US010022354B2

(12) United States Patent
Lai et al.

(10) Patent No.: US 10,022,354 B2
(45) Date of Patent: Jul. 17, 2018

(54) PYRROLIDINE AMIDE COMPOUNDS AS HISTONE DEMETHYLASE INHIBITORS

(71) Applicants: GENENTECH, INC., South San Francisco, CA (US); CONSTELLATION PHARMACEUTICALS, INC., Cambridge, MA (US)

(72) Inventors: Kwong Wah Lai, Shanghai (CN); Jun Liang, South San Francisco, CA (US); Birong Zhang, South San Francisco, CA (US); Sharada Labadie, South San Francisco, CA (US); Daniel Ortwine, South San Francisco, CA (US); Peter Dragovich, South San Francisco, CA (US); James Kiefer, South San Francisco, CA (US); Victor S. Gehling, Somerville, MA (US); Jean-Christophe Harmange, Andover, MA (US)

(73) Assignees: GENENTECH, INC., South San Francisco, CA (US); CONSTELLATION PHARMACEUTICALS INC., Cambridge, MA (US)

( * ) Notice: Subject to any disclaimer, the term of this patent is extended or adjusted under 35 U.S.C. 154(b) by 0 days.

(21) Appl. No.: 15/482,584

(22) Filed: Apr. 7, 2017

(65) Prior Publication Data
US 2017/0312252 A1 Nov. 2, 2017

Related U.S. Application Data

(63) Continuation of application No. PCT/US2015/054949, filed on Oct. 9, 2015.

(30) Foreign Application Priority Data

Oct. 10, 2014 (WO) ................ PCT/CN2014/088309

(51) Int. Cl.
C07D 237/04 (2006.01)
A61K 31/41 (2006.01)
A61K 31/4025 (2006.01)
C07D 207/04 (2006.01)

(52) U.S. Cl.
CPC .......... A61K 31/41 (2013.01); A61K 31/4025 (2013.01); C07D 207/04 (2013.01); C07D 237/04 (2013.01)

(58) Field of Classification Search
CPC ........................... C07D 207/04; C07D 237/04
See application file for complete search history.

(56) References Cited

U.S. PATENT DOCUMENTS 8,513,244 B2 * 8/2013 Gendron .............. C07D 231/14 514/236.5
2010/0261701 A1 10/2010 Kaneko et al.
2014/0275092 A1 9/2014 Albrecht et al.

FOREIGN PATENT DOCUMENTS

WO 2014164708 A1 10/2014

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Database CA, Yu, Guixue et al., "Preparation of fused pyridopyridazine inhibitors of cGMP phosphodiesterase", Database accession No. 2000:688225 abstract.
Patent Cooperation Treaty, International Searching Authority, Search Report and Written Opinion for PCT/US2015/054949, 12 pages, dated Jan. 4, 2016.
Sharma, et al., "A chromatin-mediated reversible drug-tolerant state in cancer cell subpopulations", Cell 141 (1), 39-80 (2010).

* cited by examiner

Primary Examiner — Shawquia Jackson
(74) Attorney, Agent, or Firm — Viksnins Harris Padys Malen LLP

(57) ABSTRACT

The present invention relates to compounds useful as inhibitors of one or more histone demethylases, such as KDM5. The invention also provides pharmaceutically acceptable compositions comprising compounds of the present invention and methods of using said compositions in the treatment of various disorders.

20 Claims, No Drawings

PYRROLIDINE AMIDE COMPOUNDS AS HISTONE DEMETHYLASE INHIBITORS

CROSS-REFERENCE TO RELATED APPLICATION(S)

This patent application is a continuation of International application serial no. PCT/US2015/054949, filed Oct. 9, 2015, which claims the benefit of International application serial No. PCT/CN2014/088309, filed Oct. 10, 2014, which applications are herein incorporated by reference.

TECHNICAL FIELD

Compounds useful as inhibitors of histone demethylases, such as KDM5 are provided.

BACKGROUND

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding or chromatin-modifying enzymes. Significantly, an increasing number of these enzymes have been associated with a variety of disorders such as cancer. Thus, therapeutic agents directed against this emerging class of gene regulatory enzymes promise new approaches to the treatment of human diseases.

Additionally, the relatively rapid acquisition of resistance to cancer drugs remains a key obstacle to successful cancer therapy. Substantial efforts to elucidate the molecular basis for such drug resistance have revealed a variety of mechanisms, including drug efflux, acquisition of drug binding-deficient mutants of the target, engagement of alternative survival pathways and epigenetic alterations. Rare, stochastic, resistance-conferring genetic alterations have been found within a tumor cell population selected during drug treatment. See Sharma et al., Cell 141(1):69-80 (2010). The KDM5/JARID1 family of histone demethylases was found to play a role in cancer resistance. The KDM5/JARID1 family of demethylases in humans contains four members, KDM5A, KDM5B, KDM5C and KDM5D. KDM5 family members contain five conserved domains: JmjN, ARID, JmjC, PHD and a $C_5HC_2$ zinc finger. Amino acid sequences of KDM5A, KDM5B, KDM5C and KDM5D are known and are publicly available, e.g., see UniProtKB/Swiss-Prot (see e.g., KDM5A (e.g., P29375-1 and P29375-2), KDM5B (e.g., Q9UGL1-1 and Q9UGL1-2), KDM5C (e.g., P41229-1, P41229-2, P41229-3 and P41229-4) and KDM5D (e.g., Q9BY66-1, Q9BY66-2 and Q9BY66-3). There is currently a need for compounds that inhibit of KDM5 demethylases for treating hyperproliferative diseases, preventing drug resistance, and/or for improving the efficacy of other cancer treatments (e.g. targeted therapies, chemotherapies, and radiotherapies.

SUMMARY OF THE INVENTION

One aspect provides a compound of formula (I):

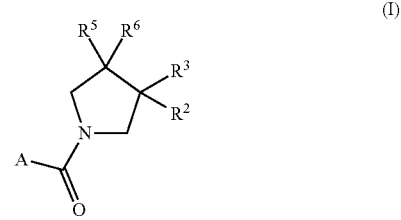

or a salt thereof, wherein:
A is selected from the group consisting of:

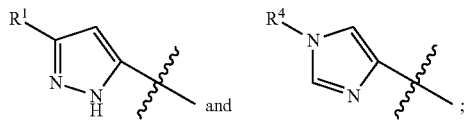

$R^1$ is halo, —$N(R^x)_2$, $C_{1-6}$alkyl, $C_{2-6}$alkenyl, $C_{2-6}$alkynyl, 3-8 membered carbocyclyl, $C_{1-6}$alkoxy, 5-10 membered aryl, 5-10 membered heteroaryl, or 3-8 membered heterocyclyl, wherein said $C_{1-6}$alkyl, $C_{1-6}$alkenyl, $C_{1-6}$alkynyl, 3-8 membered carbocyclyl, $C_{1-6}$alkoxy, 5-10 membered aryl, 5-10 membered heteroaryl, and 3-8 membered heterocyclyl are optionally substituted with one or more groups independently selected from the group consisting of oxo, hydroxy, halo, $C_{1-3}$alkoxy, 3-8 membered carbocyclyl, 5-10 membered aryl, —$N(R^x)_2$, —$N(R^x)C(O)R^x$, and $C_{1-3}$alkyl;

each $R^x$ is independently selected from the group consisting of H and $C_{1-6}$alkyl, that is optionally substituted with one or more groups independently selected from the group consisting of halo, hydroxy, and $C_{1-3}$alkoxy;

$R^2$ is 5-10 membered carbocyclyl, 5-10 membered heterocyclyl, 5-10 membered aryl, 5-10 membered heteroaryl, —$OR^a$, —$C(O)N(R^a)_2$, or $NR^aR^b$, wherein each 5-10 membered carbocyclyl, 5-10 membered heterocyclyl, 5-10 membered aryl, and 5-10 membered heteroaryl is optionally substituted with one or more groups $R^d$;

$R^a$ and $R^b$ are each independently selected from the group consisting of H, $C_{1-6}$alkyl, $C_{2-6}$alkenyl, $C_{2-6}$alkynyl, 3-8 membered carbocyclyl, 3-8 membered heterocyclyl, 5-10 membered aryl, 5-10 membered heteroaryl —$C(O)R^c$, —$CO_2R^c$, —$C(O)N(R^c)_2$, —$C(O)SR^c$, and —$C(O)C(O)R^c$, wherein each $C_{1-6}$alkyl, $C_{2-6}$alkenyl, $C_{2-6}$alkynyl, 3-8 membered carbocyclyl, 3-8 membered heterocyclyl, 5-10 membered aryl, and 5-10 membered heteroaryl is optionally substituted with one or more groups independently selected from the group consisting of halo, nitro, cyano, oxo, $C_{1-4}$alkyl, $C_{2-4}$alkenyl, $C_{2-4}$alkynyl, 3-8 membered carbocyclyl, —$OR^c$, —$SR^c$, —$N(R^c)_2$, —$C(O)R^c$, —$CO_2R^c$, —$C(O)N(R^c)_2$, —$C(O)SR^c$, —$C(O)C(O)R^c$, —$S(O)R^c$, —$SO_2R^c$, —$SO_2N(R^c)_2$, —$N(R^c)C(O)R^c$, —$N(R^c)C(O)N(R^c)_2$, —$N(R^c)SO_2R^c$, —$N(R^c)SO_2N(R^c)_2$, —$N(R^c)N(R^c)_2$, —$N(R^c)C(=N(R^c))N(R^c)_2$, —$C(=N)N(R^c)_2$, —$C=NOR^c$, and —$C(=N(R^c))N(R^c)_2$;

each $R^c$ is independently selected from the group consisting of H, $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl, wherein each $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl is optionally substituted with one or more groups $R^h$;

each $R^d$ is independently selected from the group consisting of halo, nitro, cyano, oxo, $C_{1-6}$alkyl, $C_{2-6}$alkenyl, $C_{2-6}$alkynyl, 3-8 membered carbocyclyl, 3-8 membered heterocyclyl, 5-10 membered aryl, 5-10 membered heteroaryl, —$OR^e$, —$SR^e$, —$N(R^e)_2$, —$C(O)R^e$, —$CO_2R^e$, —$C(O)N(R^e)_2$, —$C(O)SR^e$, —$C(O)C(O)R^e$, —$S(O)R^e$, —$SO_2R^e$, —$SO_2N(R^e)_2$, —$N(R^e)C(O)R^e$, —$N(R^e)C(O)N(R^e)_2$, —$N(R^e)SO_2R^e$, —$N(R^e)SO_2N(R^e)_2$, —$N(R^e)N(R^e)_2$, —$N(R^e)C(=N(R^e))N(R^e)_2$, —$C(=N)N(R^e)_2$, —$C=NOR^e$, and —$C(=N(R^e))N(R^e)_2$, wherein each $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl is optionally substituted with one or more groups independently selected from $R^f$;

each $R^e$ is independently selected from the group consisting of H, $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl, wherein each $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl is optionally substituted with one or more groups independently selected from the group consisting of $C_{1-4}$alkyl, $C_{2-4}$alkenyl, $C_{2-4}$alkynyl, 3-8 membered carbocyclyl, 3-8 membered heterocyclyl, 5-10 membered aryl and 5-10 membered heteroaryl;

each $R^f$ is independently selected from the group consisting of halo, nitro, cyano, oxo, $C_{1-4}$alkyl, $C_{2-4}$alkenyl, $C_{2-4}$alkynyl, 3-8 membered carbocyclyl, —$OR^g$, —$SR^g$, —$N(R^g)_2$, —$C(O)R^g$, —$CO_2R^g$, —$C(O)N(R^g)_2$, —$C(O)SR^g$, —$C(O)C(O)R^g$, —$S(O)R^g$, —$SO_2R^g$, —$SO_2N(R^g)_2$, —$N(R^g)C(O)R^g$, —$N(R^g)C(O)N(R^g)_2$, —$N(R^g)SO_2R^g$, —$N(R^g)SO_2N(R^g)_2$, —$N(R^g)N(R^g)_2$, —$N(R^g)C(=N(R^g))N(R^g)_2$, —$C(=N)N(R^g)_2$, and —$C=NOR^g$, —$C(=N(R^g))N(R^g)_2$, wherein each $C_{1-4}$alkyl, $C_{2-4}$alkenyl, $C_{2-4}$alkynyl, and 3-8 membered carbocyclyl is optionally substituted with one or more groups independently selected from the group consisting of halo, cyano, oxo, 3-8 membered carbocyclyl, —$OR^g$, —$N(R^g)_2$, —$C(O)R^g$, —$CO_2R^g$, —$C(O)N(R^g)_2$, —$SO_2R^g$, —$SO_2N(R^g)_2$, and —$N(R^g)C(O)R^g$;

each $R^g$ is independently selected from the group consisting of H, $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl, wherein each $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl is optionally substituted with one or more groups independently selected from the group consisting of $C_{1-4}$alkyl, $C_{2-4}$alkenyl, $C_{2-4}$alkynyl, 3-8 membered carbocyclyl, 3-8 membered heterocyclyl, 5-10 membered aryl and 5-10 membered heteroaryl; and each $R^h$ is independently selected from the group consisting of halo, nitro, cyano, oxo, $C_{1-4}$alkyl, $C_{2-4}$alkenyl, $C_{2-4}$alkynyl, 3-8 membered carbocyclyl, 3-8 membered heterocyclyl, 5-10 membered aryl, 5-10 membered heteroaryl, —$N(R^k)_2$, and, —$OR^k$, wherein each $C_{1-4}$alkyl, $C_{2-4}$alkenyl, $C_{2-4}$alkynyl, 3-8 membered carbocyclyl, 3-8 membered heterocyclyl, 5-10 membered aryl and 5-10 membered heteroaryl is optionally substituted with one or more groups independently selected from the group consisting of halo, hydroxy, $C_{1-4}$alkoxy, cyano, oxo, $C_{1-4}$alkyl, $C_{2-4}$alkenyl, $C_{2-4}$alkynyl, 3-8 membered carbocyclyl, and 5-10 membered aryl;

each $R^k$ is independently selected from the group consisting of H, $C_{1-4}$alkyl, $C_{2-4}$alkenyl, $C_{2-4}$alkynyl, 3-8 membered carbocyclyl, and 5-10 membered aryl wherein any $C_{1-4}$alkyl, $C_{2-4}$alkenyl, $C_{2-4}$alkynyl, 3-8 membered carbocyclyl, and 5-10 membered aryl carbocyclyl is optionally substituted with one or more groups independently selected from the group consisting of halo, cyano, oxo hydroxy, and 3-8 membered carbocyclyl; and $R^3$ is H or $C_{1-6}$alkyl;

$R^4$ is H, $C_{1-6}$alkyl, $C_{2-6}$alkenyl, $C_{2-6}$alkynyl, or 3-8 membered carbocyclyl, 5-10 membered aryl, 5-10 membered heteroaryl wherein each $C_{1-6}$alkyl, $C_{2-6}$alkenyl, $C_{2-6}$alkynyl, and 3-8 membered carbocyclyl, 5-10 membered aryl, 5-10 membered heteroaryl is optionally substituted with one or more groups independently selected from halo, hydroxy, cyano, $C_{1-6}$alkoxy, and 3-8 membered carbocyclyl; and $R^5$ is H, halo, or $C_{1-6}$alkyl, and $R^6$ is H, $C_{1-6}$alkyl, $C_{2-6}$alkenyl, $C_{2-6}$alkynyl, halo, hydroxy, or 3-8 membered carbocyclyl, wherein each $C_{1-6}$alkyl, $C_{2-6}$alkenyl, $C_{2-6}$alkynyl, and 3-8 membered carbocyclyl, is optionally substituted with one or more groups independently selected from halo, hydroxy, cyano, $C_{1-6}$alkoxy, and 3-8 membered carbocyclyl; or $R^5$ and $R^6$ taken together with the atom to which they are attached form a 3-8 membered carbocyclyl or a 3-8 membered heterocyclyl, which 3-8 membered carbocyclyl and 3-8 membered heterocyclyl are optionally substitutes with one or more groups independently selected from halo, hydroxy, cyano, $C_{1-6}$alkoxy, and 3-8 membered carbocyclyl.

Another aspect includes a composition, comprising a compound of formula (I), or a pharmaceutically acceptable salt thereof, and a pharmaceutically acceptable adjuvant, carrier, or vehicle.

Another aspect includes a method of treating a disease associated with KDM5 activity, comprising administering an therapeutically effective amount of a compound of formula (I), or a pharmaceutically acceptable salt thereof, to a patient in need thereof.

Another aspect includes the use of a compound of formula (I), or a pharmaceutically acceptable salt thereof, in therapy.

Another aspect includes the use of a compound of formula (I), or a pharmaceutically acceptable salt thereof, in treating a disease associated with KDM5 activity.

Another aspect includes the use of a compound of formula (I), or a pharmaceutically acceptable salt thereof, in the manufacture of a medicament for the treatment of a disease associated with KDM5 activity.

Another aspect includes a method of increasing the efficacy of a cancer treatment comprising a cancer therapy agent, comprising administering to a patient (a) an effective amount of a compound of formula (I), or a pharmaceutically acceptable salt thereof, and (b) an effective amount of the cancer therapy agent.

Another aspect includes a method of treating an individual with cancer who has an increased likelihood of developing resistance to a cancer therapy agent comprising administering to the individual (a) an effective amount of a compound of formula (I), or a pharmaceutically acceptable salt thereof, and (b) an effective amount of the cancer therapy agent.

Another aspect includes a processes and synthetic intermediates that are useful for preparing a compound of formula (I), or a salt thereof.

Another aspect includes compounds for the study of histone demethylases, such as KDM5, the study of intracellular signal transduction pathways mediated by such histone demethylases, and the comparative evaluation of modulators of these demethylases.

DETAILED DESCRIPTION

Definitions

Definitions of specific functional groups and chemical terms are described in more detail below. Chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are included.

Unless otherwise stated, all tautomeric forms of the compounds are included. For example, when the group A includes a pyrazole ring, it can be either tautomeric form shown below:

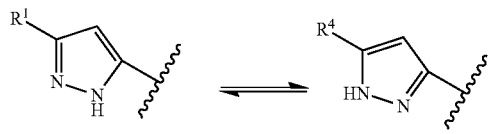

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are included. Such compounds are useful, for example, as analytical tools, as probes in biological assays, or as therapeutic agents.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "a compound as described herein" includes the compounds described in Examples 1-432 and salts thereof, as well as compounds of formula (I) and salts thereof.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic, bicyclic, or spiro ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, the term "cycloalkylene" refers to a bivalent cycloalkyl group. In certain embodiments, a cycloalkylene group is a 1,1-cycloalkylene group (i.e., a spiro-fused ring). Exemplary 1,1-cycloalkylene groups include

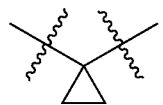

In other embodiments, a cycloalkylene group is a 1,2-cycloalkylene group or a 1,3-cycloalkylene group. Exemplary 1,2-cycloalkylene groups include

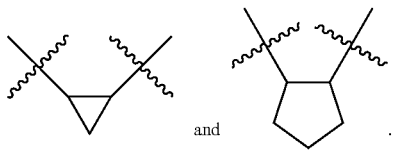 [SMILES: *C1CC1* ; *C1CCCC1*]

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "aryl" used alone or as part of a larger moiety as in "aralkyl", "aralkoxy", or "aryloxyalkyl", refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As used herein, the term "inhibitor" refers to a compound that binds to and inhibits a KDM5 enzyme with measurable affinity and activity. In certain embodiments, an inhibitor has an IC$_{50}$ and/or binding constant of less about 50 µM, less than about 1 µM, less than about 500 nM, less than about 100 nM, or less than about 10 nM.

The terms "measurable affinity" and "measurably inhibit," as used herein, refer to a measurable reduction in activity of a KDM5 enzyme between: (i) a sample comprising a compound a compound as described herein and such KDM5 enzyme, and (ii) an equivalent sample comprising such KDM5 enzyme, in the absence of said compound.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound or pharmaceutically acceptable salt thereof as described herein. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound or pharmaceutically acceptable salt thereof as described herein that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound as described herein is used to delay development of a disease or disorder or to slow the progression of a disease or disorder. Those individuals in need of treatment include those already with the condition or disorder as well as those prone to have the condition or disorder, (for example, through a genetic mutation or aberrant expression of a gene or protein) or those in which the condition or disorder is to be prevented.

Exemplary Values

In one embodiment the compound is a compound of formula (Ia):

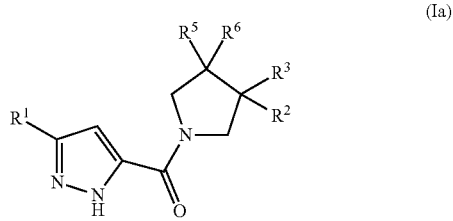

or a salt thereof.

In one embodiment R¹ is C₁₋₆alkyl, wherein said C₁₋₆alkyl is optionally substituted with one or more groups independently selected from the group consisting of oxo, hydroxy, halo, C₁₋₃alkoxy, 3-8 membered carbocyclyl, 5-10 membered aryl, —N(Rᵃ)₂, —N(Rᵃ)C(O)Rᵃ, and C₁₋₃alkyl.

In one embodiment R¹ is halo, —N(Rᵃ)₂, 3-8 membered carbocyclyl, C₁₋₆alkoxy, 5-10 membered aryl, wherein said 3-8 membered carbocyclyl and 5-10 membered aryl are optionally substituted with one or more groups independently selected from the group consisting of oxo, hydroxy, halo, C₁₋₃alkoxy, 3-8 membered carbocyclyl, 5-10 membered aryl, —N(Rᵃ)₂, —N(Rᵃ)C(O)Rᵃ, and C₁₋₃alkyl.

In one embodiment R¹ is bromo, cyclohexyl, isopropyl, isobutyl, cyclopentyl, 1-methoxyethyl, cyclopropyl, cyclobutyl, amino, 4-phenylbut-2-yl, butyl, phenethyl, cyclopentyl, 1-(acetylamino)ethyl, or 1-(hydroxymethylcarbonylamino)ethyl.

In one embodiment R¹ is isopropyl.

In one embodiment the compound is a compound of formula (Ib):

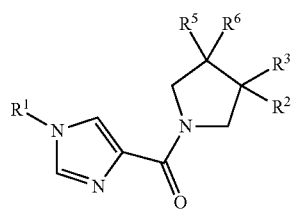

or a salt thereof.

In one embodiment R⁴ is H, methyl, or isopropyl.

In one embodiment R² is selected from the group consisting of:

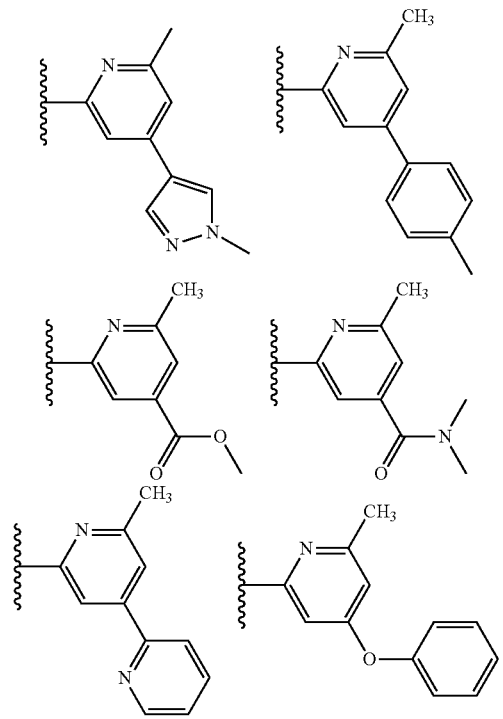

-continued

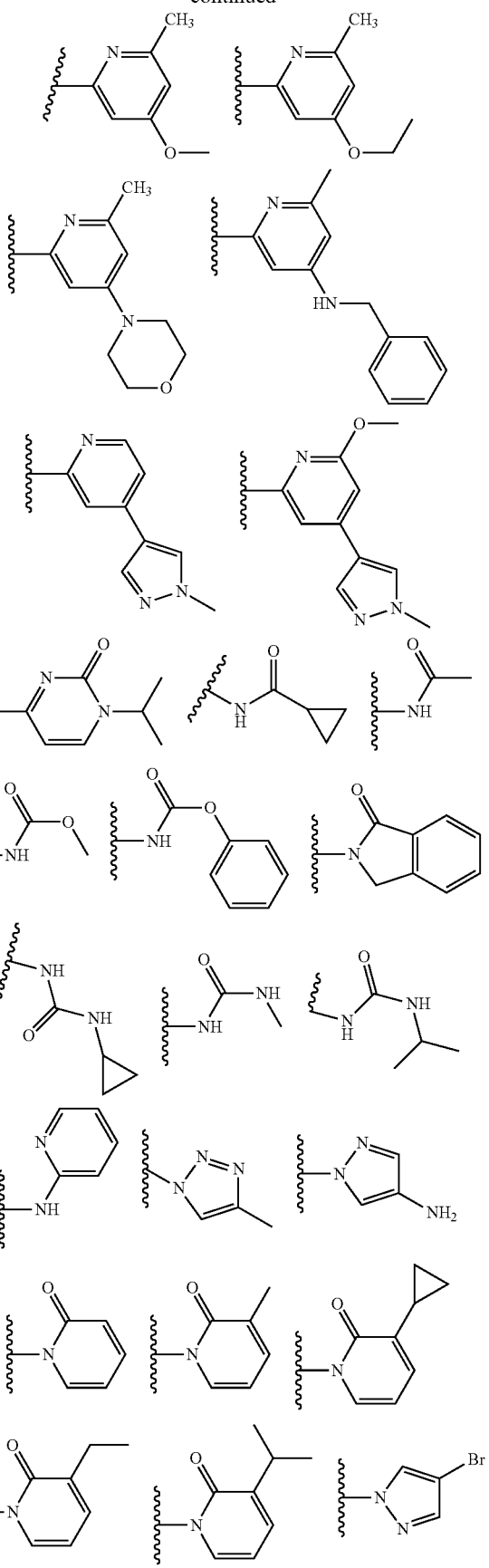

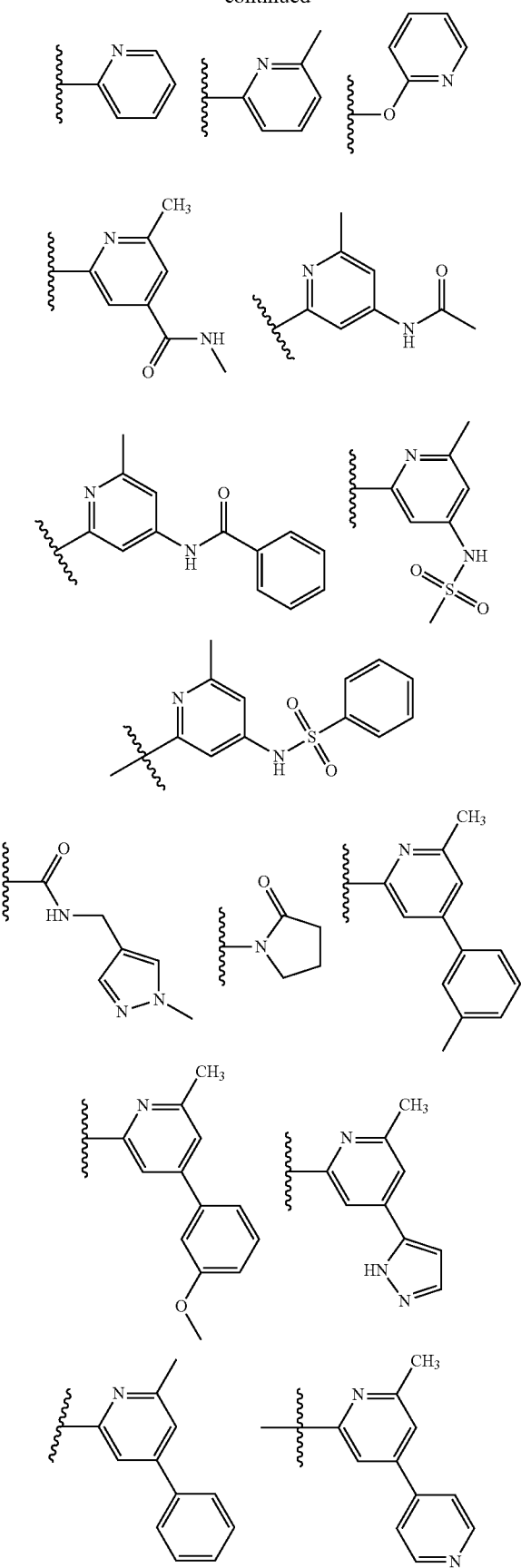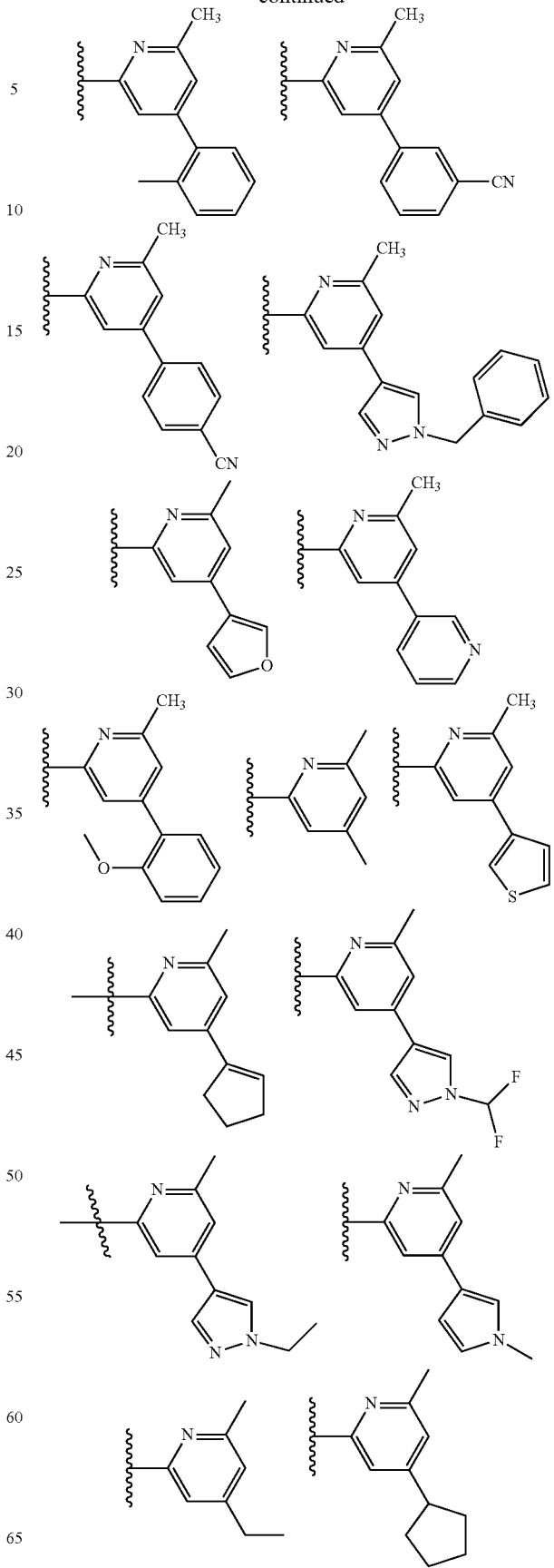

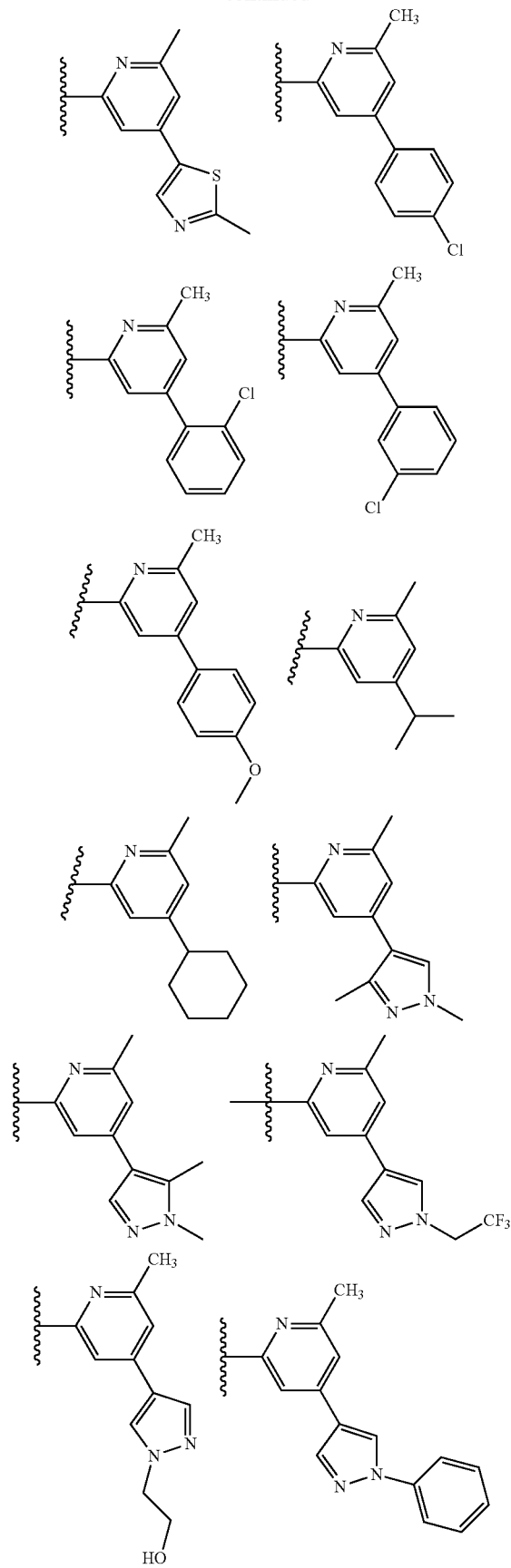
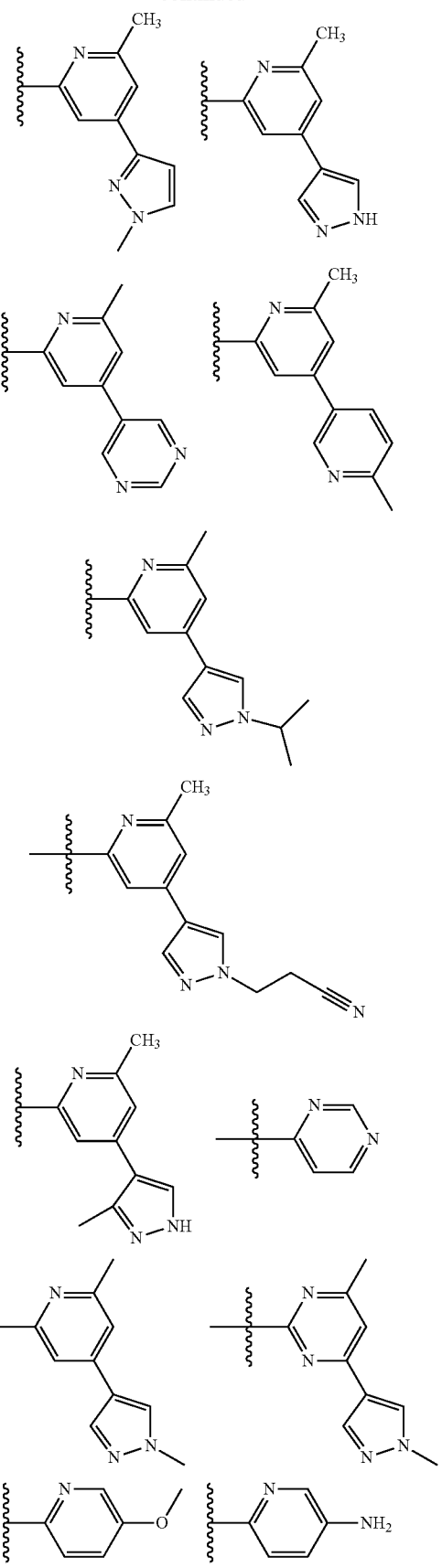

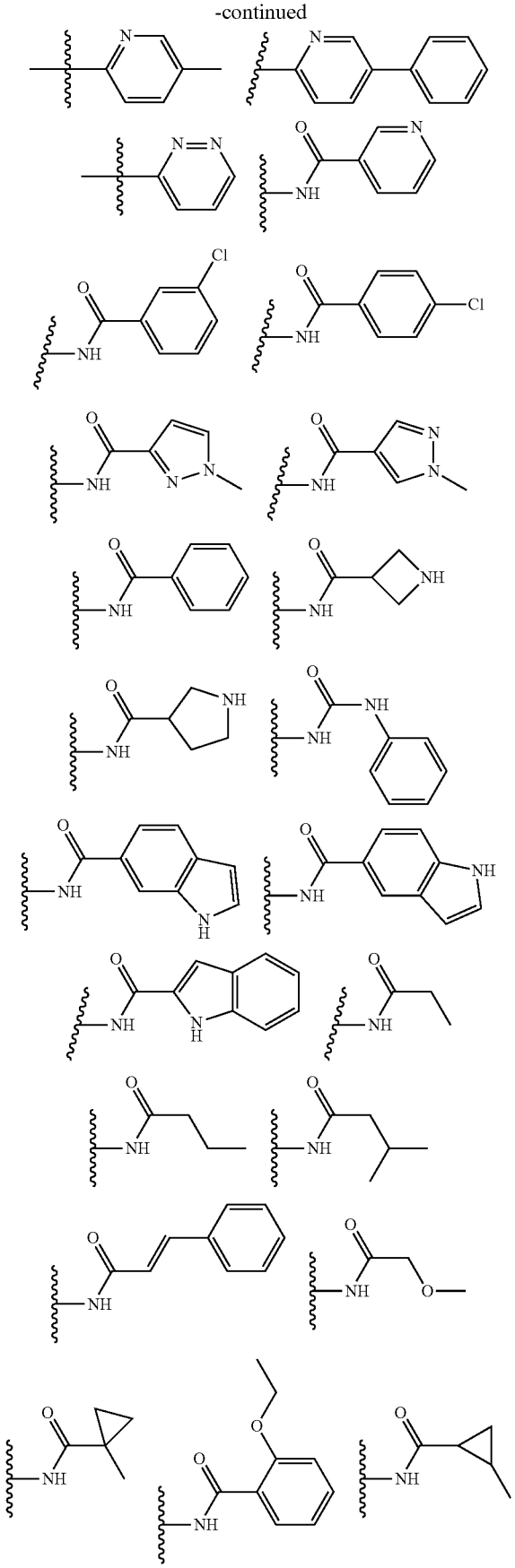
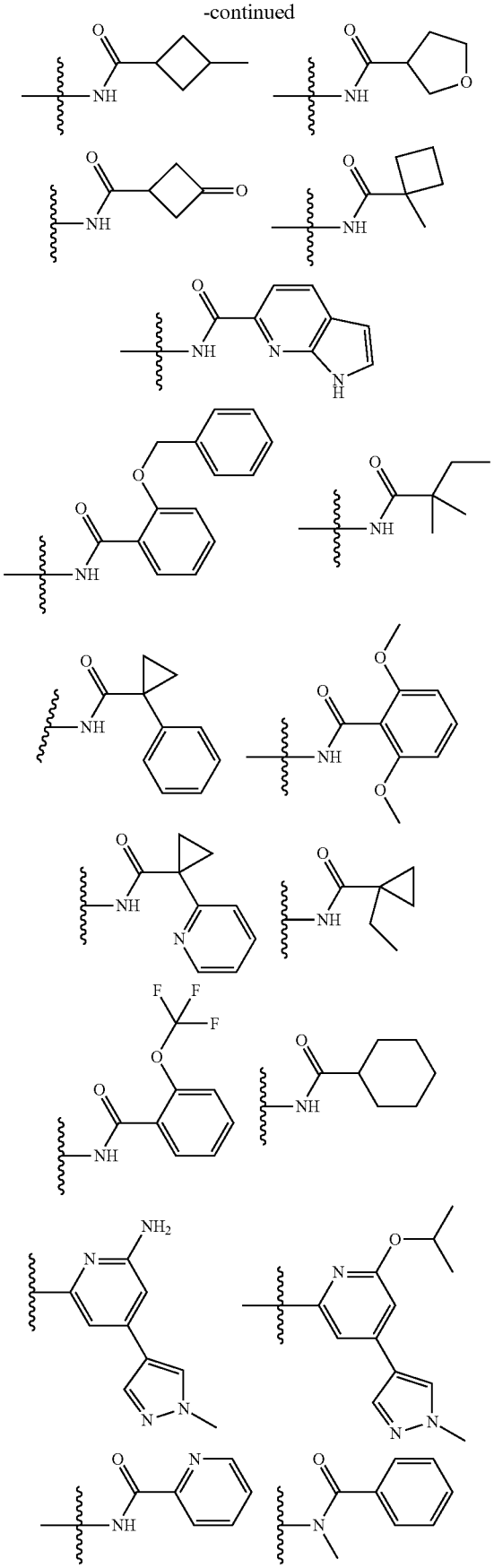

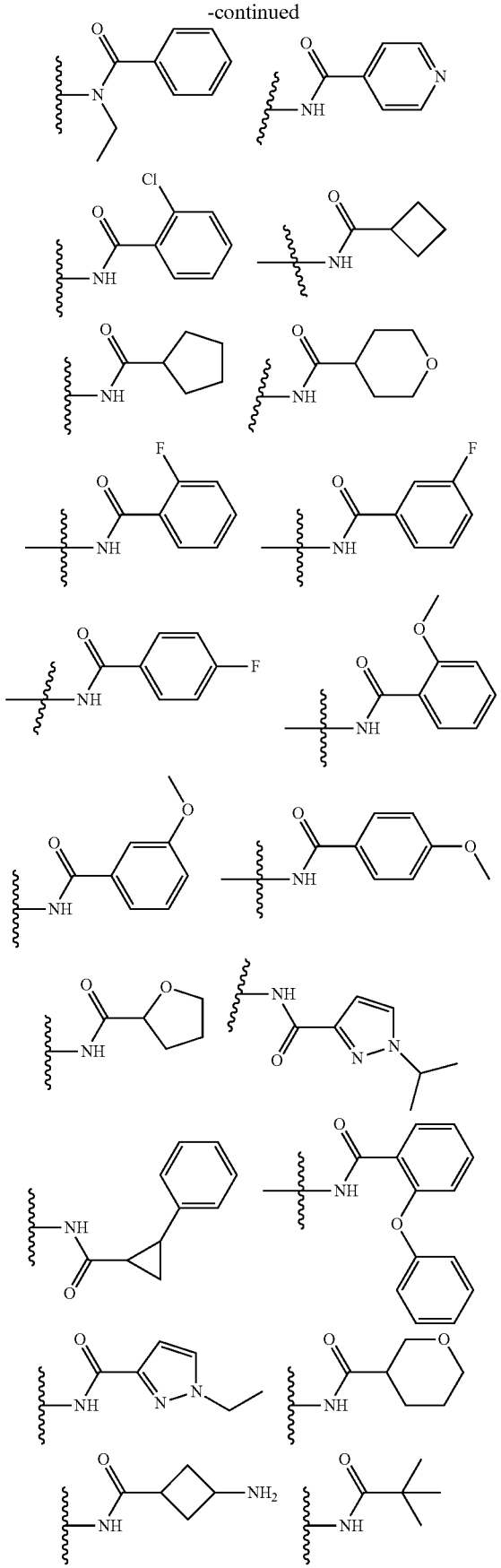
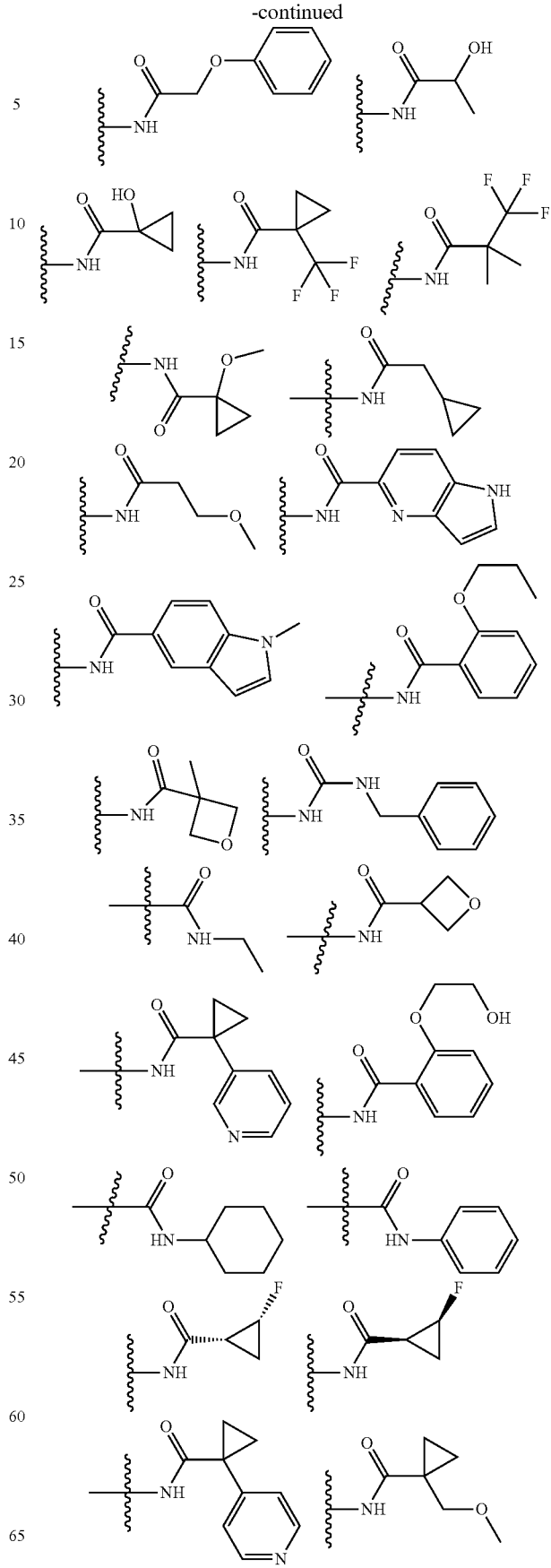

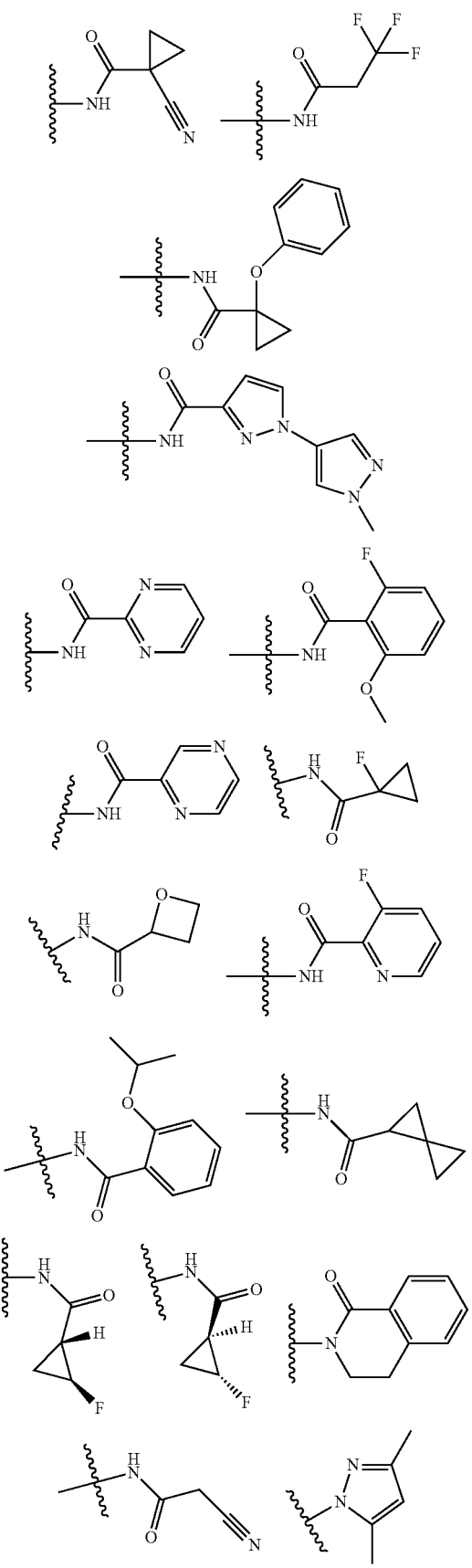
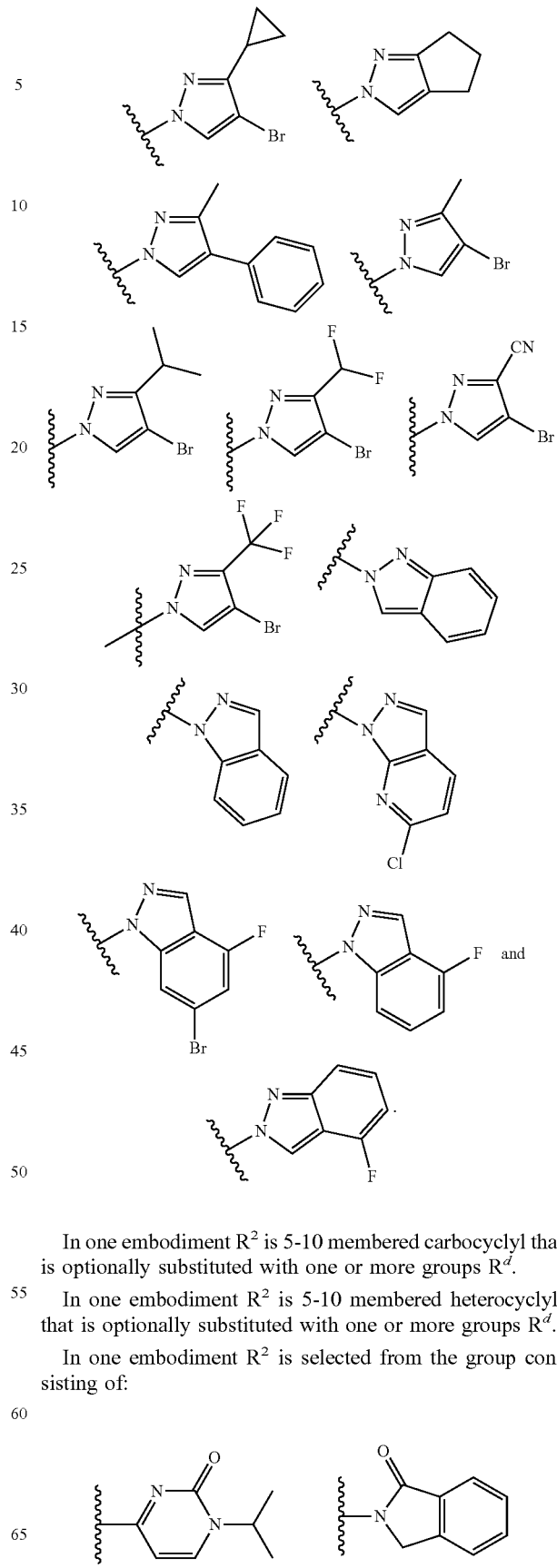
In one embodiment $R^2$ is 5-10 membered carbocyclyl that is optionally substituted with one or more groups $R^d$.
In one embodiment $R^2$ is 5-10 membered heterocyclyl, that is optionally substituted with one or more groups $R^d$.
In one embodiment $R^2$ is selected from the group consisting of:
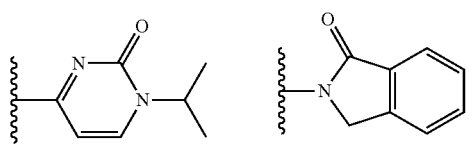

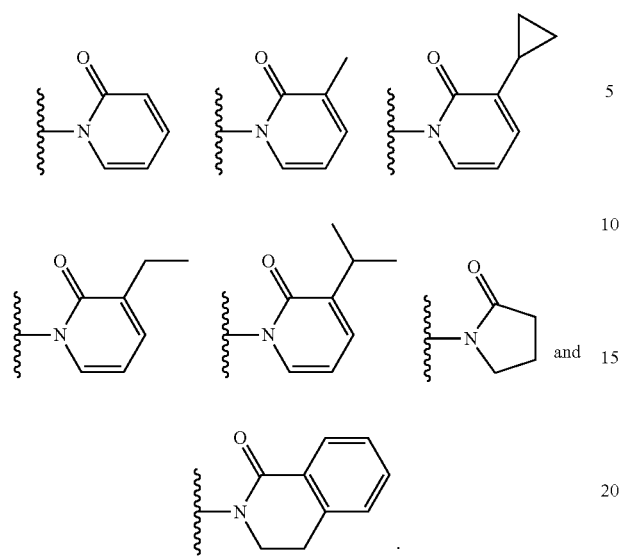
In one embodiment $R^2$ is 5-10 membered aryl that is optionally substituted with one or more groups $R^d$.
In one embodiment $R^2$ is:
In one embodiment $R^2$ is 5-10 membered heteroaryl that is optionally substituted with one or more groups $R^d$.
In one embodiment $R^2$ is selected from the group consisting of:
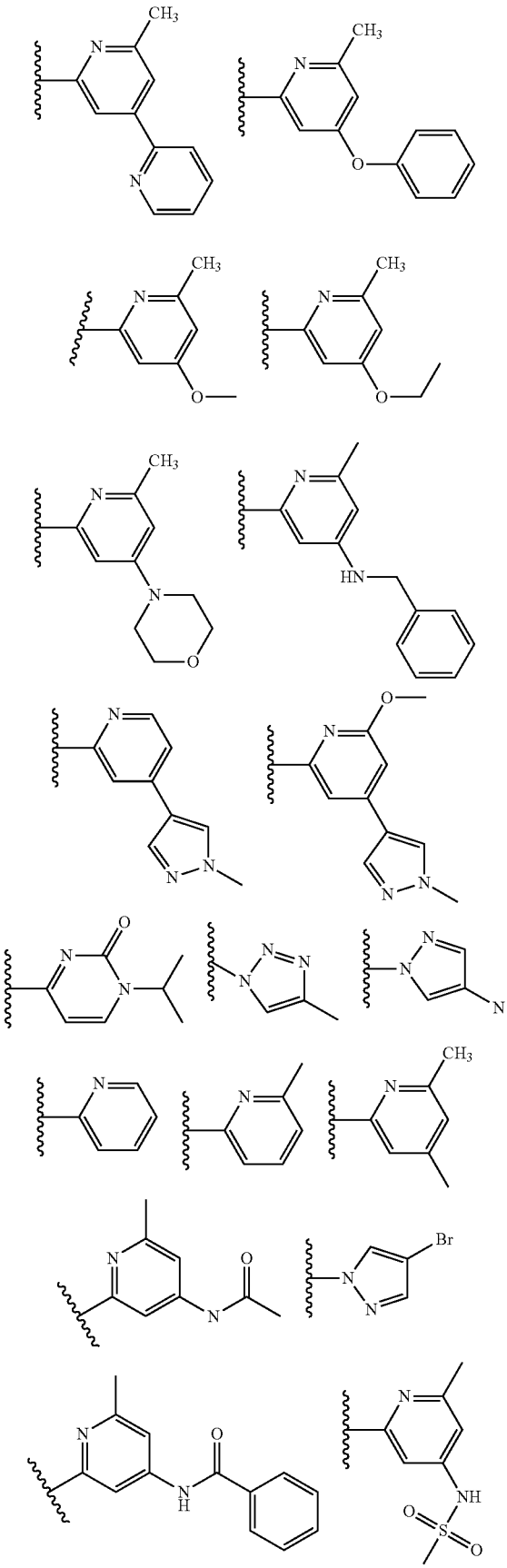

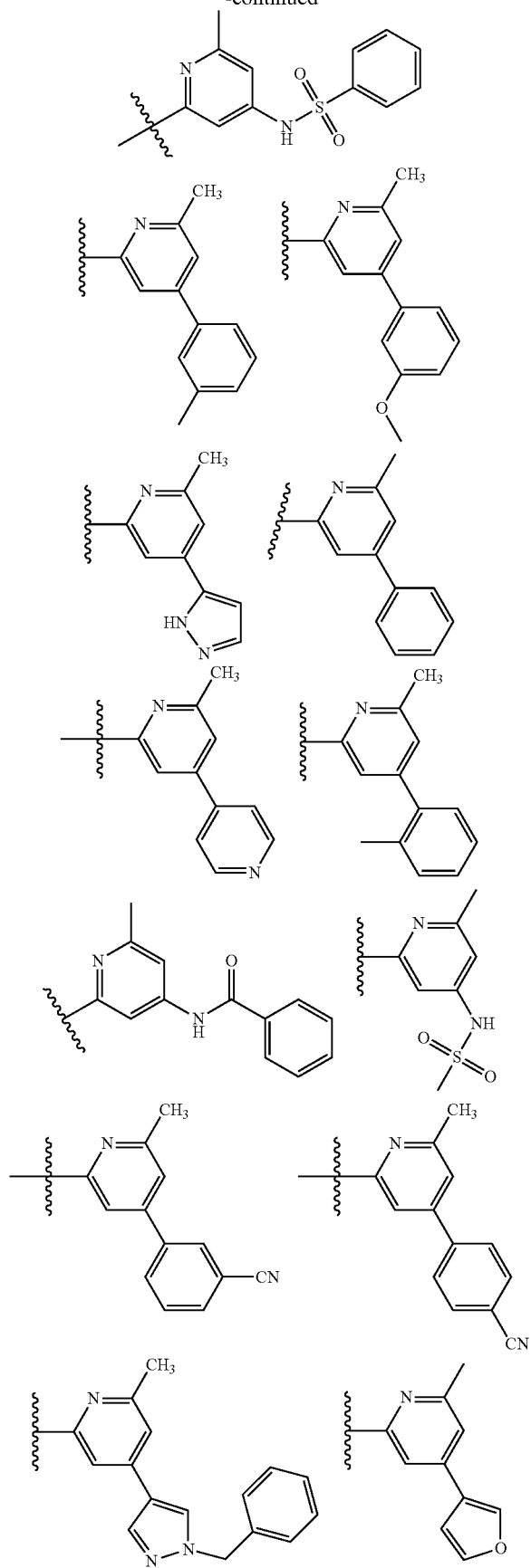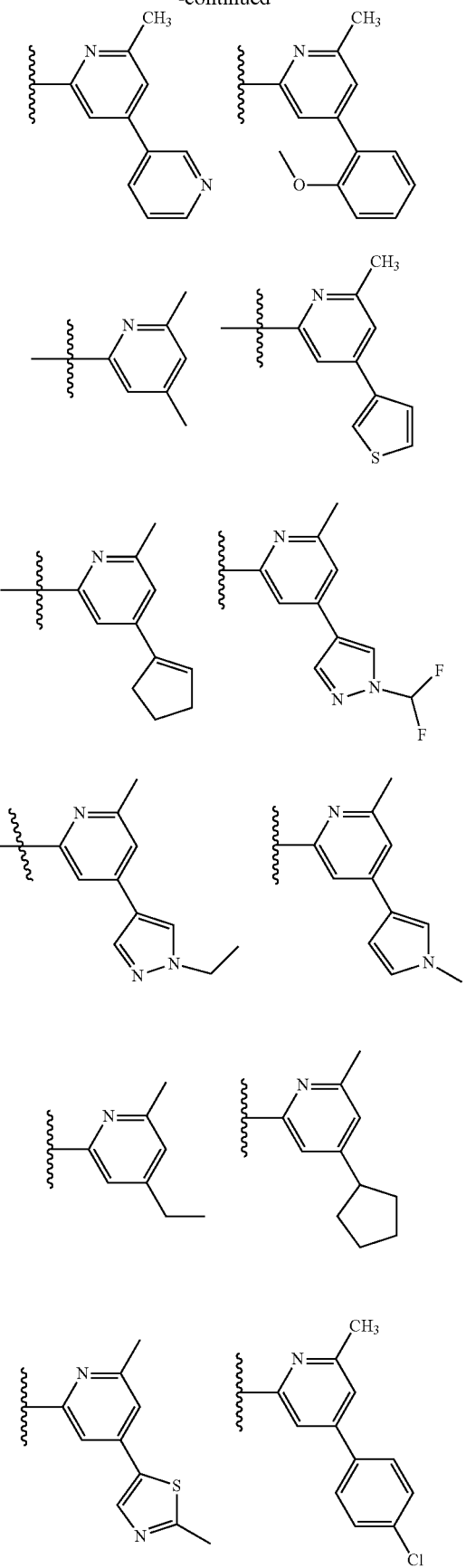

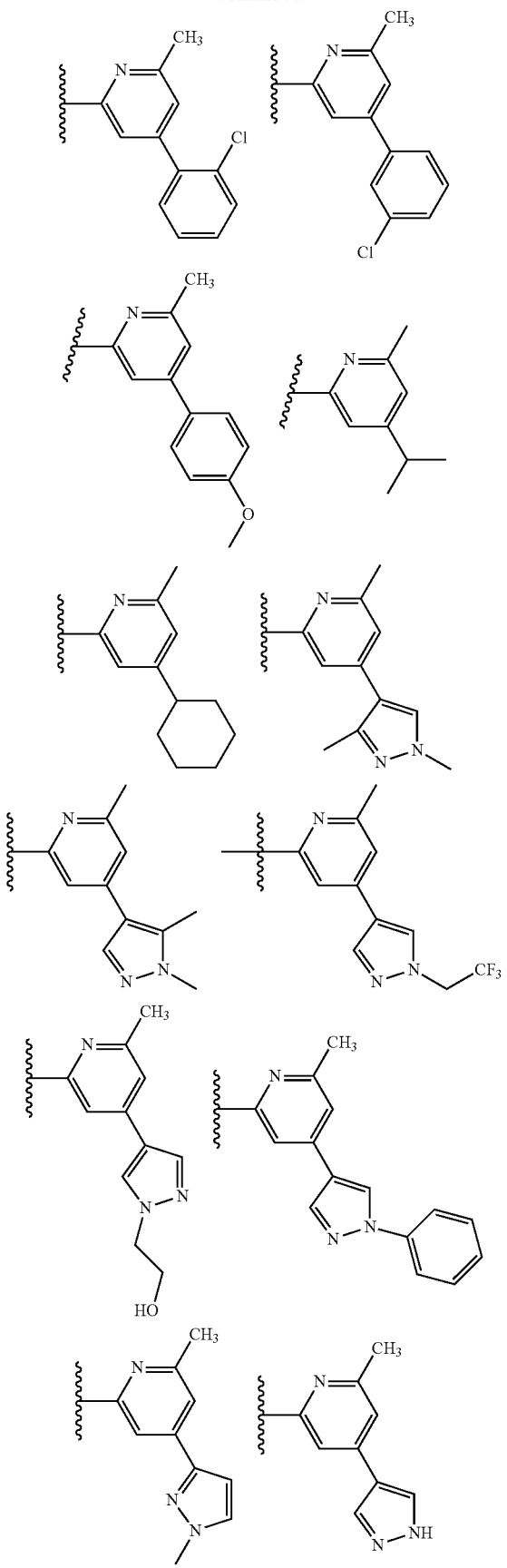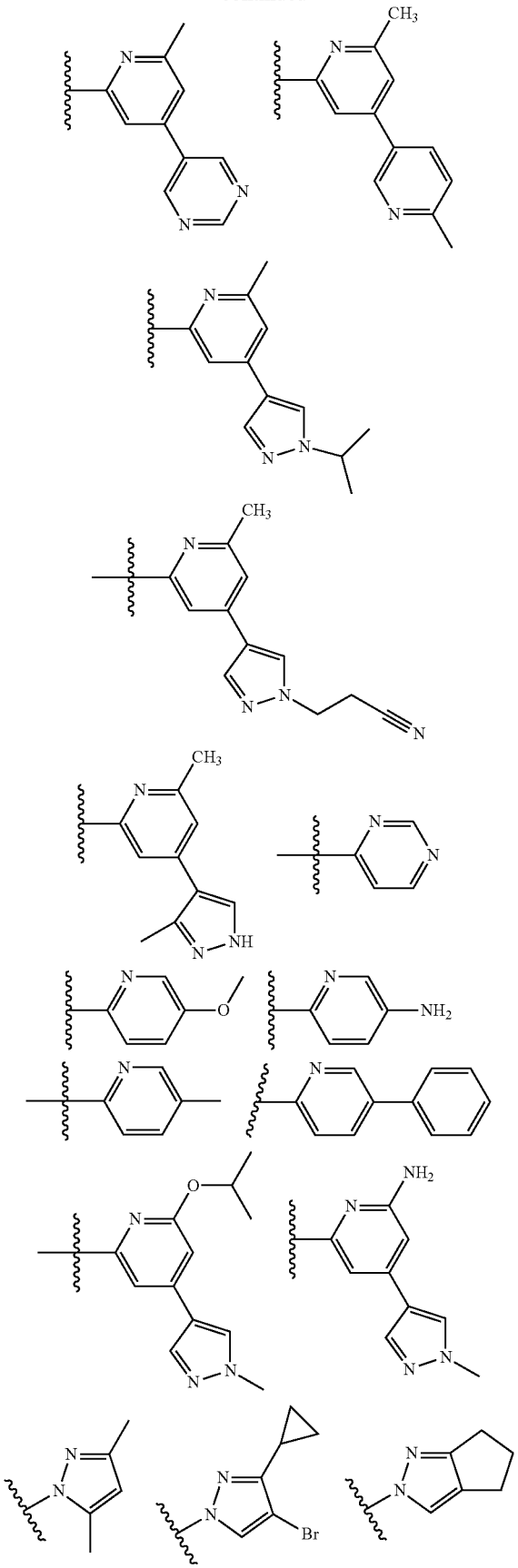

-continued
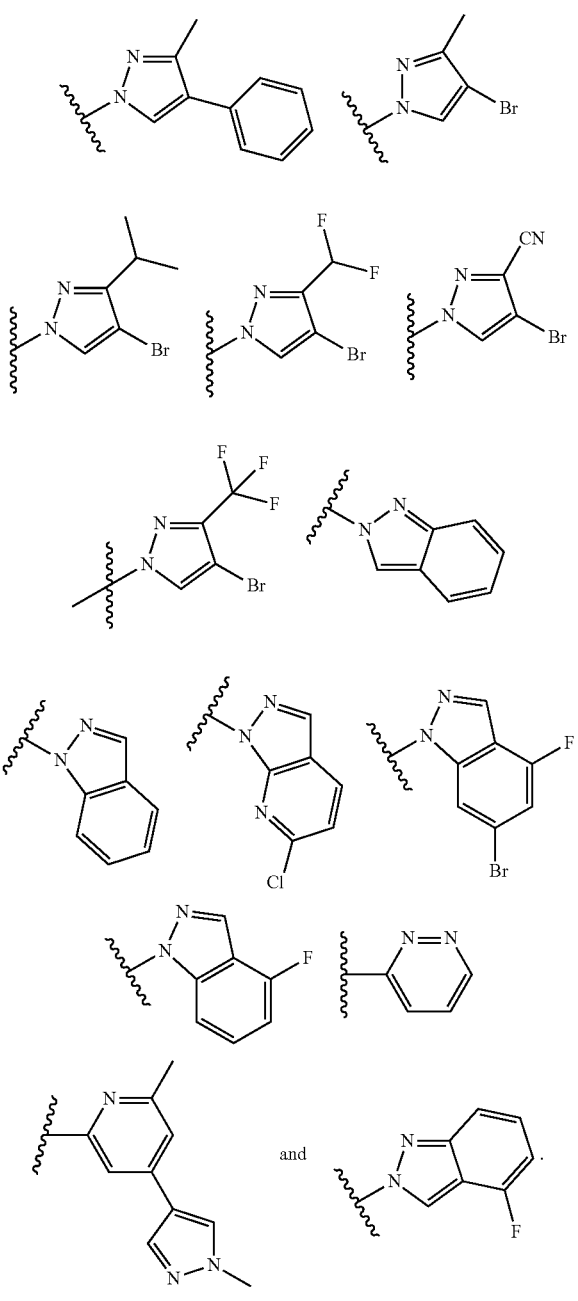
In one embodiment R² is —OR$^a$.
In one embodiment R² is:
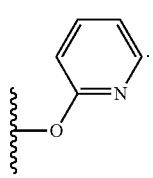 [SMILES: *Oc1ccccn1]
In one embodiment R² is NR$^a$R$^b$.
In one embodiment R² is selected from the group consisting of:
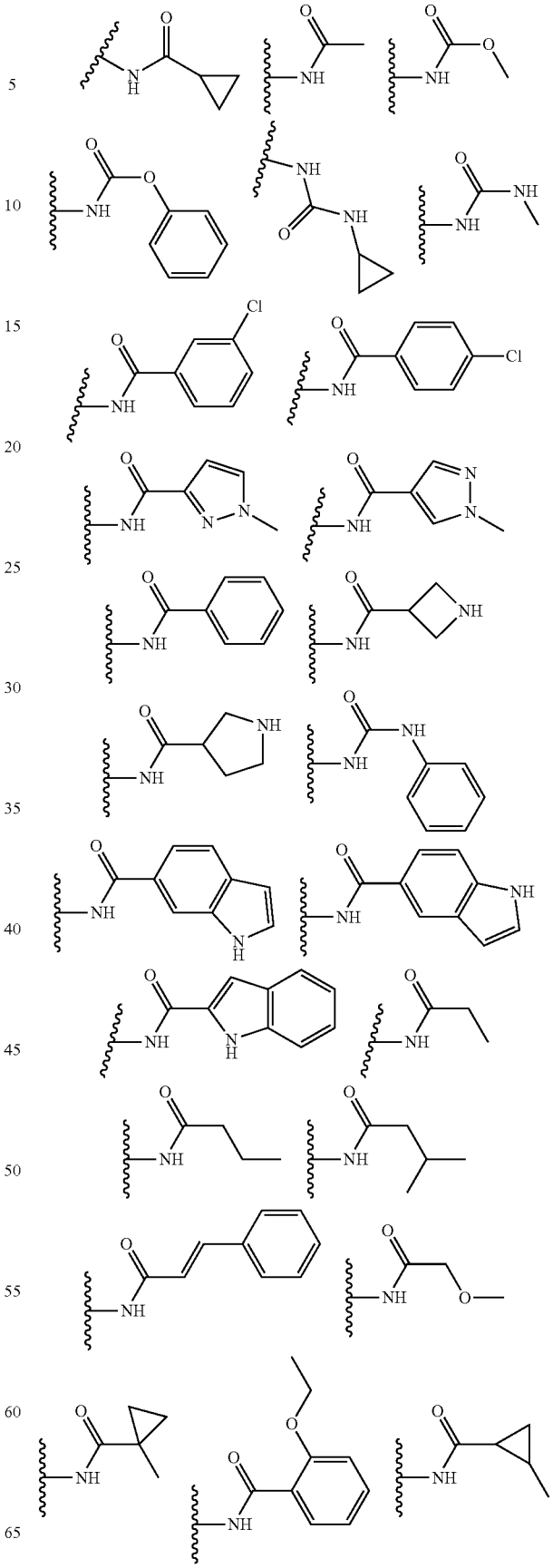

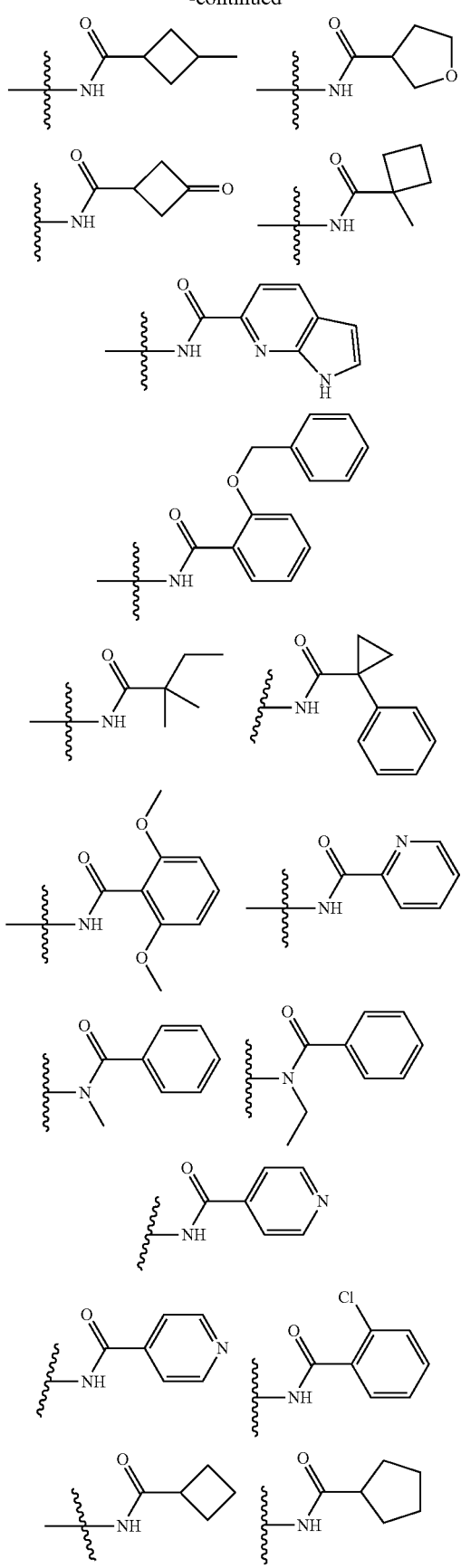
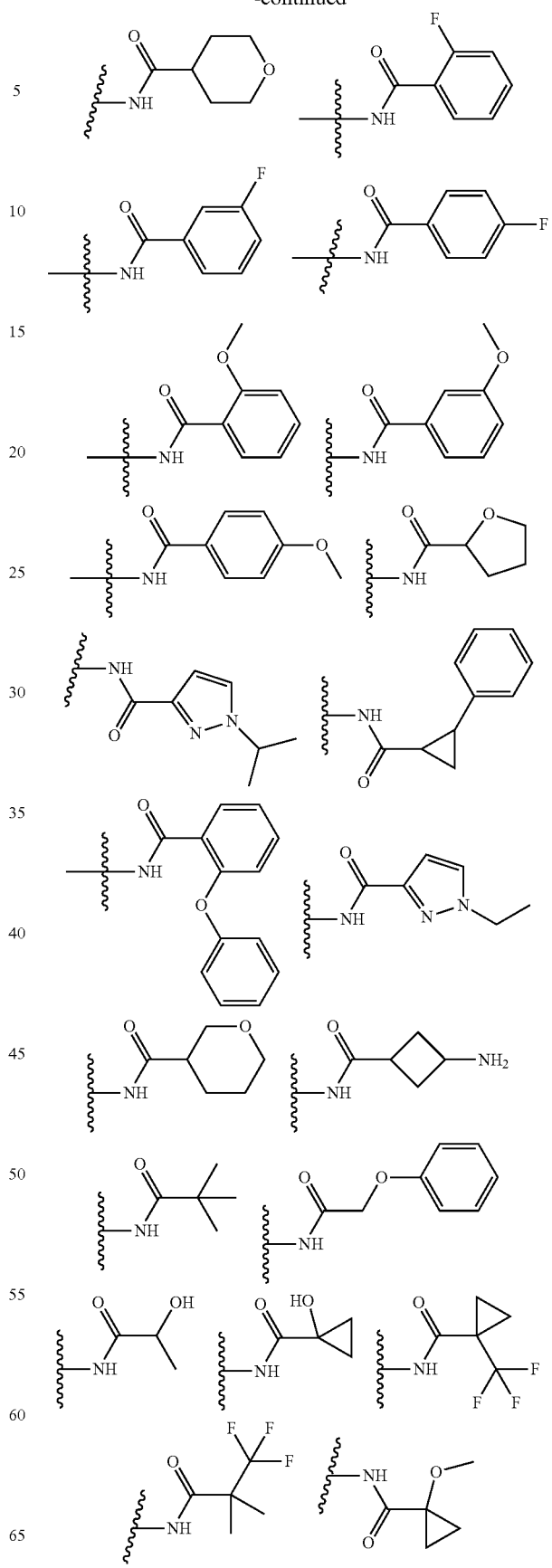

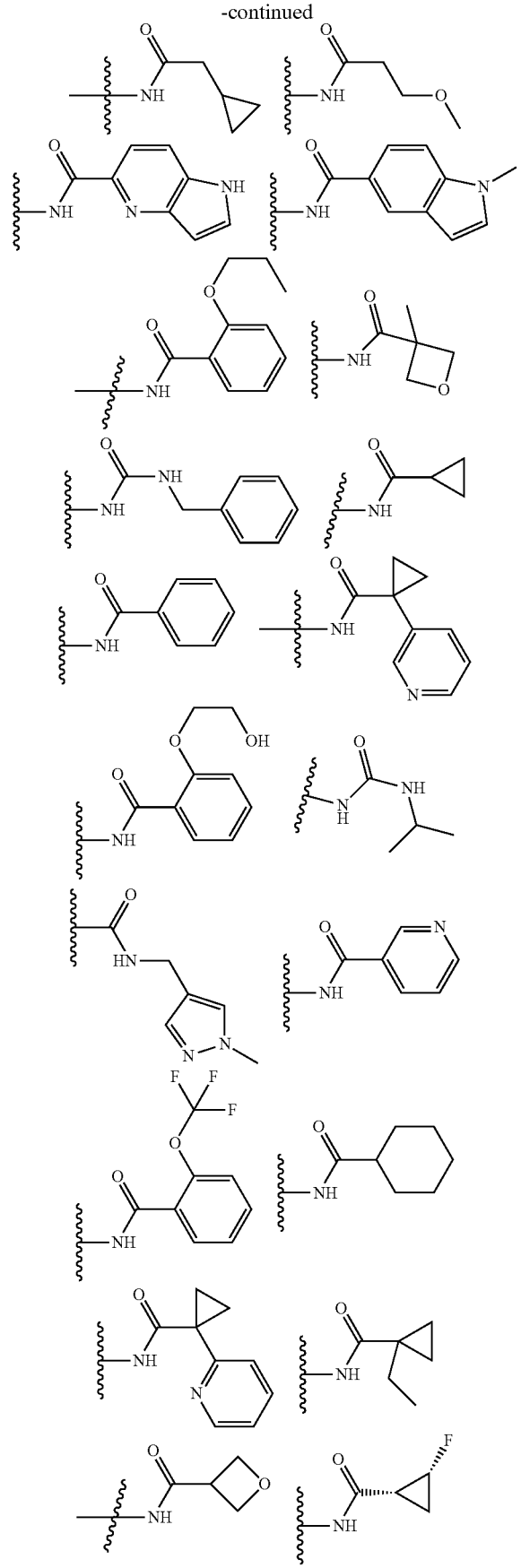
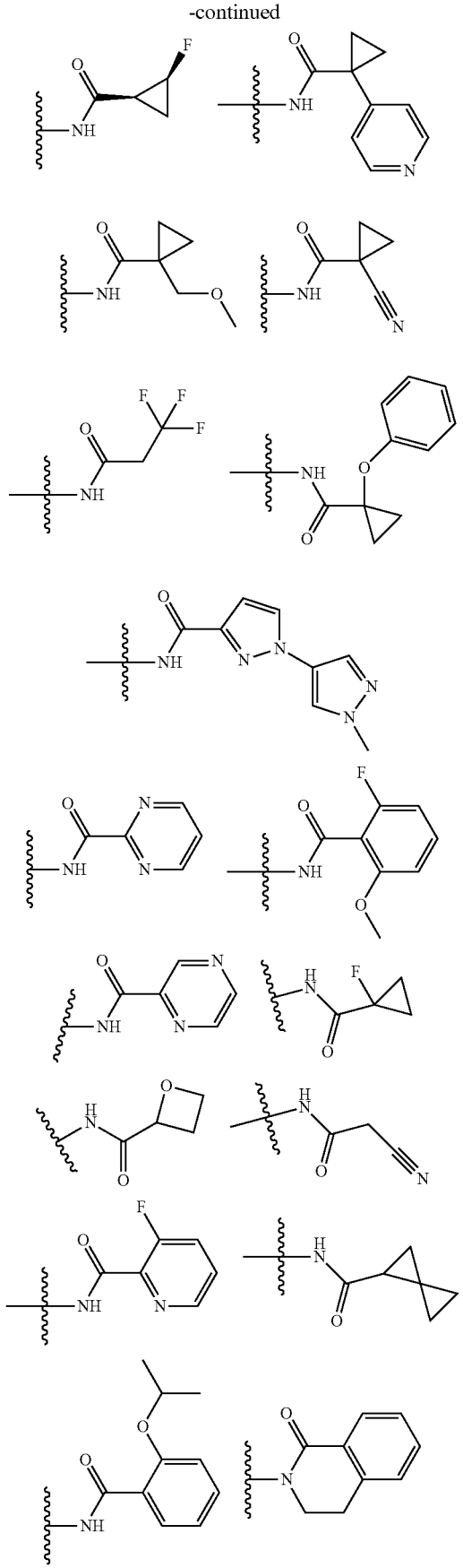

-continued

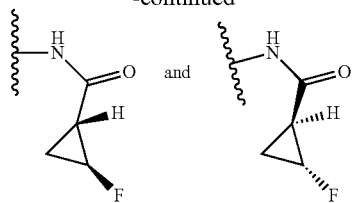

In one embodiment R² is —C(O)N(Rᵃ)₂.

In one embodiment R² is selected from the group consisting of:

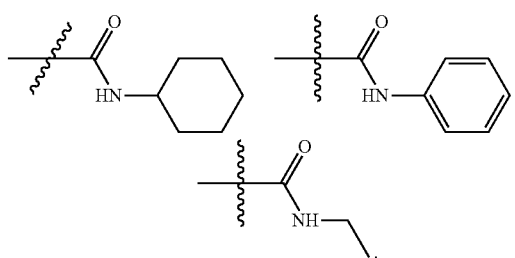

In one embodiment R³ is H.
In one embodiment R³ is methyl.
In one embodiment R⁵ is H
In one embodiment R⁶ is $C_{1-6}$alkyl or hydroxy.
In one embodiment R⁶ is methyl or hydroxy.
In one embodiment R⁶ is H.
In one embodiment R⁵ and R⁶ taken together with the atom to which they are attached form a 3-8 membered carbocyclyl or a 3-8 membered heterocyclyl, which 3-8 membered carbocyclyl and 3-8 membered heterocyclyl are optionally substitutes with one or more groups independently selected from halo, hydroxy, cyano, $C_{1-6}$alkoxy, and 3-8 membered carbocyclyl.
In one embodiment R⁵ and R⁶ taken together with the atom to which they are attached form a cyclopropyl ring.
In another embodiment the compound is selected from the group consisting of:

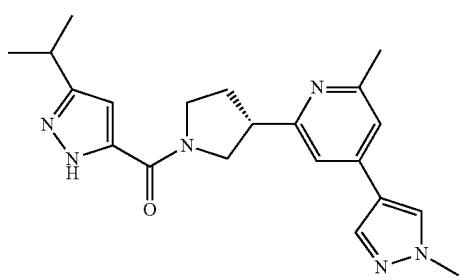

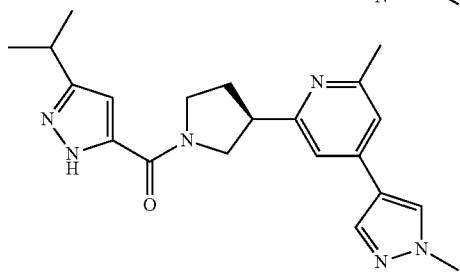

-continued

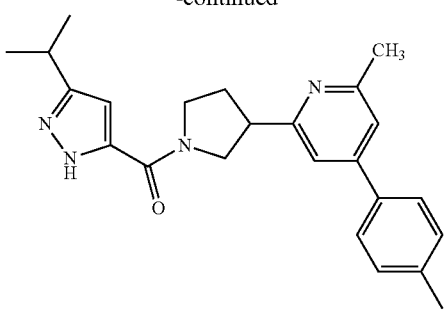

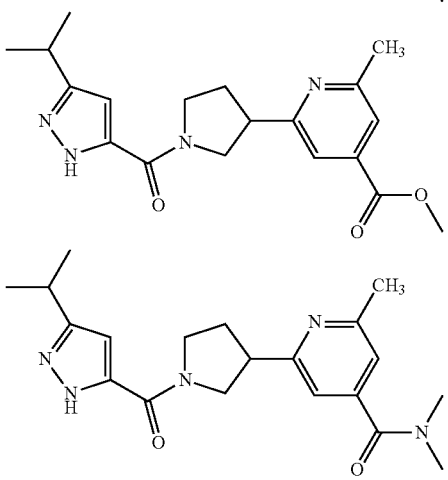

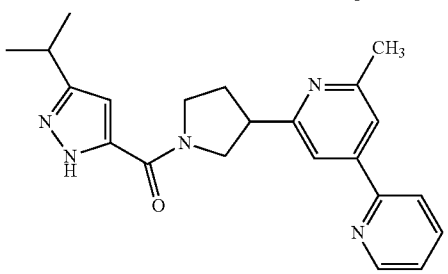

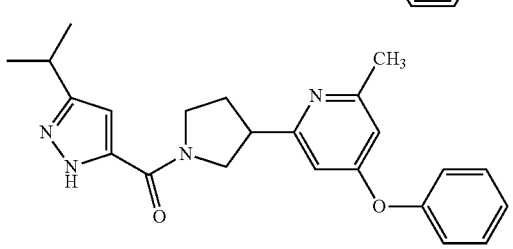

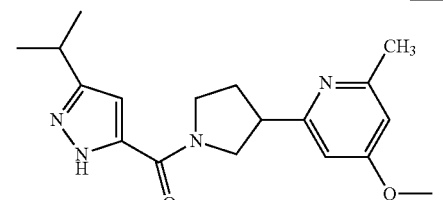

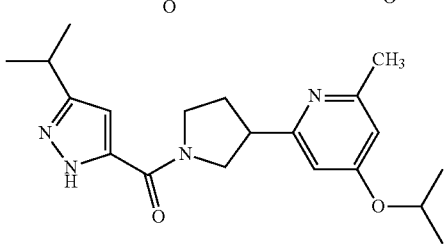

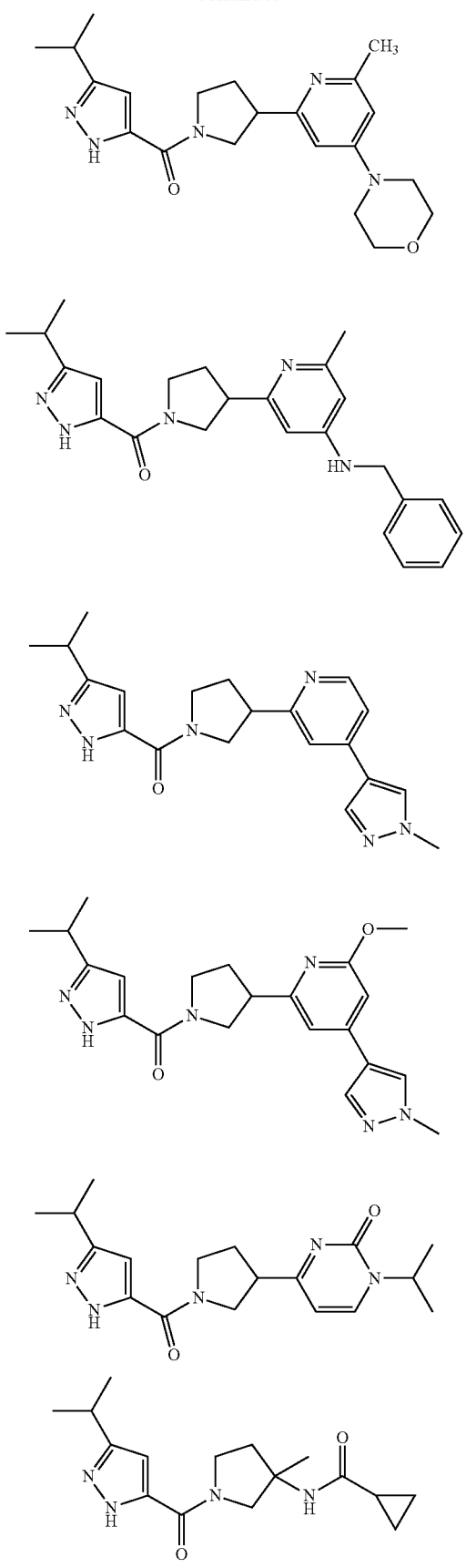
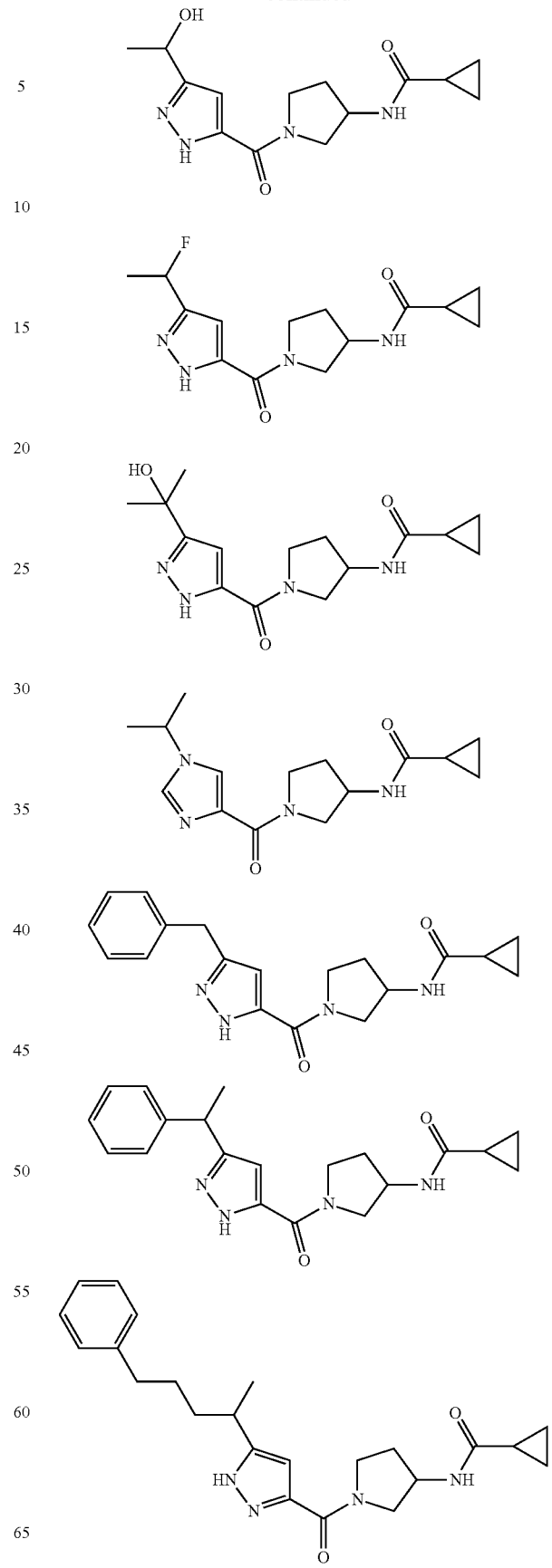

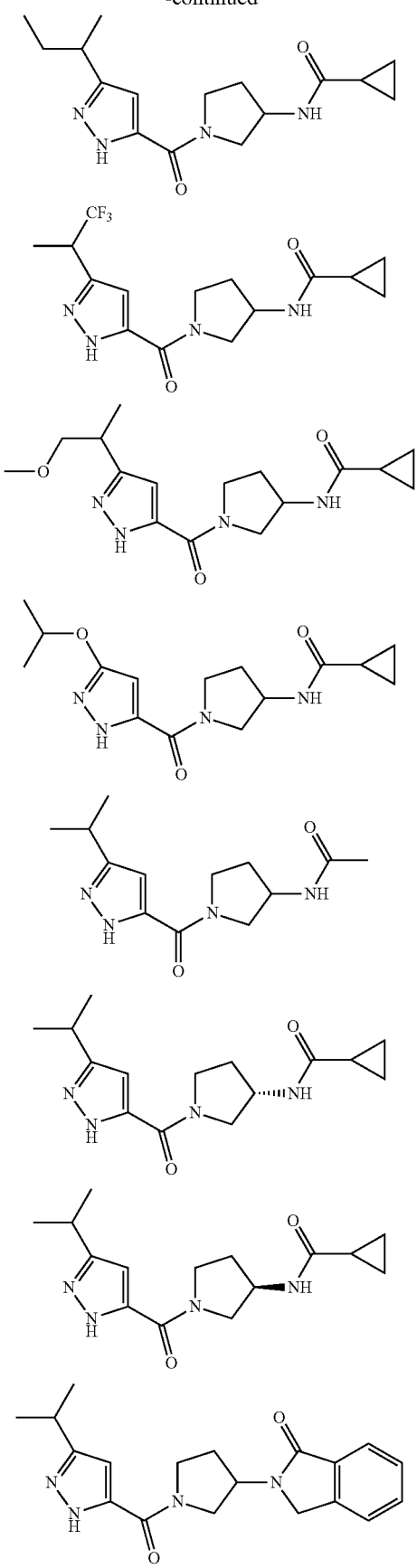
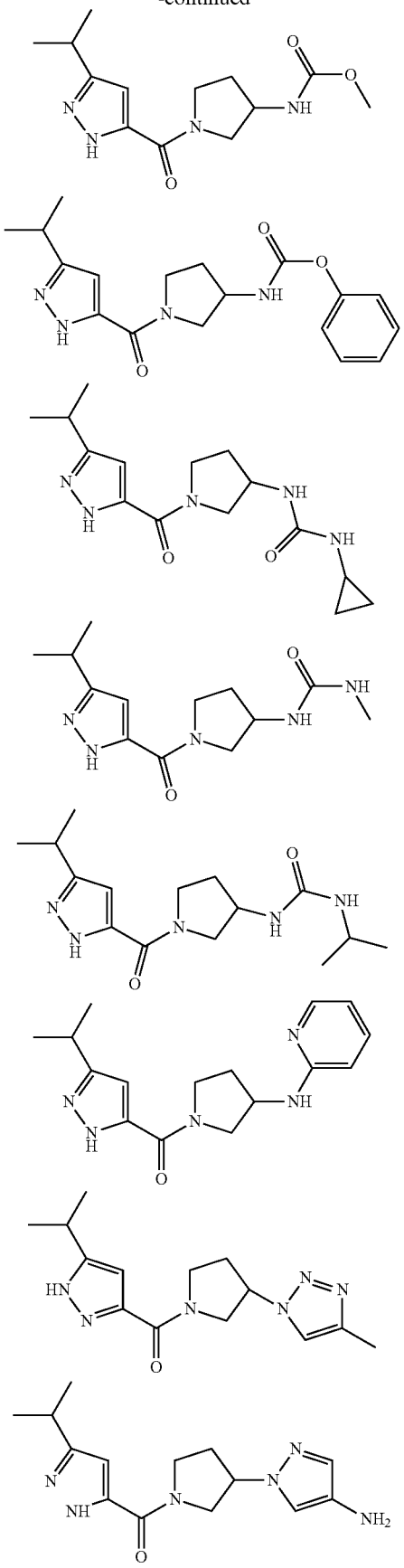

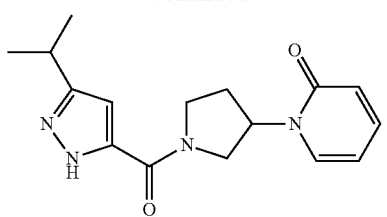
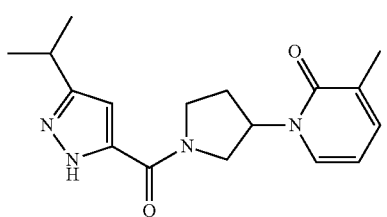
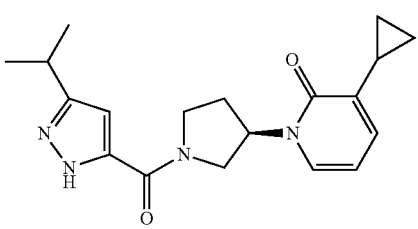
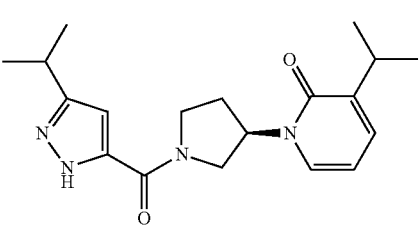
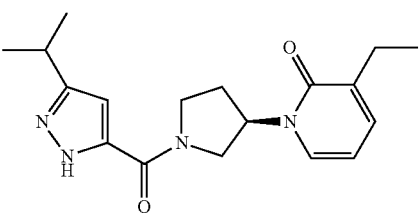
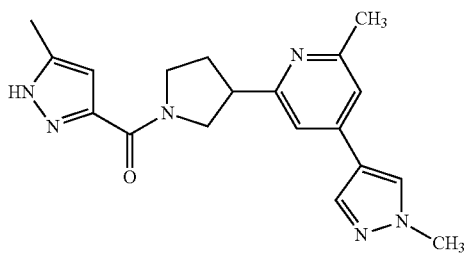
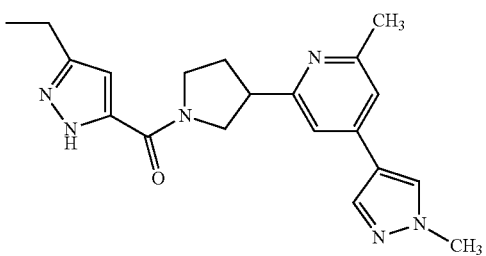
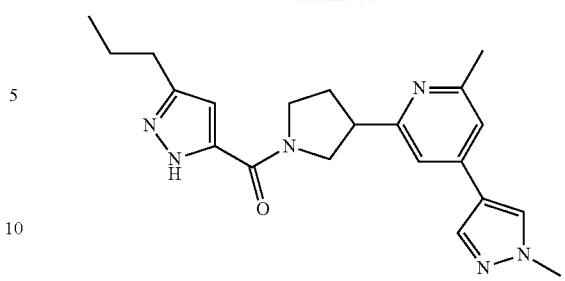
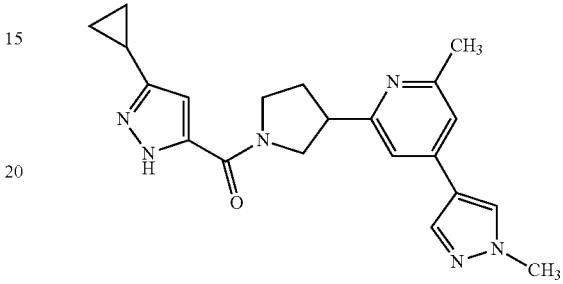
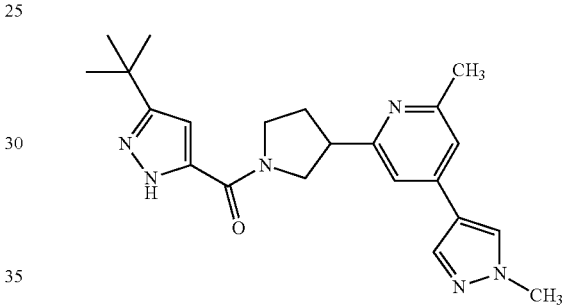
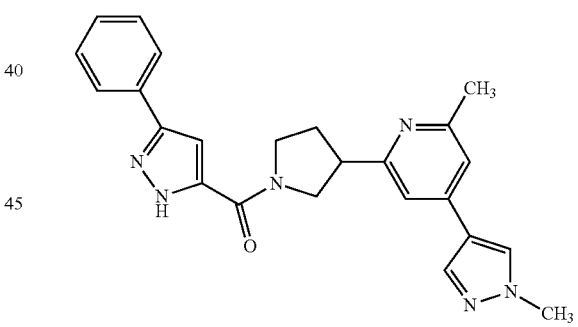
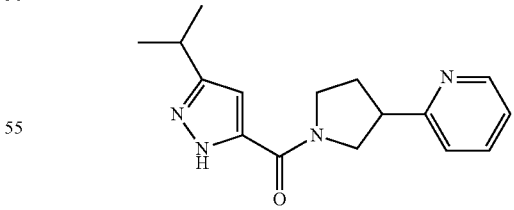
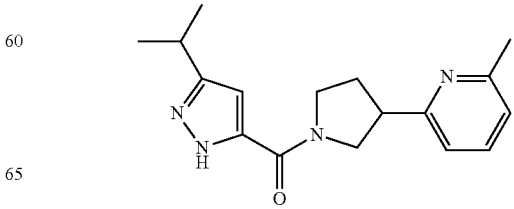

-continued
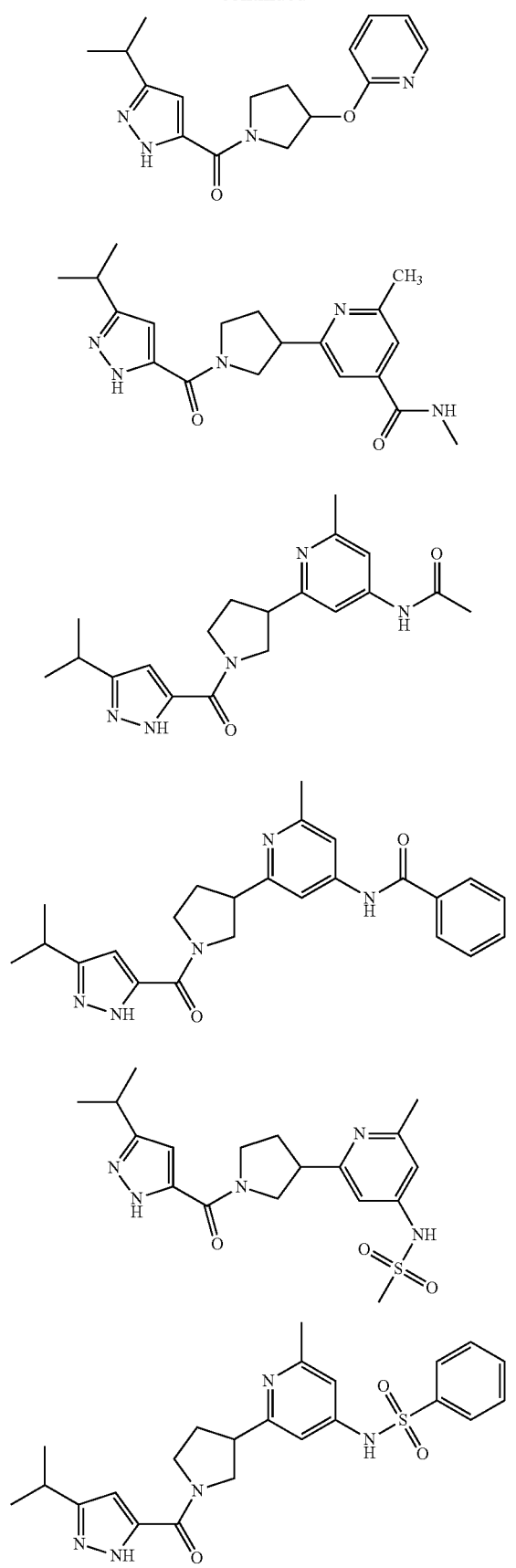
-continued
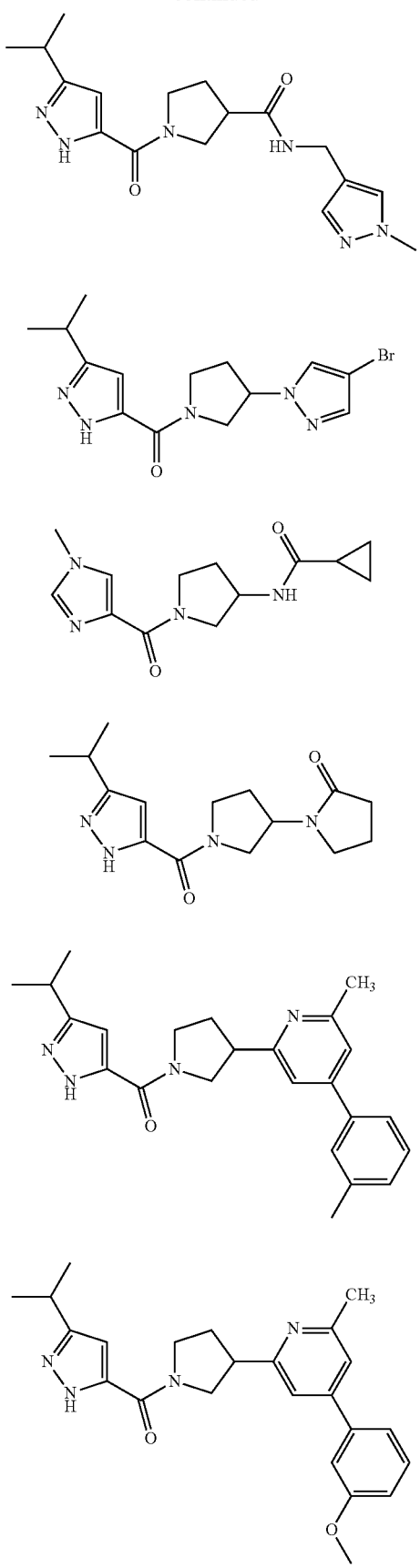

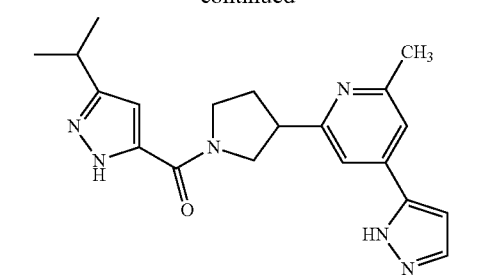
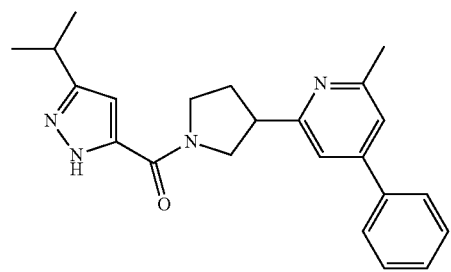
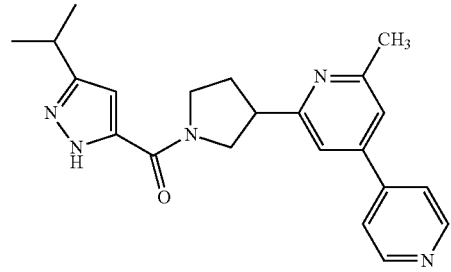
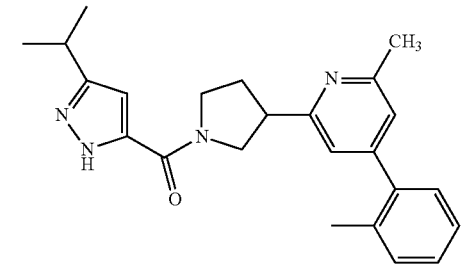
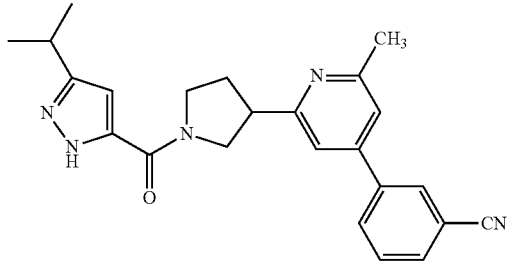
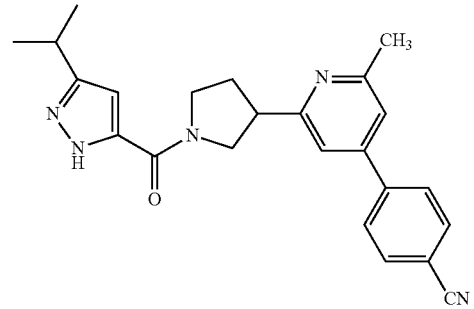
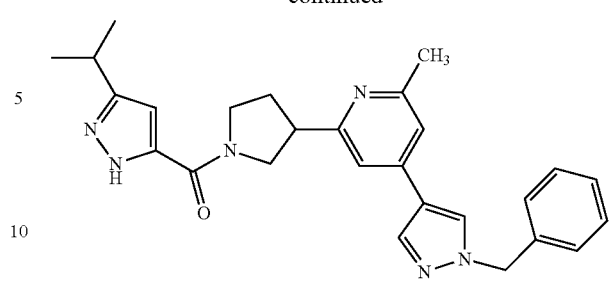
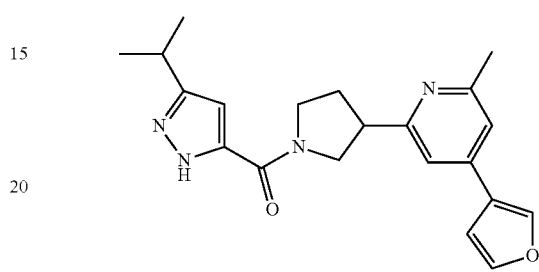
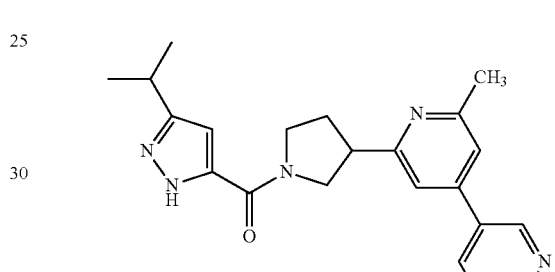
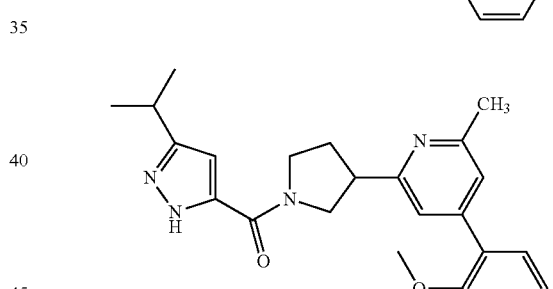
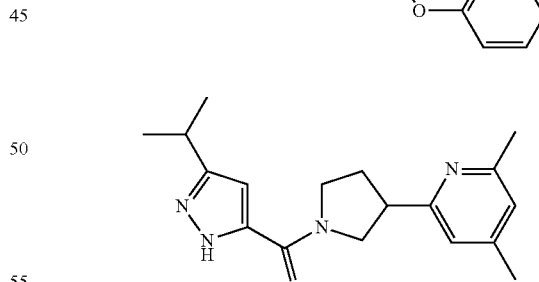
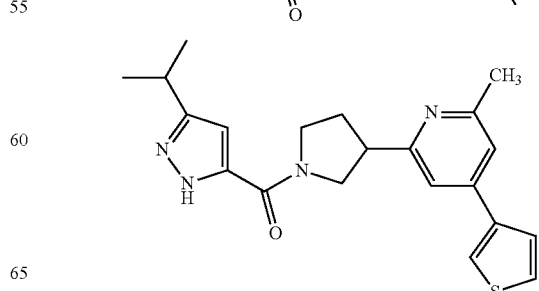

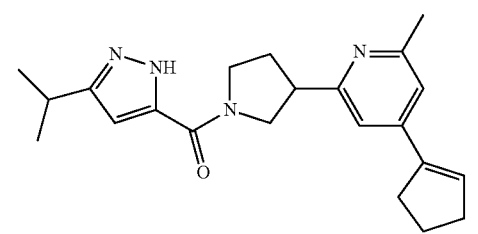
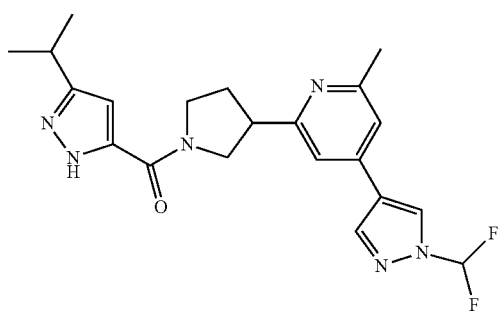
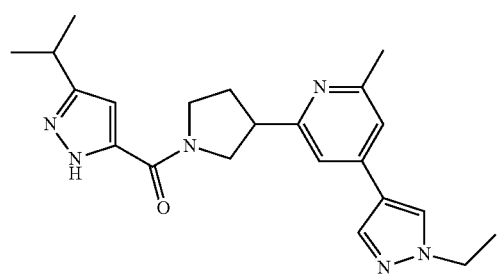
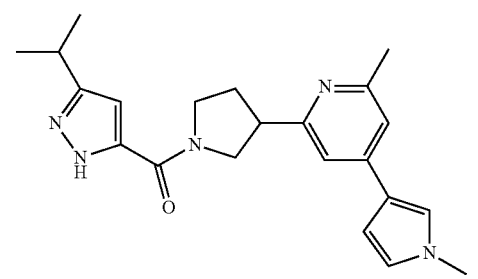
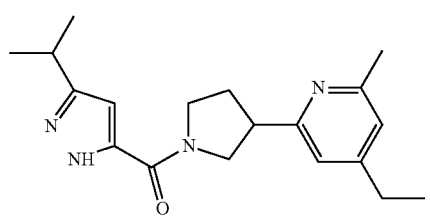
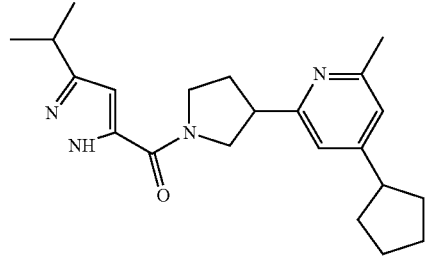
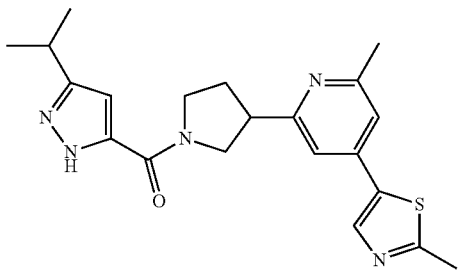
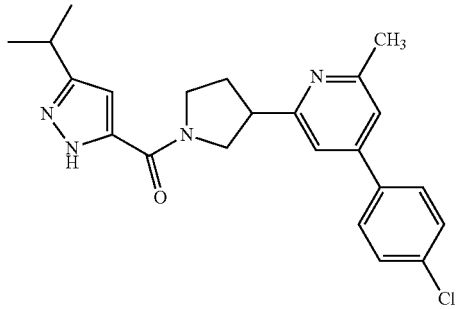
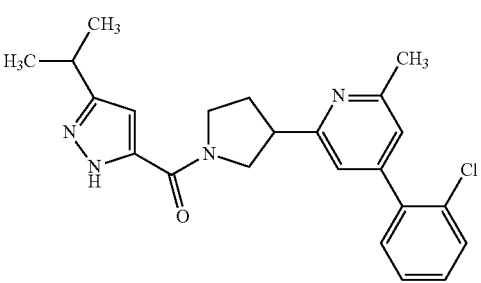
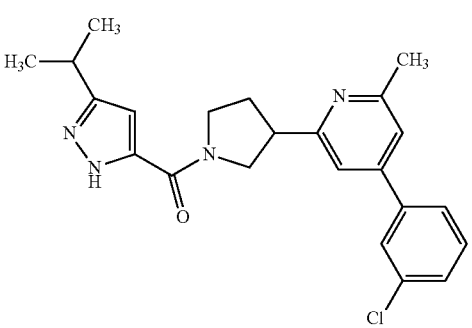
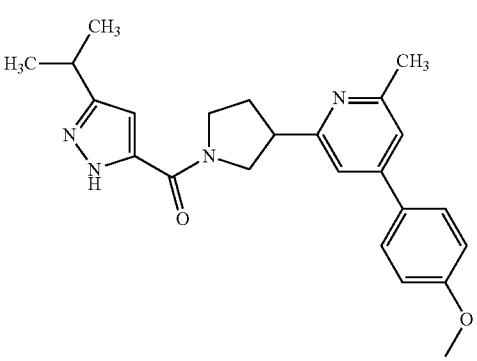

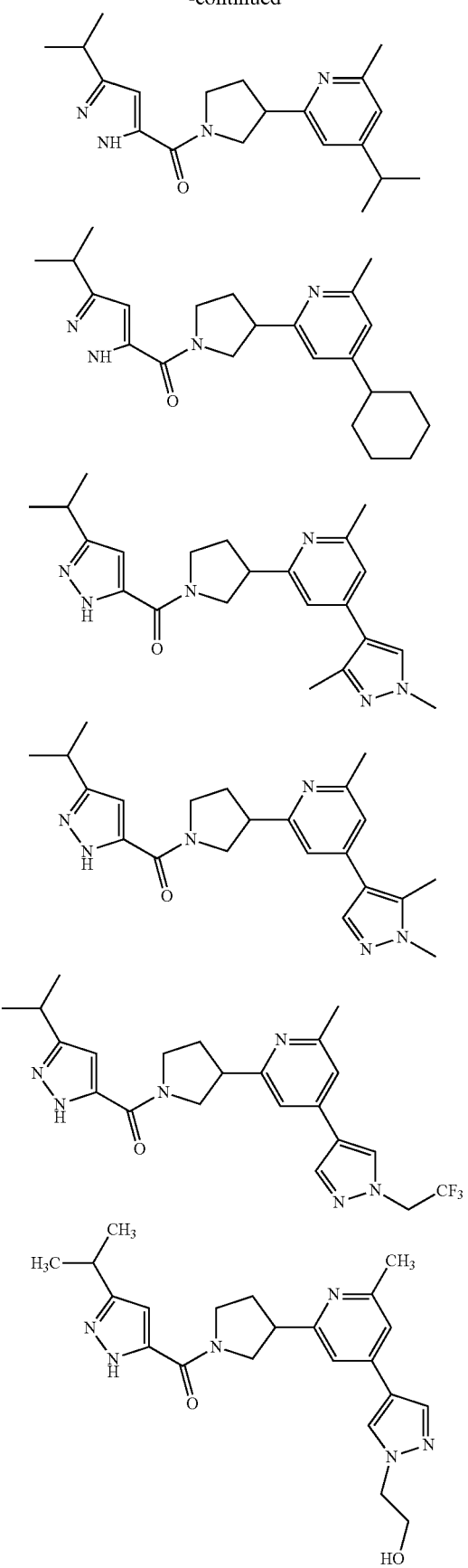
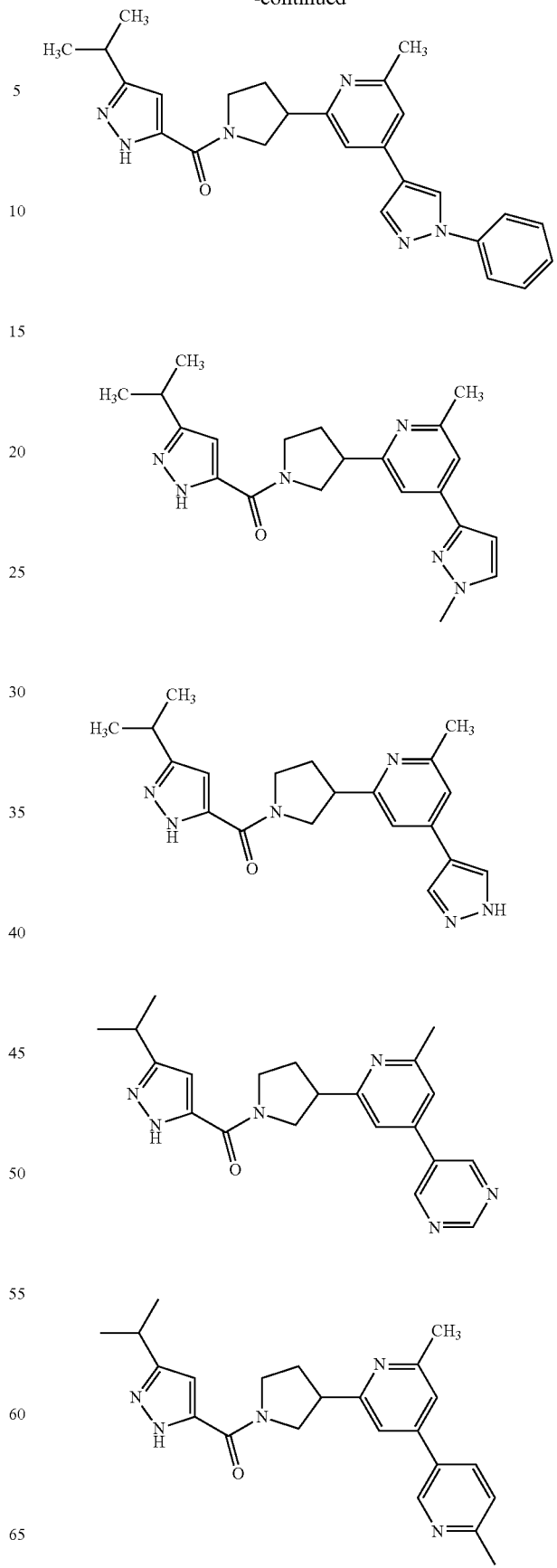

51
-continued
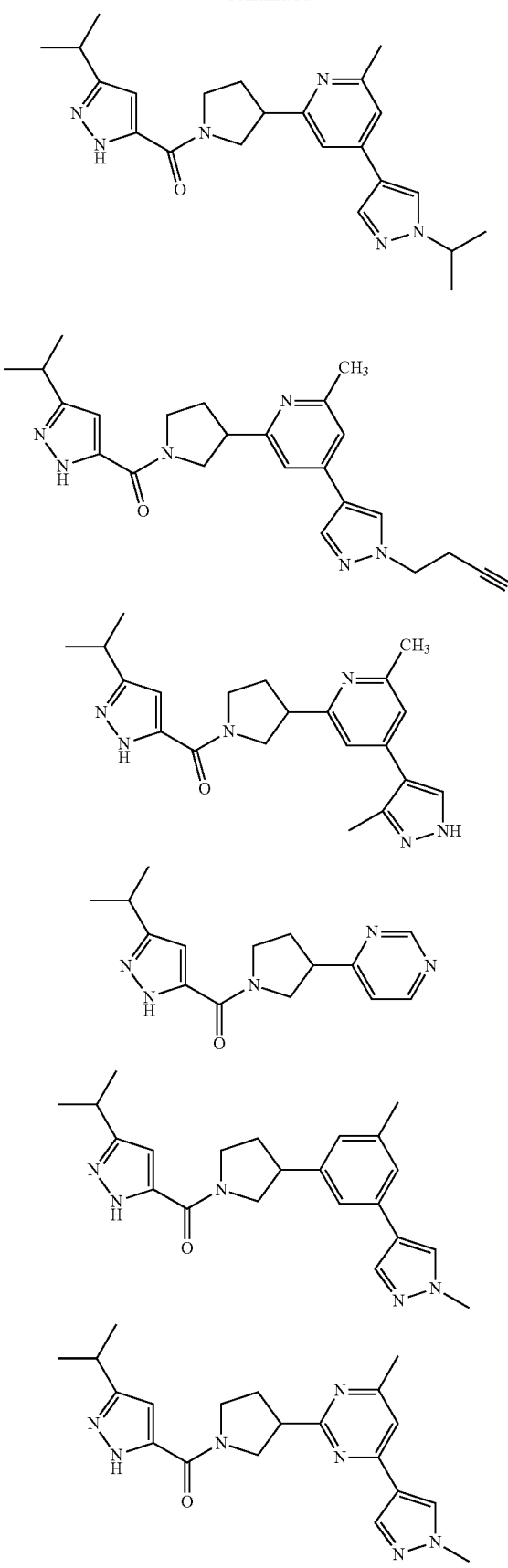
52
-continued
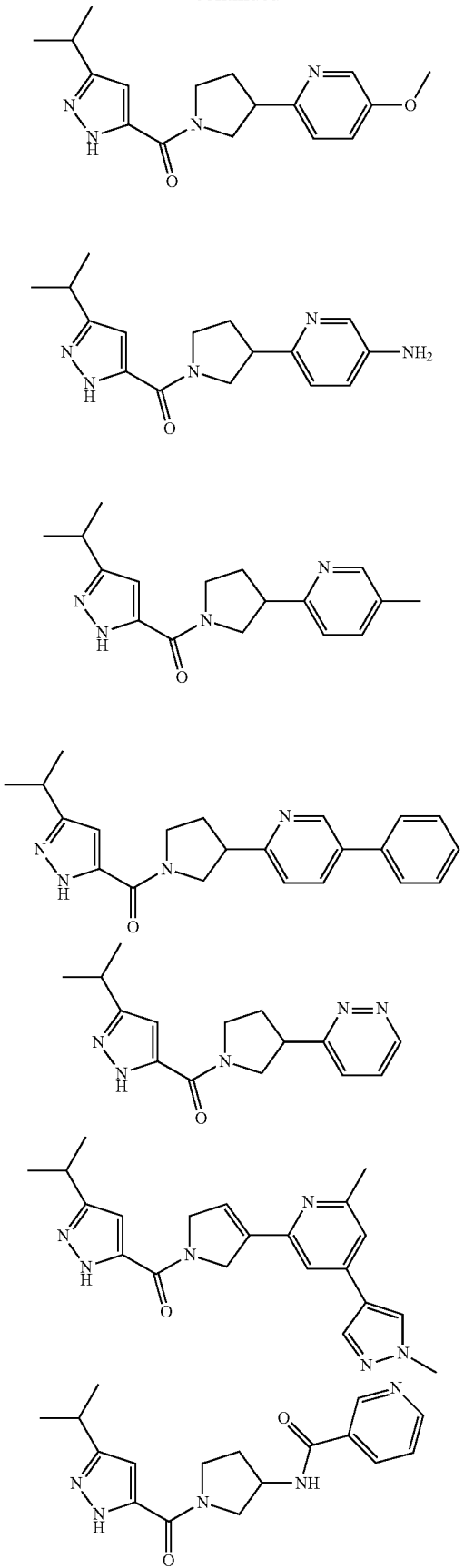

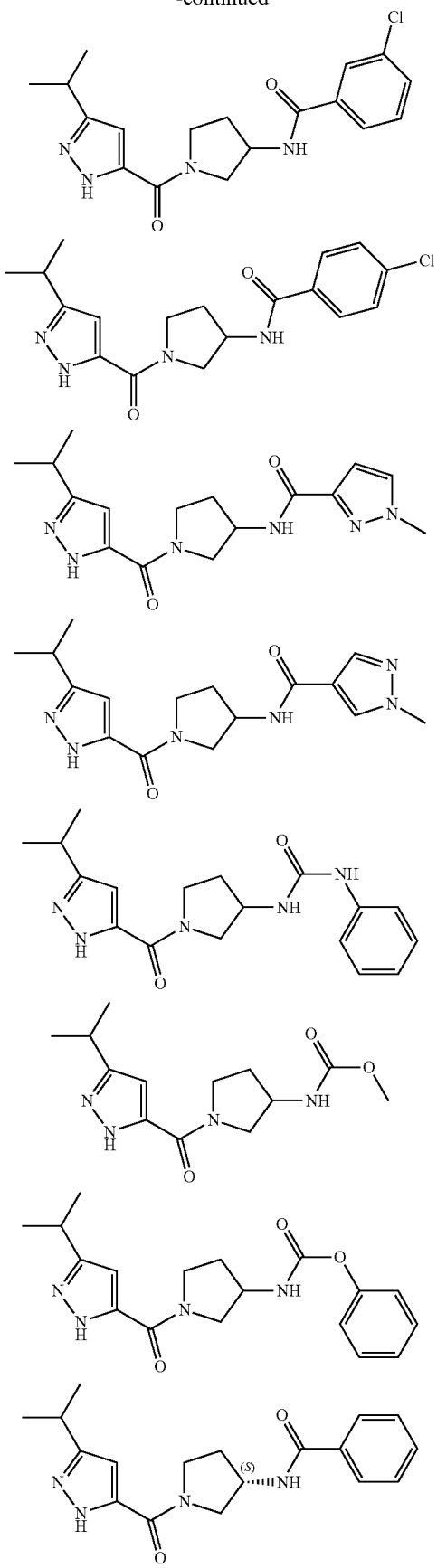
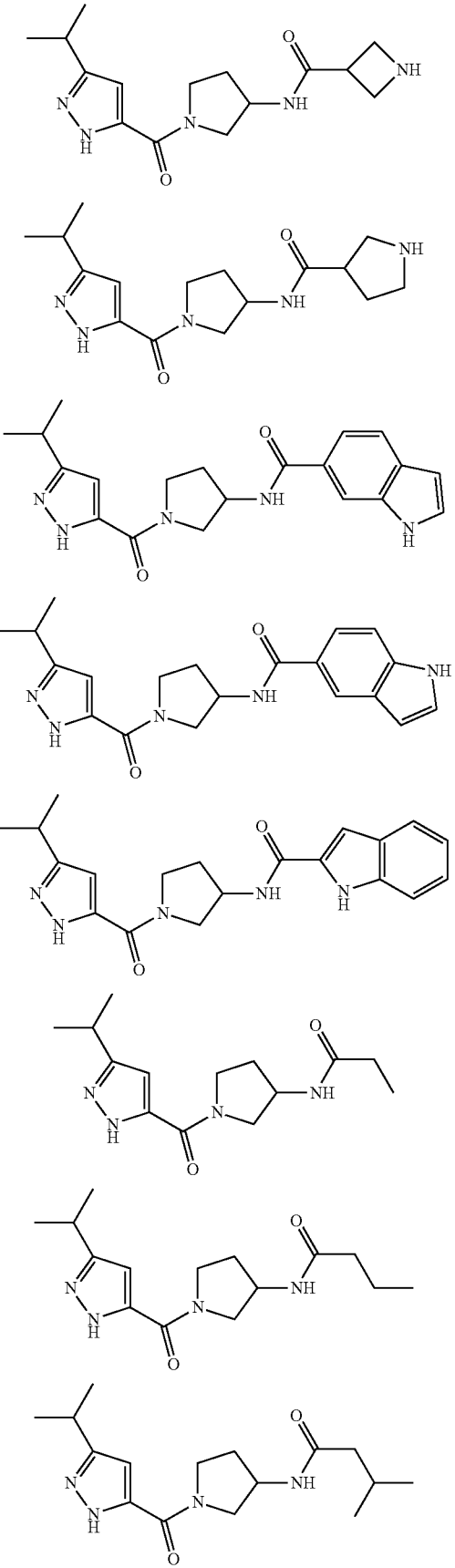

55
-continued
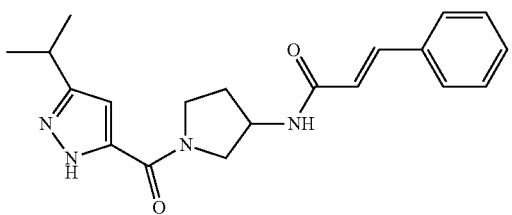
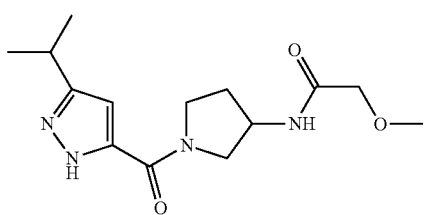
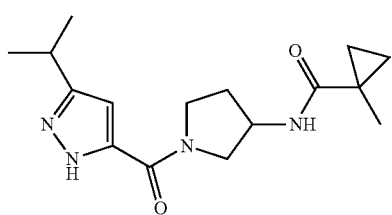
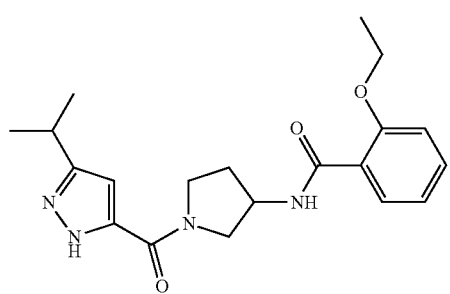
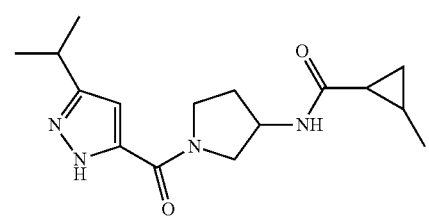
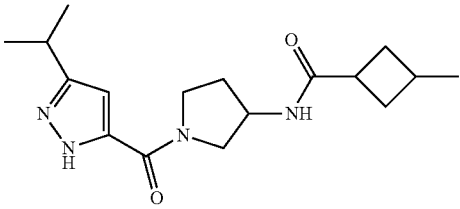
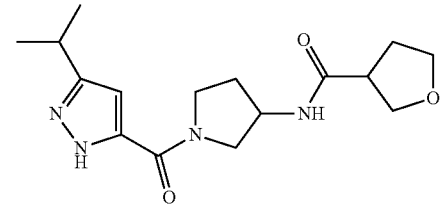
56
-continued
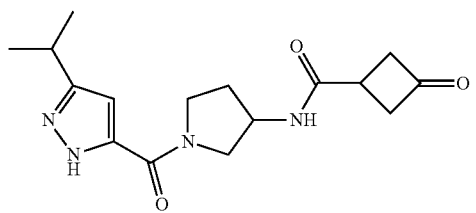
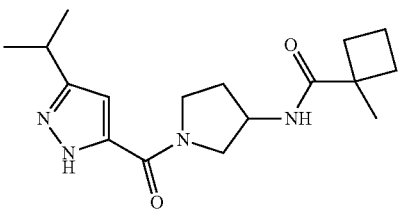
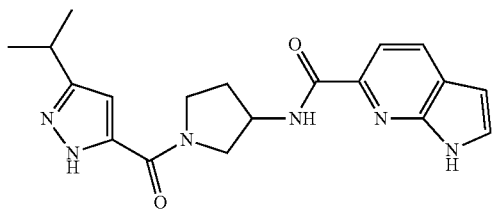
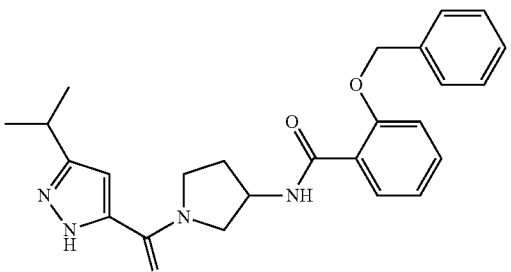
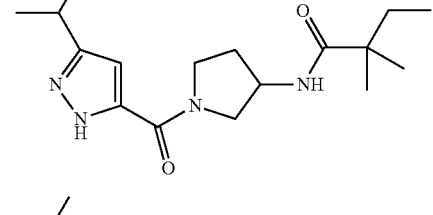
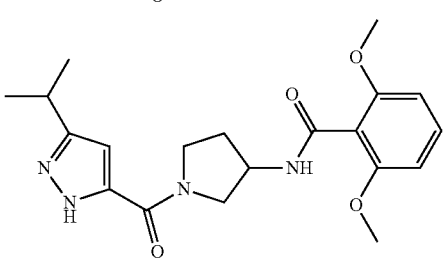

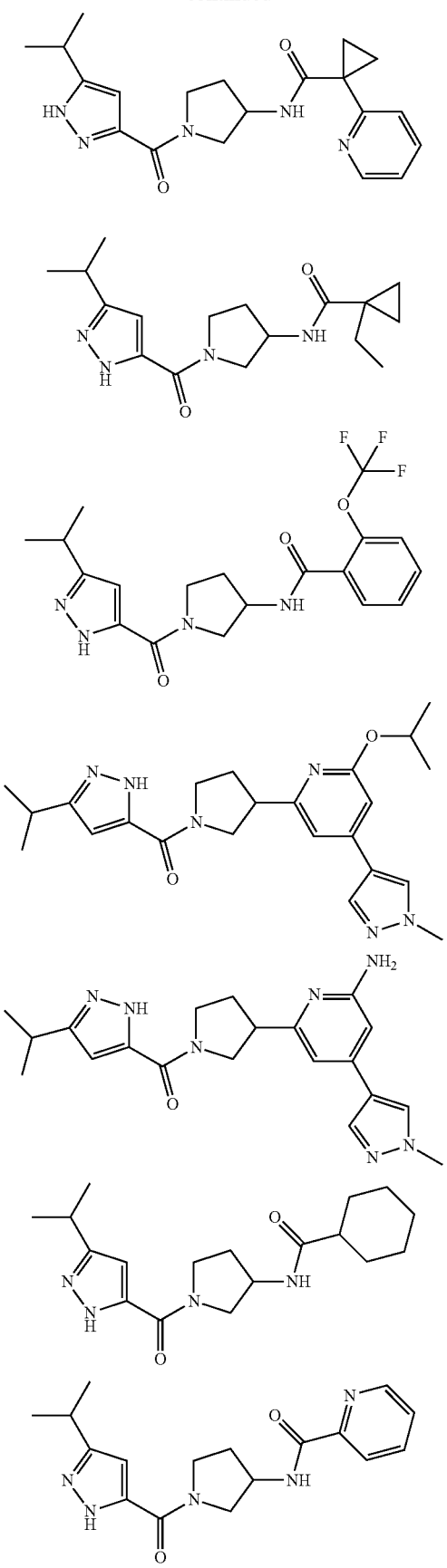
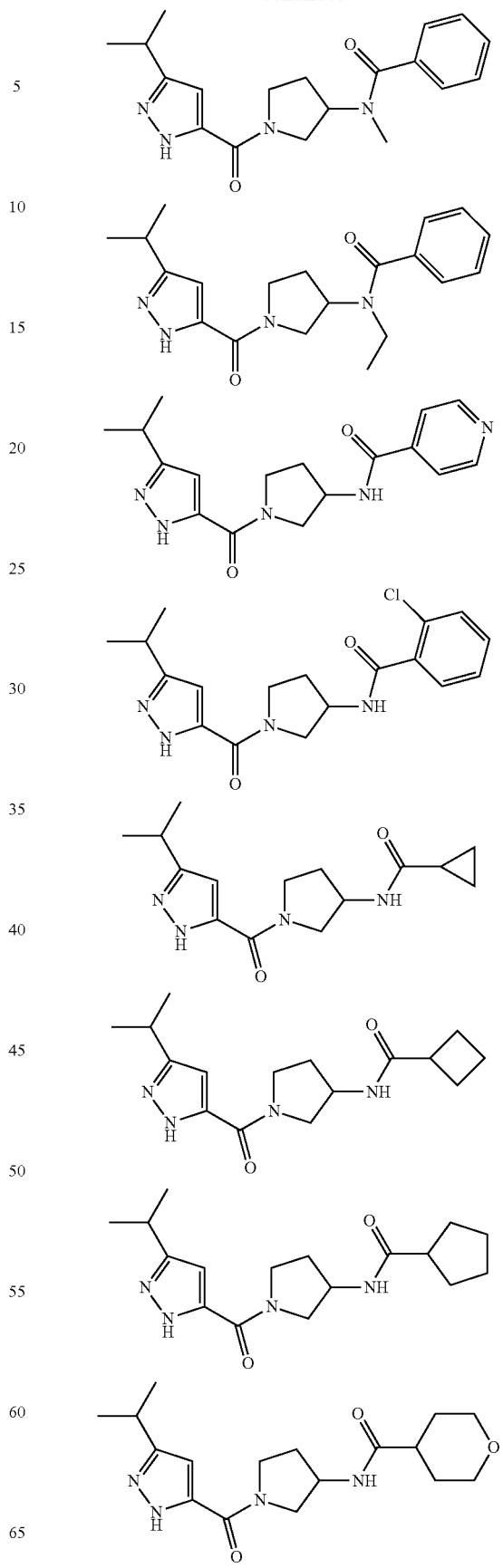

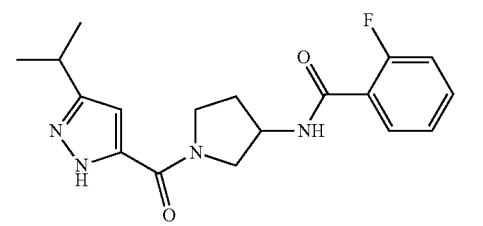
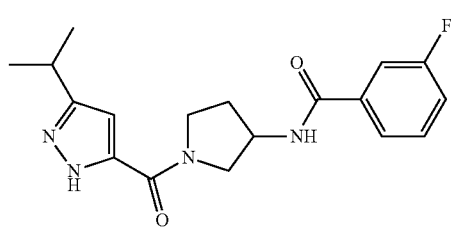
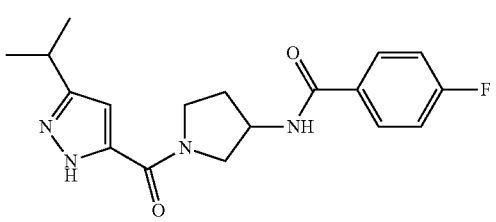
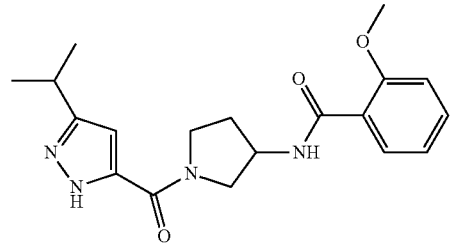
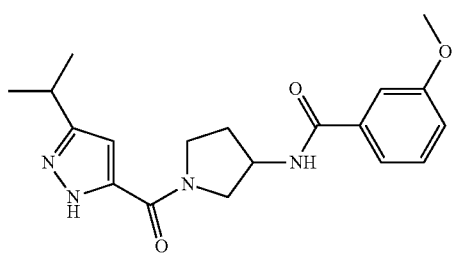
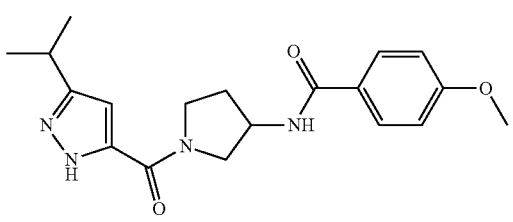
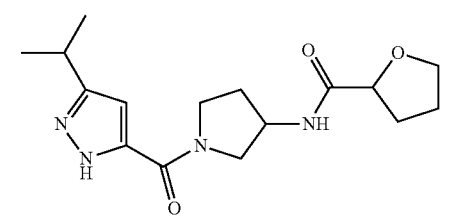
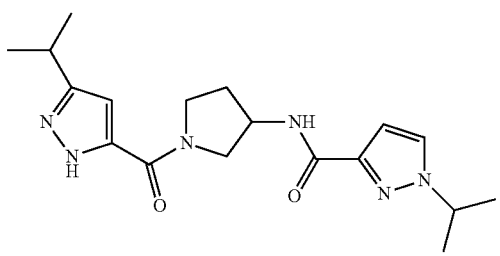
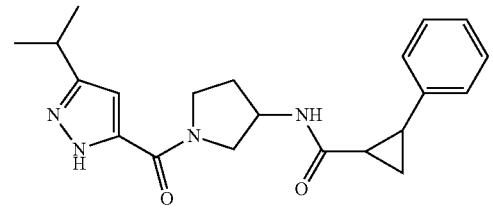
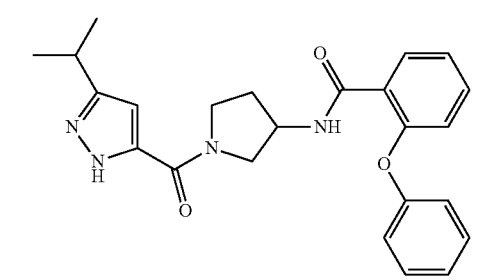
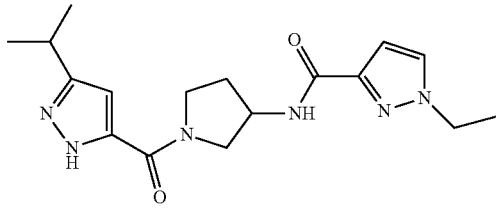
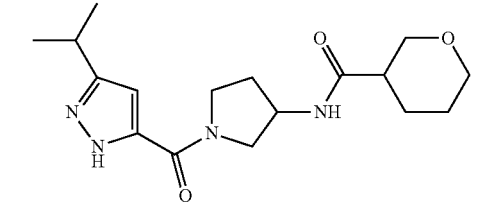
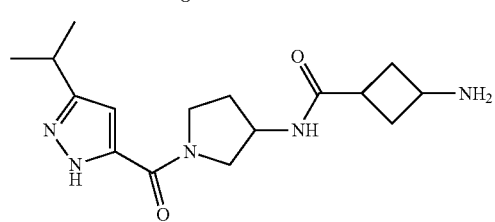
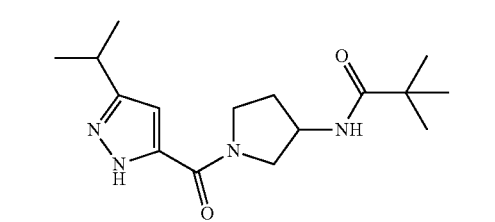

61
-continued
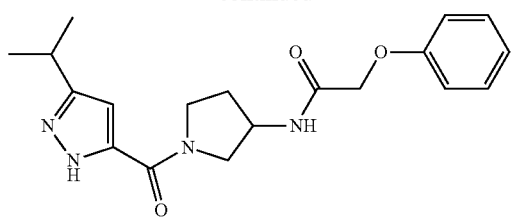
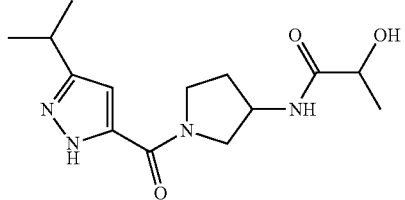
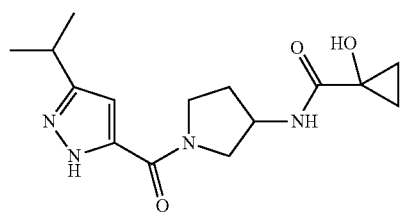
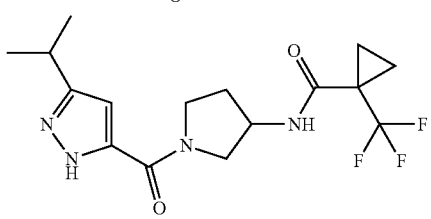
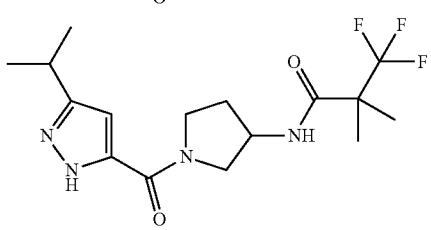
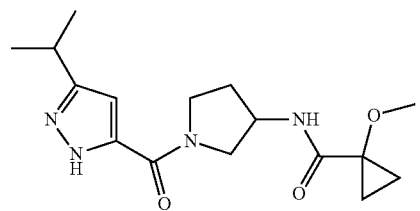
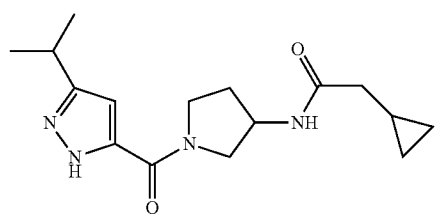
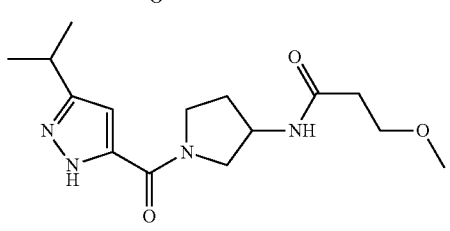
62
-continued
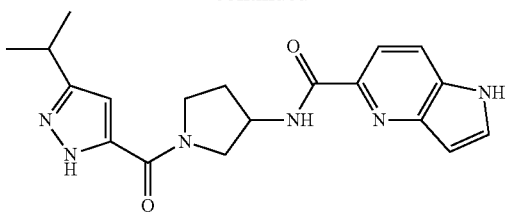
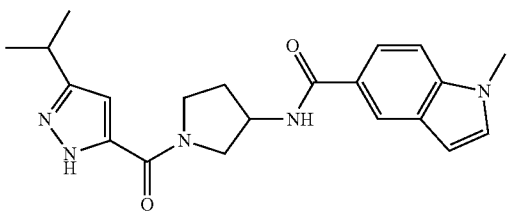
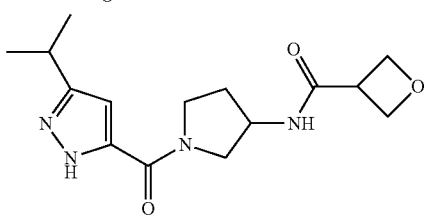
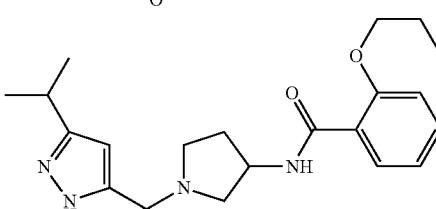
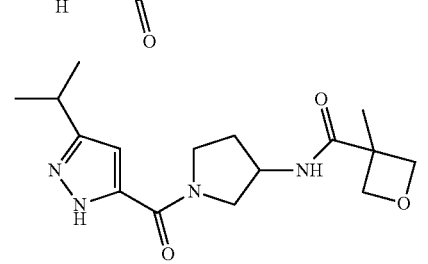
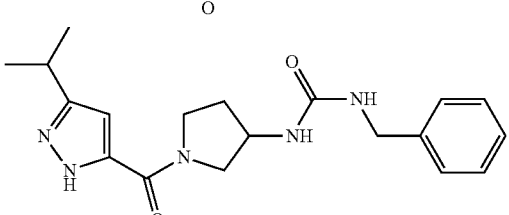
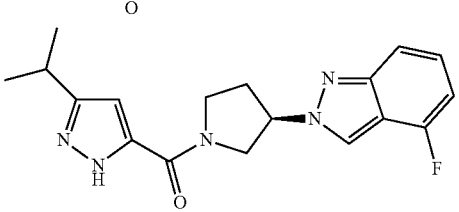
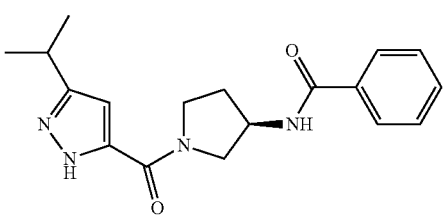

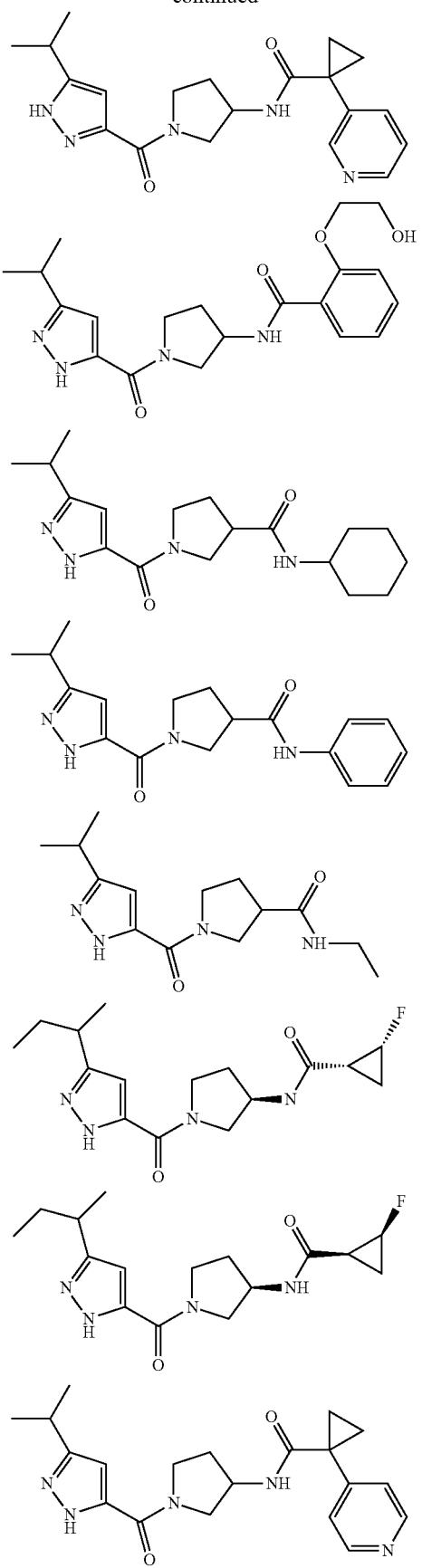
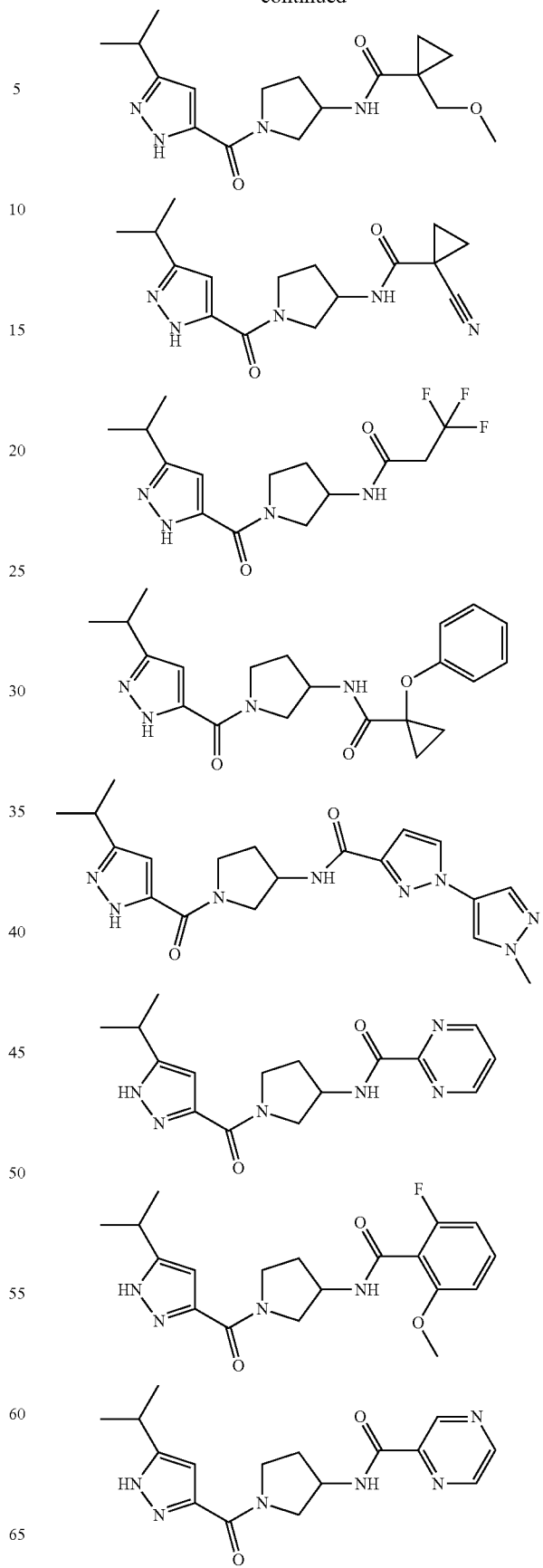

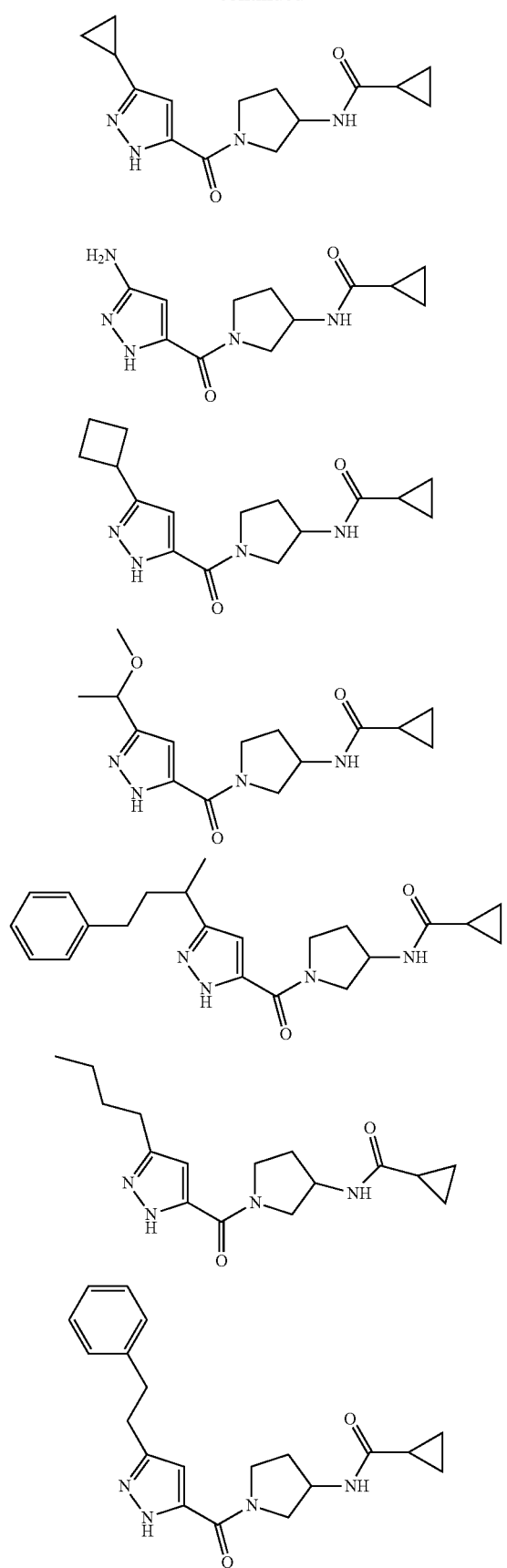
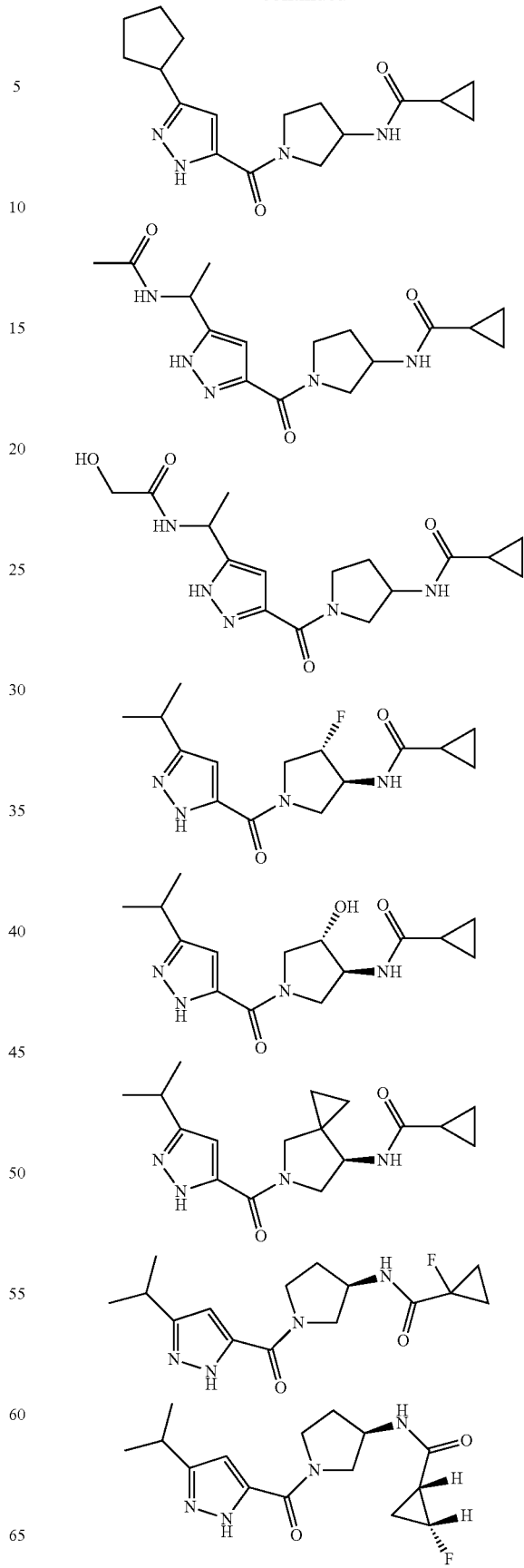

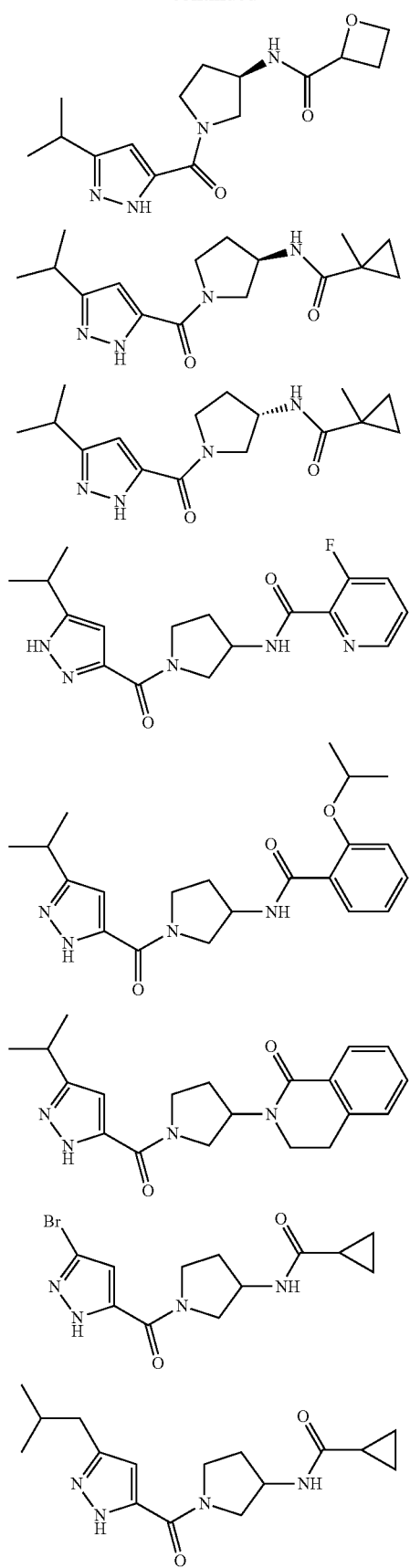
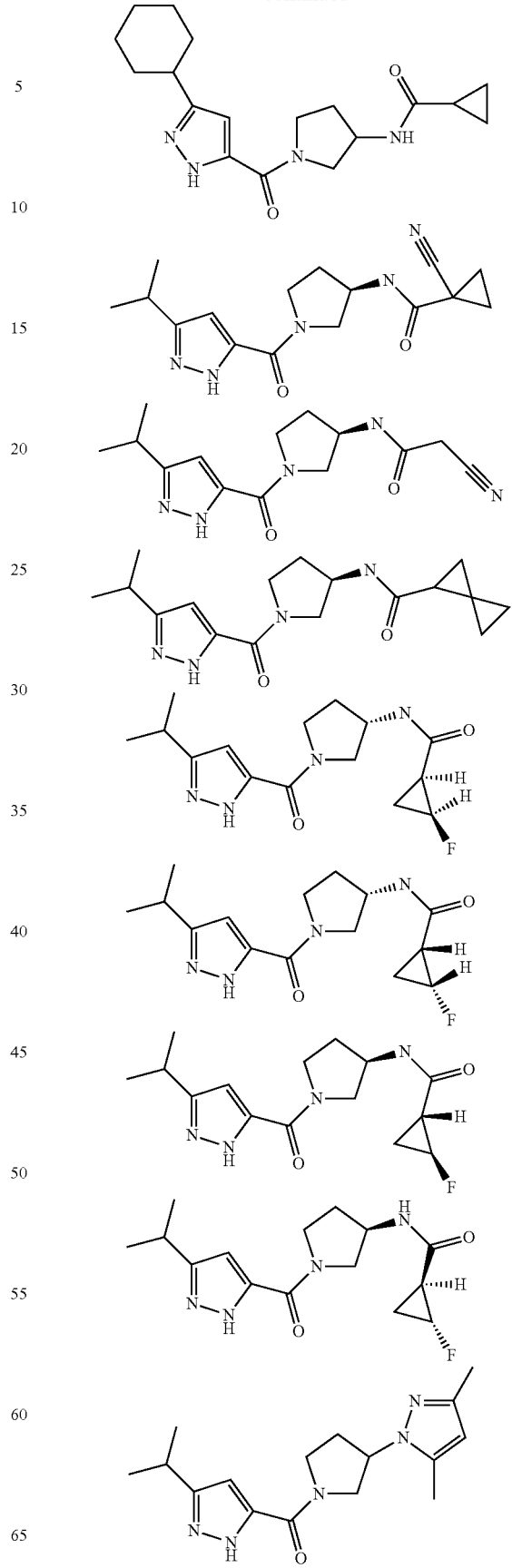

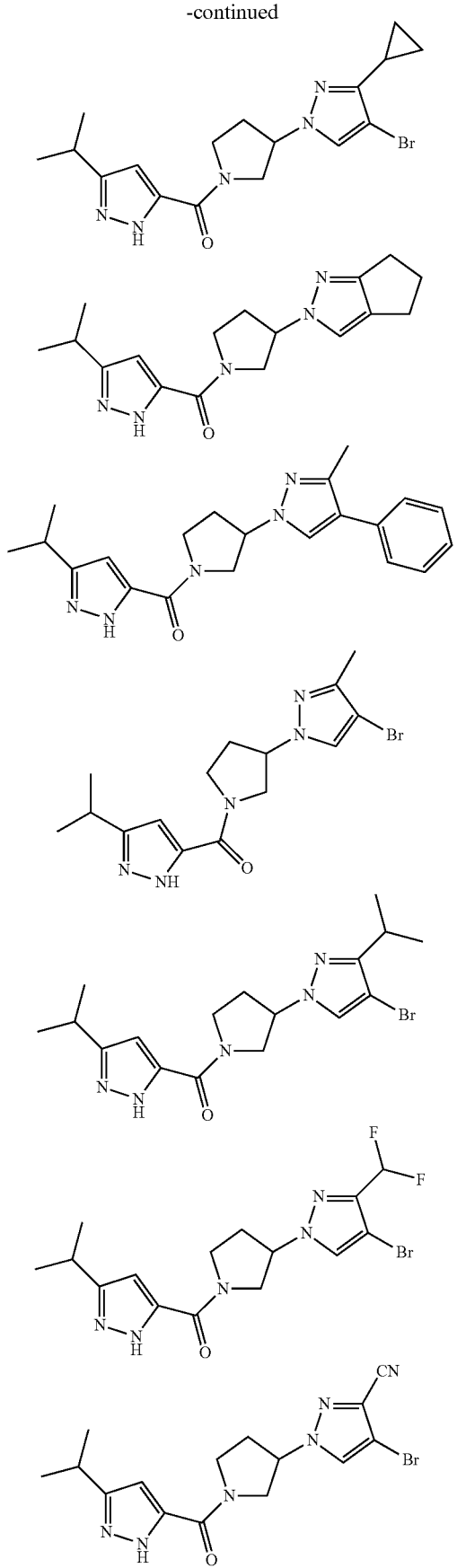
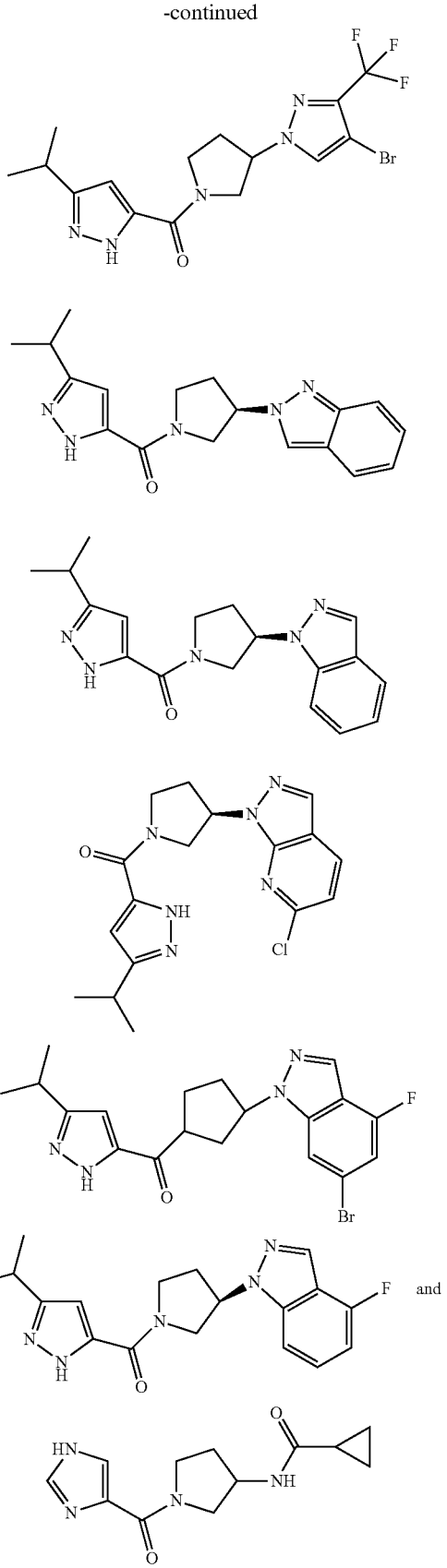
and salts thereof.

In one embodiment the compound is not:

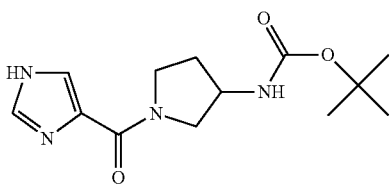 [SMILES: CC(C)(C)OC(=O)NC1CCN(C(=O)c2c[nH]cn2)C1]

or a salt thereof.

Uses, Formulation and Administration

Pharmaceutically Acceptable Compositions

Another aspect includes a pharmaceutical composition comprising a compound as described herein or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit KDM5. In certain embodiments, the composition is formulated for administration to a patient in need thereof certain embodiments.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound as described herein may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound as described herein is formulated as a solid dosage form for oral administration. Solid dosage forms for oral administration include capsules, tablets, pills, powders, and granules. In certain embodiments, the solid oral dosage form comprising a compound as described herein further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound as described herein optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polyethylene glycols and the like.

In another embodiment, a composition comprises microencapsulated compound as described herein, and optionally, further comprises one or more excipients.

In another embodiment, compositions comprise liquid dosage formulations comprising a compound as described herein for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound as described herein, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound as described herein with suitable non-irritating excipients or carriers such as cocoa butter, polyethylene glycol or a suppository wax, for example those which are solid at ambient temperature but liquid at body temperature and therefore melt in the rectum or vaginal cavity and release the compound.

Example dosage forms for topical or transdermal administration of a compound as described herein include ointments, pastes, creams, lotions, gels, powders, solutions, sprays, inhalants or patches. The compound as described herein is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound as described herein in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound as described herein may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a compound as described herein in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound as described herein, and further comprises about 95-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound as described herein, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound as described herein for the inhibition of KDM5. Compounds as described herein may also be used to inhibit the removal of methyl marks on histone lysine residues, including inhibiting the removal of methyl marks from mono-, di- or tri-methylation of histones H1, H2A, H2B, H3 and H4, such as H3K4 (including for example the KDM5 substrate H3K4me3), thereby altering interactions of these histone proteins with DNA and/or other proteins, and altering certain subsequent genetic or protein expression. Compounds as described herein may also be used to inhibit KDM5 and reduce drug-tolerant cells, thereby treating or preventing drug-resistant diseases, such as drug-resistant cancer. In certain embodiments, the disease can be treated using a compound as described herein to prevent resistance from forming, for example before targets of chemotherapies become mutated to confer resistance to such chemotherapies.

In certain embodiments, the binding or inhibition activity of a compound as described herein may be determined by running a competition experiment where the is incubated with the KDM5 enzyme bound to known radioligands. Detailed conditions for assaying a compound as an inhibitor of KDM5 or a mutant thereof are set forth in the Examples below.

In certain embodiments, detection of KDM5 activity is achieved with in vitro assays, which can be either direct binding (non-catalytic) or enzymatic (catalytic) assays. Types of substrates that are used in such assays may include: short synthetic peptides corresponding to a number of residues from the N-terminus of histone sequences comprising the target lysine residue, single recombinant histone polypeptides, histone octamers reconstituted with recombinant histone proteins, and reconstituted nucleosomes (using reconstituted octamers and specific recombinant DNA fragments). The reconstituted nucleosomes may be mononucleosomes or oligonucleosomes.

Another aspect includes a method of treating or preventing a disease responsive to the inhibition of KDM5 activity in a patient. The method includes administering a therapeutically effective amount of a compound as described hereinto a patient in need thereof.

Another aspect includes the use of a compound as described herein, in therapy. Another aspect includes the use of a pharmaceutical composition comprising a compound as described herein, in therapy.

Another aspect includes the use of a compound as described herein, in treating a disease associated with KDM5 activity. Another aspect includes the use of a pharmaceutical composition comprising a compound as described herein, in treating a disease associated with KDM5 activity.

Another aspect includes the use of a compound as described herein, in the manufacture of a medicament for the treatment of a disease associated with KDM5 activity. Another aspect includes the use of a pharmaceutical composition comprising a compound as described herein, in the manufacture of a medicament for the treatment of a disease associated with KDM5 activity.

In certain embodiments, the disease or condition is a hyperproliferative disease, cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Another aspect includes a method for treating, ameliorating or preventing cancer, drug-resistant cancer or another proliferative disorder by administration of an effective amount of a compound as described herein to a mammal, for example a human, in need of such treatment. In certain embodiments, the disease to be treated is cancer or drug resistant cancer.

Examples of cancers that may be treated using the compounds and methods described herein include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, androgen dependent cancer, angioimmunoblastic T-cell lymphoma, angiomyolipoma, angiosarcoma, astrocytoma, atypical teratoid rhabdoid tumor, B-cell chronic lymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chrondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer. Waldenstrom's macroglobulinemia, Warthin's tumor and Wilms' tumor.

Another embodiment includes a method for the treatment of benign proliferative disorders. Examples of benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma and juvenile polyposis syndrome.

Another embodiment includes a therapeutic method useful for modulating protein methylation, gene expression, cell proliferation, cell differentiation and/or apoptosis in vivo in diseases mentioned above, in particular cancer, comprising administering to a patient in need of such therapy a pharmacologically active and therapeutically effective amount of one or more of the compounds as described herein.

Another embodiment includes a method for regulating endogenous or heterologous promoter activity by contacting a cell with a compound as described herein.

Another embodiment includes the use of a compound as described herein for the production of pharmaceutical compositions which are employed for the treatment and/or prophylaxis and/or amelioration of the diseases, disorders, illnesses and/or conditions as mentioned herein.

Another embodiment includes the use of a compound as described herein for the production of pharmaceutical compositions which are employed for the treatment and/or prophylaxis of diseases and/or disorders responsive or sensitive to the inhibition of histone demethylases, particularly those diseases mentioned above, such as e.g. cancer.

Compounds as described herein may be administered using any amount and any route of administration effective for treating or lessening the severity of the disorder. The exact amount required will vary from patient to patient, depending on the species, age, and general condition of the patient, for example the severity of the disorder, the particular compound, its mode of administration, and the like. The total daily usage of a compound as described herein by a given patient will be decided by the attending physician within the scope of sound medical judgment. The specific effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Another embodiment includes a method of inhibiting KDM5 activity in a biological sample comprising contacting said biological sample with a compound as described herein.

The term "biological sample", as used herein, includes, without limitation, a cell, cell cultures or extracts thereof; biopsied material obtained from a mammal or extracts thereof; and blood, saliva, urine, feces, semen, tears, or other body fluids or extracts thereof.

Co-Administration of Compounds and Other Agents

The compound as described herein may be employed alone or in combination with other agents for treatment. For example, the second agent of the pharmaceutical combination formulation or dosing regimen may have complementary activities to the compound as described herein such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound as described herein, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound as described herein and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $P^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from antimicrotubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/1695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl)propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenyl-ethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-Smith-Kline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

The amount of both the compound as described herein and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound as described herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 μg/kg body weight/day of the additional therapeutic agent can be administered.

Another aspect includes treating or preventing drug resistance in a patient using a compound as described herein. For example, a method of treating or preventing drug resistant cancer in a patient comprises administering a therapeutically effective amount of a compound as described herein to the patient alone or in combination with a cytotoxic agent. In certain embodiments, the individual is selected for treatment with a cytotoxic agent (e.g., targeted therapies, chemotherapies, and/or radiotherapies). In certain embodiments, the individual starts treatment comprising administration of a compound as described herein prior to treatment with the cytotoxic agent. In certain embodiments, the individual concurrently receives treatment comprising the compound as described herein and the cytotoxic agent. In certain embodiments, the compound as described herein increases the period of cancer sensitivity and/or delays development of cancer resistance.

In particular, provided herein are methods of treating cancer in an individual comprising administering to the individual (a) a compound as described herein and (b) a cytotoxic agent (e.g., targeted therapy, chemotherapy, and/or radiotherapy). In certain embodiments, the respective amounts of the compound as described herein and the cytotoxic agent are effective to increase the period of cancer sensitivity and/or delay the development of cancer cell resistance to the cancer therapy agent. In certain embodiments, the respective amounts of the compound as described herein and the cytotoxic agent are effective to increase efficacy of a cancer treatment comprising the cancer therapy agent. For example, in certain embodiments, the respective amounts of the compound as described herein and the cytotoxic agent are effective to increase efficacy compared to a treatment (e.g., standard of care treatment) (e.g., standard of care treatment) comprising administering an effective amount of the cancer therapy agent without (in the absence of) the compound as described herein. In certain embodiments, the respective amounts of the compound as described herein and cytotoxic agent are effective to increase response (e.g., complete response) compared to a treatment (e.g., standard of care treatment) comprising administering an effective amount of cytotoxic agent without (in the absence of) the compound as described herein.

Also provided herein are methods of increasing efficacy of a cancer treatment comprising a cytotoxic agent in an individual comprising administering to the individual (a) an effective amount of a compound as described herein and (b) an effective amount of the cytotoxic agent.

Provided herein are methods of treating cancer in an individual wherein cancer treatment comprising administering to the individual (a) an effective amount of a compound as described herein and (b) an effective amount of a cytotoxic agent, wherein the cancer treatment has increased efficacy compared to a treatment (e.g., standard of care treatment) comprising administering an effective amount of cytotoxic agent without (in the absence of) the compound as described herein.

In addition, provided herein are methods of delaying and/or preventing development of cancer resistant to a cancer therapy agent in an individual, comprising administering to the individual (a) an effective amount of a compound as described herein and (b) an effective amount of the cytotoxic agent.

Provided herein are methods of treating an individual with cancer who has an increased likelihood of developing resistance to a cancer therapy agent comprising administering to the individual (a) an effective amount of a compound as described herein and (b) an effective amount of the cytotoxic agent.

Further provided herein are methods of increasing sensitivity to a cancer therapy agent in an individual with cancer comprising administering to the individual (a) an effective amount of a compound as described herein and (b) an effective amount of the cytotoxic agent.

Provided herein are also methods of extending the period of a cancer therapy agent sensitivity in an individual with cancer comprising administering to the individual (a) an effective amount of a compound as described herein and (b) an effective amount of the cytotoxic agent.

Provided herein are methods of extending the duration of response to a cytotoxic agent in an individual with cancer comprising administering to the individual (a) an effective amount of a compound as described herein and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine, di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound as described herein is concomitantly administered with the cytotoxic agent (e.g., targeted therapy, chemotherapy, and/or radiotherapy). In certain embodiments, the compound as described herein is administered prior to and/or concurrently with the cytotoxic agent (e.g., targeted therapy, chemotherapy, and/or radiotherapy).

In certain embodiments of any of the methods, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer. In certain embodiments, the cancer is melanoma.

EXEMPLIFICATION

As depicted in the Examples below, in certain exemplary embodiments, compounds are prepared according to the following general procedures. It will be appreciated that, although the general methods depict the synthesis of certain compounds, the following general methods, and other methods known to one of ordinary skill in the art, can typically be applied to all compounds and subclasses and species of each of these compounds, as described herein.

The general synthetic methods illustrated in Schemes 1-4 and the general LCMS isolations procedures identified as LCMS Method A—LCMS Method F were used to prepare the compounds of Examples 1-247 as detailed below.

amide 1 provided ketone 2, which was transformed to pyridine 3 upon hydrogenation. Treatment of compound 3 with triflic anhydride gave intermediate 4. Suzuki coupling of triflate 4 with a boronic acid or boronate ester 5 gave compound 6. Deprotection of Boc group, followed by amide coupling with carboxylic acid 7 resulted in pyrrolidine amide 8. Alternatively, removal of Boc group in intermediate 4, followed by amide coupling with a carboxylic acid 7 gave intermediate 9. Subsequently, Suzuki coupling of intermediate 9 with a boronic acid or boronate ester also led to

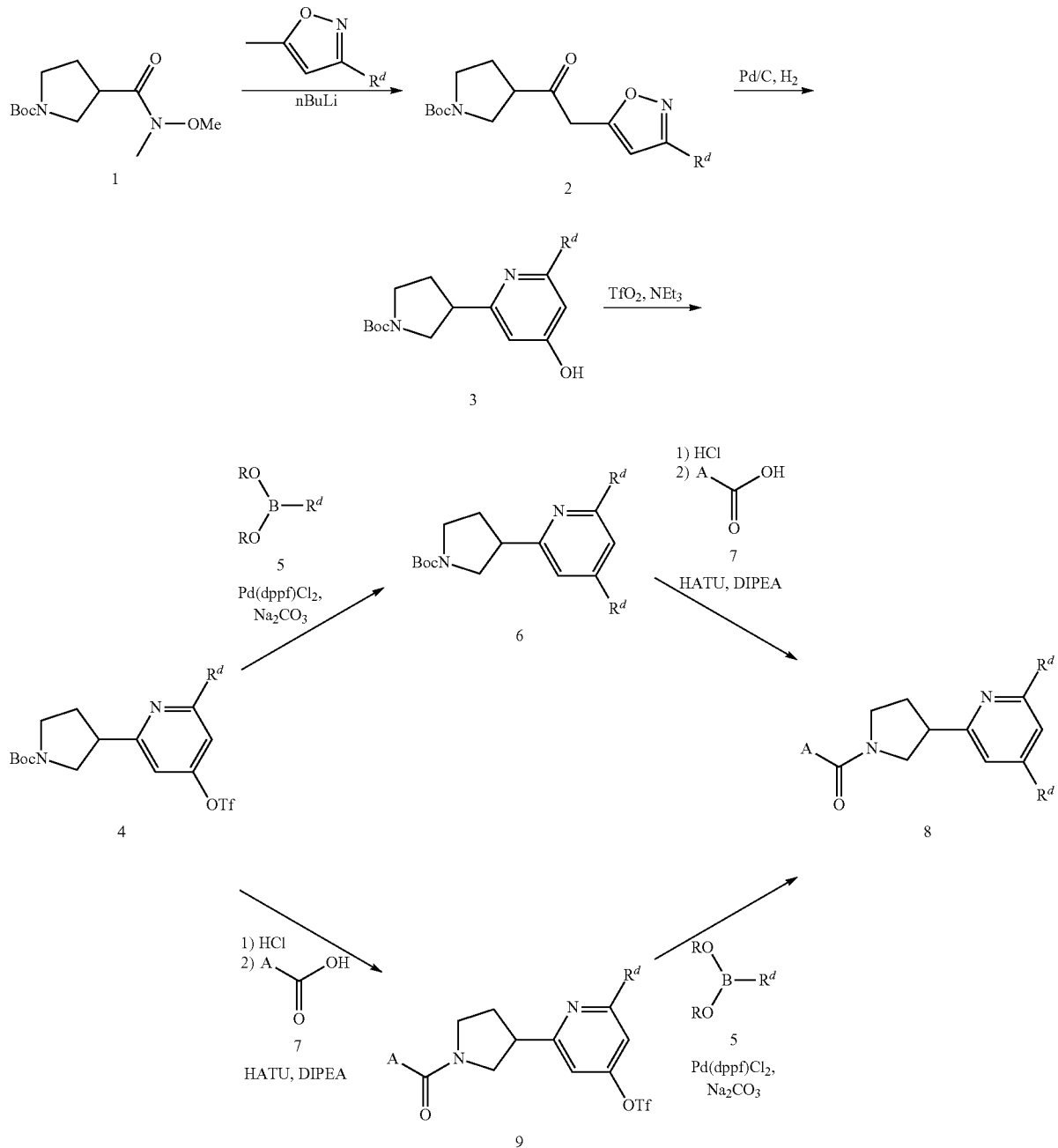

The general synthesis of compounds 8 is illustrated in Scheme 1. Organolithium addition to a pyrrolidine Weinreb compound 8. Besides Suzuki coupling with a boronate ester or boronic acid, the triflate 9 could also be transformed into compound 8, through Stille coupling reaction, or carbonylation, or Buchwald coupling reaction, etc.

Scheme 2 (Method B)

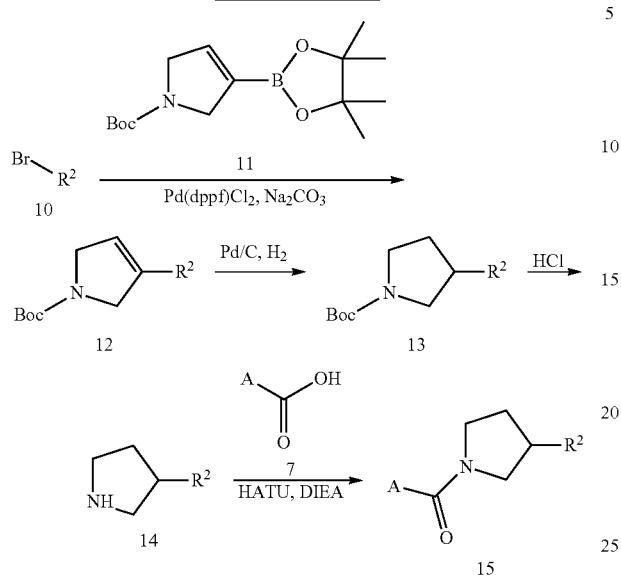

An alternative synthesis of compound 15 is illustrated in Scheme 2. Suzuki coupling of an aryl bromide 10 with a boronate ester 11 gave 2,5-dihydropyrrole 12. This was followed by hydrogenation to provide pyrrolidine intermediate 13, which was subsequently deprotected with hydrochloric acid to give pyrrolidine 14. Amide coupling with a carboxylic acid 7 then led to compound 15.

Scheme 3 (Method C)

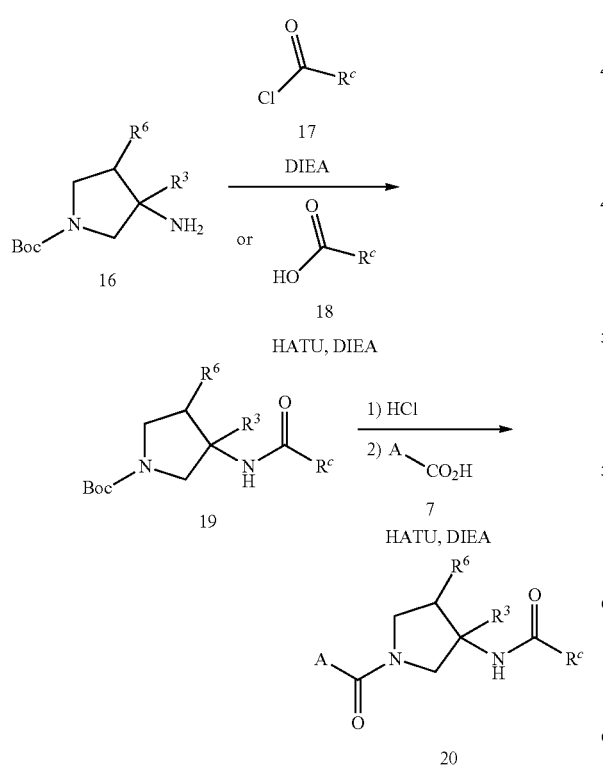

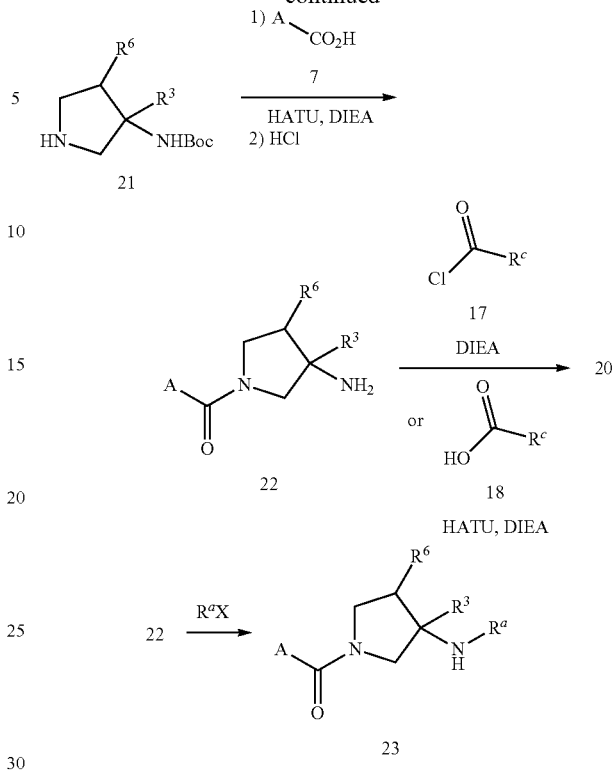

A general synthesis of compound 20 is described in Scheme 3. 3-amino pyrrolidine 16 reacted with an acid chloride 17 or a carboxylic acid 18 to give amide 19. This was followed by deprotection of Boc group, and subsequent amide formation with a carboxylic acid 7 gave pyrrolidine amide 20. Alternatively, pyrrolidine 21 could be coupled with a carboxylic acid 7 to give amide 22. Subsequent removal of Boc group, and coupling with an acid chloride, or a carboxylic acid, produced compound 20. In addition, the amino group in compound 22 could react with other reagents. For example, reaction of 22 with an isocyanate gave rise to a urea. Compound 22 could also undergo SNAr reaction with an aryl fluoride, to form a C—N bond. Alternatively, it could also form an heterocycle.

Scheme 4 (Method D)

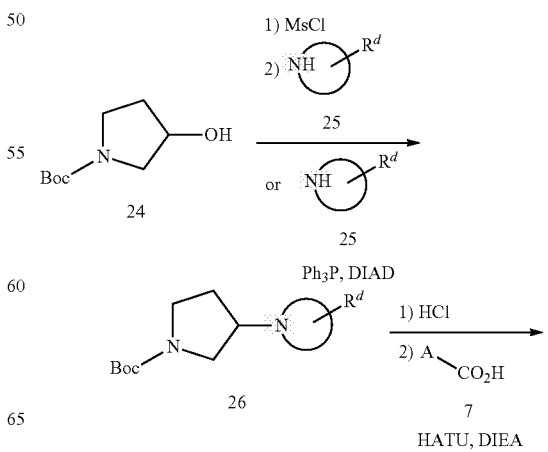

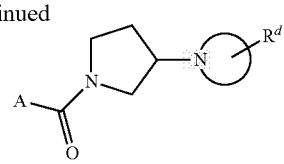

27

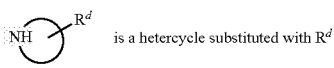

is a heterocycle substituted with $R^d$

A general synthesis of compound 27 is described in Scheme 4. 3-hydroxypyrrolidine 24 was converted to its mesylate, which upon treatment with a heterocyclic compound 25 provided compound 26. Alternatively, coupling of 3-hydroxypyrrolidine 24 and the heterocycle 25 could also be achieved by a Mitsunobu reaction. After de-protection of Boc group in 26, amide coupling with a carboxylic acid 7 then afforded compound 27.

LCMS Method A (Agilent 10-80 AB, ELSD, 2 Min)

Experiments were performed on an Agilent 1200 HPLC (with a PDA detector) with Agilent 6110 MSD mass spectrometer using ESI as ionization source using an Xtimate C18, 3 um, 30×2.1 mm and a 1.2 mL/min flow rate. Solvent A was water containing 0.038% TFA, and solvent B was acetonitrile containing 0.02% TFA. A gradient was run: starting with 10% A and 90% B, going to 20% A and 80% B within 0.9 min, then holding at 20% A and 80% B for 0.6 min. Total run time was 2 min.

LCMS Method B (Agilent 0-30 AB, ELSD, 2 Min)

Experiments were performed on an Agilent 1200 HPLC (with a PDA detector) with Agilent 6110 MSD mass spectrometer using ESI as ionization source using an Xtimate C18, 3 urn, 30×2.1 mm and a 1.2 mL/min flow rate. Solvent A was water containing 0.038% TFA, and solvent B was acetonitrile containing 0.02% TFA. A gradient was run: starting at 100% A, going to 30% A and 70% B within 0.9 min, then holding at 30% A and 70% B for 0.6 min. Total run time was 2 min.

LCMS Method C (Agilent 0-60 AB, ELSD, 2 Min)

Experiments were performed on an Agilent 1200 HPLC (with a PDA detector) with Agilent 6110 MSD mass spectrometer using ESI as ionization source using an Xtimate C18, 3 um, 30×2.1 mm and a 1.2 mL/min flow rate. Solvent A was water containing 0.038% TFA, and solvent B was acetonitrile containing 0.02% TFA. A gradient was run: starting with 100% A and going to 40% A and 60% B within 0.9 min, then holding at 40% A and 60% B for 0.6 min. Total run time was 2 min.

LCMS Method D (Agilent 30-90 AB, ELSD, 2 Min)

Experiments were performed on an Agilent 1200 HPLC (with a PDA detector) with Agilent 6110 MSD mass spectrometer using ESI as ionization source using an Xtimate C18, 3 urn, 30×2.1 mm and a 1.2 mL/min flow rate. Solvent A was water containing 0.038% TFA, and solvent B was acetonitrile containing 0.02% TFA. A gradient was run: starting with 30% A and 70% B, going to 10% A and 90% B within 0.9 min, then holding at 10% A and 90% B for 0.6 min. Total run time was 2 min.

LCMS Method E (SHIMADZU 5-95 AB, ELSD, 1.5 Min)

Experiments were performed on a SHIMADZU 20A HPLC (with a PDA detector) with SHIMADZU 2010EV MSD mass spectrometer using ESI as ionization source using an Merk RP-18e 2×25 mm column and a 1.5 mL/min flow rate. Solvent A was water containing 0.038% TFA, and solvent B was acetonitrile containing 0.02% TFA. A gradient was run: starting with 95% A and 5% B, going to 5% A and 95% B over the next 0.7 min. This solvent ratio was maintained for 0.4 min before returning to 95% A and 5% B over the next 0.4 min. Total run time was 1.5 min.

LCMS Method F (Agilent 5-95 AB, ELSD, 10 Min)

Experiments were performed on an Agilent 6140 quadrupole LC/MS system linked to a HPLC Agilent 1200 system with a UV detector monitoring at 254 nm, and mass spectrometry scanning 90-1300 amu in ESI+ ionization mode. This system uses an Agilent SB C18 (1.8 urn 30×2.1 mm) column, maintained at 25° C. and a 0.4 mL/min flow rate. Solvent A was water containing 0.05% TFA, and solvent B was acetonitrile containing 0.05% TFA. A gradient was run: starting with 95% A and 5% B for the first 0.3 min, going to 5% A and 95% B over the next 6.5 min. This solvent ratio was maintained for 1.5 min before returning to 95% A and 5% B over the next 0.1 min. Total run time was 10 min.

Examples 1 and 2

S)-(3-Isopropyl-1H-pyrazol-5-yl)(3-(6-methyl-4-(1-methyl-1H-pyrazol-4-yl)pyridin-2-yl)pyrrolidin-1-yl)methanone; and (R)-(3-Isopropyl-1H-pyrazol-5-yl)(3-(6-methyl-4-(1-methyl-1H-pyrazol-4-yl) pyridin-2-yl)pyrrolidin-1-yl)methanone Step 1

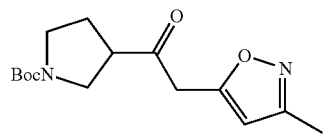 [SMILES: Cc1cc(CC(=O)C2CCN(C(=O)OC(C)(C)C)C2)on1]

tert-butyl 3-(2-(3-methylisoxazol-5-yl)acetyl)pyrrolidine-1-carboxylate

To a cooled (−78° C.) rigorously stirred solution of 3,5-dimethylisoxazole (31.4 mL, 1.1 eqiv., 0.319 mol) in THF (175 mL), a 2.6 M n-BuLi solution (123 mL, 1.1 eqiv., 0.319 mol) in hexane was added under argon. The reaction mixture was stirred at −78° C. for 60 min and a solution of tert-butyl 3-(methoxy(methyl)carbamoyl)pyrrolidine-1-carboxylate (75 g, 1.0 eqiv., 0.2906 mol) in 300 mL of THF was added at this temperature to the reaction mixture. The mixture was kept at −78° C. for another 60 min, then warmed to room temperature overnight. The mixture was quenched with solution of NH$_4$Cl (2 M, 500 mL). The organic layer was separated, dried over sodium sulfate, and evaporated. Crude product was purified by flash column chromatography on silica gel eluting with hexane/EtOAc to give the desired product (50 g, 58.5% yield) as an oil.

Step 2

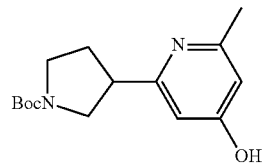 [SMILES: Cc1cc(O)cc(C2CCN(C(=O)OC(C)(C)C)C2)n1]

tert-butyl 3-(4-hydroxy-6-methylpyridin-2-yl)pyrrolidine-1-carboxylate

To a solution of tert-butyl 3-(2-(3-methylisoxazol-5-yl)acetyl)pyrrolidine-1-carboxylate (52 g, 1.0 eqiv.) in methanol (1400 mL) was added Pd/C (10%) (5.2 g) and the mixture was hydrogenated at 30 atm at 90° C. for 20 hrs. The reaction mixture was passed through Celite plug and the filtrate was evaporated on rotavap to yield (50 g) of the desired product which was used in the next step without further purification.
Step 3

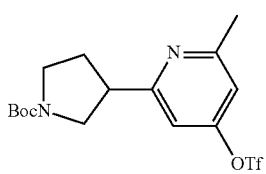 [SMILES: Cc1cc(OS(=O)(=O)C(F)(F)F)cc(C2CCN(C(=O)OC(C)(C)C)C2)n1]

tert-butyl 3-(6-methyl-4-(((trifluoromethyl)sulfonyl)oxy)pyridin-2-yl)pyrrolidine-1-carboxylate Trifluoromethane sulfonic anhydride (38 mL, 1.07 eqiv., 0.134 mol) was added drop wise to a mixture of tert-butyl 3-(4-hydroxy-6-methylpyridin-2-yl)pyrrolidine-1-carboxylate (35 g, 1.0 eqiv., 0.127 mol) and triethylamine (21 mL, 1.2 eqiv., 0.151 mol) in $CH_2Cl_2$ (350 mL) cooled with an ice bath. The mixture was allowed to warm to 10° C., then it was diluted with $CH_2Cl_2$ (100 mL), washed with saturated $NaHCO_3$ (3×100 mL), dried $Na_2SO_4$ and then concentrated. Crude product was purified by flash column chromatography on silica gel eluting with hexane-EtOAc to give the desired product (30 g, 58% yield) as solid.
Step 4

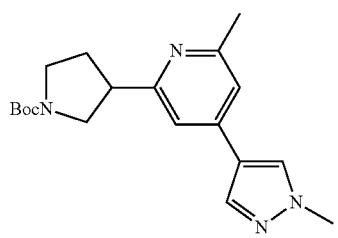 [SMILES: Cc1cc(-c2cnn(C)c2)cc(C2CCN(C(=O)OC(C)(C)C)C2)n1]

tert-Butyl 3-(6-methyl-4-(1-methyl-1H-pyrazol-4-yl)pyridin-2-yl)pyrrolidine-1-carboxylate To a solution of tert-butyl 4-(6-methyl-4-(((trifluoromethyl)sulfonyl)oxy)pyridin-2-yl)piperidine-1-carboxylate (500 mg, 1.22 mmol), 1-methyl-4-(4,4,5,5-tetramethyl-1,3,2-dioxaborolan-2-yl)-1H-pyrazole (127 mg, 0.61 mmol) and $Na_2CO_3$ (388 mg, 3.66 mmol) in $DME:H_2O$ (5:1, 10 mL) was added $Pd(dppf)Cl_2$ (9 mg, 12.2 μmol). The reaction mixture was purged with nitrogen and then heated at 100° C. in a microwave reactor for 30 min. After cooling to room temperature, the reaction mixture was concentrated and the residue was dissolved in EtOAc (180 mL) and washed with $H_2O$ (150 mL×2). The organic phase was dried over anhydrous $Na_2SO_4$, filtered and the filtrate was concentrated to dryness. The residue was purified by column chromatography eluting with 0-7% MeOH in DCM to give the desired product (355 mg, 85% yield) as yellow oil which was used directly for the next step without further purification.
Step 5

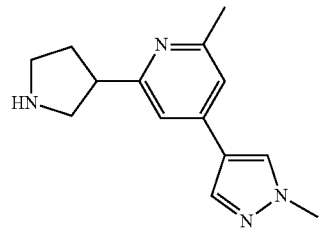 [SMILES: Cc1cc(-c2cnn(C)c2)cc(C2CCNC2)n1]

2-Methyl-4-(1-methyl-1H-pyrazol-4-yl)-6-(pyrrolidin-3-yl)pyridine

To a solution of tert-butyl 3-(6-methyl-4-(1-methyl-1H-pyrazol-4-yl)pyridin-2-yl)pyrrolidine-1-carboxylate (710 mg, 2.07 mmol) in EtOAc (2 mL) was added dropwise HCl/EtOAc (5 mL) and stirred at room temperature for 2 hrs. The reaction mixture was concentrated to dryness to give the desired product (510 mg, 88% yield) as yellow solid which was used directly for the next step without further purification. $^1$H NMR (400 MHz, $CD_3OD$) δ 8.63 (s, 1H), 8.32 (s, 1H), 8.14 (s, 1H), 7.97 (s, 1H), 4.00 (s, 3H), 3.96-3.86 (m, 2H), 3.72-3.65 (m, 2H), 3.52-3.45 (m, 1H), 2.77 (s, 3H), 2.72-2.64 (m, 1H), 2.46-2.36 (m, 1H).
Step 6

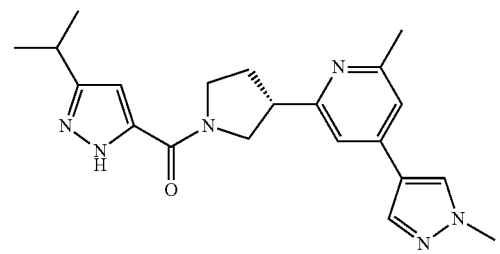 [SMILES: Cc1cc(-c2cnn(C)c2)cc([C@H]2CCN(C(=O)c3cc(C(C)C)n[nH]3)C2)n1]

Example 1

(S)-(3-Isopropyl-1H-pyrazol-5-yl)(3-(6-methyl-4-(1-methyl-1H-pyrazol-4-yl)pyridin-2-yl)pyrrolidin-1-yl)methanone

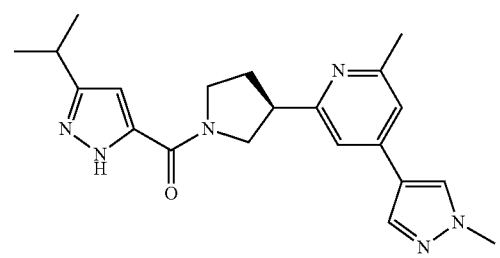 [SMILES: Cc1cc(-c2cnn(C)c2)cc([C@@H]2CCN(C(=O)c3cc(C(C)C)n[nH]3)C2)n1]

Example 2

(R)-(3-Isopropyl-1H-pyrazol-5-yl)(3-(6-methyl-4-(1-methyl-1H-pyrazol-4-yl)pyridin-2-yl)pyrrolidin-1-yl)methanone To a stirred solution of 3-isopropyl-1H-pyrazole-5-carboxylic acid (133 mg, 0.86 mmol) in DMF (5 mL) was added DIPEA (372 mg, 2.88 mmol) and HATU (395 mg, 1.04 mmol) at room temperature. The mixture was stirred at room temperature for 10 min, then 2-methyl-4-(1-methyl-1H-pyrazol-4-yl)-6-(pyrrolidin-3-yl)pyridine hydrochloride (200 mg, 0.72 mmol) was added and stirred at room temperature for 2 hrs. The mixture was diluted with EtOAc (200 mL), washed with brine (90 mL×3), dried over anhydrous Na$_2$SO$_4$, filtered, the filtrate was concentrated to give a residue which was purified by preparative TLC (DCM/MeOH=10:1) to give a mixture of enantiomers (130 mg, 48% yield) as white solid, which was purified by chiral SFC to give two enantiomers Example 1 (with arbitrarily assigned stereochemistry) (44.7 mg, 16% yield) and Example 2 (with arbitrarily assigned stereochemistry) (34.5 mg, 13% yield).

Example 1: $^1$H NMR (400 MHz, CDCl$_3$) δ 7.84 (s, 1H), 7.77-7.75 (m, 1H), 7.13-7.11 (m, 2H), 6.50, 6.48 (2s, 1H), 4.33-4.29 (m, 0.5H), 4.22-4.14 (m, 1H), 4.03-4.92 (m, 1H), 3.97 (s, 3H), 3.78-3.70 (m, 0.5H), 3.64-3.55 (m, 1H), 3.07-3.01 (in, 1H), 2.55 (s, 3H), 2.40-2.25 (m, 2H), 1.33-1.28 (m, 6H). LCMS (ESI) m/z: 378.9 [M+H]$^+$, RT=0.673 min (LCMS method E).

Example 2: $^1$H NMR (400 MHz, CDCl$_3$) δ 7.84 (s, 1H), 7.74 (s, 1H), 7.12-7.11 (m, 1H), 7.10 (s, 1H), 6.50, 6.48 (2s, 1H), 4.33-4.29 (m, 0.5H), 4.21-4.11 (m, 1H), 4.07-3.90 (m, 2H), 4.01 (s, 3H), 3.78-3.71 (m, 0.5H), 3.65-3.54 (m, 1H), 3.09-3.00 (m, 1H), 2.54 (s, 3H), 2.46-2.28 (m, 2H), 1.33-1.28 (m, 6H). LCMS (ESI) m/z: 379.0 [M+H]$^+$, RT=0.673 min (LCMS method E).

Example 3

Step 1

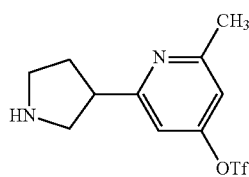 [SMILES: Cc1cc(OS(=O)(=O)C(F)(F)F)cc(C2CCNC2)n1]

2-Methyl-6-(pyrrolidin-3-yl)pyridin-4-yl trifluoromethanesulfonate

To a solution of 2-(1-(tert-butoxycarbonyl)pyrrolidin-3-yl)-6-methylpyridin-4-yl trifluoro methanesulfonate (1.5 g, 3.6 mmol) in DCM (60 mL) was added TFA (9 mL), the mixture was stirred at room temperature for 1.5 hrs. The mixture was poured into aqueous saturated NaHCO$_3$ (200 mL), extracted with EtOAc (100 mL×3), dried over anhydrous Na$_2$SO$_4$, filtered and concentrated to give the desired product (1.0 g, 90% yield) as a pale brown oil. LCMS (ESI) m/z: 310.9 [M+H]$^+$.

Step 2

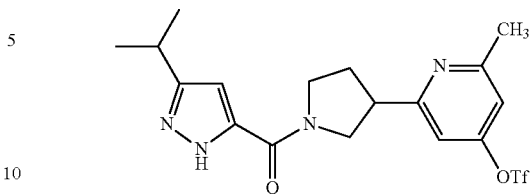

2-(1-(3-Isopropyl-1H-pyrazole-5-carbonyl)pyrrolidin-3-yl)-6-methylpyridin-4-yl Trifluoro Methanesulfonate To a solution of 2-methyl-6-(pyrrolidin-3-yl)pyridin-4-yl trifluoromethanesulfonate (1.0 g, 3.2 mmol) and 3-isopropyl-1H-pyrazole-5-carboxylic acid (600 mg, 3.9 mmol), TEA (1.0 g, 9.9 mmol) in DCM (150 mL) was added PyBrOP (1.8 g, 3.9 mmol). The mixture was stirred at room temperature for 30 min, then diluted with DCM (100 mL), washed with brine (200 mL×3), dried over anhydrous Na$_2$SO$_4$, filtered and concentrated to give the crude product which was purified by flash column chromatography on silica gel eluting with 0-5% MeOH in DCM to give the desired product (1.1 g, 78% yield) as a pale brown solid. LCMS (ESI) m/z: 446.9 [M+H]$^+$.

Step 3

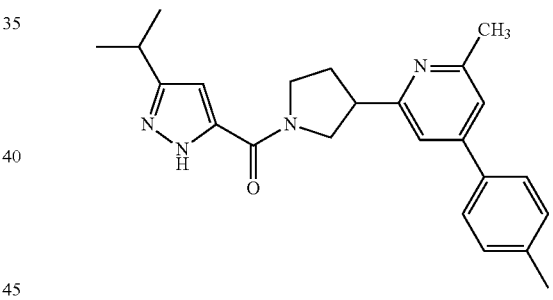

(3-Isopropyl-1H-pyrazol-5-yl)(3-(6-methyl-4-(p-tolyl)pyridin-2-yl)pyrrolidin-1-yl) methanone A mixture of 2-(1-(3-isopropyl-1H-pyrazole-5-carbonyl)pyrrolidin-3-yl)-6-methylpyridin-4-yl trifluoro methanesulfonate (50 mg, 0.11 mmol) and p-tolylboronic acid (23 mg, 0.17 mmol), K$_2$CO$_3$ (46 mg, 0.33 mmole), Pd(dppf)Cl$_2$ (10 mg, 0.01 mmol) in dioxane (2 mL) and H$_2$O (0.5 mL) was heated at 110° C. in a microwave reactor for 30 min. The mixture was filtered through a silica gel pad, washed with EtOAc, concentrated to give the crude product which was purified by preparative TLC (DCM:MeOH=20:1) to give the desired product (16 mg, 37% yield) as a brown solid. $^1$H NMR (400 MHz, CDCl$_3$) δ 7.49-7.17 (m, 2H), 7.26 (m, 4H), 6.46 (s, 1H), 4.30-3.54 (m, 5H), 3.04 (m, 1H), 2.57 (2s, 3H), 2.47-2.25 (m, 5H), 1.28 (m, 6H). LCMS (ESI) m/z: 388.9 [M+H]$^+$, RT=0.743 min (LCMS Method E).

Example 4

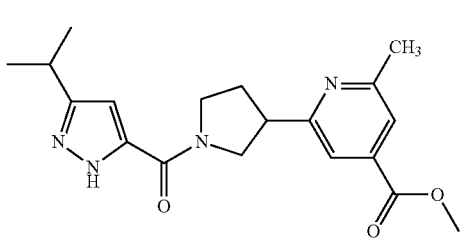 [SMILES: COC(=O)c1cc(C)nc(C2CCN(C(=O)c3cc(C(C)C)n[nH]3)C2)c1]

Methyl 2-(1-(3-isopropyl-1H-pyrazole-5-carbonyl)pyrrolidin-3-yl)-6-methylisonicotinate To a solution of 2-(1-(3-isopropyl-1H-pyrazole-5-carbonyl)pyrrolidin-3-yl)-6-methylpyridin-4-yl trifluoromethanesulfonate (100 mg, 0.2 mmol) and TEA (80 mg, 0.8 mmol) in DMF (5 mL) and MeOH (2.5 mL) were added Pd(OAc)$_2$ (10 mg, 0.08 mmole) and dppp (20 mg, 0.04 mmole). The mixture was stirred at 70° C. for 16 hrs under an atmosphere of carbon monoxide. After cooling to room temperature, the reaction mixture was diluted with EtOAc (100 mL), washed with brine (30 mL×3), dried over anhydrous Na$_2$SO$_4$, filtered and concentrated to give a residue which was purified by preparative TLC (DCM:MeOH=15:1) to give the desired product (45 mg, 63% yield) as a white solid. $^1$H NMR (400 MHz, CD$_3$OD) δ 8.25-8.28 (m, 2H), 6.67 (s, 1H), 4.59-4.54 (m, 0.5H), 4.34-4.17 (m, 2H), 4.14-3.84 (m, 4.5H), 4.02 (s, 3H), 3.12-3.05 (m, 1H), 2.89 (2s, 3H), 1.32 (m, 6H); LCMS (ESI) m/z: 357.0 [M+H]$^+$, RT=0.933 min (LCMS Method A).

Example 5

Step 1

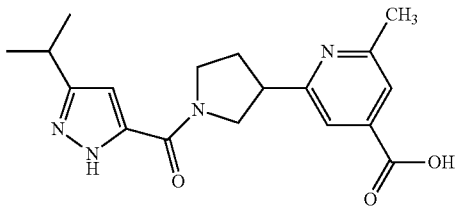 [SMILES: Cc1cc(C(=O)O)cc(C2CCN(C(=O)c3cc(C(C)C)n[nH]3)C2)n1]

2-(1-(3-Isopropyl-1H-pyrazole-5-carbonyl)pyrrolidin-3-yl)-6-methylisonicotinic Acid To a solution of methyl 2-(1-(3-isopropyl-1H-pyrazole-5-carbonyl)pyrrolidin-3-yl)-6-methylisonicotinate (33 mg, 0.1 mmol) in H$_2$O (5 mL) and MeOH (5 mL) were added LiOH (40 mg, 1.0 mmol). The mixture was stirred at room temperature for 2 hrs. The mixture was acidified to pH=2.0 with diluted aqueous HCl, extracted with DCM/MeOH=10/1 (20 mL×3), concentrated to give crude desired product (28 mg, 90% yield) as a white solid.

Step 2

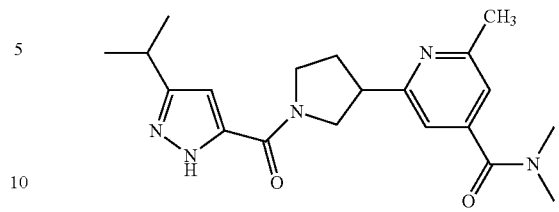

2-(1-(3-Isopropyl-1H-pyrazole-5-carbonyl)pyrrolidin-3-yl)-N,N,6-trimethylisonicotinamide To a solution of 2-(1-(3-isopropyl-1H-pyrazole-5-carbonyl)pyrrolidin-3-yl)-6-methylisonicotinic acid (28 mg, 0.8 mmol), dimethylamine hydrochloride (26 mg, 0.32 mmol), TEA (50 mg, 0.5 mmol) in DCM (10 mL) was added PyBrOP (46 mg, 0.1 mmol), the mixture was stirred at room temperature for 1 hr. The mixture was concentrated to give the crude product which was purified by preparative TLC (DCM/MeOH=10:1) to give the desired product (13 mg, 43% yield) as a white solid. $^1$H NMR (400 MHz, CD$_3$OD) δ 7.90 (s, 1H), 7.83 (d, J=1.6 Hz, 1H), 6.61 (s, 1H), 4.56 (mz, 0.5H), 4.32-4.12 (m, 1.5H), 4.09-3.68 (m, 3H), 3.12 (s, 3H), 3.09-2.99 (m, 1H), 2.95 (s, 3H), 2.83 (2s, 3H), 2.64-2.26 (m, 2H), 1.32 (m, 6H). LCMS (ESI) m/z: 370.1 [M+H]$^+$, RT=0.711 min (LCMS Method A).

Example 6

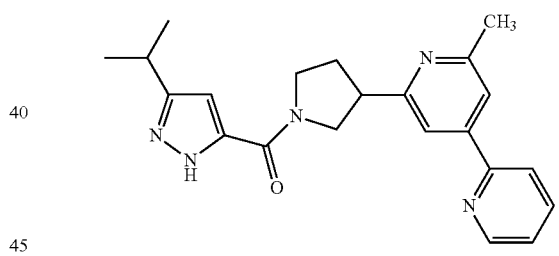

(3-isopropyl-1H-pyrazol-5-yl)(3-(6'-methyl-[2,4'-bipyridin]-2'-yl)pyrrolidin-1-yl)methanone A mixture of 2-(1-(3-isopropyl-1H-pyrazole-5-carbonyl)pyrrolidin-3-yl)-6-methylpyridin-4-yl trifluoromethanesulfonate (50 mg, 0.11 mmol) and 2-(tributylstannyl)pyridine (66 mg, 0.18 mmol), LiCl (7 mg, 0.15 mmol), Pd(PPh$_3$)Cl$_2$ (10 mg, 0.01 mmol) in DMF (2 mL) and H$_2$O (0.5 mL) was heated at 120° C. in a microwave reactor for 30 min. After cooling to room temperature, the mixture was filtered through a silica-gel pad, washed with EtOAc and concentrated to give a residue which was purified by preparative TLC (DCM/MeOH=10:1) to give the desired product (8.8 mg, 21% yield) as a white solid. $^1$H NMR (400 MHz, CD$_3$OD) δ 8.67 (d, J=4.4 Hz, 1H), 8.07-7.89 (m, 2H), 7.83-7.69 (m, 2H), 7.51-7.42 (m, 1H), 6.53 (2s, 1H), 4.43 (m, 0.5H), 4.28-3.82 (m, 3H), 3.76-3.55 (m, 1.5H), 3.12-2.96 (m, 1H), 2.60 (2s, 3H), 2.52-2.24 (m, 2H), 1.33-1.25 (m, 6H). LCMS (ESI) m/z: 376.1 [M+H]$^+$, RT=0.829 min (LCMS method A).

Example 7

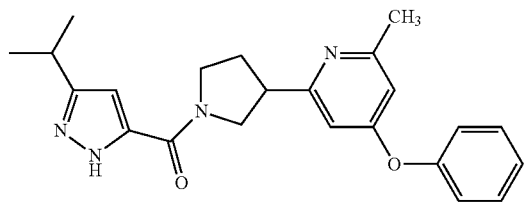 [SMILES: Cc1cc(Oc2ccccc2)cc(C2CCN(C(=O)c3cc(C(C)C)n[nH]3)C2)n1]

(3-Isopropyl-1H-pyrazol-5-yl)(3-(6-methyl-4-phenoxypyridin-2-yl)pyrrolidin-1-yl)methanone A mixture of (3-(4-bromo-6-methylpyridin-2-yl)pyrrolidin-1-yl)(3-isopropyl-1H-pyrazol-5-yl)methanone (40 mg, 0.10 mmol), phenol (56.4 mg, 0.6 mmol), CuI (57.2 mg, 0.3 mmol), $K_3PO_4$ (63.6 mg, 0.3 mmol), picolinic acid (37 mg, 0.3 mmol) in DMSO (4 mL) was heated at 120° C. in microwave reactor for 30 min. The reaction mixture was washed with water (20 mL), extracted with EtOAc (20 mL). The organic phase was dried over anhydrous $Na_2SO_4$, concentrated and the residue was purified with preparative TLC (5% MeOH in DCM) to give the crude product which was further purified by preparative HPLC to give the desired product (2.0 mg, 2% yield). $^1$H NMR (400 MHz, $CD_3OD$) δ 7.49-7.44 (m, 2H), 7.30-7.27 (m, 1H), 7.05-7.15 (m, 2H), 6.72-6.70 (m 1H), 6.65-6.55 (n, 1H), 6.49 (s, 1H), 4.42-4.12 (m, 1H), 4.08-3.90 (m, 1.5H), 3.88-3.63 (m, 1.5H), 3.55-3.45 (m, 1H), 3.12-2.96 (m, 1H), 2.44, 2.42 (2s, 3H), 2.40-2.12 (m, 2H), 1.31-1.28 (m, 6H). LCMS (ESI) m/z: 391.1 $[M+H]^+$, RT=0.736 min (LCMS Method E).

Example 8

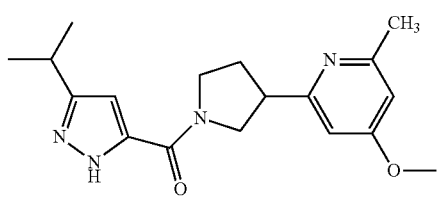 [SMILES: COc1cc(C)nc(C2CCN(C(=O)c3cc(C(C)C)n[nH]3)C2)c1]

(3-Isopropyl-1H-pyrazol-5-yl)(3-(4-methoxy-6-methylpyridin-2-yl)pyrrolidin-1-yl) methanone A mixture of (3-(4-bromo-6-methylpyridin-2-yl)pyrrolidin-1-yl)(3-isopropyl-1H-pyrazol-5-yl) methanone (40 mg, 0.11 mmol) and MeONa (2 mL, 4 mmole) in DMSO (2 mL) was heated at 90° C. for 16 h. The mixture was diluted with EtOAc (20 mL), washed with brine (20 mL×3), concentrated to give a residue which was purified by preparative TLC (DCM/MeOH=10:1) to give the desired product (23.1 mg, 72% yield) as a white solid. $^1$H NMR (400 MHz, $CD_3OD$) δ 6.70-6.80 (m, 2H), 6.49 (2s, 1H), 4.44-4.11 (m, 1H), 4.09-3.87 (m, 2H), 3.84 (m, 3H), 3.78-3.61 (m, 1H), 3.59-3.45 (m, 1H), 3.02 (m, 1H), 2.46 (2s, 3H), 2.40-2.13 (m, 2H), 1.28 (m, 6H); LCMS (ESI) m/z: 376.1 $[M+H]^+$, RT=0.829 min (LCMS method A).

Example 9

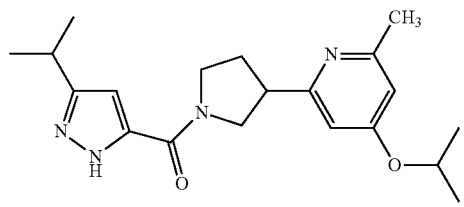 [SMILES: Cc1cc(OC(C)C)cc(C2CCN(C(=O)c3cc(C(C)C)n[nH]3)C2)n1]

(3-(4-Isopropoxy-6-methylpyridin-2-yl)pyrrolidin-1-yl)(3-isopropyl-1H-pyrazol-5-yl)methanone Sodium metal (25 mg, 1.06 mmol) was added into i-PrOH (3 mL) at room temperature. The mixture was stirred at 60° C. for 2 hrs. (3-(4-bromo-6-methylpyridin-2-yl)pyrrolidin-1-yl)(3-isopropyl-1H-pyrazol-5-yl)methanone (100 mg, 0.27 mmol) was added into the reaction mixture and stirred at 60° C. for 16 hrs. After cooling to room temperature, the reaction mixture was diluted with DCM (15 mL) and washed with $H_2O$ (10 mL), brine (10 mL). The organic phase was dried over anhydrous $Na_2SO_4$, concentrated and the residue was purified by preparative TLC (9% MeOH in DCM) to give the desired product (4.0 mg, 4% yield) as a white solid. $^1$H NMR (400 MHz, $CDCl_3$) δ 12.92 (s, 1H), 6.77 (s, 2H), 6.40 (s, 1H), 4.60-4.80 (m, 1H), 4.31-4.14 (m, 1H), 3.94-3.48 (m, 4H), 3.05-2.85 (m, 1H), 2.41 (s, 3H), 2.35-1.97 (m, 2H), 1.29-1.21 (in, 12H). LCMS (ESI) m/z: 356.9 $[M+H]^+$, RT=0.730 min (LCMS Method E).

Example 10

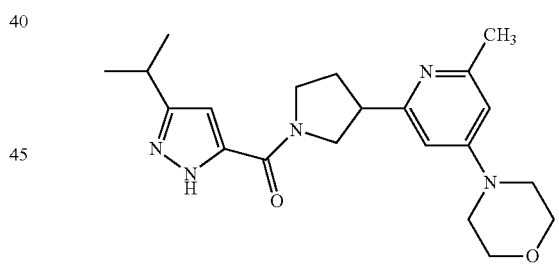

(3-Isopropyl-1H-pyrazol-5-yl)(3-(6-methyl-4-morpholinopyridin-2-yl)pyrrolidin-1-yl)methanone A mixture of 2-(1-(3-isopropyl-1H-pyrazole-5-carbonyl)pyrrolidin-3-yl)-6-methylpyridin-4-yl trifluoromethanesulfonate (50 mg, 0.11 mmol) and morpholine (1 mL) was heated at 120° C. in microwave reactor for 30 min. The mixture concentrated to give a residue which was purified by preparative TLC (DCM/MeOH=10:1) to give the desired product (17.7 mg, 41% yield) as a white solid. $^1$H NMR (400 MHz, $CDCl_3$) δ 6.52-6.29 (m, 3H), 4.24-4.14 (m, 0.5H), 4.09-3.94 (m, 1H), 3.89-3.71 (m, 5.5H), 3.68-3.48 (m, 2H), 3.26 (m, 4H), 3.02-2.86 (m, 1H), 2.51 (s, 3H), 2.30-2.26 (m, 2H), 1.22 (m, 6H). LCMS (ESI) m/z: 384.1 $[M+H]^+$, RT=0.771 min (LCMS Method A).

Example 11

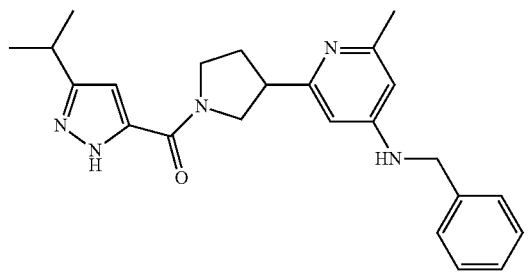 [SMILES: Cc1cc(NCc2ccccc2)cc(C2CCN(C(=O)c3cc(C(C)C)n[nH]3)C2)n1]

(3-(4-(Benzylamino)-6-methylpyridin-2-yl)pyrrolidin-1-yl)(3-isopropyl-1H-pyrazol-5-yl)methanone A solution of 2-(1-(3-isopropyl-1H-pyrazole-5-carbonyl)pyrrolidin-3-yl)-6-methylpyridin-4-yl trifluoromethanesulfonate (80 mg, 179.2 μmol) in benzyl amine (96.0 mg, 896.0 μmol) was heated in microwave reactor at 120° C. for 30 min. After cooling to room temperature, the mixture was concentrated and the residue was purified by preparative HPLC (Base) to give the desired product (2.1 mg, 3% yield) as yellow solid. $^1$H NMR (400 MHz, CDCl$_3$) δ 7.36-7.31 (m, 5H), 6.46, 6.45 (2s, 1H), 6.27-6.25 (m, 2H), 4.36 (m, 2H), 4.23-4.19 (m, 1H), 4.10-4.03 (m, 1H), 3.96-3.81 (m, 2H), 3.72-3.65 (m, 1H), 3.53-3.44 (m, 1H), 3.06-2.98 (m, 1H), 2.41 (s, 3H), 2.32-2.18 (m, 2H), 1.32-1.28 (m, 6H). LCMS (ESI) m/z: 404.2 [M+H]$^+$, RT=1.087 min (LCMS method C).

Method B

Example 12

Step 1

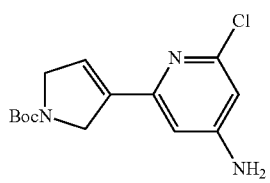 [SMILES: CC(C)(C)OC(=O)N1CC=C(c2cc(N)cc(Cl)n2)C1]

tert-Butyl 3-(4-amino-6-chloropyridin-2-yl)-2,5-dihydro-1H-pyrrole-1-carboxylate To a solution of tert-butyl 3-(4,4,5,5-tetramethyl-1,3,2-dioxaborolan-2-yl)-2,5-dihydro-1H-pyrrole-1-carboxylate (10 g, 34 mmol), 2,6-dichloropyridin-4-amine (8.3 g, 51 mmol) and Na$_2$CO$_3$ (11 g, 0.10 mol) in Dioxane/H$_2$O (5:1, 240 mL) was added Pd(dppf)Cl$_2$ (1.2 g, 1.7 mmol) at room temperature. The mixture was heated at 70° C. for 16 hrs under a N$_2$ atmosphere. After cooling to room temperature, the reaction mixture was filtered, concentrated and the residue was diluted with EtOAc (500 mL) and washed with H$_2$O (400 mL×2), brine (400 mL). The organic phase was dried over anhydrous Na$_2$SO$_4$, filtered and concentrated to dryness. The residue was purified by flash column chromatography eluting with 0-50% EtOAc in hexanes) to give the desired product (5 g, 50% yield) as white solid.

Step 2

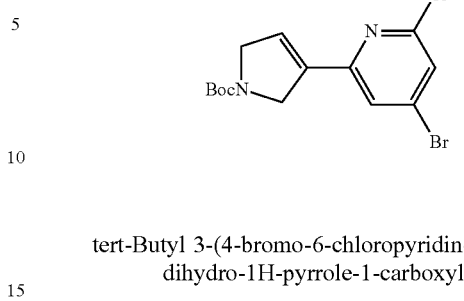

tert-Butyl 3-(4-bromo-6-chloropyridin-2-yl)-2,5-dihydro-1H-pyrrole-1-carboxylate To a solution of tert-butyl 3-(4-amino-6-chloropyridin-2-yl)-2,5-dihydro-1H-pyrrole-1-carboxylate (4 g, 14 mmol), t-BuONO (1.8 g, 18 mmol) in CH$_3$CN (150 mL) was added CuBr$_2$ (4.5 g, 20 mmol) at 0° C. and stirred at 0° C. for 1 hr. Then the reaction mixture was warmed up to room temperature for 2 hrs under N$_2$ atmosphere. The reaction mixture was concentrated and the residue was diluted with EtOAc (300 mL), washed with H$_2$O (250 mL), NH$_3$.H$_2$O (18%, 250 mL×3), brine (250 mL). The organic phase was dried over anhydrous Na$_2$SO$_4$, filtered and the filtrate was concentrated to dryness. The residue was purified by silica gel column chromatography eluting with 0-9% MeOH in DCM) to give the desired product (2.4 g, 49% yield) as yellow solid.

Step 3

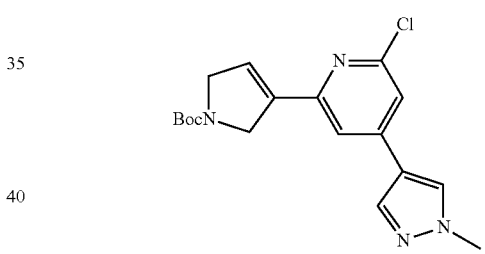

tert-Butyl 3-(6-chloro-4-(1-methyl-1H-pyrazol-4-yl)pyridin-2-yl)-2,5-dihydro-1H-pyrrole-1-carboxylate To a solution of tert-butyl 3-(4-bromo-6-chloropyridin-2-yl)-2,5-dihydro-1H-pyrrole-1-carboxylate (3 g, 8.3 mmol), 1-methyl-4-(4,4,5,5-tetramethyl-1,3,2-dioxaborolan-2-yl)-1H-pyrazole (2.6 g, 13 mmol) and Na$_2$CO$_3$ (2.6 g, 25 mmol) in dioxane/H$_2$O (5:1, 150 mL) was added Pd(dppf)Cl$_2$ (305 mg, 0.42 mmol) at room temperature. The mixture was heated at 80° C. for 3 hrs under N$_2$ atmosphere. After cooling to room temperature, the reaction mixture was filtered, concentrated and the residue was diluted with EtOAc (200 mL) and washed with H$_2$O (150 mL), brine (150 mL). The organic phase was dried over anhydrous Na$_2$SO$_4$, filtered and the filtrate was concentrated to dryness. The residue was purified by silica gel column chromatography eluting with 0-9% MeOH in DCM) to give the desired product (2.5 g, 83% yield) as yellow solid. $^1$H NMR (400 MHz, CDCl$_3$) δ 7.86, 7.83 (2s, 1H), 7.78, 7.74 (2s, 1H), 7.28 (s, 1H), 7.11 (s, 1H), 6.7, 6.6 (2s, 1H), 4.60-4.50 (m, 2H), 4.43-4.30 (m, 2H), 3.99 (s., 3H), 1.53, 1.52 (2s, 9H).

Step 4

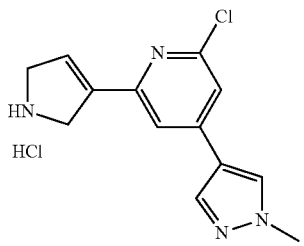 [SMILES: Cl ; Cn1cc(-c2cc(Cl)nc(C3=CCNC3)c2)cn1]

2-Chloro-6-(2,5-dihydro-1H-pyrrol-3-yl)-4-(1-methyl-1H-pyrazol-4-yl)pyridine Hydrochloride To a stirred solution of tert-butyl 3-(6-chloro-4-(1-methyl-1H-pyrazol-4-yl)pyridin-2-yl)-2,5-dihydro-1H-pyrrole-1-carboxylate (2.5 g, 6.9 mmol) in EtOAc (2 mL) was added dropwise HCl/EtOAc (5 mL, 20 mmol, 4 M) and stirred at room temperature for 1 hr. The reaction mixture was concentrated and the solid was washed with EtOAc (50 mL×2) to give the crude desired product (1.8 g) as yellow solid. $^1$H NMR (400 MHz, CD$_3$OD) δ 8.35 (s, 1H), 8.16 (s, 1H), 7.89 (s, 1H), 7.60 (s, 1H), 6.81 (s, 1H), 4.53 (s, 2H), 4.36 (s, 2H), 4.00, 3.98 (2s, 3H).

Step 5

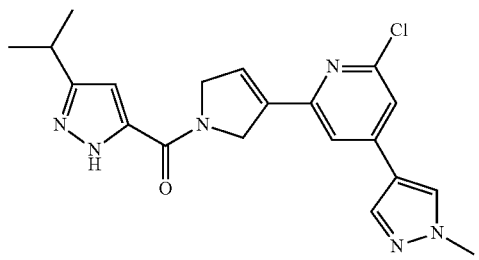 [SMILES: CC(C)c1cc(C(=O)N2CCC(c3cc(-c4cnn(C)c4)cc(Cl)n3)C2)[nH]n1]

(3-(6-Chloro-4-(1-methyl-1H-pyrazol-4-yl)pyridin-2-yl)-2,5-dihydro-1H-pyrrol-1-yl)(3-isopropyl-1H-pyrazol-5-yl)methanone To a stirred solution of 3-isopropyl-1H-pyrazole-5-carboxylic acid (1.1 g, 7.3 mmol) in DMF (20 mL) was added DIEA (3.1 g, 24 mmol) and HATU (3.2 g, 8.5 mmol) and stirred at room temperature for 10 min before the addition of 2-chloro-6-(2,5-dihydro-1H-pyrrol-3-yl)-4-(1-methyl-1H-pyrazol-4-yl)pyridine hydrochloride (1.8 g, 6.1 mmol). The mixture was stirred at room temperature for 2 hrs under a N$_2$ atmosphere. The mixture was diluted with EtOAc (250 mL), washed with H$_2$O (240 mL×3). The organic phase was dried over anhydrous Na$_2$SO$_4$, filtered and the filtrate was concentrated and purified by silica gel column chromatography eluting with 0-10% MeOH in DCM to give the desired product (1.8 g, 75% yield) as yellow solid. $^1$H NMR (400 MHz, DMSO-d$_6$) δ 8.55, 8.50 (2s, 1H), 8.22, 8.19 (2s, 1H), 7.99, 7.84 (2s, 1H), 7.64 (s, 1H), 6.91, 6.87 (2s, 1H), 6.51, 6.50 (2s, 1H), 5.06 (m, 1H), 4.90 (m, 1H), 4.68 (m, 1H), 4.54 (m, 1H), 3.93, 3.89 (2s, 3H), 3.01-2.97 (m, 1H), 1.27-1.24 (m, 6H).

Step 6

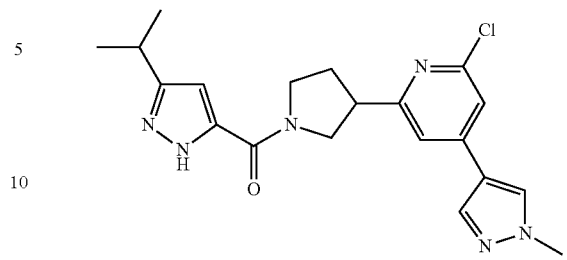

(3-(6-Chloro-4-(1-methyl-1H-pyrazol-4-yl)pyridin-2-yl)pyrrolidin-1H)(3-isopropyl-1H-pyrazol-5-yl)methanone To a stirred solution of (3-(6-Chloro-4-(1-methyl-1H-pyrazol-4-yl)pyridin-2-yl)-2,5-dihydro-1H-pyrrol-1-yl)(3-isopropyl-1H-pyrazol-5-yl)methanone (1.4 g, 3.5 mmol) in THF (150 mL) was added PtO$_2$ (500 mg, 2.2 mmol) and stirred under hydrogen at room temperature for one week. The reaction mixture was filtered and the filtrate was concentrated give the desired product (1.3 g, 92% yield) as yellow solid. $^1$H NMR (400 MHz, CDCl$_3$) δ 7.84 (s, 1H), 7.80, 7.78 (2s, 1H), 7.28 (s, 1H), 7.22, 7.21 (2s, 1H), 6.46, 6.45 (2s, 1H), 4.32-4.26 (m, 0.5H), 4.20-4.10 (m, 1H), 4.08-3.99 (m, 0.5H), 3.98, 3.97 (2s, 3H), 3.96-3.87 (m, 1H), 3.75-3.2 (m, 1H), 3.62-3.54 (m, 1H), 3.19-3.18 (m, 1H), 3.04-3.02 (m, 1H), 2.47-2.29 (m, 2H), 1.32-1.28 (m, 6H).

Step 7

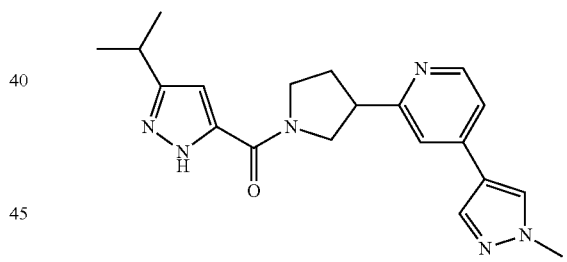

(3-Isopropyl-1H-pyrazol-5-yl)(3-(4-(1-methyl-1H-pyrazol-4-yl)pyridin-2-yl) pyrrolidin-1-yl) Methanone A solution of (3-(6-chloro-4-(1-methyl-1H-pyrazol-4-yl)pyridin-2-yl)pyrrolidin-1-yl)(3-isopropyl-1H-pyrazol-5-yl)methanone (50 mg, 0.13 mmol), Pd/C (10 mg) in MeOH (10 mL) was stirred under 1 atm H$_2$ for 16 hrs and filtered through a pad of Celite. The filtrate was concentrated and the residue was purified by preparative HPLC to give the desired product (10 mg, 22% yield) as a white solid. $^1$H NMR (400 MHz, CD$_3$OD) δ 8.41 (s, 1H), 8.21 (s, 1H), 8.01 (s, 1H), 7.58 (s, 1H), 7.47 (s, 1H), 6.52 (s, 1H), 4.50-4.40 (in, 0.5H), 4.30-4.20 (in, 0.5H), 4.19-3.90 (m, 5H), 3.80-3.50 (m, 2H), 3.10-2.90 (m, 1H), 2.50-2.10 (m, 2H), 1.31-1.28 (m, 6H). LCMS (ESI) m/z: 365.2 [M+H]$^+$, RT=0.665 min (LCMS method E).

Example 13

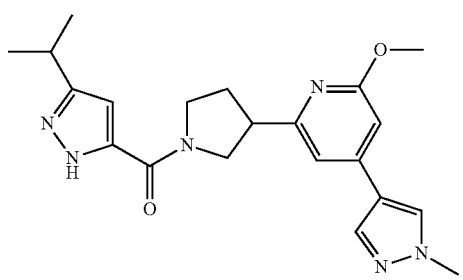 [SMILES: COc1cc(-c2cnn(C)c2)cc(C2CCN(C(=O)c3cc(C(C)C)n[nH]3)C2)n1]

(3-Isopropyl-1H-pyrazol-5-yl)(3-(6-methoxy-4-(1-methyl-1H-pyrazol-4-yl)pyridin-2-yl) pyrrolidin-1-yl)methanone Na (57.6 mg) was added into CH$_3$OH (8 mL) at room temperature and the mixture was stirred for 1 hr. (3-(6-chloro-4-(1-methyl-1H-pyrazol-4-yl)pyridin-2-yl)pyrrolidin-1-yl)(3-isopropyl-1H-pyrazol-5-yl) methanone (100 mg, 0.25 mmol) was added to this mixture. The mixture was stirred at 70° C. for 16 hrs. The reaction mixture was concentrated and the residue was purified by preparative HPLC to give the desired product (4 mg, 4% yield) as a white solid. $^1$H NMR (400 MHz, DMSO-d$_6$) δ 7.79 (s, 1H), 7.70 (m, 1H), 6.88 (m, 1H), 6.66 (m, 1H), 6.45, 6.42 (2s, 1H), 4.11-3.87 (m, 9H), 3.56-3.46 (m, 1H), 3.12-3.00 (m, 1H), 2.43-2.27 (m, 2H), 1.31-1.27 (m, 6H). LCMS (ESI) m/z: 398.4 [M+H]$^+$, RT=0.776 min (LCMS method E).

Example 14

Step 1

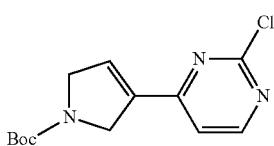

tert-Butyl 3-(2-chloropyrimidin-4-yl)-2,5-dihydro-1H-pyrrole-1-carboxylate

A mixture of 2,4-dichloropyrimidine (1.0 g, 6.7 mmol), tert-butyl 3-(4,4,5,5-tetramethyl-1,3,2-dioxaborolan-2-yl)-2,5-dihydro-1H-pyrrole-1-carboxylate (1.6 g, 5.4 mmol), Pd(dppf)Cl$_2$ (0.5 g, 0.34 mmol), Na$_2$CO$_3$ (1.4 g, 13 mmol) in Dioxane/H$_2$O (12 mL, 5:1) was stirred at 80° C. for 2 hrs. After cooling to room temperature, the reaction mixture was washed with H$_2$O (10 mL), and extracted with EtOAc (15 mL). The organic phase was dried with anhydrous Na$_2$SO$_4$, filtered and concentrated. The residue was purified with flash column chromatography on silica gel eluting with 20% EtOAc in hexanes to give the desired product (0.8 g, 42% yield) as a white solid. $^1$H NMR (400 MHz, CDCl$_3$) δ 8.60-8.57 (m, 1H), 7.27, 7.10 (2s, 1H), 6.94, 6.87 (2s, 1H), 4.51 (s, 2H), 4.36-4.20 (m, 2H), 1.51-1.49 (m, 9H).

Step 2

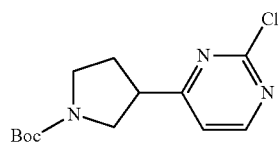 [SMILES: CC(C)(C)OC(=O)N1CCC(c2ccnc(Cl)n2)C1]

tert-Butyl 3-(2-chloropyrimidin-4-yl)pyrrolidine-1-carboxylate

A mixture of tert-butyl 3-(2-chloropyrimidin-4-yl)-2,5-dihydro-1H-pyrrole-1-carboxylate (800 mg, 2.8 mmol), PtO$_2$ (129 mg, 0.57 mmol) in THF (10 mL) was stirred under 1 atm of H$_2$ at room temperature for 12 hrs. The suspension was filtered through a pad of celite. The filtrate was concentrated and the residue was purified with column chromatograph on silica gel eluting with 20% EtOAc in hexanes to give the desired product (0.28 g, 35% yield) as a white solid. $^1$H NMR (400 MHz, CDCl$_3$) δ 8.55 (d, J=4.8 Hz, 1H), 7.16 (d, J=4.4 Hz, 1H), 3.88-3.70 (m, 1H), 3.64-3.44 (m, 4H), 2.30-2.18 (m, 2H), 1.47 (s, 9H).

Step 3

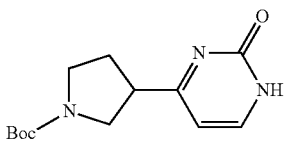 [SMILES: CC(C)(C)OC(=O)N1CCC(c2cc[nH]c(=O)n2)C1]

tert-Butyl 3-(2-oxo-1,2-dihydropyrimidin-4-yl)pyrrolidine-1-carboxylate

A mixture of tert-butyl 3-(2-chloropyrimidin-4-yl) pyrrolidine-1-carboxylate (1.2 g, 4.1 mmol), 1,4-diazabicyclo[2.2.2]octane (0.23 g, 2.1 mmol), K$_2$CO$_3$ (1.0 g, 7.4 mmol) in Dioxane/H$_2$O (10 mL/10 mL) was stirred at room temperature for 12 hrs. The reaction mixture was concentrated and extracted with DCM (15 mL). The organic phase was dried over Na$_2$SO$_4$, filtered and concentrated. The residue was purified with column chromatograph on silica gel eluting with 9% MeOH in DCM to give desired product (0.6 g, 64% yield) as a white solid.

Step 4

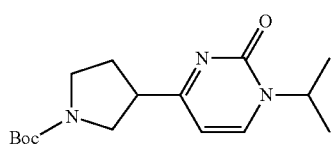 [SMILES: CC(C)n1ccc(C2CCN(C(=O)OC(C)(C)C)C2)nc1=O]

tert-Butyl 3-(1-isopropyl-2-oxo-1,2-dihydropyrimidin-4-yl)pyrrolidine-1-carboxylate A mixture of tert-butyl 3-(2-oxo-1,2-dihydropyrimidin-4-yl)pyrrolidine-1-carboxylate (300 mg, 1.1 mmol), 2-iodopropane (211 mg, 1.2 mmol), Cs$_2$CO$_3$ (737 mg, 2.3 mmol) in DMF (8 mL) was stirred at 60° C. for 5 hrs. After cooling down to room temperature, the reaction mixture was washed with H$_2$O (10 mL), and extracted with DCM (10 mL×3). The reaction mixture was concentrated to give the crude product (200 mg, 57% yield) as yellow oil, contaminated with O-isopropyl pyrimidine Step 5

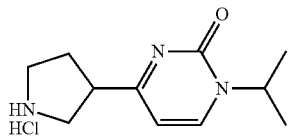

Isopropyl-4-(pyrrolidin-3-yl)pyrimidin-2(1H)-one Hydrochloride

To a mixture of tert-butyl 3-(1-isopropyl-2-oxo-1,2-dihydropyrimidin-4-yl)pyrrolidine-1-carbo-xylate and O-iPr pyrimidine (200 mg, 0.65 mmol) in EtOAc (4 mL) was added 4M HCl/EtOAc (4 mL) at room temperature. The mixture was stirred at room temperature for 2 hrs and then concentrated to dryness to give the crude product (150 mg, 95% yield) as yellow solid, which was directly taken to the next step.

Step 6

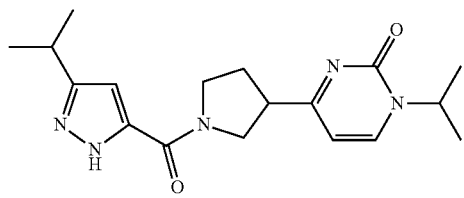 [SMILES: CC(C)c1cc(C(=O)N2CCC(c3ccn(C(C)C)c(=O)n3)C2)[nH]n1]

1-Isopropyl-4-(1-(3-isopropyl-1H-pyrazole-5-carbonyl)pyrrolidin-3-yl)pyrimidin-2(1H)-one A mixture of 3-isopropyl-1H-pyrazole-5-carboxylic acid (114 mg, 0.74 mmol), HATU (393 mg, 1.0 mmol), N-ethyl-N-isopropylpropan-2-amine (382 mg, 3.0 mmol) in DMF (5 mL) was stirred at room temperature for 10 min. A solution of the mixture of 1-isopropyl-4-(pyrimidin-3-yl)pyrimidin-2(1H)-one hydrochloride and 2-isopropoxy-4-(pyrrolidin-3-yl)pyrimidine hydro chloride (180 mg, 0.74 mmol) in DMF (4 mL) was added into the mixture. The reaction mixture was stirred at room temperature for 2 hrs and then washed with H$_2$O (15 mL), extracted with EtOAc (15 mL). The organic phase was washed with H$_2$O (15 mL×3), then washed with brine (10 mL), dried over anhydrous Na$_2$SO$_4$. The mixture was filtered. The filtrate was concentrated via rotavap to give a residue which was purified with preparative HPLC to give the desired product (50 mg, 20% yield) as white solid. $^1$H NMR (400 MHz, CD$_3$OD) δ 8.17-8.14 (m, 1H), 6.63-6.59 (m, 1H), 6.49 (s, 1H), 4.44-4.30 (m, 0.5H), 4.27-3.93 (m, 2H), 3.87-3.82 (m, 1H), 3.76-3.63 (m, 0.5H), 3.59-3.42 (m, 1H), 3.12-2.94 (m, 1H), 2.51-2.11 (m, 2H), 1.43-1.29 (m, 12H); LCMS (ESI) m/z: 344.1 [M+H]$^+$, RT=1.033 min (LCMS method C).

Method C

Example 15

Step 1

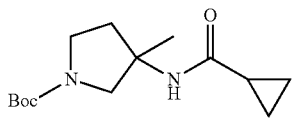 [SMILES: CC1(NC(=O)C2CC2)CCN(C(=O)OC(C)(C)C)C1]

tert-Butyl 3-(cyclopropanecarboxamido)-3-methylpyrrolidine-1-carboxylate

To a solution of tert-butyl 3-amino-3-methylpyrrolidine-1-carboxylate (560 mg, 2.80 mmol) in DCM (5 mL) was added DIEA (0.93 mL, 5.59 mmol), then cyclopropanecarbonyl chloride (300 mg, 2.80 mmol) was added dropwise at 0° C. The resulting mixture was stirred at room temperature for 1 hour. The reaction was quenched with water, and then extracted with DCM (50 mL×3). Combined organic layers were washed with H$_2$O (50 mL), dried over anhydrous Na$_2$SO$_4$, filtered and concentrated. The residue was purified by column chromatograph on silica gel eluted with 0-30% EtOAc in hexanes to give the desired product (680 mg, 91% yield) as light yellow oil. $^1$H NMR (400 MHz, CDCl$_3$) δ 5.56 (s, 1H), 3.60-3.32 (m, 4H), 1.85-1.82 (m, 1H), 1.29-1.26 (m, 2H), 0.93-0.85 (m, 4H).

Step 2

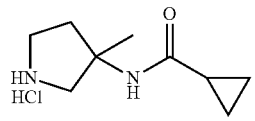

N-(3-methylpyrrolidin-3-yl)cyclopropanecarboxamide Hydrochloride

To a solution of tert-butyl 3-(cyclopropanecarboxamido)-3-methylpyrrolidine-1-carboxylate (680 mg, 2.53 mmol) in EtOAc (3 mL) was added dropwise HCl/EtOAc (5 mL). The mixture was stirred at room temperature for 1 hr. Then the reaction mixture was concentrated and the crude product was used in the next step directly.

Step 3

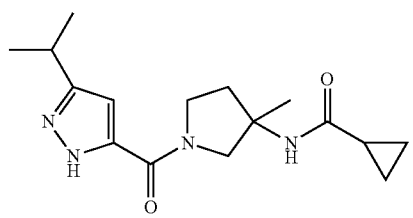 [SMILES: CC(C)c1cc(C(=O)N2CCC(C)(NC(=O)C3CC3)C2)[nH]n1]

N-(1-(3-isopropyl-1H-pyrazole-5-carbonyl)-3-methylpyrrolidin-3-yl)cyclopropanecarboxamide To a solution of 3-isopropyl-1H-pyrazole-5-carboxylic acid (431 mg, 2.79 mmol) in DMF (6 mL) were added HATU (1.38 g, 3.63 mmol) and DIEA (1.85 mL, 11.18 mmol) and then stirred at room temperature for 5 minutes before the addition of N-(3-methylpyrrolidin-3-yl)cyclopropane carboxamide hydrochloride (572 mg, 2.79 mmol) was added. The resulting mixture was stirred at room temperature for 16 hrs. The reaction mixture was filtered and the crude product was purified by preparative HPLC (Gemini C18, 150×25 mm×10 μm, 26-56% MeCN/H₂O) to give the desired product (210 mg, 25% yield) as white solid. ¹H NMR (400 MHz, DMSO-d₆) δ 8.09 (s, 1H), 6.41 (s, 1H), 4.17-4.14 (m, 0.5H), 3.88-3.72 (m, 2H), 3.55-3.52 (m, 1H), 3.38-3.35 (m, 0.5H), 2.96-2.93 (m, 1H), 2.31-2.19 (m, 1H), 1.88-1.72 (m, 1H), 1.56-1.53 (m, 1H), 1.38 (s, 3H), 1.22 (d, J=7.2 Hz, 6H), 0.63-0.57 (m, 4H). LCMS (ESI) m/z: 305.1 [M+H]⁺, RT=0.904 min (LCMS Method E).

Example 16

Step 1

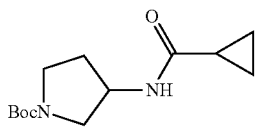

tert-Butyl 3-(cyclopropanecarboxamido)pyrrolidine-1-carboxylate

To a stirred solution of tert-butyl 3-aminopyrrolidine-1-carboxylate (15.0 g, 80.5 mmol) in DCM (45 mL) was added TEA (24.5 g, 241.6 mmol) and cooled to 0° C. in an ice bath. Then cyclopropanecarbonyl chloride (10.1 g, 96.6 mmol) was added dropwise into the mixture and stirred at room temperature for 2 hrs. The mixture was diluted with DCM (200 mL) and washed with H₂O (180 mL×3). The organic phase was dried over anhydrous Na₂SO₄, filtered and the filtrate was concentrated to give the desired product (18.0 g, 88% yield) as brown oil. ¹H NMR (400 MHz, CDCl₃) δ 6.00-5.96 (m, 1H), 4.51-4.43 (m, 1H), 3.65-3.56 (m, 1H), 3.46-3.35 (m, 2H), 3.30-3.11 (m, 1H), 2.20-2.08 (m, 1H), 1.83 (br. s., 1H), 1.38-1.31 (m, 1H), 1.01-0.92 (m, 2H), 0.79-0.69 (m, 2H).

Step 2

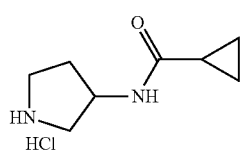 [SMILES: O=C(NC1CCNC1)C1CC1 ; Cl]

N-(Pyrrolidin-3-yl)cyclopropanecarboxamide Hydrochloride

To a stirred solution of tert-butyl 3-(cyclopropanecarboxamido)pyrrolidine-1-carboxylate (7 g, 27.5 mmol) in EtOAc (10 mL) was added dropwise HCl/EtOAc (35 mL, 140 mmol, 4 M) and stirred at room temperature for 1 hr. The reaction mixture was concentrated and the solid was washed with EtOAc (50 mL×3) to give the desired product (5.0 g, 96% yield) as yellow solid. ¹H NMR (400 MHz, CD₃OD) δ 4.45-4.37 (m, 1H), 3.55-3.45 (m, 2H), 3.40-3.33 (m, 1H), 3.25-3.20 (m, 1H), 2.38-2.26 (m, 1H), 2.36-2.27 (m, 1H), 1.70-1.58 (m, 1H), 0.90-0.83 (m, 2H), 0.83-0.75 (m, 2H).

Step 3

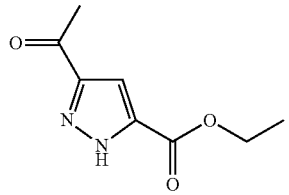

Ethyl 3-acetyl-1H-pyrazole-5-carboxylate

To a solution of 3-butyn-2-one (5 g, 73 mmol) in H₂O (80 mL) was added ethyl diazoacetate (12.5 g, 110 mmol). The mixture was stirred at room temperature for 4 hrs, and then filtered to give the desired product (10 g, 74% yield) as a white solid. ¹HNMR (400 MHz, CD₃OD) δ 7.38, 7.21 (m, 1H), 4.43-4.34 (m, 2H), 2.55, 2.52 (2s, 3H), 1.39-1.32 (m, 3H).

Step 4

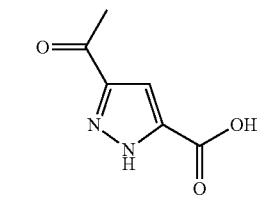

3-acetyl-1H-pyrazole-5-carboxylic Acid

To a solution of ethyl 3-acetyl-1H-pyrazole-5-carboxylate (1 g, 5.5 mmol) in a mixture of MeOH (5 mL) and H₂O (5 mL) was added NaOH (1.1 g, 27 mmol). The mixture was stirred at room temperature for 2 hrs before being acidified by conc. HCl to pH 2.o, and then filtered to give the desired product (800 mg, 94% yield) as a white solid.

Step 5

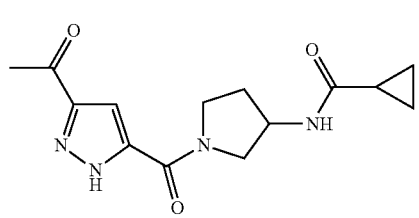 [SMILES: CC(=O)c1cc(C(=O)N2CCC(NC(=O)C3CC3)C2)[nH]n1]

N-(1-(3-acetyl-1H-pyrazole-5-carbonyl)pyrrolidin-3-yl)cyclopropanecarboxamide

To a solution of 3-acetyl-1H-pyrazole-5-carboxylic acid (800 mg, 5 mmol) in DMF (15 mL) was added N-pyrrolidin-3-ylcyclopropanecarboxamide (1.2 g, 8 mmol), HATU (3 g, 8 mmol) and DIEA (2.8 mL, 16 mmol). The mixture was stirred at room temperature for 15 hrs and then concentrated to dryness under reduced pressure. The residue was partitioned between water (8 mL) and EtOAc (30 mL). The aqueous layer was extracted with EtOAc (20 mL×2) and combined organic layers were dried over anhydrous Na₂SO₄, filtered, concentrated, and purified by silica gel column chromatography eluting with 0-5% MeOH in DCM to give the desired product (1.8 g, 53% yield) as a white solid. LCMS (ESI) m/z: 290.9 [M+H]⁺, RT=0.99 min (LCMS Method C).

Step 6

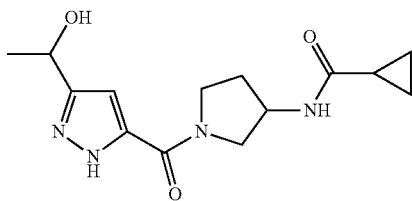 [SMILES: CC(O)c1cc(C(=O)N2CCC(NC(=O)C3CC3)C2)[nH]n1]

N-(1-(3-(1-hydroxyethyl)-1H-pyrazole-5-carbonyl) pyrrolidin-3-yl)cyclopropanecarboxamide To a solution of N-(1-(3-acetyl-1H-pyrazole-5-carbonyl) pyrrolidin-3-yl)cyclopropanecarboxamide (500 mg, 0.9 mmol) in MeOH (8 mL) was added NaBH₄ (93 mg, 2.4 mmol) at 0° C. under nitrogen atmosphere. The mixture was warmed to room temperature and stirred for 2 hrs before being concentrated under reduced pressure. The residue was treated with water (3 mL) and extracted with EtOAc (20 mL×2). The combined organic layers were dried over anhydrous Na₂SO₄, filtered, concentrated, and purified by preparative HPLC (Gemini C18 150×25 mm×10 µm, 12-42% MeCN/H₂O) to give the desired product (33.3 mg, 13% yield) as a white solid. $^1$H NMR (400 MHz, CD₃OD) δ 6.61 (s, 1H), 4.93-4.91 (m, 1H), 4.44-3.68 (m, 5H), 2.21-2.18 (m, 1H), 2.03-1.92 (m, 1H), 1.58-1.52 (m, 1H), 1.51-1.48 (m, 3H), 0.85-0.72 (m, 4H). LCMS (ESI) m/z: 293.1 [M+H]⁺, RT=0.85 min (LCMS Method C).

Example 17

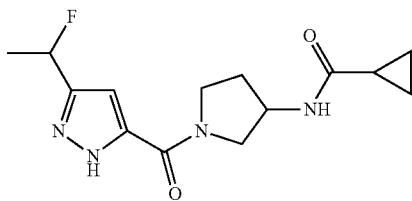 [SMILES: CC(F)c1cc(C(=O)N2CCC(NC(=O)C3CC3)C2)[nH]n1]

N-(1-(3-(1-fluoroethyl)-1H-pyrazole-5-carbonyl) pyrrolidin-3-yl)cyclopropanecarboxamide To a suspension of N-(1-(3-(1-hydroxyethyl)-1H-pyrazole-5-carbonyl)pyrrolidin-3-yl)cyclopropanecarboxamide (120 mg, 0.4 mmol) in DCM (5 mL) was added dropwise DAST (198 mg, 1 mmol) at −78° C. under a nitrogen atmosphere. After addition, the reaction was warmed to room temperature and stirred for 30 min before being quenched with saturated NaHCO₃ solution, then extracted with EtOAc (20 mL×3). The combined organic layers were dried over anhydrous Na₂SO₄, filtered, concentrated and purified by preparative HPLC (Gemini C18 150×25 mm×10 µm, 20-50% MeCN/H₂O) to give the title compound (30.8 mg, 25% yield) as a white solid. $^1$H NMR (400 MHz, CD₃OD) δ 6.78, 6.75 (2s, 1H), 5.80-5.63 (m, 1H), 4.41-4.37 (m, 1H), 4.12-3.68 (m, 4H), 2.24-2.18 (m, 1H), 2.07-1.96 (m, 1H); 1.72-1.62 (m, 3H), 1.59-1.50 (m, 1H), 0.85-0.73 (m, 4H). LCMS (ESI) m/z: 295.2 [M+H]+, RT=0.95 min (LCMS Method C).

Example 18

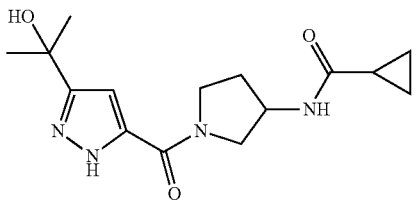 [SMILES: CC(C)(O)c1cc(C(=O)N2CCC(NC(=O)C3CC3)C2)[nH]n1]

N-(1-(3-(2-hydroxypropan-2-yl)-1H-pyrazole-5-carbonyl)pyrrolidin-3-yl)cyclopropanecarboxamide To a solution of N-[1-(3-acetyl-1H-pyrazole-5-carbonyl)pyrrolidin-3-yl]cyclopropane carboxamide (100 mg, 0.3 mmol) in THF (3 mL) was added MeMgBr (0.7 mL, 3 M in THF) at 0° C. under a nitrogen atmosphere. The mixture was warmed to room temperature and stirred for 5 hrs before being quenched with saturated NH₄Cl solution, and extracted with EtOAc (20 mL×3). The combined organic layers were dried over anhydrous Na₂SO₄, filtered, concentrated, and purified by preparative HPLC to give the desired product (8.2 mg, 8% yield) as a white solid. $^1$H NMR (400 MHz, CD₃OD) δ 6.61 (s, 1H), 4.46-4.40 (m, 1H), 4.18-3.70 (m, 3H), 2.29-2.19 (m, 1H), 2.06-1.94 (m, 1H), 1.59 (m, 7H), 0.90-0.73 (m, 4H). LCMS (ESI) m/z: 307.1 [M+H]+, RT=0.90 min (LCMS Method C).

Example 19

Step 1

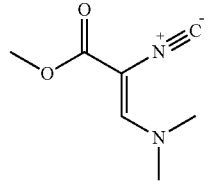

(Z)-methyl 3-(dimethylamino)-2-isocyanoacrylate

To a solution of methyl 2-isocyanoacetate (1 g, 10 mmol) in EtOH (10 mL) was added DMF-DMA (2.4 g, 20 mmol) at 0° C. under a nitrogen atmosphere and the mixture was stirred at room temperature for 24 hrs before being concentrated under reduced pressure. The residue was purified by neutral alumina column eluting with 0-20% EtOAc in hexanes to give the desired product (1 g, 64% yield) as a yellow oil.

Step 2

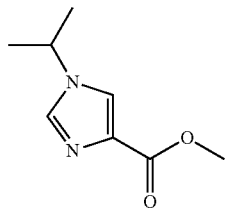

Methyl 1-isopropyl-1H-imidazole-4-carboxylate

A mixture of (Z)-methyl 3-(dimethylamino)-2-isocyano-acrylate (400 mg, 2 mmol) and isopropylamine (0.43 mL, 25 mmol) in an autoclave was stirred at 70° C. for 2 hrs. After cooling to room temperature, the reaction mixture was treated with water (3 mL) and EtOAc (20 ml×3). The combined organic layers were dried over anhydrous Na$_2$SO$_4$, filtered, concentrated to dryness to give the desired product (400 mg, 92% yield) as a yellow oil. $^1$H NMR (400 MHz, CD$_3$OD): δ 7.93 (d, J=0.8 Hz, 1H), 7.84 (s, 1H), 4.58-4.48 (m, 1H), 3.86 (s, 3H), 1.52 (d, J=6.8 Hz, 6H).

Step 3

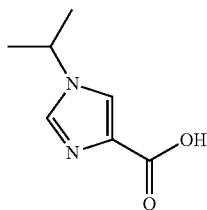

1-Isopropyl-1H-imidazole-4-carboxylic Acid

To a solution of methyl 1-isopropyl-1H-imidazole-4-carboxylate (400 mg, 2 mmol) in a mixture of MeOH (2 mL) and H$_2$O (1 mL) was added LiOH.H$_2$O (300 mg, 7 mmol). The mixture was stirred at room temperature for 2 hrs, and then concentrated under reduced pressure to dryness to give the desired crude product (750 mg) as a yellow solid.

Step 4

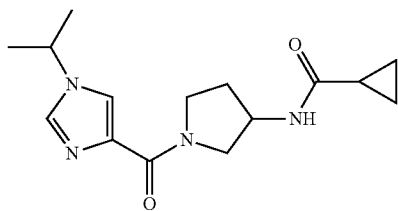 [SMILES: CC(C)n1cnc(C(=O)N2CCC(NC(=O)C3CC3)C2)c1]

N-(1-(1-isopropyl-1H-imidazole-4-carbonyl)pyrrolidin-3-yl)cyclopropanecarboxamide To a solution of 1-isopropyl-1H-imidazole-4-carboxylic acid (200 mg, 1.3 mmol) in DMF (3 mL) was added N-pyrrolidin-3-ylcyclopropanecarboxamide (260 mg, 1.7 mmol), HATU (739 mg, 2 mmol) and DIEA (0.7 mL, 4 mmol). The mixture was stirred at room temperature for 3 hrs, filtered, concentrated, and purified by preparative HPLC (Gemini 150×25 mm×10 μm, 0-30% MeCN/H$_2$O) to give the desired product (93.7 mg, 24% yield) as a white solid. $^1$H NMR (400 MHz, DMSO-d$_6$): δ 8.31-8.29 (m, 1H), 7.77-7.74 (m, 1H), 4.44-4.41 (m, 1H), 4.26-4.19 (m, 1H), 4.08-3.76 (m, 2H), 3.58-3.48 (m, 2H), 2.07-1.98 (m, 1H), 1.82-1.70 (m, 1H), 1.58-1.52 (m, 1H), 1.40-1.38 (m, 6H), 0.64-0.60 (m, 4H). LCMS (ESI) m/z: 291.1 [M+H]$^+$, RT=0.79 min (LCMS Method C).

Example 20

Step 1

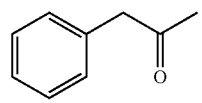

phenylpropan-2-one

Dess-Martin reagent (9.3 g, 22.0 mmol) was added into a solution of 1-phenylpropan-2-ol (2.0 g, 15 mmol) in DCM (20 mL) at room temperature. The mixture was stirred at room temperature for 12 hrs and washed with Na$_2$S$_2$O$_3$ aq. solution (20 mL), NaHCO$_3$ aq. solution (20 mL). The organic phase was dried over anhydrous Na$_2$SO$_4$ and then filtered. The filtrate was concentrated and the residue was purified by flash column chromatography on silica gel eluting with 20% EtOAc in hexanes to give the desired product (1.5 g, 76% yield) as colorless oil. $^1$H NMR (400 MHz, CDCl$_3$) δ 7.35-7.32 (m, 2H), 7.29-7.27 (m, 1H), 7.25-7.19 (m, 2H), 3.69 (s, 2H), 2.15 (s, 3H).

Step 2

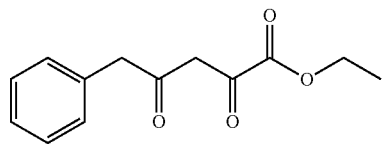 [SMILES: CCOC(=O)C(=O)CC(=O)Cc1ccccc1]

Ethyl 2,4-dioxo-5-phenylpentanoate

EtONa (8.2 mL, 8.2 mmol) in EtOH was added into a mixture of 1-phenylpropan-2-one (1.0 g, 7.5 mmol) and diethyl oxalate (1.3 g, 9.0 mmol) in EtOH (10 mL) at room temperature. The reaction mixture was stirred for 16 hrs and concentrated. The residue was dissolved in H$_2$O (10 mL), HCl (1 N) was added to adjust to pH=2.0, then extracted with DCM (15 mL×2). The organic phase was combined and dried over anhydrous Na$_2$SO$_4$. The mixture was filtered and concentrated to dryness to give the desired crude product (0.9 g, 51% yield) as yellow oil.

Step 3

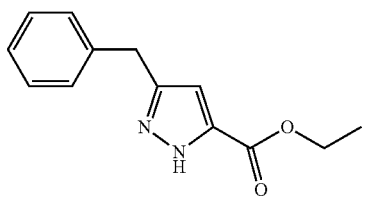 [SMILES: CCOC(=O)c1cc(Cc2ccccc2)n[nH]1]

Ethyl 3-benzyl-1H-pyrazole-5-carboxylate

A mixture of ethyl 2,4-dioxo-5-phenylpentanoate (0.9 g, 3.8 mmol), hydrazine hydrate (0.37 g, 5.8 mmol), AcOH (0.35 g, 5.8 mmol) in EtOH (10 mL) was stirred at room temperature for 12 hrs. The reaction mixture was concentrated and the residue was dissolved in DCM (10 mL) and washed with NaHCO$_3$ aqueous solution (10 mL). The organic phase was washed with brine (10 mL) and dried over anhydrous Na$_2$SO$_4$. The mixture was filtered and evaporated to dryness to give the crude product (0.5 g, 57% yield) as a yellow oil.

Step 4

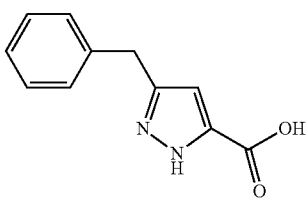 [SMILES: O=C(O)c1cc(Cc2ccccc2)n[nH]1]

3-Benzyl-1H-pyrazole-5-carboxylic Acid

LiOH (0.26 g, 11 mmol) was added into a solution of ethyl 3-benzyl-1H-pyrazole-5-carboxylate (0.5 g, 2.2 mmol) in THF/H$_2$O (5 mL/5 mL) at room temperature. The mixture was stirred for 12 hrs. To the reaction mixture was added concentrated HCl (1 N) to adjust to pH=2.0. The mixture was filtered and dried to give the desired product (0.4 g, 91% yield) as a white solid.

Step 5

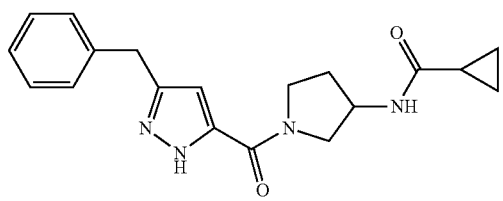 [SMILES: O=C(NC1CCN(C(=O)c2cc(Cc3ccccc3)n[nH]2)C1)C1CC1]

N-(1-(3-benzyl-1H-pyrazole-5-carbonyl) pyrrolidin-3-yl)cyclopropanecarboxamide

A mixture of 3-benzyl-1H-pyrazole-5-carboxylic acid (100 mg, 0.50 mmol), N-(pyrrolidin-3-yl) cyclopropanecarboxamide hydrochloride (94 mmg, 0.5 mmol), T$_3$P (472 mg, 0.74 mmol), Et$_3$N (200 mg, 2.0 mmol) in DMF (5 mL) was stirred at room temperature for 2 hrs. The reaction mixture was purified by preparative HPLC to give the desired product (39 mg, 23% yield) as a white solid. $^1$H NMR (400 MHz, DMSO-d$_6$) δ 13.07 (2s, 1H), 8.33, 8.31 (2s, 1H), 7.38-7.16 (m, 5H), 6.38, 6.37 (2s, 1H), 4.30-4.20 (m, 1H), 4.03-3.89 (m, 3H), 3.75-3.45 (m, 3H), 2.04-1.99 (m, 1H), 1.87-1.72 (m, 1H), 1.55-1.45 (m, 1H), 0.75-0.54 (m, 4H). LCMS (ESI) m/z: 339.1 [M+H]+, RT=1.149 min. (Method C).

Example 21

Step 1

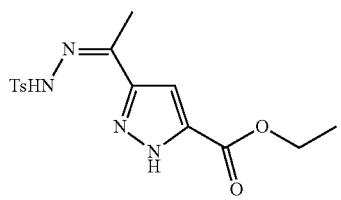

(2)-Ethyl 3-(1-(2-tosylhydrazono)ethyl)-1H-pyrazole-5-carboxylate

A mixture of methyl 5-acetyl-1H-pyrazole-3-carboxylate (500 mg, 3 mmol) and 4-methylbenzenesulfonohydrazide (554 mg, 3 mmol) in MeOH (5 mL) was heated at 60° C. for 1 hr. Then the reaction mixture was cooled to room temperature, filtered to give the desired product (800 mg, 80% yield) as a white solid. $^1$HNMR (400 MHz, DMSO-d$_6$) δ 13.68 (s, 1H), 10.61, 10.54 (2s, 1H), 7.93-7.91 (m, 1H), 7.80-7.78 (m, 1H), 7.41-7.37 (m, 2H), 6.98, 6.82 (2s, 1H), 4.33-4.25 (m, 2H), 2.38, 2.36 (2s, 3H), 2.17-2.13 (m, 3H), 1.32-1.26 (m, 2H).

Step 2

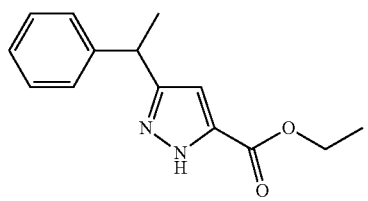 [SMILES: CCOC(=O)c1cc(C(C)c2ccccc2)n[nH]1]

Ethyl 3-(1-phenylethyl)-1H-pyrazole-5-carboxylate

To a solution of (Z)-ethyl 3-(1-(2-tosylhydrazono)ethyl)-1H-pyrazole-5-carboxylate (300 mg, 0.9 mmol) in 1,4-dioxane (5 mL) was added phenylboronic acid (163 mg, 1.3 mmol) and K$_2$CO$_3$ (370 mg, 2.7 mmol) and the mixture was heated at 110° C. for 5 hrs. After cooling to room temperature, the reaction mixture was concentrated and the residue was partitioned with water (5 mL) and EtOAc (20 mL×3). The combined organic layers were dried over anhydrous Na$_2$SO$_4$, filtered, concentrated, and purified by silica gel column chromatography eluting with 0-5% MeOH in DCM to give the desired product (250 mg, 43% yield) as a white solid. LCMS (ESI) m/z: 244.9 [M+H]+.

Step 3

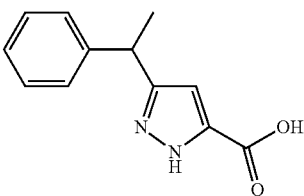 [SMILES: CC(c1ccccc1)c1cc(C(=O)O)[nH]n1]

3-(1-phenylethyl)-1H-pyrazole-5-carboxylic Acid

To a solution of ethyl 3-(1-phenylethyl)-1H-pyrazole-5-carboxylate (250 mg, 1 mmol) in a mixture of MeOH (1 mL) and H$_2$O (1 mL) was added LiOH H$_2$O (137 mg, 3 mmol). The mixture was stirred at room temperature for 2 hrs, then was concentrated under reduced pressure to dryness to give the crude desired product (300 mg) as a white solid. LCMS (ESI) m/z: 217.2 [M+H]+.

Step 4

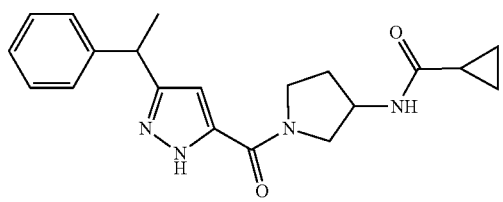 [SMILES: CC(c1ccccc1)c1cc(C(=O)N2CCC(NC(=O)C3CC3)C2)[nH]n1]

N-(1-(3-(1-phenylethyl)-1H-pyrazole-5-carbonyl) pyrrolidin-3-yl)cyclopropanecarboxamide To a solution of 3-(1-phenylethyl)-1H-pyrazole-5-carboxylic acid (300 mg, 1.4 mmol) in DMF (3 mL) was added N-pyrrolidin-3-ylcyclopropanecarboxamide (214 mg, 1.4 mmol), HATU (527 mg, 1.4 mmol) and DIEA (0.7 mL, 4.2 mmol). The mixture was stirred at room temperature for 3 hrs before being purified by preparative HPLC (Gemini C18 150×25 mm×10 um, 22-52% MeCN/H$_2$O) to give the title compound (35.7 mg, 7% yield) as a white solid. $^1$H NMR (400 MHz, DMSO-d$_6$): δ 8.31, 8.29 (2s, 1H), 7.29-7.15 (m, 5H), 6.44, 6.42 (2s, 1H), 4.26-4.15 (m, 2H), 3.98-3.81 (m, 2H), 3.63-3.48 (m, 2H), 2.10-1.94 (m, 1H); 1.83-1.70 (m, 1H), 1.54 (d, J=7.2 Hz, 3H), 1.48-1.41 (m, 1H), 0.69-0.59 (m, 4H). LCMS (ESI) m/z: 353.2 [M+H]+, RT=1.16 min (LCMS Method C).

Example 22

Step 1

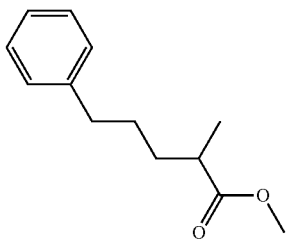

Methyl 2-methyl-5-phenylpentanoate

To a stirred solution of methyl 5-phenylpentanoate (10 g, 52.02 mmol) in THF (100 mL) was added LDA (28.7 mL, 57.32 mmol) dropwise in an ice bath. After stirring at this temperature for 30 min, MeI (8.74 mL, 140.44 mmol) was added. The reaction mixture was stirred at 20° C. for 12 hrs. The reaction was quenched with sat NH$_4$Cl (100 mL), washed with EtOAc (100 mL×2). The combined organic layers were dried over anhydrous Na$_2$SO$_4$, filtered and concentrated to give the desired product (9.6 g, 90% yield) as a yellow oil. $^1$H NMR (400 MHz, CDCl$_3$) δ: 7.28-7.15 (m, 5H), 3.65 (s, 3H), 2.62-2.58 (m, 2H), 2.48-2.43 (m, 1H), 1.67-1.47 (m, 4H), 1.13 (d, J=7.2 Hz, 3H).

Step 2

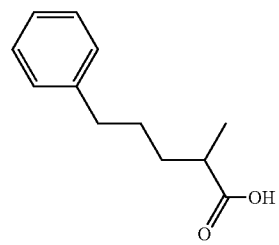

2-Methyl-5-phenylpentanoic Acid

A mixture of methyl 2-methyl-5-phenyl-pentanoate (9.6 g, 46.54 mmol) and LiOH (3.34 g, 139.62 mmol) in methanol (70 mL) and water (70 mL) was stirred at room temperature for 12 hrs. The organic solvent was removed, the mixture was diluted in water (30 mL), washed with EtOAc (100 mL). The aqueous layer was acidified by 2 N HCl to pH 6.0. The mixture was extracted EtOAc (100 mL×2). Combined organic layers were dried over anhydrous Na$_2$SO$_4$, filtered and concentrated to give the desired product (8.5 g, 95% yield) as a colorless oil. $^1$H NMR (400 MHz, CDCl$_3$) δ: 7.30-7.17 (m, 5H), 2.64-2.61 (m, 2H), 2.52-2.46 (m, 1H), 1.75-1.65 (m, 3H), 1.50-1.48 (m, 1H), 1.18 (d, J=7.2 Hz, 3H)

Step 3

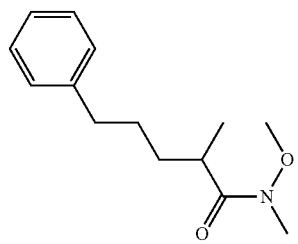 [SMILES: CON(C)C(=O)C(C)CCCc1ccccc1]

N-methoxy-N,2-dimethyl-5-phenylpentanamide

A mixture of 2-methyl-5-phenyl-pentanoic acid (8.5 g, 44.21 mmol), N,O-dimethyl hydroxyamine hydrochloride (5.18 g, 53.06 mmol), HATU (20.16 g, 53.06 mmol) and DIEA (17.11 g, 132.64 mmol) in DCM (85 mL) was stirred at room temperature for 2 hrs. The reaction mixture was diluted in DCM (50 mL), washed with 1 N HCl (150 mL), sat NaHCO$_3$ (150 mL) and brine (150 mL). The organic layer was dried over anhydrous Na$_2$SO$_4$, filtered and concentrated. The crude residue was purified by silica gel column chromatography (petroleum ether/EtOAc=30/1) to give the desired product (7.8 g, 75% yield) as colorless oil. ¹H NMR (400 MHz, CDCl₃) δ 7.30-7.16 (m, 5H), 3.66 (s, 3H), 3.18 (s, 3H), 2.90-2.88 (m, 1H), 2.65-2.56 (m, 2H), 1.77-1.73 (m, 1H), 1.64-1.58 (m, 2H), 1.45-1.41 (m, 1H), 1.11 (d, J=6.8 Hz, 3H)

Step 4

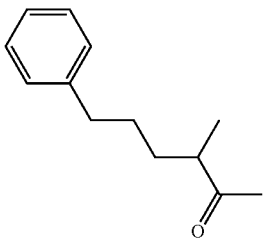

3-Methyl-6-phenylhexan-2-one

To a stirred solution of N-methoxy-N,2-dimethyl-5-phenyl-pentanamide (4 g, 17 mmol) in THF (40 mL) was added MeMgBr (6.8 mL, 20.4 mmol) in an ice bath. The reaction was stirred at room temperature for 2 hrs. The reaction was quenched with sat NH₄Cl (50 mL), washed with EtOAc (50 mL×2). The combined organic layers were dried over anhydrous Na₂SO₄, filtered and concentrated to give the desired product (2.9 g, 90% yield) as a light yellow oil. ¹H NMR (400 MHz, CDCl₃) δ: 7.28-7.14 (m, 5H), 2.62-2.57 (m, 2H), 2.52-2.50 (m, 1H), 2.09 (s, 3H), 1.60-1.57 (m, 3H), 1.40-1.38 (m, 1H), 1.06 (d, J=6.8 Hz, 3H).

Step 5

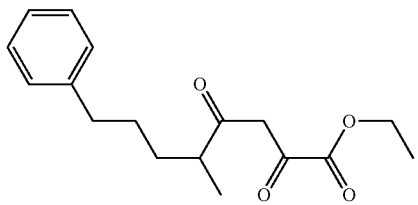 [SMILES: CCOC(=O)C(=O)CC(=O)C(C)CCCc1ccccc1]

Ethyl 5-methyl-2,4-dioxo-8-phenyloctanoate

To a stirred solution of 3-methyl-6-phenylhexan-2-one (2.9 g, 15.24 mmol) in ethanol (50 mL) was added NaOEt (1.14 g, 16.76 mmol). After stirring at room temperature for 30 min, diethyl oxalate (2.28 mL, 16.76 mmol) was added and then stirred at room temperature for 4 hrs. The solvent was removed, the mixture was partitioned with water (40 mL) and EtOAc (40 mL×2). The combined organic layers were dried over anhydrous Na₂SO₄, filtered and concentrated. The crude residue was purified by silica gel column chromatography (petroleum ether/EtOAc=20/1) to give the desired product (2.1 g, 47% yield) as yellow oil.

Step 6

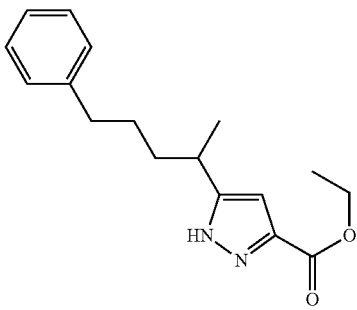 [SMILES: CCOC(=O)c1cc(C(C)CCCc2ccccc2)[nH]n1]

Ethyl 5-(5-phenylpentan-2-yl)-1H-pyrazole-3-carboxylate

A mixture of ethyl 5-methyl-2,4-dioxo-8-phenyl-octanoate (2.1 g, 7.23 mmol) and hydrazine monohydrate (0.51 mL, 8.68 mmol) in ethanol (30 mL) was stirred at room temperature for 2 hrs. The solvent was removed, the crude residue was purified by silica gel column chromatography (petroleum ether/EtOAc=5/1) to give the desired product (0.6 g, 29% yield) as a yellow oil.

Step 7

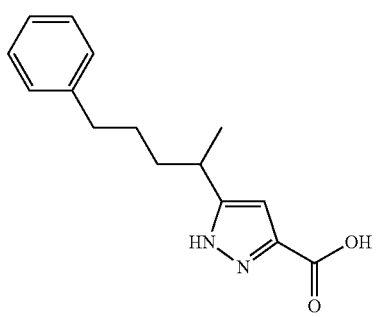 [SMILES: CC(CCCc1ccccc1)c1cc(C(=O)O)n[nH]1]

5-(5-phenylpentan-2-yl)-1H-pyrazole-3-carboxylic Acid

A mixture of ethyl 5-(1-methyl-4-phenyl-butyl)-1H-pyrazole-3-carboxylate (600 mg, 2.1 mmol) and LiOH (251 mg, 10.48 mmol) in methanol (6 mL) and water (6 mL) was stirred at room temperature for 3 hrs. The organic solvent was removed, the mixture was diluted in water (40 mL), washed with EtOAc (40 mL×2). The aqueous layer was acidified by 2 N HCl to pH=5.0. The mixture was washed with EtOAc (40 mL×2). The combined layers were dried over anhydrous Na₂SO₄, filtered and concentrated to give the crude desired product (400 mg, 74% yield) as a yellow solid. LCMS M/Z (M+H)=258.9.

Step 8

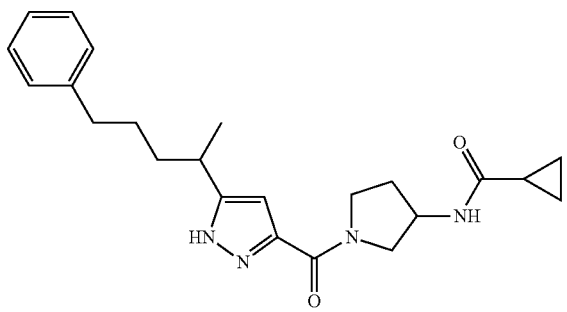 [SMILES: CC(CCCc1ccccc1)c1cc(C(=O)N2CCC(NC(=O)C3CC3)C2)n[nH]1]

N-(1-(5-(5-phenylpentan-2-yl)-1H-pyrazole-3-carbonyl)pyrrolidin-3-yl) cyclopropanecarboxamide A mixture of 5-(1-methyl-4-phenyl-butyl)-1H-pyrazole-3-carboxylic acid (150 mg, 0.58 mmol), N-pyrrolidin-3-ylcyclopropanecarboxamide hydrochloride (133 mg, 0.70 mmol), HATU (265 mg, 0.70 mmol) and DIEA (225 mg, 1.74 mmol) in DMF (3 mL) was stirred at room temperature for 12 hrs. The reaction mixture was diluted in water (20 mL), and extracted with EtOAc (20 mL×2). Combined organic layers were dried over anhydrous $Na_2SO_4$, filtered and concentrated. The crude residue was purified by preparative HPLC to give the desired product (25 mg, 11% yield) as a white solid. $^1$H NMR (400 MHz, DMSO-$d_6$) δ 7.23-7.09 (m, 5H), 6.43 (s, 1H), 4.39-4.37 (m, 1H), 4.08-3.68 (m, 4H), 2.91-2.89 (m, 1H), 2.59-2.55 (m, 2H), 2.20-2.18 (m, 1H), 1.95-1.93 (m, 1H), 1.62-1.56 (m, 5H), 1.24 (d, J=7.2 Hz, 3H), 0.84-0.71 (m, 4H). LCMS (ESI), M/Z (M+H)=395.0, RT=0.722 min (LCMS method E).

Example 23

Step 1

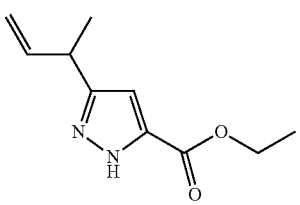

Ethyl 3-(but-3-en-2-yl)-1H-pyrazole-5-carboxylate

To a solution of ethyl 3-(1-(2-tosylhydrazono)ethyl)-1H-pyrazole-5-carboxylate (1.0 g, 2.85 mmol) and vinylboronic anhydride pyridine complex (1.03 g, 4.28 mmol) in dioxane (10 mL) was added $K_2CO_3$ (1.18 g, 8.56 mmol). The resulting mixture was heated at 110° C. for 16 hrs. After cooling to room temperature, the reaction mixture was filtered and concentrated. The residue was purified by flash column chromatography on silica gel (eluting with 0-2% MeOH in DCM) to give the crude title compound (400 mg) as a yellow oil. LCMS (ESI) m/z: 194.9 [M+H]$^+$.

Step 2

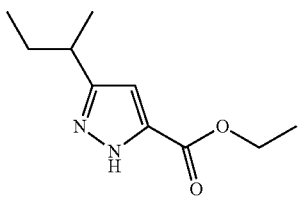

Ethyl 3-(sec-butyl)-1H-pyrazole-5-carboxylate

To a solution of ethyl 3-(but-3-en-2-yl)-1H-pyrazole-5-carboxylate (400 mg crude, 2.06 mmol) in MeOH (10 mL) was added Pd/C (10% wt., 100 mg). The mixture was stirred under $H_2$ (15 psi) at room temperature for 4 hrs. The mixture was filtered and concentrated to give desired crude product (370 mg) as a pale yellow oil. $^1$H NMR (400 MHz, CD$_3$OD): δ 6.55 (s, 1H), 4.34 (q, J=6.8 Hz, 2H), 2.83-2.79 (m, 1H), 1.69-1.61 (m, 2H), 1.37 (t, J=6.8 Hz, 3H), 1.28 (d, J=6.8 Hz, 3H), 0.87 (t, J=6.8 Hz, 3H).

Step 3

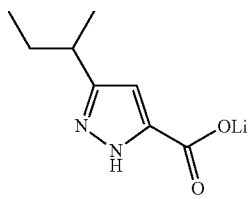

Lithium 3-(sec-butyl)-1H-pyrazole-5-carboxylate

To a solution of ethyl 3-(sec-butyl)-1H-pyrazole-5-carboxylate (100 mg, 0.51 mmol) in MeOH (2 mL) and H$_2$O (1 mL) was added lithium hydroxide monohydrate (64 mg, 1.53 mmol). The resulting mixture was stirred at room temperature for 2 hrs and concentrated to give the crude title compound (150 mg) as a white solid. LCMS (ESI) m/z: 169.1 [M-Li+H]$^+$.

Step 4

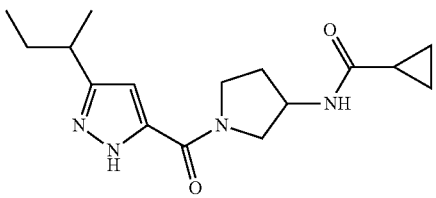 [SMILES: CCC(C)c1cc(C(=O)N2CCC(NC(=O)C3CC3)C2)[nH]n1]

N-(1-(3-(sec-butyl)-1H-pyrazole-5-carbonyl)pyrrolidin-3-yl)cyclopropanecarboxamide To a solution of lithium 3-(sec-butyl)-1H-pyrazole-5-carboxylate (150 mg crude, 0.51 mmol) and N-(pyrrolidin-3-yl)cyclopropanecarboxamide hydrochloride (97 mg, 0.51 mmol) in DMF (2 mL) was added HATU (290 mg, 0.77 mmol) and DIPEA (198 mg, 1.53 mmol). The mixture was stirred at room temperature for 16 hrs. The mixture was purified by preparative HPLC to give the title compound (26 mg, 17% yield) as a white solid. $^1$H NMR (400 MHz, DMSO-d₆) δ 8.35, 8.33 (s, 1H total), 6.41, 6.39 (s, 1H total), 4.26-4.24 (m, 1H), 3.99-3.93 (m, 2H), 3.67-3.35 (m, 2H), 2.78-2.72 (m, 1H), 2.04-2.01 (m, 1H), 1.78-1.73 (m, 1H), 1.60-1.53 (m, 3H), 1.20 (d, J=6.8 Hz, 3H), 0.80 (t, J=7.2 Hz, 3H), 0.68-0.62 (m, 4H). LCMS (ESI) m/z: 305.0 [M+H]⁺, Rt=1.081 min (LCMS Method C), Example 24

Step 1

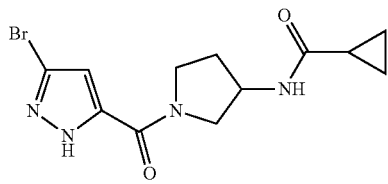 [SMILES: O=C(NC1CCN(C(=O)c2cc(Br)n[nH]2)C1)C1CC1]

N-(1-(3-bromo-1H-pyrazole-5-carbonyl)pyrrolidin-3-yl)cyclopropanecarboxamide

To a solution of 3-bromo-1H-pyrazole-5-carboxylic acid (1.0 g, 5.24 mmol) and N-(pyrrolidin-3-yl)cyclopropanecarboxamide hydrochloride (1.0 g, 5.24 mmol) in DMF (20 mL) was added HATU (2.39 g, 6.29 mmol) and DIPEA (2.03 g, 15.72 mmol). The mixture was stirred at room temperature for 16 hrs and concentrated. The residue was dissolved in EtOAc (50 mL) and washed with H₂O (10 mL). The organic phase was dried over anhydrous Na₂SO₄, filtered and concentrated. The residue was purified by flash column chromatography on silica gel (0-3% MeOH in DCM) to give the desired product (900 mg, 53% yield) as a white solid. ¹H NMR (400 MHz, DMSO-d₆) δ 13.87 (s, 1H), 8.36 (s, 1H), 6.89, 6.84 (2s, 1H), 4.31-4.26 (m, 1H), 3.89-3.34 (m, 4H), 2.06-2.01 (m, 1H), 1.89-1.72 (m, 1H), 1.53-1.50 (m, 1H), 0.67-0.64 (m, 4H). LCMS (ESI) m/z: 329.0 [M+H]⁺, RT=1.007 min (LCMS Method C).

Step 2

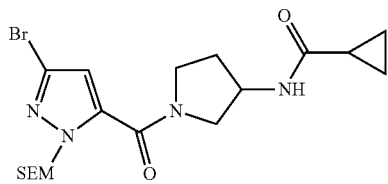 [SMILES: C[Si](C)(C)CCOCn1nc(Br)cc1C(=O)N1CCC(NC(=O)C2CC2)C1]

N-(1-(3-bromo-1-((2-(trimethylsilyl)ethoxy)methyl)-1H-pyrazole-5-carbonyl)pyrrolidin-3-yl)cyclopropanecarboxamide To a solution of N-(1-(3-bromo-1H-pyrazole-5-carbonyl)pyrrolidin-3-yl)cyclopropane carboxamide (500 mg, 1.53 mmol) in DMF (5 mL) was added NaH (60% in mineral oil, 153 mg, 3.82 mmol) portionwise at 0° C. under a nitrogen atmosphere. After stirring at 0° C. for 15 min, a solution of (2-(chloromethoxy)ethyl)trimethylsilane (280 mg, 1.68 mmol) in DMF (2 mL) was added dropwise. After addition, the resulting mixture was stirred at room temperature for 16 hrs. The reaction was quenched with saturated NH₄Cl (20 mL) and extracted with EtOAc (20 mL). The organic phase was dried over anhydrous Na₂SO₄, filtered and concentrated. The residue was purified by flash column chromatography on silica gel (eluting with 0-50% EtOAc in hexanes) to give the desired product (450 mg, 64% yield) as a colorless oil. LCMS (ESI) m/z: 457.1 [M+H]⁺.

Step 3

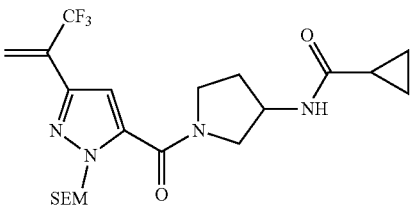 [SMILES: C=C(c1cc(C(=O)N2CCC(NC(=O)C3CC3)C2)n(COCC[Si](C)(C)C)n1)C(F)(F)F]

N-(1-(3-(3,3,3-trifluoroprop-1-en-2-yl)-1-((2-(trimethylsilyl)ethoxy)methyl)-1H-pyrazole-5-carbonyl)pyrrolidin-3-yl)cyclopropanecarboxamide To a solution of N-(1-(3-bromo-1-((2-(trimethylsilyl)ethoxy)methyl)-1H-pyrazole-5-carbonyl)pyrrolidin-3-yl)cyclopropanecarboxamide (300 mg, 0.656 mmol) and 4,4,6-trimethyl-2-(3,3,3-trifluoroprop-1-en-2-yl)-1,3,2-dioxaborinane (291 mg, 1.31 mmol) in dioxane (6 mL) and H₂O (3 mL) was added Cs₂CO₃ (642 mg, 1.97 mmol) and Pd(PPh₃)₄ (76 mg, 0.066 mmol). The resulting mixture was purged with N₂ for 1 min and then heated at 110° C. for 30 min in a microwave reactor. The reaction mixture was cooled to room temperature, extracted with EtOAc (10 mL). The organic phase was dried over anhydrous Na₂SO₄, filtered and concentrated. The residue was purified by flash column chromatography on silica gel (eluting with 0-50% EtOAc in hexanes) to give the desired product (180 mg, 62% yield) as a colorless oil. LCMS (ESI) m/z: 473.2 [M+H]⁺.

Step 4

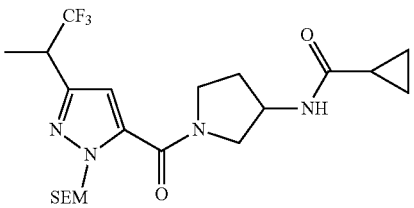 [SMILES: CC(c1cc(C(=O)N2CCC(NC(=O)C3CC3)C2)n(COCC[Si](C)(C)C)n1)C(F)(F)F]

N-(1-(3-(1,1,1-trifluoropropan-2-yl)-1-((2-(trimethylsilyl)ethoxy)methyl)-1H-pyrazole-5-carbonyl)pyrrolidin-3-yl)cyclopropanecarboxamide To a solution of N-(1-(3-(3,3,3-trifluoroprop-1-en-2-yl)-1-((2-(trimethylsilyl)ethoxy)methyl)-1H-pyrazole-5-carbonyl)pyrrolidin-3-yl)cyclopropanecarboxamide (150 mg, 0.317 mmol) in MeOH (5 mL) was added Pd/C (10% wt., 50 mg). The resulting mixture was stirred at room temperature under H₂ for 2 hrs. The reaction mixture was filtered and concentrated to give the crude desired product (150 mg) as colorless oil. LCMS (ESI) m/z: 475.2 [M+H]⁺.

Step 5

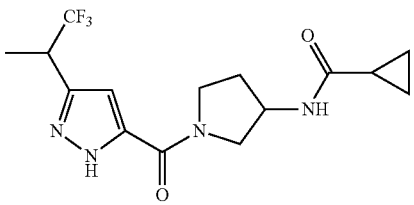 [SMILES: CC(c1cc(C(=O)N2CCC(NC(=O)C3CC3)C2)[nH]n1)C(F)(F)F]

N-(1-(3-(1,1,1-trifluoropropan-2-yl)-1H-pyrazole-5-carbonyl)pyrrolidin-3-yl) cyclopropanecarboxamide To a solution of N-(1-(3-(1,1,1-trifluoropropan-2-yl)-1-((2-(trimethylsilyl)ethoxy)methyl)-1H-pyrazole-5-carbonyl)pyrrolidin-3-yl)cyclopropanecarboxamide (150 mg, 0.316 mmol) in DCM (3 mL) was added TFA (1.5 mL) dropwise. The resulting mixture was stirred at room temperature for 2 hrs. The reaction mixture was concentrated and the residue was dissolved in EtOAc (10 mL) and adjusted the pH=8~9 using saturated NaHCO$_3$ (1 mL). The mixture was dried over anhydrous Na$_2$SO$_4$, filtered and concentrated. The residue was purified by preparative HPLC to give the desired product (26 mg, 24% yield) as a white solid. $^1$H NMR (400 MHz, CD$_3$OD) δ 6.76, 6.72 (s, 1H total), 4.46-4.40 (m, 1H), 4.35-3.58 (m, 5H), 2.29-1.96 (m, 2H), 1.65-1.52 (m, 4H), 0.89-0.75 (m, 4H). LCMS (ESI) m/z: 345.1[M+H]$^+$, RT=1.070 min (LCMS Method C).

Example 25

Step 1

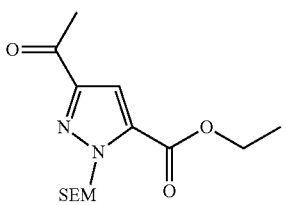 [SMILES: CCOC(=O)c1cc(C(C)=O)nn1COCC[Si](C)(C)C]

Ethyl 3-acetyl-1-((2-(trimethylsilyl)ethoxy)methyl)-1H-pyrazole-5-carboxylate

To a stirred solution of ethyl 3-acetyl-1H-pyrazole-5-carboxylate (7.5 g, 41.17 mmol) in DMF (75 mL) was added NaH (1.98 g, 49.4 mmol) in an ice bath. After stirred at this temperature for 30 min, the reaction was added SEMCl (8.24 g, 49.4 mmol) dropwise. The reaction mixture was stirred at room temperature for 12 hrs. The mixture was diluted in EtOAc (100 mL), washed with brine (100 mL×3). The organic layer was dried over anhydrous Na$_2$SO$_4$, filtered and concentrated. The residue was purified by silica gel flash column chromatography (petroleum ether:EtOAc=50:1) to give the desired product (4.8 g, 37% yield) as a colorless oil. $^1$H NMR (400 MHz, CDCl$_3$) δ 7.37 (s, 1H), 5.90 (s, 2H), 4.40-4.35 (m, 2H), 3.63 (t, J=8.0 Hz, 2H), 2.61 (s, 3H), 1.38 (t, J=6.8 Hz, 3H), 0.91 (t, J=8.0 Hz, 2H), 0.03 (s, 9H).

Step 2

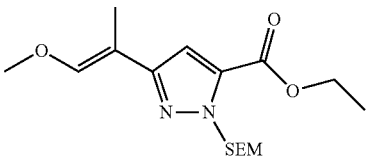 [SMILES: CCOC(=O)c1cc(/C(C)=C/OC)nn1COCC[Si](C)(C)C]

(E)-ethyl 3-(1-methoxyprop-1-en-2-yl)-1-((2-(trimethylsilyl)ethoxy)methyl)-1H-pyrazole-5-carboxylate A mixture of methoxy methyl(triphenyl)phosphonium chloride (15.8 g, 46.09 mmol) and t-BuOK (5.17 g, 46.09 mmol) in THF (90 mL) was stirred at 20° C. for 30 min. To the mixture was added ethyl 5-acetyl-2-(2-trimethylsilylethoxymethyl)pyrazole-3-carboxylate (4.8 g, 15.36 mmol) in an ice bath under N$_2$ atmosphere. The mixture was stirred at 20° C. for 12 hrs. The reaction was quenched by sat NH$_4$Cl (100 mL), and extracted with EtOAc (100 mL×2). The combined organic layers were dried over anhydrous Na$_2$SO$_4$, filtered and concentrated. The crude residue was purified by silica gel flash column chromatography (petroleum ether:EtOAc=50:1) to give the desired product (1 g, 19% yield) as a colorless oil. LCMS (ESI) M/Z (M+H)=340.9.

Step 3

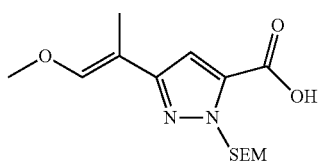 [SMILES: CO/C=C(\C)c1cc(C(=O)O)n(COCC[Si](C)(C)C)n1]

(E)-3-(1-methoxyprop-1-en-2-yl)-1-((2-(trimethylsilyl)ethoxy)methyl)-1H-pyrazole-5-carboxylic Acid A mixture of ethyl 5-[(E)-2-methoxy-1-methyl-vinyl]-2-(2-trimethylsilylethoxymethyl) pyrazole-3-carboxylate (300 mg, 0.88 mmol) and TBAF (1.15 g, 4.41 mmol) in THF (6 mL) was stirred at 20° C. for 12 hrs. The mixture was diluted in EtOAc (30 mL), washed with brine (30 mL×3). The organic layer was dried over anhydrous Na$_2$SO$_4$, filtered and concentrated to give the desired product (200 mg, 73% yield) as a yellow oil. LCMS M/Z (M+11)=312.9.

Step 4

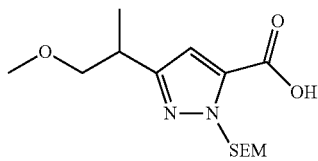 [SMILES: COCC(C)c1cc(C(=O)O)n(COCC[Si](C)(C)C)n1]

3-(1-Methoxypropan-2-yl)-1-((2-(trimethylsilyl)ethoxy)methyl)-1H-pyrazole-5-carboxylic Acid A mixture of 5-[(E)-2-methoxy-1-methyl-vinyl]-2-(2-trimethylsilylethoxymethyl)pyrazole-3-carboxylic acid (200 mg, 0.64 mmol) and Pd/C (100 mg) in ethyl acetate (4 mL)

was stirred at room temperature for 12 hrs, under 1 atm of H$_2$. The reaction mixture was filtered over a short of Celite pad. The filtrate was concentrated to give the crude desired product (200 mg, 99% yield) as a yellow solid. LCMS M/Z (M+H)=314.9.

Step 5

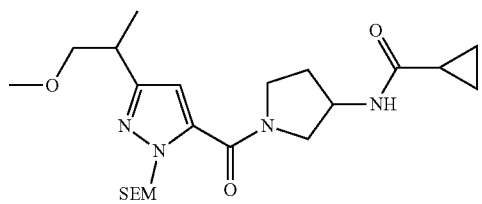 [SMILES: COCC(C)c1cc(C(=O)N2CCC(NC(=O)C3CC3)C2)n(COCC[Si](C)(C)C)n1]

N-(1-(3-(1-methoxypropan-2-yl)-1-((2-(trimethylsilyl)ethoxy)methyl)-1H-pyrazole-5-carbonyl)pyrrolidin-3-yl)cyclopropanecarboxamide A mixture of 5-(2-methoxy-1-methyl-ethyl)-2-(2-trimethylsilylethoxymethyl)pyrazole-3-carboxylic acid (200 mg, 0.64 mmol), N-pyrrolidin-3-ylcyclopropanecarboxamide hydrochloride (146 mg, 0.76 mmol), HATU (290 mg, 0.76 mmol) and DIEA (246 mg, 1.91 mmol) in DMF (5 mL) was stirred at room temperature for 12 hrs. The mixture was diluted in EtOAc (30 mL), washed with brine (30 mL×2). The organic layer was dried over anhydrous Na$_2$SO$_4$, filtered and concentrated. The crude residue was purified by preparative TLC (DCM:MeOH=20:1) to give the desired product (200 mg, 70% yield) as a yellow solid. LCMS M/Z (M+Na)=473.0.

Step 6

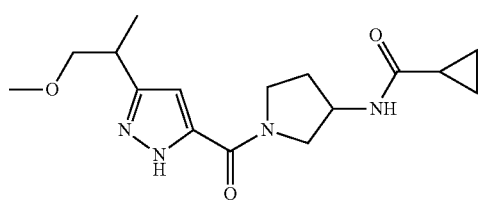 [SMILES: COCC(C)c1cc(C(=O)N2CCC(NC(=O)C3CC3)C2)[nH]n1]

N-(1-(3-(1-methoxypropan-2-yl)-1H-pyrazole-5-carbonyl)pyrrolidin-3-yl) cyclopropanecarboxamide A solution of N-[1-[5-(2-methoxy-1-methyl-ethyl)-2-(2-trimethylsilylethoxymethyl) pyrazole-3-carbonyl]pyrrolidin-3-yl]cyclopropanecarboxamide (350 mg, 0.78 mmol) in DCM (4 mL) and TFA (4 mL) was stirred at room temperature for 2 hrs. The solvent was removed, the crude residue was purified by preparative HPLC to give the desired product (38 mg, 15% yield) as a white solid. $^1$H NMR (400 MHz, DMSO-d$_6$) δ 6.54 (s, 1H), 4.41-4.39 (m, 1H), 4.14-3.82 (m, 4H), 3.39 (d, J=6.4 Hz, 2H), 3.34 (s, 3H), 3.17-3.15 (m, 1H), 2.20-1.98 (m, 1H), 1.97-1.95 (m, 1H), 1.60-1.58 (m, 1H), 1.30 (d, J=7.2 Hz, 3H), 0.87-0.73 (m, 4H). LCMS (ESI) M/Z (M+H)=321.2, RT=0.656 min (LCMS method E).

Example 26

Step 1

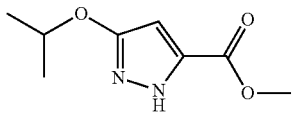

Methyl 3-isopropoxy-1H-pyrazole-5-carboxylate

To a mixture of methyl 3-hydroxy-1H-pyrazole-5-carboxylate (300 mg, 2.11 mmol) and K$_2$CO$_3$ (438 mg, 3.17 mmol) in DMF (3 mL) was added 2-iodopropane (431 mg, 2.53 mmol). The resulting mixture was stirred at room temperature for 16 hrs. The reaction was quenched with water and the mixture was extracted with EtOAc (30 mL×3). The combined organic layers were washed with water and brine, dried over anhydrous Na$_2$SO$_4$, filtered and concentrated. The residue was purified by flash column chromatograph on silica gel eluting with 0-10% EtOAc in hexanes to give the desired product (100 mg, 26% yield) as a light yellow solid. $^1$H NMR (400 MHz, CDCl$_3$) δ 6.19 (s, 1H), 4.78-4.69 (m, 1H), 3.90 (s, 3H), 1.35 (d, J=6.0 Hz, 6H).

Step 2

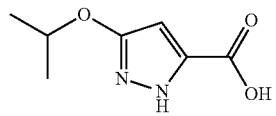

3-Isopropoxy-1H-pyrazole-5-carboxylic Acid

To a solution of methyl 3-isopropoxy-1H-pyrazole-5-carboxylate (100 mg, 0.543 mmol) in MeOH/H$_2$O (3/2, 3 mL) was added LiOH.H$_2$O (91 mg, 2.17 mmol). The resulting mixture was stirred at room temperature for 16 hrs. After removal of MeOH under reduced pressure, the mixture was acidized with 3 N HCl to pH=1.0 and then extracted with EtOAc (50 mL). The organic layer was washed with brine, dried over anhydrous Na$_2$SO$_4$, filtered and concentrated to give the desired product (80 mg, 87% yield) as a light yellow solid.

Step 3

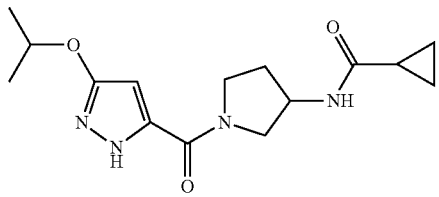 [SMILES: CC(C)Oc1cc(C(=O)N2CCC(NC(=O)C3CC3)C2)[nH]n1]

N-(1-(3-isopropoxy-1H-pyrazole-5-carbonyl)pyrrolidin-3-yl)cyclopropanecarboxamide To a solution of 3-isopropoxy-1H-pyrazole-5-carboxylic acid (70 mg, 0.411 mmol) in DMF (1.5 mL) were added HATU (235 mg, 0.617 mmol) and DIEA (0.27 mL, 1.65 mmol). After the mixture stirred for 5 min, N-(pyrrolidin-3-yl)cyclopropanecarboxamide hydrochloride (78 mg, 0.411 mmol) was added. The resulting mixture was stirred at room temperature for 16 hrs. Filtered, the mixture was purified by preparative HPLC (Gemini C18, 150×25 mm×10 μm, 14-44% MeCN/H₂O) to give the desired product (35 mg, 28% yield) as a white solid. ¹H NMR (400 MHz, CD₃OD) δ 6.14, 6.09 (2s, 1H), 4.66-4.62 (m, 1H), 4.44-4.40 (m, 1H), 4.05-3.50 (m, 4H), 2.28-2.12 (m, 1H), 2.10-1.90 (m, 1H), 1.33 (d, J=6.0 Hz, 6H), 0.87-0.84 (m, 2H), 0.77-0.74 (m, 2H). LCMS (ESI) m/z: 307.2 [M+H]⁺, RT=1.036 min (LCMS method C).

Example 27

Step 1

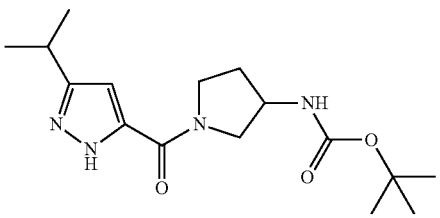 [SMILES: CC(C)c1cc(C(=O)N2CCC(NC(=O)OC(C)(C)C)C2)[nH]n1]

tert-Butyl (1-(3-isopropyl-1H-pyrazole-5-carbonyl)pyrrolidin-3-yl)carbamate

To a solution of tert-butyl N-pyrrolidin-3-ylcarbamate (1 g, 5.4 mmol) in DMF (15 ml) was added 3-isopropyl-1H-pyrazole-5-carboxylic acid (0.9 g, 5.9 mmol), DIEA (1.9 ml, 10.7 mmol) and HATU (2.6 g, 7.0 mmol). The mixture was stirred at room temperature for 15 hrs, then diluted with H₂O (20 ml), and extracted with EtOAc (60 ml×2). The combined organic layers were dried over anhydrous Na₂SO₄, filtered, concentrated and the residue was purified by silica gel flash chromatography eluted with 0-10% MeOH in DCM to give the desired product (1.3 g, 75% yield) as a white solid. LCMS (ESI) m/z: 323.0 [M+H]⁺, RT=1.11 min (LCMS Method A).

Step 2

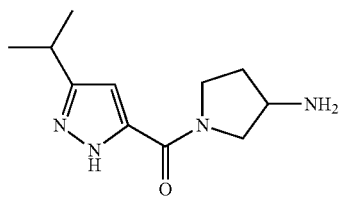 [SMILES: CC(C)c1cc(C(=O)N2CCC(N)C2)[nH]n1]

(3-Aminopyrrolidin-1-yl)(3-isopropyl-1H-pyrazol-5-yl)methanone

To a suspension of tert-butyl (1-(3-isopropyl-1H-pyrazole-5-carbonyl)pyrrolidin-3-yl)carbamate (1.3 g, 4.0 mmol) in EtOAc (7 ml) was added HCl (7 ml, 4 M in EtOAc). The mixture was stirred at room temperature for 30 min, then solvent was removed under reduced pressure to give the desired crude product (1.1 g) as a white solid. LCMS (ESI) m/z: 223.2 [M+H]⁺, RT=0.74 min (LCMS Method C).

Step 3

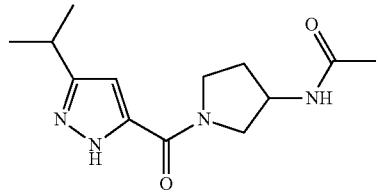 [SMILES: CC(=O)NC1CCN(C(=O)c2cc(C(C)C)n[nH]2)C1]

N-(1-(3-isopropyl-1H-pyrazole-5-carbonyl)pyrrolidin-3-yl)acetamide

To a solution of (3-aminopyrrolidin-1-yl)(3-isopropyl-1H-pyrazol-5-yl)methanone (200 mg, 0.9 mmol) in DMF (4 ml) was added acetyl acetate (119 mg, 1.2 mmol) and DIEA (0.5 ml, 2.7 mmol). The mixture was stirred at room temperature for 2 hrs, filtered and purified by preparative HPLC (Gemini C18 150×25 mm×10 μm, 11-41% MeCN/H₂O) to give the desired product (62.3 mg, 26% yield) as a white solid. ¹H NMR (400 MHz, DMSO-d₆) δ 12.91 (s, 1H), 7.78 (m, 1H), 6.39 (s, 1H), 4.22-4.20 (m, 1H), 3.97-3.90 (m, 2H), 3.64-3.50 (m, 2H), 2.97-2.94 (m, 1H), 2.02-1.99 (m, 1H), 1.81-1.74 (m, 4H), 1.22 (d, J=7.2 Hz, 6H). LCMS (ESI) m/z: 265.1 [M+H]⁺, RT=0.94 min (LCMS Method C).

Examples 28

Step 1

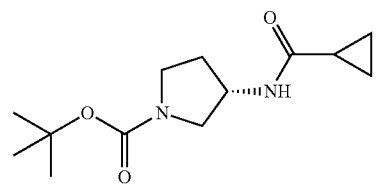 [SMILES: CC(C)(C)OC(=O)N1CC[C@H](NC(=O)C2CC2)C1]

(S)-tert-butyl 3-(cyclopropanecarboxamido)pyrrolidine-1-carboxylate

To a stirred solution of (S)-tert-butyl 3-aminopyrrolidine-1-carboxylate (1.0 g, 5.37 mmol) in DCM (5 mL) was added TEA (1.63 g, 16.11 mmol) and cooled to 0° C. Then cyclopropanecarbonyl chloride (673.5 mg, 6.44 mmol) was added drop wise into the mixture and the reaction mixture was warned to room temperature over 2 hrs. The mixture was diluted with DCM (150 mL) and washed with H₂O (120 mL×3). The organic phase was dried over anhydrous Na₂SO₄, filtered and concentrated to afford the desired product (1.2 g, 86% yield) as yellow solid which was used to the next step directly without further purification.

Step 2

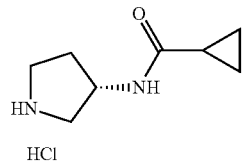 [SMILES: O=C(N[C@H]1CCNC1)C1CC1 ; Cl]

HCl

(S)—N-(pyrrolidin-3-yl)cyclopropanecarboxamide Hydrochloride

To a stirred solution of (S)-tert-butyl 3-(cyclopropanecarboxamido) pyrrolidine-1-carboxylate (1.2 g, 4.7 mmol) in EtOAc (2 mL) was added dropwise HCl/EtOAc (4 N, 3 mL, 12 mmol) at room temperature and stirred for 1 hr. The reaction mixture was concentrated and washed with EtOAc (30 mL×2) to afford the crude desired product (700 mg, 78% yield) as yellow solid.
Step 3

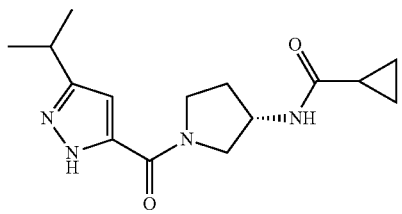 [SMILES: CC(C)c1cc(C(=O)N2CC[C@H](NC(=O)C3CC3)C2)[nH]n1]

(S)—N-(1-(3-isopropyl-1H-pyrazole-5-carbonyl) pyrrolidin-3-yl)cyclopropanecarboxamide To a stirred solution of 3-isopropyl-1H-pyrazole-5-carboxylic acid (221 mg, 1.16 mmol) in DMF (3 mL) was added DIEA (500 mg, 3.87 mmol) and HATU (539.2 mg, 1.42 mmol) at room temperature. The mixture was stirred for 10 min before (S)—N-(pyrrolidin-3-yl)cyclopropanecarboxamide hydrochloride (200 mg, 1.29 mmol) was added. The mixture was stirred at room temperature for another 2 hrs before being purified by preparative HPLC to afford the desired product (40 mg, 11% yield) as white solid. $^1$H NMR (400 MHz, CD$_3$OD) δ 6.48 (s, 1H), 4.47-4.34 (m, 1H), 4.17-3.97 (m, 1.5H), 3.85-3.80 (m, 1H), 3.78-3.64 (m, 1H), 3.55-3.52 (m, 0.5H), 3.07-3.00 (m, 1H), 2.27-2.12 (m, 1H), 2.02-1.90 (m, 1H), 1.65-1.52 (m, 1H), 1.30 (d, J=7.2 Hz, 6H), 0.90-0.79 (m, 2H), 0.79-0.69 (m, 2H). LCMS (ESI) m/z: 291.1 [M+H]$^+$, RT=1.023 min (LCMS method C).

Examples 29

Step 1

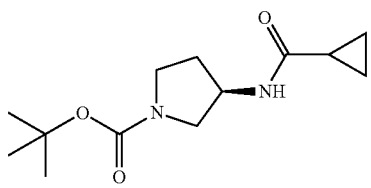 [SMILES: CC(C)(C)OC(=O)N1CC[C@@H](NC(=O)C2CC2)C1]

(R)-tert-butyl 3-(cyclopropanecarboxamido)pyrrolidine-1-carboxylate

To a solution of (R)-tert-butyl 3-aminopyrrolidine-1-carboxylate (1.0 g, 5.37 mmol) in DCM (10 mL) was added Et$_3$N (1.09 g, 10.74 mmol), followed by the addition of cyclopropanecarbonyl chloride (0.6 mL, 0.64 mmol) dropwise at 0° C. The mixture was stirred for 15 min, then quenched with H$_2$O (25 mL), and extracted with DCM (20 mL×3). Combined organic layers were dried over anhydrous Na$_2$SO$_4$ and concentrated to give desired product (1.30 g, crude) as a yellow solid.
Step 2

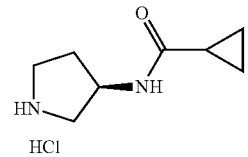 [SMILES: O=C(N[C@@H]1CCNC1)C1CC1 ; Cl]

(R)—N-(pyrrolidin-3-yl)cyclopropanecarboxamide Hydrochloride

To a solution of (R)-tert-butyl 3-(cyclopropanecarboxamido)pyrrolidine-1-carboxylate (1.3 g, 5.11 mmol) in EtOAc (10 mL) was added HCl/EtOAc (10 mL). The mixture was stirred at room temperature for 12 hrs. Then the mixture was evaporated under reduced pressure to give the crude desired product (800 mg) as a dark solid.
Step 3

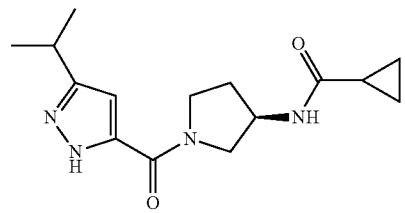 [SMILES: CC(C)c1cc(C(=O)N2CC[C@@H](NC(=O)C3CC3)C2)[nH]n1]

(R)—N-(1-(3-isopropyl-1H-pyrazole-5-carbonyl) pyrrolidin-3-yl)cyclopropane Carboxamide To a solution of 3-isopropyl-1H-pyrazole-5-carboxylic acid (220 mg, 1.43 mmol) in DMF (5 mL) was added HATU (690 mg, 1.82 mmol) and DIPEA (0.7 mL, 0.39 mmol) at room temperature. The reaction mixture was stirred for 30 min and then (R)—N-(pyrrolidin-3-yl) cyclopropanecarboxamide hydrochloride (200 mg, 1.30 mmol) was added and the mixture was stirred for another 2 hrs. Then the mixture was filtered and purified by preparative HPLC to give desired product (136.8 mg, 36% yield). $^1$H NMR (400 MHz, CD$_3$OD) δ 6.48 (s, 1H), 4.41-4.38 (m, 1H), 4.03-3.75 (m, 4H), 3.05-3.02 (m, 1H), 2.20-2.15 (m, 1H), 1.97-1.96 (m, 1H), 1.59-1.57 (n, 1H), 0.86-0.82 (m, 2H), 0.75-0.73 (m, 2H). LCMS (EST) m/z: 291.1 [M+H]$^+$, RT=0.687 min (LCMS Method E).

Example 30

Step 1

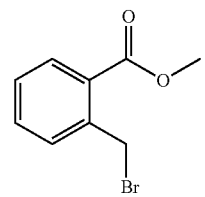

Methyl 2-(bromomethyl)benzoate

To a solution of methyl 2-methylbenzoate (1.0 g, 6.66 mmol) in CCl₄ (20 mL) was added NBS (1.3 g, 7.32 mmol) and BPO (50 mg, 0.21 mmol). The mixture was heated at 80° C. for 16 hrs. After cooling to room temperature, the reaction mixture was concentrated and the residue was dissolved in EtOAc (50 mL) and washed with H₂O (20 mL). The organic phase was dried over anhydrous Na₂SO₄, filtered and concentrated. The residue was purified by flash column chromatography on silica gel eluting with 0-10% EtOAc in hexanes to give the desired product (1.4 g crude) as a colorless oil. ¹H NMR (400 MHz, CDCl₃): δ 7.97 (d, J=7.6 Hz, 1H), 7.52-7.47 (m, 2H), 7.40-7.38 (m, 1H), 4.96 (s, 2H), 3.95 (s, 3H).

Step 2

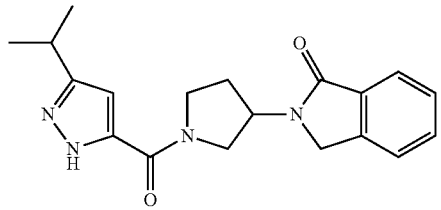 [SMILES: CC(C)c1cc(C(=O)N2CCC(N3Cc4ccccc4C3=O)C2)[nH]n1]

2-(1-(3-Isopropyl-1H-pyrazole-5-carbonyl)pyrrolidin-3-yl)isoindolin-1-one

To a solution of (3-aminopyrrolidin-1-yl)(3-isopropyl-1H-pyrazol-5-yl)methanone hydrochloride (100 mg, 0.386 mmol) and DIPEA (150 mg, 1.16 mmol) in MeCN (2 mL) was added methyl 2-(bromomethyl)benzoate (89 mg, 0.386 mmol). The mixture was stirred at room temperature for 16 hrs. The mixture was concentrated and the residue was purified by preparative HPLC (Gemini C₁₈ 150×25 mm×10 μm, 30-60-16% MeCN condition) to give the desired product (19 mg, 15% yield) as a white solid. ¹H NMR (400 MHz, CD₃OD): δ 7.80-7.76 (m, 1H), 7.64-7.49 (m, 3H), 6.53 (s, 1H), 5.01-4.96 (m, 1H), 4.60, 4.58 (s, 2H total), 4.26-4.22 (m, 1H), 4.28-3.71 (m, 4H), 3.05-3.02 (m, 1H), 2.39-2.31 (m, 2H), 1.82-1.75 (m, 1H), 1.31, 1.29 (d, J=6.8 Hz, 6H total). LCMS (LCMS Method C): Rt=1.145 min, m/z: 339.2 [M+H]⁺.

Example 31

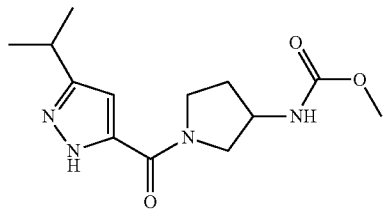 [SMILES: COC(=O)NC1CCN(C(=O)c2cc(C(C)C)n[nH]2)C1]

Methyl (1-(3-isopropyl-1H-pyrazole-5-carbonyl)pyrrolidin-3-yl)carbamate

A solution of methyl carbonochloridate (120 mg, 1.27 mmol) in DCM (1 mL) was added into a solution of (3-aminopyrrolidin-1-yl)(3-isopropyl-1H-pyrazol-5-yl)methanone hydrochloride (40 mg, 1.85 mmol), DIPEA (600 mg, 4.64 mmol) in DCM (5 mL) at 0° C. under a N₂ atmosphere. The reaction mixture was stirred at room temperature for 12 hrs. The reaction mixture was concentrated and the residue was purified by preparative HPLC to give the title product (67 mg, 18% yield) as a white solid. ¹H NMR (400 MHz, methanol-d₄) δ 6.48 (s, 1H), 4.25-4.16 (m, 1H), 4.15-4.07 (m, 0.5H), 4.05-3.95 (m, 1H), 3.84-3.80 (m, 0.5H), 3.75-3.47 (m, 5H), 3.05-3.02 (m, 1H), 2.25-2.12 (m, 1H), 2.00-1.88 (m, 1H), 1.30 (d, J=8.0 Hz, 6H). LCMS (ESI) m/z: 280.8 [M+H]⁺, RT=0.690 min.

Example 32

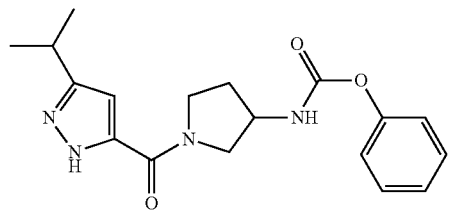 [SMILES: CC(C)c1cc(C(=O)N2CCC(NC(=O)Oc3ccccc3)C2)[nH]n1]

Phenyl (1-(3-isopropyl-1H-pyrazole-5-carbonyl)pyrrolidin-3-yl)carbamate

A solution of phenyl carbonochloridate (303 mg, 1.93 mmol) in DCM (1 mL), was added into a solution of (3-aminopyrrolidin-1-yl)(3-isopropyl-1H-pyrazol-5-yl)methanone hydrochloride (500 mg, 1.93 mmol), DIPEA (749 mg, 5.79 mmol) in DCM (5 mL) at 0° C. under a N₂ atmosphere. The reaction mixture was stirred at room temperature for 12 hrs. The reaction mixture was concentrated and the residue was purified by preparative HPLC to give the title product (10 mg, 1.5% yield) as a white solid. ¹H NMR (400 MHz, methanol-d₄) δ 7.44-7.31 (m, 2H), 7.25-7.15 (m, 1H), 7.12-7.08 (m, 2H), 6.49 (s, 1H), 4.31-4.25 (m, 0.5H), 4.20-4.02 (m, 1.5H), 3.96-3.84 (m, 1H), 3.80-3.58 (m, 2H), 3.10-2.98 (m, 1H), 2.32-2.18 (m, 1H), 2.10-2.00 (m, 1H), 1.31 (d, J 4.0 Hz, 6H). LCMS (ESI) m/z: 343.1 [M+H]⁺, RT=0.786 min.

Example 33

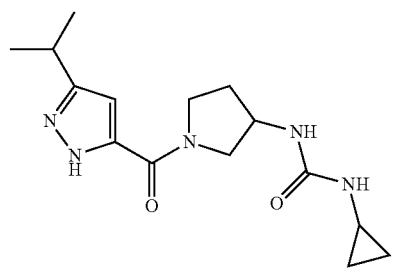 [SMILES: CC(C)c1cc(C(=O)N2CCC(NC(=O)NC3CC3)C2)[nH]n1]

1-Cyclopropyl-3-(1-(3-isopropyl-1H-pyrazole-5-carbonyl)pyrrolidin-3-yl)urea

A solution of phenyl (1-(3-isopropyl-1H-pyrazole-5-carbonyl)pyrrolidin-3-yl)carbamate (150 mg, 0.44 mmol), cyclopropanamine (38 mg, 0.68 mmol), DIEA (170 mg, 1.31 mmol) was stirred at room temperature for 12 hrs. The reaction mixture was concentrated. The residue was purified by preparative HPLC to give the desired product (46.9 mg, 35% yield) as a white solid. $^1$H NMR (400 MHz, DMSO-$d_6$) δ 12.90 (s, 1H), 6.37 (s, 1H), 6.13-5.98 (m, 2H), 4.15-4.05 (m, 1H), 4.00-3.85 (m, 1.5H), 3.64-3.44 (in, 2.5H), 2.99-2.91 (m, 1H), 2.40-2.38 (m, 1H), 2.02-1.97 (m, 1H), 1.83-1.71 (m, 1H), 1.22 (d, J=6.8 Hz, 6H), 0.58-0.49 (m, 2H), 0.34-0.25 (m, 2H). LCMS (ESI) m/z: 306.3 [M+H]$^+$, RT=0.686 min (LCMS method E).

Example 34

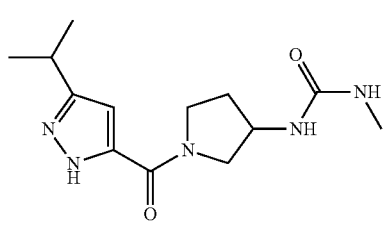

1-(1-(3-Isopropyl-1H-pyrazole-5-carbonyl) pyrrolidin-3-yl)-3-methylurea

A solution of methanamine hydrochloride (30 mg, 0.43 mmol), phenyl (1-(3-isopropyl-1H-pyrazole-5-carbonyl)-pyrrolidin-3-yl)carbamate (100 mg, 0.29 mmol) in MeCN (3 mL) was stirred at 60° C. for 12 hrs. The reaction mixture was concentrated. The residue was purified by preparative HPLC to give the desired product (47.7 mg, 40% yield) as a white solid. $^1$H NMR (400 MHz, DMSO-$d_6$) δ 12.92 (s, 1H), 6.36 (s, 1H), 6.21-6.19 (m, 1H), 5.66-5.54 (m, 1H), 4.13-4.02 (m, 1H), 4.00-3.85 (m, 1H), 3.69-3.42 (m, 2H), 3.30-3.22 (in, 1H), 3.00-2.89 (m, 1H), 2.54-2.52 (m, 3H), 2.07-1.94 (m, 1H), 1.81-1.66 (m, 1H), 1.21 (d, J=6.8 Hz, 6H). LCMS (ESI) m/z: 280.1 [M+H]$^+$, RT=0.569 min (LCMS method E).

Example 35

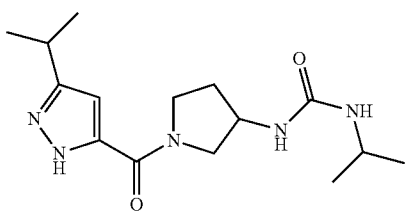 [SMILES: CC(C)NC(=O)NC1CCN(C(=O)c2cc(C(C)C)n[nH]2)C1]

1-Isopropyl-3-(1-(3-isopropyl-1H-pyrazole-5-carbonyl)pyrrolidin-3-yl)urea

A mixture of (3-aminopyrrolidin-1-yl)(3-isopropyl-1H-pyrazol-5-yl)methanone hydrochloride (200 mg, 0.77 mmol), 2-isocyanatopropane (66 mg, 0.77 mmol), DIEA (300 mg, 2.32 mmol) in CH$_3$CN (5 mL) was stirred at room temperature for 12 hrs. The reaction mixture was diluted with H$_2$O (10 mL) and extracted with EtOAc (10 mL). The organic phase was separated and then concentrated to give the crude product which was purified with preparative HPLC to give the desired product (3.6 mg, 1.5% yield) as a white solid. $^1$H NMR (400 MHz, DMSO-$d_6$) δ 12.92 (s, 1H), 6.37 (s, 1H), 6.02-6.00 (m, 1H), 5.58-5.55 (m, 1H), 4.19-3.82 (m, 3H), 3.70-3.46 (m, 3H), 2.99-2.93 (m, 1H), 2.07-1.96 (m, 1H), 1.79-1.65 (m, 1H), 1.22 (d, J=8.0 Hz, 6H), 1.10-0.90 (m, 6H). LCMS (ESI) m/z: 308.3 [M+H]$^+$, RT=0.703 min (LCMS method E).

Example 36

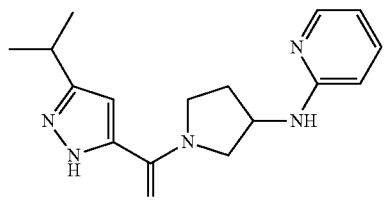

(3-Isopropyl-1H-pyrazol-5-yl)(3-(pyridin-2-ylamino)pyrrolidin-1-yl)methanone

To a solution of (3-aminopyrrolidin-1-yl)(3-isopropyl-1H-pyrazol-5-yl)methanone (200 mg, 0.9 mmol) in DMF (4 ml) was added 2-fluoropyridine (131 mg, 1.3 mmol) and Cs$_2$CO$_3$ (879 mg, 2.7 mmol). Then the mixture was stirred at 150° C. for 15 hrs. After cooling to room temperature, the reaction mixture was filtered and purified by preparative HPLC (Gemini 150×25 mm×5 μm, 50% MeCN) to give the desired product (30.7 mg, 11% yield) as a white solid. $^1$H NMR (400 MHz, CD$_3$OD) δ 8.53 (d, J=4.0 Hz, 1H), 8.03-8.00 (m, 1H), 7.87-7.85 (m, 1H), 7.45-7.42 (m, 1H), 6.78 (s, 1H), 4.26-4.25 (m, 1H), 3.94-3.92 (m, 0.5H), 3.89-3.83 (m, 3H), 3.69-3.66 (m, 1H), 3.51-3.49 (m, 0.5H), 2.26-2.21 (m, 1H), 1.93-1.83 (m, 1H), 1.28 (d, J=6.8 Hz, 6H). LCMS (ESI) m/z: 300.1 [M+H]+, RT=0.95 min (LCMS Method C).

Example 37

Step 1

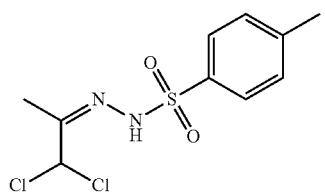 [SMILES: C/C(=N/NS(=O)(=O)c1ccc(C)cc1)C(Cl)Cl]

N'-(1,1-dichloropropan-2-ylidene)-4-methylbenzenesulfonohydrazide

To a solution of 1,1-dichloropropan-2-one (10 g, 78.76 mmol) in EtCOOH (60 mL) was added 4-methylbenzenesulfonohydrazide (13.4 g, 71.95 mmol) dropwise. The resulting mixture was stirred at room temperature for 16 hrs. The white solid was collected by filtration and washed with cyclohexane (20 mL) to give the crude desired product (18.0 g) as a white solid. $^1$H NMR (400 MHz, DMSO-$d_6$): δ 11.91 (brs, 1H), 7.80 (d, J=8.0 Hz, 2H), 7.42 (d, J=8.0 Hz, 2H), 2.38 (s, 3H), 1.84 (s, 3H).

Step 2

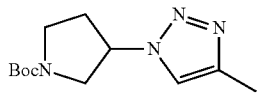 [SMILES: Cc1cn(C2CCN(C(=O)OC(C)(C)C)C2)nn1]

tert-Butyl 3-(4-methyl-1H-1,2,3-triazol-1-yl)pyrrolidine-1-carboxylate

To a solution of tert-butyl 3-aminopyrrolidine-1-carboxylate (2.0 g, 10.74 mmol) in EtOH (50 mL) was added DIPEA (8.33 g, 64.43 mmol) at 0° C. After stirring at 0° C. for 10 min, a solution of (N-(1,1-dichloropropan-2-ylidene)-4-methylbenzenesulfonohydrazide (4.12 g, 13.96 mmol) in MeCN was added to the cooled solution. The resulting mixture was stirred at room temperature for 16 hrs. After reaction, the mixture was concentrated. The residue was redissolved in EtOAc (50 mL) and washed with H$_2$O (20 mL). The organic phase was dried over anhydrous Na$_2$SO$_4$, filtered and concentrated. The residue was purified by flash column chromatography on silica gel eluting with 0-50% EtOAc in hexanes to give the desired product (2.1 g, 77% yield) as a brown oil. $^1$H NMR (400 MHz, CDCl$_3$): δ 7.28 (s, 1H), 5.15-5.12 (m, 1H), 3.91-3.86 (m, 1H), 3.79-3.58 (m, 3H), 2.45-2.39 (m, 2H), 2.36 (s, 3H), 1.48 (s, 9H).

Step 3

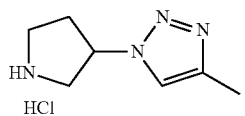

4-Methyl-1-(pyrrolidin-3-yl)-1H-1,2,3-triazole Hydrochloride

To a solution of tert-butyl 3-(4-methyl-1H-1,2,3-triazol-1-yl)pyrrolidine-1-carboxylate (1.0 g, 3.96 mmol) in EtOAc (2 mL) was added HCl/EtOAc (10 mL). The resulting mixture was stirred at room temperature for 2 hrs and concentrated to give the crude desired product (700 mg) as a brown solid. $^1$H NMR (400 MHz, CD$_3$OD): δ 8.62 (s, 1H), 5.80-5.75 (m, 1H), 3.98 (d, J=4.8 Hz, 2H), 3.64-3.60 (m, 2H), 2.81-2.67 (m, 2H), 2.55 (s, 3H).

Step 4

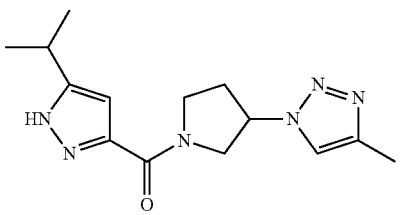 [SMILES: Cc1cn(C2CCN(C(=O)c3cc(C(C)C)[nH]n3)C2)nn1]

(5-Isopropyl-1H-pyrazol-3-yl)(3-(4-methyl-1H-1,2,3-triazol-1-yl)pyrrolidin-1-yl)methanone To a solution of 5-isopropyl-1H-pyrazole-3-carboxylic acid (160 mg, 1.04 mmol) and 4-methyl-1-(pyrrolidin-3-yl)-1H-1,2,3-triazole hydrochloride (196 mg, 1.04 mmol) in DMF (4 mL) was added HATU (593 mg, 1.56 mmol) and DIPEA (402 mg, 3.11 mmol). The mixture was stirred at room temperature for 16 hrs. The mixture was purified by prep.-HPLC (Gemini C$_{18}$150*25 mm*10 um, 15-45% MeCN condition) to give the desired product (108 mg, 36% yield) as a white solid. $^1$H NMR (400 MHz, MeOD): δ 7.86, 7.83 (s, 1H total), 6.52, 6.50 (2s, 1H), 5.33-5.29 (m, 1H), 4.46-4.42 (m, 1H), 4.17-4.11 (m, 2H), 3.85-3.82 (m, 1H), 3.05-3.00 (m, 1H), 2.58-2.49 (m, 2H), 2.32, 2.31 (2s, 1H), 1.29, 1.27 (d, J=6.8 Hz, 6H total). LCMS (LCMS Method C): Rt=1.017 min, m/z: 289.1 [M+H]$^+$.

Method D

Example 38

Step 1

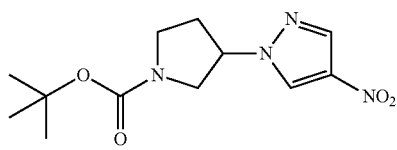 [SMILES: CC(C)(C)OC(=O)N1CCC(n2cc([N+](=O)[O-])cn2)C1]

tert-Butyl 3-(4-nitro-1H-pyrazol-1-yl)pyrrolidine-1-carboxylate

To a solution of 4-nitro-1H-pyrazole (2 g, 17.68 mmol), tert-butyl 3-hydroxypyrrolidine-1-carboxylate (3.32 g, 17.68 mmol) and PPh$_3$ (5.56 g, 21.2 mmol) in THF (20 mL) under a nitrogen atmosphere at 10° C. was added DIAD (5.3 g, 23 mmol). The reaction mixture was stirred at 10° C. for 16 hrs. The reaction mixture was concentrated and purified by flash column chromatography on silica gel, eluting with 0-50% EtOAc in hexanes to afford the desired product (4 g, 80% yield) as a white solid. LCMS (ESI) m/z: 305.1 [M+Na]$^+$, RT=1.04 min (LCMS Method A).

Step 2

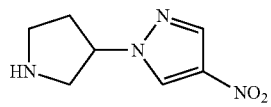 [SMILES: O=[N+]([O-])c1cnn(C2CCNC2)c1]

4-nitro-1-(pyrrolidin-3-yl)-1H-pyrazole

To the reaction mixture of tert-butyl 3-(4-nitro-1H-pyrazol-1-yl)pyrrolidine-1-carboxylate (400 mg 1.42 mmol) in EtOAc (8 mL) was added HCl/EtOAc (8 mL, 4M). The reaction mixture was stirred at 10° C. for 30 min. Then the reaction mixture was concentrated to afford the desired product (100 mg, 39% yield) as an off-white solid.

Step 3

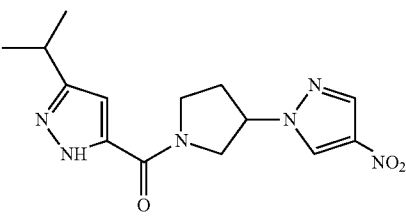

(3-isopropyl-1H-pyrazol-5-yl)(3-(4-nitro-1H-pyrazol-1-yl)pyrrolidin-1-yl)methanone To the reaction mixture of 3-isopropyl-1H-pyrazole-5-carboxylic acid (360 mg, 2.2 mmol), HATU (1.0 g, 4.4 mmol) in DMF (10 mL) was added DIEA (851 mg, 6.6 mmol). The reaction mixture was stirred at 10° C. for 30 min, then 4-nitro-1-(pyrrolidin-3-yl)-1H-pyrazole (400 mg, 2.2 mmol) was added. The reaction mixture was stirred at 10° C. for 16 hrs. The reaction mixture was concentrated and purified by flash column chromatography on silica gel, eluting with 0-2% MeOH in DCM to afford the desired product (200 mg, 40% yield) as a yellow oil. LCMS (ESI) m/z: 319.1 [M+Na]$^+$, RT=0.655 min (LCMS Method A).

Step 4

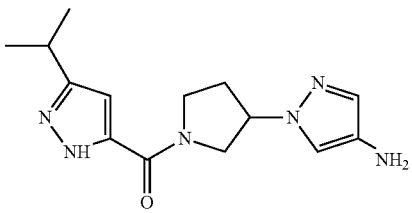 [SMILES: CC(C)c1cc(C(=O)N2CCC(n3cc(N)cn3)C2)[nH]n1]

(3-(4-amino-1H-pyrazol-1-yl)pyrrolidin-1-yl)(3-isopropyl-1H-pyrazol-5-yl)methanone To the reaction mixture of (3-isopropyl-1H-pyrazol-5-yl)(3-(4-nitro-1H-pyrazol-1-yl)pyrrolidin-1-yl)methanone (200 mg, 0.63 mmol) was added Pd/C (20 mg). The reaction mixture was stirred at 10° C. under a H$_2$ atmosphere for 16 hrs. The reaction mixture was filtered and the filtrate was concentrated and purified by preparative HPLC to afford the desired product (5 mg, 3% yield) as a white solid. $^1$H NMR (400 MHz, DMSO-d$_6$) δ 7.09 (s, 1H), 6.98 (s, 1H), 6.39 (s, 1H), 4.81 (m, 1H), 4.25-3.65 (m, 4H), 3.10-2.90 (m, 1H), 2.33-2.30 (m, 2H), 1.24 (d, J=8 Hz, 6H). LCMS (ESI) m/z: 289.1 [M+H]$^+$, RT=0.95 min (LCMS Method B).

Example 39

Step 1

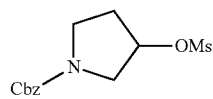 [SMILES: CS(=O)(=O)OC1CCN(C(=O)OCc2ccccc2)C1]

Benzyl 3-((methylsulfonyl)oxy)pyrrolidine-1-carboxylate

To a stirred solution of benzyl 3-hydroxypyrrolidine-1-carboxylate (500 mg, 2.26 mmol) in DCM (10 mL) was added triethylamine (686 mg, 0.94 mL, 6.78 mmol) at room temperature. The resulting mixture was cooled to 0° C. Then methanesulfonyl chloride (388 mg, 3.39 mmol) was added dropwise into the mixture and the mixture was slowly warmed to room temperature over 2 hrs under N$_2$ atmosphere. The mixture was diluted with DCM (20 mL) and washed with H$_2$O (10 mL×2), hydrochloric acid (10 ml×2, 1N), saturated NaHCO$_3$ (10 mL). The organic phase was dried over anhydrous Na$_2$SO$_4$, filtered and concentrated to give the crude desired product (600 mg) as a brown oil which was used in the next step without further purification.

Step 2

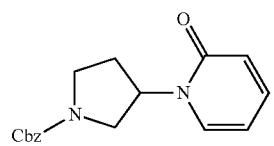 [SMILES: O=C(OCc1ccccc1)N1CCC(n2ccccc2=O)C1]

Benzyl 3-(2-oxopyridin-1(2H)-yl)pyrrolidine-1-carboxylate

To a solution of benzyl 3-((methylsulfonyl)oxy)pyrrolidine-1-carboxylate (1.0 g, 3.34 mmol), K$_2$CO$_3$ (692.5 mg, 5.01 mmol) in DMF (5 mL) was added pyridin-2(1H)-one (381.2 mg, 4.01 mmol) at room temperature. The mixture was stirred at 100° C. for 16 hrs under a N$_2$ atmosphere. After cooling to room temperature, the reaction mixture was diluted with EtOAc (120 mL), washed with H$_2$O (80 mL×2) and brine (80 mL). The organic phase was dried over anhydrous Na$_2$SO$_4$, filtered and the filtrate was concentrated to dryness. The residue obtained was purified by silica gel flash column chromatography (0-25% EtOAc in hexanes and 0-3% MeOH in DCM) to give the crude desired product (200 mg) as a colourless oil, which was used to the next step directly without further purification.

Step 3

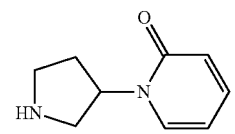

1-(Pyrrolidin-3-yl)pyridin-2(1H)-one

To a solution of benzyl 3-(2-oxopyridin-1(2H)-yl)pyrrolidine-1-carboxylate (200 mg, 0.67 mmol) in EtOH (2 mL) was added Pd/C (50 mg, wet, 10%) and the mixture was stirred at room temperature for 16 hrs under a H$_2$ balloon. The mixture was filtered and the filtrate was concentrated to dryness under reduced pressure to afford a mixture of the crude desired product (98 mg) as a colourless oil which was used to the next step directly without further purification.

Step 4

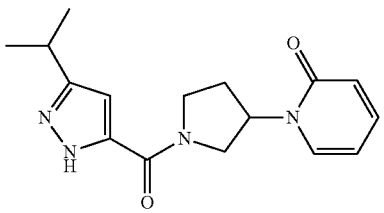 [SMILES: CC(C)c1cc(C(=O)N2CCC(n3ccccc3=O)C2)[nH]n1]

1-(1-(3-Isopropyl-1H-pyrazole-5-carbonyl)pyrrolidin-3-yl)pyridin-2(1H)-one

To a stirred solution of 3-Isopropyl-1H-pyrazole-5-carboxylic acid (100 mg, 0.65 mmol) in DMF (2 mL) was added DIEA (252 mg, 1.95 mmol) and HATU (271 mg, 0.78 mmol) at room temperature. The mixture was stirred at room temperature for 10 min before the addition of the mixture 1-(Pyrrolidin-3-yl)pyridin-2(1H)-one and 1-(Pyrrolidin-3-yl)piperidin-2-one (98 mg). The mixture was stirred at room temperature for 2 hrs and purified by preparative HPLC to afford the desired product (16 mg, 8% yield) as white solid. $^1$H NMR (400 MHz, CD$_3$OD) δ 7.64 (t, J=5.2 Hz, 1H), 7.58-7.47 (m, 1H), 6.62-6.55 (m, 1H), 6.52 (s, 1H), 6.48-6.40 (m, 1H), 5.49-5.44 (m, 1H), 4.47-4.37 (m, 0.5H), 4.25-4.16 (m, 1H), 4.12-4.07 (m, 1H), 3.94-3.75 (in, 1.5H), 3.08-3.00 (m, 1H), 2.53-2.30 (m, 2H), 1.30 (t, J=6.8 Hz, 6H). LCMS (ESI) m/z: 301.1 [M+H]$^+$, RT=0.682 min (LCMS method E).

Example 40

Step 1

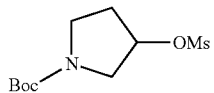

tert-butyl 3-((methylsulfonyl)oxy)pyrrolidine-1-carboxylate

To a stirred solution of tert-butyl 3-hydroxypyrrolidine-1-carboxylate (5 g, 27 mmol) in DCM (20 mL) was added triethylamine (8.1 g, 80 mmol) at room temperature. The mixture was cooled to 0° C. and then methanesulfonyl chloride (3.9 g, 34 mmol) was added dropwise into the mixture. The resulting mixture was slowly warmed to room temperature over 2 hrs under N$_2$ atmosphere. The mixture was diluted with DCM (80 mL) and washed with H$_2$O (80 mL), hydrochloric acid (80 ml×2, 1N), saturated NaHCO$_3$ (80 mL). The organic phase was dried over anhydrous Na$_2$SO$_4$, filtered and concentrated to give the crude desired product (3.8 g, 54% yield) as colourless oil which was used in the next step without further purification.

Step 2

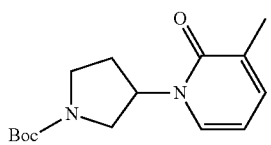 [SMILES: Cc1cccn(C2CCN(C(=O)OC(C)(C)C)C2)c1=O]

tert-Butyl 3-(3-methyl-2-oxopyridin-1(2H)-yl)pyrrolidine-1-carboxylate

To a solution of tert-Butyl 3-((methylsulfonyl)oxy)pyrrolidine-1-carboxylate (1.0 g, 3.77 mmol), K$_2$CO$_3$ (781.3 mg, 5.70 mmol) in DMF (7 mL) was added 3-Methylpyridin-2(1H)-one (493.6 mg, 4.52 mmol) at room temperature. The mixture was stirred at 100° C. for 16 hrs under a N$_2$ atmosphere. After cooling to room temperature, it was diluted with EtOAc (120 mL), washed with H$_2$O (80 mL×2) and brine (80 mL). The organic phase was dried over Na$_2$SO$_4$, filtered and concentrated to dryness to afford the crude title compounds (800 mg) as yellow oil which was used to the next step directly without further purification.

Step 3

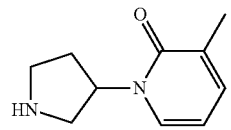

3-Methyl-1-(pyrrolidin-3-yl)pyridin-2(1H)-one

To a solution of the mixture of tert-butyl 3-(3-methyl-2-oxopyridin-1(2H)-yl)pyrrolidine-1-carboxylate and tert-butyl 3-((3-methylpyridin-2-yl)oxy)pyrrolidine-1-carboxylate (800 mg, 2.87 mmol) in EtOAc (2 mL) was added dropwise HCl/EtOAc (2 mL, 8 mmol) and stirred at room temperature for 1 hr. The reaction mixture was concentrated and the residue obtained was washed with EtOAc (30 mL×2) to afford the crude desired product (600 mg) as a yellow oil which was used to the next step directly without further purification.

Step 4

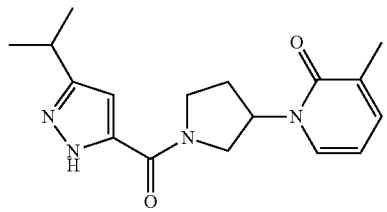 [SMILES: Cc1cccn(C2CCN(C(=O)c3cc(C(C)C)n[nH]3)C2)c1=O]

1-(1-(3-Isopropyl-1H-pyrazole-5-carbonyl)pyrrolidin-3-yl)-3-methylpyridin-2(1H)-one To a solution of 3-Isopropyl-1H-pyrazole-5-carboxylic acid (474 mg, 3.07 mmol) in DMF (3 mL) was added DIEA (1.44 g, 11.18 mmol) and HATU (1.28 g, 3.35 mmol) at room temperature. The mixture was stirred at room temperature for 10 min before the addition of the 3-Methyl-1-(pyrrolidin-3-yl)pyridin-2(1H)-one. The mixture was stirred at room temperature for 2 hrs and purified by preparative HPLC to afford the desired product (30 mg, 3.1% yield) as white solid. $^1$H NMR (400 MHz, CD$_3$OD) δ ☐☐☐ (m, 1H), 7.39 (m, 1H), 6.52, 6.51 (2s, 1H), 6.37-6.33 (m, 1H), 5.51-5.42 (m, 1H), 4.44-4.39 (m, 0.5H), 4.25-4.04 (m, 2H), 3.98-3.72 (m, 1.5H), 3.08-2.99 (m, 1H), 2.52-2.26 (m, 2H), 2.13, 2.11 (2s, 3H), 1.30 (t, J=6.6 Hz, 6H). LCMS (ESI) m/z: 315.2 [M+H]$^+$, RT=0.719 min (LCMS method E).

Example 41

Step 1

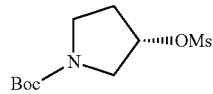

(S)-tert-butyl 3-((methylsulfonyl)oxy)pyrrolidine-1-carboxylate

To a cooled solution of tert-butyl (3S)-3-hydroxypyrrolidine-1-carboxylate (15 g, 80.11 mmol) in DCM (150 mL) was added TEA (22.3 mL, 160.22 mmol) and MsCl (7.44 mL, 96.13 mmol). The reaction mixture was stirred at 28° C. for 1 hr. The reaction mixture was diluted in DCM (100 mL), washed with 1 N HCl (100 mL), saturated NaHCO$_3$ (100 mL) and brine (100 mL). The organic layer was dried over anhydrous Na$_2$SO$_4$, filtered and concentrated to afford the desired product (19.4 g, 91% yield) as a yellow oil. $^1$H NMR (400 MHz, CDCl$_3$) δ 5.30-5.26 (m, 1H), 3.68-3.43 (m, 4H), 3.05 (s, 3H), 2.27-2.13 (m, 2H), 1.46 (s, 9H).

Step 2

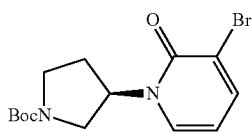

(R)-tert-butyl 3-(3-bromo-2-oxopyridin-1(2H)-yl)pyrrolidine-1-carboxylate

A mixture of 3-bromo-1H-pyridin-2-one (9 g, 51.72 mmol), tert-butyl (3S)-3-methylsulfonyl oxopyrrolidine-1-carboxylate (16.47 g, 62.07 mmol) and K$_2$CO$_3$ (14.28 g, 103.45 mmol) in DMF (90 mL) was stirred at 80° C. for 12 hours. The reaction mixture was diluted in water (150 mL), washed with EtOAc (150 mL×2). The combined organic layers were dried over anhydrous Na$_2$SO$_4$, filtered and concentrated. The residue was purified by silica gel flash column chromatography (petroleum ether/EtOAc=10/1) to afford the desired product (4.2 g, 24% yield) as a colorless oil.

Step 3

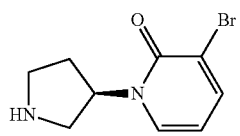

(R)-3-bromo-1-(pyrrolidin-3-yl)pyridin-2(1H)-one

To a stirred solution of tert-butyl (3R)-3-(3-bromo-2-oxo-1-pyridyl)pyrrolidine-1-carboxylate (4.2 g, 12.24 mmol) in methanol (40 mL) was added HCl/MeOH (10 mL) in an ice bath. The reaction was stirred at 30° C. for 2 hrs. The solvent was removed under reduced pressure to give the crude product (3 g) which was used in next step without further purification.

Step 4

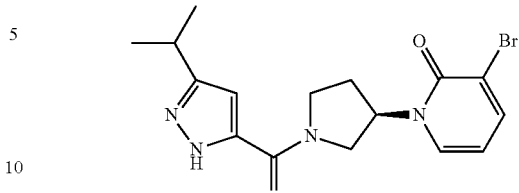

(R)-3-bromo-1-(1-(3-isopropyl-1H-pyrazole-5-carbonyl)pyrrolidin-3-yl)pyridin-2(1H)-one A mixture of (R)-3-bromo-1-(pyrrolidin-3-yl)pyridin-2(1H)-one (3 g, 12.34 mmol), 3-isopropyl-1H-pyrazole-5-carboxylic acid (2.1 g, 13.58 mmol), HATU (5.6 g, 14.81 mmol) and DIEA (6.58 mL, 37.02 mmol) in DMF (30 mL) was stirred at room temperature for 12 hrs. The mixture was diluted with EtOAc (60 mL), washed with brine (60 mL×2). The organic layer was dried over anhydrous Na$_2$SO$_4$, filtered and concentrated. The crude residue was purified by preparative TLC (DCM:MeOH=50:1) to afford the desired product (1.6 g, 34% yield) as a light yellow solid. LCMS M/Z (M+Na)=402.8.

Step 5

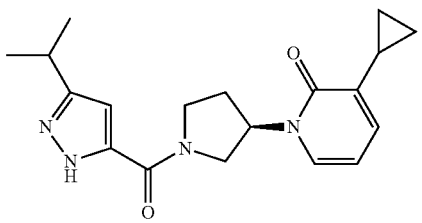 [SMILES: CC(C)c1cc(C(=O)N2CC[C@@H](n3cccc(C4CC4)c3=O)C2)[nH]n1]

(R)-3-cyclopropyl-1-(1-(3-isopropyl-1H-pyrazole-5-carbonyl)pyrrolidin-3-yl)pyridin-2(1H)-one A mixture of 3-bromo-1-[(3R)-1-(3-isopropyl-1H-pyrazole-5-carbonyl)pyrrolidin-3-yl]pyridin-2-one (200 mg, 0.53 mmol), cyclopropylboronic acid (54 mg, 0.63 mmol), Pd(dppf)Cl$_2$ (39 mg, 0.05 mmol) and Na$_2$CO$_3$ (168 mg, 1.58 mmol) in 1,4-dioxane (5 mL) and water (1 mL) was stirred at 100° C. for 12 hrs under a N$_2$ atmosphere. After cooling to room temperature, the reaction mixture was diluted in water (20 mL), washed with DCM (20 mL×2). Combined organic layers were dried over anhydrous Na$_2$SO$_4$, filtered and concentrated. The crude residue was purified by preparative HPLC to afford the desired product (31 mg, 17% yield) as a white solid. $^1$H NMR (400 MHz, DMSO-d$_6$) δ 7.46-7.44 (m, 1H), 7.10-7.08 (m, 1H), 6.53 (s, 1H), 6.37-6.32 (m, 1H), 5.51-5.46 (m, 1H), 4.44-3.77 (m, 4H), 3.06-3.01 (m, 1H), 2.50-2.32 (m, 2H), 2.06-2.01 (in, 1H), 1.30 (m, 6H), 0.95-0.90 (m, 2H), 0.63-0.58 (m, 2H). LCMS (EST) M/Z (M+H)=341.1, RT=0.762 min (LCMS method E).

Example 42

Step 1

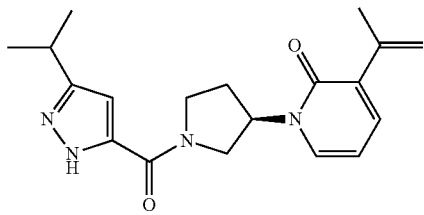 [SMILES: C=C(C)c1cccn([C@@H]2CCN(C(=O)c3cc(C(C)C)n[nH]3)C2)c1=O]

(R)-1-(1-(3-isopropyl-1H-pyrazole-5-carbonyl)pyr-rolidin-3-yl)-3-(prop-1-en-2-yl) pyridin-2(1H)-one A mixture of 3-bromo-1-[(3R)-1-(3-isopropyl-1H-pyrazole-5-carbonyl)pyrrolidin-3-yl]pyridin-2-one (300 mg, 0.79 mmol), potassium trifluoro(isopropenyl)boranuide (140 mg, 0.95 mmol), Pd(OAc)$_2$ (27 mg, 0.12 mmol), RuPhos (111 mg, 0.24 mmol) and K$_3$PO$_4$ (504 mg, 2.37 mmol) in toluene (5 mL) and water (0.5 mL) was stirred at 110° C. for 12 hrs under a N$_2$ atmosphere. After cooling to room temperature, the reaction mixture was diluted in water (20 mL), and then extracted with DCM (20 mL×2). The combined organic layers were dried over anhydrous Na$_2$SO$_4$, filtered and concentrated. The crude residue was purified by silica gel flash column chromatography (DCM/MeOH=30/1) to afford the desired product (90 mg, 25% yield) as a light yellow solid. LCMS M/Z (M+H)=340.9.

Step 2

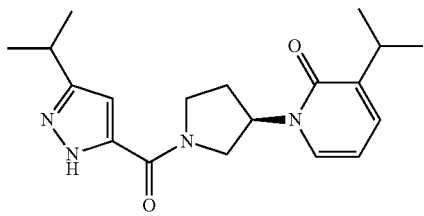

(R)-3-isopropyl-1-(1-(3-isopropyl-1H-pyrazole-5-carbonyl)pyrrolidin-3-yl)pyridin-2(1H)-one A mixture of 3-isopropenyl-1-[(3R)-1-(3-isopropyl-1H-pyrazole-5-carbonyl)pyrrolidin-3-yl]pyridin-2-one (90 mg, 0.26 mmol) and Pd/C (45 mg) in ethyl acetate (2 mL) was stirred at room temperature for 12 hrs under an atmosphere of H$_2$ balloon. The reaction was filtered over a short of Celite pad. The filtrate was concentrated and the crude residue was purified by preparative HPLC to afford the desired product (38 mg, 32% yield) as a white solid. $^1$H NMR (400 MHz, DMSO-d$_6$) δ 7.49-7.47 (m, 1H), 7.40-7.37 (m, 1H), 6.51 (s, 1H), 6.42-6.39 (m, 1H), 5.50-5.46 (m, 1H), 4.44-4.07 (m, 4H), 3.16-3.03 (m, 2H), 2.47-2.31 (m, 2H), 1.30 (m, 6H), 1.18 (m, 6H). LCMS (ESI) M/Z (M+H)=343.1, RT=0.798 min (LCMS method E).

Example 43

Step 1

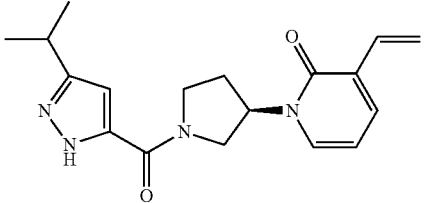 [SMILES: C=Cc1cccn([C@@H]2CCN(C(=O)c3cc(C(C)C)n[nH]3)C2)c1=O]

(R)-1-(1-(3-isopropyl-1H-pyrazole-5-carbonyl)pyr-rolidin-3-yl)-3-vinylpyridin-2(1H)-one A mixture of 3-bromo-1-[(3R)-1-(3-isopropyl-1H-pyrazole-5-carbonyl)pyrrolidin-3-yl]pyridin-2-one (200 mg, 0.53 mmol), potassium trifluoro(vinyl)boranuide (141 mg, 1.05 mmol), Pd(dppf)Cl$_2$ (39 mg, 0.05 mmol) and Na$_2$CO$_3$ (168 mg, 1.58 mmol) in 1,4-dioxane (5 mL) and water (1 mL) was stirred at 110° C. for 12 hrs, under a N$_2$ atmosphere. After cooling to room temperature, the reaction mixture was diluted in water (20 mL), and extracted with DCM (20 mL×2). The combined organic layers were dried over anhydrous Na$_2$SO$_4$, filtered and concentrated. The crude residue was purified by silica gel flash column chromatography (DCM/MeOH=30/1) to afford the desired product (50 mg, 29% yield) as a light yellow solid.

Step 2

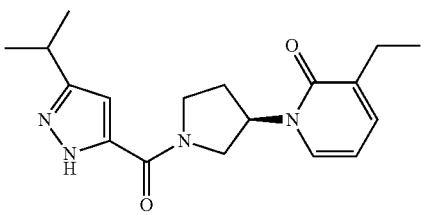 [SMILES: CCc1cccn([C@@H]2CCN(C(=O)c3cc(C(C)C)n[nH]3)C2)c1=O]

(R)-3-ethyl-1-(1-(3-isopropyl-1H-pyrazole-5-carbonyl)pyrrolidin-3-yl)pyridin-2(1H)-one A mixture of 1-[(3R)-1-(3-isopropyl-1H-pyrazole-5-carbonyl)pyrrolidin-3-yl]-3-vinylpyridin-2-one (50 mg, 0.15 mmol), Pd/C (25 mg, 0.1500 mmol) in ethyl acetate (2 mL) was stirred at room temperature for 12 hrs, under 1 atm of H$_2$. The reaction mixture was filtered over a short Celite pad and then the filtrate was concentrated. The resulting residue was purified by preparative HPLC to afford the desired product (35 mg, 70% yield) as a white solid. $^1$H NMR (400 MHz, DMSO-d$_6$) δ 7.49-7.46 (m, 1H), 7.36-7.35 (m, 1H), 6.49 (s, 1H), 6.38-6.35 (m, 114), 5.48-5.43 (m, 1H), 4.17-3.78 (m, 4H), 3.03-3.01 (m, 1H), 2.54-2.49 (m, 2H), 2.42-2.31 (m, 2H), 1.30 (m, 6H), 1.17-1.13 (m, 3H). LCMS (ESI) M/Z (M+H)=329.0, RT=0.626 min (LCMS method E).

Using the General Synthetic Method (Syn. Met.) and the General LCMS Method shown, the following compounds were also prepared.

TABLE 1

| Ex | Structure | Synth. Method | LCMS (ESI) m/z | LCMS Method | R_T (min) | NMR |
|---|---|---|---|---|---|---|
| 44 | 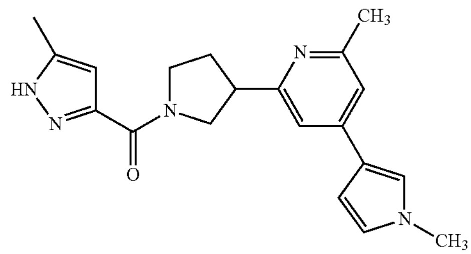 [SMILES: Cc1cc(-c2ccn(C)c2)cc(C2CCN(C(=O)c3cc(C)[nH]n3)C2)n1] | A | 351.1 | A | 0.605 | ¹H NMR (400 MHz, CDCl₃) δ 7.83 (s, 1H), 7.72 (s, 1H), 7.11 (s, 1H), 7.08 (s, 1H), 6.46, 6.45 (2s, 1H), 4.29-3.57 (m, 5H), 3.96 (s, 3H), 2.54 (s, 3H), 2.44-2.38 (m, 1H), 2.35-2.30 (m, 1H), 2.35, 2.32 (2s, 3H). |
| 45 | 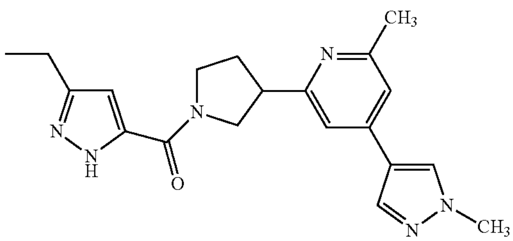 [SMILES: CCc1cc(C(=O)N2CCC(c3cc(-c4cnn(C)c4)cc(C)n3)C2)[nH]n1] | A | 365.2 | E | 2.175 | ¹H NMR (400 MHz, CDCl₃) δ 7.81 (s, 1H), 7.70 (s, 1H), 7.09 (m, 1H), 7.06 (m, 1H), 6.47, 6.46 (2s, 1H), 4.30-4.12 (m, 0.5H), 3.99-3.89 (m, 2.5H), 3.94 (s, 3H), 3.57-3.53 (m, 2H), 2.70-2.65 (m, 2H), 2.51 (s, 3H), 2.31-2.30 (m, 2H), 1.28-1.22 (m, 3H). |
| 46 | 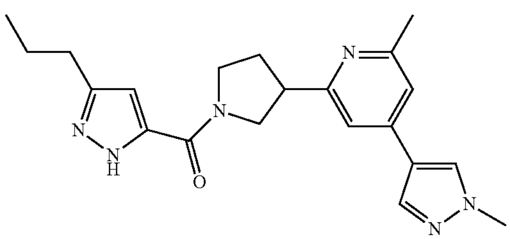 [SMILES: CCCc1cc(C(=O)N2CCC(c3cc(-c4cnn(C)c4)cc(C)n3)C2)[nH]n1] | A | 379.0 | E | 0.666 | ¹H NMR (400 MHz, CDCl₃) δ 7.84 (s, 1H), 7.73 (s, 1H), 7.12 (s, 1H), 7.09 s, 1H), 6.49, 6.47 (2s, 2H), 4.32-4.28 (m, 0.5H), 4.20-4.11 (m, 1H), 4.07-4.02 (m, 1H), 3.97 (s, 3H), 3.94-3.87 (m, 1H), 3.77-3.70 (m, 0.5H), 3.62-3.54 (m, 1H), 2.69-2.62 (m, 2H), 2.55, 2.54 (2s, 3H), 2.52-2.30 (m, 2H), 1.72-1.68 (m, 2H), 1.01-0.95 (m, 3H). |
| 47 | 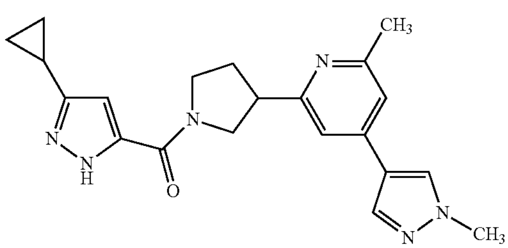 [SMILES: Cc1cc(-c2cnn(C)c2)cc(C2CCN(C(=O)c3cc(C4CC4)n[nH]3)C2)n1] | A | 377.0 | B | 1.165 | ¹H NMR (400 MHz, CDCl₃) δ 10.75 (s, 1H), 7.83 (s, 1H), 7.73 (s, 1H), 7.12-7.11 (m, 1H), 7.08 (s, 1H), 6.34, 6.32 (2s, 1H), 4.26-3.90 (m, 3H), 3.97 (s, 3H), 3.59-3.57 (m, 2H), 2.54 (s, 3H), 2.53-2.31 (m, 2H), 1.94-1.91 (m, 1H), 0.95-0.92 (m, |

TABLE 1-continued

| Ex | Structure | Synth. Method | LCMS (ESI) m/z | LCMS Method | R_T (min) | NMR |
|---|---|---|---|---|---|---|
| | | | | | | 2H), 0.78-0.74 (m, 2H). |
| 48 | 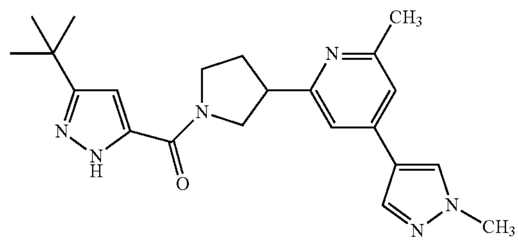 [SMILES: Cc1cc(-c2cnn(C)c2)cc(C2CCN(C(=O)c3cc(C(C)(C)C)n[nH]3)C2)n1] | A | 393.0 | C | 0.950 | $^1$H NMR (400 MHz, CDCl$_3$) δ 7.84 (s, 1H), 7.75 (s, 1H), 7.12-7.10 (m, 2H), 6.52, 6.49 (2s, 1H), 4.31-4.25 (m, 0.5H), 4.21-4.12 (m, 1H), 4.08-3.89 (m, 2H), 3.97 (s, 3H), 3.79-3.70 (m, 0.5H), 3.65-3.45 (s, 1H), 2.55, 2.54 (2s, 3H), 2.39-2.30 (m, 2H), 1.36, 1.33 (2s, 9H). |
| 49 | 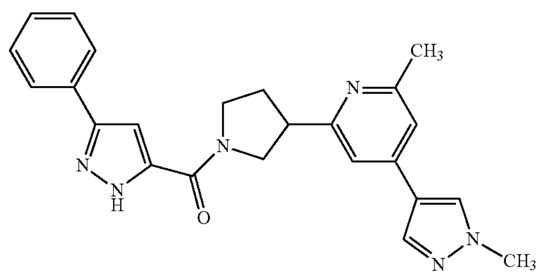 [SMILES: Cc1cc(-c2cnn(C)c2)cc(C2CCN(C(=O)c3cc(-c4ccccc4)n[nH]3)C2)n1] | A | 412.9 | B | 1.333 | $^1$H NMR (400 MHz, CDCl$_3$) δ 11.10 (s, 1H), 7.84 (s, 1H), 7.80-7.77 (m, 2H), 7.74 (s, 1H), 7.45-7.39 (m, 3H), 7.14-7.10 (m, 2H), 6.92, 6.89 (2s, 1H), 4.32-3.97 (m, 3H), 3.97 (s, 3H), 3.78-3.61 (m, 2H), 2.56 2.55 (2s, 3H), 2.52-2.35 (m, 2H). |
| 50 | 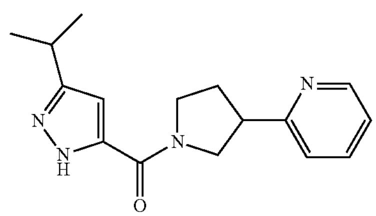 [SMILES: CC(C)c1cc(C(=O)N2CCC(c3ccccn3)C2)[nH]n1] | B | 285.0 | C | 0.886 | $^1$H NMR (400 MHz, CDCl$_3$) δ 10.70 (s, 1H), 8.60-8.57 (m, 1H), 7.68-7.64 (m, 1H), 7.24-7.17 (m, 2H), 6.50, 6.48 (2s, 1H), 4.37-4.32 (m, 0.5H), 4.22-4.14 (m, 1H), 4.08-3.85 (m, 2H), 3.79-3.71 (m, 0.5H), 3.69-3.55 (m, 1H), 3.08-2.98 (m, 1H), 2.48-2.21 (m, 2H), 1.32-1.28 (m, 6H). |
| 51 | 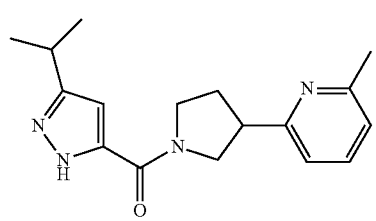 [SMILES: Cc1cccc(C2CCN(C(=O)c3cc(C(C)C)n[nH]3)C2)n1] | B | 299.0 | C | 0.884 | $^1$H NMR (400 MHz, CDCl$_3$) δ 7.55-7.51 (m, 1H), 7.05-7.01 (m, 2H), 6.49, 6.47 (2s, 1H), 4.31-4.26 (m, 0.5H), 4.16-4.07 (m, 1H), 4.03-3.85 (m, 2H), 3.75-3.68 (m, 0.5H), 3.63-3.50 (m, 1H), 3.06-2.97 (m, 1H), 2.54, 2.53 (2s, 3H), 2.43- |

TABLE 1-continued

| Ex | Structure | Synth. Method | LCMS (ESI) m/z | LCMS Method | R$_T$ (min) | NMR |
|---|---|---|---|---|---|---|
| | | | | | | 2.21 (m, 2H), 1.32-1.28 (m, 6H). |
| 52 | 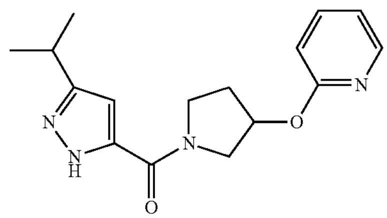 [SMILES: CC(C)c1cc(C(=O)N2CCC(Oc3ccccn3)C2)[nH]n1] | B | 301.2 | E | 0.753 | $^1$H NMR (400 MHz, CDCl$_3$) δ 11.18 (s, 1H), 8.15-8.13 (m, 1H), 7.59-7.55 (m, 1H), 6.89-6.88 (m, 1H), 6.72-6.70 (m, 1H), 6.51, 6.47 (2s, 1H), 5.70-5.65 (m, 1H), 4.17-3.92 (m, 4H), 3.04-2.99 (m, 1H), 2.29-2.24 (m, 2H), 1.28 (m, 6H). |
| 53 | 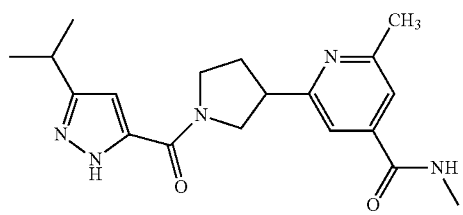 [SMILES: CNC(=O)c1cc(C)nc(C2CCN(C(=O)c3cc(C(C)C)n[nH]3)C2)c1] | A | 356.1 | A | 0.717 | $^1$H NMR (400 MHz, CDCl$_3$) δ 7.34-7.46 (m, 2H), 6.68 (s, 1H), 6.44, 6.43 (2s, 1H), 4.34-3.76 (m, 3.5H), 3.73-3.46 (m, 1.5H), 3.14-2.93 (m, 4H), 2.54 (2s, 3H), 2.47-2.14 (m, 2H), 1.27 (m, 6H). |
| 54 | 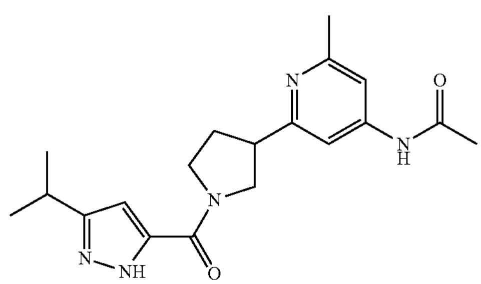 [SMILES: CC(=O)Nc1cc(C)nc(C2CCN(C(=O)c3cc(C(C)C)n[nH]3)C2)c1] | A | 356.1 | A | 0.727 | $^1$H NMR (400 MHz, CD$_3$OD) δ 7.43-7.30 (m, 2H), 6.49 (s, 1H), 4.38 (m, 0.5H), 4.24-3.46 (m, 4.5H), 3.11-2.95 (m, 1H), 2.45 (2s, 3H), 2.39-2.16 (m, 2H), 2.12 (s, 3H), 1.28 (m, 6H). |
| 55 | 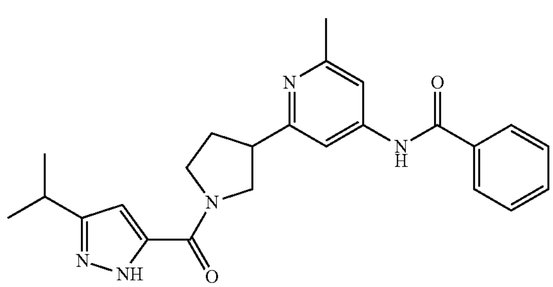 [SMILES: Cc1cc(NC(=O)c2ccccc2)cc(C2CCN(C(=O)c3cc(C(C)C)n[nH]3)C2)n1] | A | 418.1 | A | 0.893 | $^1$H NMR (400 MHz, CD$_3$OD) δ 7.93 (d, J = 7.2 Hz, 2H), 7.66-7.56 (m, 3H), 7.55-7.44 (m, 2H), 6.50 (s, 1H), 4.41 (m, 0.5H), 4.28-4.05 (m, 1H), 4.04-3.93 (m, 1H), 3.93-3.53 (m, 2.5H), 3.02 (m, 1H), 2.51 (2s, 3H), 2.46-2.17 (m, 2H), 1.29 (m, 6H) |

TABLE 1-continued

| Ex | Structure | Synth. Method | LCMS (ESI) m/z | LCMS Method | R_T (min) | NMR |
|---|---|---|---|---|---|---|
| 56 | 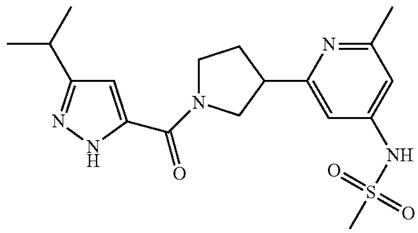 [SMILES: Cc1cc(NS(C)(=O)=O)cc(C2CCN(C(=O)c3cc(C(C)C)n[nH]3)C2)n1] | A | 392.2 | E | 0.619 | $^1$H NMR (400 MHz, CD$_3$OD) δ 6.96-6.92 (m, 2H), 6.54 (s, 1H), 4.42 (s, 0.5H), 4.20 9s, 0.5H), 4.12-4.01 (m, 2H), 3.91-3.86 (m, 1H), 3.79-3.67 (m, 1H), 3.61-3.54 (m, 1H), 3.04 (2s, 3H), 2.49 (2s, 3H), 2.44-2.39 (m, 1H), 2.27-2.15 (m, 1H), 1.32-1.29 (m, 6H). |
| 57 | 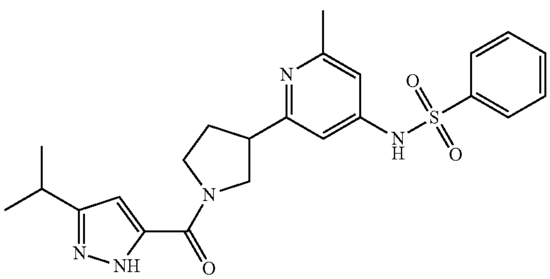 [SMILES: Cc1cc(NS(=O)(=O)c2ccccc2)cc(C2CCN(C(=O)c3cc(C(C)C)n[nH]3)C2)n1] | A | 454.2 | A | 0.862 | $^1$H NMR (400 MHz, CD$_3$OD) δ 7.84 (m, 2H), 7.60-7.33 (m, 3H), 6.93-6.70 (m, 2H), 6.53 (s, 1H), 4.33 (m, 0.5H), 3.98 (m, 2H), 3.79-3.57 (m, 1.5H), 3.53-3.39 (m, 1H), 3.03 (m, 1H), 2.44-1.97 (m, 5H), 1.39-1.23 (m, 6H). |
| 58 | 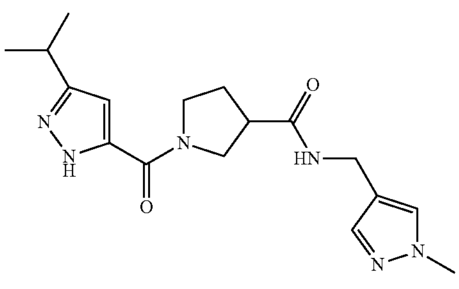 [SMILES: CC(C)c1cc(C(=O)N2CCC(C(=O)NCc3cnn(C)c3)C2)[nH]n1] | B | 345.2 | A | 0.757 | $^1$H NMR (400 MHz, DMSO-d$_6$) δ 12.91 (s, 1H), 8.31-8.29 (m, 1H), 7.55, 7.53 (2s, 1H), 7.30, 7.28 (2s, 1H), 6.30 (s, 1H), 4.10-4.07 (m, 2H), 3.77 (s, 3H), 3.30-3.70 (m, 2H), 3.00-2.80 (m, 2H), 2.00-1.80 (m, 2H), 1.21 (m, 6H). |
| 59 | 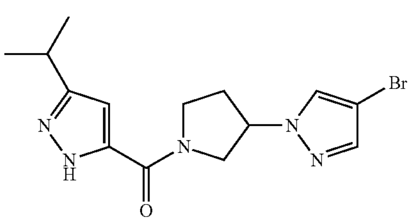 [SMILES: CC(C)c1cc(C(=O)N2CCC(n3cc(Br)cn3)C2)[nH]n1] | B | 352.1 | E | 0.783 | $^1$H NMR (400 MHz, CDCl$_3$) δ 10.29 (s, 1H), 7.49-7.48 (m, 2H), 6.55 (m, 1H), 4.99-4.92 (m, 1H), 4.39-4.37 (m, 1H), 4.14-4.12 (m, 2H), 3.91-3.86 (m, 1H), 3.06-3.01 (m, 1H), 2.49-2.43 (m, 2H), 1.32-1.30 (m, 6H). |

TABLE 1-continued

| Ex | Structure | Synth. Method | LCMS (ESI) m/z | LCMS Method | R$_T$ (min) | NMR |
|---|---|---|---|---|---|---|
| 60 | 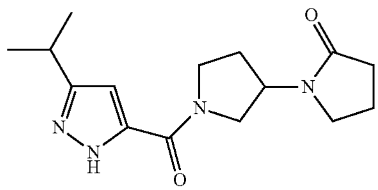 [SMILES: CC(C)c1cc(C(=O)N2CCC(N3CCCC3=O)C2)[nH]n1] | D | 313.2 | E | 0.685 | $^1$H NMR (400 MHz, CDCl$_3$) δ 6.49 (s, 1H), 4.82 (m, 1H), 4.10 (m, 1H), 3.96-3.79 (m, 2H), 3.69 (m, 1H), 3.43 (m, 2H), 3.03 (m, 1H), 2.42 (m, 2H), 2.00-2.30 (m, 4H), 1.30 (d, J = 6.8 Hz, 6H). |
| 61 | 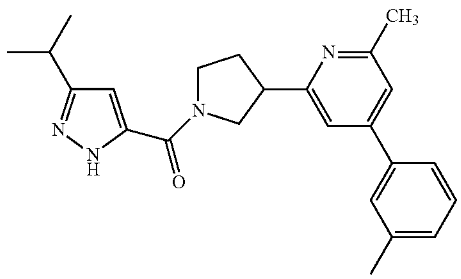 [SMILES: Cc1cccc(-c2cc(C)nc(C3CCN(C(=O)c4cc(C(C)C)n[nH]4)C3)c2)c1] | A | 388.9 | E | 0.735 | $^1$H NMR (400 MHz, CDCl$_3$) δ 7.42-7.35 (m, 3H), 7.26-7.24 (m, 3H), 6.50, 6.48 (2s, 1H), 4.35 (m, 0.5H), 4.28-3.87 (m, 3H), 3.83-3.56 (m, 1.5H), 3.13-2.99 (m, 1H), 2.60 (s, 3H), 2.53-2.27 (m, 5H), 1.30 (m, 6H). |
| 62 | 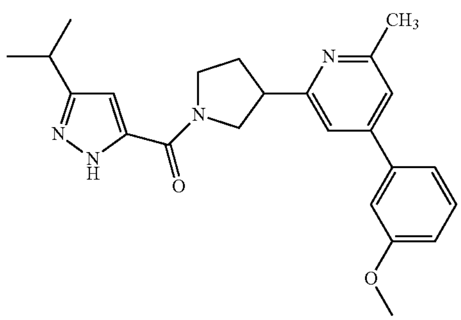 [SMILES: COc1cccc(-c2cc(C)nc(C3CCN(C(=O)c4cc(C(C)C)n[nH]4)C3)c2)c1] | A | 405.0 | E | 0.732 | $^1$H NMR (400 MHz, CDCl$_3$) δ 7.39 (m, 1H), 7.26-7.22 (m, 2H), 7.19 (m, 1H), 7.12 (s, 1H), 6.98 (m, 1H), 6.50, 6.48 (2s, 1H), 4.33 (m, 0.5H), 4.24 (m, 0.5H), 4.18-4.13 (m, 0.5H), 4.10-3.92 (m, 2H), 3.81-3.60 (m, 1.5H), 3.09-3.03 (m, 1H), 2.60, 2.59 (2s, 3H), 2.52-2.26 (m, 2H), 1.31 (m, 6H). |
| 63 | 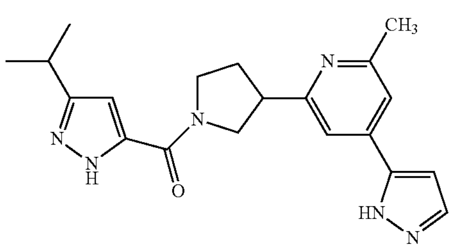 [SMILES: Cc1cc(-c2ccn[nH]2)cc(C2CCN(C(=O)c3cc(C(C)C)n[nH]3)C2)n1] | A | 385.0 | C | 0.944 | $^1$H NMR (400 MHz, CDCl$_3$) δ 7.67 (s, 1H), 7.50 (m, 1H), 7.42 (s, 1H), 6.71 (s, 1H), 6.48 (s, 1H), 4.39-4.27 (m, 0.5H), 4.23-3.83 (m, 3H), 3.79-3.56 (m, 1.5H), 3.08-2.98 (m, 1H), 2.58 (2s, 3H), 2.51-2.24 (m, 2H), 1.29 (m, 6H). |

TABLE 1-continued

| Ex | Structure | Synth. Method | LCMS (ESI) m/z | LCMS Method | R_T (min) | NMR |
|---|---|---|---|---|---|---|
| 64 | 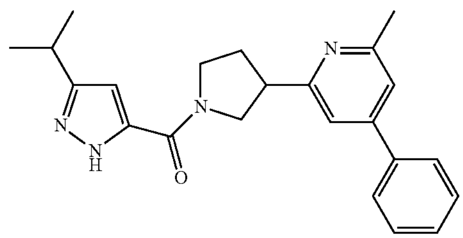 [SMILES: Cc1cc(-c2ccccc2)cc(C2CCN(C(=O)c3cc(C(C)C)n[nH]3)C2)n1] | A | 375.0 | E | 0.732 | $^1$H NMR (400 MHz, CDCl$_3$) δ 7.60 (m, 1H), 7.47-7.44 (m, 3H), 7.23 (s, 2H), 6.48 (2s, 1H), 4.36-4.31 (m, 0.5H), 4.27-4.22 (m, 0.5H), 4.18-4.13 (m, 0.5H), 4.11-4.02 (m, 1H), 4.00-3.93 (m, 1H), 3.82-3.77 (m, 0.5H), 3.72-3.61 (m, 1H), 2.60, 2.58 (2s, 3H), 2.53-2.32 (m, 2H), 1.34-1.29 (m, 6H). |
| 65 | 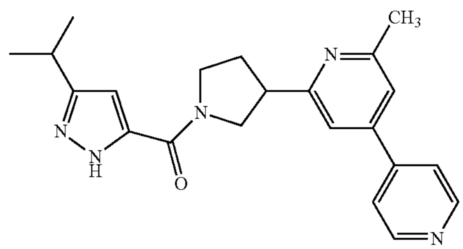 [SMILES: Cc1cc(-c2ccncc2)cc(C2CCN(C(=O)c3cc(C(C)C)n[nH]3)C2)n1] | A | 376.2 | C | 0.917 | $^1$H NMR (400 MHz, CDCl$_3$) δ 8.73 (d, J = 4.8 Hz, 2H), 7.50 (d, J = 4.0 Hz, 2H), 7.27 (m, 2H), 6.51, 6.49 (2s, 1H), 4.36 (m, 0.5H), 4.24-3.96 (m, 3H), 3.78-3.61 (m, 1.5H), 3.07-3.01 (m, 1H), 2.63, 2.62 (2s, 3H), 2.48-2.31 (m, 2H), 1.31 (m, 6H). |
| 66 | 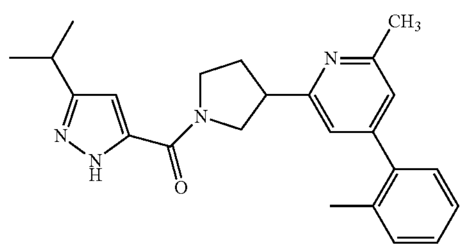 [SMILES: Cc1cc(-c2ccccc2C)cc(C2CCN(C(=O)c3cc(C(C)C)n[nH]3)C2)n1] | A | 389.0 | E | 0.724 | $^1$H NMR (400 MHz, CDCl$_3$) δ 7.29 (m, 4H), 7.19-7.18 (m, 1H), 7.02-6.99 (m, 2H), 6.49 (s, 1H), 4.34 (m, 0.5H), 4.17-3.91 (m, 3H), 3.64-3.62 (m, 1.5H), 3.02-3.2 (m, 2H), 2.59, 2.58 (2s, 3H), 2.36-2.27 (m, 2H), 2.26 (s, 3H), 1.34-1.29 (m, 6H). |
| 67 | 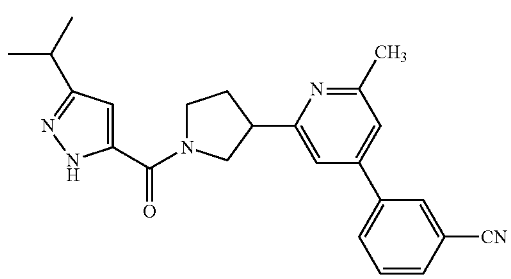 [SMILES: Cc1cc(-c2cccc(C#N)c2)cc(C2CCN(C(=O)c3cc(C(C)C)n[nH]3)C2)n1] | A | 400.2 | A | 1.78 | $^1$H NMR (400 MHz, CDCl$_3$) δ 7.89 (m, 1H), 7.83 (m, 1H), 7.73 (m, 1H), 7.62 (m, 1H), 7.22 (m, 2H), 6.51, 6.50 (2s, 1H), 4.35-4.10 (m, 2H), 3.98-3.62 (m, 3H), 3.04-3.00 (m, 1H), 2.63 (s, 3H), 2.38-2.33 (m, 2H), 1.32 (m, 6H). |

TABLE 1-continued

| Ex | Structure | Synth. Method | LCMS (ESI) m/z | LCMS Method | R$_T$ (min) | NMR |
|---|---|---|---|---|---|---|
| 68 | 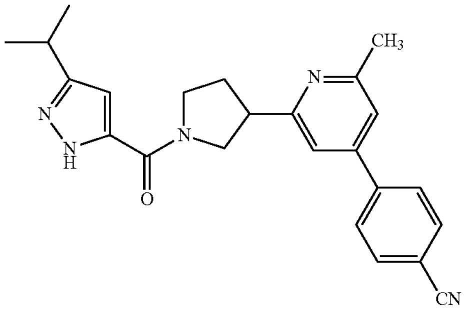 [SMILES: Cc1cc(-c2ccc(C#N)cc2)cc(C2CCN(C(=O)c3cc(C(C)C)n[nH]3)C2)n1] | A | 400.0 | E | 0.73 | $^1$H NMR (400 MHz, CDCl$_3$) δ 7.79 (d, J = 8.0 Hz, 2H), 7.71 (d, J = 8.0 Hz, 2H), 7.24 (m, 2H), 6.51, 6.49 (2s, 1H), 4.35-4.09 (m, 2H), 4.01-3.68 (m, 3H), 3.05-3.02 (m, 1H), 2.62 (2s, 3H), 2.37-2.33 (m, 2H), 1.32 (m, 6H). |
| 69 | 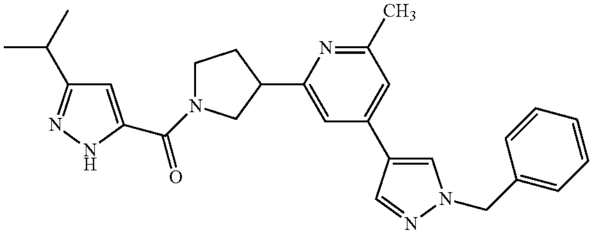 [SMILES: Cc1cc(-c2cnn(Cc3ccccc3)c2)cc(C2CCN(C(=O)c3cc(C(C)C)n[nH]3)C2)n1] | A | 455.0 | C | 1.165 | $^1$H NMR (400 MHz, CDCl$_3$) δ 7.89 (s, 1H), 7.73 (s, 1H), 7.41-7.35 (m, 2H), 7.30-7.28 (m, 3H), 7.11-7.00 (m, 2H), 6.48, 6.46 (2s, 1H), 5.36 (s, 2H), 4.30-4.20 (m, 0.5H), 4.20-4.11 (m, 1H), 4.05-3.90 (m, 1H), 3.89-3.80 (m, 1H), 3.75-3.70 (m, 0.5H), 3.61-3.52 (m, 1H), 3.09-2.99 (m, 1H), 2.53, 2.52 (2s, 3H), 2.44-2.31 (m, 2H), 1.33-1.25 (m, 6H). |
| 70 | 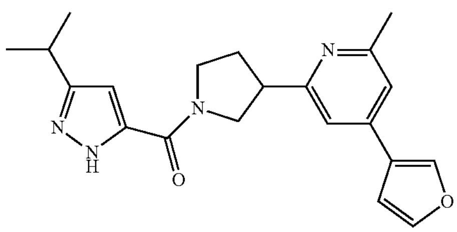 [SMILES: Cc1cc(-c2ccoc2)cc(C2CCN(C(=O)c3cc(C(C)C)n[nH]3)C2)n1] | A | 365.0 | C | 1.023 | $^1$H NMR (400 MHz, CDCl$_3$) δ 7.86 (s, 1H), 7.53 (s, 1H), 7.17-7.08 (m, 2H), 6.73 (s, 1H), 6.50, 6.48 (2s, 1H), 4.36-4.27 (m, 1H), 4.23-4.10 (m, 1H), 4.08-3.96 (m, 1H), 3.96-3.86 (m, 1H), 3.79-3.68 (m, 1H), 3.60 (m, 1H), 3.09-2.95 (m, 1H), 2.57, 2.56 (2s, 3H), 2.42-2.24 (m, 1H), 1.23-1.35 (m, 6H). |
| 71 | 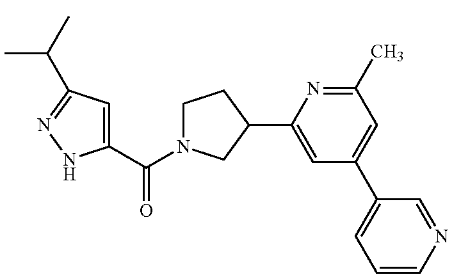 [SMILES: Cc1cc(-c2cccnc2)cc(C2CCN(C(=O)c3cc(C(C)C)n[nH]3)C2)n1] | A | 376.2 | C | 2.304 | $^1$H NMR (400 MHz, DMSO-d$_6$) δ 8.87 (s, 1H), 8.69 (d, J = 4.8 Hz, 1H), 7.90 (d, J = 8.0 Hz, 1H), 7.42 (dd, J = 8.0, 4.8 Hz, 1H), 7.27-7.23 (m, 2H), 6.50, 6.49 (2s, 1H), 4.35-4.34 (m, 0.5H), 4.20-4.09 (m, 3H), 3.98-3.92 (m, 1H), 3.04-3.02 (m, 1H), 2.63 (s, 3H), 2.39-2.34 (m, 2H), 1.32-1.28 (m, 6H). |

TABLE 1-continued

| Ex | Structure | Synth. Method | LCMS (ESI) m/z | LCMS Method | R_T (min) | NMR |
|---|---|---|---|---|---|---|
| 72 | 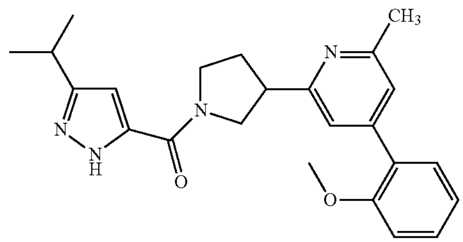 [SMILES: COc1ccccc1-c1cc(C)nc(C2CCN(C(=O)c3cc(C(C)C)n[nH]3)C2)c1] | A | 405.0 | E | 0.740 | $^1$H NMR (400 MHz, CDCl$_3$) δ 7.39 (m, 1H), 7.30-7.18 (m, 2H), 7.18 (m, 1H), 7.03-6.97 (m, 2H), 6.47, 6.45 (2s, 1H), 4.29-3.94 (m, 3H), 3.90, 3.88 (2s, 3H), 3.80-3.50 (m, 2H), 3.06-2.90 (m, 1H), 2.56, 2.55 (2s, 3H), 2.45-2.27 (m, 2H), 1.29-1.25 (m, 6H). |
| 73 | 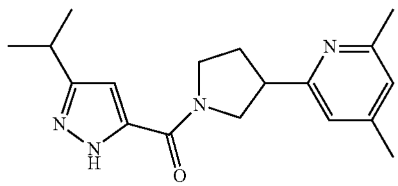 [SMILES: Cc1cc(C)nc(C2CCN(C(=O)c3cc(C(C)C)n[nH]3)C2)c1] | A | 313.1 | C | 0.931 | $^1$H NMR (400 MHz, CDCl$_3$) δ 6.88-6.85 (m, 2H), 6.49 (2s, 1H), 4.30-4.26 (m, 0.5H), 4.17-4.08 (m, 1H), 4.02-3.84 (m, 2H), 3.76-3.68 (m, 0.5H), 3.61-3.47 (m, 1H), 3.05-3.00 (m, 1H), 2.50, 2.49 (2s, 3H), 2.45-2.25 (m, 2H), 2.30 (s, 3H), 1.32-1.28 (m, 6H). |
| 74 | 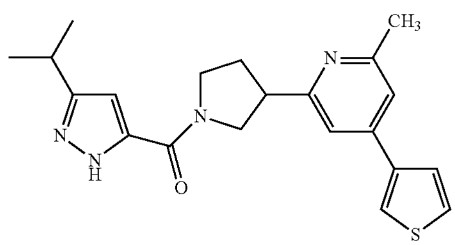 [SMILES: Cc1cc(-c2ccsc2)cc(C2CCN(C(=O)c3cc(C(C)C)n[nH]3)C2)n1] | A | 381.0 | C | 1.014 | $^1$H NMR (400 MHz, CDCl$_3$) δ 7.61 (s, 1H), 7.45-7.35 (m, 2H), 7.25-7.15 (m, 2H), 6.48, 6.46 (2s, 1H), 4.38-4.25 (m, 0.5H), 4.20-4.08 (m, 1H), 4.06-3.89 (m, 2H), 3.76-3.69 (m, 0.5H), 3.66-3.55 (m, 1H), 3.06-2.96 (m, 1H), 2.56, 2.55 (2s, 3H), 2.47-2.24 (m, 2H), 1.28 (m, 6H). |
| 75 | 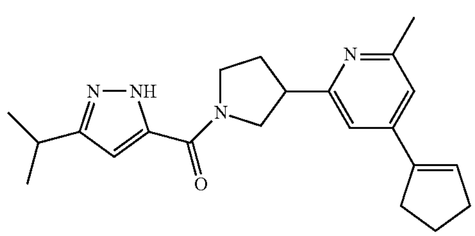 [SMILES: Cc1cc(C2=CCCC2)cc(C2CCN(C(=O)c3cc(C(C)C)n[nH]3)C2)n1] | A | 365.2 | C | 1.101 | $^1$H NMR (400 MHz, CDCl$_3$) δ 7.03 (s, 2H), 6.49-6.47 (m, 1H), 6.40 (s, 1H), 4.26-4.12 (m, 1H), 4.10-3.87 (m, 2H), 3.83-3.72 (m, 1H), 3.68-3.52 (m, 1H), 3.14-3.00 (m, 1H), 2.72 (m, 2H), 2.64-2.54 (m, 2H), 2.53 (s, 3H), 2.52-2.28 (m, 2H), 2.08 (m, 2H), 1.34 (m, 6H). |
| 76 | 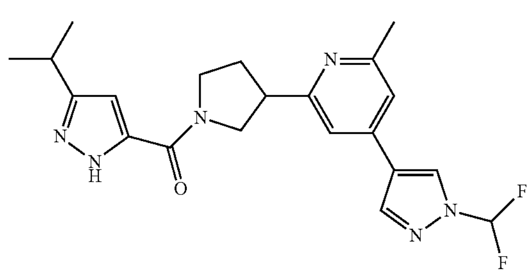 [SMILES: Cc1cc(-c2cnn(C(F)F)c2)cc(C2CCN(C(=O)c3cc(C(C)C)n[nH]3)C2)n1] | A | 415.2 | C | 2.098 | $^1$H NMR (400 MHz, CDCl$_3$) δ 8.17 (s, 1H), 7.99 (s, 1H), 7.24 (m, 1H), 7.18 (m, 1H), 7.15 (s, 1H), 6.51, 6.49 (2s, 1H), 4.35-4.30 (m, 0.5H), 4.21-4.14 (m, 1H), 4.10-3.92 (m, 2H), 3.79-3.71 (m, 0.5H), 3.65- |

TABLE 1-continued

| Ex | Structure | Synth. Method | LCMS (ESI) m/z | LCMS Method | R$_T$ (min) | NMR |
|---|---|---|---|---|---|---|
| | | | | | | 3.56 (m, 1H), 3.08-2.99 (m, 1H), 2.58 (2s, 3H), 2.36-3.32 (m, 2H), 1.33-1.29 (m, 6H). |
| 77 | 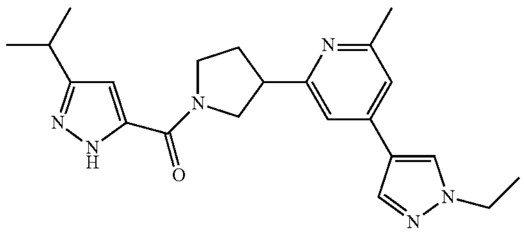 [SMILES: CCn1cc(-c2cc(C)nc(C3CCN(C(=O)c4cc(C(C)C)n[nH]4)C3)c2)cn1] | A | 393.2 | C | 1.028 | $^1$H NMR (400 MHz, CDCl$_3$) δ 7.84 (s, 1H), 7.76 (m, 1H), 7.11 (m, 2H), 6.50, 6.48 (2s, 1H), 4.32 (m, 1H), 4.27-4.09 (m, 3H), 4.09-3.87 (m, 2H), 3.79-3.68 (m, 1H), 3.57 (m, 1H), 3.09-2.94 (m, 1H), 2.54 (s, 3H), 2.48-2.22 (m, 2H), 1.59-1.47 (m, 3H), 1.29 (m, 6H). |
| 78 | 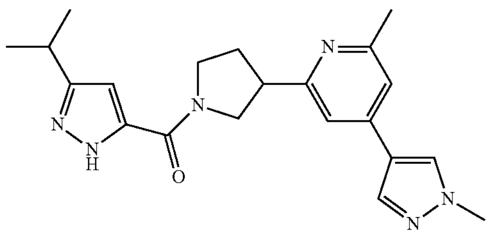 [SMILES: Cc1cc(-c2cnn(C)c2)cc(C2CCN(C(=O)c3cc(C(C)C)n[nH]3)C2)n1] | A | 378.2 | C | 1.058 | $^1$H NMR (400 MHz, CDCl$_3$) δ 7.09-7.00 (m, 2H), 6.77 (s, 1H), 6.49 (s, 1H), 6.38 (s 1H), 6.22 (s, 1H), 4.36-4.26 (m, 1H), 4.22-3.87 (m, 3H), 3.80-3.69 (m, 4H), 3.68-3.53 (m, 1H), 3.09-2.95 (m, 1H), 2.57 (2s, 3H), 2.51-2.24 (m, 2H), 1.36-1.24 (m, 6H). |
| 79 | 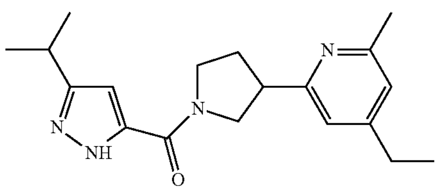 [SMILES: CCc1cc(C)nc(C2CCN(C(=O)c3cc(C(C)C)n[nH]3)C2)c1] | A | 327.1 | C | 0.990 | $^1$H NMR (400 MHz, CDCl$_3$) δ 6.89-6.83 (m, 2H), 6.49, 6.46 (2s, 1H), 4.30-3.87 (m, 5H), 3.05-3.02 (m, 1H), 2.61-2.59 (m, 2H), 2.51 (s, 3H), 2.50-2.30 (m, 2H), 1.33-1.23 (m, 9H).. |
| 80 | 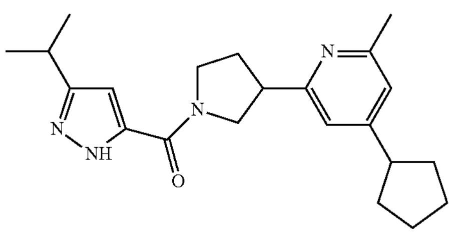 [SMILES: Cc1cc(C2CCCC2)cc(C2CCN(C(=O)c3cc(C(C)C)n[nH]3)C2)n1] | A | 367.1 | C | 1.115 | $^1$H NMR (400 MHz, CDCl$_3$) δ 6.91-6.88 (m, 2H), 6.49, 6.46 (2s, 1H), 4.27-3.52 (m, 5H), 3.18-3.02 (m, 1H), 2.93-2.90 (m, 2H), 2.51 (s, 3H), 2.50-2.30 (m, 2H), 2.06-1.90 (m, 2H), 1.84-1.70 (m, 5H), 1.32-1.28 (m, 6H). |
| 81 | 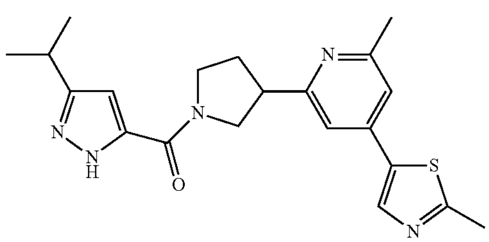 [SMILES: Cc1cc(-c2cnc(C)s2)cc(C2CCN(C(=O)c3cc(C(C)C)n[nH]3)C2)n1] | A | 396.2 | C | 1.722 | $^1$H NMR (400 MHz, CDCl$_3$) δ 7.97 (s, 1H), 7.16-7.13 (m, 2H), 6.51, 6.49 (2s, 1H), 4.35-4.30 (m, 0.5H), 4.22-4.123 (m, 1H), 4.07-4.00 (m, 1H), 3.95-3.89 (m, 1H), 3.78-3.71 (m, 0.5H), 3.64-3.52 (m, 1H), 3.09-2.99 (m, 1H), 2.77 (s, 3H), 2.57 (2s, |

TABLE 1-continued

| Ex | Structure | Synth. Method | LCMS (ESI) m/z | LCMS Method | R_T (min) | NMR |
|---|---|---|---|---|---|---|
| | | | | | | 3H), 2.47-2.31 (m, 2H), 1.33-1.29 (m, 6H). |
| 82 | 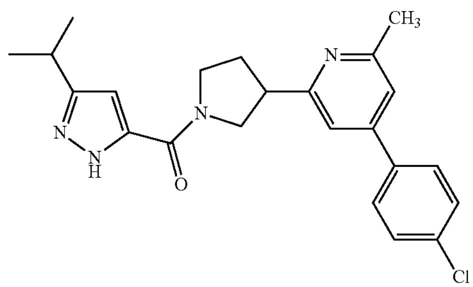 [SMILES: Cc1cc(-c2ccc(Cl)cc2)cc(C2CCN(C(=O)c3cc(C(C)C)n[nH]3)C2)n1] | A | 409.1 | E | 0.765 | $^1$H NMR (400 MHz, CDCl$_3$) δ 7.55 (m, 2H), 7.45 (m, 2H), 7.20 (m, 2H), 6.48, 6.47 (2s, 1H), 4.33-4.21 (m, 1H), 4.18-3.86 (m, 2H), 3.79-3.58 (m, 1.5H), 3.13-3.02 (m, 0.5H), 2.60, 2.59 (2s, 3H), 2.50-2.20 (m, 2H) 1.34-1.29 (m, 6H). |
| 83 | 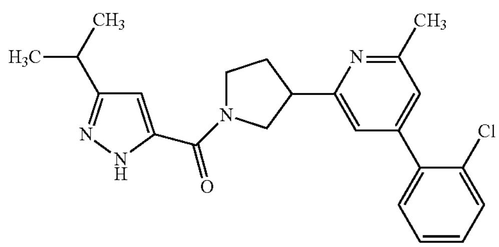 [SMILES: Cc1cc(-c2ccccc2Cl)cc(C2CCN(C(=O)c3cc(C(C)C)n[nH]3)C2)n1] | A | 409.3 | C | 1.134 | $^1$H NMR (400 MHz, CDCl$_3$) δ 7.50-7.49 (m, 1H), 7.37-7.30 (m, 3H), 7.20-7.12 (m, 2H), 6.49 (s, 1H), 4.37-3.64 (m, 5H), 3.04-3.00 (m, 1H), 2.61 (s, 3H), 2.37-2.34 (m, 1H), 1.32-1.29 (m, 6H). |
| 84 | 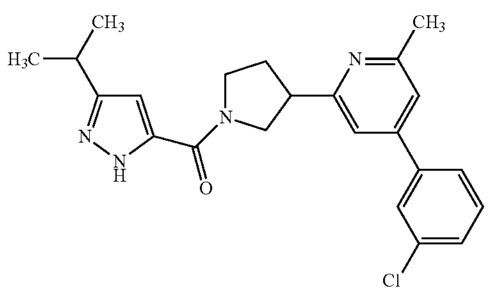 [SMILES: Cc1cc(-c2cccc(Cl)c2)cc(C2CCN(C(=O)c3cc(C(C)C)n[nH]3)C2)n1] | A | 409.1 | C | 1.156 | $^1$H NMR (400 MHz, CDCl$_3$) δ 7.59-7.49 (m, 1H), 7.48-7.45 (m, 1H), 7.42-7.41 (m, 2H), 7.23-7.21 (m, 2H), 6.51, 6.49 (2s, 1H1H), 4.35-3.60 (m, 1H), 2.62 (s, 3H), 2.61-2.34 (m, 2H), 1.33-1.29 (m, 6H). |
| 85 | 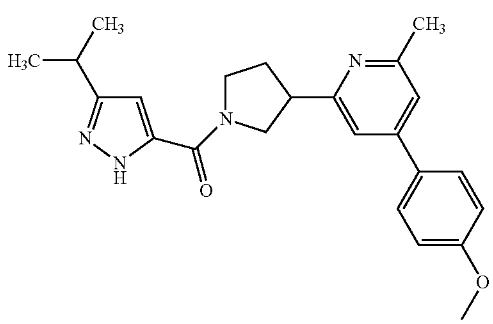 [SMILES: COc1ccc(-c2cc(C)nc(C3CCN(C(=O)c4cc(C(C)C)n[nH]4)C3)c2)cc1] | A | 405.2 | C | 1.094 | $^1$H NMR (400 MHz, CDCl$_3$) δ 7.57 (d, J = 8.4 Hz, 2H), 7.23-7.20 (m, 2H), 7.02-6.99 (m, 2H), 6.50, 6.48 (2s, 1H), 4.33-3.50 (m, 8H), 3.05-3.00 (m, 1H), 2.60 (s, 3H), 2.59-2.33 (m, 2H), 1.30-1.28 (m, 6H). |
| 86 | 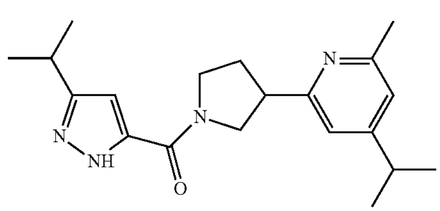 [SMILES: Cc1cc(C(C)C)cc(C2CCN(C(=O)c3cc(C(C)C)n[nH]3)C2)n1] | A | 341.2 | C | 1.012 | $^1$H NMR (400 MHz, CDCl$_3$) δ 7.27 (s, 1H), 6.90-6.87 (m, 2H), 6.49, 6.46 (2s, 1H), 4.29-3.54 (m, 5H), 3.04-3.00 (m, 1H), 2.83-2.82 (m, 1H), 2.52 (s, 3H), 2.51-2.28 (m, 2H), 1.32-1.23 (m, 12H). |

TABLE 1-continued

| Ex | Structure | Synth. Method | LCMS (ESI) m/z | LCMS Method | R$_T$ (min) | NMR |
|---|---|---|---|---|---|---|
| 87 | 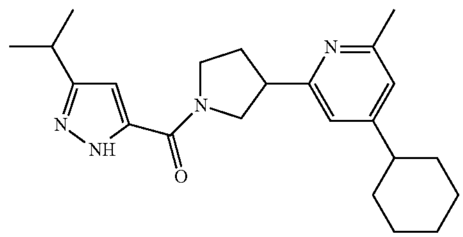 [SMILES: Cc1cc(C2CCCCC2)cc(C2CCN(C(=O)c3cc(C(C)C)n[nH]3)C2)n1] | A | 381.3 | C | 1.143 | $^1$H NMR (400 MHz, CDCl$_3$) δ 6.89-6.85 (m, 2H), 6.48, 6.45 (2s, 1H1), 4.27-3.50 (m, 5H), 3.20-2.90 (m, 1H), 2.51 (s, 3H), 2.50-2.20 (m, 3H), 1.86-1.80 (m, 6H), 1.39-1.36 (m, 4H), 1.32-1.27 (m, 6H). |
| 88 | 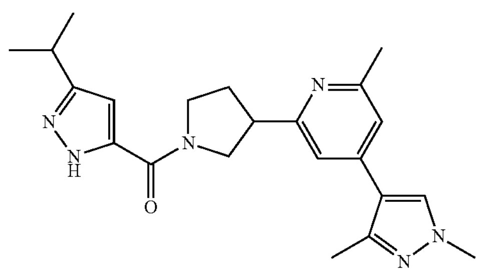 [SMILES: Cc1cc(-c2cn(C)nc2C)cc(C2CCN(C(=O)c3cc(C(C)C)n[nH]3)C2)n1] | A | 393.3 | E | 0.679 | $^1$H NMR (400 MHz, CDCl$_3$) δ 7.60 (s, 1H), 7.08 (s, 2H), 6.50, 6.48 (2s, 1H), 4.33-4.28 (m, 0.5H), 4.23-4.18 (m, 0.5H), 4.13-4.06 (m, 1H), 4.04-3.98 (m, 0.5H), 3.95-3.94 (m, 0.5H), 3.89 (s, 3H), 3.80-3.60 (m, 2H), 3.10-3.03 (m, 1H), 2.58 (s, 3H), 2.48-2.32 (m, 2H), 2.43 (s, 3H), 1.33-1.29 (m, 6H). |
| 89 | 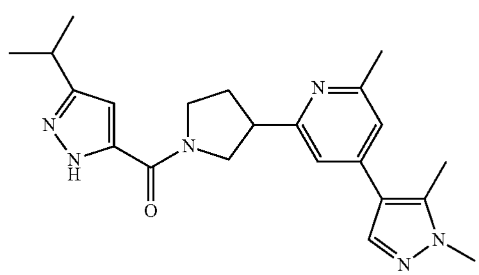 [SMILES: Cc1cc(-c2cnn(C)c2C)cc(C2CCN(C(=O)c3cc(C(C)C)n[nH]3)C2)n1] | A | 393.2 | E | 0.674 | $^1$H NMR (400 MHz, CDCl$_3$) δ 7.64 (s, 1H), 7.06-7.04 (m, 2H), 6.49, 6.48 (2s, 1H), 4.33-4.28 (m, 0.5H), 4.23-4.18 (m, 0.5H), 4.14-4.07 (m, 1H), 4.04-4.00 (m, 0.5H), 3.96-3.92 (m, 0.5H), 3.87 (s, 3H), 3.80-3.60 (m, 2H), 3.10-3.02 (m, 1H), 2.57 (2s, 3H), 2.48-2.30 (m, 2H), 2.45 (s, 1H), 1.34-1.29 (m, 6H). |
| 90 | 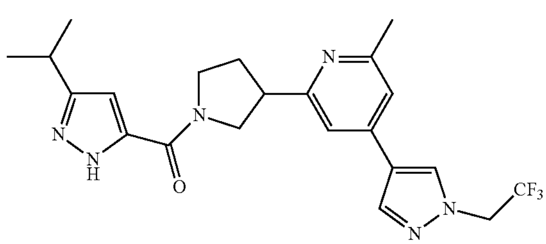 [SMILES: Cc1cc(-c2cnn(CC(F)(F)F)c2)cc(C2CCN(C(=O)c3cc(C(C)C)n[nH]3)C2)n1] | A | 447.2 | E | 0.718 | $^1$H NMR (400 MHz, CDCl$_3$) δ 7.94 (s, 1H), 7.88 (s, 1H), 7.15-7.12 (m, 2H), 6.51, 6.48 (2s, 1H), 4.77 (m, 2H), 4.34-4.29 (m, 0.5H), 4.22-3.13 (m, 1H), 4.09-3.89 (m, 2H), 3.80-3.72 (m, 0.5H), 3.68-3.55 (m, 1H), 3.08-3.01 (m, 1H), 2.57 (2s, 3H), 2.50-2.29 (m, 2H), 1.33-1.29 (m, 6H). |

TABLE 1-continued
| Ex | Structure | Synth. Method | LCMS (ESI) m/z | LCMS Method | R$_T$ (min) | NMR |
|---|---|---|---|---|---|---|
| 91 | 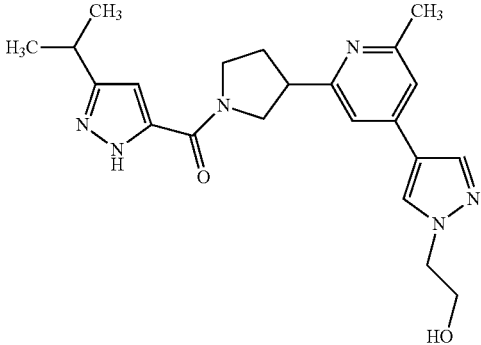 [SMILES: Cc1cc(-c2cnn(CCO)c2)cc(C2CCN(C(=O)c3cc(C(C)C)n[nH]3)C2)n1] | A | 409.3 | C | 0.931 | $^1$H NMR (400 MHz, CDCl$_3$) δ 7.87 (s, 1H), 7.83 (s, 1H), 7.13-7.09 (m, 2H), 6.50, 6.48 (2s, 1H), 4.32-4.31 (m, 2H), 4.30-3.58 (m, 7H), 3.05-3.02 (m, 1H), 2.55 (s, 3H), 2.54-2.32 (m, 2H), 1.33-1.28 (m, 6H). |
| 92 | 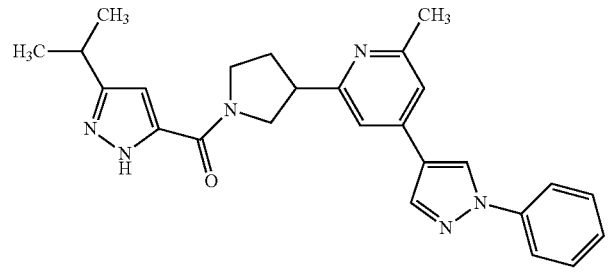 [SMILES: Cc1cc(-c2cnn(-c3ccccc3)c2)cc(C2CCN(C(=O)c3cc(C(C)C)n[nH]3)C2)n1] | A | 441.2 | C | 1.147 | $^1$H NMR (400 MHz, CDCl$_3$) δ 8.28 (s, 1H), 8.06 (s, 1H), 7.76-7.74 (m, 2H), 7.53-7.49 (m, 2H), 7.38-7.36 (m, 1H), 7.22-7.19 (m, 2H), 6.51, 6.49 (2s, 1H), 4.34-3.62 (m, 5H), 3.05-3.00 (m, 1H), 2.59 (s, 3H), 2.58-2.34 (m, 1H), 1.33-1.28 (m, 6H). |
| 93 | 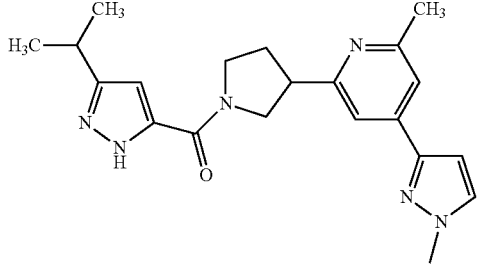 [SMILES: Cc1cc(-c2ccn(C)n2)cc(C2CCN(C(=O)c3cc(C(C)C)n[nH]3)C2)n1] | A | 379.2 | C | 0.984 | $^1$H NMR (400 MHz, CDCl$_3$) δ 7.44-7.43 (m, 3H), 6.62 (s, 1H), 6.50-6.47 (m, 1H), 4.32-3.64 (m, 8H), 3.05-3.00 (m, 1H), 2.58 (s, 3H), 2.57-2.33 (m, 2H), 1.32-1.28 (m, 6H). |
| 94 | 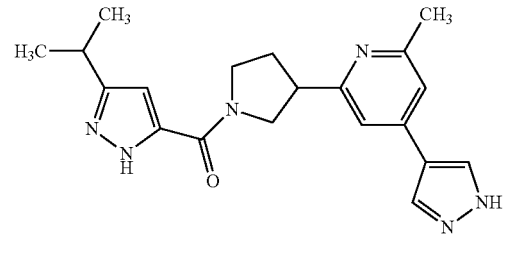 [SMILES: Cc1cc(-c2cn[nH]c2)cc(C2CCN(C(=O)c3cc(C(C)C)n[nH]3)C2)n1] | A | 365.0 | C | 0.939 | $^1$H NMR (400 MHz, CDCl$_3$) δ 7.96 (s, 2H), 7.17-7.13 (m, 2H), 6.51, 6.49 (2s, 1H), 4.34-3.58 (m, 5H), 3.05-3.01 (m, 1H), 2.57 (s, 3H), 2.56-2.32 (m, 2H), 1.33-1.28 (m, 6H). |
| 95 | 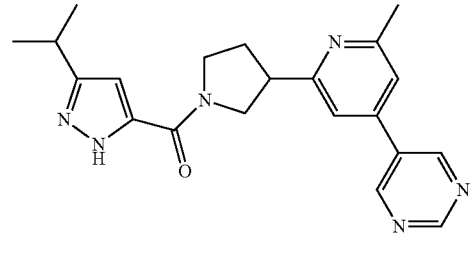 [SMILES: Cc1cc(-c2cncnc2)cc(C2CCN(C(=O)c3cc(C(C)C)n[nH]3)C2)n1] | A | 377.1 | C | 0.926 | $^1$H NMR (400 MHz, CDCl$_3$) δ 10.42 (s, 1H), 9.30 (s, 1H), 8.98 (s, 2H), 7.26-7.23 (m, 2H), 6.51 (2s, 1H), 4.39-4.35 (m, 0.5H), 4.24-4.17 (m, 1H), 4.14-4.09 (m, 0.5H), 4.04-3.93 (m, 1H), 3.81-3.62 (m, 2H), 3.05-3.00 (m, 1H), 2.65 (2s, 3H), 2.39-2.37 (m, 2H), 1.33-1.29 (m, 6H). |

TABLE 1-continued

| Ex | Structure | Synth. Method | LCMS (ESI) m/z | LCMS Method | R_T (min) | NMR |
|---|---|---|---|---|---|---|
| 96 | 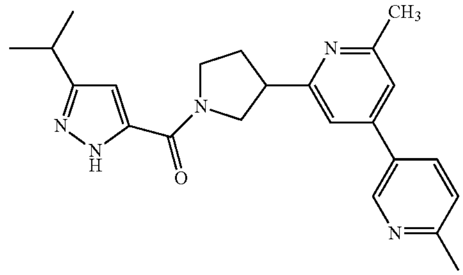 [SMILES: Cc1ccc(-c2cc(C)nc(C3CCN(C(=O)c4cc(C(C)C)n[nH]4)C3)c2)cn1] | A | 390.3 | E | 0.653 | $^1$H NMR (400 MHz, CDCl$_3$) δ 8.75 (s, 1H), 7.79 (m, 1H), 7.27-7.20 (m, 3H), 6.48, 6.47 (2s, 1H), 4.35-4.30 (m, 0.5H), 4.23-43.91 (m, 3H), 3.77-3.59 (m, 1.5H), 3.06-3.00 (m, 1H), 2.62-2.59 (m, 6H), 2.50-2.32 (m, 2H), 1.31-1.27 (m, 6H). |
| 97 | 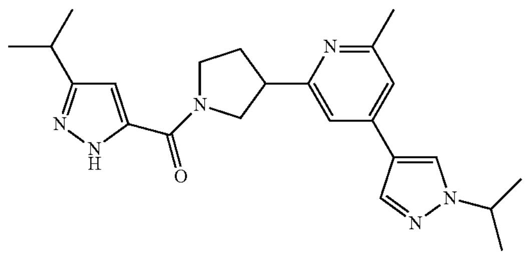 [SMILES: Cc1cc(-c2cnn(C(C)C)c2)cc(C2CCN(C(=O)c3cc(C(C)C)n[nH]3)C2)n1] | A | 407.1 | C | 1.235 | $^1$H NMR (400 MHz, CD$_3$OD) δ 8.72 (m, 1H), 8.30 (s, 1H), 8.11-7.93 (m, 2H), 6.86 (2s, 1H), 4.71-4.49 (m, 1H), 4.36-4.16 (m, 1H), 4.05 (m, 1H), 3.97-3.73 (m, 2H), 3.23-3.06 (m, 1H), 2.85-2.72 (m, 3H), 2.71-2.37 (m, 2H), 1.66-1.49 (m, 6H), 1.36 (m, 6H). |
| 98 | 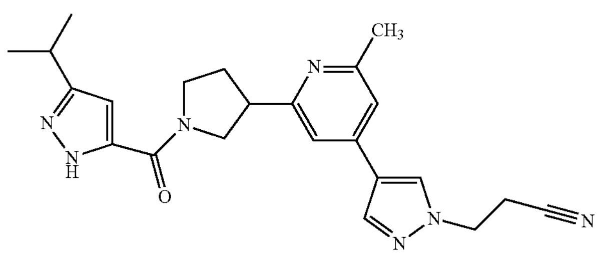 [SMILES: Cc1cc(-c2cnn(CCC#N)c2)cc(C2CCN(C(=O)c3cc(C(C)C)n[nH]3)C2)n1] | A | 418.1 | C | 0.986 | $^1$H NMR (400 MHz, CDCl$_3$) δ 7.91-7.87 (m, 2H), 7.14-7.11 (m, 2H), 6.50, 6.48 (2s, 1H), 4.46 (t, J = 6.4 Hz, 2H), 4.17-3.43 (m, 5H), 3.05-2.99 (m, 3H), 2.56, 2.55 (2s, 3H), 2.36-2.29 (m, 2H), 1.33-1.28 (m, 6H). |
| 99 | 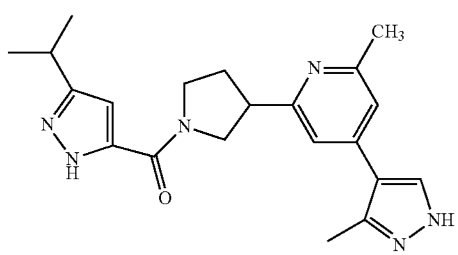 [SMILES: Cc1cc(-c2c[nH]nc2C)cc(C2CCN(C(=O)c3cc(C(C)C)n[nH]3)C2)n1] | A | 379.2 | C | 0.935 | $^1$H NMR (400 MHz, CDCl$_3$) δ 7.77 (s, 1H), 7.09-7.05 (m, 2H) 6.50, 6.49 (2s, 1H), 4.34-3.60 (m, 5H), 3.05-3.00 (m, 1H), 2.58 (s, 3H), 2.57-2.34 (m, 5H), 1.33-1.28 (m, 6H). |
| 100 | 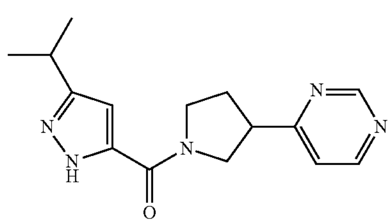 [SMILES: CC(C)c1cc(C(=O)N2CCC(c3ccncn3)C2)[nH]n1] | B | 286.1 | E | 0.686 | $^1$H NMR (400 MHz, DMSO-d$_6$) δ 12.93, 12.89 (2s, 1H), 9.12 (s, 1H), 8.74-8.72 (m, 1H), 7.54-7.50 (m, 1H), 6.37 (s, 1H), 4.39-4.30 (m, 0.5H), 4.14-3.83 (m, 2H), 3.71-3.48 (m, 2.5H), 3.02-2.81 (m, 1H), 2.38-1.99 (m, 2H), 1.23-1.20 (m, 6H). |

TABLE 1-continued
| Ex | Structure | Synth. Method | LCMS (ESI) m/z | LCMS Method | R_T (min) | NMR |
|---|---|---|---|---|---|---|
| 101 | 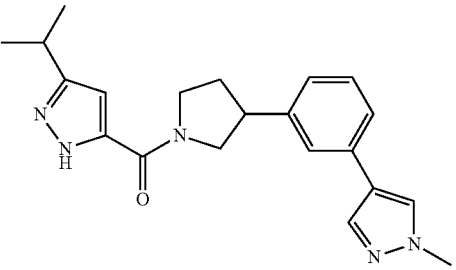 [SMILES: CC(C)c1cc(C(=O)N2CCC(c3cccc(-c4cnn(C)c4)c3)C2)[nH]n1] | B | 284.0 | E | 0.761 | ¹H NMR (400 MHz, CDCl₃) δ 7.75 (s, 1H), 7.61 (s, 1H), 7.21-7.18 (m, 2H), 6.96 (s, 1H), 6.50, 6.46 (2s, 1H), 4.35-4.30 (m, 0.5H), 4.24-4.12 (m, 1H), 4.07-3.87 (m, 4H), 3.79-3.67 (m, 1.5H), 3.49-3.37 (m, 1H), 3.10-2.99 (m, 1H), 2.46-2.26 (m, 4H), 2.21-2.05 (m, 1H), 1.33-1.28 (m, 6H). |
| 102 | 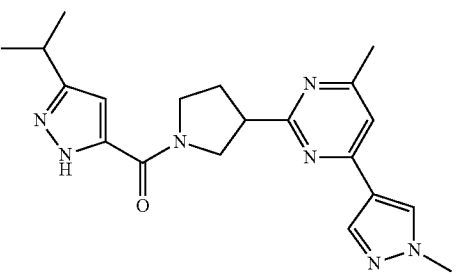 [SMILES: Cc1cc(-c2cnn(C)c2)nc(C2CCN(C(=O)c3cc(C(C)C)n[nH]3)C2)n1] | B | 380.2 | C | 1.056 | ¹H NMR (400 MHz, CDCl₃) δ 8.02 (m, 1H), 7.97 (s, 1H), 7.12 (m, 1H), 6.49 (2s, 1H), 3.27-4.24 (m, 1H), 4.22-4.08 (m, 1.5H), 4.01-3.98 (m, 0.5H), 3.96 (2s, 3H), 3.82-3.64 (m, 2H), 3.11-3.03 (m, 1H), 2.48-2.37 (m, 5H), 1.32-1.29 (m, 6H). |
| 103 | 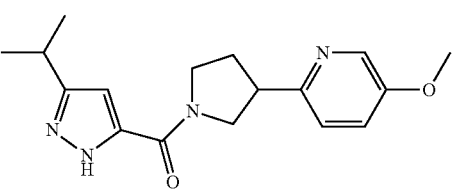 [SMILES: COc1ccc(C2CCN(C(=O)c3cc(C(C)C)n[nH]3)C2)nc1] | B | 315.1 | E | 0.666 | ¹H NMR (400 MHz, CDCl₃) δ 8.28, 8.26 (2s, 1H), 7.19 (s, 2H), 6.49, 6.46 (2s, 1H), 4.30-4.21 (m, 1H), 4.15-4.08 (m, 0.5H), 4.05-4.01 (m, 1H), 3.8 (m, 0.5H), 3.86 (2s, 3H), 3.83-3.75 (m, 1H), 3.70-3.54 (m, 1H), 3.16-3.05 (m, 2H), 1.33-1.29 (m, 6H). |
| 104 | 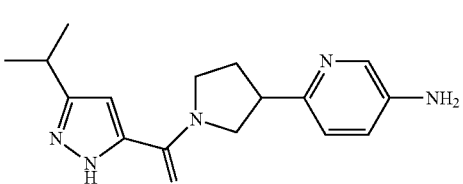 | B | 300.1 | C | 0.874 | ¹H NMR (400 MHz, DMSO-d₆) δ 12.90, 12.86 (2s, 1H), 7.88 (s, 1H), 7.01-6.95 (m, 1H), 6.94-6.85 (m, 1H), 6.38 (s, 1H), 5.17 (s, 2H), 4.26-4.09 (m, 1.5H), 3.87-3.67 (m, 2.5H), 3.52-3.45 (m, 1H), 3.00-2.90 (m, 1H), 2.25-2.00 (m, 2H), 1.23-1.21 (m, 6H). |
| 105 | 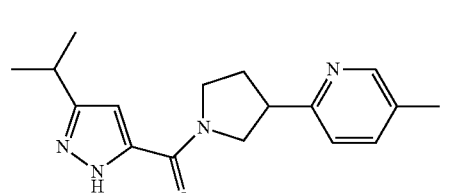 | B | 299.1 | C | 0.623 | ¹H NMR (400 MHz, CDCl₃) δ 8.40 (d, J = 8.0 Hz, 1H), 7.47-7.46 (m, 1H), 7.14 (d, J = 8.0 Hz, 1H), 6.46, 6.44 (2s, 1H), 4.31-3.73 (m, 4.5H), 3.65-3.53 (m, 1H), 3.09-3.03 (m, 1H), 2.49-2.21 (m, 4.5H), 1.32-1.28 (m, 6H). |

TABLE 1-continued

| Ex | Structure | Synth. Method | LCMS (ESI) m/z | LCMS Method | R$_T$ (min) | NMR |
|---|---|---|---|---|---|---|
| 106 | 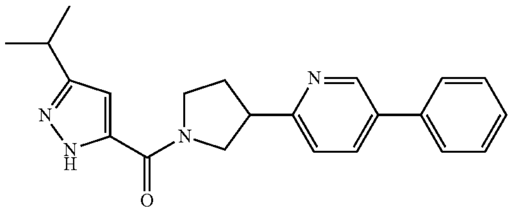 [SMILES: CC(C)c1cc(C(=O)N2CCC(c3ccc(-c4ccccc4)cn3)C2)[nH]n1] | B | 361.1 | E | 0.836 | ¹H NMR (400 MHz, DMSO-d$_6$) δ 12.93, 12.88 (2s, 1H), 8.81 (s, 1H), 8.02-8.00 (m, 1H), 7.70-7.67 (m, 2H), 7.59-7.38 (m, 4H), 6.40 (s, 1H), 4.39-4.34 (m, 0.5H), 4.15-4.11 (m, 2H), 3.75-3.52 (m, 2.5H), 2.95-2.90 (m, 1H), 2.30-2.07 (m, 2H), 1.21-1.18 (m, 6H). |
| 107 | 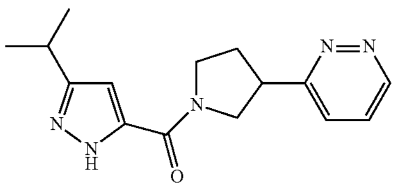 [SMILES: CC(C)c1cc(C(=O)N2CCC(c3cccnn3)C2)[nH]n1] | B | 308.1 | E | 0.649 | ¹H NMR (400 MHz, CDCl$_3$) δ 9.13 (2s, 1H), 7.49-7.41 (m, 2H), 6.52 (s, 1H), 4.50-3.78 (m, 5H), 3.06-3.00 (m, 1H), 2.55-2.30 (m, 2H). 1.29 (m, 6H). |
| 108 | 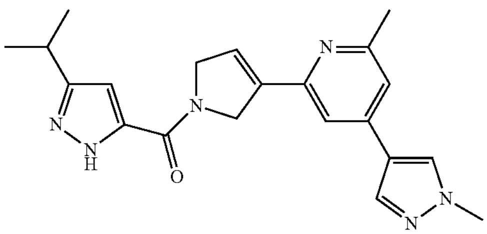 [SMILES: Cc1cc(-c2cnn(C)c2)cc(C2=CCN(C(=O)c3cc(C(C)C)n[nH]3)C2)n1] | A | 377.0 | E | 0.869 | ¹H NMR (400 MHz, CDCl$_3$) δ 7.87 (m, 1H), 7.79 (s, 0.5H), 7.33 (s, 0.5H), 7.23 (s, 1H), 7.14 (m, 1H), 6.76 (s, 0.5H), 6.67-6.57 (m, 1.5H), 5.12 (m, 1H), 4.95 (m, 1H), 4.88 (m, 1H), 4.71 (m, 1H), 3.99, 3.98 (2s, 3H), 3.18-3.11 (m, 1H), 2.59, 2.58 (2s, 3H), 1.37-1.34 (m, 6H). |
| 109 | 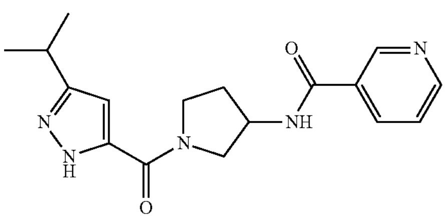 [SMILES: CC(C)c1cc(C(=O)N2CCC(NC(=O)c3cccnc3)C2)[nH]n1] | C | 328.1 | A | 0.536 | ¹H NMR (400 MHz, DMSO-d$_6$) δ 12.93, 12.91 (2s, 1H), 8.97 (m, 1H), 8.77 (m, 1H), 8.67 (s, 1H), 8.20-8.10 (m, 1H), 7.47 (s, 1H), 6.36 (s, 1H), 4.53-4.33 (m, 1H), 4.12-4.10 (m, 0.5H), 4.04-3.90 (m, 1H), 3.80-3.70 (m, 0.5H), 3.69-3.47 (m, 2H), 3.00-2.82 (m, 1H), 2.22-1.83 (m, 2H), 1.28-1.09 (m, 6H). |
| 110 | 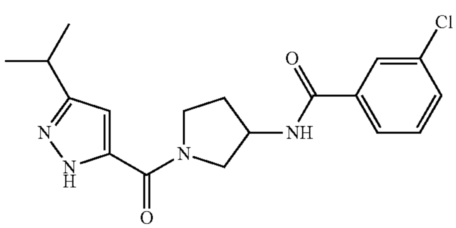 [SMILES: CC(C)c1cc(C(=O)N2CCC(NC(=O)c3cccc(Cl)c3)C2)[nH]n1] | C | 361.1 | E | 0.807 | ¹H NMR (400 MHz, DMSO-d$_6$) δ 12.91, 12.88 (2s, 1H), 8.69, 8.68 (2s, 1H), 7.88 (d, J = 8.0 Hz, 1H), 7.83-7.76 (m, 1H), 7.57 (d, J = 8.0 Hz, 1H), 7.49-7.45 (m, 1H), 6.36 (s, 1H), 4.53-4.33 (m, 1H), 4.15-4.05 (m, 0.5H), 4.04-3.80 (m, 1.5H), 3.75-3.47 (m, 2H), 3.00-2.82 (m, 1H), 2.22- |

TABLE 1-continued

| Ex | Structure | Synth. Method | LCMS (ESI) m/z | LCMS Method | R$_T$ (min) | NMR |
|---|---|---|---|---|---|---|
| | | | | | | 1.83 (m, 2H), 1.28-1.09 (m, 6H). |
| 111 | 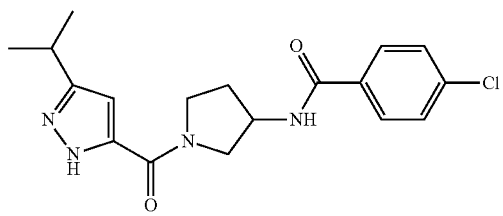 [SMILES: CC(C)c1cc(C(=O)N2CCC(NC(=O)c3ccc(Cl)cc3)C2)[nH]n1] | C | 361.1 | E | 0.802 | $^1$H NMR (400 MHz, DMSO-d$_6$) δ 12.91, 12.89 (2s, 1H), 8.67, 8.65 (2s, 1H), 7.88 (m, 2H), 7.54-7.51 (m, 2H), 6.38 (s, 1H), 4.49-4.34 (m, 1H), 4.12-4.10 (m, 0.5H), 4.03-2.89 (m, 1H), 3.85-3.80 (m 0.5H), 3.75-3.44 (m, 2H), 3.01-2.85 (m, 1H), 2.21-1.86 (m, 2H), 1.29-1.12 (m, 6H). |
| 112 | 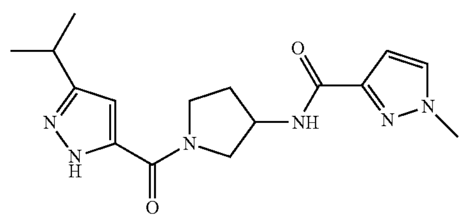 [SMILES: CC(C)c1cc(C(=O)N2CCC(NC(=O)c3ccn(C)n3)C2)[nH]n1] | C | 331.2 | E | 0.690 | $^1$H NMR (400 MHz, CD$_3$OD) δ 7.62-7.61 (m, 1H), 6.72-6.70 (m, 1H), 6.47 (s, 1H), 4.63-4.58 (m, 1H), 4.30-4.20 (m, 0.5H), 4.15-3.85 (m, 5H), 3.84-3.77 (m, 0.5H), 3.72-3.59 (m, 0.5H), 3.04-3.00 (m, 0.5H), 3.05-2.95 (m, 1H), 2.29-2.24 (m, 1H), 2.12-2.07 (m, 1H), 1.30-1.27 (m, 6H). |
| 113 | 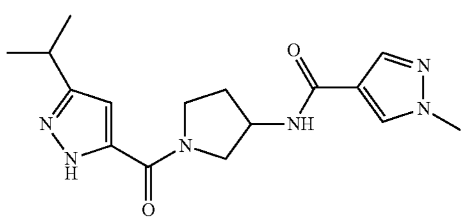 [SMILES: CC(C)c1cc(C(=O)N2CCC(NC(=O)c3cnn(C)c3)C2)[nH]n1] | C | 331.1 | E | 0.677 | $^1$H NMR (400 MHz, CD$_3$OD) δ 8.06, 8.04 (2s, 1H), 7.91, 7.89 (2s, 1H), 6.47 (s, 1H), 4.65-4.49 (m, 1H), 4.30-4.20 (m, 0.5H), 4.14-3.95 (m, 1H), 3.95-3.85 (m, 4H), 3.80-3.54 (m, 1.5H), 3.10-2.90 (m, 1H), 2.34-2.19 (m, 1H), 2.12-1.95 (m, 1H), 1.28 (m, 6H). |
| 114 | 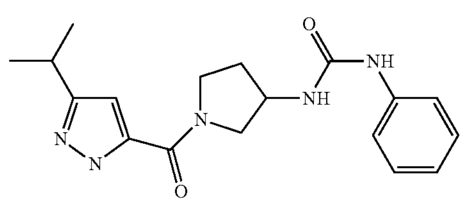 [SMILES: CC(C)c1cc(C(=O)N2CCC(NC(=O)Nc3ccccc3)C2)[nH]n1] | C | 342.2 | E | 0.761 | $^1$H NMR (400 MHz, CD$_3$OD) δ 7.36-7.28 (m, 2H), 7.27-7.19 (m, 2H), 6.99-6.93 (m, 1H), 6.47 (s, 1H), 4.41-4.29 (m, 1H), 4.18-3.99 (m, 1.5H), 3.93-3.80 (m, 1H), 3.77-3.63 (m, 1H), 3.60-3.50 (m, 0.5H), 3.09-2.96 (m, 1H), 2.32-2.18 (m, 1H), 2.05-1.88 (m, 1H), 1.28 (m, 6H). |
| 115 | 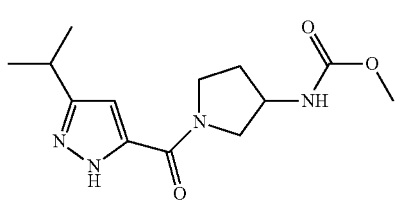 [SMILES: COC(=O)NC1CCN(C(=O)c2cc(C(C)C)n[nH]2)C1] | C | 280.8 | E | 0.690 | $^1$H NMR (400 MHz, CD$_3$OD) δ 6.48 (s, 1H), 4.25-4.16 (m, 1H), 4.15-4.07 (m, 0.5H), 4.05-3.95 (m, 1H), 3.84-3.80 (m, 0.5H), 3.75-3.47 (m, 5H), 3.05-3.02 (m, 1H), 2.25-2.12 (m, |

TABLE 1-continued
| Ex | Structure | Synth. Method | LCMS (ESI) m/z | LCMS Method | R_T (min) | NMR |
|---|---|---|---|---|---|---|
| | | | | | | 1H), 2.00-1.88 (m, 1H), 1.38-1.29 (m, 6H). |
| 116 | 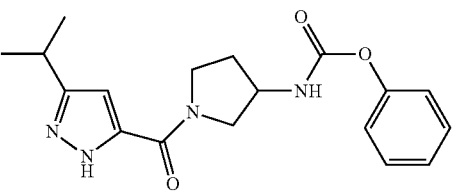 [SMILES: CC(C)c1cc(C(=O)N2CCC(NC(=O)Oc3ccccc3)C2)[nH]n1] | C | 343.1 | E | 0.786 | $^1$H NMR (400 MHz, CD$_3$OD) δ 7.44-7.31 (m, 2H), 7.25-7.15 (m, 1H), 7.12-7.08 (m, 2H), 6.49 (s, 1H), 4.31-4.25 (m, 0.5H), 4.20-4.02 (m, 1.5H), 3.96-3.84 (m, 1H), 3.80-3.58 (m, 2H), 3.10-2.98 (m, 1H), 2.32-2.18 (m, 1H), 2.10-2.00 (m, 1H), 1.31 (d, J = 6.8 Hz, 6H). |
| 117 | 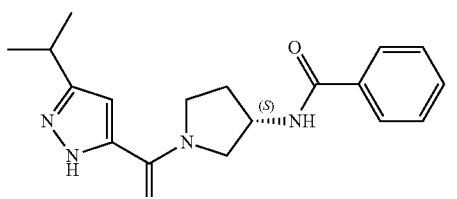 | C | 327.1 | E | 0.755 | $^1$H NMR (400 MHz, CDCl$_3$) δ 7.87-7.73 (m, 2H), 7.54-7.46 (m, 1H), 7.41 (d, J = 7.2 Hz, 2H), 6.73 (s, 1H), 6.44 (s, 1H), 4.88-4.69 (m, 1H), 4.22-4.16 (m, 1H), 4.00-3.88 (m, 2H), 3.85-3.75 (m, 1H), 3.07-2.93 (m, 1H), 2.39-2.25 (m, 1H), 2.21 (m, 1H), 2.13-1.99 (m, 1H), 1.28 (d, J = 6.8 Hz, 6H). |
| 118 | 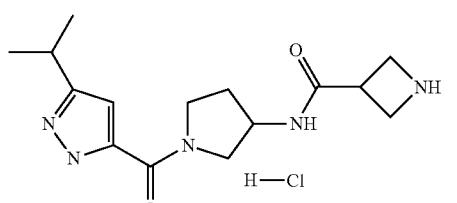 | C | 306.1 | B | 0.953 | $^1$H NMR (400 MHz, CD$_3$OD) δ 6.87-6.77 (m, 1H), 4.47 (m, 1H), 4.27-4.12 (m, 4H), 4.00 (m, 1H), 3.92-3.55 (m, 4H), 3.20-3.10 (m, 1H), 2.36-2.19 (m, 1H), 2.13-1.98 (m, 1H), 1.37-1.34 (m, 6H). |
| 119 | 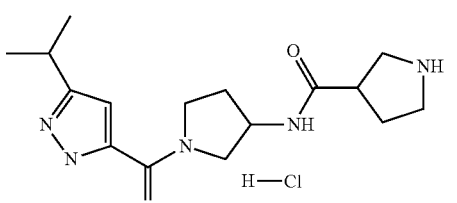 | C | 320.2 | B | 0.998 | $^1$H NMR (400 MHz, CD$_3$OD) δ 6.82-6.71 (m, 1H), 4.44 (m, 1H), 4.14-4.10 (m, 0.5H), 4.07-3.94 (m, 1H), 3.89-3.72 (m, 2H), 3.61-3.58 (m, 0.5H), 3.54-3.34 (m, 4H), 3.25-3.08 (m, 2H), 2.38-1.97 (m, 5H), 1.36-1.33 (m, 6H). |
| 120 | 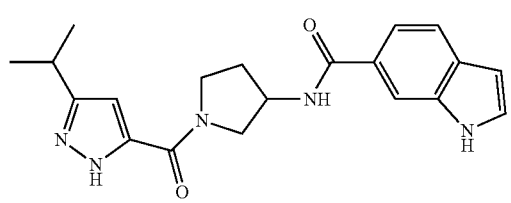 [SMILES: CC(C)c1cc(C(=O)N2CCC(NC(=O)c3ccc4cc[nH]c4c3)C2)[nH]n1] | C | 366.1 | E | 0.776 | $^1$H NMR (400 MHz, DMSO-d$_6$) δ 11.36 (s, 1H), 8.48-8.53 (m, 1H), 7.94 (d, J = 6.8 Hz, 1H), 7.52-7.59 (m, 2H), 7.48-7.51 (m, 1H), 6.47 (m, 1H), 6.42, 6.40 (2s, 1H), 4.53-4.47 (m, 1H), 4.13-4.04 (m, 2H), 3.80-3.70 (m, 3H), 2.98-2.93 (m, 1H), 2.19-2.12 (m, 1H), |

TABLE 1-continued

| Ex | Structure | Synth. Method | LCMS (ESI) m/z | LCMS Method | R_T (min) | NMR |
|---|---|---|---|---|---|---|
| | | | | | | 2.04-1.97 (m, 1H), 1.23-1.20 (m, 6H). |
| 121 | 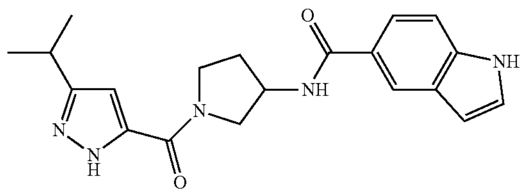 [SMILES: CC(C)c1cc(C(=O)N2CCC(NC(=O)c3ccc4[nH]ccc4c3)C2)[nH]n1] | C | 366.2 | E | 0.757 | $^1$H NMR (400 MHz, DMSO-$d_6$) δ 11.31 (s, 1H), 8.43 (m, 1H), 8.14 (m, 1H), 7.67-7.60 (m, 1H), 7.44-7.37 (m, 2H), 6.52 (m, 1H), 6.42, 6.40 (2s, 1H), 4.53-4.45 (m, 1H), 4.17-3.89 (m, 3H), 3.82-3.67 (m, 2H), 2.99-2.93 (m, 1H), 2.20-2.11 (m, 1H), 2.06-1.96 (m, 1H), 1.23-1.21 (m, 6H). |
| 122 | 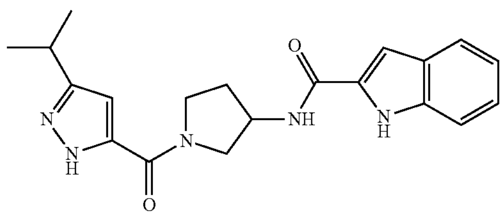 [SMILES: CC(C)c1cc(C(=O)N2CCC(NC(=O)c3cc4ccccc4[nH]3)C2)[nH]n1] | C | 366.2 | E | 0.804 | $^1$H NMR (400 MHz, DMSO-$d_6$) δ 12.93 (2s, 1H), 11.56 (2s, 1H), 8.57 (m, 1H), 7.60 (m, 1H), 7.44-7.38 (m, 1H), 7.22-7.14 (m, 2H), 7.02 (m, 1H), 6.40 (s, 1H), 4.51 (m, 1H), 4.05-3.56 (m, 5H), 3.00-2.94 (m, 1H), 2.23-2.12 (m, 1H), 2.04-1.94 (m, 1H), 1.24-1.21 (m, 6H). |
| 123 | 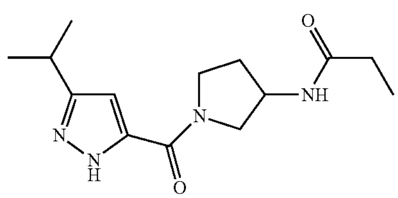 [SMILES: CCC(=O)NC1CCN(C(=O)c2cc(C(C)C)n[nH]2)C1] | C | 279.1 | A | 0.743 | $^1$H NMR (400 MHz, CDCl$_3$) δ 6.46-6.43 (m, 1H), 6.16 (s, 1H), 4.55 (m, 1H), 4.12-3.56 (m, 4H), 3.01-2.98 (m, 1H), 2.28-2.13 (m, 3H), 2.06-1.86 (m, 1H), 1.31-1.25 (m, 6H), 1.17-1.08 (m, 3H). |
| 124 | 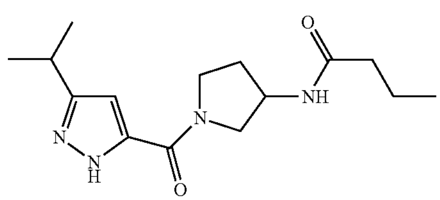 [SMILES: CCCC(=O)NC1CCN(C(=O)c2cc(C(C)C)n[nH]2)C1] | C | 293.2 | A | 0.829 | $^1$H NMR (400 MHz, CDCl$_3$) δ 6.45-6.41 (m, 2H), 4.54 (m, 1H), 4.10-3.55 (m, 4H), 3.00-2.97 (m, 1H), 2.28-2.08 (m, 3H), 2.01-1.89 (m, 1H), 1.65-1.61 (m, 2H), 1.28-1.25 (m, 6H), 0.91-0.87 (m, 3H). |
| 125 | 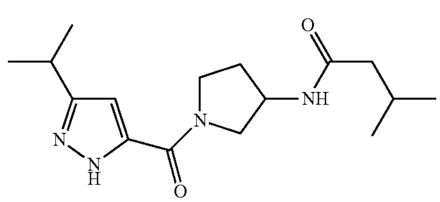 [SMILES: CC(C)CC(=O)NC1CCN(C(=O)c2cc(C(C)C)n[nH]2)C1] | C | 307.2 | A | 0.890 | $^1$H NMR (400 MHz, CDCl$_3$) δ 6.44-6.41 (m, 1H), 5.57 (m, 1H), 4.52-4.50 (m, 1H), 4.08-3.45 (m, 4H), 3.03-2.89 (m, 1H), 2.27-1.78 (m, 5H), 1.27-1.20 (m, 6H), 0.91-0.84 (m, 6H). |

TABLE 1-continued
| Ex | Structure | Synth. Method | LCMS (ESI) m/z | LCMS Method | R_T (min) | NMR |
|---|---|---|---|---|---|---|
| 126 | 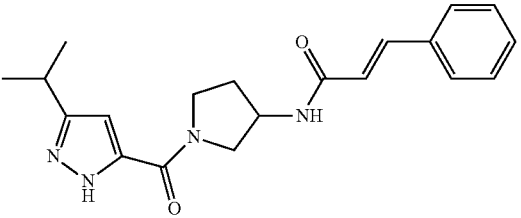 [SMILES: CC(C)c1cc(C(=O)N2CCC(NC(=O)/C=C/c3ccccc3)C2)[nH]n1] | C | 353.1 | A | 0.997 | $^1$H NMR (400 MHz, CD$_3$OD) δ 7.63-7.49 (m, 3H), 7.45-7.30 (m, 3H), 6.69-6.57 (m, 1H), 6.50-6.49 (m, 1H), 4.60-4.46 (m, 1H), 4.22-3.56 (m, 4H), 3.11-2.95 (m, 1H), 2.33-2.20 (m, 1H), 2.09-1.95 (m, 1H), 1.32-1.29 (m, 6H). |
| 127 | 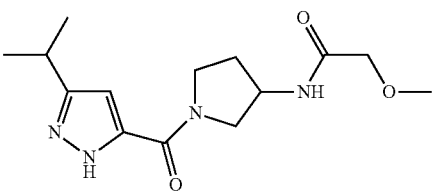 [SMILES: COCC(=O)NC1CCN(C(=O)c2cc(C(C)C)n[nH]2)C1] | C | 295.1 | A | 0.704 | $^1$H NMR (400 MHz, CDCl$_3$) δ 6.79-6.63 (m, 0.5H), 6.48-6.47 (m, 1H), 4.60-4.57 (m, 1H), 4.17-4.13 (m, 0.5H), 4.01-3.72 (m, 4.5H), 3.66-3.54 (m, 0.5H), 3.40-3.39 (m, 3H), 3.08-2.94 (m, 1H), 2.36-2.15 (m, 1H), 2.11-1.84 (m, 1H), 1.29-1.27 (m, 6H). |
| 128 | 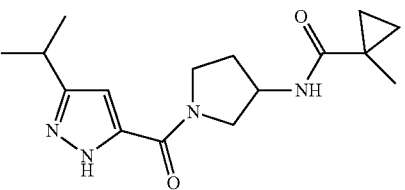 [SMILES: CC(C)c1cc(C(=O)N2CCC(NC(=O)C3(C)CC3)C2)[nH]n1] | C | 305.2 | A | 0.875 | $^1$H NMR (400 MHz, CD$_3$OD) δ 6.47 (s, 1H), 4.44-4.43 (m, 1H), 4.22-4.03 (m, 1H), 3.99-3.83 )m, 1H), 3.81-3.71 (m, 1H), 3.68-3.45 (m, 1H), 3.05-3.02 (m, 1H), 2.21-2.20 (m, 1H), 2.07-1.91 (m, 1H), 1.35-1.27 (m, 9H), 1.13-1.03 (m, 2H), 0.65-0.56 (m, 2H). |
| 129 | 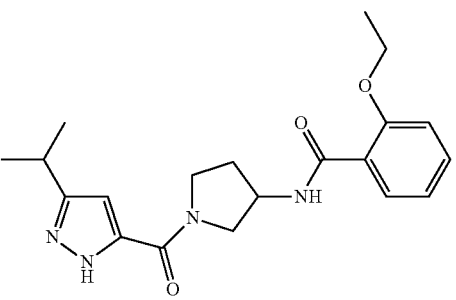 [SMILES: CCOc1ccccc1C(=O)NC1CCN(C(=O)c2cc(C(C)C)n[nH]2)C1] | C | 371.2 | A | 1.001 | $^1$H NMR (400 MHz, CD$_3$OD) δ 7.92-7.80 (m, 1H), 7.52-7.41 (m, 1H), 7.13-6.99 (m, 2H), 6.50-6.49 (m, 1H), 4.66-4.60 (m, 1H), 4.26-4.02 (m, 4H), 3.97-3.63 (m, 2H), 3.09-2.97 (m, 1H), 2.39-2.23 (m, 1H), 2.18-2.02 (m, 1H), 1.43-1.37 (m, 3H), 1.31-1.29 (m, 6H). |
| 130 | 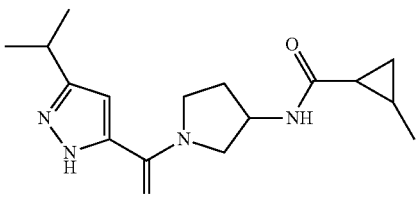 | C | 305.2 | A | 0.874 | $^1$H NMR (400 MHz, CD$_3$OD) δ 6.48 (s, 1H), 4.46-4.32 (m, 1H), 4.15-3.49 (m, 4H), 3.09-2.97 (m, 1H), 2.22-2.12 (m, 1H), 2.02-1.89 (m, 1H), 1.37-1.25 (m, 8H), 1.13-1.01 (m, 4H), 0.62-0.52 (m, 1H). |

US 10,022,354 B2
TABLE 1-continued
| Ex | Structure | Synth. Method | LCMS (ESI) m/z | LCMS Method | R_T (min) | NMR |
|---|---|---|---|---|---|---|
| 131 | 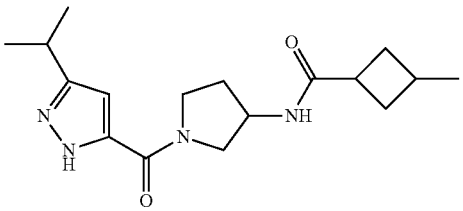 [SMILES: CC1CC(C(=O)NC2CCN(C(=O)c3cc(C(C)C)n[nH]3)C2)C1] | C | 319.2 | A | 0.933 | ¹H NMR (400 MHz, CD₃OD) δ 6.47 (s, 1H), 4.39-4.37 (m, 1H), 4.24-3.41 (m, 4H), 3.14-2.81 (m, 2H), 2.49-2.10 (m, 4H), 2.00-1.67 (m, 3H), 1.30 (d, J = 7.2 Hz, 6H), 1.15-1.12 (m, 1.5H), 1.06-1.02 (m, 1.5H). |
| 132 | 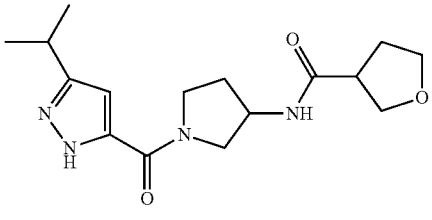 [SMILES: CC(C)c1cc(C(=O)N2CCC(NC(=O)C3CCOC3)C2)[nH]n1] | C | 320.8 | E | 0.661 | ¹H NMR (400 MHz, CD₃OD) δ 6.48 (s, 1H), 4.47-4.31 (m, 1H), 4.15-3.49 (m, 8H), 3.08-2.95 (m, 2H), 2.30-2.16 (m, 1H), 2.15-2.03 (m, 2H), 2.02-1.88 (m, 1H), 1.30 (d, J = 6.8 Hz, 6H). |
| 133 | 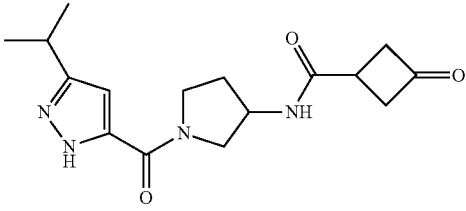 [SMILES: CC(C)c1cc(C(=O)N2CCC(NC(=O)C3CC(=O)C3)C2)[nH]n1] | C | 319.1 | A | 0.718 | ¹H NMR (400 MHz, CD₃OD) δ 6.48 (s, 1H), 4.51-4.36 (m, 1H), 4.17-3.52 (m, 4H), 3.31-3.13 (m, 5H), 3.04-3.01 (m, 1H), 2.25-2.21 (m, 1H), 2.06-1.90 (m, 1H), 1.31-1.29 (m, 6H). |
| 134 | 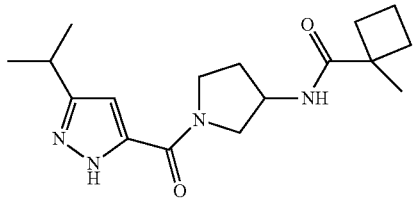 [SMILES: CC(C)c1cc(C(=O)N2CCC(NC(=O)C3(C)CCC3)C2)[nH]n1] | C | 318.9 | E | 0.701 | ¹H NMR (400 MHz, DMSO-d₆) δ 7.64, 7.62 (2s, 1H), 6.39, 6.37 (2s, 1H), 4.26-4.20 (m, 1H), 4.02 (dd, J = 6.4, 12.0 Hz, 0.5H), 3.95-3.81 (m, 0.5H), 3.68-3.52 (m, 2H), 3.51-3.41 (m, 0.5H), 3.33 (dd, J = 4.8, 12.0 Hz, 0.5H), 2.98-2.90 (m, 1H), 2.33-2.19 (m, 2H), 2.10-1.93 (m, 1H), 1.89-1.74 (m, 2H), 1.72-1.54 (m, 3H), 1.28 (d, J = 6.4 Hz, 3H), 1.20 (d, J = 6.8 Hz, 6H). |
| 135 | 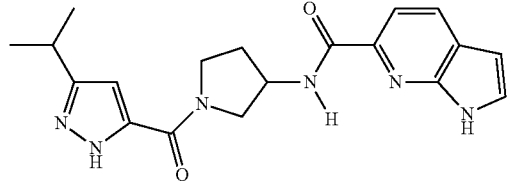 [SMILES: CC(C)c1cc(C(=O)N2CCC(NC(=O)c3ccc4cc[nH]c4n3)C2)[nH]n1] | C | 367.1 | A | 0.959 | ¹H NMR (400 MHz, DMSO-d₆) δ 12.96, 12.92 (2s, 1H), 11.79 (s, 1H), 8.48 (m, 1H), 8.12-8.08 (m, 1H), 7.80-7.75 (m, 1H), 7.66 (s, 1H), 6.55 (s, 1H), 6.40 (s, 1H), 4.54-4.52 (m, 1H), 4.16-3.53 (m, 4H), 2.99-2.94 (m, 1H), 2.20-2.00 (m, 2H), 1.24-1.20 (m, 6H). |

TABLE 1-continued

| Ex | Structure | Synth. Method | LCMS (ESI) m/z | LCMS Method | R$_T$ (min) | NMR |
|---|---|---|---|---|---|---|
| 136 | 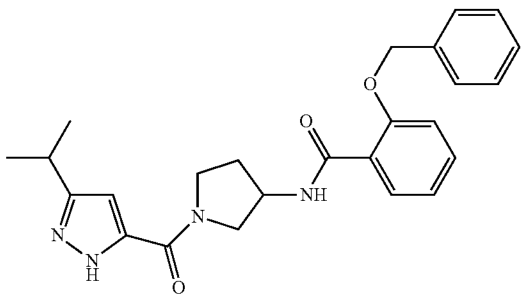 [SMILES: CC(C)c1cc(C(=O)N2CCC(NC(=O)c3ccccc3OCc3ccccc3)C2)[nH]n1] | C | 433.1 | A | 1.087 | $^1$H NMR (400 MHz, DMSO-d$_6$) δ 12.78 (s, 1H), 8.33 (m, 1H), 7.72-7.60 (m, 1H), 7.50-7.46 (m, 3H), 7.38-7.33 (m, 3H), 7.23 (m, 1H), 7.04-7.00 (m, 1H), 6.39, 6.37 (2s, 1H), 5.19, 5.18 (2s, 2H), 4.42-4.38 (m, 1H), 4.10-4.05 (m, 0.5H), 3.85-3.80 (m, 0.5H), 3.73-3.68 (m, 1H), 3.48-3.43 (m, 2H), 2.99-2.93 (m, 1H), 2.10-1.92 (m, 1H), 1.68-1.63 (m, 1H), 1.24-1.20 (m, 6H). |
| 137 | 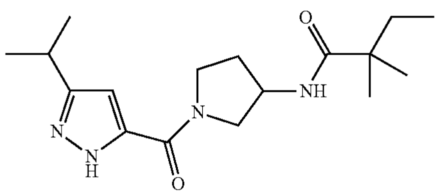 [SMILES: CCC(C)(C)C(=O)NC1CCN(C(=O)c2cc(C(C)C)n[nH]2)C1] | C | 321.2 | A | 0.956 | $^1$H NMR (400 MHz, CD$_3$OD) δ 6.54, 6.52 (2s, 1H), 4.47-4.42 (m, 1H), 4.17-3.48 (m, 4H), 3.08-3.04 (m, 1H), 2.30-2.16 (m, 1H), 2.05-1.92 (m, 1H), 1.65-1.50 (m, 2H), 1.33-1.31 (m, 6H), 1.18-1.14 (m, 6H), 0.86-0.81 (m, 3H). |
| 138 | 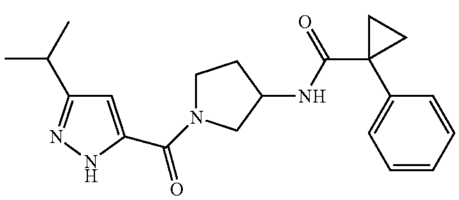 [SMILES: CC(C)c1cc(C(=O)N2CCC(NC(=O)C3(c4ccccc4)CC3)C2)[nH]n1] | C | 367.2 | A | 1.023 | $^1$H NMR (400 MHz, CD$_3$OD) δ 7.41-7.28 (m, 5H), 6.45 (s, 1H), 4.45-4.32 (m, 1H), 4.13-3.32 (m, 4H), 3.0-6-2.95 (m, 1H), 2.18-2.03 (m, 1H), 1.90-1.82 (m, 1H), 1.51-1.44 (m, 2H), 1.31-1.27 (m, 6H), 1.11-1.06 (m, 2H). |
| 139 | 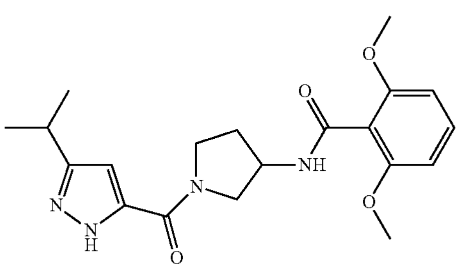 [SMILES: COc1cccc(OC)c1C(=O)NC1CCN(C(=O)c2cc(C(C)C)n[nH]2)C1] | C | 387.2 | A | 0.904 | $^1$H NMR (400 MHz, CD$_3$OD) δ 7.35-7.26 (m, 1H), 6.67-6.63 (m, 2H), 6.52 (s, 1H), 4.62-4.51 (m, 1H), 4.14-4.00 (m, 2H), 3.92-3.65 (m, 2H), 3.80 (s, 3H), 3.74 (s, 3H), 3.10-2.98 (m, 1H), 2.34-2.19 (m, 1H), 2.14-2.02 (m, 1H), 1.30 (d, J = 6.8 Hz, 6H). |
| 140 | 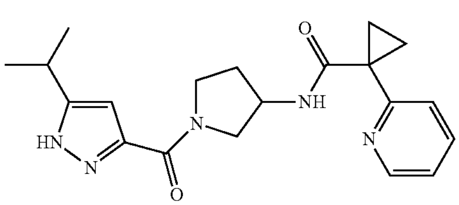 [SMILES: CC(C)c1cc(C(=O)N2CCC(NC(=O)C3(c4ccccn4)CC3)C2)n[nH]1] | C | 368.1 | C | 0.931 | $^1$H NMR (400 MHz, CD$_3$OD) δ 8.49-8.44 (m, 1H), 7.80-7.72 (m, 1H), 7.38-7.31 (m, 1H), 7.30-7.24 (m, 1H), 6.46 (s, 1H), 4.53-4.42 (m, 1H), 4.16-3.49 (m, 4H), 3.09-2.98 (m, 1H), 2.26-2.14 (m, 1H), 2.03-1.91 (m, 1H), 1.58-1.44 (m, |

TABLE 1-continued

| Ex | Structure | Synth. Method | LCMS (ESI) m/z | LCMS Method | R$_T$ (min) | NMR |
|---|---|---|---|---|---|---|
| | | | | | | 2H), 1.35-1.22 (m, 2H), 1.29 (d, J = 6.8 Hz, 6H). |
| 141 | 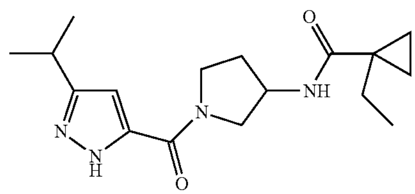 [SMILES: CCC1(C(=O)NC2CCN(C(=O)c3cc(C(C)C)n[nH]3)C2)CC1] | C | 319.2 | C | 1.130 | $^1$H NMR (400 MHz, MeOD) δ 6.52, 6.50 (2s, 1H), 4.42-4.39 (m, 1H), 4.13-3.48 (m, 4H), 3.05-3.02 (m, 1H), 2.20-2.17 (m, 1H), 2.00-1.95 (m, 1H), 1.62-1.58 (m, 2H), 1.28 (d, J = 7.2 Hz, 6H), 0.99-0.94 (m, 5H), 0.60-0.59 (m, 2H) |
| 142 | 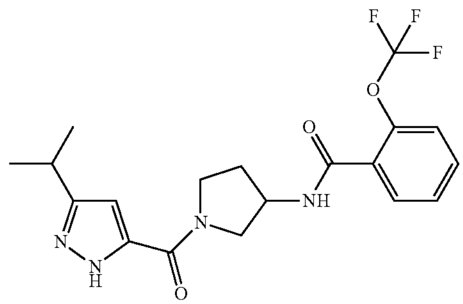 [SMILES: CC(C)c1cc(C(=O)N2CCC(NC(=O)c3ccccc3OC(F)(F)F)C2)[nH]n1] | C | 411.1 | A | 0.995 | $^1$H NMR (400 MHz, MeOD) δ 7.62-7.38 (m, 4H), 6.53 (s, 1H), 4.63-4.60 (m, 1H), 4.21-3.62 (m, 4H), 3.06-3.04 (m, 1H), 2.31-2.29 (m, 1H), 2.12-2.09 (m, 1H), 1.32 (d, J = 7.2 Hz, 6H) |
| 143 | 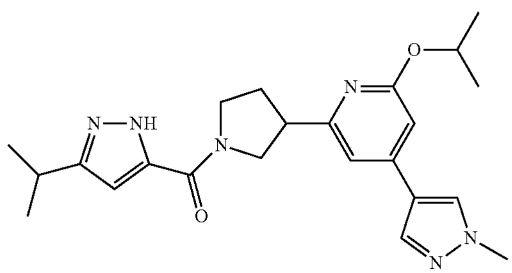 [SMILES: CC(C)Oc1cc(-c2cnn(C)c2)cc(C2CCN(C(=O)c3cc(C(C)C)n[nH]3)C2)n1] | B | 428.8 | E | 0.819 | $^1$H NMR (400 MHz, CDCl$_3$) δ 8.41 (m, 1H), 8.08 (m, 1H), 7.22 (s, 1H), 6.95 (s, 1H), 6.41 (s, 1H), 5.23-5.14 (m, 1H), 3.88-3.72 (m, 3H), 3.70-3.68 (m, 3H), 3.66-3.50 (m, 2H), 3.49-2.93 (1H), 2.40-2.10 (m, 2H), 1.29-0.94 (m, 12H). |
| 144 | 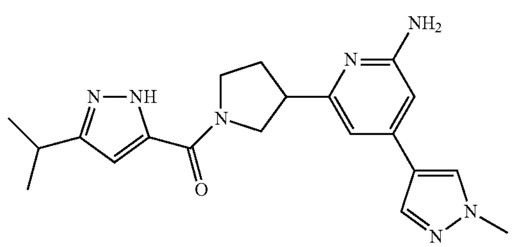 [SMILES: CC(C)c1cc(C(=O)N2CCC(c3cc(-c4cnn(C)c4)cc(N)n3)C2)[nH]n1] | B | 380.2 | E | 0.684 | $^1$H NMR (400 MHz, CDCl$_3$) δ 7.79 (s, 1H), 7.69 (s, 1H), 6.68 (s, 1H), 6.51 (s, 1H), 6.48 (s, 1H), 4.77 (s, 2H), 4.26-4.24 (m, 1H), 4.23 (m, 1H), 3.98 (s, 3H), 3.90 (m, 1H), 3.73-3.71 (m, 1H), 3.50-3.48 (m, 1H), 3.05-3.01 (m, 1H), 2.29-2.26 (s, 2H), 1.32-1.29 (m, 6H). |
| 145 | 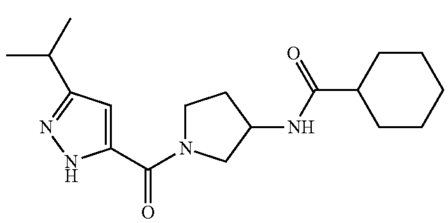 [SMILES: CC(C)c1cc(C(=O)N2CCC(NC(=O)C3CCCCC3)C2)[nH]n1] | C | 333.2 | E | 0.768 | $^1$H NMR (400 MHz, CDCl$_3$) δ 6.51-6.19 (m, 1H), 5.63 (m, 1H), 4.58-4.56 (m. 1H), 4.15-3.59 (m, 4H), 3.04-3.01 (m, 1H), 2.06-1.95 (m, 2H), 1.86-1.78 (m, 5H), 1.43-1.41 (m, 2H), 1.32-1.30 (m, 6H), 1.28-1.24 (m, 2H). |

TABLE 1-continued

| Ex | Structure | Synth. Method | LCMS (ESI) m/z | LCMS Method | R$_T$ (min) | NMR |
|---|---|---|---|---|---|---|
| 146 | 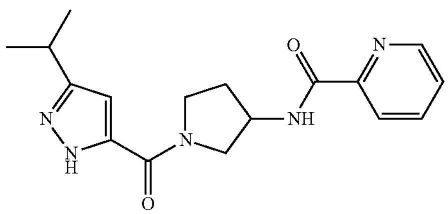 [SMILES: CC(C)c1cc(C(=O)N2CCC(NC(=O)c3ccccn3)C2)[nH]n1] | C | 328.1 | E | 0.726 | ¹H NMR (400 MHz, CDCl₃) δ 8.56-8.54 (m, 1H), 8.20 (m, 1H), 7.86 (m, 1H), 7.44 (m, 1H), 6.49, 6.45 (2s, 1H), 4.80-4.75 (m, 1H), 4.26-3.84 (m, 4H), 3.05-3.00 (m, 1H), 2.37-2.07 (m, 2H), 1.31-1.28 (m, 6H). |
| 147 | 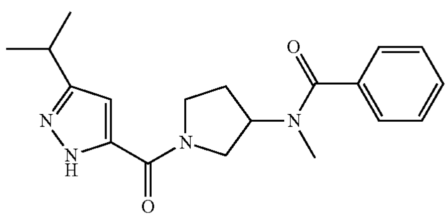 [SMILES: CC(C)c1cc(C(=O)N2CCC(N(C)C(=O)c3ccccc3)C2)[nH]n1] | C | 341.1 | E | 0.785 | ¹H NMR (400 MHz, CDCl₃) δ 7.43-7.41 (m, 5H), 6.53-6.50 (m, 1H), 4.14 (m, 1H), 3.96-3.50 (m, 4H), 3.30 (s, 3H), 2.23-2.13 (m, 3H), 1.32-1.29 (m, 6H). |
| 148 | 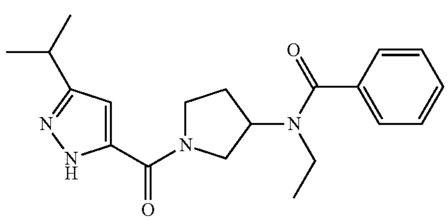 [SMILES: CCN(C(=O)c1ccccc1)C1CCN(C(=O)c2cc(C(C)C)n[nH]2)C1] | C | 355.2 | E | 0.773 | ¹H NMR (400 MHz, CDCl₃) δ 7.43-7.38 (m, 5H), 6.51-6.48 (m, 1H), 4.59 (m, 1H), 4.16-3.36 (m, 6H), 3.05-3.00 (m, 1H), 2.19-2.17 (m, 2H), 1.34-1.23 (m, 9H). |
| 149 | 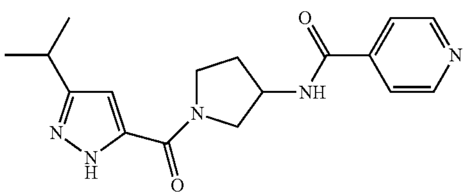 [SMILES: CC(C)c1cc(C(=O)N2CCC(NC(=O)c3ccncc3)C2)[nH]n1] | C | 328.2 | E | 0.600 | ¹H NMR (400 MHz, CDCl₃) δ 8.67 (m, 2H), 7.74 (s, 2H), 6.33 (s, 1H), 4.76 (s, 1H), 4.05-3.70 (m, 4H), 2.95-2.93 (m, 1H), 2.30-2.05 (m, 2H), 1.23 (s, 6H). |
| 150 | 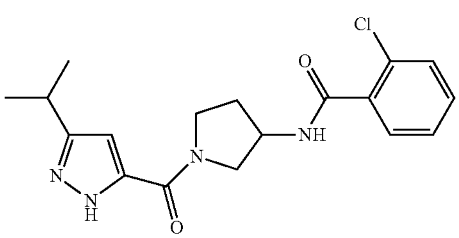 [SMILES: CC(C)c1cc(C(=O)N2CCC(NC(=O)c3ccccc3Cl)C2)[nH]n1] | C | 361.2 | E | 0.736 | ¹H NMR (400 MHz, CDCl₃) δ 7.66-7.65 (m, 1H), 7.39-7.32 (m, 3H), 6.50 (s, 1H), 4.77 (s, 1H), 4.21-3.80 (m, 4H), 3.02 (m, 1H), 2.35-2.05 (m, 2H), 1.30 (d, J = 6.8 Hz, 6H). |
| 151 | 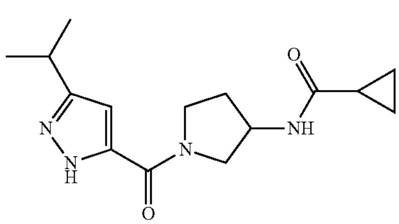 | C | 313.1 | E | 0.697 | ¹H NMR (400 MHz, CD₃OD) δ 6.50-6.47 (m, 1H), 6.02 (s, 1H), 4.61-4.59 (m, 1H), 4.09-3.75 (m, 4H), 3.04-3.00 (m, 1H), 2.23-2.21 (m, 2H), 1.38-1.37 (m, 1H), 1.32-1.30 (m, 6H), 1.00-0.98 (m, 2H), 0.76-0.75 (m, 2H). |

TABLE 1-continued

| Ex | Structure | Synth. Method | LCMS (ESI) m/z | LCMS Method | R_T (min) | NMR |
|---|---|---|---|---|---|---|
| 152 | 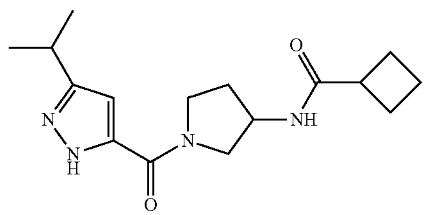 [SMILES: CC(C)c1cc(C(=O)N2CCC(NC(=O)C3CCC3)C2)[nH]n1] | C | 305.1 | E | 0.737 | $^1$H NMR (400 MHz, CDCl$_3$) δ 6.51, 6.48 (2s, 1H), 5.61 (m, 1H), 4.57 (m, 1H), 4.15-3.74 (m, 4H), 3.04-2.98 (m, 1H), 2.29-2.24 (m, 2H), 2.16-2.13 (m, 2H), 1.97-1.89 (m, 2H), 1.31-1.30 (m, 6H). |
| 153 | 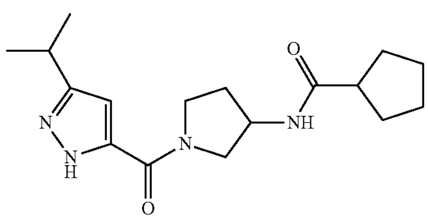 [SMILES: CC(C)c1cc(C(=O)N2CCC(NC(=O)C3CCCC3)C2)[nH]n1] | C | 341.2 | E | 0.767 | $^1$H NMR (400 MHz, CDCl$_3$) δ 6.52, 6.49 (2s, 1H), 5.62 (s, 1H), 4.57 (m, 1H), 4.15-3.75 (m, 4H), 3.04-3.01 (m, 1H), 2.49-2.48 (m, 1H), 2.20-2.16 (m, 2H), 1.90-1.75 (m, 8H), 1.32-1.30 (m, 6H). |
| 154 | 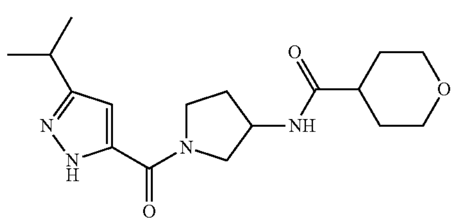 [SMILES: CC(C)c1cc(C(=O)N2CCC(NC(=O)C3CCOCC3)C2)[nH]n1] | C | 335.1 | E | 0.677 | $^1$H NMR (400 MHz, CDCl$_3$) δ 6.51, 6.50 (2s, 1H), 5.76 (m, 1H), 4.57 (m, 1H), 4.14-3.75 (m, 8H), 2.03-3.02 (m, 1H), 2.34-1.80 (m, 7H), 1.32-1.30 (m, 6H). |
| 155 | 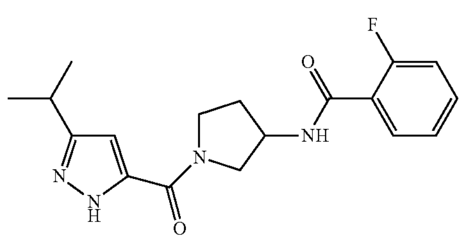 [SMILES: CC(C)c1cc(C(=O)N2CCC(NC(=O)c3ccccc3F)C2)[nH]n1] | C | 345.1 | E | 0.771 | $^1$H NMR (400 MHz, CDCl$_3$) δ 8.10-8.07 (m, 1H), 7.49 (m, 1H), 7.15-7.10 (m, 1H), 6.86-6.85 (m, 1H), 6.52 (2s, 1H), 4.79 (m, 1H), 4.27-3.82 (m, 4H), 3.05-3.00 (m. 1H), 2.35-2.02 (m, 2H), 1.32-1.29 (m, 6H). |
| 156 | 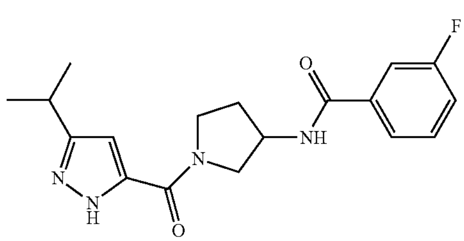 [SMILES: CC(C)c1cc(C(=O)N2CCC(NC(=O)c3cccc(F)c3)C2)[nH]n1] | C | 345.1 | E | 0.785 | $^1$H NMR (400 MHz, CDCl$_3$) δ 7.55-7.53 (m, 2H). 7.41-7.38 (m, 1H), 7.23-7.20 (m, 1H), 6.49 (s, 1H), 4.76-4.75 (m, 1H), 4.20-3.81 (m, 4H), 3.02-3.00 (m, 1H), 3.36-2.06 (m, 2H), 1.30-1.24 (m, 6H). |
| 157 | 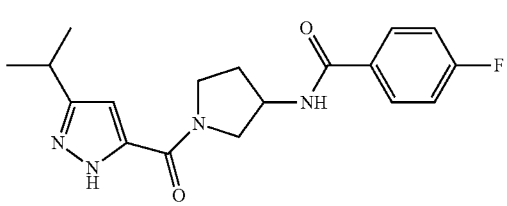 [SMILES: CC(C)c1cc(C(=O)N2CCC(NC(=O)c3ccc(F)cc3)C2)[nH]n1] | C | 345.2 | E | 0.771 | $^1$H NMR (400 MHz, CDCl$_3$) δ 7.79 (d, J = 8.4 Hz, 2H), 7.12 (t, J = 8.4 Hz, 2H), 6.53-6.51 (m, 1H), 6.24 (s, 1H), 4.78-4.76 (m, 1H), 4.22-3.76 (m, 4H), 3.05-3.00 (m 1H), 2.34-2.03 (m, 2H), 1.32-1.29 (m, 6H). |

TABLE 1-continued

| Ex | Structure | Synth. Method | LCMS (ESI) m/z | LCMS Method | R$_T$ (min) | NMR |
|---|---|---|---|---|---|---|
| 158 | 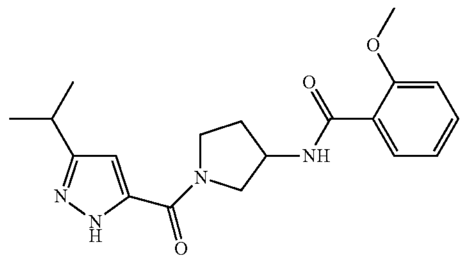 [SMILES: COc1ccccc1C(=O)NC1CCN(C(=O)c2cc(C(C)C)n[nH]2)C1] | C | 357.2 | E | 0.767 | ¹H NMR (400 MHz, CDCl$_3$) δ 8.21-8.19 (m, 1H), 8.15 (s, 1H), 7.48-7.41 (m, 1H), 7.11-7.10 (m, 1H), 7.08-6.98 (m, 1H), 6.53-6.49 (m, 1H), 4.81-4.75 (m, 1H), 4.81-3.83 (m, 7H), 3.04-3.00 (m, 1H), 2.31-2.02 (m, 1H), 1.32-1.28 (m, 6H). |
| 159 | 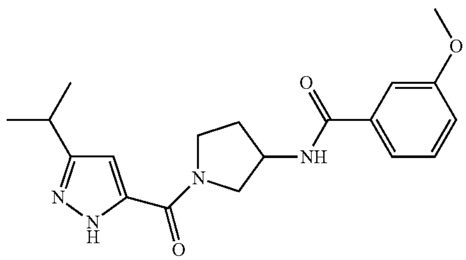 [SMILES: COc1cccc(C(=O)NC2CCN(C(=O)c3cc(C(C)C)n[nH]3)C2)c1] | C | 357.2 | E | 0.765 | ¹H NMR (400 MHz, CDCl$_3$) δ 7.37-7.04 (m, 3H), 7.04 (m, 1H), 6.50, 6.45 (2s, 1H), 4.77-4.75 (m, 1H), 4.02-3.76 (m, 4H), 3.04-2.99 (m, 1H), 2.37-2.02 (m, 2H), 1.29 (d, J = 6.8 Hz, 6H). |
| 160 | 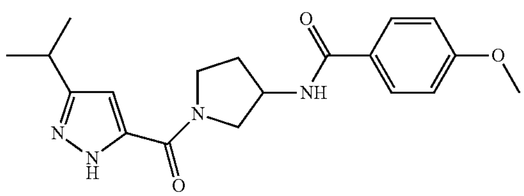 [SMILES: COc1ccc(C(=O)NC2CCN(C(=O)c3cc(C(C)C)n[nH]3)C2)cc1] | C | 357.2 | E | 0.773 | ¹H NMR (400 MHz, CDCl$_3$) δ 7.76 (m, 2H), 6.91 (m, 2H), 6.48 (s, 1H), 4.75 (m, 1H), 3.98-3.76 (m, 7H), 3.03-2.98 (m, 1H), 2.35-2.03 (m, 2H), 1.29 (d, J = 6.8 Hz, 6H). |
| 161 | 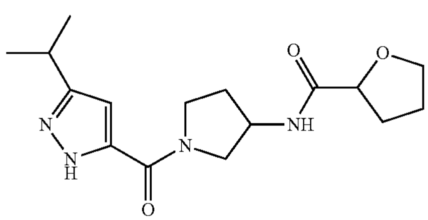 [SMILES: CC(C)c1cc(C(=O)N2CCC(NC(=O)C3CCCO3)C2)[nH]n1] | C | 321.1 | E | 0.694 | ¹H NMR (400 MHz, CDCl$_3$) δ 6.85 (s, 1H), 6.50-6.45 (m, 1H), 4.57-4.55 (m, 1H), 4.35-4.33 (m, 1H), 3.96-3.76 (m, 6H), 3.04-3.01 (m, 1H), 2.32-1.87 (m, 6H), 1.30 (d, J = 7.2 Hz, 6H). |
| 162 | 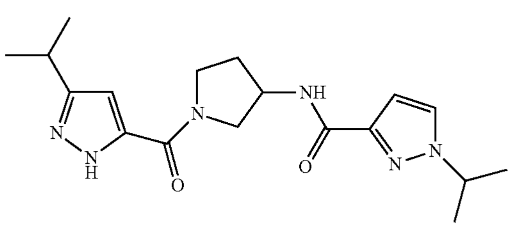 [SMILES: CC(C)c1cc(C(=O)N2CCC(NC(=O)c3ccn(C(C)C)n3)C2)[nH]n1] | C | 359.3 | E | 0.753 | ¹H NMR (400 MHz, CDCl$_3$) δ 7.44-7.42 (m, 1H), 6.81-6.78 (m, 1H), 6.48-6.42 (m, 1H), 4.76-4.78 (m, 1H), 4.55-4.47 (m, 1H), 3.94-3.80 (m, 4H), 3.05-3.01 (m, 1H), 2.31-2.04 (m, 2H), 1.50-1.29 (m, 6H). |
| 163 | 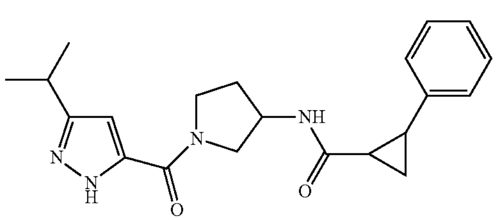 [SMILES: CC(C)c1cc(C(=O)N2CCC(NC(=O)C3CC3c3ccccc3)C2)[nH]n1] | C | 367.2 | E | 0.799 | ¹H NMR (400 MHz, CDCl$_3$) δ 7.20-7.06 (m, 5H), 6.49-6.46 (m, 1H), 6.01 (s, 1H), 4.60 (m, 1H), 4.13-3.72 (m, 4H), 3.03-3.00 (m, 1H), 2.23-2.05 (m, 1H), 2.05-1.89 (m, 3H), 1.30-1.25 (m, 8H). |

TABLE 1-continued

| Ex | Structure | Synth. Method | LCMS (ESI) m/z | LCMS Method | R$_T$ (min) | NMR |
|---|---|---|---|---|---|---|
| 164 | 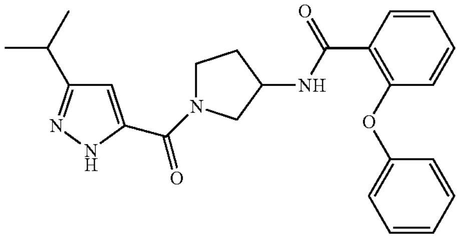 [SMILES: CC(C)c1cc(C(=O)N2CCC(NC(=O)c3ccccc3Oc3ccccc3)C2)[nH]n1] | C | 419.2 | E | 0.833 | ¹H NMR (400 MHz, CDCl₃) δ 8.24-5.20 (m, 1H), 7.82-7.80 (m, 1H), 7.44-6.88 (m, 7H), 6.41-6.39 (m, 1H), 4.76-4.70 (m, 1H), 4.14-3.65 (m, 4H), 3.03-2.99 (m, 1H), 2.21-1.87 (m, 2H), 1.31-1.23 (m, 6H). |
| 165 | 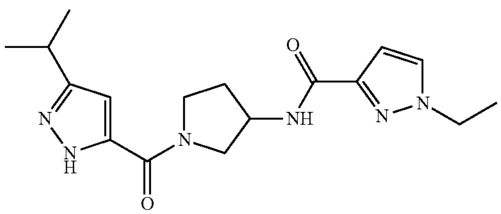 [SMILES: CCn1ccc(C(=O)NC2CCN(C(=O)c3cc(C(C)C)n[nH]3)C2)n1] | C | 345.1 | E | 3.066 | ¹H NMR (400 MHz, CDCl₃) δ 7.58 (s, 1H), 7.41 (s, 1H), 7.39-7.21 (m, 1H), 6.45-, 6.32 (2s, 1H), 4.78-4.70 (m, 1H), 4.21-4.16 (m, 2H), 2.88-3.82 (m, 4H), 3.04-2.99 (m, 1H), 2.28-2.20 (m, 2H), 1.51-1.47 (m, 3H), 1.29-1.27 (m, 6H). |
| 166 | 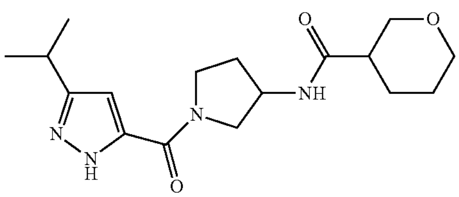 [SMILES: CC(C)c1cc(C(=O)N2CCC(NC(=O)C3CCCOC3)C2)[nH]n1] | C | 335.1 | E | 2.694 | ¹H NMR (400 MHz, CDCl₃) δ 6.44 (s, 1H), 4.54 (m, 1H), 3.87-3.65 (m, 8H), 3.02-3.00 (m, 1H), 2.45 (s, 1H), 1.91-1.29 (m, 6H), 1.30-1.28 (m, 6H). |
| 167 | 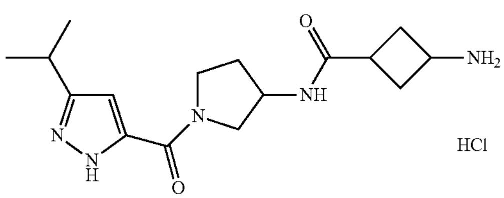 [SMILES: CC(C)c1cc(C(=O)N2CCC(NC(=O)C3CC(N)C3)C2)[nH]n1 ; Cl] | C | 320.1 | E | 1.024 | ¹H NMR (400 MHz, CD₃OD) δ 6.80-6.74 (2s, 1H), 4.44 (m, 1H), 3.74 (m, 4H), 3.31 (s, 1H), 3.14-3.12 (m, 2H), 2.57-2.55 (m, 2H), 2.45-2.27 (m, 4H), 1.37-1.33 (m, 6H). |
| 168 | 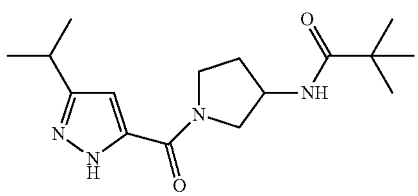 [SMILES: CC(C)c1cc(C(=O)N2CCC(NC(=O)C(C)(C)C)C2)[nH]n1] | C | 307.2 | C | 1.117 | ¹H NMR (400 MHz, DMSO-d₆) δ 7.52 (s, 1H), 6.39, 6.37 (2s, 1H), 4.26-4.22 (m, 1H), 4.03-3.57 (m, 4H), 2.97-2.90 (m, 1H), 2.04-2.95 (m, 1H), 1.82-1.75 (m, 1H), 1.20 (d, J = 6.8 Hz, 6H), 1.07, 1.06 (s, 9H). |
| 169 | 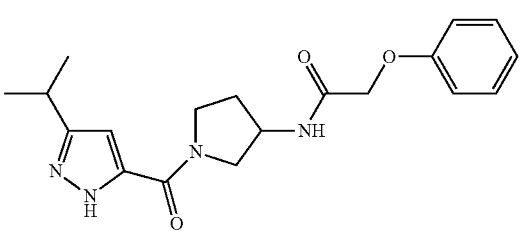 [SMILES: CC(C)c1cc(C(=O)N2CCC(NC(=O)COc3ccccc3)C2)[nH]n1] | C | 357.2 | C | 1.168 | ¹H NMR (400 MHz, DMSO-d₆) δ 8.36 (s, 1H), 7.31-7.25 (m, 2H), 6.97-6.91 (m, 3H), 6.41, 6.40 (2s, 1H), 4.49-4.47 (m, 2H), 4.36-4.33 (m, 1H), 4.03-3.58 (m, 4H), 2.99-2.94 (m, 1H), 2.10-2.05 (m, 1H), 1.88-1.82 (m, 1H), 1.22 (d, J = 6.8 Hz, 6H). |
| 170 | 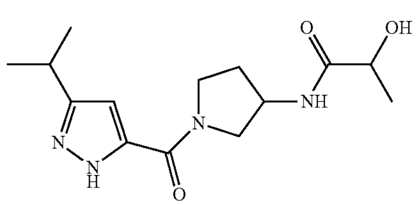 [SMILES: CC(O)C(=O)NC1CCN(C(=O)c2cc(C(C)C)n[nH]2)C1] | C | 295.1 | C | 0.931 | ¹H NMR (400 MHz, DMSO-d₆) δ 7.89 (s, 1H), 6.40, 6.38 (2s, 1H), 4.26-4.21 (m, 1H), 4.03-3.68 (m, 5H), 2.99-2.92 (m, 1H), 2.08-1.83 (m, 2H), 1.22-1.17 (m, 9H). |

TABLE 1-continued

| Ex | Structure | Synth. Method | LCMS (ESI) m/z | LCMS Method | R_T (min) | NMR |
|---|---|---|---|---|---|---|
| 171 | 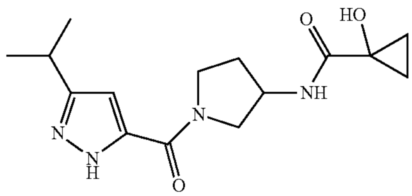 [SMILES: CC(C)c1cc(C(=O)N2CCC(NC(=O)C3(O)CC3)C2)[nH]n1] | C | 307.1 | C | 0.975 | $^1$H NMR (400 MHz, DMSO-$d_6$) δ 12.90 (s, 1H), 8.03 (s, 1H), 6.38 (s, 1H), 6.22 (s, 1H), 4.31-4.29 (m, 1H), 4.05-3.44 (m, 4H), 2.96-2.92 (m, 1H), 2.02-1.95 (m, 2H), 1.22 (d, J =7.2 Hz, 6H), 1.04-1.01 (m, 2H), 0.84-0.80 (m, 2H). |
| 172 | 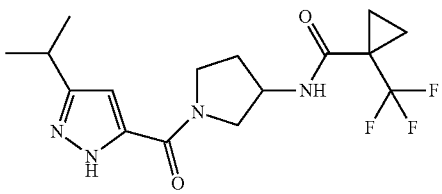 [SMILES: CC(C)c1cc(C(=O)N2CCC(NC(=O)C3(C(F)(F)F)CC3)C2)[nH]n1] | C | 359.1 | C | 1.142 | $^1$H NMR (400 MHz, CD$_3$OD) δ 6.49 (2s, 1H), 4.45-4.41 (m, 1H), 4.16-3.66 (m, 4H), 3.05-3.01 (m, 1H), 2.24-2.19 (m, 1H), 2.02-1.93 (m, 1H), 1.30-1.24 (m, 10H). |
| 173 | 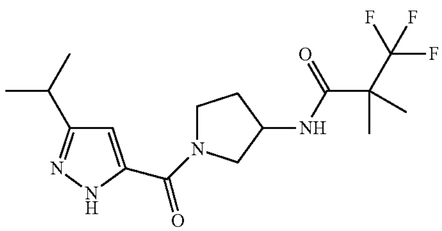 [SMILES: CC(C)c1cc(C(=O)N2CCC(NC(=O)C(C)(C)C(F)(F)F)C2)[nH]n1] | C | 361.1 | C | 1.182 | $^1$H NMR (400 MHz, CD$_3$OD) δ 6.48 (s, 1H), 4.48-4.43 (m, 1H), 4.38-3.53 (m, 4H), 3.05-3.01 (m, 1H), 2.23-2.18 (m, 1H), 2.02-1.95 (m, 1H), 1.43, 1.41 (2s, 6H), 1.30 (d, J = 6.8 Hz, 6H). |
| 174 | 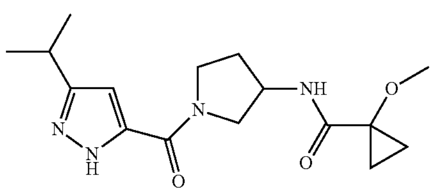 [SMILES: COC1(C(=O)NC2CCN(C(=O)c3cc(C(C)C)n[nH]3)C2)CC1] | C | 321.1 | C | 1.048 | $^1$H NMR (400 MHz, CD$_3$OD): δ 6.52 (s, 1H), 4.49-4.42 (m, 1H), 4.18-3.67 (m, 4H), 3.31-3.29 (s, 3H), 3.05-3.01 (m, 1H), 2.26-2.21 (m, 1H), 2.09-2.03 (m, 1H), 1.29 (d, J = 7.2 Hz, 6H), 1.17-1.05 (m, 4H). |
| 175 | 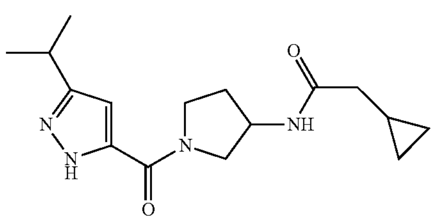 [SMILES: CC(C)c1cc(C(=O)N2CCC(NC(=O)CC3CC3)C2)[nH]n1] | C | 305.1 | C | 1.061 | $^1$H NMR (400 MHz, DMSO-$d_6$) δ 12.82 (s, 1H), 7.93-7.91 (m, 1H), 6.30 (s, 1H), 4.18-4.11 (m, 1H), 3.94-3.82 (m, 2H), 3.59-3.43 (m, 2H), 2.90-2.87 (m, 1H), 1.99-1.87 (m, 3H), 1.75-1.69 (m, 1H), 1.14 (d, J = 6.8 Hz, 6H), 0.87-0.85 (m, 1H), 0.36-0.31 (m, 2H), 0.03-0.00 (m, 2H). |
| 176 | 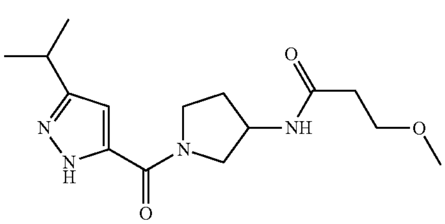 [SMILES: COCCC(=O)NC1CCN(C(=O)c2cc(C(C)C)n[nH]2)C1] | C | 309.1 | C | 0.974 | $^1$H NMR (400 MHz, DMSO-$d_6$) δ 12.90 (s, 1H), 8.15-8.14 (m, 1H), 6.38 (s, 1H), 4.28-4.21 (m, 1H), 4.02-3.91 (m, 1H), 3.68-3.57 (m, 2H), 3.55-3.47 (m, 3H), 3.20, 3.18 (2s, 3H), 2.97-2.91 (m, 1H), 2.33-2.28 (m, 2H), 2.03-1.98 (m, 1H), 1.88-1.76 (m, 1H), 1.22 (d, J = 6.4 Hz, 6H). |

| Ex | Structure | Synth. Method | LCMS (ESI) m/z | LCMS Method | R$_T$ (min) | NMR |
|---|---|---|---|---|---|---|
| 177 | 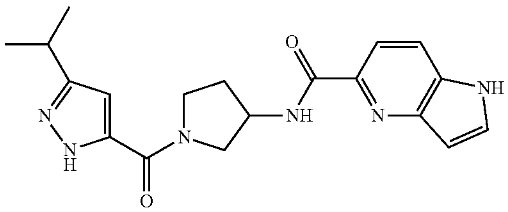 | C | 367.1 | C | 1.061 | $^1$H NMR (400 MHz, DMSO-d$_6$) δ 12.93, 12.89 (m, 1H), 11.61 (s, 1H), 8.73-8.70 (m, 1H), 7.89-7.87 (m, 2H), 7.85-7.82 (m, 1H), 6.65 (s, 1H), 6.38 (s, 1H), 4.52-4.50 (m, 1H), 4.18-4.16 (m, 1H), 3.88-3.86 (m, 1H), 3.77-3.69 (m, 1H), 3.56-3.51 (m, 1H), 2.98-2.93 (m, 1H), 2.14-2.08 (m, 2H), 1.23-1.20 (m, 6H). |
| 178 | 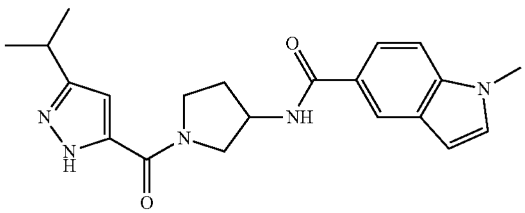 [SMILES: CC(C)c1cc(C(=O)N2CCC(NC(=O)c3ccc4c(ccn4C)c3)C2)[nH]n1] | C | 380.2 | C | 1.182 | $^1$H NMR (400 MHz, DMSO-d$_6$) δ 12.89 (s, 1H), 8.44 (m, 1H), 8.14-8.13 (m, 1H), 7.71-7.67 (m, 1H), 7.47-7.44 (m, 1H), 7.39-7.38 (m, 1H), 6.50 (m, 1H), 6.38 (s, 1H), 4.52-4.47 (m, 1H), 4.18-3.92 (m, 2H), 3.80 (s, 3H), 3.76-3.65 (m, 1H), 3.57-3.50 (m, 1H), 2.99-2.91 (m, 1H), 2.18-2.11 (m, 1H), 2.01-1.98 (m, 1H), 1.22-1.20 (m, 6H). |
| 179 | 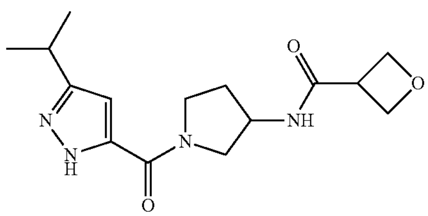 [SMILES: CC(C)c1cc(C(=O)N2CCC(NC(=O)C3COC3)C2)[nH]n1] | C | 307.1 | C | 0.944 | $^1$H NMR (400 MHz, DMSO-d$_6$) δ 12.92 (s, 1H), 8.18-8.16 (m, 1H), 6.39 (s, 1H), 4.61-4.56 (m, 4H), 4.32-4.26 (m, 1H), 4.01-3.85 (m, 2H), 3.74-3.64 (m, 2H), 3.62-3.51 (m, 1H), 2.99-2.92 (m, 1H), 2.10-2.01 (m, 1H), 1.22 (d, J = 7.2 Hz, 6H). |
| 180 | 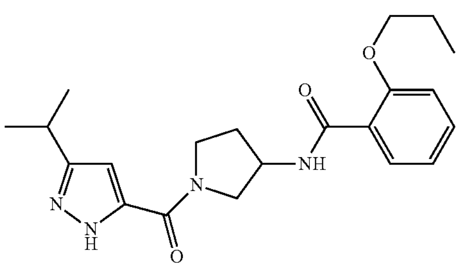 [SMILES: CCCOc1ccccc1C(=O)NC1CCN(C(=O)c2cc(C(C)C)n[nH]2)C1] | C | 385.2 | C | 1.268 | $^1$H NMR (400 MHz, DMSO-d$_6$) δ 12.94, 12.91 (2s, 1H), 8.32-8.30 (m, 1H), 7.71-7.67 (m, 1H), 7.48-7.41 (m, 1H), 7.11-7.00 (m, 2H), 6.39, 6.38 (2s, 1H), 4.50-4.45 (m, 1H), 4.10-3.92 (m, 4H), 3.71-3.54 (m, 2H), 2.98-2.93 (m, 1H), 2.20-2.11 (m, 1H), 2.02-1.90 (m, 1H), 1.73-1.66 (m, 2H), 1.22 (d, J = 6.0 Hz, 6H), 0.92-0.87 (m, 3H). |
| 181 | 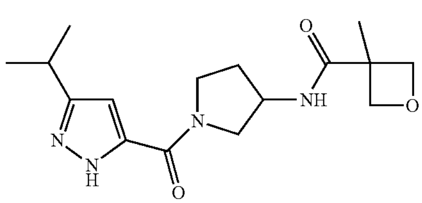 [SMILES: CC(C)c1cc(C(=O)N2CCC(NC(=O)C3(C)COC3)C2)[nH]n1] | C | 321.1 | C | 0.985 | $^1$H NMR (400 MHz, DMSO-d$_6$) δ 12.91 (s, 1H), 8.04, 8.03 (2s, 1H), 6.41, 6.39 (2s, 1H), 4.71-4.66 (m, 2H), 4.28-4.22 (m, 3H), 4.24-3.81 (m, 1H), 3.69-3.53 (m, 2H), 2.98-2.94 (m, 1H), 2.04-2.01 (m, 1H), 1.82-1.79 (m, |

TABLE 1-continued

| Ex | Structure | Synth. Method | LCMS (ESI) m/z | LCMS Method | R$_T$ (min) | NMR |
|---|---|---|---|---|---|---|
| | | | | | | 1H), 1.47, 1.45 (2s, 3H), 1.22 (d, J = 7.2 Hz, 6H). |
| 182 | 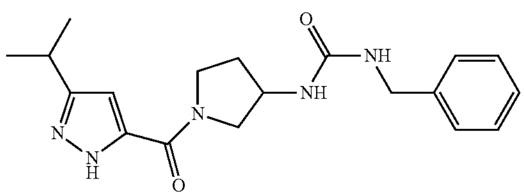 [SMILES: CC(C)c1cc(C(=O)N2CCC(NC(=O)NCc3ccccc3)C2)[nH]n1] | C | 363.2 | E | 0.762 | $^1$H NMR (400 MHz, CD$_3$OD) δ 7.33-7.13 (m, 4H), 6.46 (s, 1H), 4.30 (m, 2H), 4.15-3.93 (m, 1.5H), 3.85-3.62 (m, 2.5H), 3.56-3.43 (m, 1H), 3.04-3.00 (m, 1H), 2.30-2.12 (m, 1H), 2.00-1.88 (m, 1H), 1.28 (d, J = 7.2 Hz, 6H). |
| 183 | 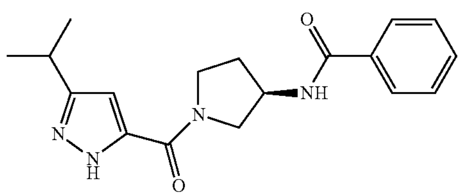 [SMILES: CC(C)c1cc(C(=O)N2CC[C@@H](NC(=O)c3ccccc3)C2)[nH]n1] | C | 349.1 | E | 0.758 | $^1$H NMR (400 MHz, CDCl$_3$) δ 7.82-7.78 (m, 2H), 7.52 (m, 1H), 7.41 (m, 2H), 6.35 (s, 1H), 6.46 (s, 1H), 4.77 (t, J = 6.0 Hz, 1H), 4.20-3.78 (m, 4H), 3.03-2.98 (m, 1H), 2.34-2.02 (m, 2H), 1.28 (d, J = 6.8 Hz, 6H). |
| 184 | 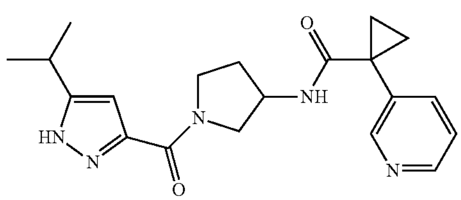 [SMILES: CC(C)c1cc(C(=O)N2CCC(NC(=O)C3(c4cccnc4)CC3)C2)n[nH]1] | C | 368.1 | E | 0.906 | $^1$H NMR (400 MHz, CD$_3$OD) δ 8.55-8.53 (m, 1H), 8.44-8.41 (m, 1H), 7.85-7.80 (m, 1H), 7.42-7.38 (m, 1H), 6.43 (s, 1H), 4,42-4,36 (m, 1H), 4.12-4.07, 3.92-3.51 (m, 4H), 3.02-2.97 (m, 1H), 2.17-2.08 (m, 1H), 1.91-1.80 (m, 1H), 1.56-1.48 (m, 2H), 1.27 (d, J = 7.2 Hz, 6H), 1.13-1.07 (m, 2H). |
| 185 | 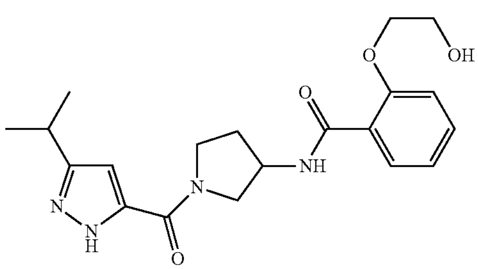 [SMILES: CC(C)c1cc(C(=O)N2CCC(NC(=O)c3ccccc3OCCO)C2)[nH]n1] | C | 387.2 | C | 1.122 | $^1$H NMR (400 MHz, CD$_3$OD) δ 7.93-7.88 (m, 1H), 7.52-7.46 (m, 1H), 7.15-7.02 (m, 2H), 6.49 (s, 1H), 4.66-4.58 (m, 1H), 4.25-4.13 (m, 2H), 4.03-3.67 (m, 6H), 3.08-2.99 (m, 1H), 2.39-2.25 (m, 1H), 2.19-2.10 (m, 1H), 1.29 (d, J = 4.0 Hz, 3H). |
| 186 | 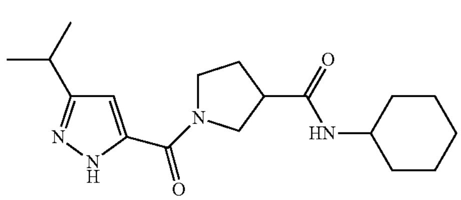 [SMILES: CC(C)c1cc(C(=O)N2CCC(C(=O)NC3CCCCC3)C2)[nH]n1] | C | 305.0 | E | 0.870 | $^1$H NMR (400 MHz, CD$_3$OD) δ 6.48 (s, 1H), 4.60 (m, 1H), 4.17-3.60 (m, 5H), 3.04-3.01 (m, 1H), 2.16-1.19 (m, 19H). |
| 187 | 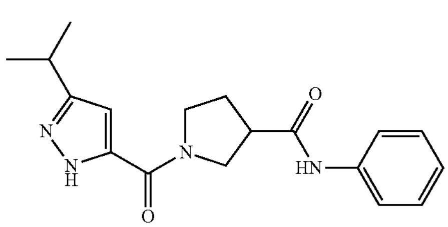 [SMILES: CC(C)c1cc(C(=O)N2CCC(C(=O)Nc3ccccc3)C2)[nH]n1] | C | 327.2 | E | 0.775 | $^1$H NMR (400 MHz, CD$_3$OD) δ 7.60-7.56 (m, 2H), 7.34-7.12 (m, 1H), 7.11 (m, 1H), 6.53 (s, 1H), 4.27-3.83 (m, 4H), 3.27-3.04 (m, 2H), 2.34-2.25 (m, 2H), 1.33-1.31 (m, 6H). |

TABLE 1-continued

| Ex | Structure | Synth. Method | LCMS (ESI) m/z | LCMS Method | R$_T$ (min) | NMR |
|---|---|---|---|---|---|---|
| 188 | 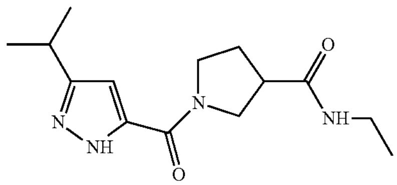 [SMILES: CCNC(=O)C1CCN(C(=O)c2cc(C(C)C)n[nH]2)C1] | C | 279.1 | E | 0.665 | $^1$H NMR (400 MHz, CD$_3$OD) δ 6.48 (s, 1H), 4.19-4.18 (m, 1H), 3.95-3.80 (m, 4H), 3.24-3.20 (m, 2H), 3.05-2.99 (m, 2H), 2.16-2.10 (m, 2H), 1.30-1.28 (m, 6H), 1.15-1.10 (m, 3H). |
| 189 | 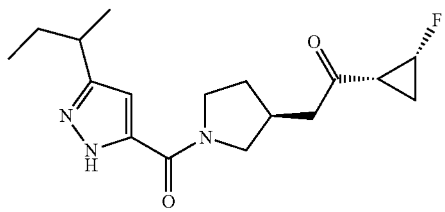 [SMILES: CCC(C)c1cc(C(=O)N2CC[C@@H](CC(=O)[C@H]3C[C@H]3F)C2)[nH]n1] | C | 323.0 | C | 1.050 | $^1$H NMR (400 MHz, CD$_3$OD) δ 6.55 (s, 1H), 4.86-4.64 (m, 1H), 4.55-4.40 (m, 1H), 4.22-3.54 (m, 4H), 2.91-2.78 (m, 1H), 2.35-2.17 (m, 1H), 2.10-1.92 (m, 1H), 1.88-1.75 (m, 1H), 1.74-1.56 (m, 3H), 1.31 (d, J = 6.8 Hz, 3H), 1.16-1.00 (m, 1H), 0.90 (t, J = 6.8 Hz, 3H). |
| 190 | 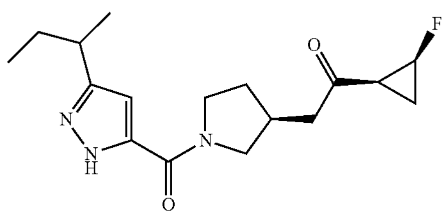 [SMILES: CCC(C)c1cc(C(=O)N2CC[C@@H](CC(=O)[C@@H]3C[C@@H]3F)C2)[nH]n1] | C | 323.0 | C | 1.051 | $^1$H NMR (400 MHz, CD$_3$OD) δ 6.52 (s, 1H), 4.84-4.61 (m, 1H), 4.54-4.40 (m, 1H), 4.26-3.48 (m, 4H), 2.94-2.71 (m, 1H), 2.33-2.18 (m, 1H), 2.10-1.94 (m, 1H), 1.86-1.77 (m, 1H), 1.74-1.57 (m, 3H), 1.30 (m, 3H), 1.14-1.03 (m, 1H), 0.90 (m, 3H). |
| 191 | 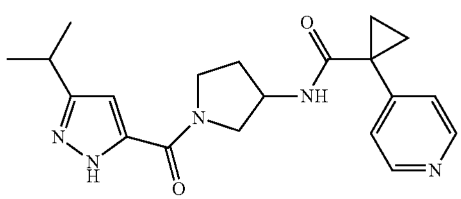 [SMILES: CC(C)c1cc(C(=O)N2CCC(NC(=O)C3(c4ccncc4)CC3)C2)[nH]n1] | C | 368.1 | C | 0.888 | $^1$H NMR (400 MHz, CD$_3$OD) δ 8.49-8.46 (m, 2H), 7.40-7.35 (m, 2H), 6.48 (s, 1H), 4.49-4.43 (m, 1H), 4.22-3.46 (m, 4H), 3.15-2.96 (m, 1H), 2.22-2.14 (m, 1H), 1.20-1.91 (m, 1H), 1.59-1.50 (m, 2H), 1.34-1.29 (m, 6H), 1.24-1.18 (m, 2H). |
| 192 | 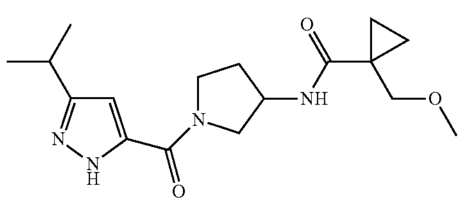 [SMILES: COCC1(C(=O)NC2CCN(C(=O)c3cc(C(C)C)n[nH]3)C2)CC1] | C | 335.2 | C | 1.079 | $^1$H NMR (400 MHz, CD$_3$OD) δ 6.53 (s, 1H), 4.52-4.40 (m, 1H), 4.21-3.66 (m, 4H), 3.62-3.46 (m, 2H), 3.38 (s, 3H), 3.09-3.02 (m, 1H), 2.36-2.17 (m, 1H), 2.10-1.92 (m, 1H), 1.32 (d, J = 7.2 Hz, 6H), 1.21-1.08 (m, 2H), 0.84-0.71 (m, 2H). |
| 193 | 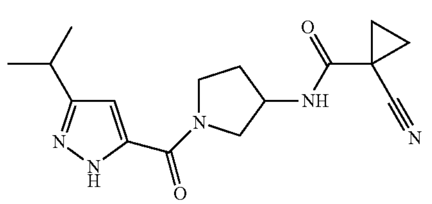 [SMILES: CC(C)c1cc(C(=O)N2CCC(NC(=O)C3(C#N)CC3)C2)[nH]n1] | C | 316.2 | C | 1.051 | $^1$H NMR (400 MHz, CD$_3$OD) δ 6.51 (s, 1H), 4.54-4.41 (m, 1H), 4.27-3.52 (m, 4H), 3.09-3.02 (m, 1H), 2.34-2.18 (m, 1H), 2.15-1.98 (m, 1H), 1.70-1.49 (m, |

TABLE 1-continued

| Ex | Structure | Synth. Method | LCMS (ESI) m/z | LCMS Method | R$_T$ (min) | NMR |
|---|---|---|---|---|---|---|
| | | | | | | 4H), 1.32 (d, J = 7.2 Hz, 6H). |
| 194 | 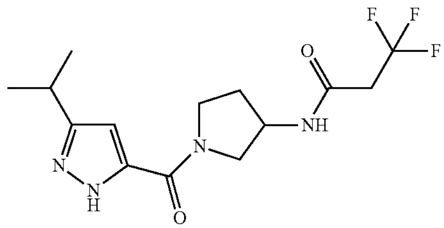 [SMILES: CC(C)c1cc(C(=O)N2CCC(NC(=O)CC(F)(F)F)C2)[nH]n1] | C | 333.1 | C | 1.063 | $^1$H NMR (400 MHz, CD$_3$OD) δ 6.51 (s, 1H), 4.57-4.36 (m, 1H), 4.23-3.51 (m, 4H), 3.32-3.13 (m, 2H), 3.09-3.02 (m, 1H), 2.34-2.18 (m, 1H), 2.09-1.89 (m, 1H), 1.32 (d, J = 7.2 Hz, 6H). |
| 195 | 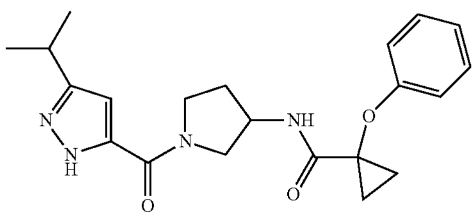 [SMILES: CC(C)c1cc(C(=O)N2CCC(NC(=O)C3(Oc4ccccc4)CC3)C2)[nH]n1] | C | 383.1 | C | 1.192 | $^1$H NMR (400 MHz, CD$_3$OD) δ 7.27-7.21 (m, 2H), 7.00-6.82 (m, 3H), 6.47, 6.42 (2s, 1H), 4.52-4.42 (m, 1H), 4.12-3.45 (m, 4H), 3.09-2.98 (m, 1H), 2.20-2.17 (m, 1H), 2.00-1.82 (m, 1H), 1.58-1.45 (m, 2H), 1.35-1.22 (m, 6H), 1.18-1.11 (m, 2H). |
| 196 | 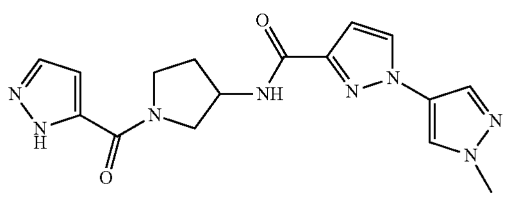 [SMILES: Cn1cc(-n2ccc(C(=O)NC3CCN(C(=O)c4ccn[nH]4)C3)n2)cn1] | C | 397.1 | E | 0.724 | $^1$H NMR (400 MHz, CDCl$_3$) δ 7.77, 7.76 (2s, 1H), 7.70 (s, 1H), 7.64 (s, 1H), 6.97-6.93 (m, 1H), 6.47, 6.40 (2s, 1H), 4.82-4.76 (m, 1H), 4.24-4.19 (m, 1H), 3.95, 3.92 (2s, 3H), 3.90-3.80 (m, 3H), 3.05-3.00 (m, 1H), 2.31-2.04 (m, 2H), 1.31-1.28 (m, 6H). |
| 197 | 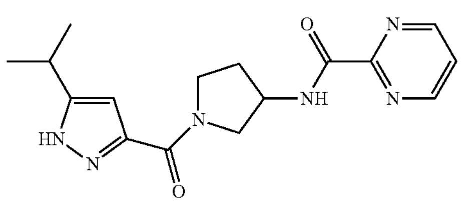 [SMILES: CC(C)c1cc(C(=O)N2CCC(NC(=O)c3ncccn3)C2)n[nH]1] | C | 329.1 | C | 0.975 | $^1$H NMR (400 MHz, CD$_3$OD) δ 8.96-8.94 (m, 2H), 7.66-7.63 (m, 1H), 6.55, 6.54 (2s, 1H), 4.71-4.68 (m, 1H), 4.29-3.71 (m, 5H), 3.07-3.02 (m, 1H), 2.37-2.17 (m, 2H), 1.32-1.29 (m, 6H). |
| 198 | 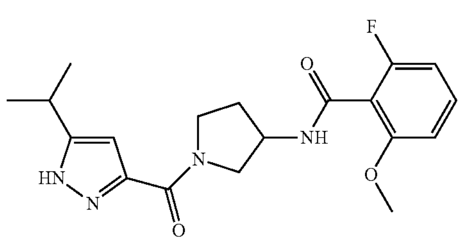 [SMILES: COc1cccc(F)c1C(=O)NC1CCN(C(=O)c2cc(C(C)C)[nH]n2)C1] | C | 375.1 | C | 1.097 | $^1$H NMR (400 MHz, CD$_3$OD) δ 7.39-7.36 (m, 2H), 6.89-6.85 (m, 1H), 6.76-6.72 (m, 1H), 6.54, 6.53 (2s, 1H), 4.61-4.58 (m, 1H), 4.15-3.74 (m, 5H), 3.07-3.03 (m, 1H), 2.30-2.07 (m, 2H), 1.30 (d, J = 6.8 Hz, 6H). |

TABLE 1-continued

| Ex | Structure | Synth. Method | LCMS (ESI) m/z | LCMS Method | R$_T$ (min) | NMR |
|---|---|---|---|---|---|---|
| 199 | 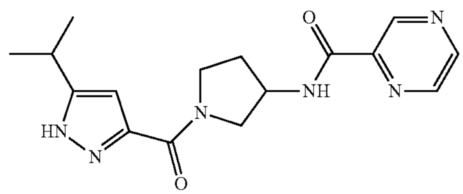 [SMILES: CC(C)c1cc(C(=O)N2CCC(NC(=O)c3cnccn3)C2)n[nH]1] | C | 329.1 | C | 1.017 | $^1$H NMR (400 MHz, CD$_3$OD) δ 9.23, 9.21 (2s, 1H), 8.77 (s, 1H), 8.67 (s, 1H), 6.53 (s, 1H), 4.69-4.68 (m, 1H), 4.29-3.69 (m, 5H), 3.04-3.01 (m, 1H), 2.34-2.14 (m, 2H), 1.31-1.28 (m, 6H). |
| 200 | 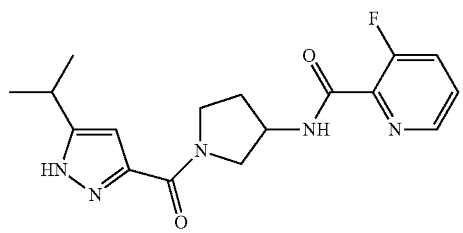 [SMILES: CC(C)c1cc(C(=O)N2CCC(NC(=O)c3ncccc3F)C2)n[nH]1] | C | 346.1 | C | 1.047 | $^1$H NMR (400 MHz, CD$_3$OD) δ 8.45 (m, 1H), 7.74-7.70 (m, 1H), 7.62-7.59 (m, 1H), 6.52, 6.51 (2s, 1H), 4.67-4.62 (m, 1H), 4.25-3.74 (m, 5H), 3.04-3.01 (m, 1H), 2.33-2.12 (m, 2H), 1.30-1.28 (m, 6H). |
| 201 | 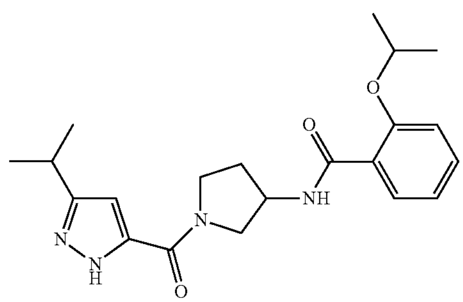 [SMILES: CC(C)Oc1ccccc1C(=O)NC1CCN(C(=O)c2cc(C(C)C)n[nH]2)C1] | C | 385.2 | C | 1.252 | $^1$H NMR (400 MHz, CD$_3$OD) δ 7.91-7.86 (m, 1H), 7.50-7.40 (m, 1H), 7.13-7.10 (m, 1H), 7.05-7.00 (m, 1H), 6.49 (s, 1H), 4.81-4.73 (m, 1H), 4.62 (br. s., 1H), 4.22-4.04 (m, 2H), 3.91-3.86 (m, 0.5H), 3.79-3.69 (m, 1.5H), 3.09-2.96 (m, 1H), 2.38-2.23 (m, 1H), 2.19-2.02 (m, 1H), 1.38-1.24 (m, 12H). |
| 202 | 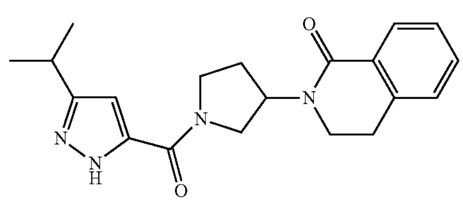 [SMILES: CC(C)c1cc(C(=O)N2CCC(N3CCc4ccccc4C3=O)C2)[nH]n1] | C | 353.1 | C | 1.188 | $^1$H NMR (400 MHz, CD$_3$OD) δ 7.97-7.94 (m, 1H), 7.50-7.47 (m, 1H), 7.38-7.36 (m, 1H), 7.30-7.28 (m, 1H), 6.57 (s, 1H), 5.39-5.33 (m, 1H), 4.22-4.20 (m, 1H), 3.97-3.90 (m, 2H), 3.69-3.59 (m, 3H), 3.06-3.02 (m, 3H), 2.28-2.20 (m, 2H), 1.32-1.29 (m, 6H). |
| 203 | 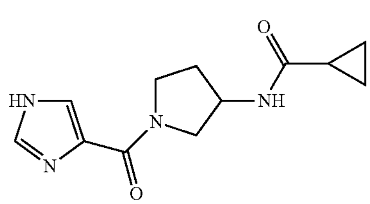 [SMILES: O=C(NC1CCN(C(=O)c2c[nH]cn2)C1)C1CC1] | C | 249.1 | B | 0.327 | $^1$H NMR (400 MHz, CD$_3$OD) δ 7.76 (m, 1H), 7.62 (m, 1H), 4.48-4.36 (m, 1H), 4.21-3.46 (m, 4H), 2.33-2.12 (m, 1H), 2.08-1.90 (m, 1H), 1.64-1.53 (m, 1H), 0.88-0.72 (m, 4H). |

TABLE 1-continued
| Ex | Structure | Synth. Method | LCMS (ESI) m/z | LCMS Method | $R_T$ (min) | NMR |
|---|---|---|---|---|---|---|
| 204 | 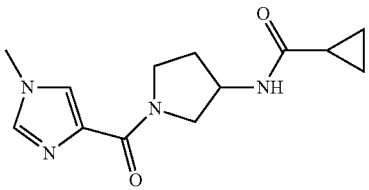 [SMILES: Cn1cnc(C(=O)N2CCC(NC(=O)C3CC3)C2)c1] | C | 263.1 | C | 1.149 | $^1$H NMR (400 MHz, CD$_3$OD) δ 7.64-7.62 (m, 1H), 4.41-4.40 (m, 1H), 4.38-3.31 (m, 7H), 2.20-2.19 (m, 1H), 1.95-1.93 (m, 1H), 1.60-1.57 (m, 1H), 0.86-0.73 (m, 4H). |
| 205 | 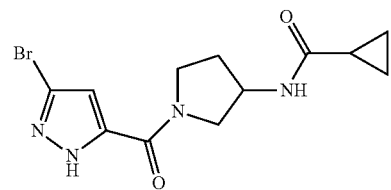 [SMILES: O=C(NC1CCN(C(=O)c2cc(Br)n[nH]2)C1)C1CC1] | C | 329.0 | C | 1.007 | $^1$H NMR (400 MHz, CD$_3$OD) δ 13.87 (s, 1H), 8.36 (s, 1H), 6.89, 6.84 (2s, 1H), 4.31-4.26 (m, 1H), 3.89-3.34 (m, 4H), 2.06-2.01 (m, 1H), 1.89-1.72 (m, 1H), 1.53-1.50 (m, 1H), 0.67-0.64 (m, 4H). |
| 206 | 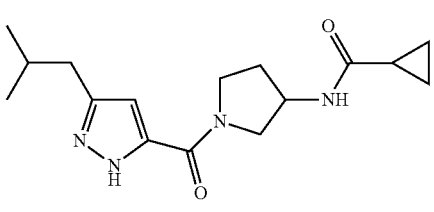 [SMILES: CC(C)Cc1cc(C(=O)N2CCC(NC(=O)C3CC3)C2)[nH]n1] | C | 305.1 | E | 0.733 | $^1$H NMR (400 MHz, CD$_3$OD) δ 6.51, 6.50 (2s, 1H), 4.43-4.40 (m, 1H), 4.14-3.53 (m, 4H), 2.57 (m, 2H), 2.24-2.17 (m, 1H), 2.05-1.95 (m, 2H), 1.62-1.58 (m, 1H), 0.96 (d, J = 6.4 Hz, 6H), 0.87-0.75 (m, 4H). |
| 207 | 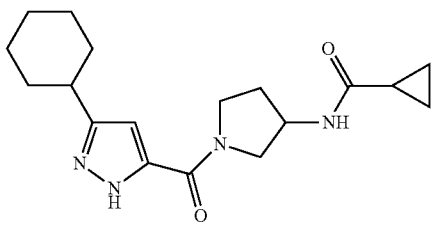 [SMILES: O=C(NC1CCN(C(=O)c2cc(C3CCCCC3)n[nH]2)C1)C1CC1] | C | 331.2 | A | 0.973 | $^1$H NMR (400 MHz, CD$_3$OD) δ 6.47 (s, 1H), 4.44-4.34 (m, 1H), 4.18-3.43 (m, 4H), 2.75-2.65 (m, 1H), 2.25-2.14 (m, 1H), 2.03-1.94 (m, 3H), 1.87-1.70 (m, 3H), 1.65-1.54 (m, 1H), 1.48-1.29 (m, 5H), 0.89-0.71 (m, 4H). |
| 208 | 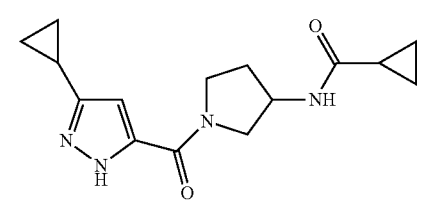 [SMILES: O=C(NC1CCN(C(=O)c2cc(C3CC3)n[nH]2)C1)C1CC1] | C | 289.1 | A | 0.724 | $^1$H NMR (400 MHz, CD$_3$OD) δ 6.42-6.28 (m, 1H), 4.45-4.33 (m, 1H), 4.15-3.47 (m, 4H), 2.31-2.11 (m, 1H), 2.06-1.86 (m, 2H), 1.67-1.45 (m, 1H), 1.02-0.96 (m, 2H), 0.89-0.81 (m, 2H), 0.80-0.76 (m, 4H). |
| 209 | 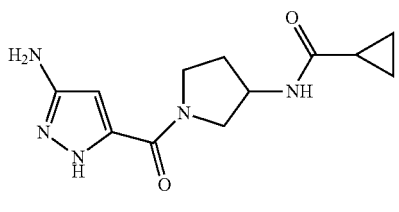 [SMILES: Nc1cc(C(=O)N2CCC(NC(=O)C3CC3)C2)[nH]n1] | C | 264.1 | B | 0.622 | $^1$H NMR (400 MHz, CD$_3$OD) δ 5.94, 5.90 (2s, 1H), 4.44-4.36 (m, 1H), 4.06-3.49 (m, 4H), 2.27-2.14 (m, 1H), 2.03-1.91 (m, 1H), 1.62-1.55 (m, 1H), 0.86-0.74 (m, 4H). |

TABLE 1-continued

| Ex | Structure | Synth. Method | LCMS (ESI) m/z | LCMS Method | R_T (min) | NMR |
|---|---|---|---|---|---|---|
| 210 | 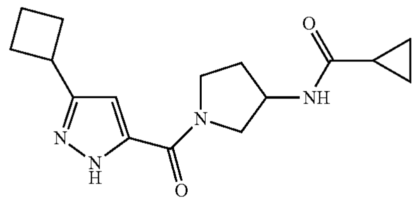 [SMILES: O=C(NC1CCN(C(=O)c2cc(C3CCC3)n[nH]2)C1)C1CC1] | C | 303.1 | E | 0.712 | $^1$H NMR (400 MHz, CD$_3$OD) δ 6.54, 6.53 (2s, 1H), 4.42-4.37 (m, 1H), 4.14-4.10 (m, 0.5H), 4.08-3.98 (m, 1H), 3.78-3.69 (m, 1H), 3.68-3.57 (m, 1H), 3.55-3.51 (m, 0.5H), 2.46-2.32 (m, 2H), 2.29-2.15 (m, 3H), 2.14-2.02 (m, 1H), 2.01-1.88 (m, 2H), 1.65-1.53 (m, 1H), 0.89-0.80 (m, 2H), 0.79-0.70 (m, 2H). |
| 211 | 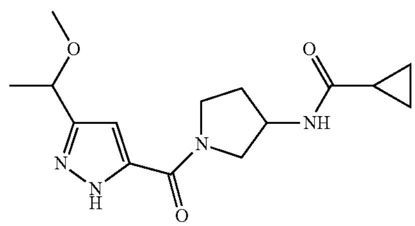 [SMILES: COC(C)c1cc(C(=O)N2CCC(NC(=O)C3CC3)C2)[nH]n1] | C | 307.0 | C | 0.93 | $^1$H NMR (400 MHz, CD$_3$OD) δ 6.67 (s, 1H), 4.58-4.50 (m, 1H), 4.49-4.40 (m, 1H), 4.13-3.69 (m, 4H). 3.29 (s, 3H), 2.30-2.20 (m, 1H), 2.08-1.93 (m, 1H), 1.61-1.52 (m, 1H), 1.50 (d, J = 6.8 Hz, 3H), 0.89-0.72 (m, 4H). |
| 212 | 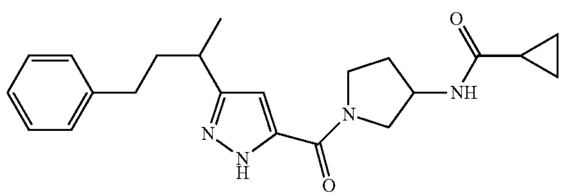 [SMILES: CC(CCc1ccccc1)c1cc(C(=O)N2CCC(NC(=O)C3CC3)C2)[nH]n1] | C | 381.1 | C | 1.25 | $^1$H NMR (400 MHz, CD$_3$OD) δ 7.28-7.21 (m, 2H), 7.19-7./10 (m, 3H), 6.52 (s, 1H), 4.46-4.37 (m, 1H), 4.18-3.70 (m, 4H), 2.97-2.88 (m, 1H), 2.60-2.50 (m, 2H), 2.25-2.17 (m, 1H), 2.06-1.89 (m, 3H), 1.61-1.53 (m, 1H), 1.31 (d, J = 6.4 Hz, 3H), 0.89-0.70 (m, 4H),. |
| 213 | 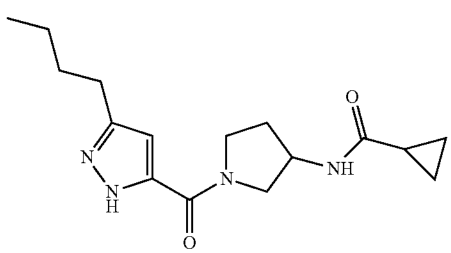 [SMILES: CCCCc1cc(C(=O)N2CCC(NC(=O)C3CC3)C2)[nH]n1] | C | 305.0 | A | 1.440 | $^1$H NMR (400 MHz, CD$_3$OD) δ 6.50 (s, 1H), 4.62 (m, 1H), 4.43-4.41 (m, 1H), 3.86-3.71 (m, 4H), 2.71-2.68 (m, 2H), 2.10-2.08 (m, 1H), 1.98-1.96 (m, 1H), 1.68-1.39 (m, 6H), 0.98-0.75 (m, 7H). |
| 214 | 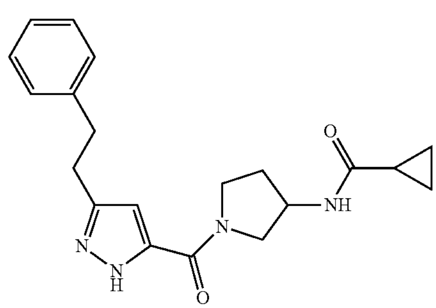 [SMILES: O=C(NC1CCN(C(=O)c2cc(CCc3ccccc3)n[nH]2)C1)C1CC1] | C | 353.2 | A | 0.770 | $^1$H NMR (400 MHz, CD$_3$OD) δ 7.26-7.14 (m, 5H), 6.43 (s, 1H), 4.42-4.39 (m, 1H), 4.05-3.71 (m, 4H), 2.97 (m, 4H), 2.23-2.17 (m, 1H), 1.96-1.92 (m, 1H), 1.60-1.57 (m, 1H), 0.86-0.74 (m, 4H). |

TABLE 1-continued

| Ex | Structure | Synth. Method | LCMS (ESI) m/z | LCMS Method | R$_T$ (min) | NMR |
|---|---|---|---|---|---|---|
| 215 | 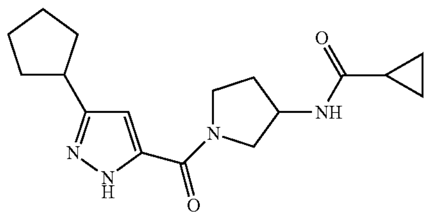 [SMILES: O=C(NC1CCN(C(=O)c2cc(C3CCCC3)n[nH]2)C1)C1CC1] | C | 317.0 | E | 0.747 | $^1$H NMR (400 MHz, CD$_3$OD) δ 6.49 (s, 1H), 4.43-4.30 (m, 1H), 4.10-3.74 (m, 4H), 3.15-3.11 (m, 1H), 2.20-1.81 (m, 4H), 1.71-1.60 (m, 7H), 0.86-0.73 (m, 4H). |
| 216 | 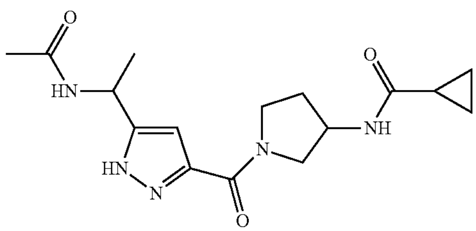 [SMILES: CC(=O)NC(C)c1cc(C(=O)N2CCC(NC(=O)C3CC3)C2)n[nH]1] | C | 334.0 | C | 0.874 | $^1$H NMR (400 MHz, CD$_3$OD) δ 6.62 (s, 1H), 5.20-5.10 (m, 1H), 4.47-4.35 (m, 1H), 4.15-3.50 (m, 4H), 2.30-2.15 (m, 1H), 1.97 (s, 3H), 2.02-1.91 (m, 1H), 1.62-1.54 (m, 1H), 1.50 (d, J = 6.4 Hz, 3H), 0.88-0.80 (m, 2H), 0.78-0.70 (m, 2H). |
| 217 | 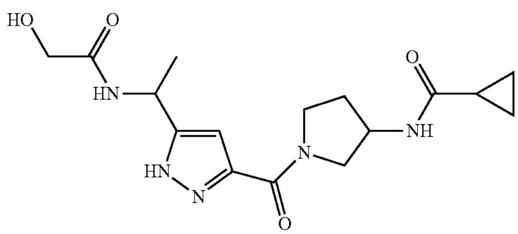 [SMILES: CC(NC(=O)CO)c1cc(C(=O)N2CCC(NC(=O)C3CC3)C2)n[nH]1] | C | 350.0 | C | 0.846 | $^1$H NMR (400 MHz, CD$_3$OD) δ 6.65 (s, 1H), 5.32-5.25 (m, 1H), 4.48-4.35 (m, 1H), 4.01 (s, 2H), 4.12-3.50 (m, 1H), 2.30-2.15 (m, 1H), 2.12-1.90 (m, 1H), 1.62-1.52 (m, 1H), 1.54 (d, J = 6.8 Hz, 3H), 0.88-0.80 (m, 2H), 0.78-0.70 (m, 2H). |
| 218 | 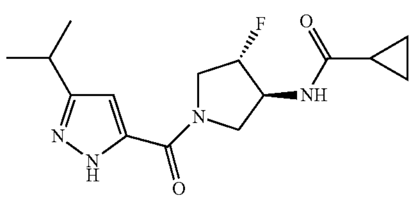 [SMILES: CC(C)c1cc(C(=O)N2C[C@H](NC(=O)C3CC3)[C@@H](F)C2)[nH]n1] | C | 309.1 | C | 1.055 | $^1$H NMR (400 MHz, DMSO-d$_6$) δ 13.02 (s, 1H), 8.48-8.46 (m, 1H), 6.45 (s, 1H), 5.13-4.97 (m, 1H), 4.35-4.07 (m, 3H), 3.81-3.60 (m, 2H), 3.00-2.96 (m, 1H), 1.57-1.51 (m, 1H), 1.23 (d, J = 7.2 Hz, 6H), 0.70-0.66 (m, 4H). |
| 219 | 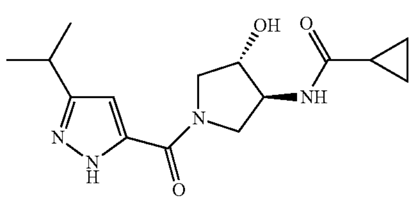 [SMILES: CC(C)c1cc(C(=O)N2C[C@H](NC(=O)C3CC3)[C@@H](O)C2)[nH]n1] | C | 307.2 | C | 0.976 | $^1$H NMR (400 MHz, DMSO-d$_6$) δ 12.94 (s, 1H), 8.30-8.28 (m, 1H), 6.41 (s, 1H), 5.34 (m, 1H), 4.04-3.93 (m, 3H), 3.67-3.61 (m, 2H), 3.41-3.34 (m, 1H), 2.97-2.92 (m, 1H), 1.54-1.49 (m, 1H), 1.21 (d, J = 7.2 Hz, 6H), 0.67-0.62 (m, 4H). |
| 220 | 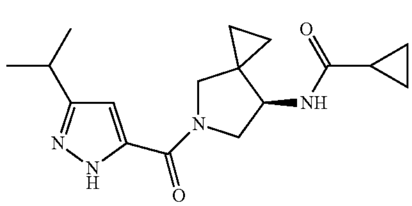 [SMILES: CC(C)c1cc(C(=O)N2C[C@H](NC(=O)C3CC3)C3(CC3)C2)[nH]n1] | C | 317.1 | A | 0.889 | $^1$H NMR (400 MHz, CD$_3$OD) δ 6.51 (s, 1H), 4.29-3.39 (m, 5H), 3.15-2.94 (m, 1H), 1.73-1.58 (m, 1H), 1.32 (d, J = 6.8 Hz, 6H), 0.99-0.61 (m, 8H). |

TABLE 1-continued

| Ex | Structure | Synth. Method | LCMS (ESI) m/z | LCMS Method | R$_T$ (min) | NMR |
|---|---|---|---|---|---|---|
| 221 | 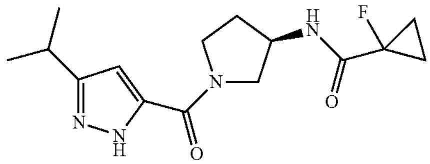 [SMILES: CC(C)c1cc(C(=O)N2CC[C@@H](NC(=O)C3(F)CC3)C2)[nH]n1] | C | 309.2 | F | 4.08 | $^1$H NMR (DMSO-d6) δ: 12.89 (d, J = 11.1 Hz, 1H), 8.66-8.52 (m, 1H), 6.38 (s, 1H), 4.45-4.28 (m, 1H), 4.19-3.97 (m, 1H), 3.80-3.59 (m, 2H), 3.57-3.40 (m, 1H), 2.97 (p, J = 6.9 Hz, 1H), 2.21-1.86 (m, 2H), 1.35-1.12 (m, 10H) |
| 222 | 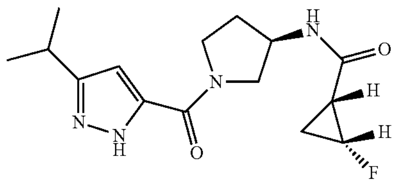 [SMILES: CC(C)c1cc(C(=O)N2CC[C@@H](NC(=O)[C@H]3C[C@H]3F)C2)[nH]n1] | C | 309.2 | F | 3.78 | $^1$H NMR (DMSO-d6) δ: 12.90 (d, J = 10.1 Hz, 1H), 8.36 (d, J = 6.4 Hz, 1H), 6.38 (s, 1H), 4.93-4.64 (m, 1H), 4.34-4.20 (m, 1H), 4.09-3.89 (m, 1H), 3.80-3.47 (m, 3H), 2.97 (p, J = 6.9 Hz, 1H), 2.19-1.97 (m, 1H), 1.89-1.67 (m, 2H), 1.61-1.43 (m, 1H), 1.22 (d, J = 6.9 Hz, 6H), 1.09-0.91 (m, 1H) |
| 223 | 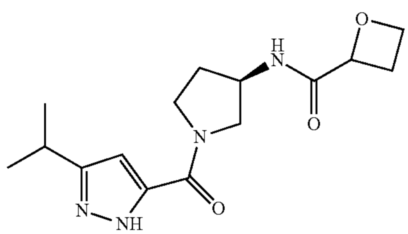 [SMILES: CC(C)c1cc(C(=O)N2CC[C@@H](NC(=O)C3CCO3)C2)[nH]n1] | C | 307.2 | F | 3.59 | $^1$H NMR (DMSO-d6) δ: 12.90 (d, J = 7.6 Hz, 1H), 8.23 (t, J = 8.5 Hz, 1H), 6.38 (d, J = 2.4 Hz, 1H), 4.98-4.86 (m, 1H), 4.65-4.46 (m, 2H), 4.43-4.26 (m, 1H), 4.20-4.07 (m, 1H), 4.05-3.82 (m, 1H), 3.81-3.67 (m, 1H), 3.67-3.56 (m, 1H), 3.56-3.40 (m, 1H), 3.04-2.78 (m, 2H), 2.48-2.41 (m, 1H), 2.19-1.81 (m, 2H), 1.22 (d, J = 6.9 Hz, 6H) |
| 224 | 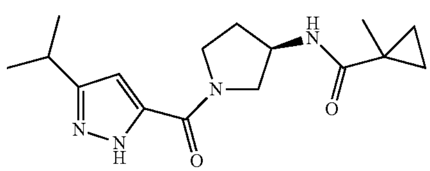 [SMILES: CC(C)c1cc(C(=O)N2CC[C@@H](NC(=O)C3(C)CC3)C2)[nH]n1] | C | 305.2 | F | 4.13 | $^1$H NMR (DMSO-d6) δ: 12.88 (d, J = 11.6 Hz, 1H), 7.50 (d, J = 6.6 Hz, 1H), 6.37 (t, J = 2.4 Hz, 1H), 4.35-4.20 (m, 1H), 4.14-3.78 (m, 2H), 3.69-3.58 (m, 1H), 3.51-3.35 (m, 1H), 2.97 (p, J = 7.0 Hz, 1H), 2.15-1.95 (m, 1H), 1.95-1.78 (m, 1H), 1.25 (d, J = 4.6 Hz, 3H), 1.22 (d, J = 6.9 Hz, 6H), 1.01-0.89 (m, 2H), 0.55-0.44 (m, 2H) |
| 225 | 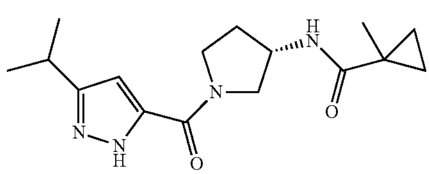 [SMILES: CC(C)c1cc(C(=O)N2CC[C@H](NC(=O)C3(C)CC3)C2)[nH]n1] | C | 305.2 | F | 4.12 | $^1$H NMR (DMSO-d6) δ: 12.88 (d, J = 11.5 Hz, 1H), 7.50 (d, J = 6.6 Hz, 1H), 6.37 (t, J = 2.4 Hz, 1H), 4.35-4.20 (m, 1H), 4.14-3.94 (m, 1H), 3.73-3.57 (m, 2H), 3.51-3.34 (m, 1H), 2.97 (p, J = 6.9 Hz, 1H), 2.12-1.77 (m, 2H), 1.25 (d, J = 4.6 Hz, 3H), 1.22 |

TABLE 1-continued

| Ex | Structure | Synth. Method | LCMS (ESI) m/z | LCMS Method | R$_T$ (min) | NMR |
|---|---|---|---|---|---|---|
| | | | | | | (d, J = 6.9 Hz, 6H), 1.01-0.89 (m, 2H), 0.55-0.44 (m, 2H) |
| 226 | 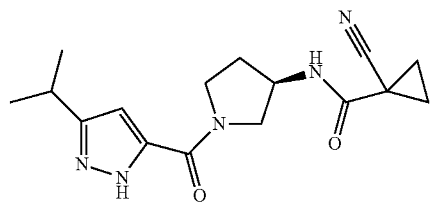 [SMILES: CC(C)c1cc(C(=O)N2CC[C@@H](NC(=O)C3(C#N)CC3)C2)[nH]n1] | C | 316.2 | F | 4.01 | $^1$H NMR (DMSO-d6) δ: 12.89 (s, 1H), 8.31 (d, J = 6.5 Hz, 1H), 6.43-6.34 (m, 1H), 4.38-4.22 (m, 1H), 4.15-3.93 (m, 1H), 3.80-3.56 (m, 2H), 3.54-3.39 (m, 1H), 3.04-2.88 (m, 1H), 2.14-1.83 (m, 2H), 1.62-1.47 (m, 4H), 1.22 (d, J = 6.9 Hz, 6H) |
| 227 | 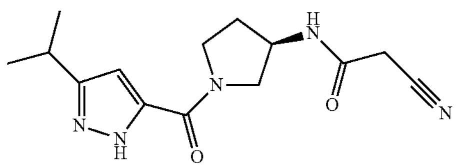 [SMILES: CC(C)c1cc(C(=O)N2CC[C@@H](NC(=O)CC#N)C2)[nH]n1] | C | 290.2 | F | 3.65 | $^1$H NMR (DMSO-d6) δ: 12.91 (d, J = 9.2 Hz, 1H), 8.52 (t, J = 5.6 Hz, 1H), 6.38 (s, 1H), 4.34-4.19 (m, 1H), 4.06-3.73 (m, 2H), 3.69-3.60 (m, 2H), 3.59-3.51 (m, 1H), 3.47-3.35 (m, 1H), 2.97 (p, J = 6.9 Hz, 1H), 2.17-1.98 (m, 1H), 1.93-1.72 (m, 1H), 1.22 (d, J = 6.9 Hz, 6H) |
| 228 | 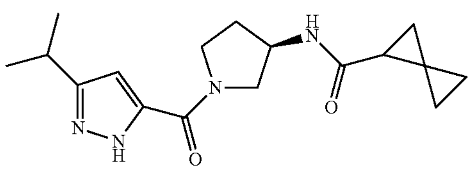 [SMILES: CC(C)c1cc(C(=O)N2CC[C@@H](NC(=O)C3CC34CC4)C2)[nH]n1] | C | 317.2 | F | 4.17 | $^1$H NMR (DMSO-d6) δ: 12.89 (d, J = 11.9 Hz, 1H), 8.12 (t, J = 6.7 Hz, 1H), 6.37 (d, J = 7.1 Hz, 1H), 4.32-4.17 (m, 1H), 4.06-3.87 (m, 1H), 3.75-3.49 (m, 2H), 3.04-2.90 (m, 1H), 2.15-1.95 (m, 1H), 1.94-1.85 (m, 1H), 1.85-1.69 (m, 1H), 1.31-1.23 (m, 2H), 1.22 (dd, J = 6.9, 1.1 Hz, 6H), 1.19-1.10 (m, 1H), 0.88-0.73 (m, 3H), 0.72-0.54 (m, 1H) |
| 229 | 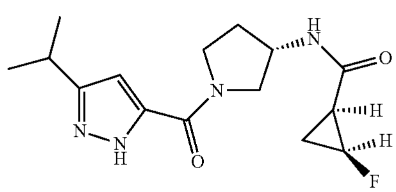 [SMILES: CC(C)c1cc(C(=O)N2CC[C@H](NC(=O)[C@@H]3C[C@@H]3F)C2)[nH]n1] | C | 309.2 | F | 3.78 | $^1$H NMR (DMSO-d6) δ: 12.90 (d, J = 10.1 Hz, 1H), 8.36 (d, J = 6.4 Hz, 1H), 6.38 (t, J = 2.4 Hz, 1H), 4.92-4.64 (m, 1H), 4.34-4.18 (m, 1H), 4.09-3.88 (m, 1H), 3.82-3.46 (m, 2H), 3.45-3.32 (m, 1H), 2.97 (p, J = 6.9 Hz, 1H), 2.19-1.95 (m, 1H), 1.94-1.68 (m, 2H), 1.63-1.41 (m, 1H), 1.10-0.90 (m, 1H) |
| 230 | 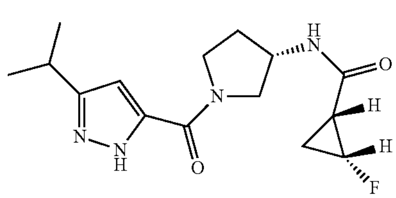 [SMILES: CC(C)c1cc(C(=O)N2CC[C@H](NC(=O)[C@H]3C[C@H]3F)C2)[nH]n1] | C | 309.2 | F | 3.77 | $^1$H NMR (DMSO-d6) δ: 12.90 (d, J = 10.7 Hz, 1H), 8.38 (d, J = 6.6 Hz, 1H), 6.38 (dd, J = 5.9, 2.0 Hz, 1H), 4.95-4.61 (m, 1H), 4.37-4.20 (m, 1H), 4.11-3.89 (m, 1H), 3.75-3.47 (m, 2H), |

TABLE 1-continued

| Ex | Structure | Synth. Method | LCMS (ESI) m/z | LCMS Method | R_T (min) | NMR |
|---|---|---|---|---|---|---|
| | | | | | | 3.42-3.32 (m, 1H), 3.06-2.90 (m, 1H), 2.21-1.98 (m, 1H), 1.96-1.68 (m, 2H), 1.64-1.42 (m, 1H), 0.99 (tdd, J = 10.2, 8.6, 5.2 Hz, 1H) |
| 231 | 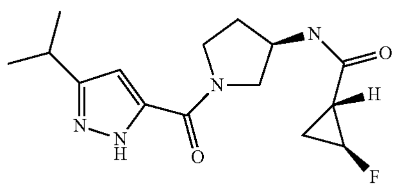 [SMILES: CC(C)c1cc(C(=O)N2CC[C@@H](NC(=O)[C@H]3C[C@@H]3F)C2)[nH]n1] | C | 309.2 | F | 4.02 | $^1$H NMR (DMSO-d6) δ: 12.91 (s, 1H), 8.51 (d, J = 6.6 Hz, 1H), 6.39 (s, 1H), 4.91-4.61 (m, 1H), 4.30-4.16 (m, 1H), 4.09-3.85 (m, 1H), 3.81-3.48 (m, 2H), 3.46-3.33 (m, 1H), 3.07-2.89 (m, 1H), 2.18-1.96 (m, 2H), 1.91-1.67 (m, 1H), 1.48-1.28 (m, 1H), 1.16-1.00 (m, 1H) |
| 232 | 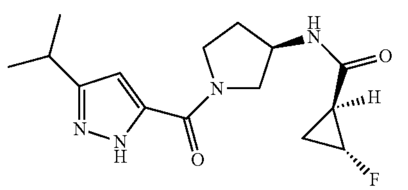 [SMILES: CC(C)c1cc(C(=O)N2CC[C@@H](NC(=O)[C@@H]3C[C@H]3F)C2)[nH]n1] | C | 309.2 | F | 4.01 | $^1$H NMR (DMSO-d6) δ: 12.90 (s, 1H), 8.51 (d, J = 6.7 Hz, 1H), 6.39 (s, 1H), 4.90-4.62 (m, 1H), 4.24 (s, 1H), 3.96 (d, J = 17.5 Hz, 1H), 3.78-3.48 (m, 2H), 3.06-2.88 (m, 1H), 2.21-1.97 (m, 2H), 1.93-1.72 (m, 1H), 1.45-1.27 (m, 1H), 1.22 (dd, J = 6.9, 2.1 Hz, 6H), 1.16-1.00 (m, 1H) |
| 233 | 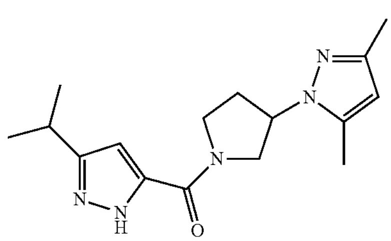 [SMILES: Cc1cc(C)n(C2CCN(C(=O)c3cc(C(C)C)n[nH]3)C2)n1] | D | 302.2 | F | 4.59 | $^1$H NMR (DMSO-d6) δ: 12.90 (d, J = 24.5 Hz, 1H, 6.39 (d, J = 2.1 Hz, 1H), 5.81 (d, J = 6.4 Hz, 1H), 5.04-4.78 (m, 1H), 4.33-4.09 (m, 1H), 4.01 (dd, J = 11.5, 6.6 Hz, 1H), 3.94-3.73 (m, 1H), 3.72-3.51 (m, 1H), 3.02-2.88 (m, 1H), 2.31-2.17 (m, 5H), 2.07 (s, 3H), 1.22 (dd, J = 6.9, 5.8 Hz, 6H) |
| 234 | 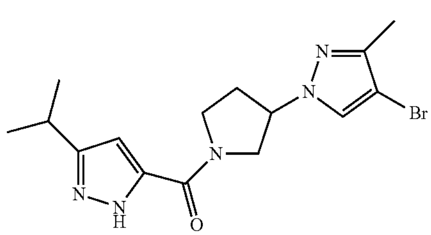 [SMILES: Cc1nn(C2CCN(C(=O)c3cc(C(C)C)n[nH]3)C2)cc1Br] | D | 392.2 | F | 5.32 | $^1$H NMR (DMSO-d6) δ: 12.92 (s, 1H), 7.95 (d, J = 7.9 Hz, 1H), 6.40 (d, J = 6.5 Hz, 1H), 4.96-4.82 (m, 1H), 4.26-3.93 (m, 2H), 3.91-3.75 (m, 1H), 3.72-3.51 (m, 1H), 3.04-2.88 (m, 1H), 2.40-2.31 (m, 1H), 2.31-2.21 (m, 1H), 1.86-1.72 (m, 1H), 1.22 (dt, J = 6.9, 2.6 Hz, 6H), 0.91-0.80 (m, 2H), 0.77-0.65 (m, 2H) |

TABLE 1-continued

| Ex | Structure | Synth. Method | LCMS (ESI) m/z | LCMS Method | R<sub>T</sub> (min) | NMR |
|---|---|---|---|---|---|---|
| 235 | 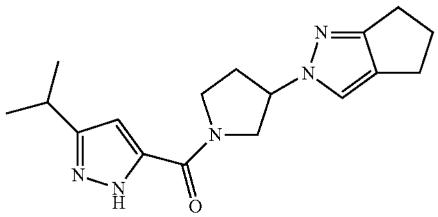 [SMILES: CC(C)c1cc(C(=O)N2CCC(n3cc4c(n3)CCC4)C2)[nH]n1] | D | 314.2 | F | 4.75 | ¹H NMR (DMSO-d6) δ: 12.91 (d, J = 14.4 Hz, 1H), 7.39 (d, J = 8.2 Hz, 0.5H), 7.11 (d, J = 3.3 Hz, 0.5H), 6.39 (s, 1H), 4.98-4.80 (m, 1H), 4.10-3.96 (m, 1H), 3.94-3.76 (m, 1H), 3.75-3.54 (m, 1H), 3.04-2.88 (m, 1H), 2.76-2.65 (m, 1H), 2.60-2.51 (m, 4H), 2.38-2.20 (m, 3H), 1.22 (dd, J = 6.9, 3.2 Hz, 6H) |
| 236 | 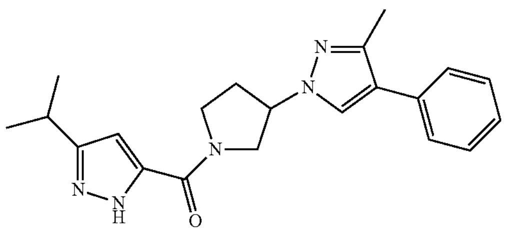 [SMILES: Cc1nn(C2CCN(C(=O)c3cc(C(C)C)n[nH]3)C2)cc1-c1ccccc1] | D | 364.2 | F | 5.42 | ¹H NMR (DMSO-d6) δ: 12.92 (d, J = 11.3 Hz, 1H), 8.03 (d, J = 9.5 Hz, 1H), 7.49-7.41 (m, 2H), 7.41-7.33 (m, 2H), 7.29-7.16 (m, 1H), 6.40 (s, 1H), 5.03-4.88 (m, 1H), 4.40-4.16 (m, 1H), 4.14-4.00 (m, 1H), 4.02-3.85 (m, 1H), 3.82-3.85 (m, 1H), 3.04-2.89 (m, 1H), 2.47-2.33 (m, 2H), 2.30 (d, J = 5.1 Hz, 3H), 1.22 (dd, J = 6.9, 2.8 Hz, 6H) |
| 237 | 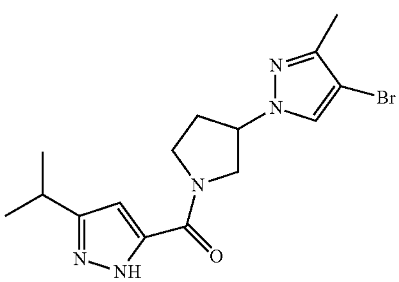 [SMILES: Cc1nn(C2CCN(C(=O)c3cc(C(C)C)n[nH]3)C2)cc1Br] | D | 366.1 | F | 5.07 | ¹H NMR (DMSO-d6) δ: 12.92 (s, 1H), 7.99 (d, J = 8.0 Hz, 1H), 6.40 (s, 1H), 5.02-4.84 (m, 1H), 4.36-4.13 (m, 1H), 4.10-3.97 (m, 1H), 3.95-3.79 (m, 1H), 3.75-3.54 (m, 1H), 3.06-2.87 (m, 1H), 2.43-2.24 (m, 2H), 2.11 (d, J = 4.3 Hz, 3H), 1.22 (dd, J = 6.9, 2.7 Hz, 6H) |
| 238 | 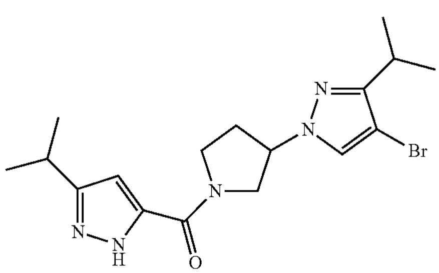 [SMILES: CC(C)c1cc(C(=O)N2CCC(n3cc(Br)c(C(C)C)n3)C2)[nH]n1] | D | 394.1 | F | 5.81 | ¹H NMR (DMSO-d6) δ: 12.93 (s, 1H), 7.97 (d, J = 8.1 Hz, 1H), 6.40 (s, 1H), 5.02-4.86 (m, 1H), 4.35-3.97 (m, 2H), 3.96-3.79 (m, 1H), 3.78-3.53 (m, 1H), 3.06-2.85 (m, 2H), 2.43-2.35 (m, 1H), 2.35-2.24 (m, 1H), 1.34-1.10 (m, 12H) |
| 239 | 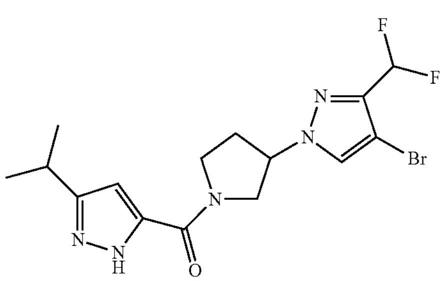 [SMILES: CC(C)c1cc(C(=O)N2CCC(n3cc(Br)c(C(F)F)n3)C2)[nH]n1] | D | 402.1 | F | 5.26 | ¹H NMR (DMSO-d6) δ: 12.93 (d, J = 10.4 Hz, 1H), 8.28 (d, J = 8.3 Hz, 1H), 6.99 (td, J = 53.0, 4.0 Hz, 1H), 6.40 (d, J = 3.6 Hz, 1H), 5.32-4.88 (m, 1H), 4.55-4.19 (m, 1H), 4.17-3.80 (m, 2H), 3.78-3.50 (m, 1H), 3.13-2.82 (m, 1H), 2.48-2.28 (m, 2H), 1.22 (dd, J = 6.9, 2.6 Hz, 6H) |

TABLE 1-continued

| Ex | Structure | Synth. Method | LCMS (ESI) m/z | LCMS Method | R_T (min) | NMR |
|---|---|---|---|---|---|---|
| 240 | 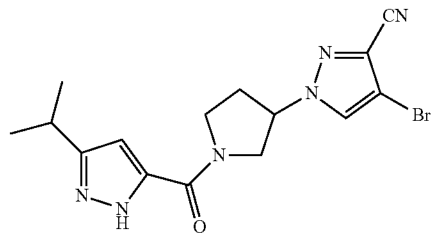 [SMILES: CC(C)c1cc(C(=O)N2CCC(n3cc(Br)c(C#N)n3)C2)[nH]n1] | D | 377.1 | F | 5.09 | $^1$H NMR (DMSO-d6) δ: 12.94 (d, J = 12.5 Hz, 1H), 8.48 (d, J = 8.8 Hz, 1H), 6.41 (d, J = 3.5 Hz, 1H), 5.27-5.07 (m, 1H), 4.39-4.24 (m, 1H), 4.15-3.85 (m, 2H), 3.76-3.58 (m, 1H), 3.07-2.86 (m, 1H), 2.48-2.29 (m, 2H), 1.22 (dd, J = 6.9, 2.4 Hz, 6H) |
| 241 | 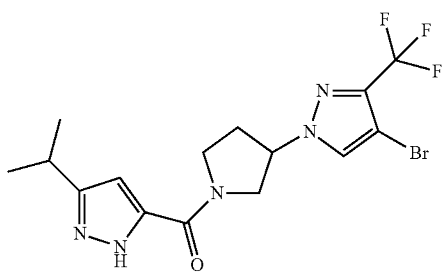 [SMILES: CC(C)c1cc(C(=O)N2CCC(n3cc(Br)c(C(F)(F)F)n3)C2)[nH]n1] | D | 420.2 | F | 5.55 | $^1$H NMR (DMSO-d6) δ: 12.95 (s, 1H), 8.49-8.34 (m, 1H), 6.41 (s, 1H), 5.22-5.03 (m, 1H), 4.30 (d, J = 33.1 Hz, 1H), 4.12-3.85 (m, 2H), 3.77-3.59 (m, 1H), 3.04-2.88 (m, 1H), 2.48-2.28 (m, 2H), 1.33-1.10 (m, 6H) |
| 242 | 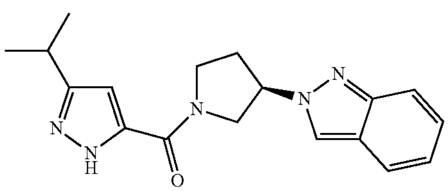 [SMILES: CC(C)c1cc(C(=O)N2CC[C@@H](n3cc4ccccc4n3)C2)[nH]n1] | D | 324.2 | F | 4.82 | $^1$H NMR (400 MHz, DMSO-d6) δ 8.52-8.38 (m, 1H), 7.75-7.67 (m, 1H), 7.63-7.56 (m, 1H), 7.27-7.19 (m, 1H), 7.08-6.98 (m, 1H), 6.49-6.36 (m, 1H), 5.45-5.26 (m, 1H), 4.47-4.31 (m, 1H), 4.20-4.00 (m, 2H), 3.89-3.66 (m, 1H), 3.02-2.90 (m, 1H), 2.62-2.52 (m, 2H), 1.26-1.11 (m, 6H) |
| 243 | 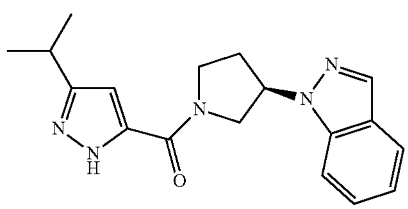 [SMILES: CC(C)c1cc(C(=O)N2CC[C@@H](n3ncc4ccccc43)C2)[nH]n1] | D | 324.2 | F | 5.14 | $^1$H NMR (400 MHz, DMSO-d6) δ 8.09 (d, J = 1.3 Hz, 1H), 7.85-7.67 (m, 2H), 7.41 (dtd, J = 8.0, 6.8, 1.1 Hz, 1H), 7.25-7.09 (m, 1H), 6.48-6.34 (m, 1H), 5.57-5.47 (m, 1H), 4.41-3.70 (m, 4H), 3.00-2.88 (m, 1H), 2.40 (dt, J = 12.5, 6.5 Hz, 2H), 1.26-1.15 (m, 6H) |
| 244 | 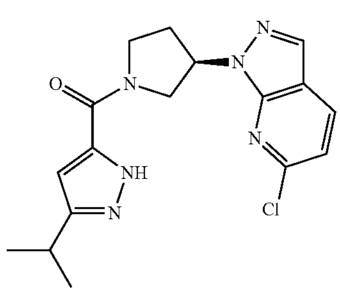 | D | 359.1 | F | 5.34 | $^1$H NMR (400 MHz, DMSO-d6) δ 8.33 (d, J = 8.3, 4.4 Hz, 1H), 8.24 (d, J = 3.4 Hz, 1H), 7.33 (dd, J = 8.4, 4.8 Hz, 1H), 6.41 (s, 1H), 5.58 (s, 1H), 4.41-3.70 (m, 4H), 3.06-2.81 (m, 1H), 2.46-2.25 (m, 2H), 1.28-1.15 (m, 6H) |

| Ex | Structure | Synth. Method | LCMS (ESI) m/z | LCMS Method | R_T (min) | NMR |
|---|---|---|---|---|---|---|
| 245 | 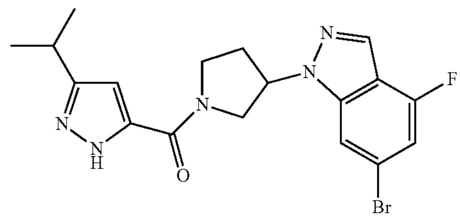 [SMILES: CC(C)c1cc(C(=O)N2CCC(n3ncc4c(F)cc(Br)cc43)C2)[nH]n1] | D | 420.1 | F | 5.98 | $^1$H NMR (400 MHz, DMSO-d6) δ 12.91 (d, J = 34.2 Hz, 1H), 8.38-8.21 (m, 1H), 8.10-7.91 (m, 1H), 7.30-7.09 (m, 1H), 6.41 (dd, J = 4.9, 2.1 Hz, 1H), 5.69-5.37 (m, 1H), 4.45-3.58 (m, 5H), 3.06-2.90 (m, 1H), 2.40-2.31 (m, 1H), 1.28-1.15 (m, 6H) |
| 246 | 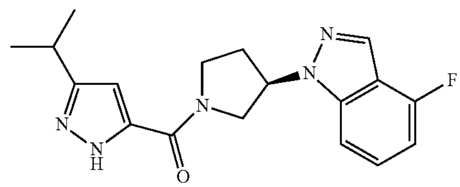 [SMILES: CC(C)c1cc(C(=O)N2CC[C@@H](n3ncc4c(F)cccc43)C2)[nH]n1] | D | 342.2 | F | 5.38 | $^1$H NMR (400 MHz, DMSO-d6) δ 12.91 (s, 1H), 8.31-8.14 (m, 1H), 7.62 (t, J = 9.0 Hz, 1H), 7.50-7.34 (m, 1H), 7.04-67.88 (m, 1H), 6.41 (dd, J = 4.4, 2.1 Hz, 1H), 5.63-5.41 (m, 1H), 4.47-3.58 (m, 4H), 3.06-2.84 (m, 1H), 2.46-2.25 (m, 2H), 1.30-1.11 (m, 6H) |
| 247 | 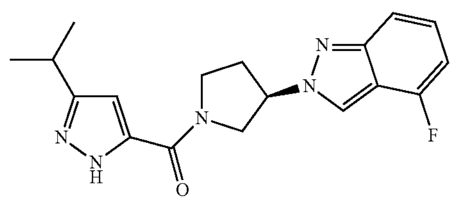 [SMILES: CC(C)c1cc(C(=O)N2CC[C@@H](n3cc4c(F)cccc4n3)C2)[nH]n1] | D | 342.2 | F | 4.85 | $^1$H NMR (400 MHz, DMSO-d6) δ 8.67 (d, J = 7.9 Hz, 1H), 7.56-7.38 (m, 1H), 7.32-7.09 (m, 1H), 6.88-6.67 (m, 1H), 6.51-6.30 (m, 1H), 5.51-5.20 (m, 1H), 4.55-4.31 (m, 1H), 4.27-3.94 (m, 2H), 3.91-3.66 (m, 1H), 3.08-2.82 (m, 1H), 1.38-1.07 (m, 6H) |

Example 248

KDM5 Enzyme Assay Procedure

Full length KDM5A enzyme was expressed and purified inhouse. Biotin-H3K4me3 peptide was purchased from New England Biolabs. HTRF reagents (containing Eu-labeled H3K4me1-2 antibody, and streptavidin-XL665) were purchased from Cis-Bio International. Plates were read on an Envision multi-label plate reader (Perkin Elmer).

The HTRF assay mixture contained 2 nM full length KDM5A enzyme, 100 nM H3K4Me3 peptide substrate, 1 uM 2-OG, 100 uM $Fe^{2+}$, 500 uM ascorbate. 50 mM HEPES pH 7.0 buffer, 0.01% Triton-X 100, 2 mM DTT, 0.25% DMSO at a final volume of 10 uL.

The enzyme reaction was carried out at room temperature in black Proxiplate 384-Plus plate (Corning. Costar) within 30 minutes, in the presence of varying concentration of a test compound. At the end of enzyme reaction, 5 uL of 1 mM EDTA were added to quench the reaction and then the detection reagents (5 uL) were added to give final concentrations of 0.5 nM Eu-labeled H3K4me1-2 antibody, and 50 nM streptavidin-XL665. The plates were incubated at room temperature for 60 minutes and then read in the Envision plate reader. The readouts were transformed into % inhibition, and IC50 value of a test compounds was generated by using four parameters curve fitting (Model 205 in XLFIT5, iDBS).

Example 249

KDM5 Cell Assay Procedure

PC9 cells were seeded in a 384 well plate (2000 cells/well) with a test compound and incubated for 120 hours at 37° C. H3K4Me3 mark level was assessed using HTRF reagents from CisBio. Briefly, media was removed and cells were lysed in 20 μL of Epigeneous Cell Histone lysis buffer C for 45 min at 26° C., shaking. 10 μL of 4 μg/mL acceptor antibody (H3K4me3-d2) and 10 μL of 1.2 μg/mL donor antibody (Total H3-K) in Cell Histone detection buffer were added and the mixture was incubated at 26° C. for 1 hour. Assay plate was read subsequently on Envision (Perkin Elmer). Each compound was run in duplicate. Data were normalized to DMSO treated wells as the low response and $EC_{50}$'s were calculate using a four-parameter fit.

Data for the compounds of Examples 1-247 from the assays described in Examples 248 and 249 is provided in the following table.

TABLE 2
| Ex | Structure | KDM5A HTRF IC$_{50}$ (nM) | H3K4Me3 PC9 HTRF EC$_{50}$ (nM) |
|---|---|---|---|
| 1 | 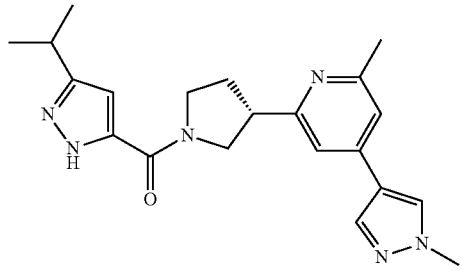 [SMILES: Cc1cc(-c2cnn(C)c2)cc([C@H]2CCN(C(=O)c3cc(C(C)C)n[nH]3)C2)n1] | | 0.17 |
| 2 | 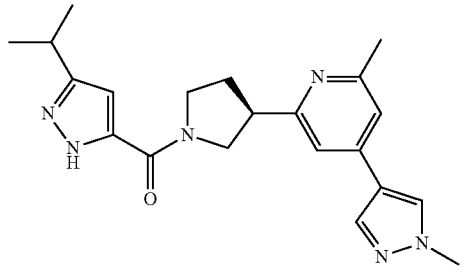 [SMILES: Cc1cc(-c2cnn(C)c2)cc([C@@H]2CCN(C(=O)c3cc(C(C)C)n[nH]3)C2)n1] | | 0.84 |
| 3 | 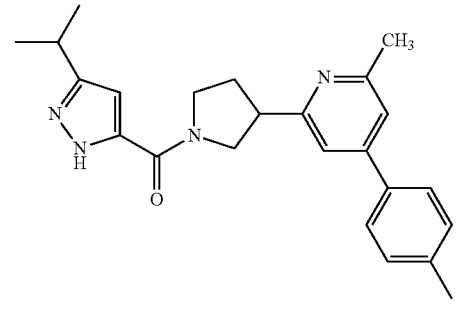 [SMILES: Cc1ccc(-c2cc(C)nc(C3CCN(C(=O)c4cc(C(C)C)n[nH]4)C3)c2)cc1] | | 0.22 |
| 4 | 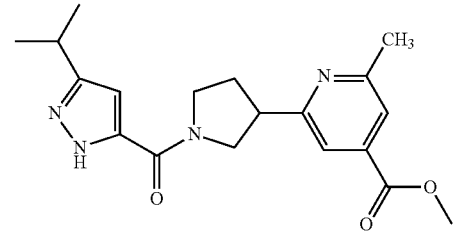 [SMILES: COC(=O)c1cc(C)nc(C2CCN(C(=O)c3cc(C(C)C)n[nH]3)C2)c1] | | 12 |
| 5 | 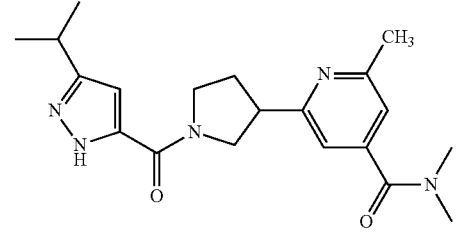 [SMILES: Cc1cc(C(=O)N(C)C)cc(C2CCN(C(=O)c3cc(C(C)C)n[nH]3)C2)n1] | | 7.4 |

TABLE 2-continued
| Ex | Structure | KDM5A HTRF IC$_{50}$ (nM) | H3K4Me3 PC9 HTRF EC$_{50}$ (nM) |
|---|---|---|---|
| 6 | 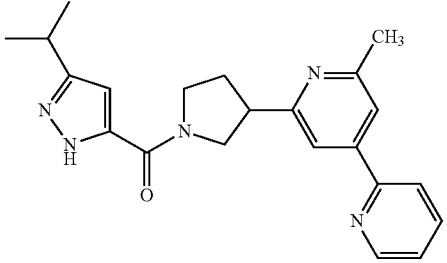 [SMILES: Cc1cc(-c2ccccn2)cc(C2CCN(C(=O)c3cc(C(C)C)n[nH]3)C2)n1] | 1 | |
| 7 | 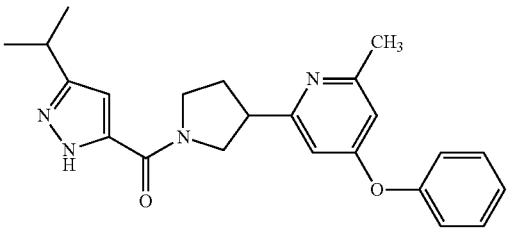 | 0.13 | |
| 8 | 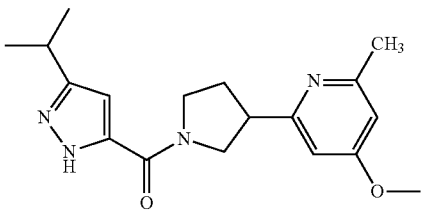 [SMILES: COc1cc(C)nc(C2CCN(C(=O)c3cc(C(C)C)n[nH]3)C2)c1] | 1.4 | |
| 9 | 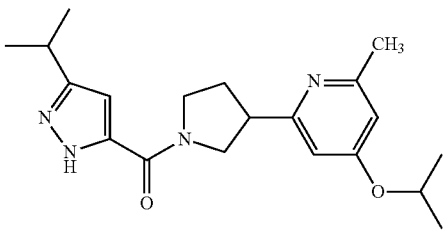 [SMILES: Cc1cc(OC(C)C)cc(C2CCN(C(=O)c3cc(C(C)C)n[nH]3)C2)n1] | 8.6 | |
| 10 | 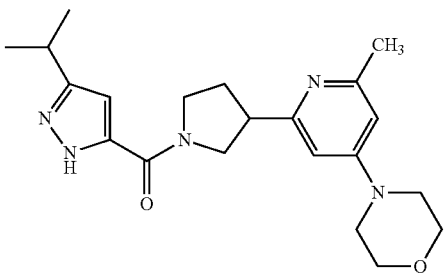 [SMILES: Cc1cc(N2CCOCC2)cc(C2CCN(C(=O)c3cc(C(C)C)n[nH]3)C2)n1] | 14 | |

TABLE 2-continued

| Ex | Structure | KDM5A HTRF IC$_{50}$ (nM) | H3K4Me3 PC9 HTRF EC$_{50}$ (nM) |
|---|---|---|---|
| 11 | 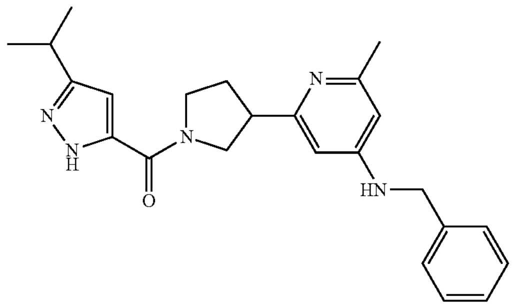 [SMILES: Cc1cc(NCc2ccccc2)cc(C2CCN(C(=O)c3cc(C(C)C)n[nH]3)C2)n1] | 11 | |
| 12 | 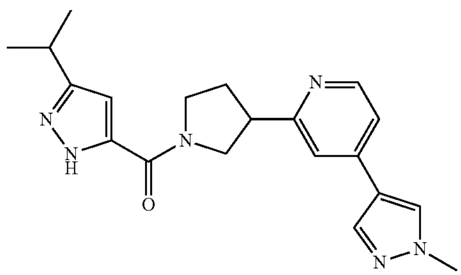 | 0.57 | 23 |
| 13 | 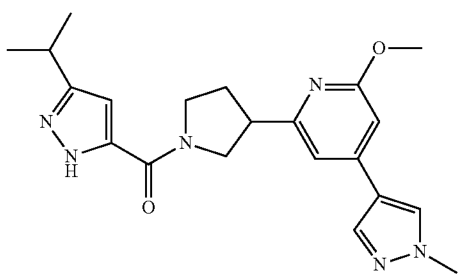 [SMILES: COc1cc(-c2cnn(C)c2)cc(C2CCN(C(=O)c3cc(C(C)C)n[nH]3)C2)n1] | 0.094 | |
| 14 | 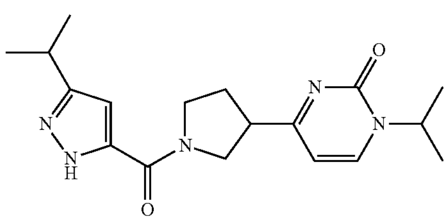 [SMILES: CC(C)c1cc(C(=O)N2CCC(c3ccn(C(C)C)c(=O)n3)C2)[nH]n1] | 0.19 | |
| 15 | 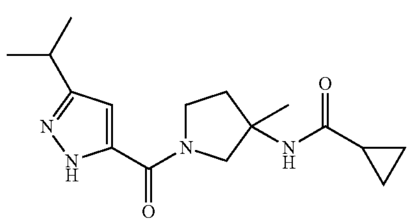 [SMILES: CC(C)c1cc(C(=O)N2CCC(C)(NC(=O)C3CC3)C2)[nH]n1] | 2 | |
| 16 | 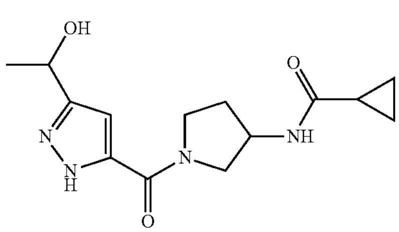 [SMILES: CC(O)c1cc(C(=O)N2CCC(NC(=O)C3CC3)C2)[nH]n1] | 0.91 | |

TABLE 2-continued

| Ex | Structure | KDM5A HTRF IC$_{50}$ (nM) | H3K4Me3 PC9 HTRF EC$_{50}$ (nM) |
|---|---|---|---|
| 17 | 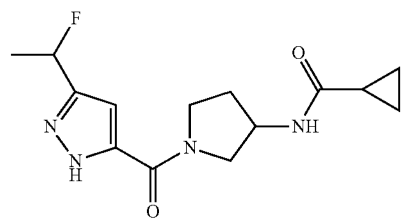 [SMILES: CC(F)c1cc(C(=O)N2CCC(NC(=O)C3CC3)C2)[nH]n1] | 25 | |
| 18 | 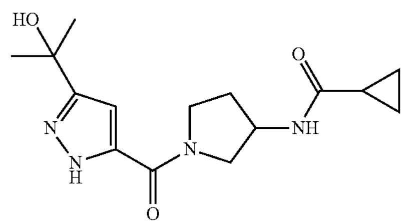 [SMILES: CC(C)(O)c1cc(C(=O)N2CCC(NC(=O)C3CC3)C2)[nH]n1] | 0.74 | |
| 19 | 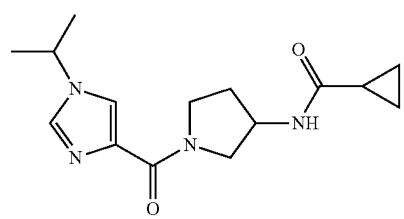 [SMILES: CC(C)n1cnc(C(=O)N2CCC(NC(=O)C3CC3)C2)c1] | 0.21 | 26 |
| 20 | 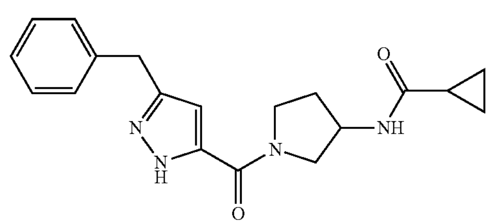 [SMILES: O=C(NC1CCN(C(=O)c2cc(Cc3ccccc3)n[nH]2)C1)C1CC1] | 4.8 | |
| 21 | 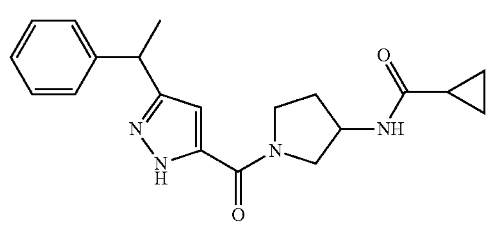 [SMILES: CC(c1ccccc1)c1cc(C(=O)N2CCC(NC(=O)C3CC3)C2)[nH]n1] | 0.65 | |
| 22 | 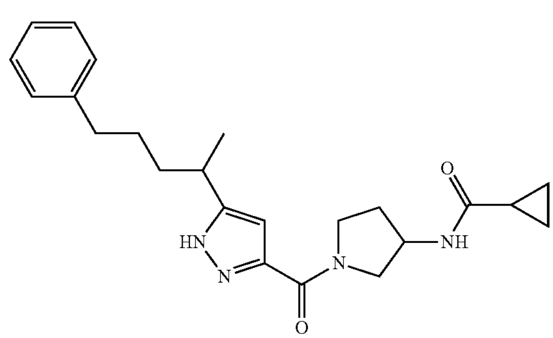 [SMILES: CC(CCCc1ccccc1)c1cc(C(=O)N2CCC(NC(=O)C3CC3)C2)n[nH]1] | 0.12 | 11 |

TABLE 2-continued
| Ex | Structure | KDM5A HTRF IC$_{50}$ (nM) | H3K4Me3 PC9 HTRF EC$_{50}$ (nM) |
|---|---|---|---|
| 23 | 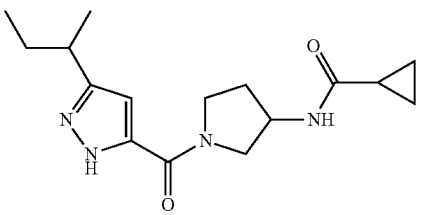 [SMILES: CCC(C)c1cc(C(=O)N2CCC(NC(=O)C3CC3)C2)[nH]n1] | 0.21 | |
| 24 | 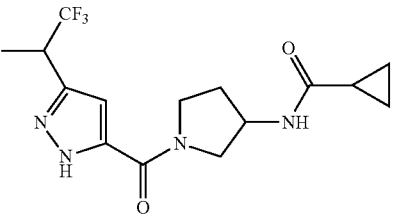 [SMILES: CC(c1cc(C(=O)N2CCC(NC(=O)C3CC3)C2)[nH]n1)C(F)(F)F] | 1.2 | |
| 25 | 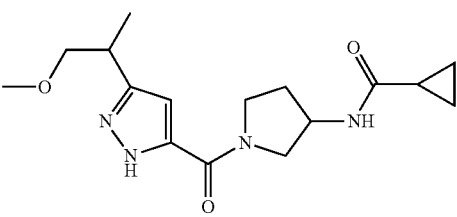 [SMILES: COCC(C)c1cc(C(=O)N2CCC(NC(=O)C3CC3)C2)[nH]n1] | 0.93 | |
| 26 | 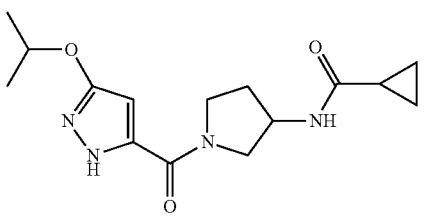 | 8.4 | |
| 27 | 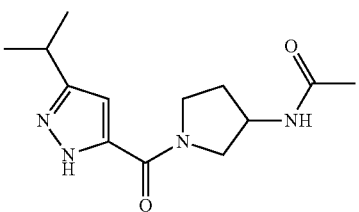 [SMILES: CC(=O)NC1CCN(C(=O)c2cc(C(C)C)n[nH]2)C1] | 11 | |
| 28 | 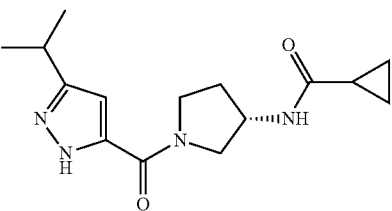 [SMILES: CC(C)c1cc(C(=O)N2CC[C@H](NC(=O)C3CC3)C2)[nH]n1] | 0.13 | |
| 29 | 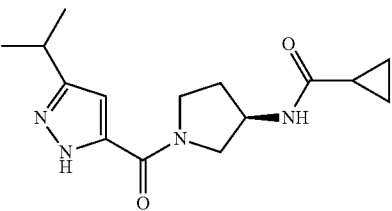 | 0.049 | 0.93 |

TABLE 2-continued

| Ex | Structure | KDM5A HTRF IC$_{50}$ (nM) | H3K4Me3 PC9 HTRF EC$_{50}$ (nM) |
|---|---|---|---|
| 30 | 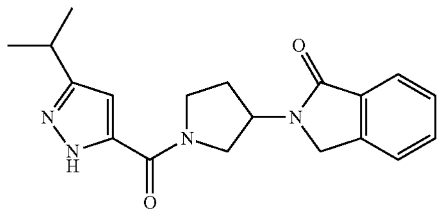 [SMILES: CC(C)c1cc(C(=O)N2CCC(N3Cc4ccccc4C3=O)C2)[nH]n1] | 0.14 | 15 |
| 31 | 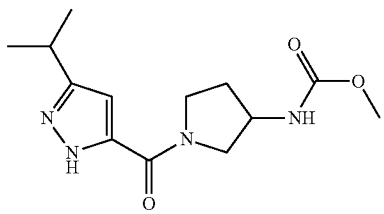 [SMILES: COC(=O)NC1CCN(C(=O)c2cc(C(C)C)n[nH]2)C1] | 0.59 | |
| 32 | 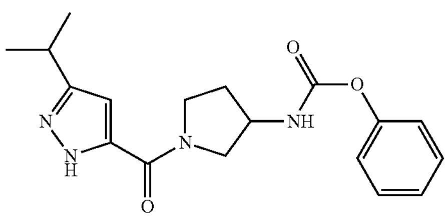 [SMILES: CC(C)c1cc(C(=O)N2CCC(NC(=O)Oc3ccccc3)C2)[nH]n1] | 2.1 | |
| 33 | 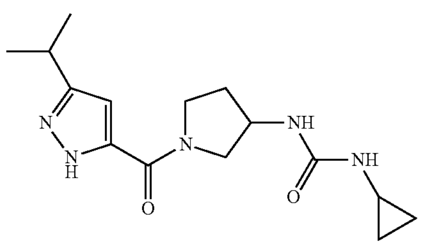 [SMILES: CC(C)c1cc(C(=O)N2CCC(NC(=O)NC3CC3)C2)[nH]n1] | 0.087 | 3.3 |
| 34 | 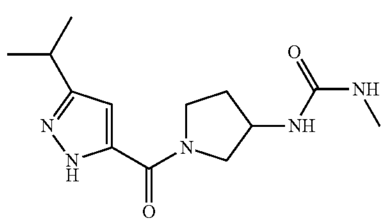 [SMILES: CNC(=O)NC1CCN(C(=O)c2cc(C(C)C)n[nH]2)C1] | 0.058 | 2.3 |
| 35 | 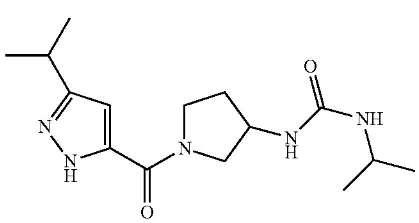 [SMILES: CC(C)NC(=O)NC1CCN(C(=O)c2cc(C(C)C)n[nH]2)C1] | 0.083 | |

TABLE 2-continued

| Ex | Structure | KDM5A HTRF IC$_{50}$ (nM) | H3K4Me3 PC9 HTRF EC$_{50}$ (nM) |
|---|---|---|---|
| 36 | 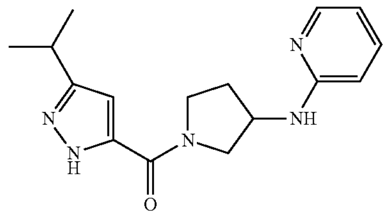 [SMILES: CC(C)c1cc(C(=O)N2CCC(Nc3ccccn3)C2)[nH]n1] | 11 | |
| 37 | 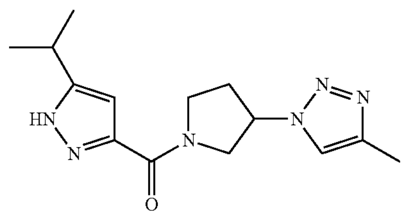 [SMILES: Cc1cn(C2CCN(C(=O)c3cc(C(C)C)[nH]n3)C2)nn1] | 5.8 | |
| 38 | 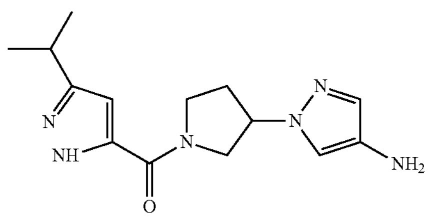 [SMILES: CC(C)C(=N)/C=C(\N)C(=O)N1CCC(n2cc(N)cn2)C1] | 1.8 | |
| 39 | 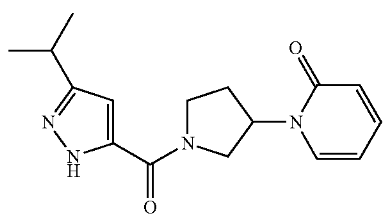 [SMILES: CC(C)c1cc(C(=O)N2CCC(n3ccccc3=O)C2)[nH]n1] | 1.2 | |
| 40 | 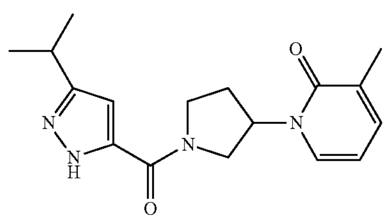 [SMILES: Cc1cccn(C2CCN(C(=O)c3cc(C(C)C)n[nH]3)C2)c1=O] | 0.058 | 3.7 |
| 41 | 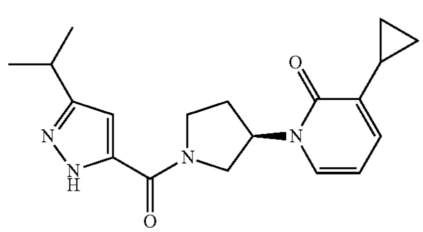 [SMILES: CC(C)c1cc(C(=O)N2CC[C@@H](n3cccc(C4CC4)c3=O)C2)[nH]n1] | 0.051 | 6.8 |
| 42 | 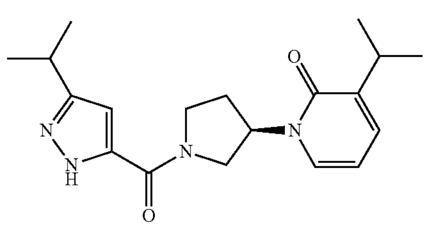 [SMILES: CC(C)c1cc(C(=O)N2CC[C@@H](n3cccc(C(C)C)c3=O)C2)[nH]n1] | 0.082 | |

TABLE 2-continued

| Ex | Structure | KDM5A HTRF IC$_{50}$ (nM) | H3K4Me3 PC9 HTRF EC$_{50}$ (nM) |
|---|---|---|---|
| 43 | 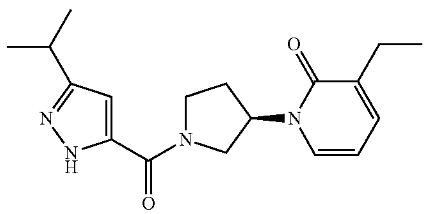 [SMILES: CCc1cccn([C@@H]2CCN(C(=O)c3cc(C(C)C)n[nH]3)C2)c1=O] | 0.039 | |
| 44 | 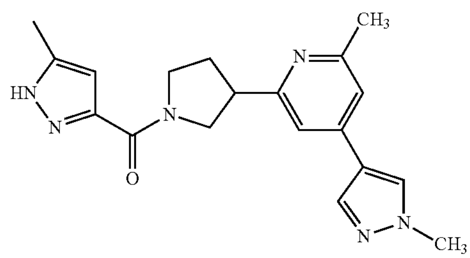 | 2.7 | |
| 45 | 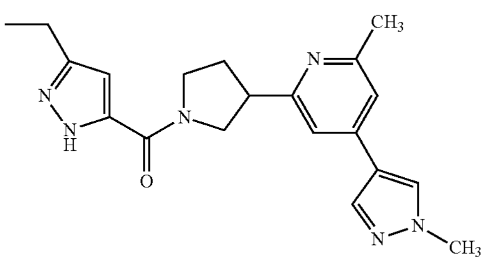 [SMILES: CCc1cc(C(=O)N2CCC(c3cc(-c4cnn(C)c4)cc(C)n3)C2)[nH]n1] | 0.91 | |
| 46 | 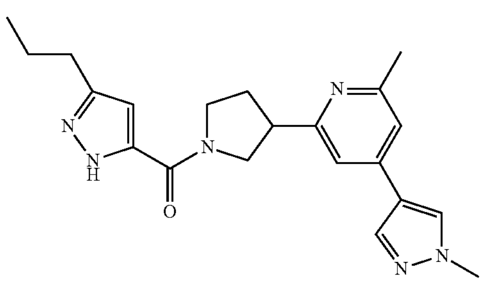 [SMILES: CCCc1cc(C(=O)N2CCC(c3cc(-c4cnn(C)c4)cc(C)n3)C2)[nH]n1] | 0.54 | |
| 47 | 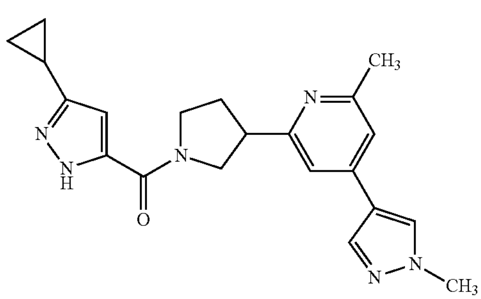 [SMILES: Cc1cc(-c2cnn(C)c2)cc(C2CCN(C(=O)c3cc(C4CC4)n[nH]3)C2)n1] | 0.4 | |

TABLE 2-continued

| Ex | Structure | KDM5A HTRF IC$_{50}$ (nM) | H3K4Me3 PC9 HTRF EC$_{50}$ (nM) |
|---|---|---|---|
| 48 | 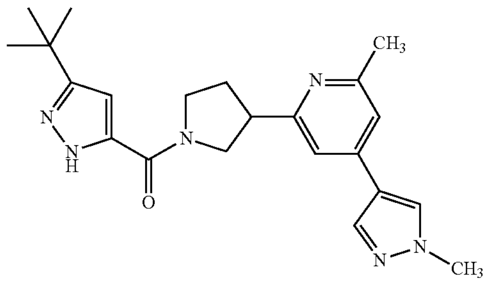 [SMILES: Cc1cc(-c2cnn(C)c2)cc(C2CCN(C(=O)c3cc(C(C)(C)C)n[nH]3)C2)n1] | 0.9 | |
| 49 | 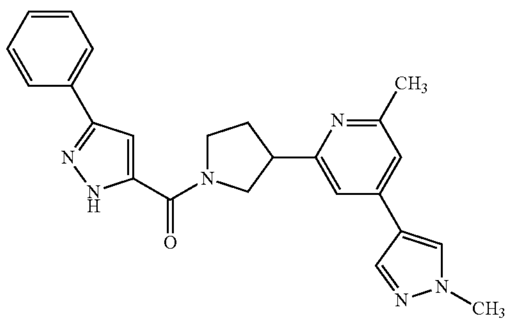 [SMILES: Cc1cc(-c2cnn(C)c2)cc(C2CCN(C(=O)c3cc(-c4ccccc4)n[nH]3)C2)n1] | 3.6 | |
| 50 | 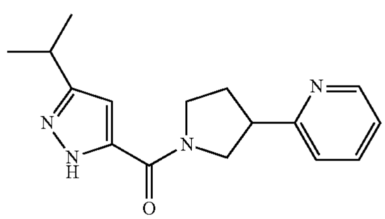 [SMILES: CC(C)c1cc(C(=O)N2CCC(c3ccccn3)C2)[nH]n1] | 6.1 | |
| 51 | 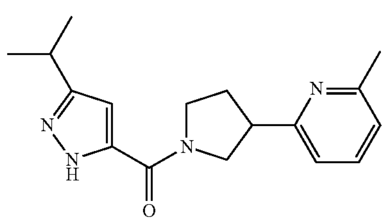 [SMILES: Cc1cccc(C2CCN(C(=O)c3cc(C(C)C)n[nH]3)C2)n1] | 2.4 | |
| 52 | 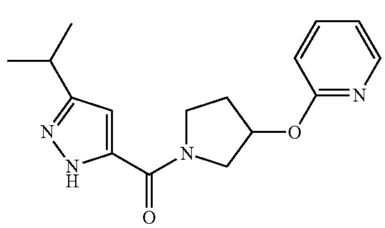 [SMILES: CC(C)c1cc(C(=O)N2CCC(Oc3ccccn3)C2)[nH]n1] | 14 | |
| 53 | 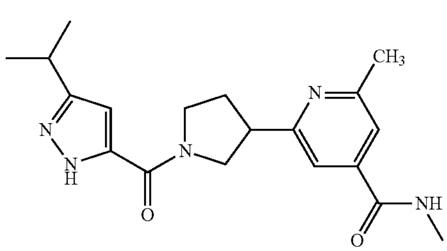 [SMILES: CNC(=O)c1cc(C)nc(C2CCN(C(=O)c3cc(C(C)C)n[nH]3)C2)c1] | 4.2 | |

TABLE 2-continued

| Ex | Structure | KDM5A HTRF IC$_{50}$ (nM) | H3K4Me3 PC9 HTRF EC$_{50}$ (nM) |
|---|---|---|---|
| 54 | 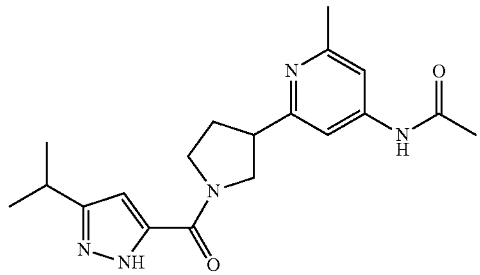 [SMILES: CC(=O)Nc1cc(C)nc(C2CCN(C(=O)c3cc(C(C)C)n[nH]3)C2)c1] | | 1.7 |
| 55 | 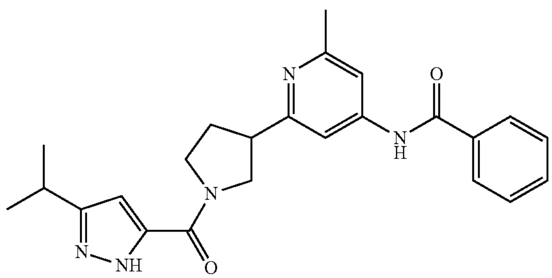 [SMILES: Cc1cc(NC(=O)c2ccccc2)cc(C2CCN(C(=O)c3cc(C(C)C)n[nH]3)C2)n1] | | 1.2 |
| 56 | 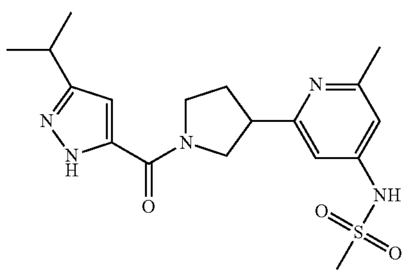 [SMILES: Cc1cc(NS(C)(=O)=O)cc(C2CCN(C(=O)c3cc(C(C)C)n[nH]3)C2)n1] | | 16 |
| 57 | 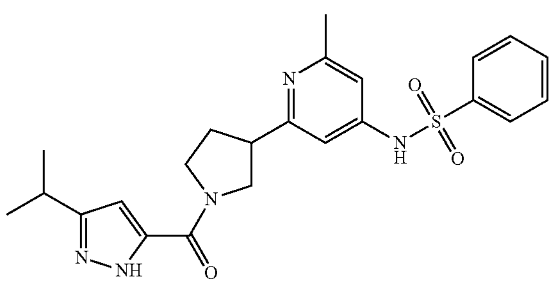 [SMILES: Cc1cc(NS(=O)(=O)c2ccccc2)cc(C2CCN(C(=O)c3cc(C(C)C)n[nH]3)C2)n1] | | 17 |
| 58 | 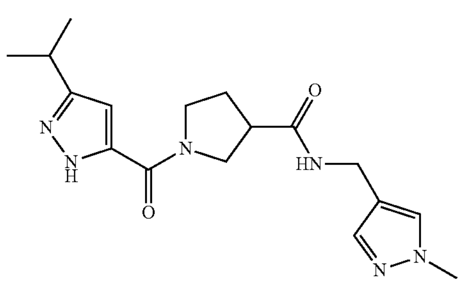 [SMILES: CC(C)c1cc(C(=O)N2CCC(C(=O)NCc3cnn(C)c3)C2)[nH]n1] | | 15 |

TABLE 2-continued
| Ex | Structure | KDM5A HTRF IC$_{50}$ (nM) | H3K4Me3 PC9 HTRF EC$_{50}$ (nM) |
|---|---|---|---|
| 59 | 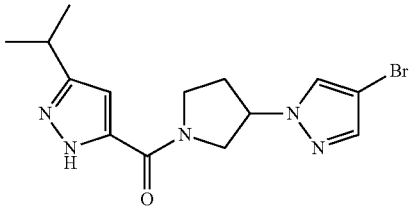 [SMILES: CC(C)c1cc(C(=O)N2CCC(n3cc(Br)cn3)C2)[nH]n1] | 0.74 | 30 |
| 60 | 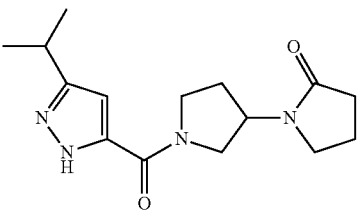 [SMILES: CC(C)c1cc(C(=O)N2CCC(N3CCCC3=O)C2)[nH]n1] | 7.1 | |
| 61 | 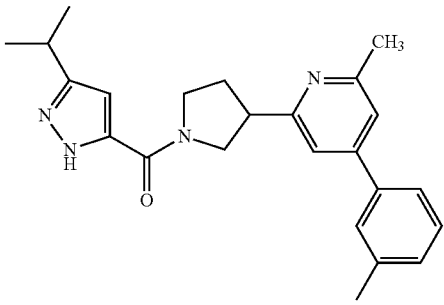 [SMILES: Cc1cccc(-c2cc(C)nc(C3CCN(C(=O)c4cc(C(C)C)n[nH]4)C3)c2)c1] | 0.12 | |
| 62 | 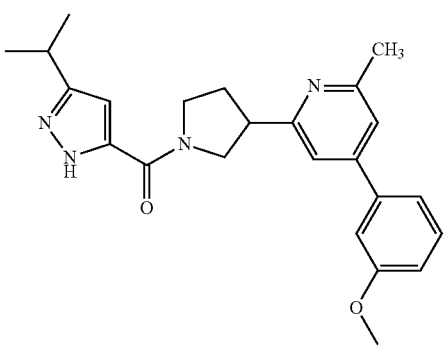 [SMILES: COc1cccc(-c2cc(C)nc(C3CCN(C(=O)c4cc(C(C)C)n[nH]4)C3)c2)c1] | 0.22 | |
| 63 | 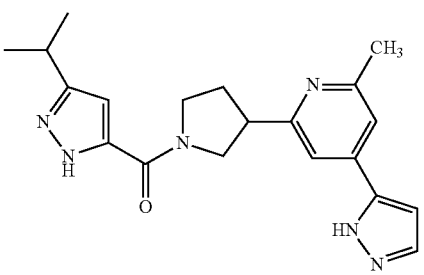 [SMILES: Cc1cc(-c2ccn[nH]2)cc(C2CCN(C(=O)c3cc(C(C)C)n[nH]3)C2)n1] | 0.35 | |

TABLE 2-continued
| Ex | Structure | KDM5A HTRF IC$_{50}$ (nM) | H3K4Me3 PC9 HTRF EC$_{50}$ (nM) |
|---|---|---|---|
| 64 | 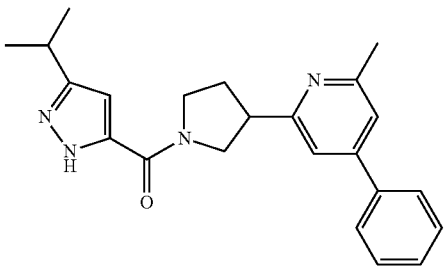 [SMILES: Cc1cc(-c2ccccc2)cc(C2CCN(C(=O)c3cc(C(C)C)n[nH]3)C2)n1] | | 0.23 |
| 65 | 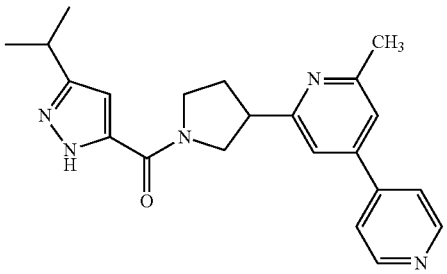 [SMILES: Cc1cc(-c2ccncc2)cc(C2CCN(C(=O)c3cc(C(C)C)n[nH]3)C2)n1] | | 0.37 |
| 66 | 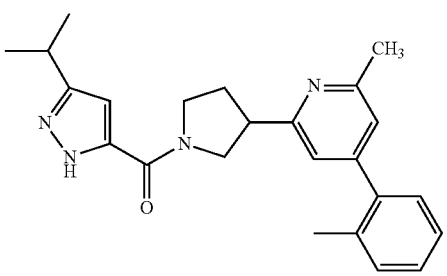 [SMILES: Cc1cc(-c2ccccc2C)cc(C2CCN(C(=O)c3cc(C(C)C)n[nH]3)C2)n1] | | 0.25 |
| 67 | 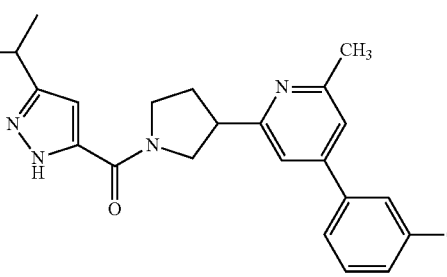 | | 0.35 |
| 68 | 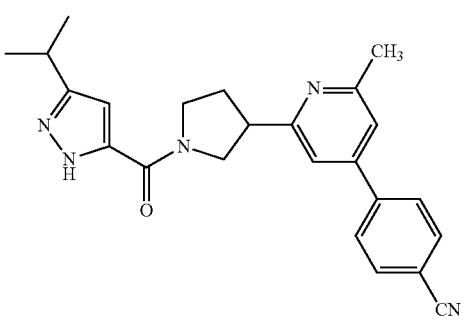 [SMILES: Cc1cc(-c2ccc(C#N)cc2)cc(C2CCN(C(=O)c3cc(C(C)C)n[nH]3)C2)n1] | | 0.29 |

TABLE 2-continued

| Ex | Structure | KDM5A HTRF IC$_{50}$ (nM) | H3K4Me3 PC9 HTRF EC$_{50}$ (nM) |
|---|---|---|---|
| 69 | 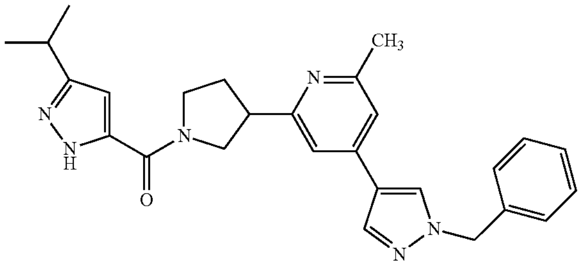 [SMILES: Cc1cc(-c2cnn(Cc3ccccc3)c2)cc(C2CCN(C(=O)c3cc(C(C)C)n[nH]3)C2)n1] | 0.11 | 15 |
| 70 | 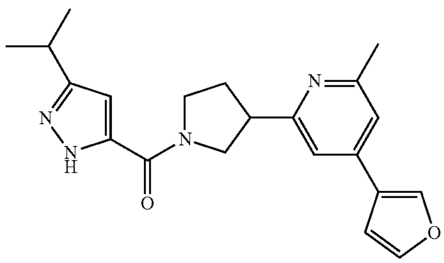 [SMILES: Cc1cc(-c2ccoc2)cc(C2CCN(C(=O)c3cc(C(C)C)n[nH]3)C2)n1] | 0.27 | |
| 71 | 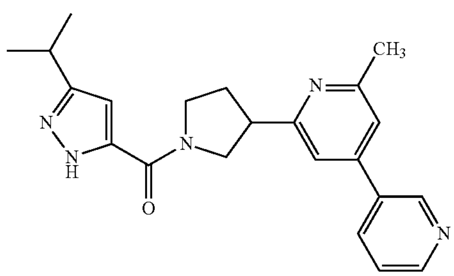 [SMILES: Cc1cc(-c2cccnc2)cc(C2CCN(C(=O)c3cc(C(C)C)n[nH]3)C2)n1] | 0.47 | |
| 72 | 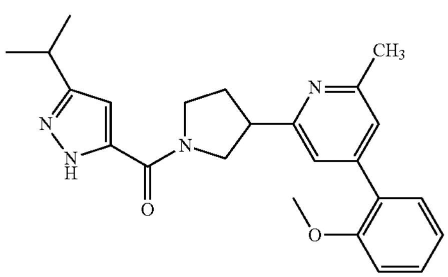 [SMILES: COc1ccccc1-c1cc(C)nc(C2CCN(C(=O)c3cc(C(C)C)n[nH]3)C2)c1] | 0.24 | |
| 73 | 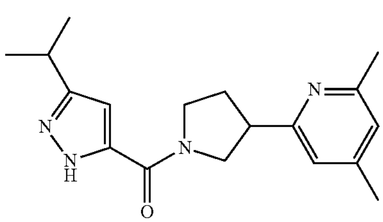 [SMILES: Cc1cc(C)nc(C2CCN(C(=O)c3cc(C(C)C)n[nH]3)C2)c1] | 1.1 | |

TABLE 2-continued

| Ex | Structure | KDM5A HTRF IC$_{50}$ (nM) | H3K4Me3 PC9 HTRF EC$_{50}$ (nM) |
|---|---|---|---|
| 74 | 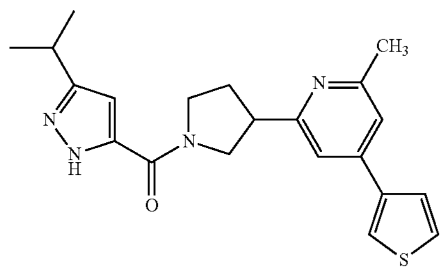 [SMILES: Cc1cc(-c2ccsc2)cc(C2CCN(C(=O)c3cc(C(C)C)n[nH]3)C2)n1] | 0.22 | |
| 75 | 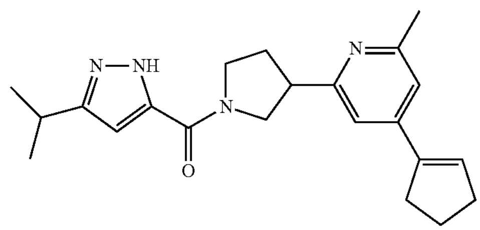 [SMILES: Cc1cc(C2=CCCC2)cc(C2CCN(C(=O)c3cc(C(C)C)n[nH]3)C2)n1] | 0.54 | |
| 76 | 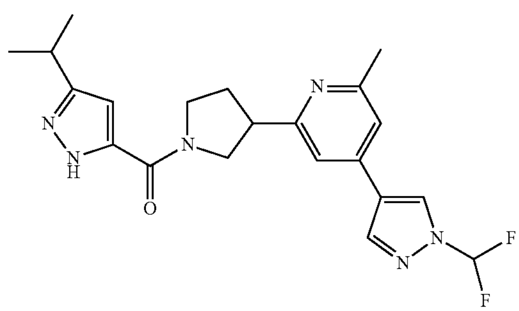 [SMILES: Cc1cc(-c2cnn(C(F)F)c2)cc(C2CCN(C(=O)c3cc(C(C)C)n[nH]3)C2)n1] | 1.7 | |
| 77 | 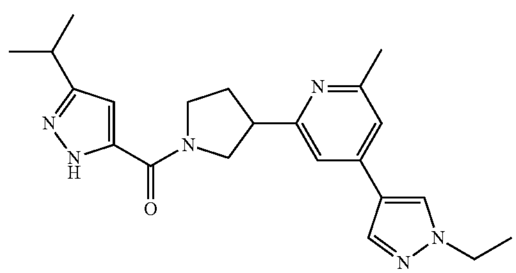 [SMILES: CCn1cc(-c2cc(C)nc(C3CCN(C(=O)c4cc(C(C)C)n[nH]4)C3)c2)cn1] | 0.67 | |
| 78 | 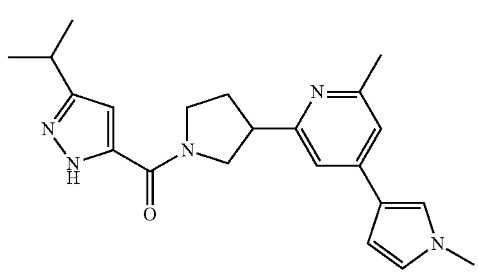 [SMILES: Cc1cc(-c2ccn(C)c2)cc(C2CCN(C(=O)c3cc(C(C)C)n[nH]3)C2)n1] | 0.34 | |

TABLE 2-continued

| Ex | Structure | KDM5A HTRF IC$_{50}$ (nM) | H3K4Me3 PC9 HTRF EC$_{50}$ (nM) |
|---|---|---|---|
| 79 | 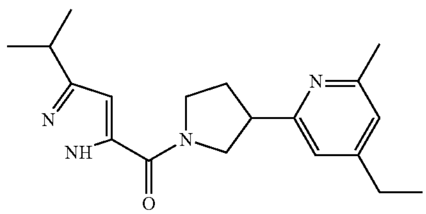 [SMILES: CCc1cc(C)nc(C2CCN(C(=O)/C(N)=C/C(=N)C(C)C)C2)c1] | | 1.4 |
| 80 | 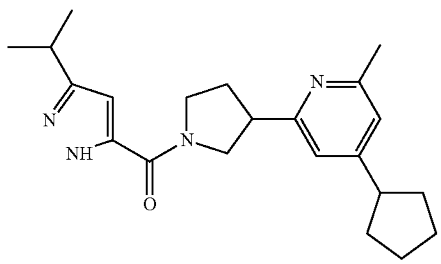 [SMILES: Cc1cc(C2CCCC2)cc(C2CCN(C(=O)/C(N)=C/C(=N)C(C)C)C2)n1] | | 0.98 |
| 81 | 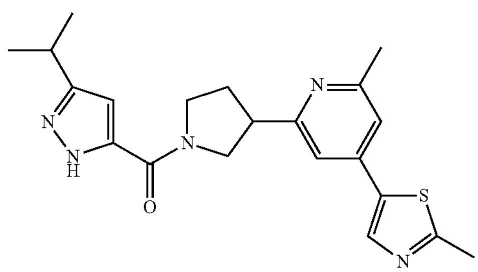 [SMILES: Cc1cc(-c2cnc(C)s2)cc(C2CCN(C(=O)c3cc(C(C)C)n[nH]3)C2)n1] | | 0.67 |
| 82 | 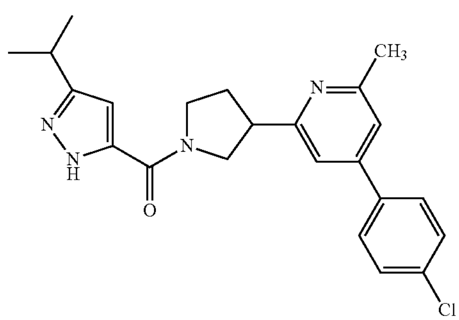 [SMILES: Cc1cc(-c2ccc(Cl)cc2)cc(C2CCN(C(=O)c3cc(C(C)C)n[nH]3)C2)n1] | | 0.16 |
| 83 | 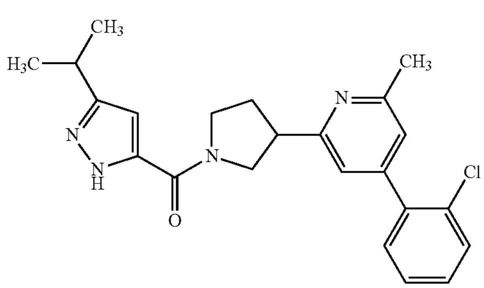 [SMILES: Cc1cc(-c2ccccc2Cl)cc(C2CCN(C(=O)c3cc(C(C)C)n[nH]3)C2)n1] | | 0.26 |

TABLE 2-continued

| Ex | Structure | KDM5A HTRF IC$_{50}$ (nM) | H3K4Me3 PC9 HTRF EC$_{50}$ (nM) |
|---|---|---|---|
| 84 | 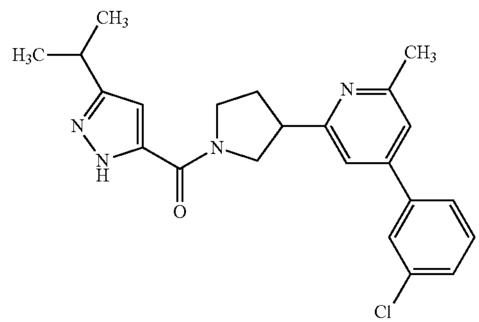 [SMILES: Cc1cc(-c2cccc(Cl)c2)cc(C2CCN(C(=O)c3cc(C(C)C)n[nH]3)C2)n1] | | 0.4 |
| 85 | 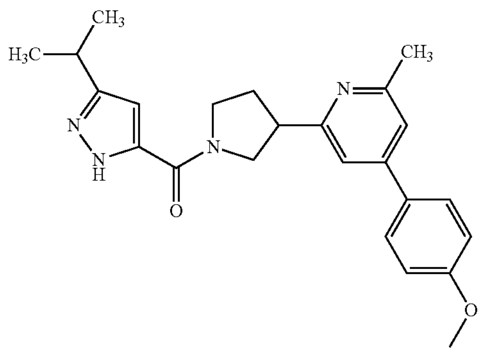 [SMILES: COc1ccc(-c2cc(C)nc(C3CCN(C(=O)c4cc(C(C)C)n[nH]4)C3)c2)cc1] | | 0.27 |
| 86 | 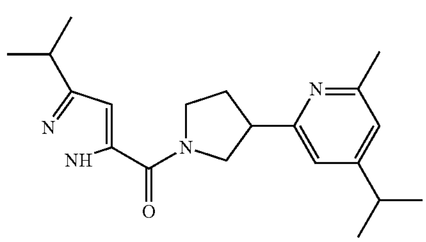 [SMILES: Cc1cc(C(C)C)cc(C2CCN(C(=O)/C(N)=C/C(=N)C(C)C)C2)n1] | | 1.1 |
| 87 | 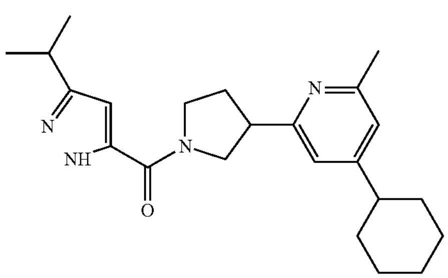 [SMILES: Cc1cc(C2CCCCC2)cc(C2CCN(C(=O)/C(N)=C/C(=N)C(C)C)C2)n1] | | 0.64 |
| 88 | 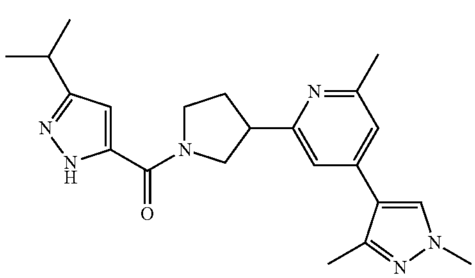 [SMILES: Cc1cc(-c2cn(C)nc2C)cc(C2CCN(C(=O)c3cc(C(C)C)n[nH]3)C2)n1] | | 0.44 |

TABLE 2-continued
| Ex | Structure | KDM5A HTRF IC$_{50}$ (nM) | H3K4Me3 PC9 HTRF EC$_{50}$ (nM) |
|---|---|---|---|
| 89 | 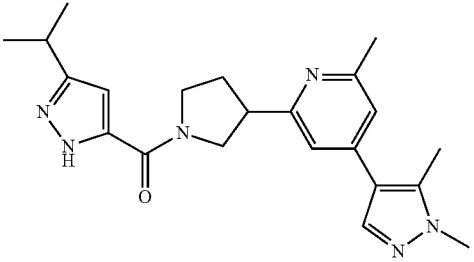 [SMILES: Cc1cc(-c2cnn(C)c2C)cc(C2CCN(C(=O)c3cc(C(C)C)n[nH]3)C2)n1] | 0.37 | |
| 90 | 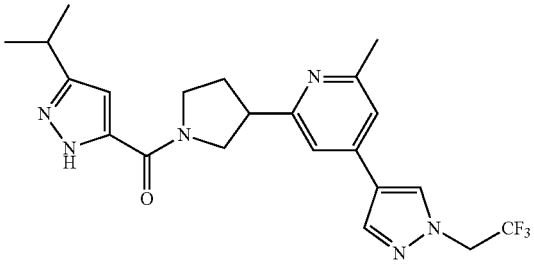 [SMILES: Cc1cc(-c2cnn(CC(F)(F)F)c2)cc(C2CCN(C(=O)c3cc(C(C)C)n[nH]3)C2)n1] | 0.4 | |
| 91 | 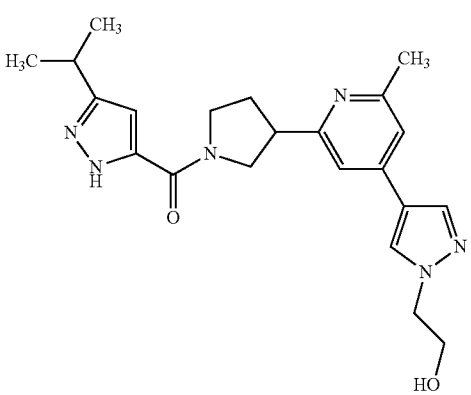 [SMILES: Cc1cc(-c2cnn(CCO)c2)cc(C2CCN(C(=O)c3cc(C(C)C)n[nH]3)C2)n1] | 0.41 | |
| 92 | 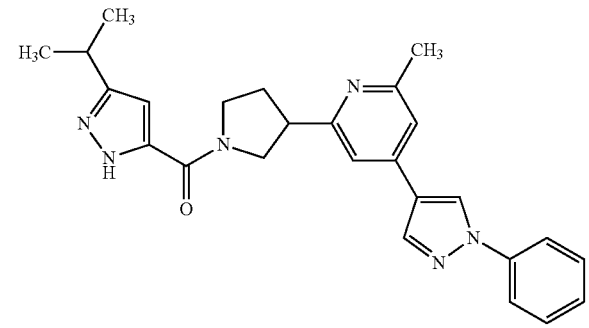 [SMILES: Cc1cc(-c2cnn(-c3ccccc3)c2)cc(C2CCN(C(=O)c3cc(C(C)C)n[nH]3)C2)n1] | 0.3 | |

TABLE 2-continued

| Ex | Structure | KDM5A HTRF IC$_{50}$ (nM) | H3K4Me3 PC9 HTRF EC$_{50}$ (nM) |
|---|---|---|---|
| 93 | 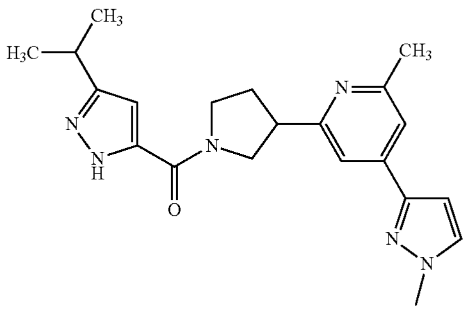 [SMILES: Cc1cc(-c2ccn(C)n2)cc(C2CCN(C(=O)c3cc(C(C)C)n[nH]3)C2)n1] | | 0.79 |
| 94 | 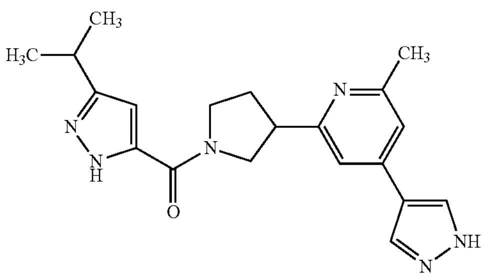 [SMILES: Cc1cc(-c2cn[nH]c2)cc(C2CCN(C(=O)c3cc(C(C)C)n[nH]3)C2)n1] | | 0.21 |
| 95 | 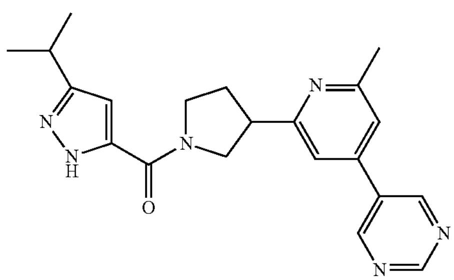 [SMILES: Cc1cc(-c2cncnc2)cc(C2CCN(C(=O)c3cc(C(C)C)n[nH]3)C2)n1] | | 2.7 |
| 96 | 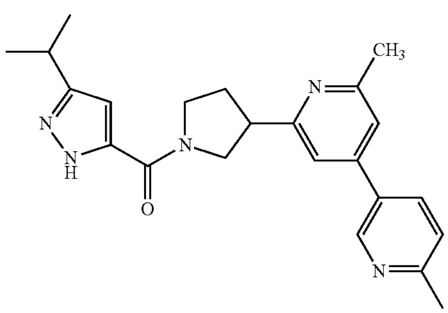 [SMILES: Cc1ccc(-c2cc(C)nc(C3CCN(C(=O)c4cc(C(C)C)n[nH]4)C3)c2)cn1] | | 0.62 |
| 97 | 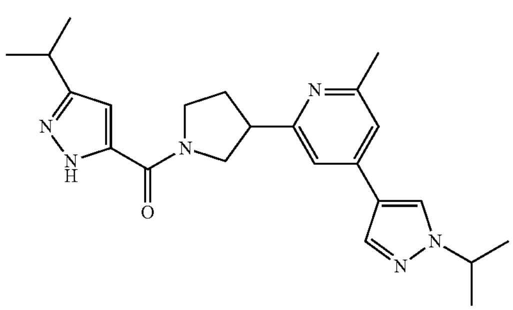 [SMILES: Cc1cc(-c2cnn(C(C)C)c2)cc(C2CCN(C(=O)c3cc(C(C)C)n[nH]3)C2)n1] | | 0.5 |

TABLE 2-continued

| Ex | Structure | KDM5A HTRF IC$_{50}$ (nM) | H3K4Me3 PC9 HTRF EC$_{50}$ (nM) |
|---|---|---|---|
| 98 | 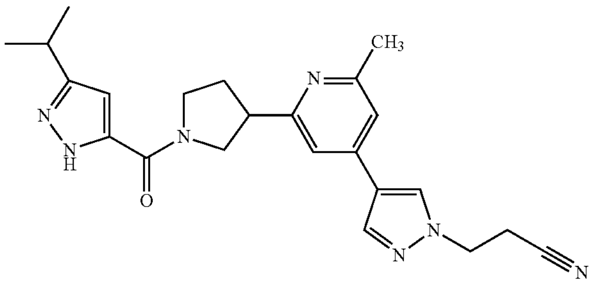 [SMILES: Cc1cc(-c2cnn(CCC#N)c2)cc(C2CCN(C(=O)c3cc(C(C)C)n[nH]3)C2)n1] | | 0.32 |
| 99 | 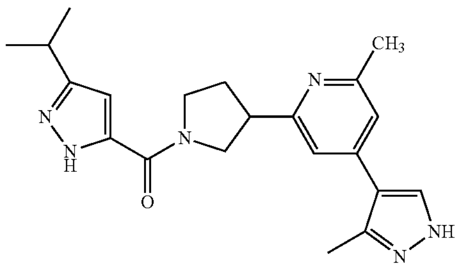 [SMILES: Cc1cc(-c2c[nH]nc2C)cc(C2CCN(C(=O)c3cc(C(C)C)n[nH]3)C2)n1] | | 0.13 |
| 100 | 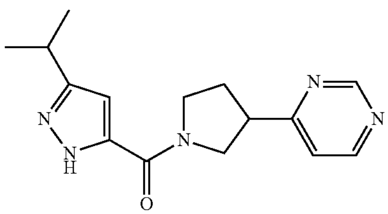 [SMILES: CC(C)c1cc(C(=O)N2CCC(c3ccncn3)C2)[nH]n1] | | 9.8 |
| 101 | 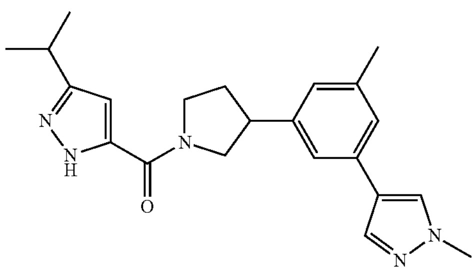 [SMILES: Cc1cc(-c2cnn(C)c2)cc(C2CCN(C(=O)c3cc(C(C)C)n[nH]3)C2)c1] | | 16 |
| 102 | 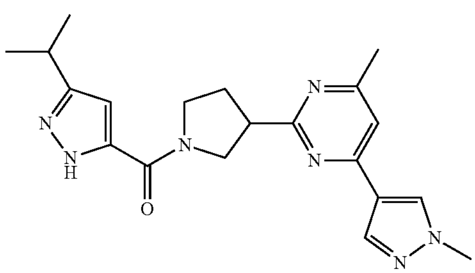 [SMILES: Cc1cc(-c2cnn(C)c2)nc(C2CCN(C(=O)c3cc(C(C)C)n[nH]3)C2)n1] | | 0.76 |
| 103 | 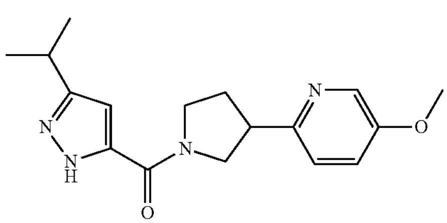 [SMILES: COc1ccc(C2CCN(C(=O)c3cc(C(C)C)n[nH]3)C2)nc1] | | 1.6 |

TABLE 2-continued

| Ex | Structure | KDM5A HTRF IC$_{50}$ (nM) | H3K4Me3 PC9 HTRF EC$_{50}$ (nM) |
|---|---|---|---|
| 104 | 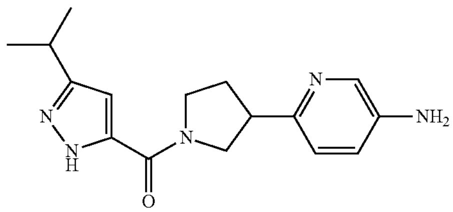 [SMILES: CC(C)c1cc(C(=O)N2CCC(c3ccc(N)cn3)C2)[nH]n1] | 3.3 | |
| 105 | 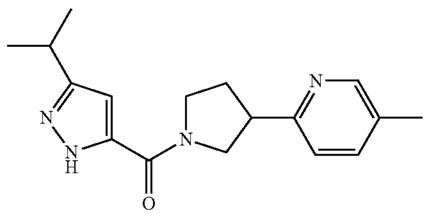 [SMILES: Cc1ccc(C2CCN(C(=O)c3cc(C(C)C)n[nH]3)C2)nc1] | 2.3 | |
| 106 | 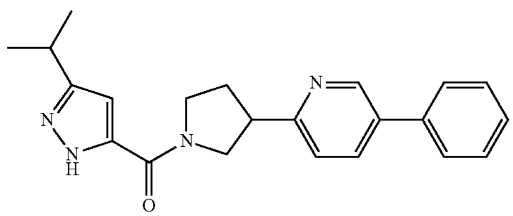 [SMILES: CC(C)c1cc(C(=O)N2CCC(c3ccc(-c4ccccc4)cn3)C2)[nH]n1] | 1.4 | |
| 107 | 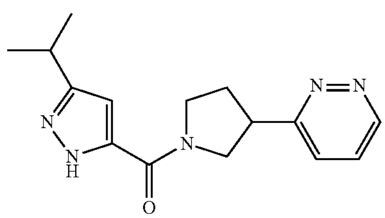 [SMILES: CC(C)c1cc(C(=O)N2CCC(c3cccnn3)C2)[nH]n1] | 0.5 | |
| 108 | 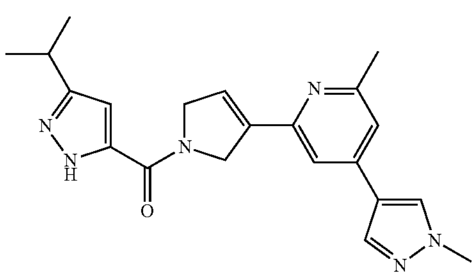 [SMILES: Cc1cc(-c2cnn(C)c2)cc(C2=CCN(C(=O)c3cc(C(C)C)n[nH]3)C2)n1] | 18 | |
| 109 | 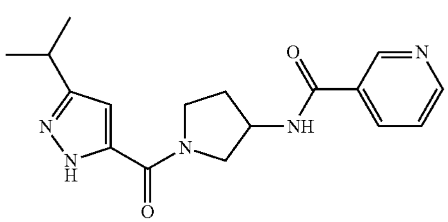 [SMILES: CC(C)c1cc(C(=O)N2CCC(NC(=O)c3cccnc3)C2)[nH]n1] | 0.76 | |

TABLE 2-continued

| Ex | Structure | KDM5A HTRF IC$_{50}$ (nM) | H3K4Me3 PC9 HTRF EC$_{50}$ (nM) |
|---|---|---|---|
| 110 | 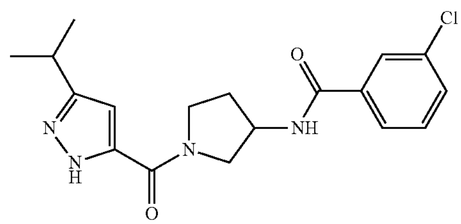 [SMILES: CC(C)c1cc(C(=O)N2CCC(NC(=O)c3cccc(Cl)c3)C2)[nH]n1] | 0.25 | |
| 111 | 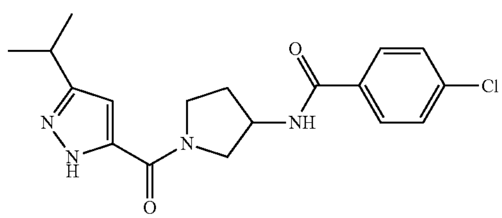 [SMILES: CC(C)c1cc(C(=O)N2CCC(NC(=O)c3ccc(Cl)cc3)C2)[nH]n1] | 0.75 | |
| 112 | 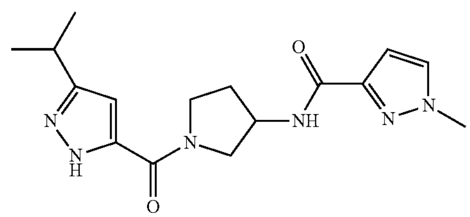 [SMILES: CC(C)c1cc(C(=O)N2CCC(NC(=O)c3ccn(C)n3)C2)[nH]n1] | 0.066 | |
| 113 | 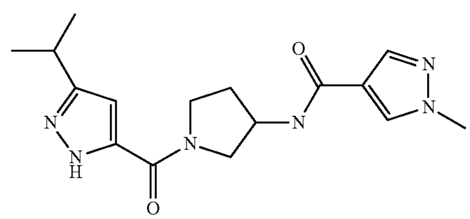 [SMILES: CC(C)c1cc(C(=O)N2CCC(NC(=O)c3cnn(C)c3)C2)[nH]n1] | 0.9 | |
| 114 | 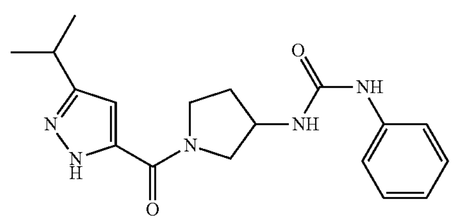 [SMILES: CC(C)c1cc(C(=O)N2CCC(NC(=O)Nc3ccccc3)C2)[nH]n1] | 0.28 | |
| 115 | 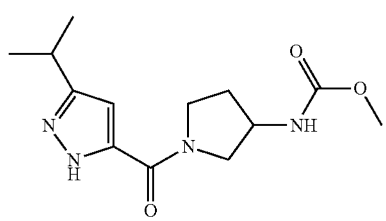 [SMILES: COC(=O)NC1CCN(C(=O)c2cc(C(C)C)n[nH]2)C1] | 0.59 | |
| 116 | 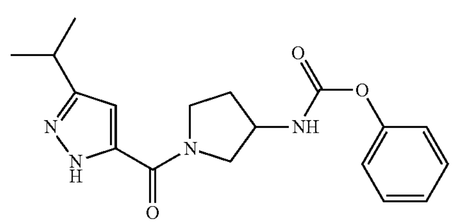 [SMILES: CC(C)c1cc(C(=O)N2CCC(NC(=O)Oc3ccccc3)C2)[nH]n1] | 2.1 | |

TABLE 2-continued

| Ex | Structure | KDM5A HTRF IC$_{50}$ (nM) | H3K4Me3 PC9 HTRF EC$_{50}$ (nM) |
|---|---|---|---|
| 117 | 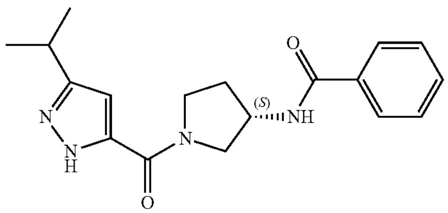 | 0.077 | 8.2 |
| 118 | 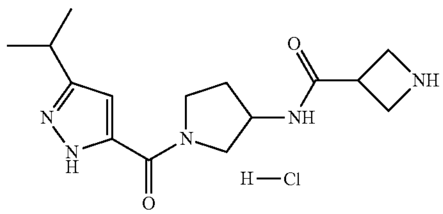 | 5.2 | |
| 119 | 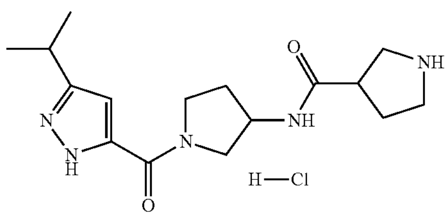 | 11 | |
| 120 | 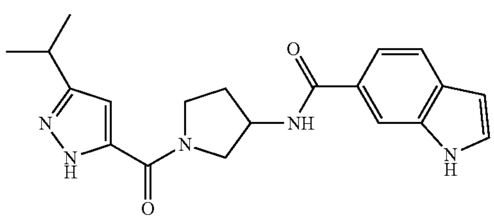 [SMILES: CC(C)c1cc(C(=O)N2CCC(NC(=O)c3ccc4cc[nH]c4c3)C2)[nH]n1] | 0.053 | |
| 121 | 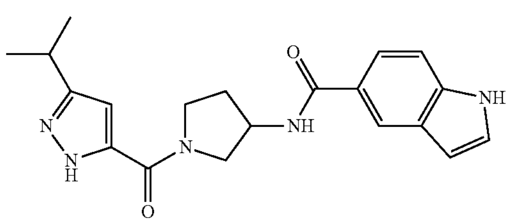 [SMILES: CC(C)c1cc(C(=O)N2CCC(NC(=O)c3ccc4[nH]ccc4c3)C2)[nH]n1] | 0.066 | |
| 122 | 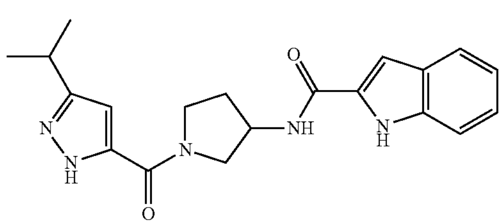 [SMILES: CC(C)c1cc(C(=O)N2CCC(NC(=O)c3cc4ccccc4[nH]3)C2)[nH]n1] | 0.49 | |

TABLE 2-continued

| Ex | Structure | KDM5A HTRF IC$_{50}$ (nM) | H3K4Me3 PC9 HTRF EC$_{50}$ (nM) |
|---|---|---|---|
| 123 | 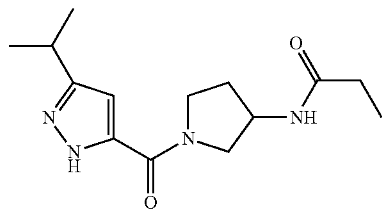 [SMILES: CCC(=O)NC1CCN(C(=O)c2cc(C(C)C)n[nH]2)C1] | 0.26 | |
| 124 | 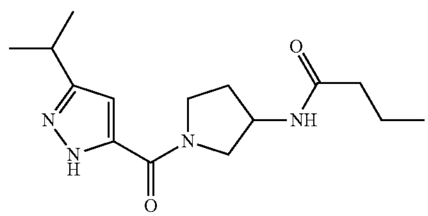 [SMILES: CCCC(=O)NC1CCN(C(=O)c2cc(C(C)C)n[nH]2)C1] | 0.15 | |
| 125 | 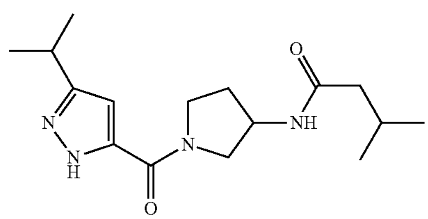 [SMILES: CC(C)CC(=O)NC1CCN(C(=O)c2cc(C(C)C)n[nH]2)C1] | 0.32 | |
| 126 | 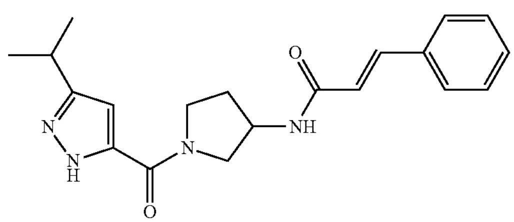 [SMILES: CC(C)c1cc(C(=O)N2CCC(NC(=O)/C=C/c3ccccc3)C2)[nH]n1] | 0.89 | |
| 127 | 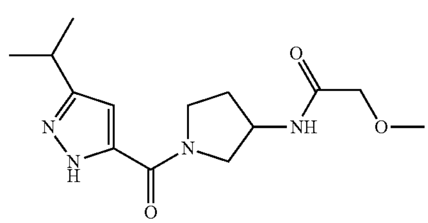 [SMILES: COCC(=O)NC1CCN(C(=O)c2cc(C(C)C)n[nH]2)C1] | 0.42 | |
| 128 | 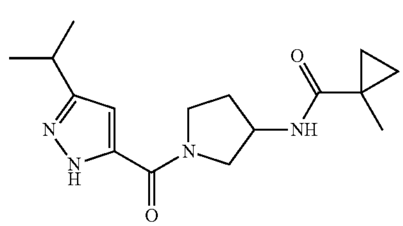 [SMILES: CC(C)c1cc(C(=O)N2CCC(NC(=O)C3(C)CC3)C2)[nH]n1] | 0.059 | 4.4 |

TABLE 2-continued

| Ex | Structure | KDM5A HTRF IC$_{50}$ (nM) | H3K4Me3 PC9 HTRF EC$_{50}$ (nM) |
|---|---|---|---|
| 129 | 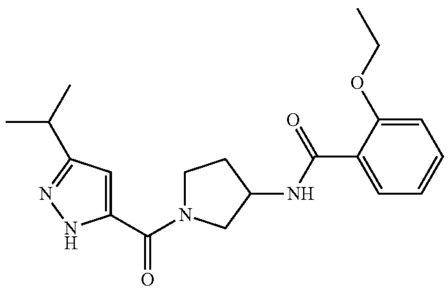 [SMILES: CCOc1ccccc1C(=O)NC1CCN(C(=O)c2cc(C(C)C)n[nH]2)C1] | 0.047 | |
| 130 | 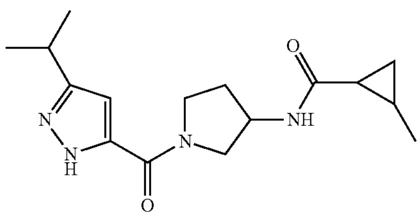 [SMILES: CC(C)c1cc(C(=O)N2CCC(NC(=O)C3CC3C)C2)[nH]n1] | 0.14 | |
| 131 | 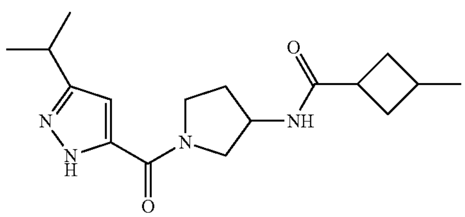 [SMILES: CC1CC(C(=O)NC2CCN(C(=O)c3cc(C(C)C)n[nH]3)C2)C1] | 0.84 | |
| 132 | 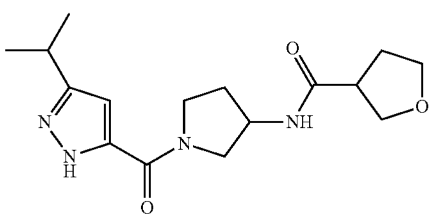 [SMILES: CC(C)c1cc(C(=O)N2CCC(NC(=O)C3CCOC3)C2)[nH]n1] | 0.12 | |
| 133 | 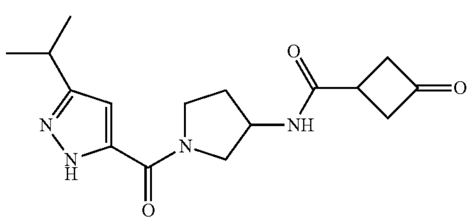 [SMILES: CC(C)c1cc(C(=O)N2CCC(NC(=O)C3CC(=O)C3)C2)[nH]n1] | 0.3 | |
| 134 | 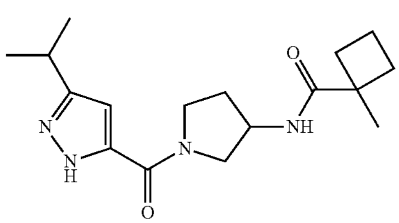 [SMILES: CC(C)c1cc(C(=O)N2CCC(NC(=O)C3(C)CCC3)C2)[nH]n1] | 0.071 | 6.4 |

TABLE 2-continued

| Ex | Structure | KDM5A HTRF IC$_{50}$ (nM) | H3K4Me3 PC9 HTRF EC$_{50}$ (nM) |
|---|---|---|---|
| 135 | 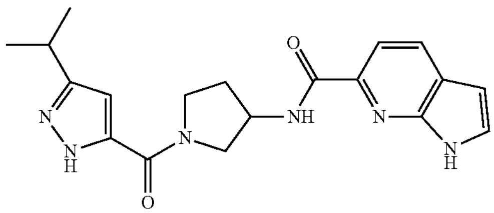 [SMILES: CC(C)c1cc(C(=O)N2CCC(NC(=O)c3ccc4cc[nH]c4n3)C2)[nH]n1] | 0.076 | 4.9 |
| 136 | 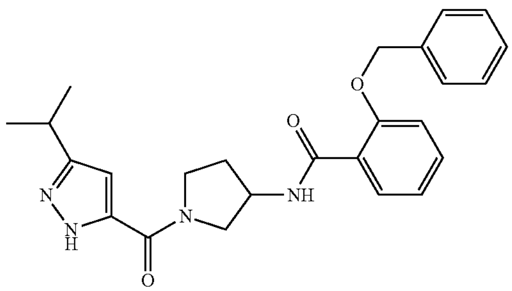 [SMILES: CC(C)c1cc(C(=O)N2CCC(NC(=O)c3ccccc3OCc3ccccc3)C2)[nH]n1] | 0.054 | 2.5 |
| 137 | 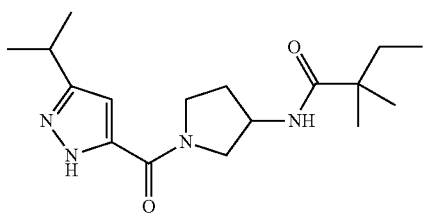 [SMILES: CCC(C)(C)C(=O)NC1CCN(C(=O)c2cc(C(C)C)n[nH]2)C1] | 0.27 | |
| 138 | 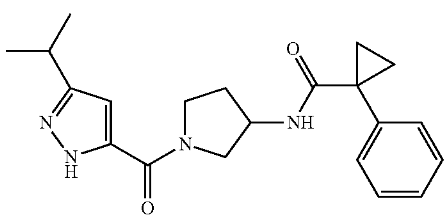 [SMILES: CC(C)c1cc(C(=O)N2CCC(NC(=O)C3(c4ccccc4)CC3)C2)[nH]n1] | 0.26 | |
| 139 | 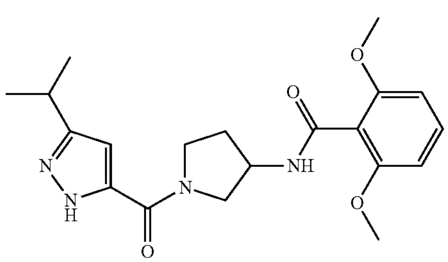 [SMILES: COc1cccc(OC)c1C(=O)NC1CCN(C(=O)c2cc(C(C)C)n[nH]2)C1] | 3 | |
| 140 | 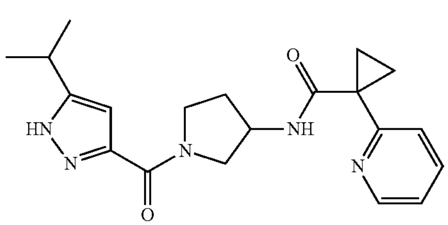 [SMILES: CC(C)c1cc(C(=O)N2CCC(NC(=O)C3(c4ccccn4)CC3)C2)n[nH]1] | 0.21 | |

TABLE 2-continued
| Ex | Structure | KDM5A HTRF IC$_{50}$ (nM) | H3K4Me3 PC9 HTRF EC$_{50}$ (nM) |
|---|---|---|---|
| 141 | 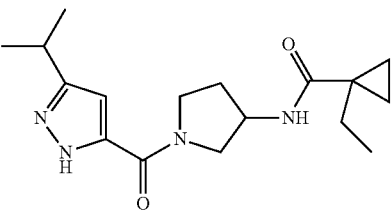 [SMILES: CCC1(C(=O)NC2CCN(C(=O)c3cc(C(C)C)n[nH]3)C2)CC1] | 0.14 | 6.5 |
| 142 | 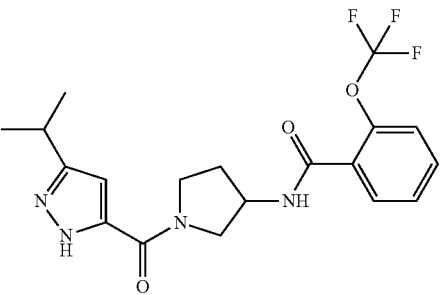 [SMILES: CC(C)c1cc(C(=O)N2CCC(NC(=O)c3ccccc3OC(F)(F)F)C2)[nH]n1] | 1.5 | |
| 143 | 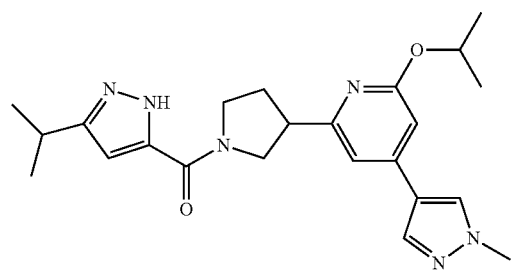 [SMILES: CC(C)Oc1cc(-c2cnn(C)c2)cc(C2CCN(C(=O)c3cc(C(C)C)n[nH]3)C2)n1] | 1.5 | |
| 144 | 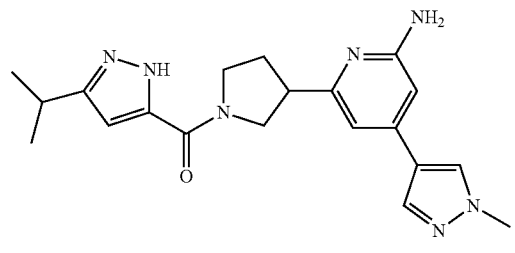 [SMILES: CC(C)c1cc(C(=O)N2CCC(c3cc(-c4cnn(C)c4)cc(N)n3)C2)[nH]n1] | 0.13 | |
| 145 | 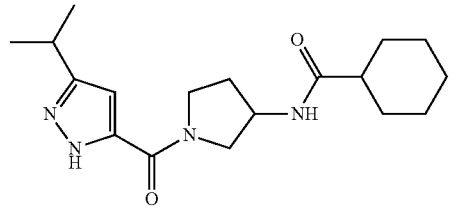 [SMILES: CC(C)c1cc(C(=O)N2CCC(NC(=O)C3CCCCC3)C2)[nH]n1] | 1.9 | |
| 146 | 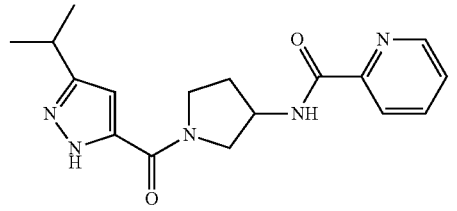 [SMILES: CC(C)c1cc(C(=O)N2CCC(NC(=O)c3ccccn3)C2)[nH]n1] | 0.18 | |

TABLE 2-continued

| Ex | Structure | KDM5A HTRF IC$_{50}$ (nM) | H3K4Me3 PC9 HTRF EC$_{50}$ (nM) |
|---|---|---|---|
| 147 | 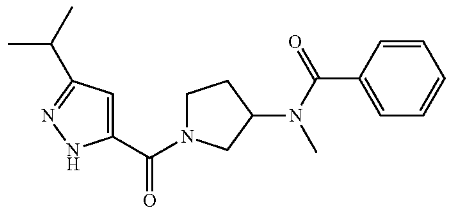 [SMILES: CC(C)c1cc(C(=O)N2CCC(N(C)C(=O)c3ccccc3)C2)[nH]n1] | 8.9 | |
| 148 | 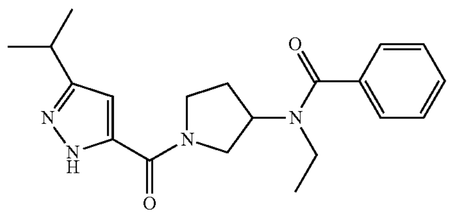 [SMILES: CCN(C(=O)c1ccccc1)C1CCN(C(=O)c2cc(C(C)C)n[nH]2)C1] | 12 | |
| 149 | 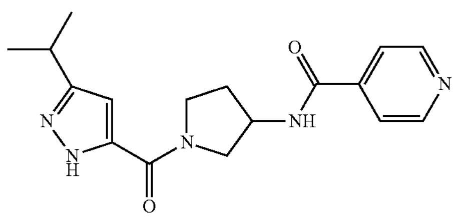 [SMILES: CC(C)c1cc(C(=O)N2CCC(NC(=O)c3ccncc3)C2)[nH]n1] | 2.5 | |
| 150 | 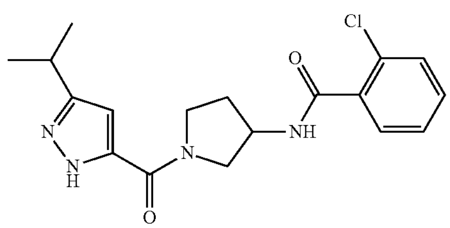 [SMILES: CC(C)c1cc(C(=O)N2CCC(NC(=O)c3ccccc3Cl)C2)[nH]n1] | 0.098 | |
| 151 | 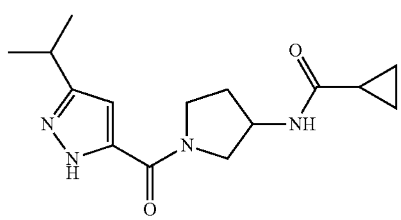 | 0.065 | 1.7 |
| 152 | 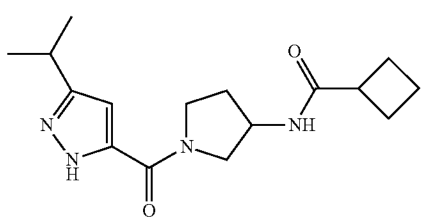 [SMILES: CC(C)c1cc(C(=O)N2CCC(NC(=O)C3CCC3)C2)[nH]n1] | 0.083 | |
| 153 | 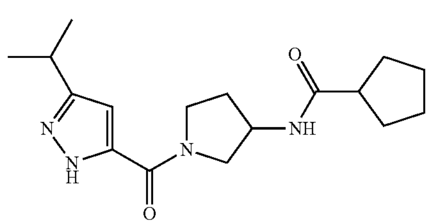 [SMILES: CC(C)c1cc(C(=O)N2CCC(NC(=O)C3CCCC3)C2)[nH]n1] | 0.12 | |

TABLE 2-continued

| Ex | Structure | KDM5A HTRF IC$_{50}$ (nM) | H3K4Me3 PC9 HTRF EC$_{50}$ (nM) |
|---|---|---|---|
| 154 | 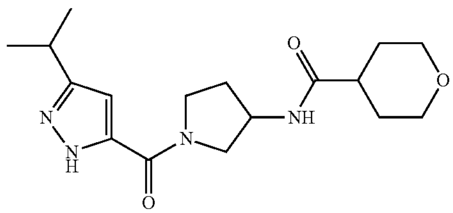 [SMILES: CC(C)c1cc(C(=O)N2CCC(NC(=O)C3CCOCC3)C2)[nH]n1] | | 0.4 |
| 155 | 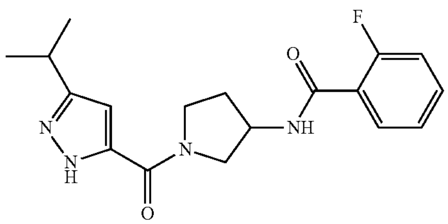 [SMILES: CC(C)c1cc(C(=O)N2CCC(NC(=O)c3ccccc3F)C2)[nH]n1] | | 0.075 |
| 156 | 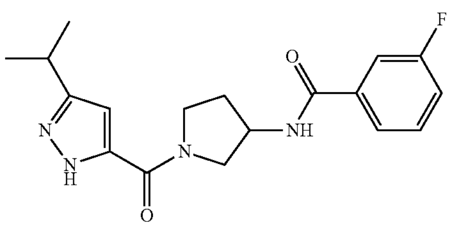 [SMILES: CC(C)c1cc(C(=O)N2CCC(NC(=O)c3cccc(F)c3)C2)[nH]n1] | | 0.074 |
| 157 | 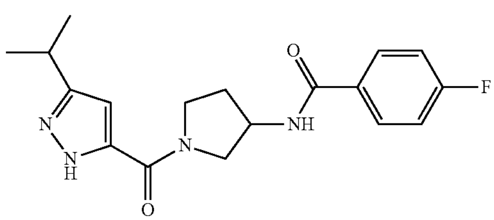 [SMILES: CC(C)c1cc(C(=O)N2CCC(NC(=O)c3ccc(F)cc3)C2)[nH]n1] | | 0.2 |
| 158 | 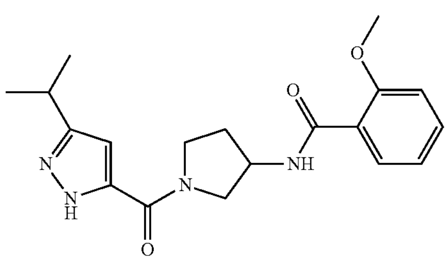 [SMILES: COc1ccccc1C(=O)NC1CCN(C(=O)c2cc(C(C)C)n[nH]2)C1] | | 0.073 |
| 159 | 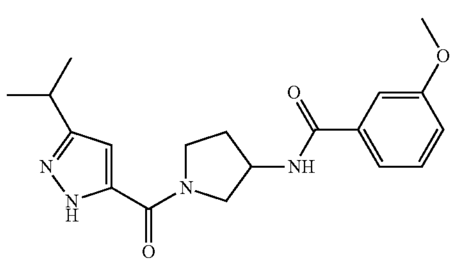 [SMILES: COc1cccc(C(=O)NC2CCN(C(=O)c3cc(C(C)C)n[nH]3)C2)c1] | | 0.12 |

TABLE 2-continued

| Ex | Structure | KDM5A HTRF IC$_{50}$ (nM) | H3K4Me3 PC9 HTRF EC$_{50}$ (nM) |
|---|---|---|---|
| 160 | 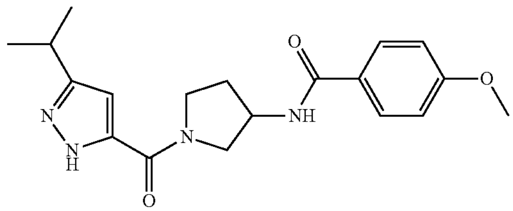 [SMILES: COc1ccc(C(=O)NC2CCN(C(=O)c3cc(C(C)C)n[nH]3)C2)cc1] | 0.27 | |
| 161 | 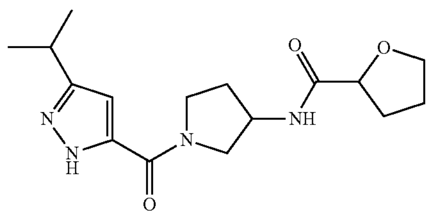 [SMILES: CC(C)c1cc(C(=O)N2CCC(NC(=O)C3CCCO3)C2)[nH]n1] | 0.38 | |
| 162 | 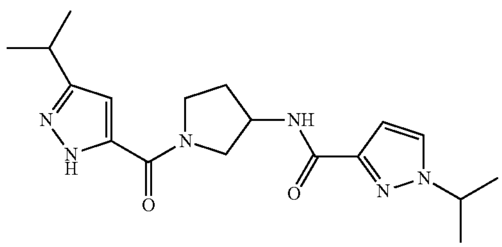 [SMILES: CC(C)c1cc(C(=O)N2CCC(NC(=O)c3ccn(C(C)C)n3)C2)[nH]n1] | 5.1 | |
| 163 | 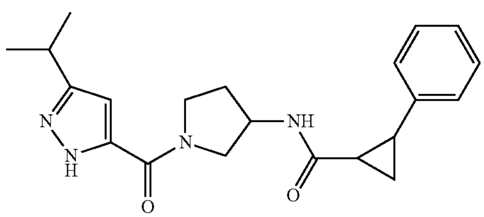 [SMILES: CC(C)c1cc(C(=O)N2CCC(NC(=O)C3CC3c3ccccc3)C2)[nH]n1] | 0.58 | |
| 164 | 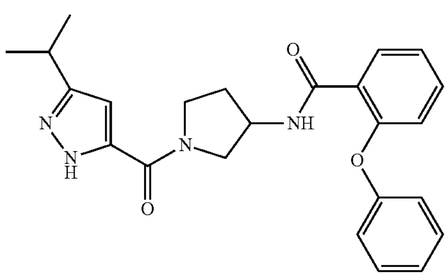 [SMILES: CC(C)c1cc(C(=O)N2CCC(NC(=O)c3ccccc3Oc3ccccc3)C2)[nH]n1] | 0.7 | |
| 165 | 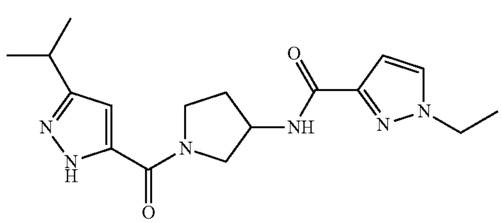 [SMILES: CCn1ccc(C(=O)NC2CCN(C(=O)c3cc(C(C)C)n[nH]3)C2)n1] | 0.11 | |

TABLE 2-continued

| Ex | Structure | KDM5A HTRF IC$_{50}$ (nM) | H3K4Me3 PC9 HTRF EC$_{50}$ (nM) |
|---|---|---|---|
| 166 | 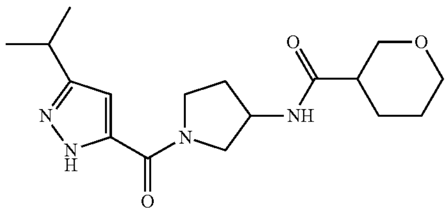 [SMILES: CC(C)c1cc(C(=O)N2CCC(NC(=O)C3CCCOC3)C2)[nH]n1] | 0.52 | |
| 167 | 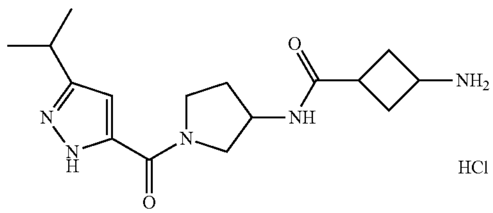 [SMILES: CC(C)c1cc(C(=O)N2CCC(NC(=O)C3CC(N)C3)C2)[nH]n1 ; Cl] | 17 | |
| 168 | 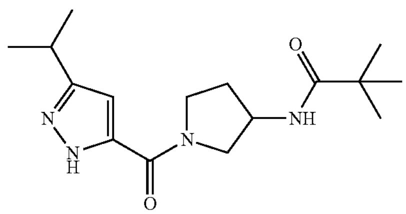 [SMILES: CC(C)c1cc(C(=O)N2CCC(NC(=O)C(C)(C)C)C2)[nH]n1] | 0.2 | |
| 169 | 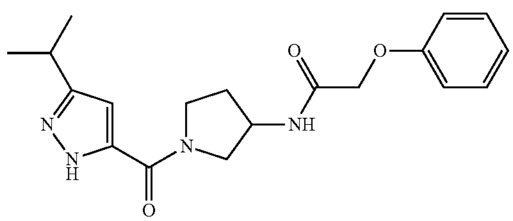 [SMILES: CC(C)c1cc(C(=O)N2CCC(NC(=O)COc3ccccc3)C2)[nH]n1] | 3.1 | |
| 170 | 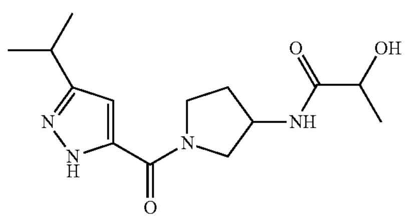 [SMILES: CC(O)C(=O)NC1CCN(C(=O)c2cc(C(C)C)n[nH]2)C1] | 1.6 | |
| 171 | 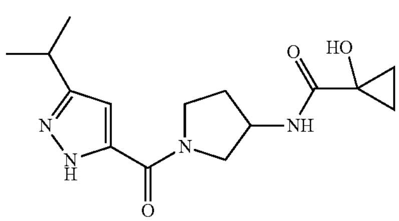 [SMILES: CC(C)c1cc(C(=O)N2CCC(NC(=O)C3(O)CC3)C2)[nH]n1] | 0.2 | 8.6 |
| 172 | 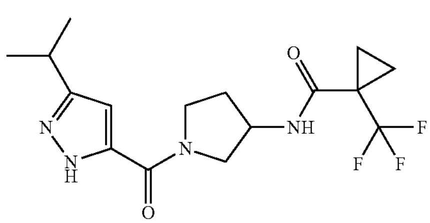 [SMILES: CC(C)c1cc(C(=O)N2CCC(NC(=O)C3(C(F)(F)F)CC3)C2)[nH]n1] | 0.92 | |

TABLE 2-continued

| Ex | Structure | KDM5A HTRF IC$_{50}$ (nM) | H3K4Me3 PC9 HTRF EC$_{50}$ (nM) |
|---|---|---|---|
| 173 | 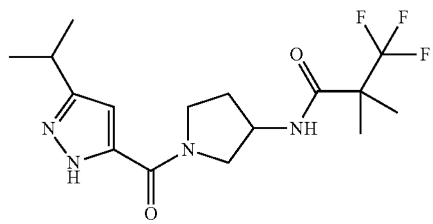 [SMILES: CC(C)c1cc(C(=O)N2CCC(NC(=O)C(C)(C)C(F)(F)F)C2)[nH]n1] | 1.6 | |
| 174 | 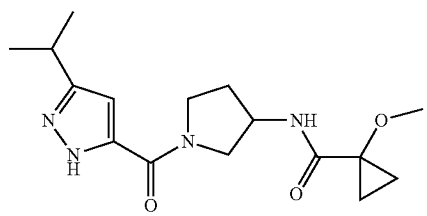 [SMILES: COC1(C(=O)NC2CCN(C(=O)c3cc(C(C)C)n[nH]3)C2)CC1] | 0.21 | |
| 175 | 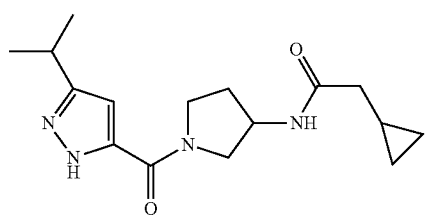 [SMILES: CC(C)c1cc(C(=O)N2CCC(NC(=O)CC3CC3)C2)[nH]n1] | 0.4 | |
| 176 | 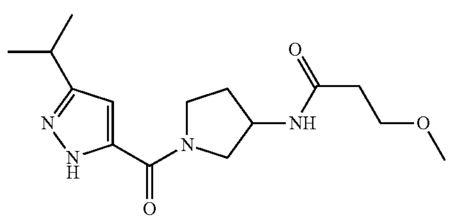 [SMILES: COCCC(=O)NC1CCN(C(=O)c2cc(C(C)C)n[nH]2)C1] | 1.1 | |
| 177 | 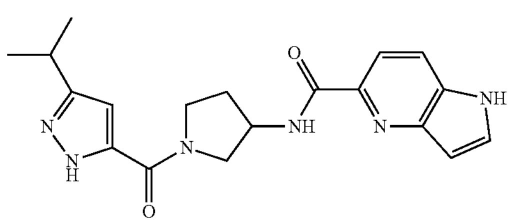 | 0.078 | |
| 178 | 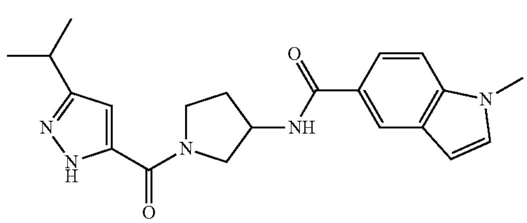 [SMILES: CC(C)c1cc(C(=O)N2CCC(NC(=O)c3ccc4c(ccn4C)c3)C2)[nH]n1] | 0.08 | |

TABLE 2-continued

| Ex | Structure | KDM5A HTRF IC$_{50}$ (nM) | H3K4Me3 PC9 HTRF EC$_{50}$ (nM) |
|---|---|---|---|
| 179 | 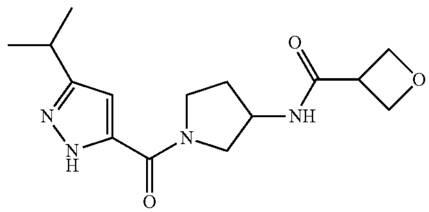 [SMILES: CC(C)c1cc(C(=O)N2CCC(NC(=O)C3COC3)C2)[nH]n1] | 0.24 | |
| 180 | 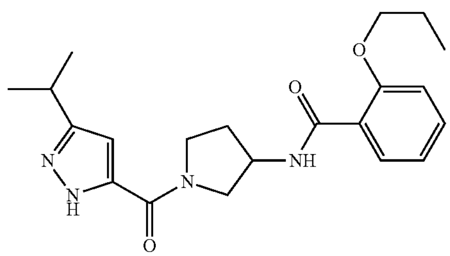 [SMILES: CCCOc1ccccc1C(=O)NC1CCN(C(=O)c2cc(C(C)C)n[nH]2)C1] | 0.065 | 3.2 |
| 181 | 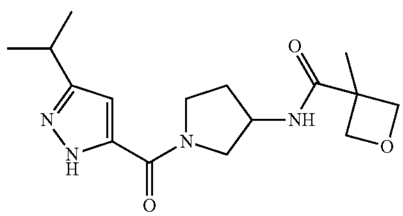 [SMILES: CC(C)c1cc(C(=O)N2CCC(NC(=O)C3(C)COC3)C2)[nH]n1] | 0.3 | |
| 182 | 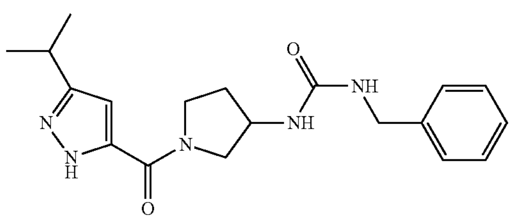 [SMILES: CC(C)c1cc(C(=O)N2CCC(NC(=O)NCc3ccccc3)C2)[nH]n1] | 20 | |
| 183 | 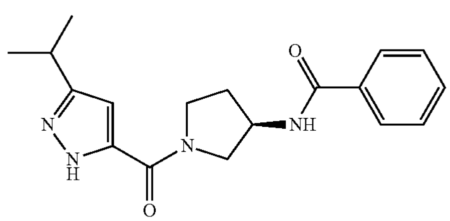 [SMILES: CC(C)c1cc(C(=O)N2CC[C@@H](NC(=O)c3ccccc3)C2)[nH]n1] | 0.078 | 4.8 |
| 184 | 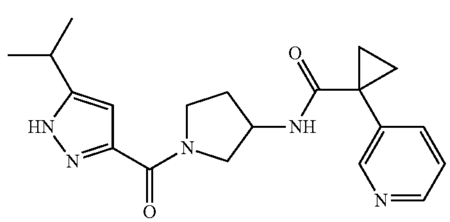 [SMILES: CC(C)c1cc(C(=O)N2CCC(NC(=O)C3(c4cccnc4)CC3)C2)n[nH]1] | 1.2 | |

TABLE 2-continued

| Ex | Structure | KDM5A HTRF IC$_{50}$ (nM) | H3K4Me3 PC9 HTRF EC$_{50}$ (nM) |
|---|---|---|---|
| 185 | 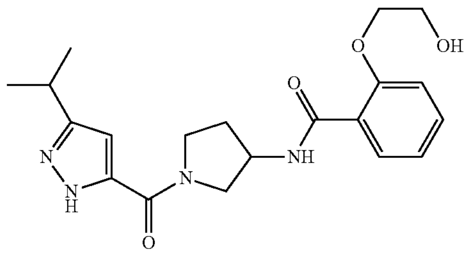 [SMILES: CC(C)c1cc(C(=O)N2CCC(NC(=O)c3ccccc3OCCO)C2)[nH]n1] | 0.11 | |
| 186 | 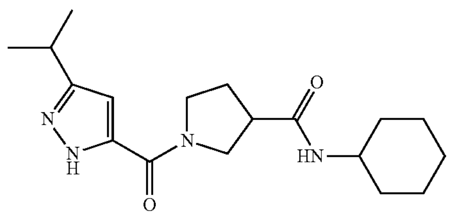 [SMILES: CC(C)c1cc(C(=O)N2CCC(C(=O)NC3CCCCC3)C2)[nH]n1] | 7.7 | |
| 187 | 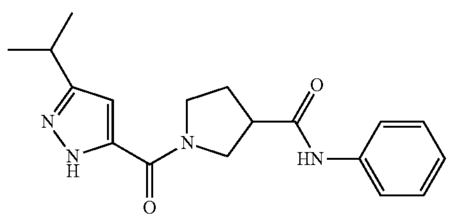 [SMILES: CC(C)c1cc(C(=O)N2CCC(C(=O)Nc3ccccc3)C2)[nH]n1] | 6.5 | |
| 188 | 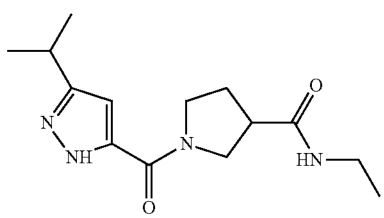 [SMILES: CCNC(=O)C1CCN(C(=O)c2cc(C(C)C)n[nH]2)C1] | 22 | |
| 189 | 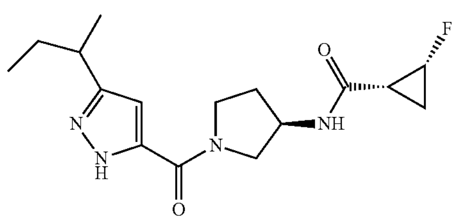 [SMILES: CCC(C)c1cc(C(=O)N2CC[C@@H](NC(=O)[C@H]3C[C@H]3F)C2)[nH]n1] | 0.038 | |
| 190 | 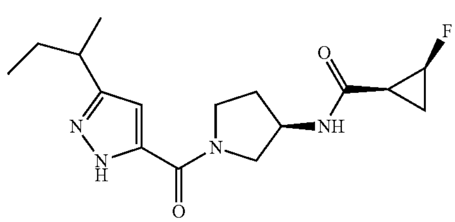 [SMILES: CCC(C)c1cc(C(=O)N2CC[C@@H](NC(=O)[C@@H]3C[C@@H]3F)C2)[nH]n1] | 0.037 | |

TABLE 2-continued

| Ex | Structure | KDM5A HTRF IC$_{50}$ (nM) | H3K4Me3 PC9 HTRF EC$_{50}$ (nM) |
|---|---|---|---|
| 191 | 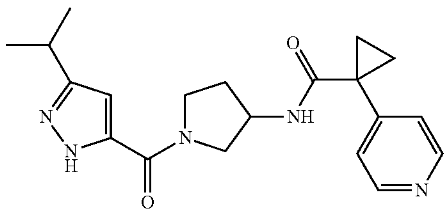 [SMILES: CC(C)c1cc(C(=O)N2CCC(NC(=O)C3(c4ccncc4)CC3)C2)[nH]n1] | 2 | |
| 192 | 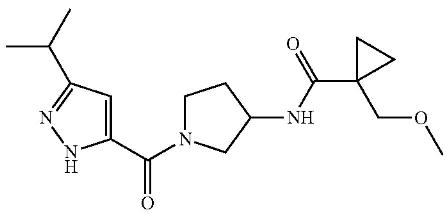 [SMILES: COCC1(C(=O)NC2CCN(C(=O)c3cc(C(C)C)n[nH]3)C2)CC1] | 0.58 | |
| 193 | 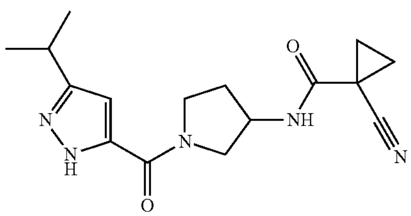 [SMILES: CC(C)c1cc(C(=O)N2CCC(NC(=O)C3(C#N)CC3)C2)[nH]n1] | 0.41 | |
| 194 | 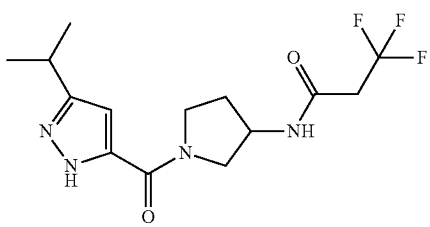 [SMILES: CC(C)c1cc(C(=O)N2CCC(NC(=O)CC(F)(F)F)C2)[nH]n1] | 0.46 | |
| 195 | 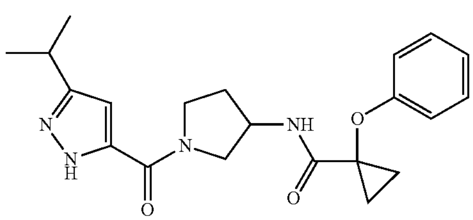 [SMILES: CC(C)c1cc(C(=O)N2CCC(NC(=O)C3(Oc4ccccc4)CC3)C2)[nH]n1] | 3.5 | |
| 196 | 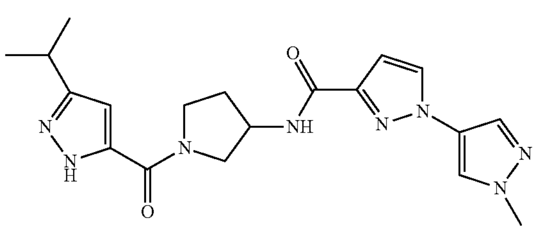 [SMILES: CC(C)c1cc(C(=O)N2CCC(NC(=O)c3ccn(-c4cnn(C)c4)n3)C2)[nH]n1] | 0.11 | |
| 197 | 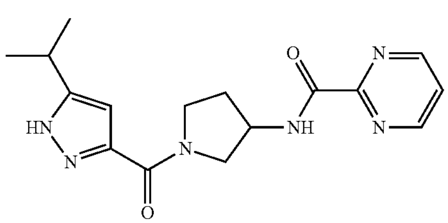 [SMILES: CC(C)c1cc(C(=O)N2CCC(NC(=O)c3ncccn3)C2)n[nH]1] | 0.31 | |

TABLE 2-continued

| Ex | Structure | KDM5A HTRF IC$_{50}$ (nM) | H3K4Me3 PC9 HTRF EC$_{50}$ (nM) |
|---|---|---|---|
| 198 | 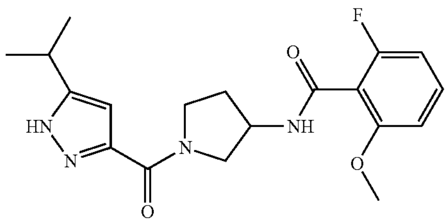 [SMILES: COc1cccc(F)c1C(=O)NC1CCN(C(=O)c2cc(C(C)C)[nH]n2)C1] | 1.2 | |
| 199 | 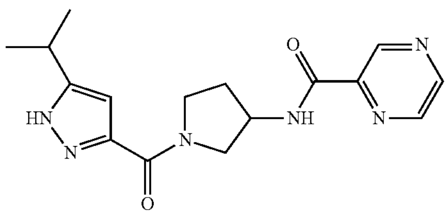 [SMILES: CC(C)c1cc(C(=O)N2CCC(NC(=O)c3cnccn3)C2)n[nH]1] | 1.1 | |
| 200 | 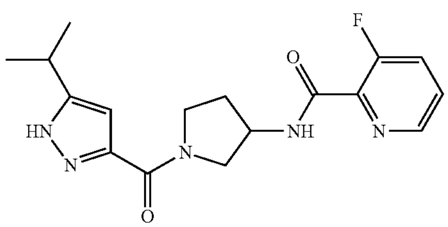 [SMILES: CC(C)c1cc(C(=O)N2CCC(NC(=O)c3ncccc3F)C2)n[nH]1] | 0.25 | |
| 201 | 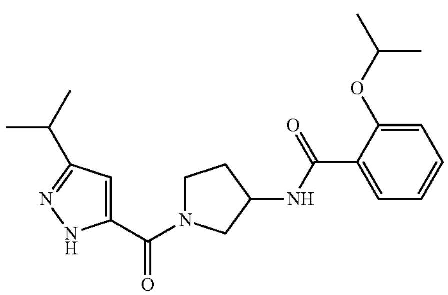 [SMILES: CC(C)Oc1ccccc1C(=O)NC1CCN(C(=O)c2cc(C(C)C)n[nH]2)C1] | 0.092 | |
| 202 | 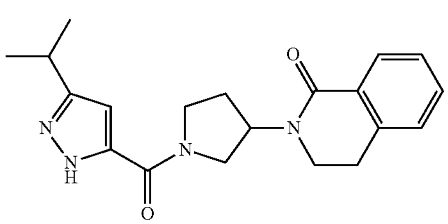 [SMILES: CC(C)c1cc(C(=O)N2CCC(N3CCc4ccccc4C3=O)C2)[nH]n1] | 1.5 | |
| 203 | 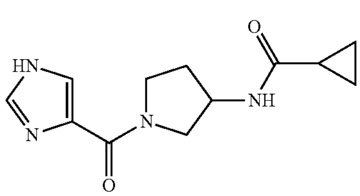 [SMILES: O=C(NC1CCN(C(=O)c2c[nH]cn2)C1)C1CC1] | 6.2 | |

TABLE 2-continued

| Ex | Structure | KDM5A HTRF IC$_{50}$ (nM) | H3K4Me3 PC9 HTRF EC$_{50}$ (nM) |
|---|---|---|---|
| 204 | 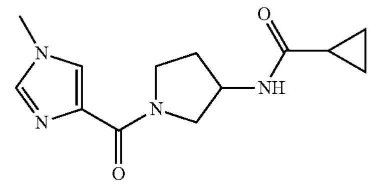 [SMILES: Cn1cnc(C(=O)N2CCC(NC(=O)C3CC3)C2)c1] | 2.2 | |
| 205 | 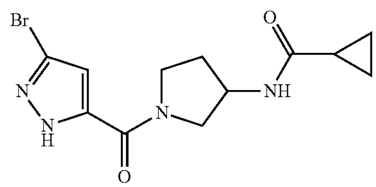 [SMILES: O=C(NC1CCN(C(=O)c2cc(Br)n[nH]2)C1)C1CC1] | 14 | |
| 206 | 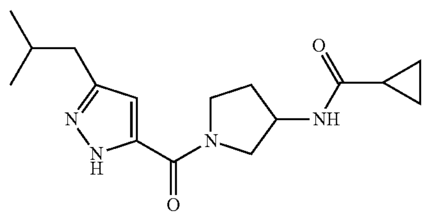 [SMILES: CC(C)Cc1cc(C(=O)N2CCC(NC(=O)C3CC3)C2)[nH]n1] | 0.3 | |
| 207 | 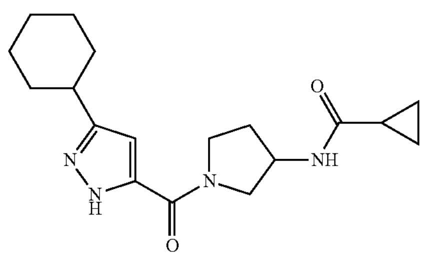 [SMILES: O=C(NC1CCN(C(=O)c2cc(C3CCCCC3)n[nH]2)C1)C1CC1] | 0.42 | |
| 208 | 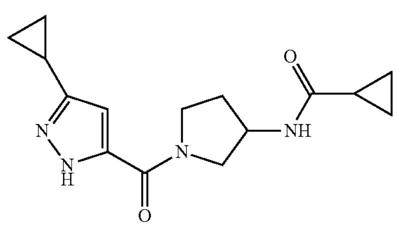 [SMILES: O=C(NC1CCN(C(=O)c2cc(C3CC3)n[nH]2)C1)C1CC1] | 0.19 | |
| 209 | 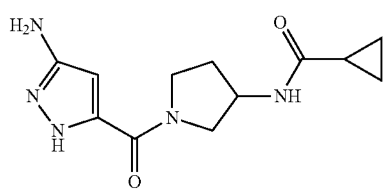 [SMILES: Nc1cc(C(=O)N2CCC(NC(=O)C3CC3)C2)[nH]n1] | 17 | |
| 210 | 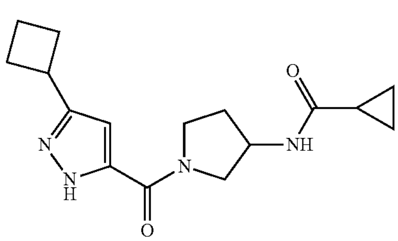 [SMILES: O=C(NC1CCN(C(=O)c2cc(C3CCC3)n[nH]2)C1)C1CC1] | 0.16 | 6.7 |

TABLE 2-continued

| Ex | Structure | KDM5A HTRF IC$_{50}$ (nM) | H3K4Me3 PC9 HTRF EC$_{50}$ (nM) |
|---|---|---|---|
| 211 | 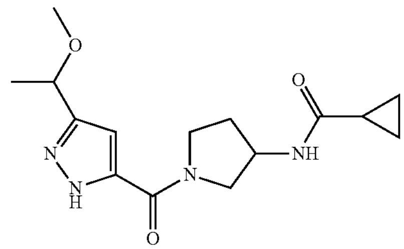 [SMILES: COC(C)c1cc(C(=O)N2CCC(NC(=O)C3CC3)C2)[nH]n1] | 2.6 | |
| 212 | 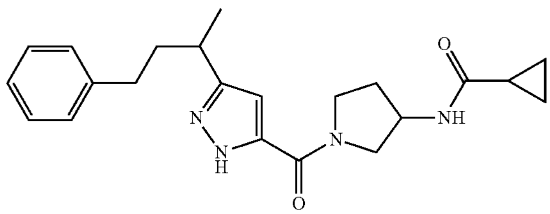 [SMILES: CC(CCc1ccccc1)c1cc(C(=O)N2CCC(NC(=O)C3CC3)C2)[nH]n1] | 0.12 | 11 |
| 213 | 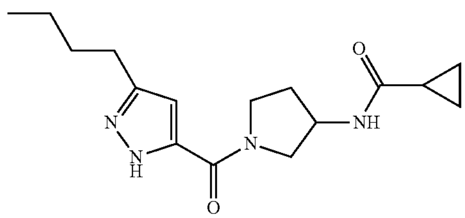 [SMILES: CCCCc1cc(C(=O)N2CCC(NC(=O)C3CC3)C2)[nH]n1] | 0.81 | |
| 214 | 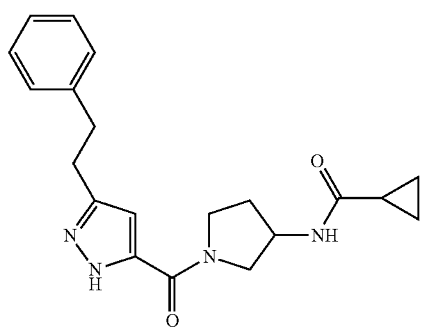 [SMILES: O=C(NC1CCN(C(=O)c2cc(CCc3ccccc3)n[nH]2)C1)C1CC1] | 2.7 | |
| 215 | 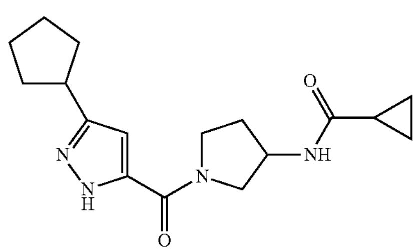 [SMILES: O=C(NC1CCN(C(=O)c2cc(C3CCCC3)n[nH]2)C1)C1CC1] | 0.23 | |
| 216 | 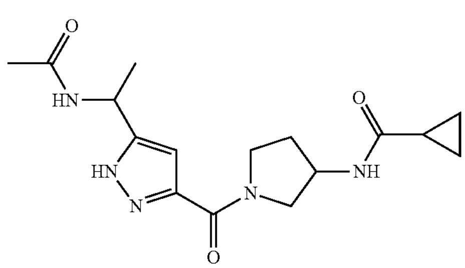 [SMILES: CC(=O)NC(C)c1cc(C(=O)N2CCC(NC(=O)C3CC3)C2)n[nH]1] | 6.6 | |

TABLE 2-continued

| Ex | Structure | KDM5A HTRF IC$_{50}$ (nM) | H3K4Me3 PC9 HTRF EC$_{50}$ (nM) |
|---|---|---|---|
| 217 | 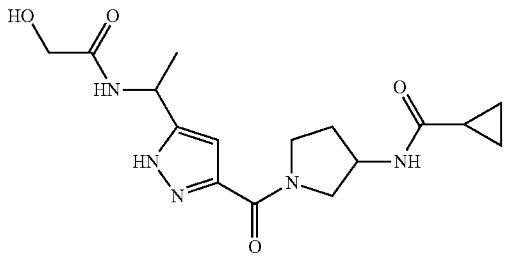 [SMILES: CC(NC(=O)CO)c1cc(C(=O)N2CCC(NC(=O)C3CC3)C2)n[nH]1] | 3.2 | |
| 218 | 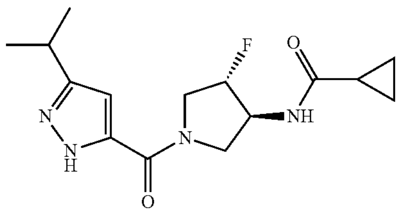 [SMILES: CC(C)c1cc(C(=O)N2C[C@H](NC(=O)C3CC3)[C@@H](F)C2)[nH]n1] | 0.05 | 1.7 |
| 219 | 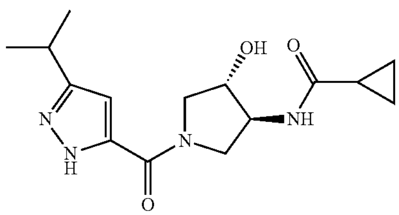 [SMILES: CC(C)c1cc(C(=O)N2C[C@H](NC(=O)C3CC3)[C@@H](O)C2)[nH]n1] | 0.046 | 1.8 |
| 220 | 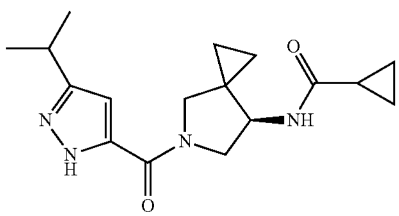 [SMILES: CC(C)c1cc(C(=O)N2C[C@H](NC(=O)C3CC3)C3(CC3)C2)[nH]n1] | 0.16 | 2.5 |
| 221 | 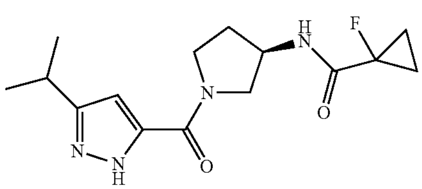 [SMILES: CC(C)c1cc(C(=O)N2CC[C@@H](NC(=O)C3(F)CC3)C2)[nH]n1] | 0.051 | 2.1 |
| 222 | 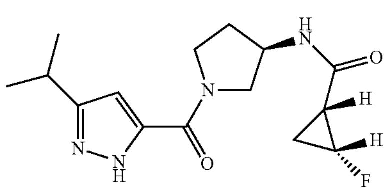 [SMILES: CC(C)c1cc(C(=O)N2CC[C@@H](NC(=O)[C@H]3C[C@H]3F)C2)[nH]n1] | 0.025 | 1.3 |
| 223 | 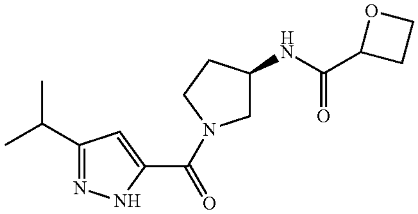 [SMILES: CC(C)c1cc(C(=O)N2CC[C@@H](NC(=O)C3CCO3)C2)[nH]n1] | 0.36 | |

TABLE 2-continued

| Ex | Structure | KDM5A HTRF IC$_{50}$ (nM) | H3K4Me3 PC9 HTRF EC$_{50}$ (nM) |
|---|---|---|---|
| 224 | 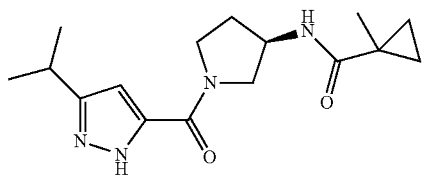 [SMILES: CC(C)c1cc(C(=O)N2CC[C@@H](NC(=O)C3(C)CC3)C2)[nH]n1] | 0.074 | 1.4 |
| 225 | 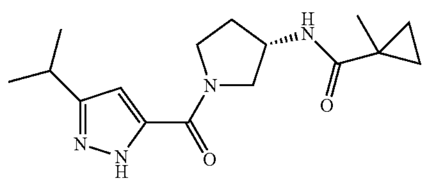 [SMILES: CC(C)c1cc(C(=O)N2CC[C@H](NC(=O)C3(C)CC3)C2)[nH]n1] | 0.11 | 14 |
| 226 | 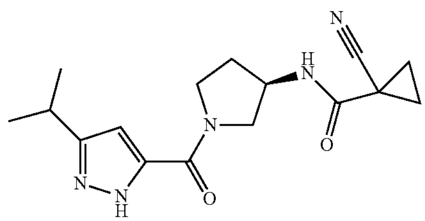 [SMILES: CC(C)c1cc(C(=O)N2CC[C@@H](NC(=O)C3(C#N)CC3)C2)[nH]n1] | 0.23 | |
| 227 | 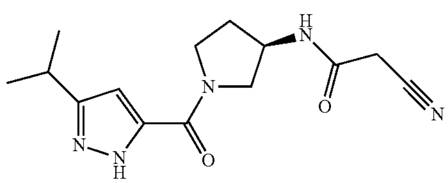 [SMILES: CC(C)c1cc(C(=O)N2CC[C@@H](NC(=O)CC#N)C2)[nH]n1] | 0.24 | |
| 228 | 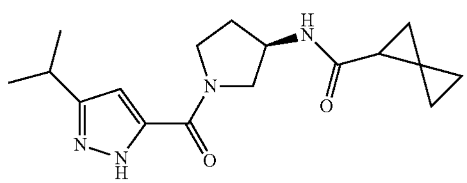 [SMILES: CC(C)c1cc(C(=O)N2CC[C@@H](NC(=O)C3CC34CC4)C2)[nH]n1] | 0.078 | 1.1 |
| 229 | 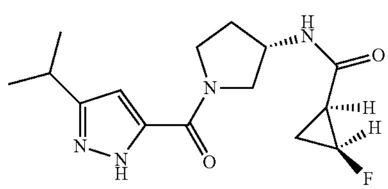 [SMILES: CC(C)c1cc(C(=O)N2CC[C@H](NC(=O)[C@@H]3C[C@@H]3F)C2)[nH]n1] | 0.11 | |
| 230 | 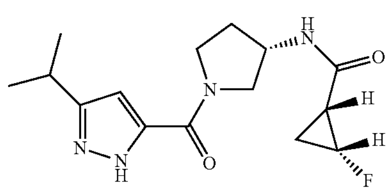 [SMILES: CC(C)c1cc(C(=O)N2CC[C@H](NC(=O)[C@H]3C[C@H]3F)C2)[nH]n1] | 0.14 | |
| 231 | 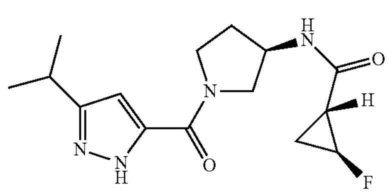 [SMILES: CC(C)c1cc(C(=O)N2CC[C@@H](NC(=O)[C@H]3C[C@@H]3F)C2)[nH]n1] | 0.33 | |

TABLE 2-continued

| Ex | Structure | KDM5A HTRF IC$_{50}$ (nM) | H3K4Me3 PC9 HTRF EC$_{50}$ (nM) |
|---|---|---|---|
| 232 | 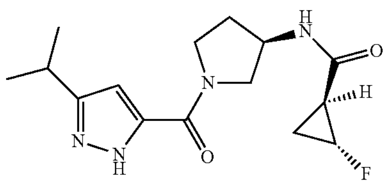 [SMILES: CC(C)c1cc(C(=O)N2CC[C@@H](NC(=O)[C@@H]3C[C@H]3F)C2)[nH]n1] | 0.14 | 5 |
| 233 | 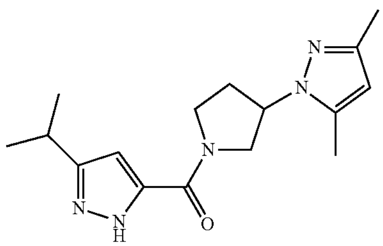 [SMILES: Cc1cc(C)n(C2CCN(C(=O)c3cc(C(C)C)n[nH]3)C2)n1] | 12 | |
| 234 | 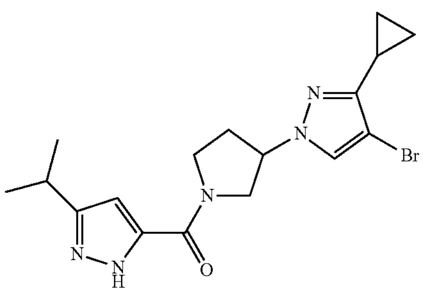 [SMILES: CC(C)c1cc(C(=O)N2CCC(n3cc(Br)c(C4CC4)n3)C2)[nH]n1] | 0.16 | 19 |
| 235 | 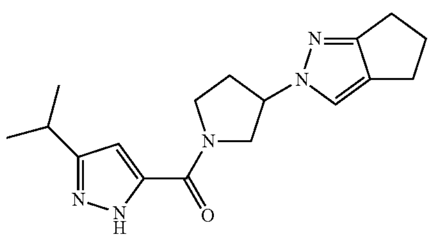 [SMILES: CC(C)c1cc(C(=O)N2CCC(n3cc4c(n3)CCC4)C2)[nH]n1] | 0.34 | |
| 236 | 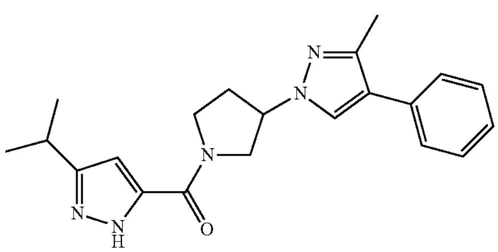 [SMILES: Cc1nn(C2CCN(C(=O)c3cc(C(C)C)n[nH]3)C2)cc1-c1ccccc1] | 0.32 | |
| 237 | 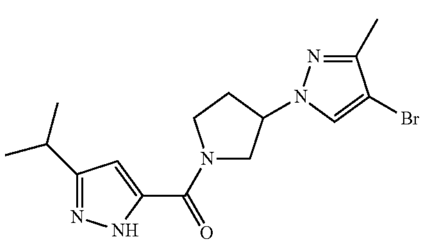 [SMILES: Cc1nn(C2CCN(C(=O)c3cc(C(C)C)n[nH]3)C2)cc1Br] | 0.36 | |

TABLE 2-continued
| Ex | Structure | KDM5A HTRF IC$_{50}$ (nM) | H3K4Me3 PC9 HTRF EC$_{50}$ (nM) |
|---|---|---|---|
| 238 | 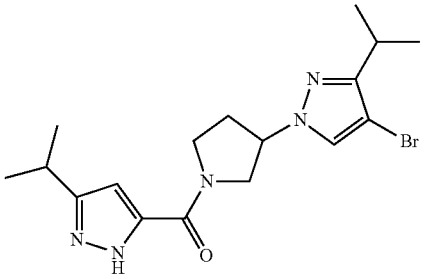 [SMILES: CC(C)c1cc(C(=O)N2CCC(n3cc(Br)c(C(C)C)n3)C2)[nH]n1] | 0.15 | 7 |
| 239 | 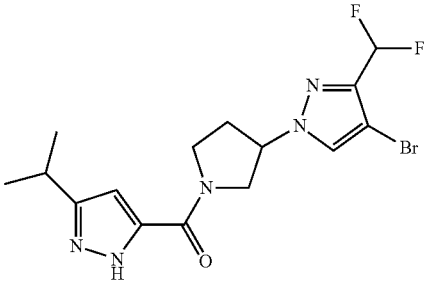 [SMILES: CC(C)c1cc(C(=O)N2CCC(n3cc(Br)c(C(F)F)n3)C2)[nH]n1] | 0.35 | |
| 240 | 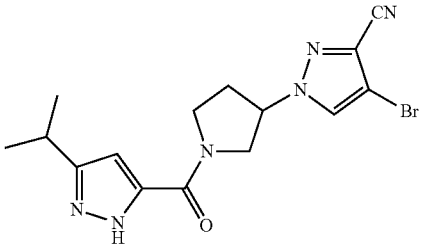 [SMILES: CC(C)c1cc(C(=O)N2CCC(n3cc(Br)c(C#N)n3)C2)[nH]n1] | 2.1 | |
| 241 | 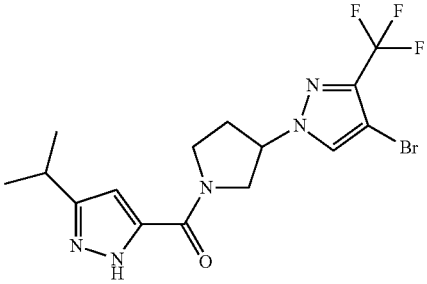 [SMILES: CC(C)c1cc(C(=O)N2CCC(n3cc(Br)c(C(F)(F)F)n3)C2)[nH]n1] | | |
| 242 | 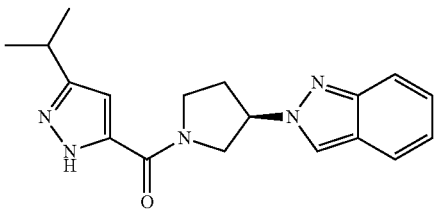 [SMILES: CC(C)c1cc(C(=O)N2CC[C@@H](n3cc4ccccc4n3)C2)[nH]n1] | 0.35 | |

TABLE 2-continued
| Ex | Structure | KDM5A HTRF IC$_{50}$ (nM) | H3K4Me3 PC9 HTRF EC$_{50}$ (nM) |
|---|---|---|---|
| 243 | 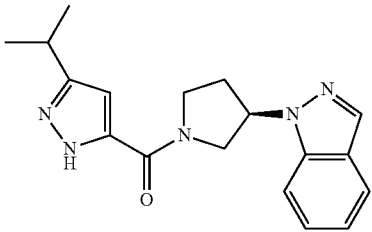 [SMILES: CC(C)c1cc(C(=O)N2CC[C@@H](n3ncc4ccccc43)C2)[nH]n1] | 0.92 | |
| 244 | 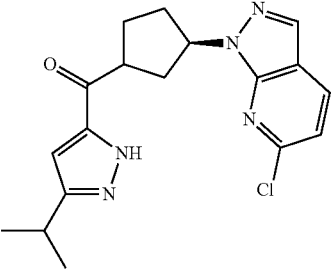 [SMILES: CC(C)c1cc(C(=O)C2CC[C@@H](n3ncc4ccc(Cl)nc43)C2)[nH]n1] | 0.84 | |
| 245 | 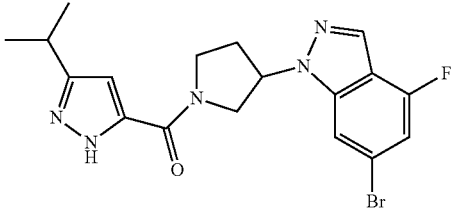 [SMILES: CC(C)c1cc(C(=O)N2CCC(n3ncc4c(F)cc(Br)cc43)C2)[nH]n1] | 0.91 | |
| 246 | 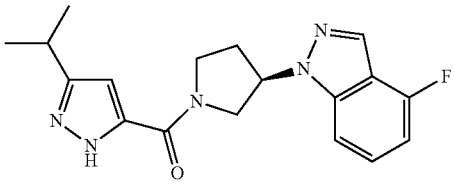 [SMILES: CC(C)c1cc(C(=O)N2CC[C@@H](n3ncc4c(F)cccc43)C2)[nH]n1] | 0.3 | 23 |
| 247 | 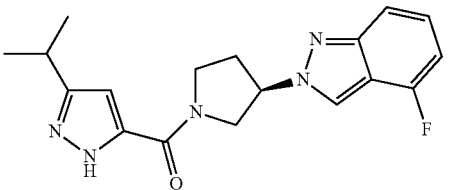 [SMILES: CC(C)c1cc(C(=O)N2CC[C@@H](n3cc4c(F)cccc4n3)C2)[nH]n1] | 0.43 | |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I):

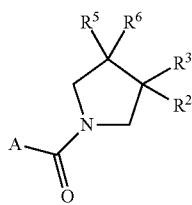

or a salt thereof, wherein:

A is selected from the group consisting of:

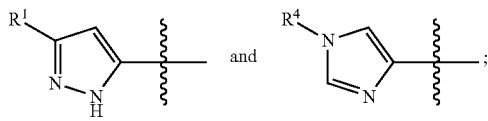

$R^1$ is halo, $-N(R^x)_2$, $C_{1-6}$alkyl, $C_{2-6}$alkenyl, $C_{2-6}$alkynyl, 3-8 membered carbocyclyl, $C_{1-6}$alkoxy, 5-10 membered aryl, 5-10 membered heteroaryl, or 3-8 membered heterocyclyl, wherein said $C_{1-6}$alkyl, $C_{1-6}$alkenyl, $C_{1-6}$alkynyl, 3-8 membered carbocyclyl, $C_{1-6}$alkoxy, 5-10 membered aryl, 5-10 membered heteroaryl, and 3-8 membered heterocyclyl are optionally substituted with one or more groups independently selected from the group consisting of oxo, hydroxy, halo, $C_{1-3}$alkoxy, 3-8 membered carbocyclyl, 5-10 membered aryl, $-N(R^x)_2$, $-N(R^x)C(O)R^x$, and $C_{1-3}$alkyl;

each $R^x$ is independently selected from the group consisting of H and $C_{1-6}$alkyl, that is optionally substituted with one or more groups independently selected from the group consisting of halo, hydroxy, and $C_{1-3}$alkoxy;

$R^2$ is 5-10 membered carbocyclyl, 5-10 membered heterocyclyl, 5-10 membered aryl, 5-10 membered heteroaryl, $-OR^a$, $-C(O)N(R^a)_2$, or $NR^aR^b$, wherein each 5-10 membered carbocyclyl, 5-10 membered heterocyclyl, 5-10 membered aryl, and 5-10 membered heteroaryl is optionally substituted with one or more groups $R^d$;

$R^a$ and $R^b$ are each independently selected from the group consisting of H, $C_{1-6}$alkyl, $C_{2-6}$alkenyl, $C_{2-6}$alkynyl, 3-8 membered carbocyclyl, 3-8 membered heterocyclyl, 5-10 membered aryl, 5-10 membered heteroaryl $-C(O)R^c$, $-CO_2R^c$, $-C(O)N(R^c)_2$, $-C(O)SR^c$, and $-C(O)C(O)R^c$, wherein each $C_{1-6}$alkyl, $C_{2-6}$alkenyl, $C_{2-6}$alkynyl, 3-8 membered carbocyclyl, 3-8 membered heterocyclyl, 5-10 membered aryl, and 5-10 membered heteroaryl is optionally substituted with one or more groups independently selected from the group consisting of halo, nitro, cyano, oxo, $C_{1-4}$alkyl, $C_{2-4}$alkynyl, 3-8 membered carbocyclyl, $-OR^c$, $-SR^c$, $-N(R^c)_2$, $-C(O)R^c$, $-C(O)N(R^c)_2$, $-C(O)SR^c$, $-C(O)C(O)R^c$, $-S(O)R^c$, $-SO_2N(R^c)_2$, $-N(R^c)C(O)R^c$, $-N(R^c)C(O)N(R^c)_2$, $-N(R^c)SO_2R^c$, $-N(R^c)SO_2N(R^c)_2$, $-N(R^c)N(R^c)_2$, $-N(R^c)C(=N(R^c))N(R^c)_2$, $-C(=N)N(R^c)_2$, $-C=NOR^c$, and $-C(=N(R^c))N(R^c)_2$;

each $R^c$ is independently selected from the group consisting of H, $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl, wherein each $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl is optionally substituted with one or more groups $R^h$;

each $R^d$ is independently selected from the group consisting of halo, nitro, cyano, oxo, $C_{1-6}$alkyl, $C_{2-6}$alkenyl, $C_{2-6}$alkynyl, 3-8 membered carbocyclyl, 3-8 membered heterocyclyl, 5-10 membered aryl, 5-10 membered heteroaryl, $-OR^e$, $-SR^e$, $-N(R^e)_2$, $-C(O)R^e$, $-CO_2R^e$, $-C(O)N(R^e)_2$, $-C(O)SR^e$, $-C(O)C(O)R^e$, $-S(O)R^e$, $-SO_2R^e$, $-SO_2N(R^e)_2$, $-N(R^e)C(O)R^e$, $-N(R^e)C(O)N(R^e)_2$, $-N(R^e)SO_2R^e$, $-N(R^e)SO_2N(R^e)_2$, $-N(R^e)N(R^e)_2$, $-N(R^e)C(=N(R^e))N(R^e)_2$, $-C(=N)N(R^e)_2$, $-C=NOR^e$, and $-C(=N(R^e))N(R^e)_2$, wherein each $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl is optionally substituted with one or more groups independently selected from $R^f$;

each $R^e$ is independently selected from the group consisting of H, $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl, wherein each $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl is optionally substituted with one or more groups independently selected from the group consisting of $C_{1-4}$alkyl, $C_{2-4}$alkenyl, $C_{2-4}$alkynyl, 3-8 membered carbocyclyl, 3-8 membered heterocyclyl, 5-10 membered aryl and 5-10 membered heteroaryl;

each $R^f$ is independently selected from the group consisting of halo, nitro, cyano, oxo, $C_{1-4}$alkyl, $C_{2-4}$alkenyl, $C_{2-4}$alkynyl, 3-8 membered carbocyclyl, $-OR^g$, $-SR^g$, $-N(R^g)_2$, $-C(O)R^g$, $-CO_2R^g$, $-C(O)N(R^g)_2$, $-C(O)SR^g$, $-C(O)C(O)R^g$, $-S(O)R^g$, $-SO_2R^g$, $-SO_2N(R^g)_2$, $-N(R^g)C(O)R^g$, $-N(R^g)C(O)N(R^g)_2$, $-N(R^g)SO_2R^g$, $-N(R^g)SO_2N(R^g)_2$, $-N(R^g)N(R^g)_2$, $-N(R^g)C(=N(R^g))N(R^g)_2$, $-C(=N)N(R^g)_2$, and $-C=NOR^g$, $-C(=N(R^g))N(R^g)_2$, wherein each $C_{1-4}$alkyl, $C_{2-4}$alkenyl, $C_{2-4}$alkynyl, and 3-8 membered carbocyclyl is optionally substituted with one or more groups independently selected from the group consisting of halo, cyano, oxo, 3-8 membered carbocyclyl, $-OR^g$, $-N(R^g)_2$, $-C(O)R^g$, $-CO_2R^g$, $-C(O)N(R^g)_2$, $-SO_2R^g$, $-SO_2N(R^g)_2$, and $-N(R^g)C(O)R^g$;

each $R^g$ is independently selected from the group consisting of H, $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl, wherein each $C_{1-6}$alkyl, $C_{2-6}$alkenyl, $C_{2-6}$alkynyl, 3-8 membered carbocyclyl, 3-8 membered heterocyclyl, 5-10 membered aryl and 5-10 membered heteroaryl is optionally substituted with one or more groups independently selected from the group consisting of $C_{1-4}$alkyl, $C_{2-4}$alkenyl, $C_{2-4}$alkynyl, 3-8 membered carbocyclyl, 3-8 membered heterocyclyl, 5-10 membered aryl and 5-10 membered heteroaryl; and each $R^h$ is independently selected from the group consisting of halo, nitro, cyano, oxo, $C_{1-4}$alkyl, $C_{2-4}$alkenyl, $C_{2-4}$alkynyl, 3-8 membered carbocyclyl, 3-8 membered heterocyclyl, 5-10 membered aryl, 5-10 membered heteroaryl, —N($R^k$)$_2$, and, —O$R^k$, wherein each $C_{1-4}$alkyl, $C_{2-4}$alkenyl, $C_{2-4}$alkynyl, 3-8 membered carbocyclyl, 3-8 membered heterocyclyl, 5-10 membered aryl and 5-10 membered heteroaryl is optionally substituted with one or more groups independently selected from the group consisting of halo, hydroxy, $C_{1-4}$alkoxy, cyano, oxo, $C_{1-4}$alkyl, $C_{2-4}$alkenyl, $C_{2-4}$alkynyl, 3-8 membered carbocyclyl, and 5-10 membered aryl;

each $R^k$ is independently selected from the group consisting of H, $C_{1-4}$alkyl, $C_{2-4}$alkenyl, $C_{2-4}$alkynyl, 3-8 membered carbocyclyl, and 5-10 membered aryl wherein any $C_{1-4}$alkyl, $C_{2-4}$alkenyl, $C_{2-4}$alkynyl, 3-8 membered carbocyclyl, and 5-10 membered aryl carbocyclyl is optionally substituted with one or more groups independently selected from the group consisting of halo, cyano, oxo hydroxy, and 3-8 membered carbocyclyl; and $R^3$ is H or $C_{1-6}$alkyl;

$R^4$ is $C_{1-6}$alkyl, $C_{2-6}$alkenyl, $C_{2-6}$alkynyl, or 3-8 membered carbocyclyl, 5-10 membered aryl, 5-10 membered heteroaryl wherein each $C_{1-6}$alkyl, $C_{2-6}$alkenyl, $C_{2-6}$alkynyl, and 3-8 membered carbocyclyl, 5-10 membered aryl, 5-10 membered heteroaryl is optionally substituted with one or more groups independently selected from halo, hydroxy, cyano, $C_{1-6}$alkoxy, and 3-8 membered carbocyclyl; and $R^5$ is H, halo, or $C_{1-6}$alkyl, and $R^6$ is H, $C_{1-6}$alkyl, $C_{2-6}$alkenyl, $C_{2-6}$alkynyl, halo, hydroxy, or 3-8 membered carbocyclyl, wherein each $C_{1-6}$alkyl, $C_{2-6}$alkenyl, $C_{2-6}$alkynyl, and 3-8 membered carbocyclyl, is optionally substituted with one or more groups independently selected from halo, hydroxy, cyano, $C_{1-6}$alkoxy, and 3-8 membered carbocyclyl; or $R^5$ and $R^6$ taken together with the atom to which they are attached form a 3-8 membered carbocyclyl or a 3-8 membered heterocyclyl, which 3-8 membered carbocyclyl and 3-8 membered heterocyclyl are optionally substitutes with one or more groups independently selected from halo, hydroxy, cyano, $C_{1-6}$alkoxy, and 3-8 membered carbocyclyl.

2. The compound of claim 1 which is a compound of formula (Ia):

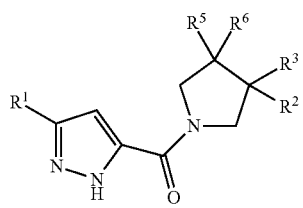

(Ia)

or a salt thereof.

3. The compound of claim 1 wherein $R^1$ is bromo, cyclohexyl, isopropyl, isobutyl, cyclopentyl, 1-methoxyethyl, cyclopropyl, cyclobutyl, amino, 4-phenylbut-2-yl, butyl, phenethyl, cyclopentyl, 1-(acetylamino)ethyl, or 1-(hydroxymethylcarbonylamino)ethyl.

4. The compound of claim 1 wherein $R^1$ is isopropyl.

5. The compound of claim 1 which is a compound of formula (Ib):

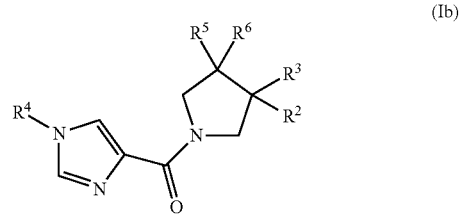

(Ib)

or a salt thereof.

6. The compound of claim 1 wherein $R^2$ is selected from the group consisting of:

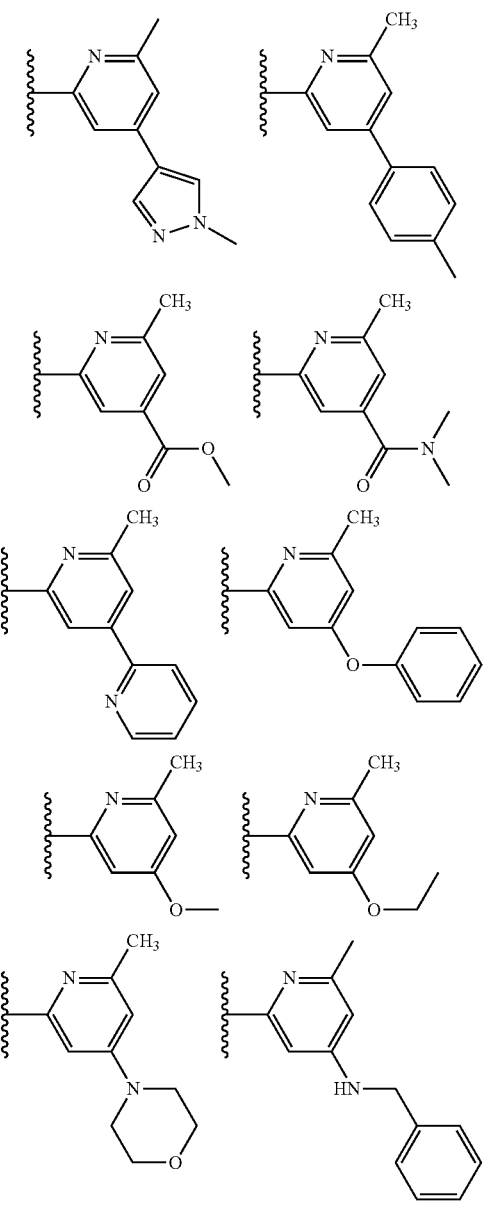

317
-continued
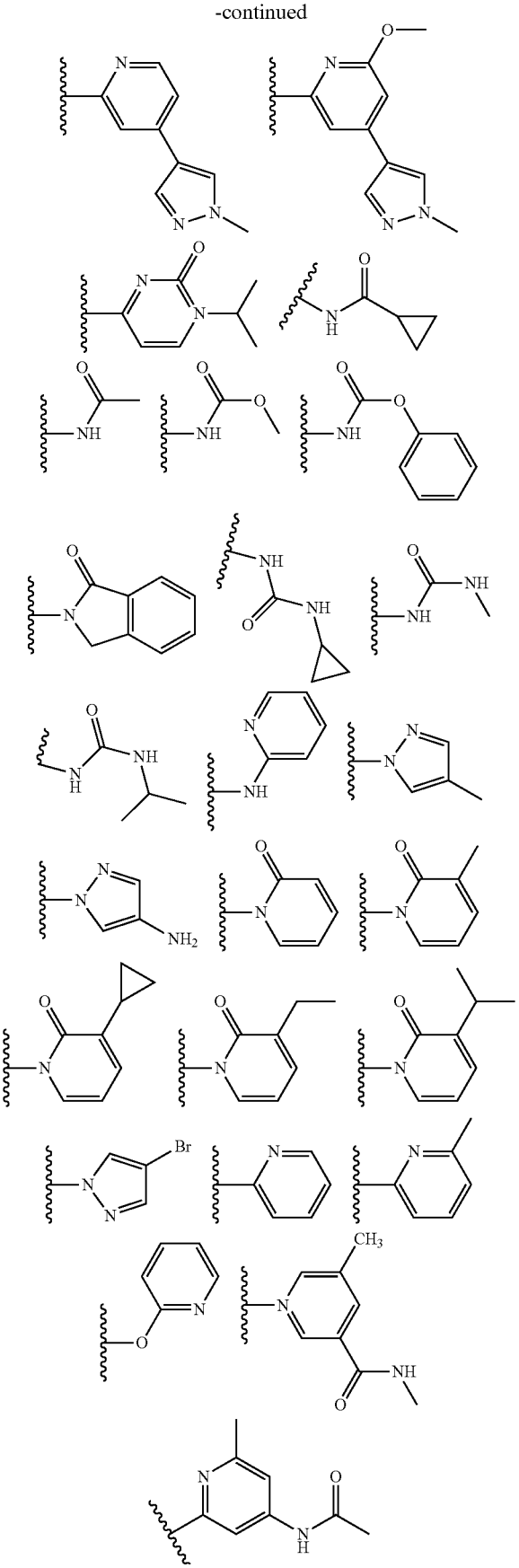
318
-continued
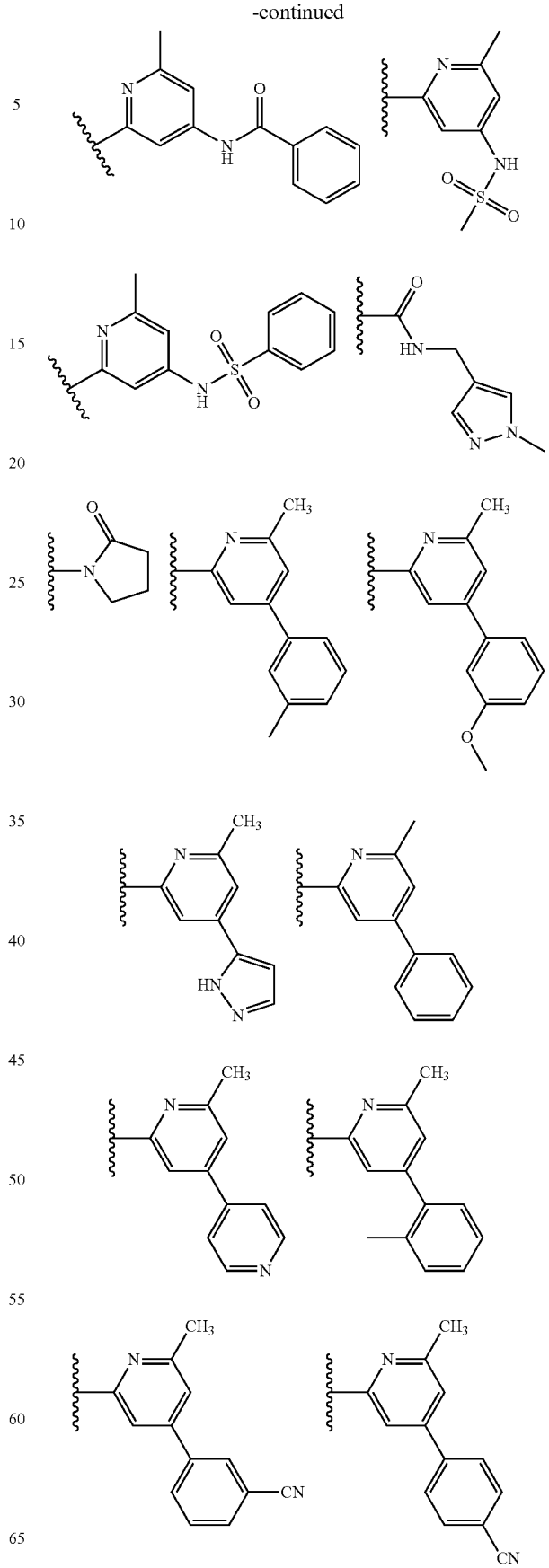

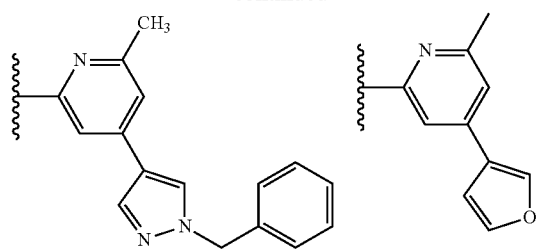
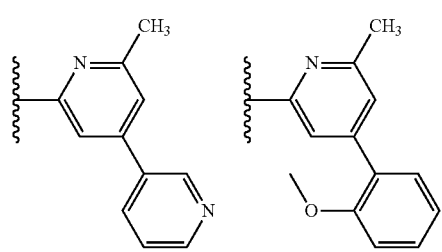
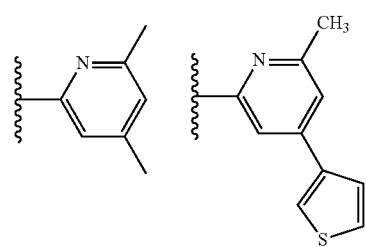
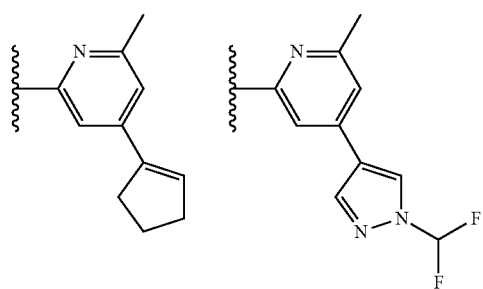
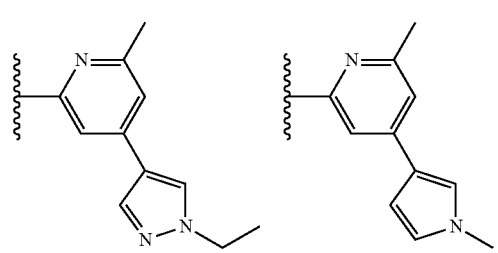
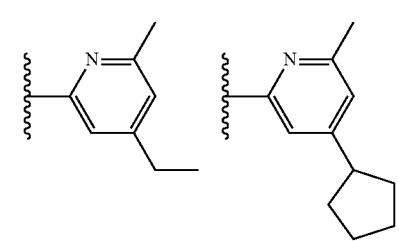
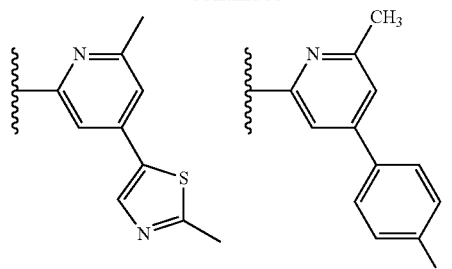
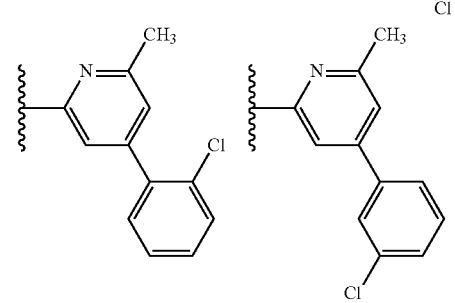
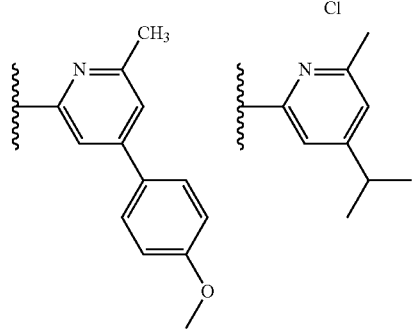
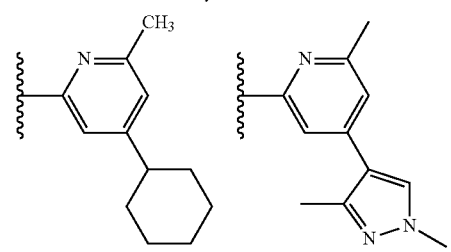
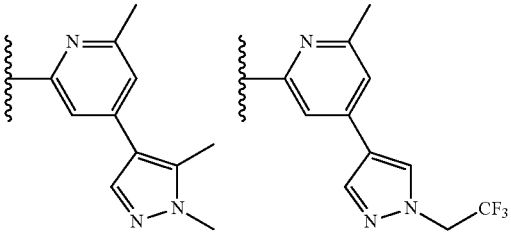
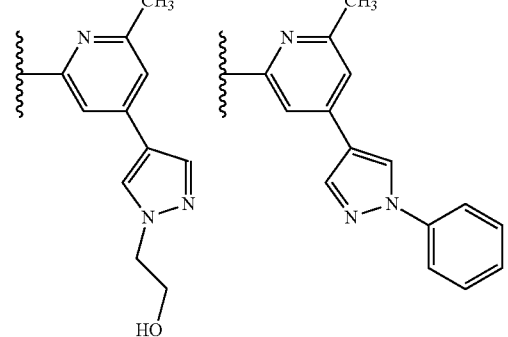

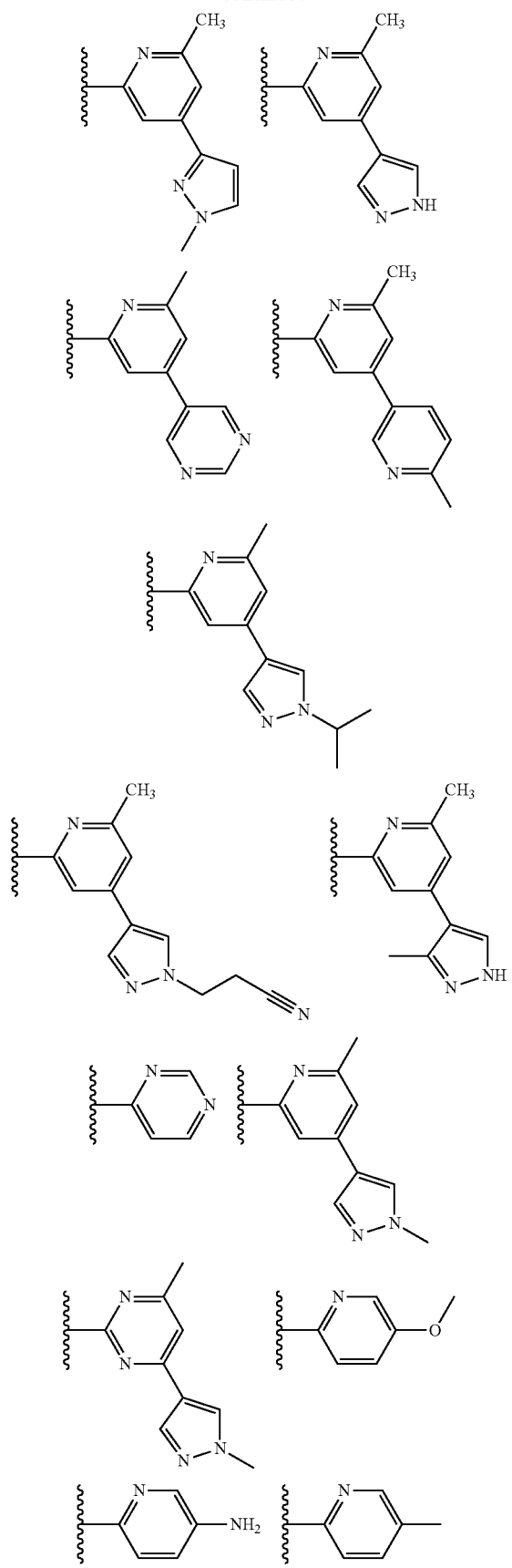
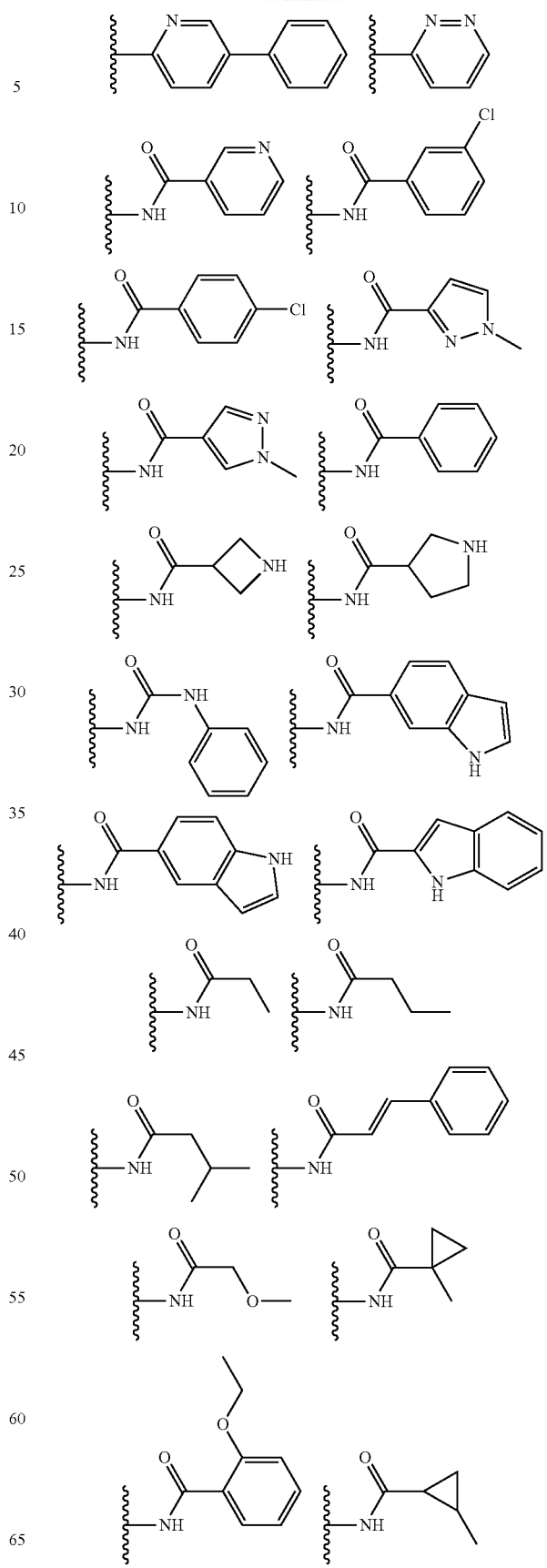

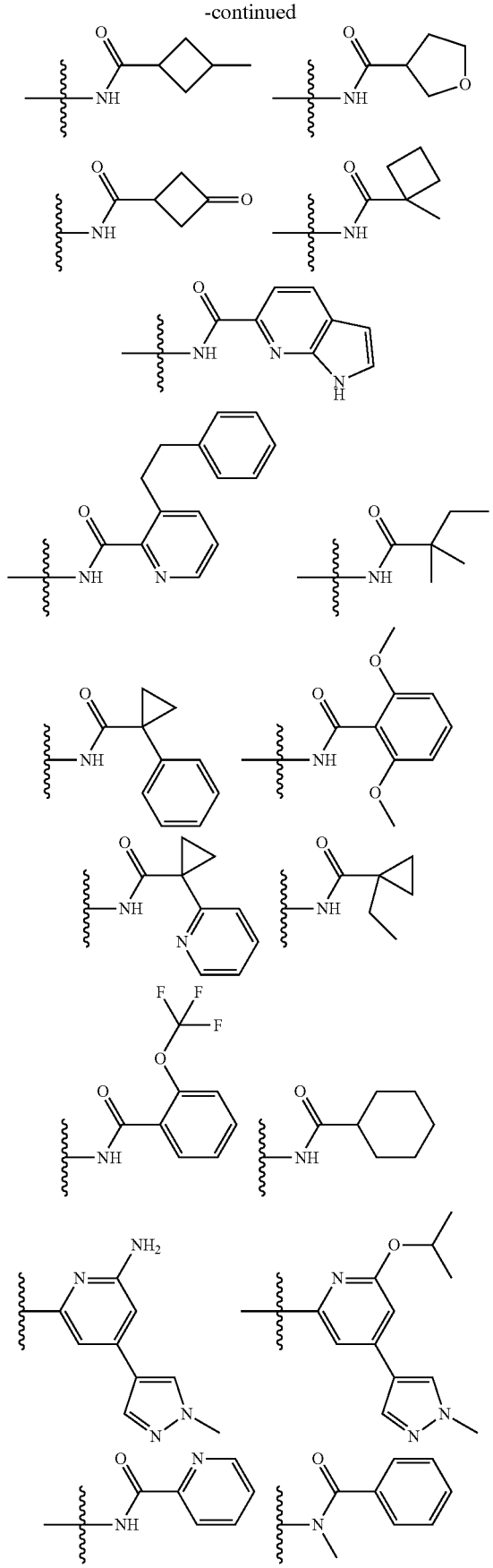
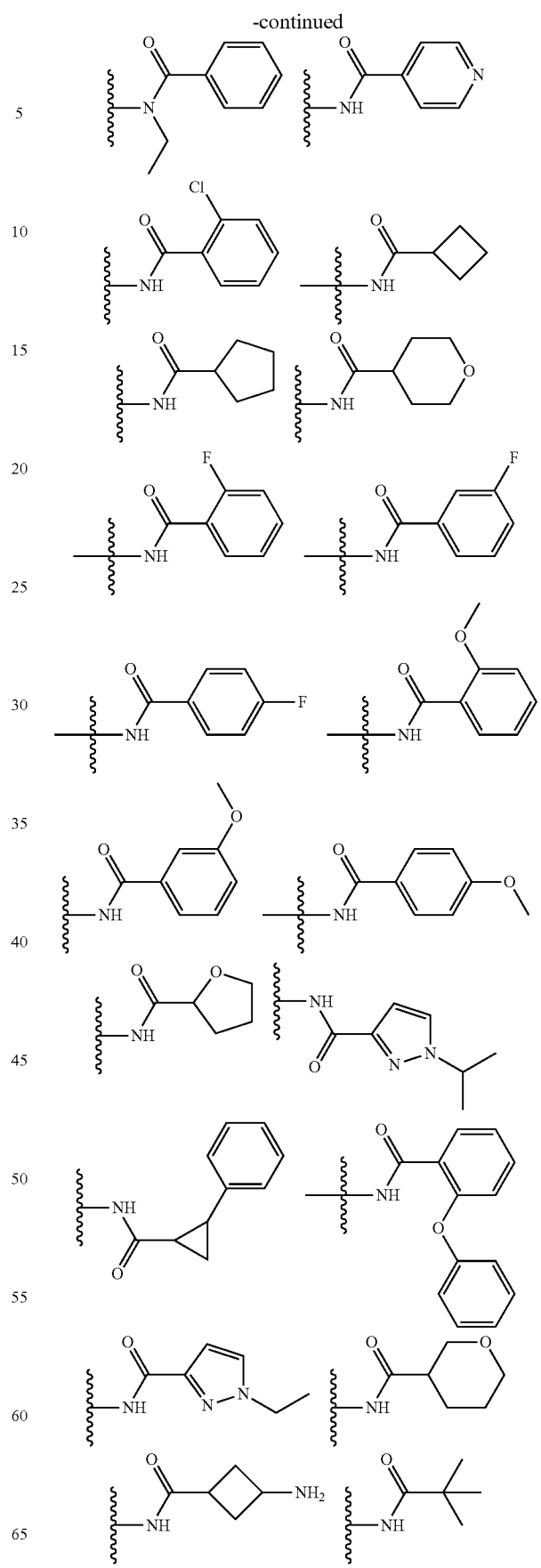

325
-continued
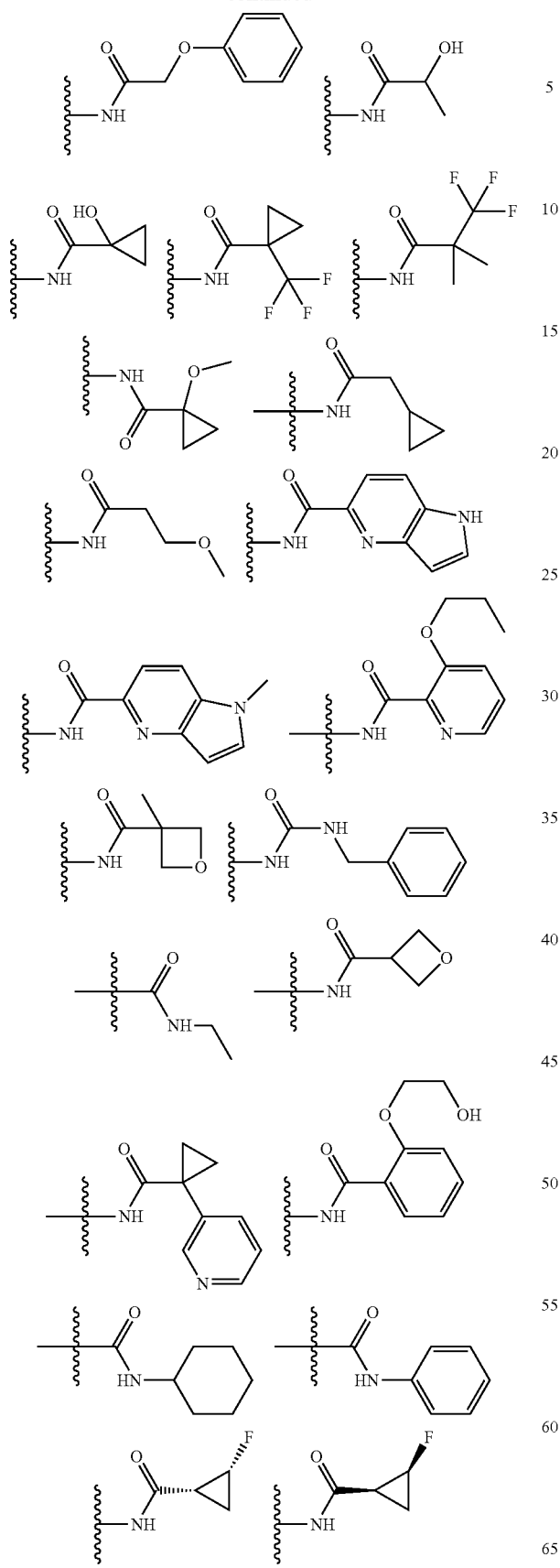
326
-continued
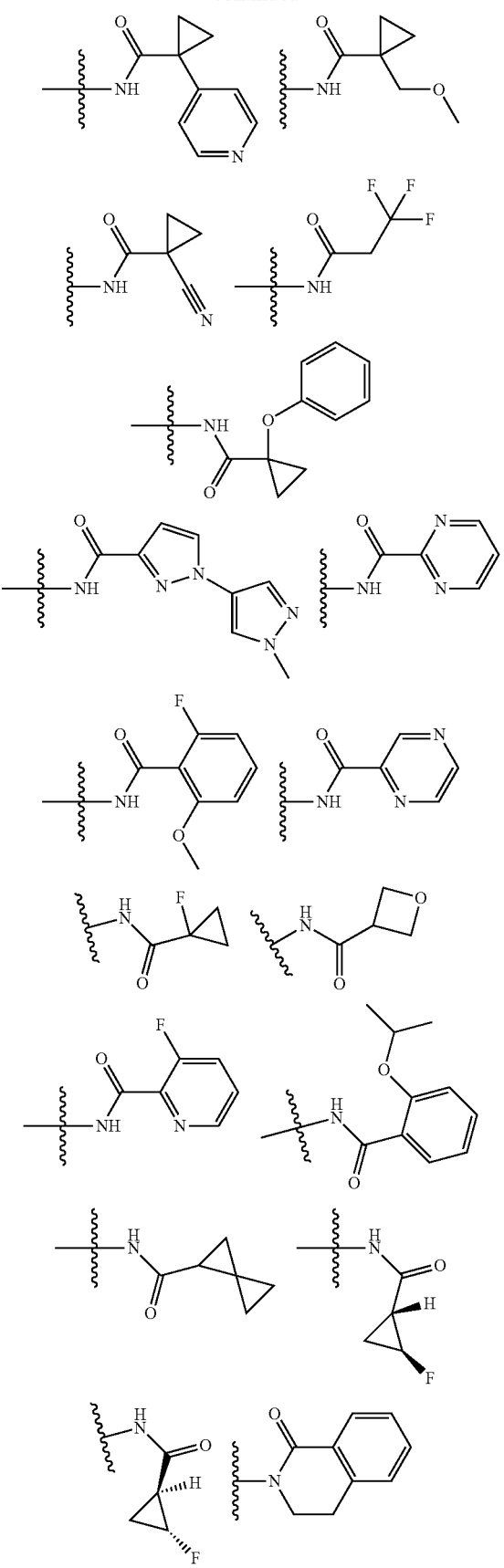

-continued

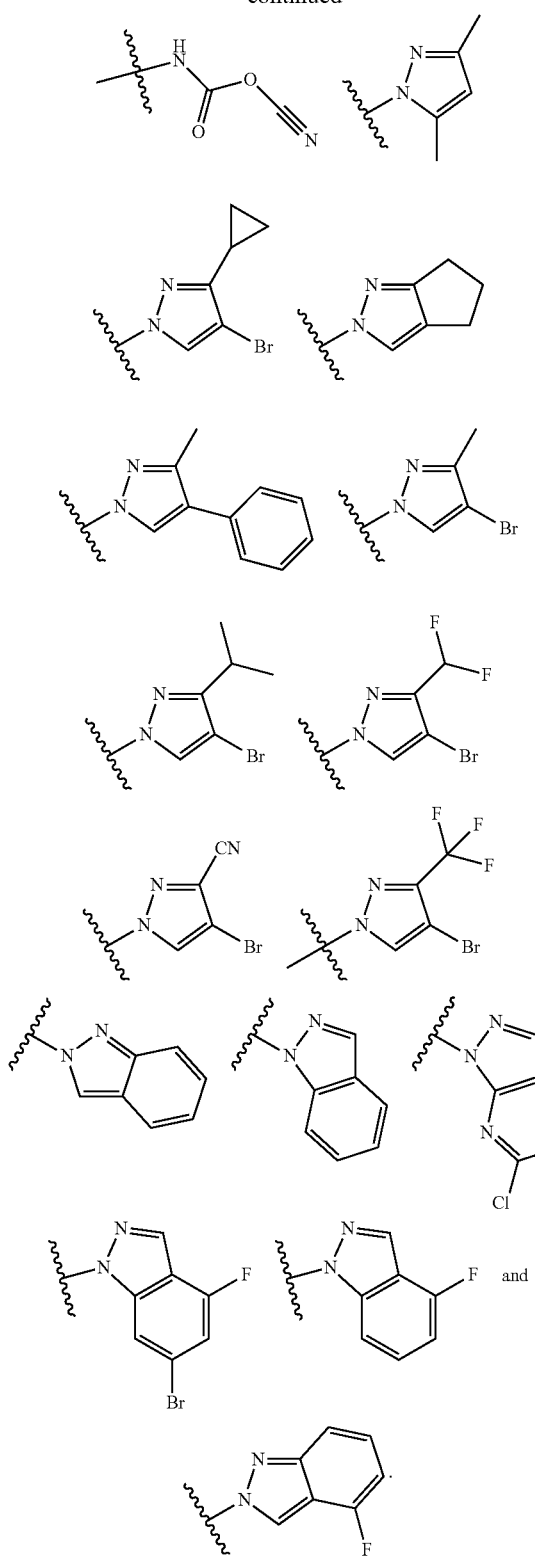

7. The compound of claim 1 wherein $R^2$ is 5-10 membered heterocyclyl, that is optionally substituted with one or more groups $R^d$.

8. The compound of claim 1 wherein $R^2$ is selected from the group consisting of:

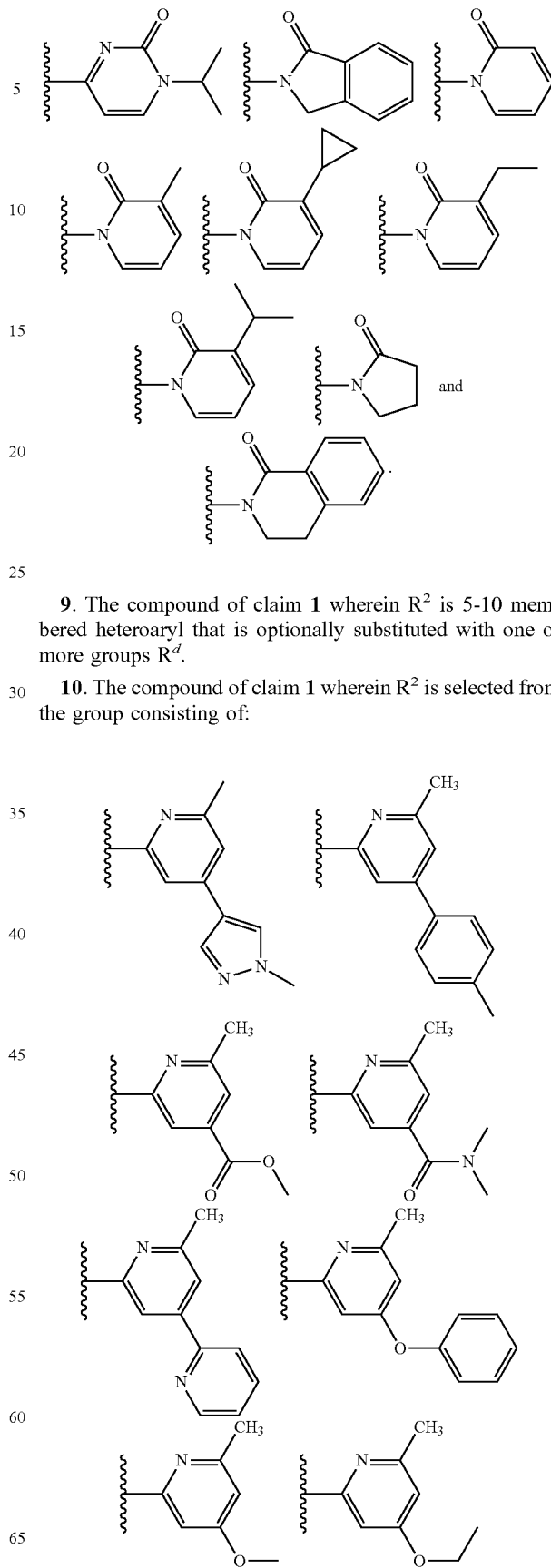

9. The compound of claim 1 wherein $R^2$ is 5-10 membered heteroaryl that is optionally substituted with one or more groups $R^d$.

10. The compound of claim 1 wherein $R^2$ is selected from the group consisting of:

329
-continued
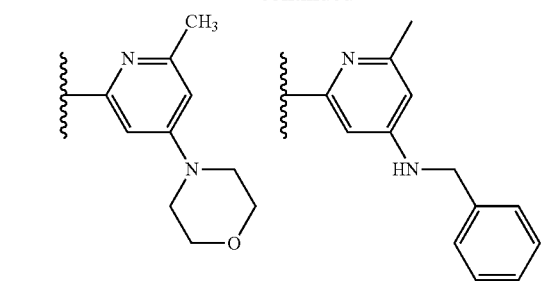
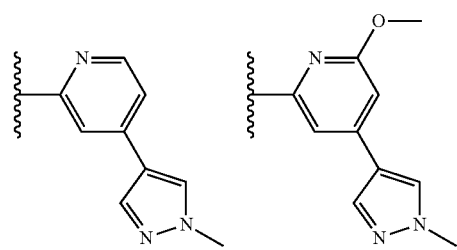
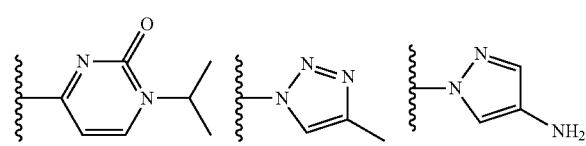
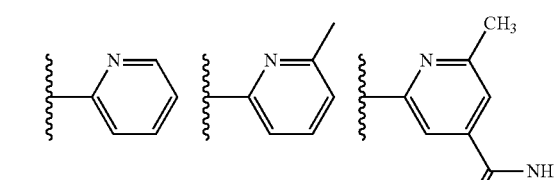
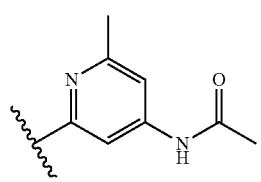
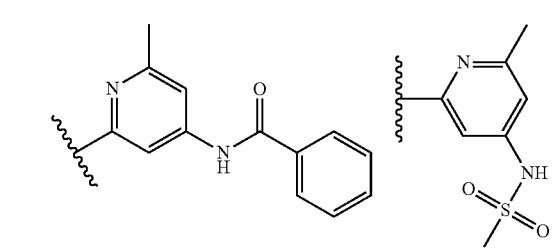
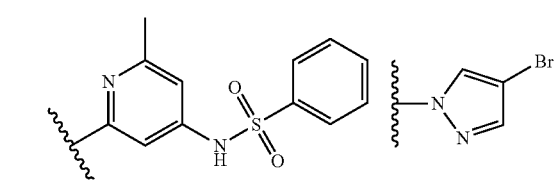
330
-continued
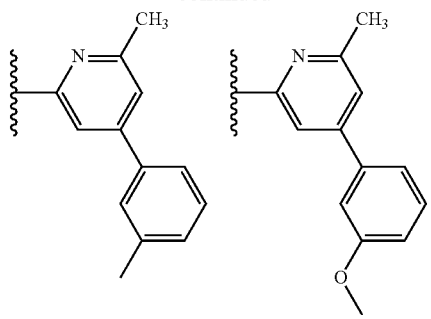
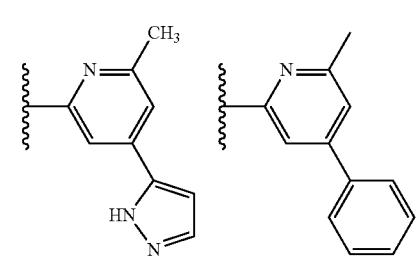
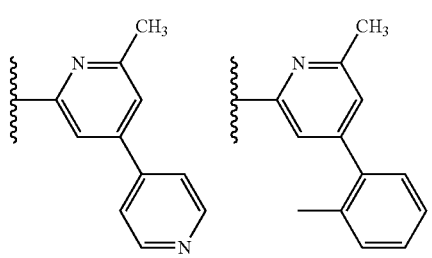
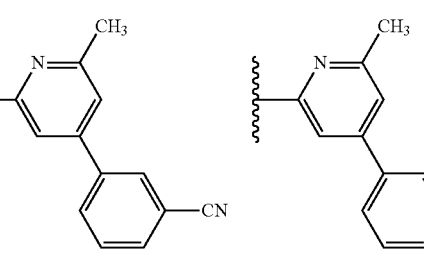
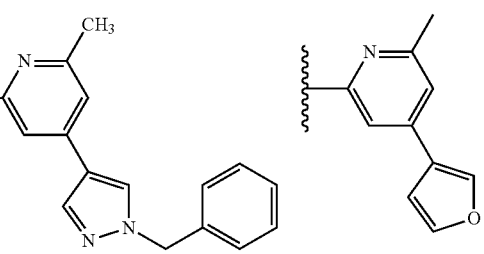
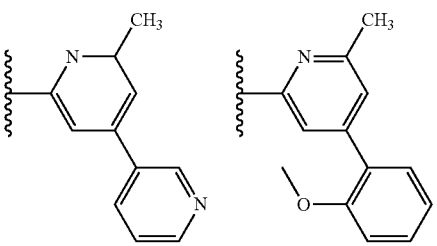

331
-continued
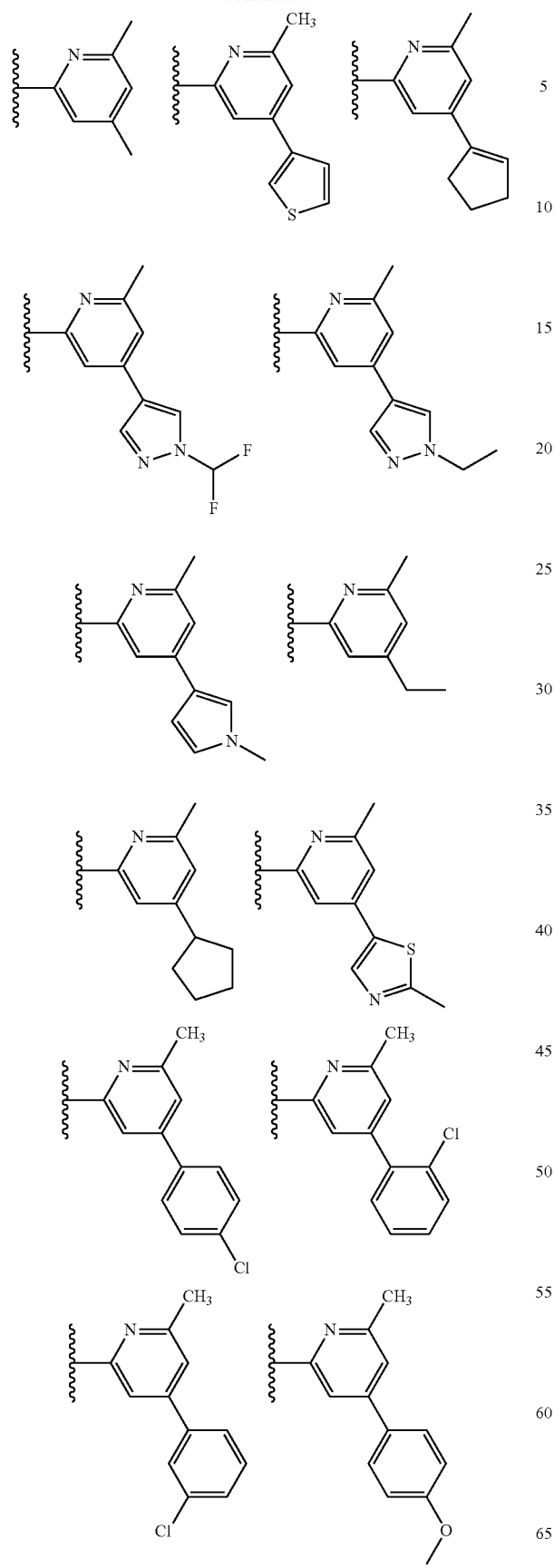
332
-continued
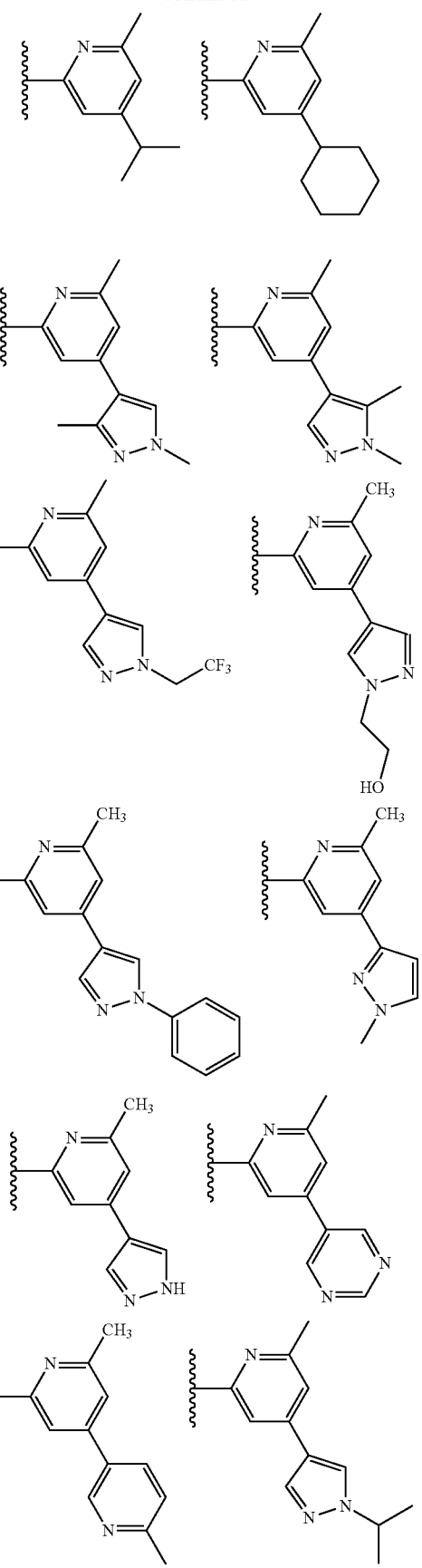

333
-continued
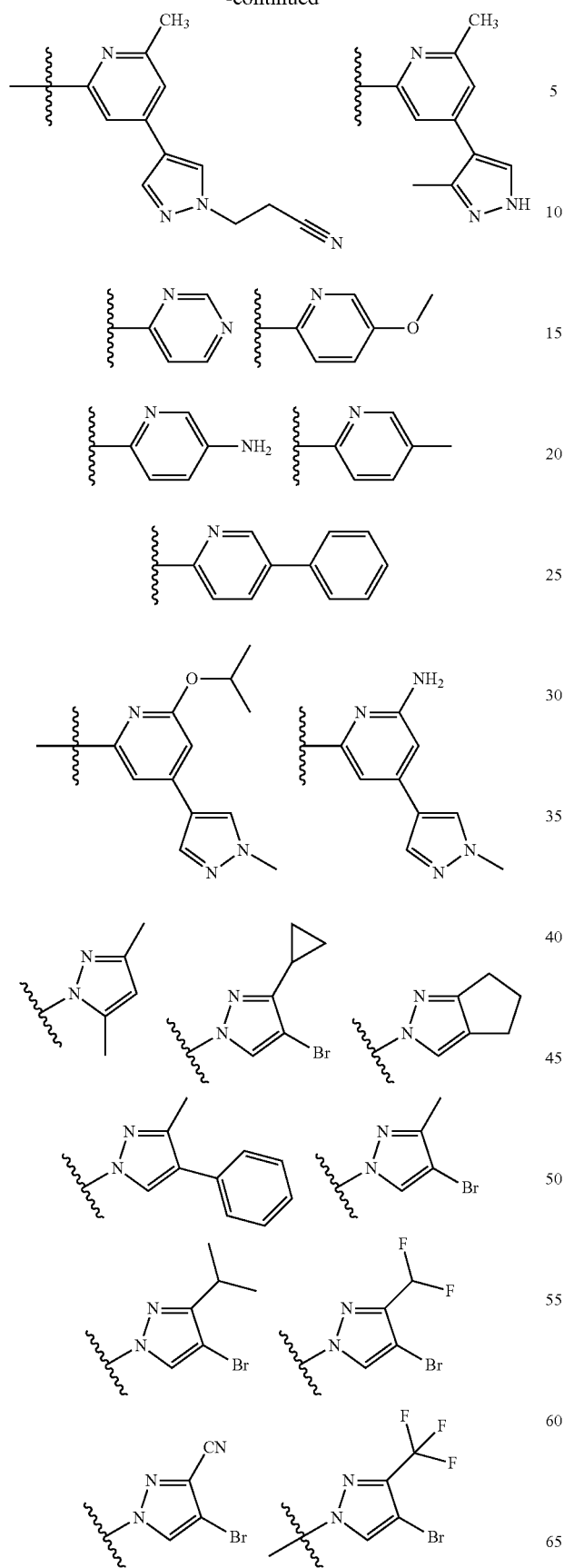
334
-continued
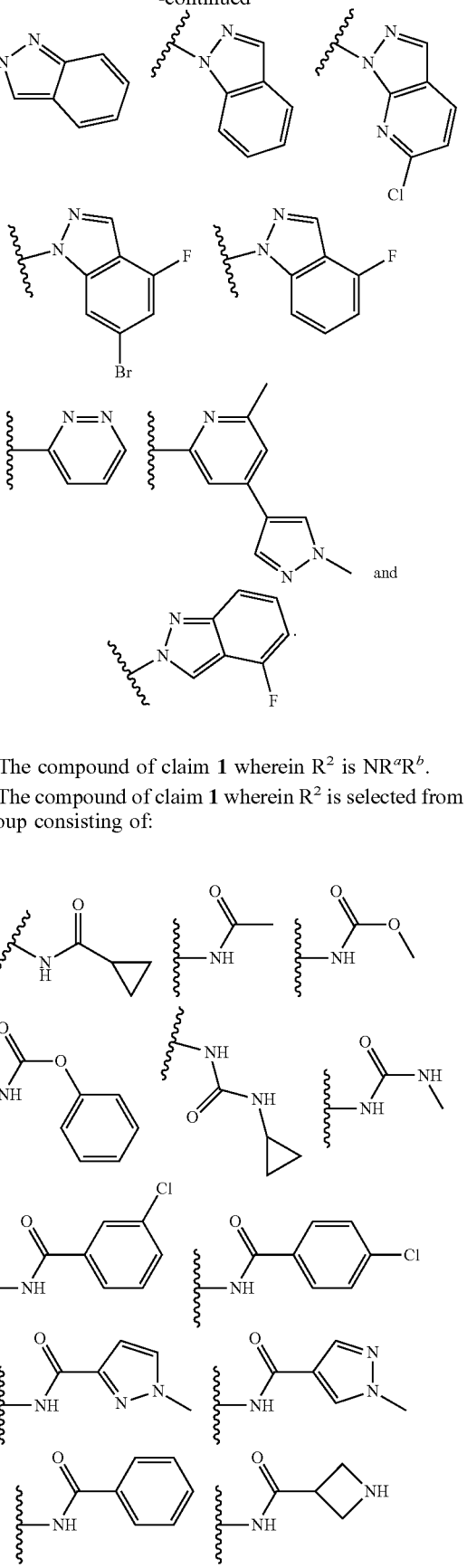
11. The compound of claim 1 wherein $R^2$ is $NR^aR^b$.
12. The compound of claim 1 wherein $R^2$ is selected from the group consisting of:

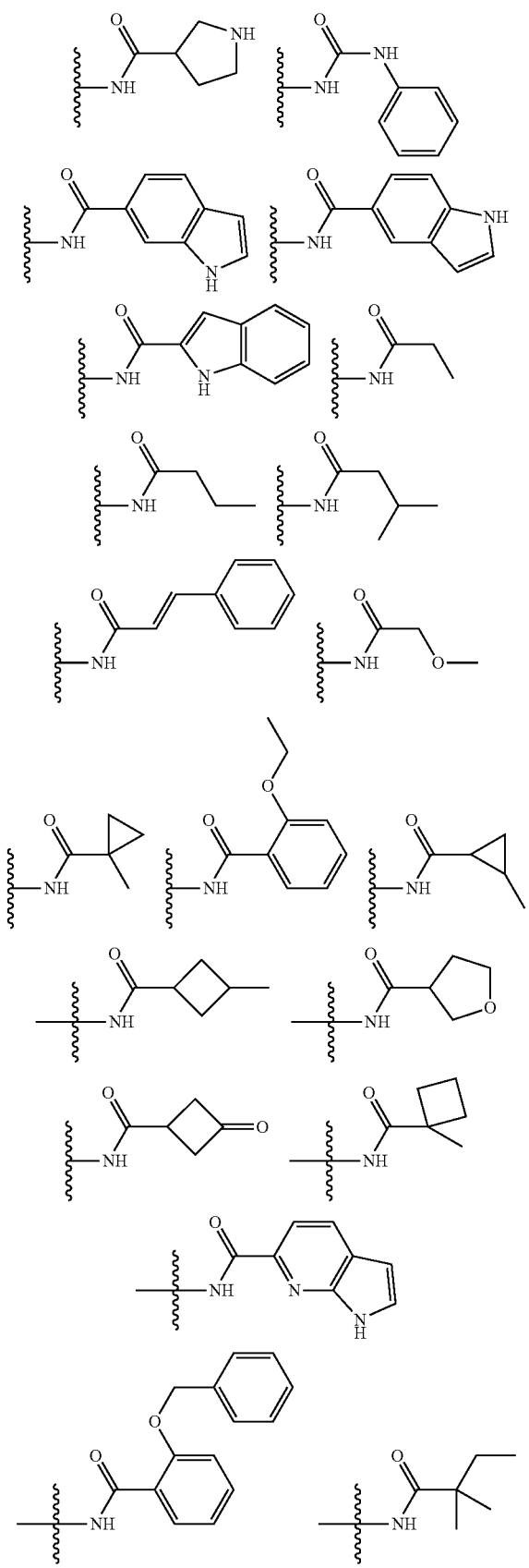
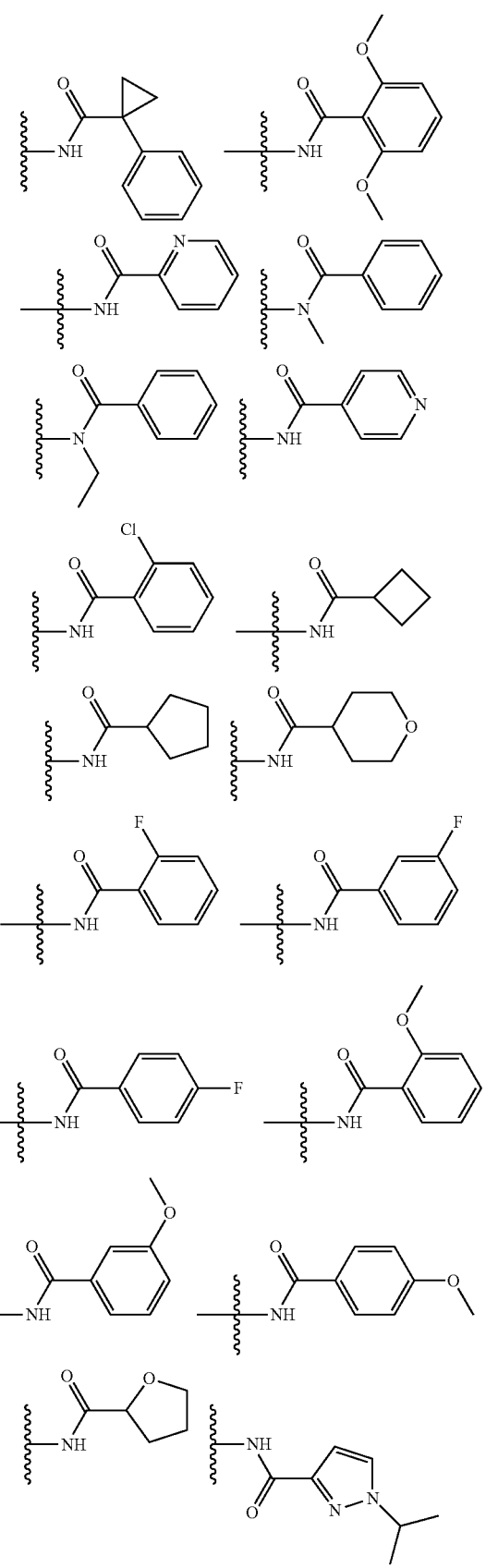

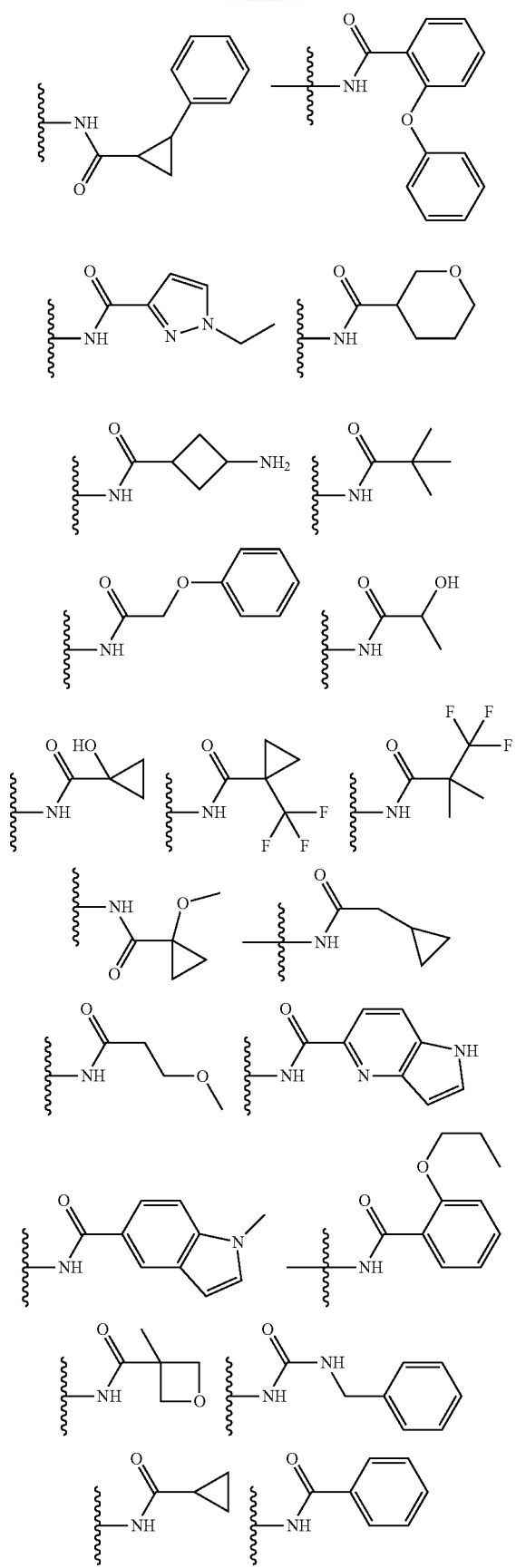
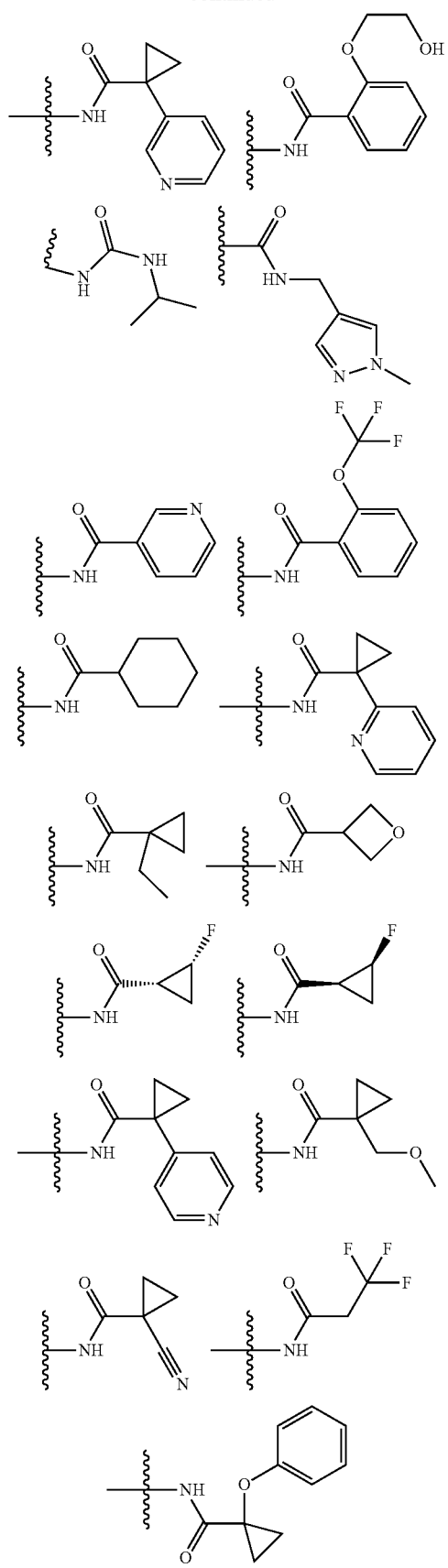

-continued

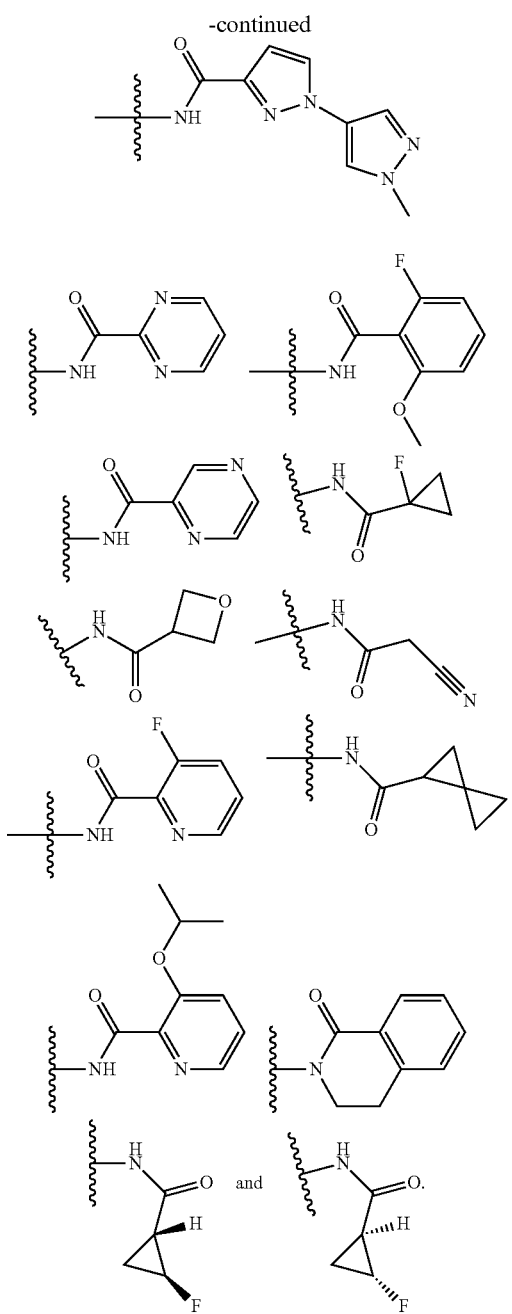

13. The compound of claim 1 wherein $R^2$ is —C(O)N$(R^a)_2$.

14. The compound of claim 1 wherein $R^2$ is selected from the group consisting of:

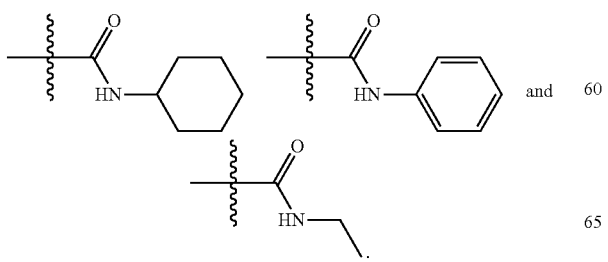

15. The compound of claim 1 wherein $R^3$ is H.

16. The compound of claim 1 wherein $R^5$ is H.

17. The compound of claim 1 wherein $R^6$ is methyl or hydroxy.

18. The compound of claim 1 wherein $R^6$ is H.

19. A compound which is selected from the group consisting of:

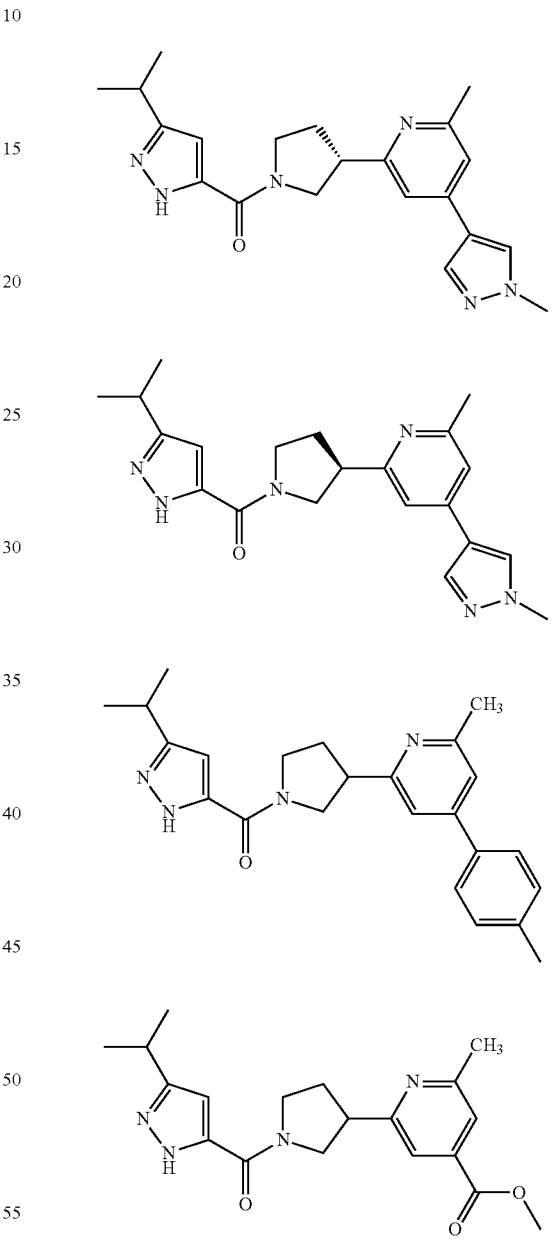

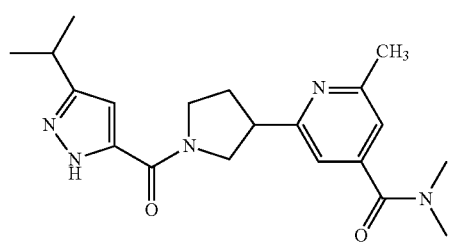

341
-continued
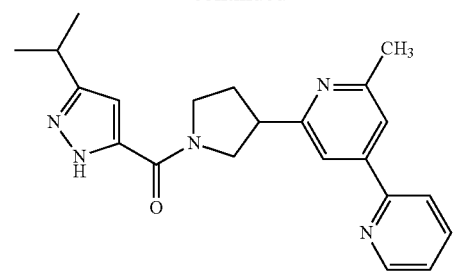
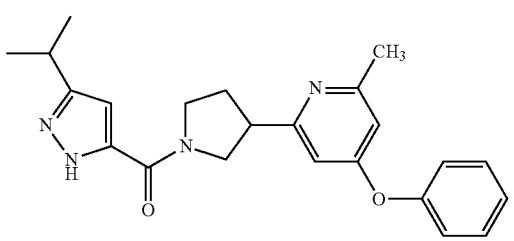
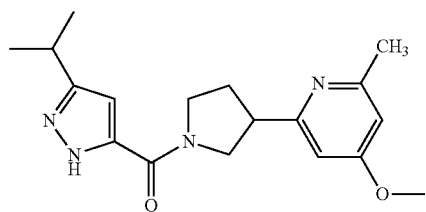
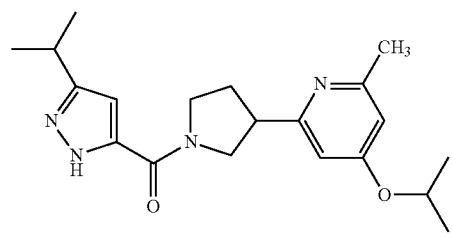
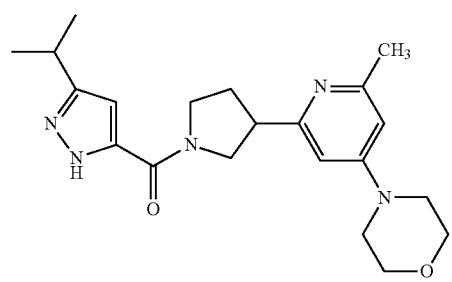
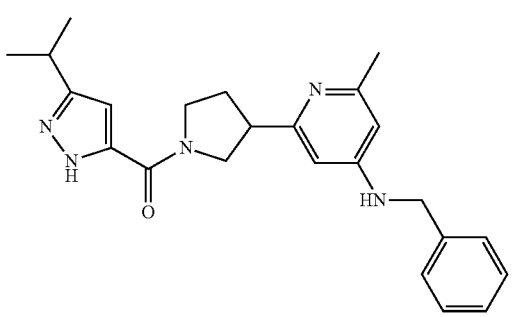
342
-continued
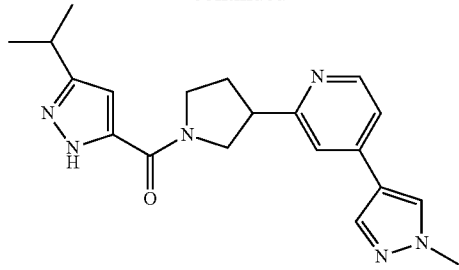
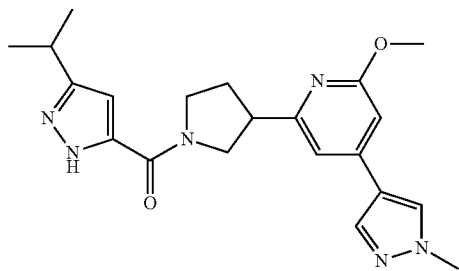
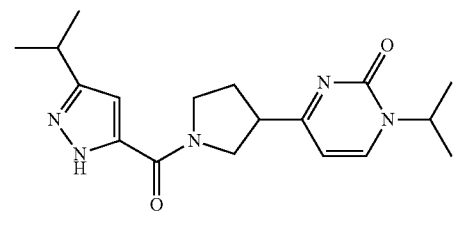
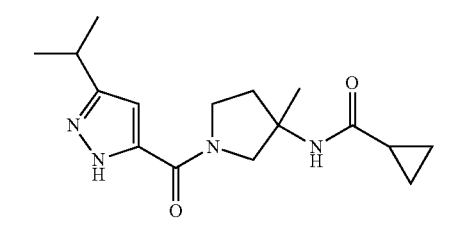
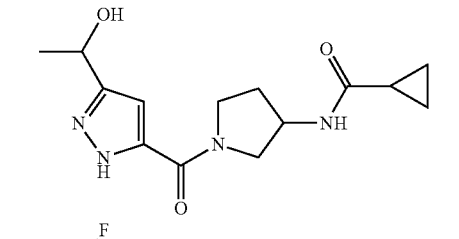
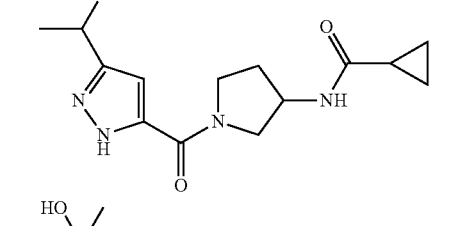
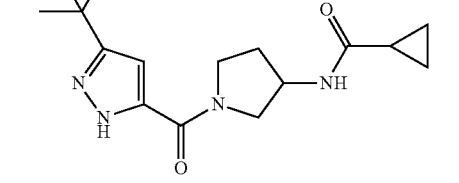

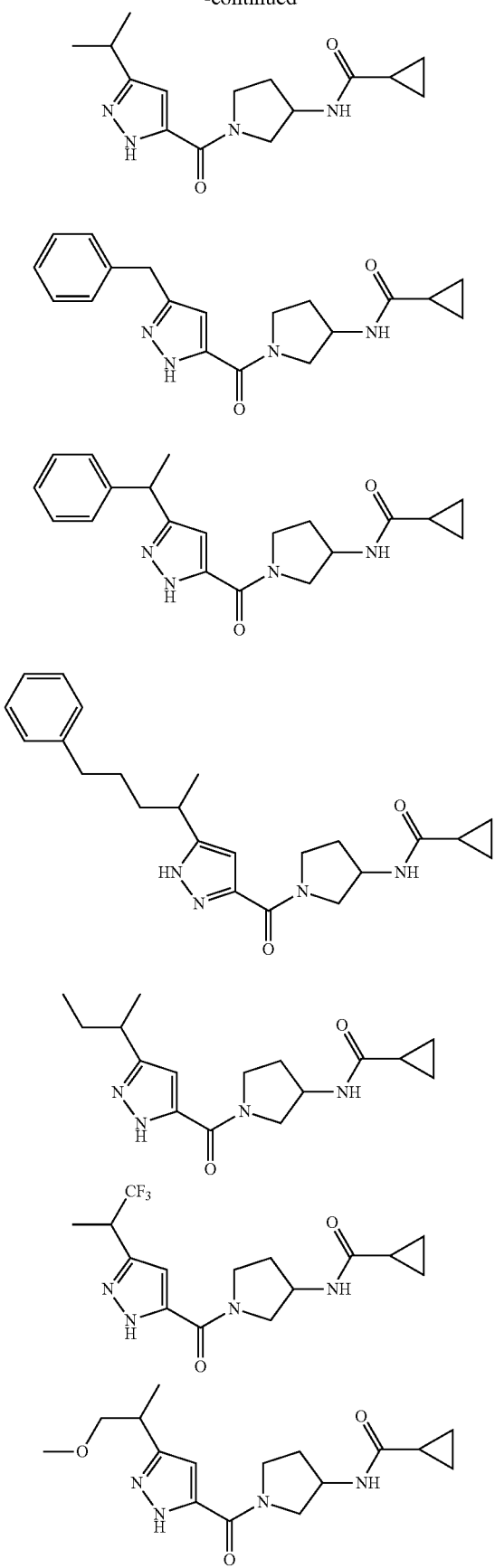
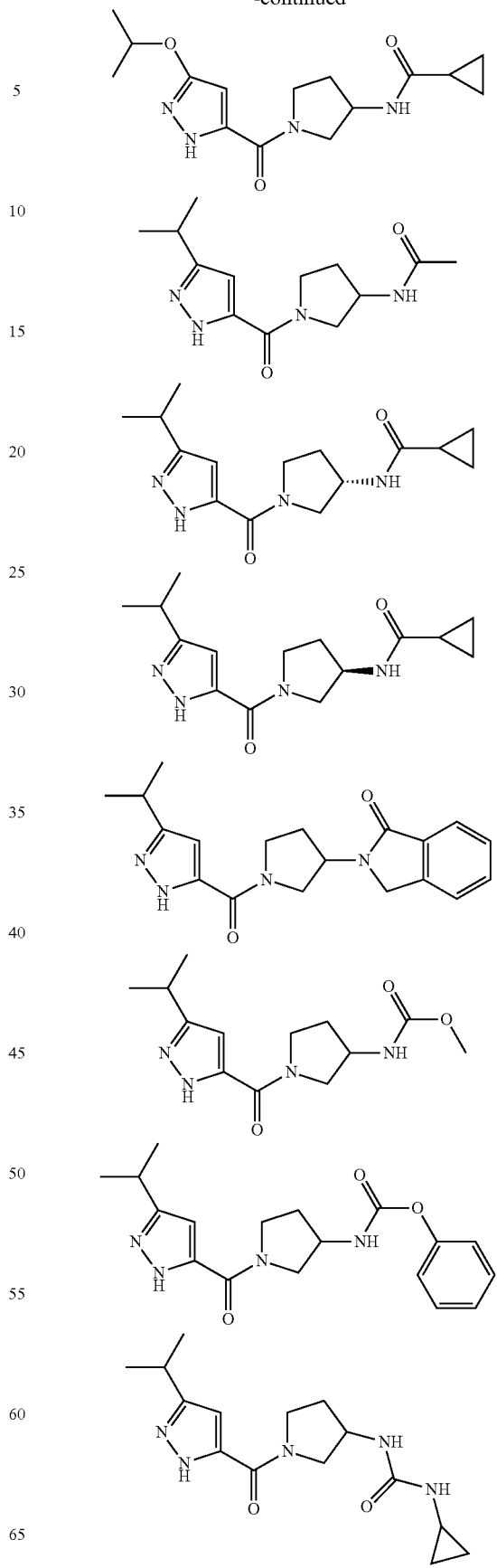

345
-continued
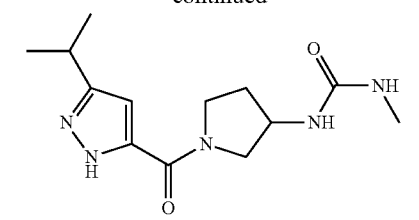
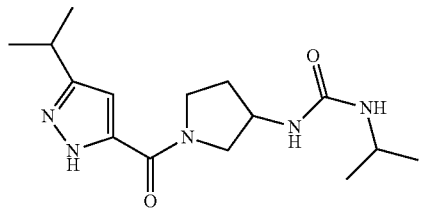
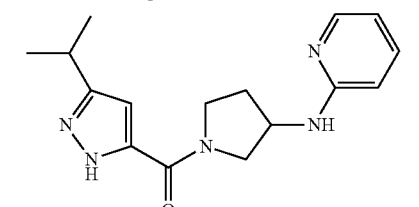
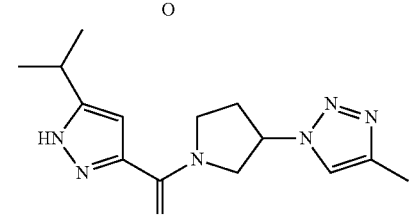
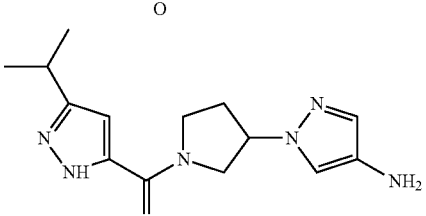
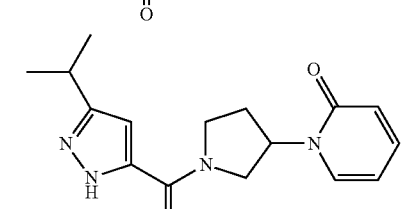
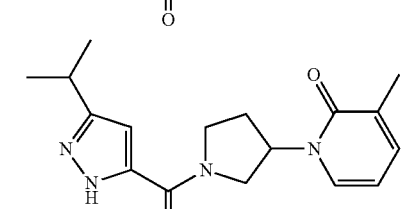
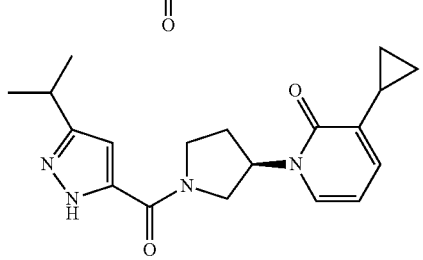
346
-continued
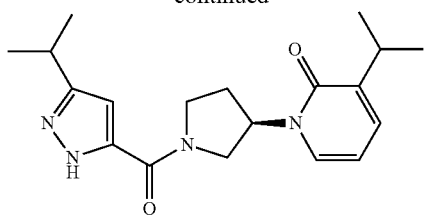
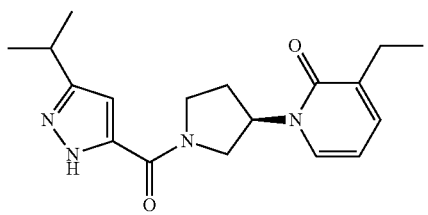
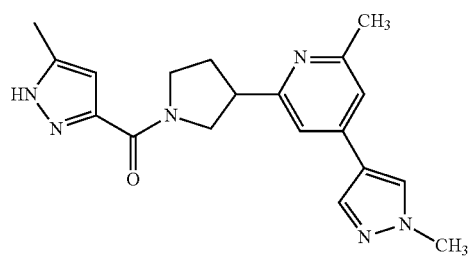
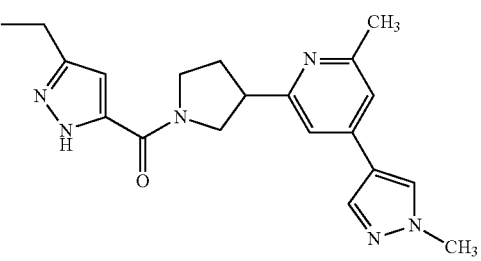
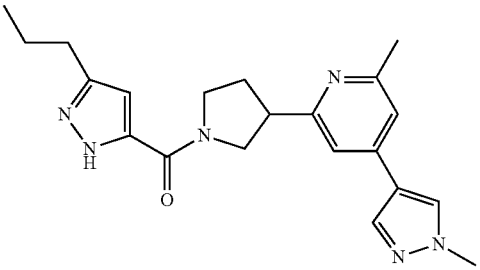
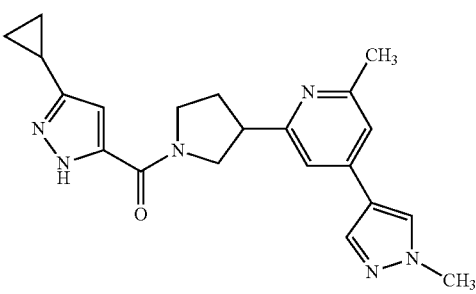

347
-continued
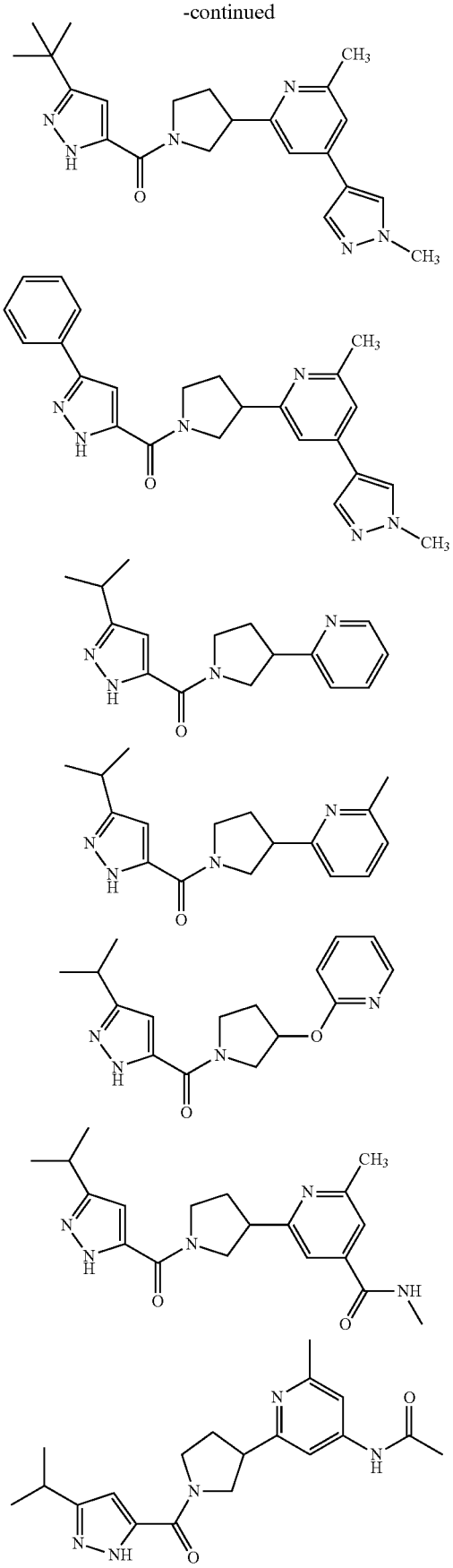
348
-continued
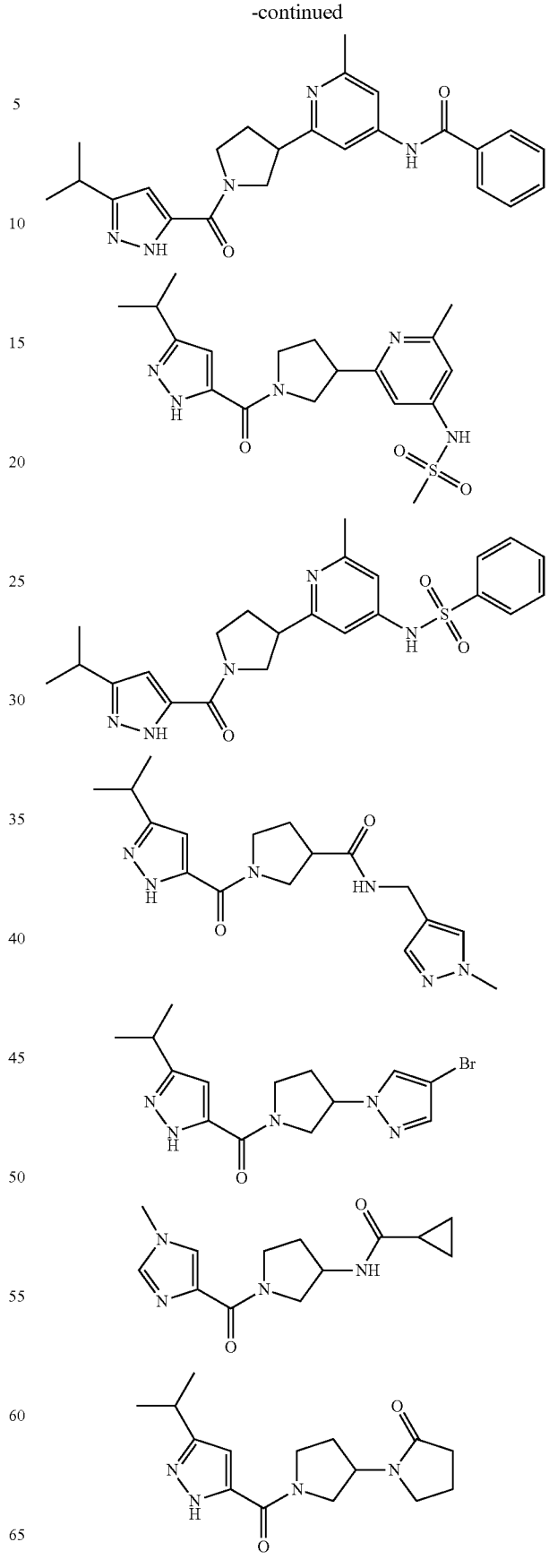

349
-continued
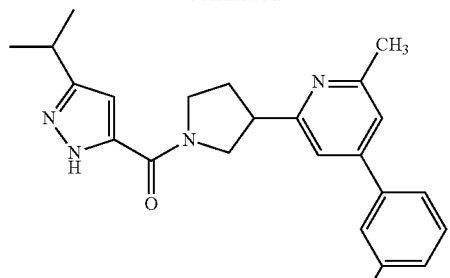
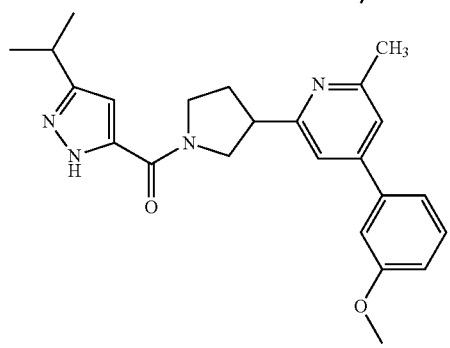
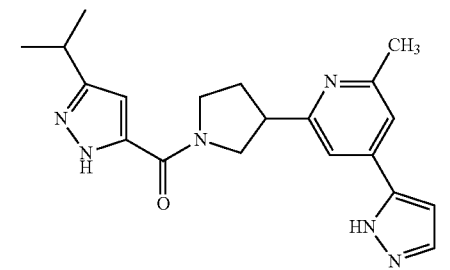
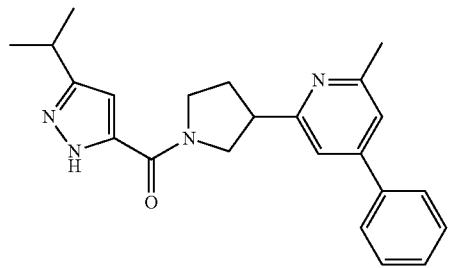
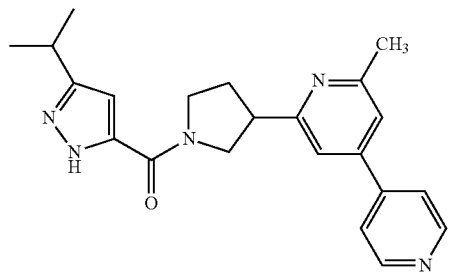
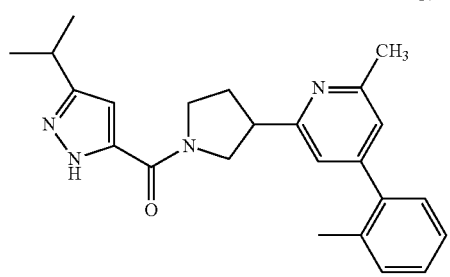
350
-continued
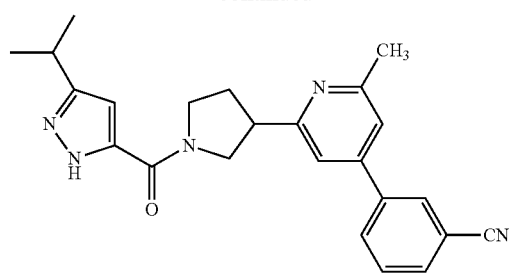
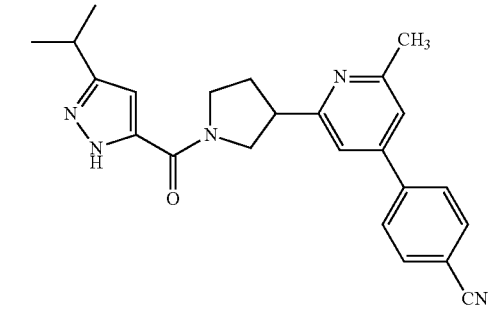
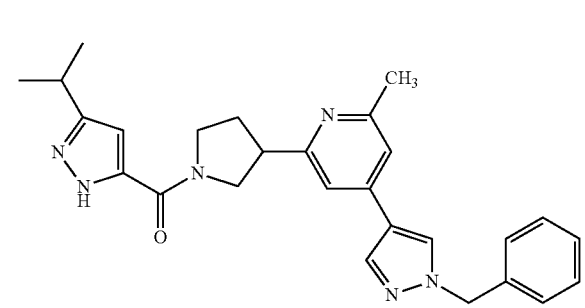
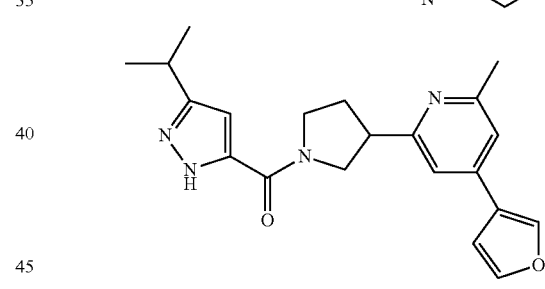
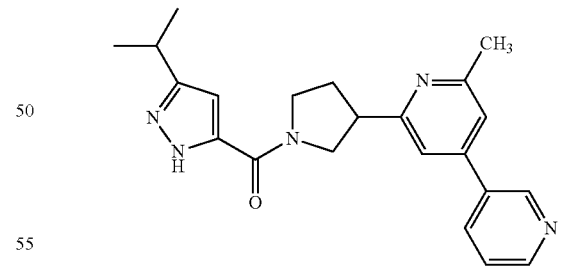
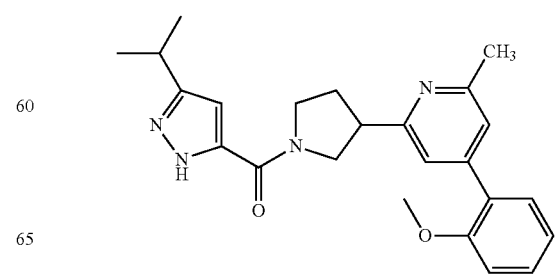

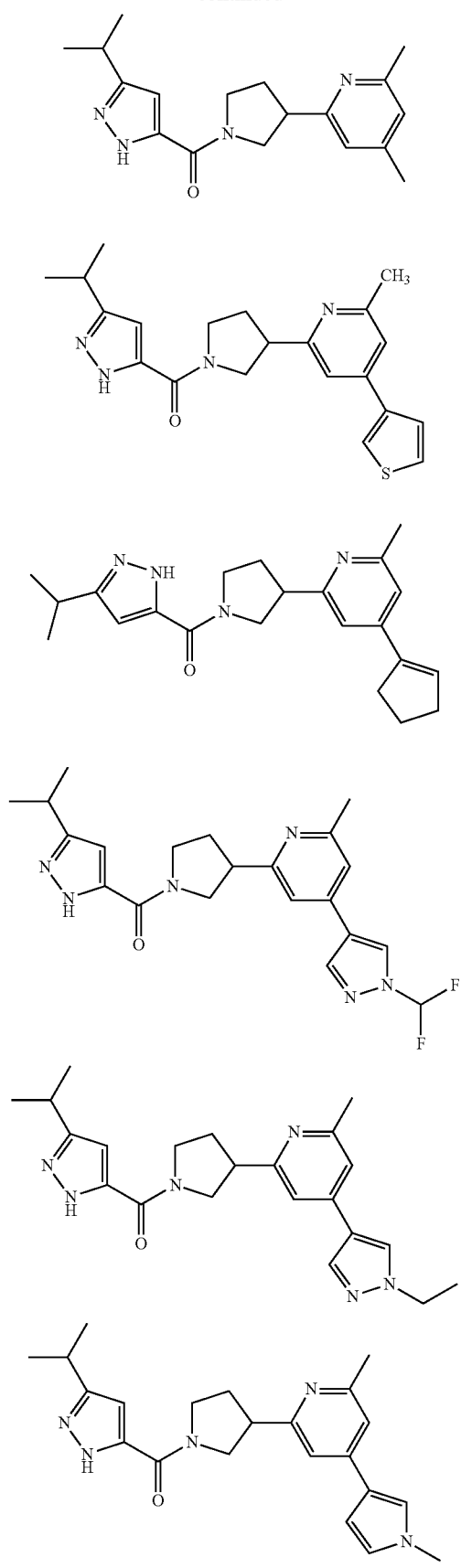
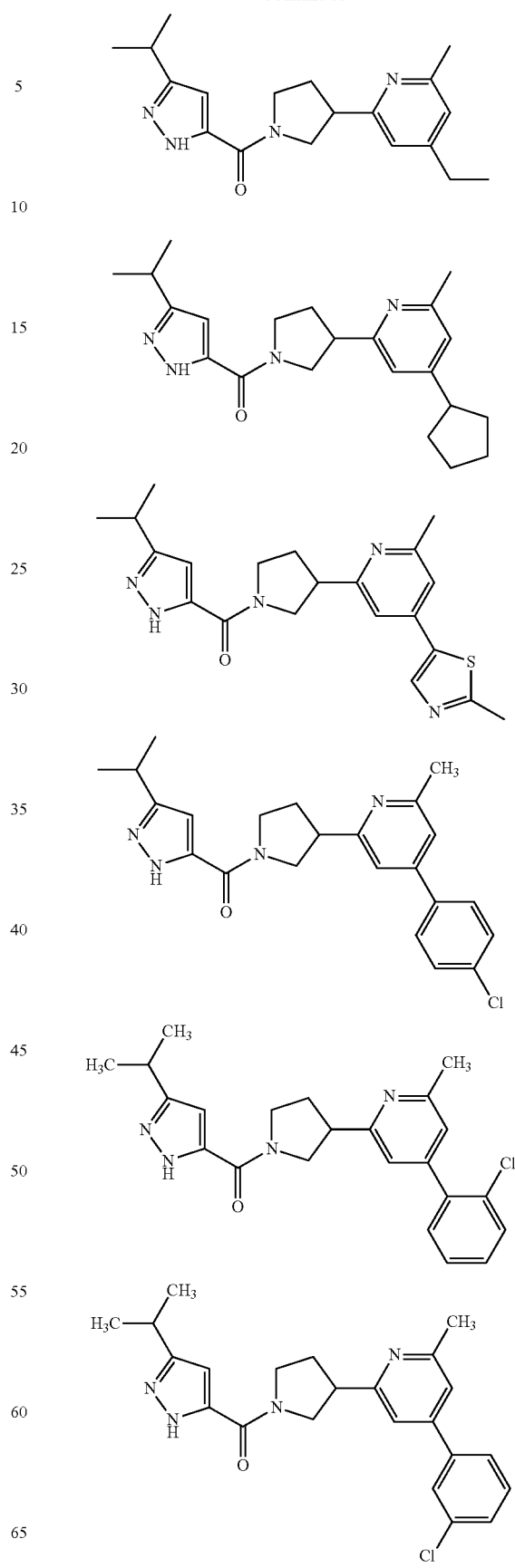

353
-continued
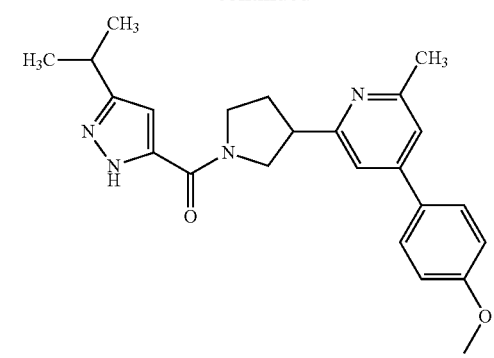
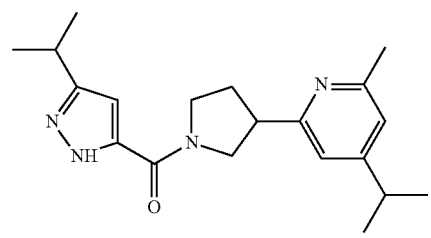
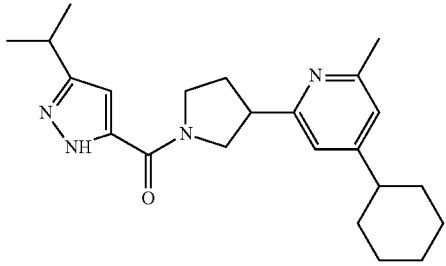
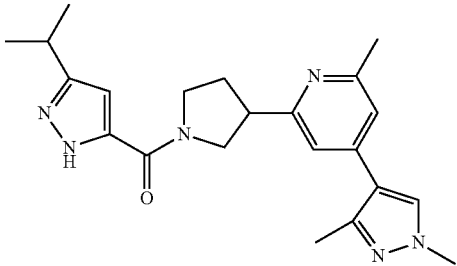
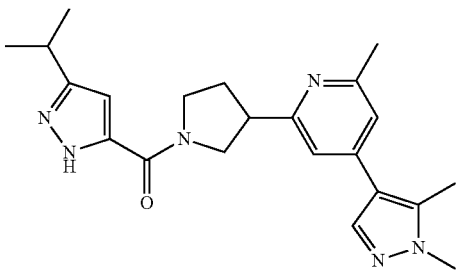
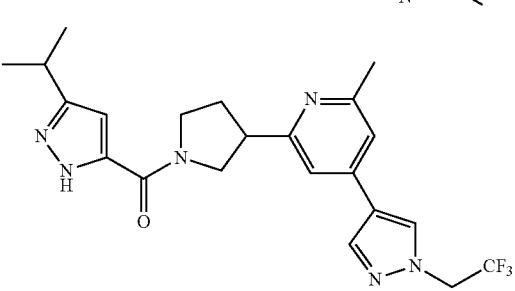
354
-continued
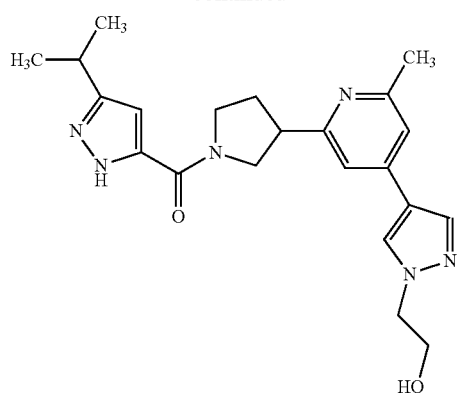
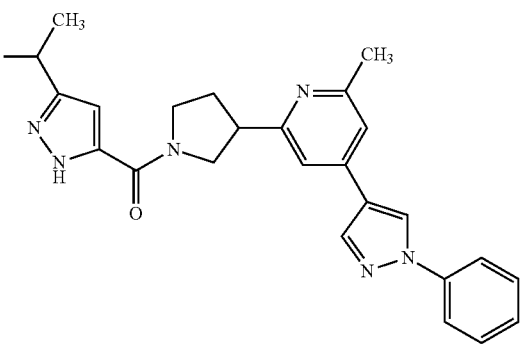
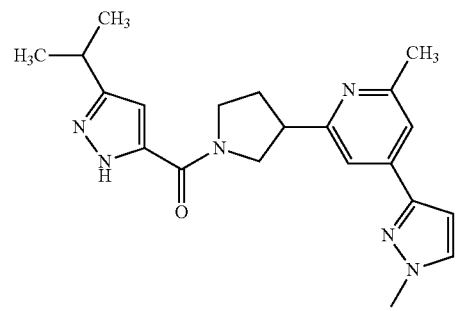
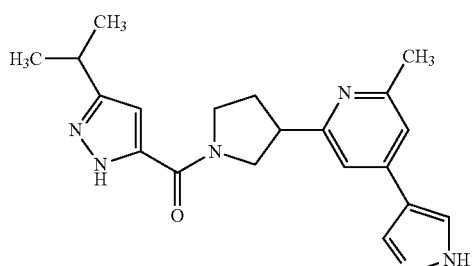
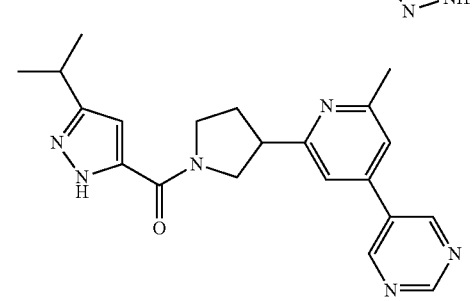

355
-continued
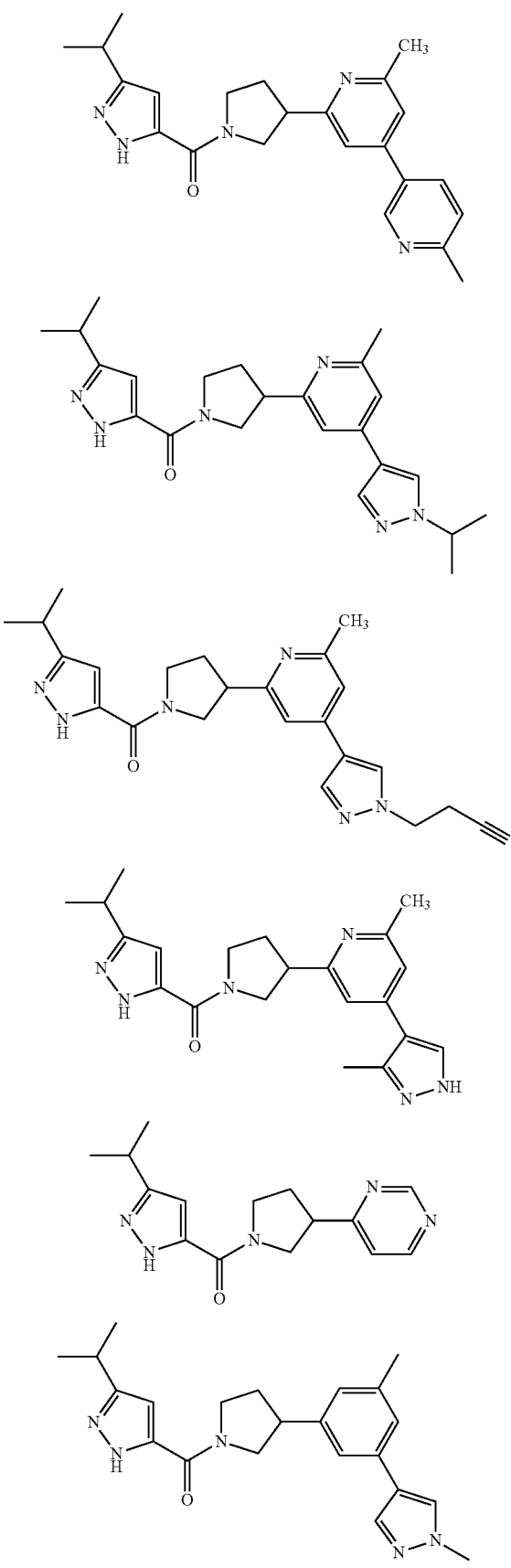
356
-continued
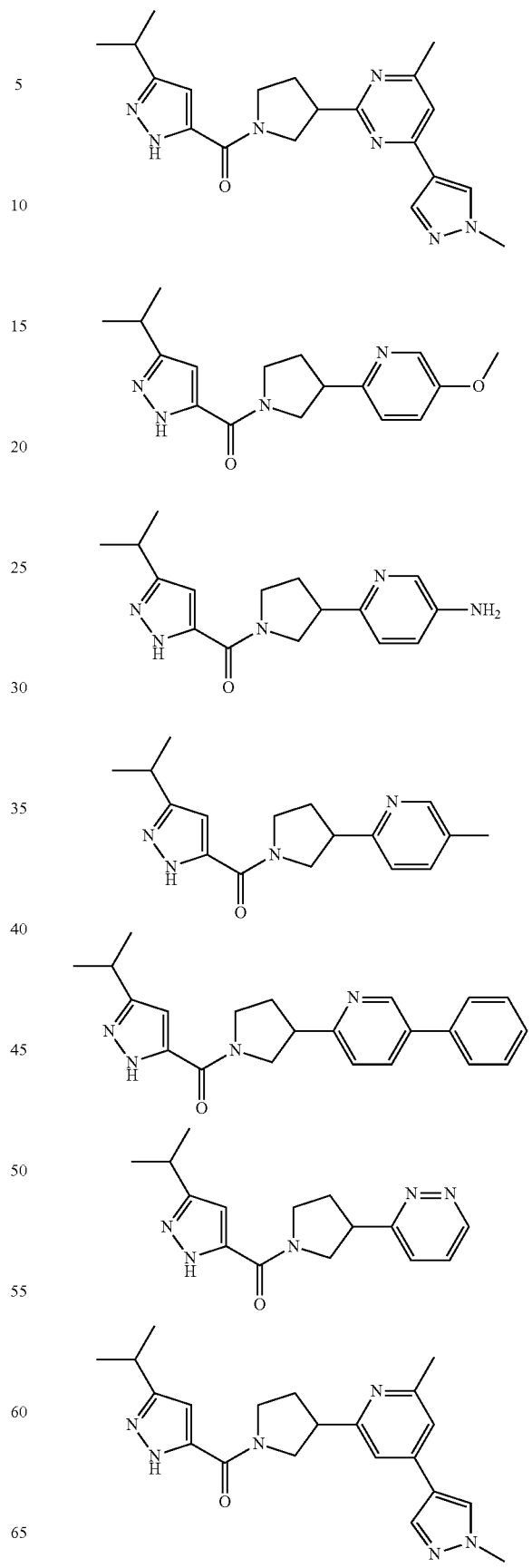

357
-continued
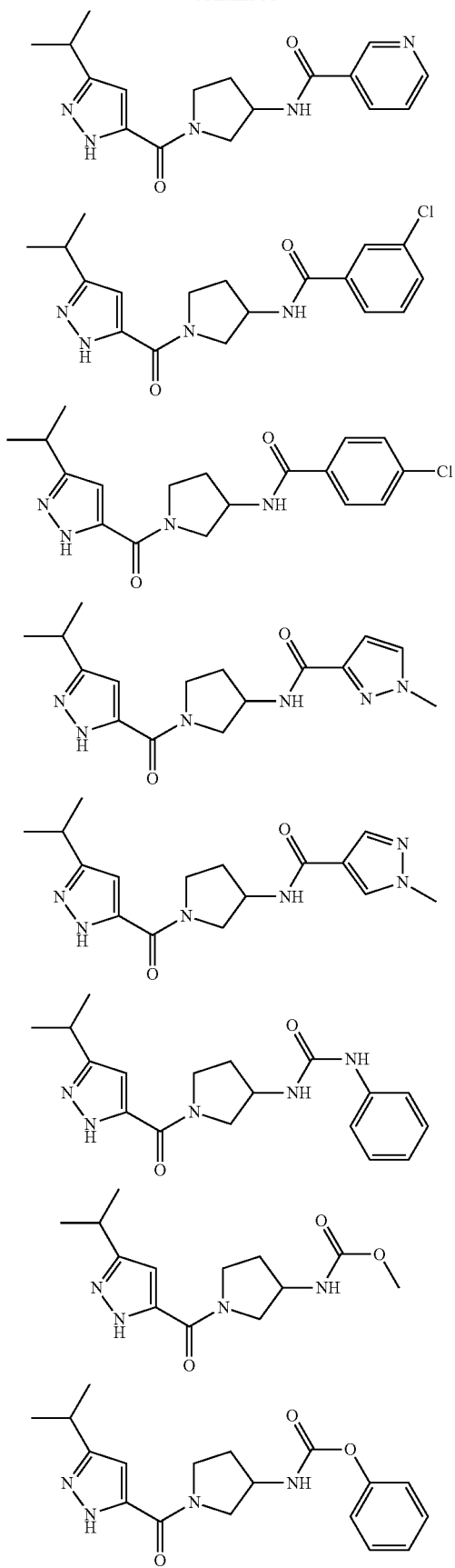
358
-continued
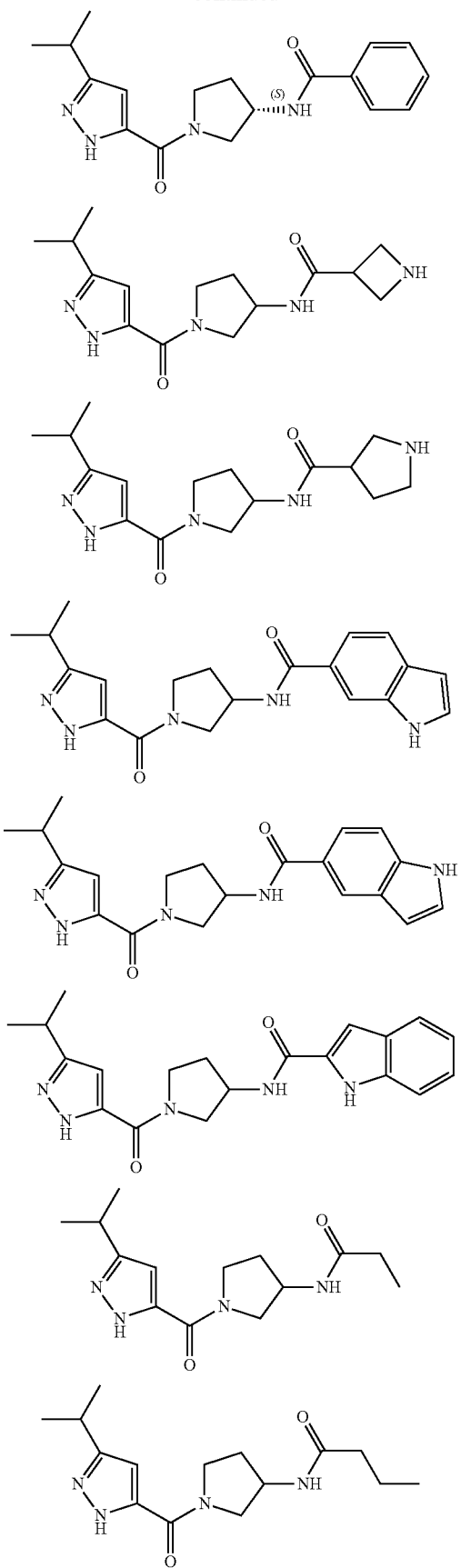

359
-continued
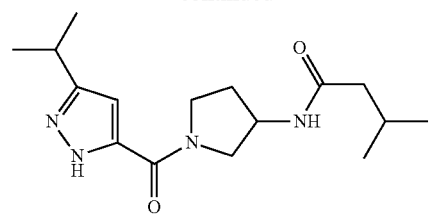
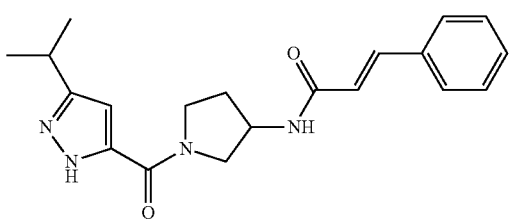
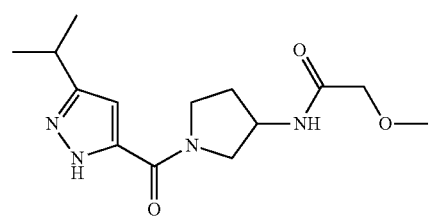
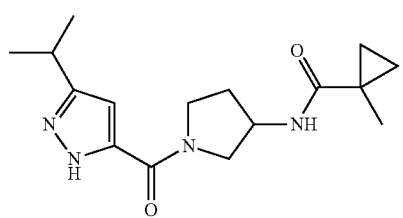
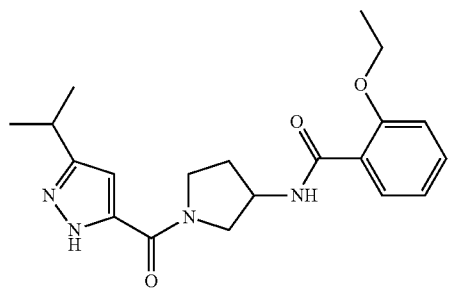
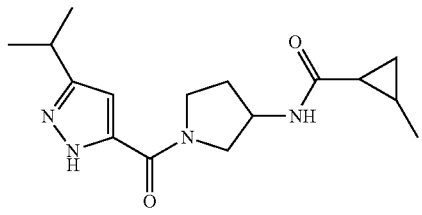
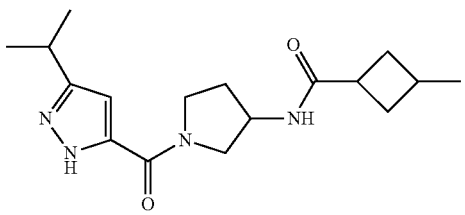
360
-continued
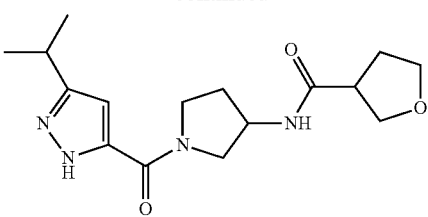
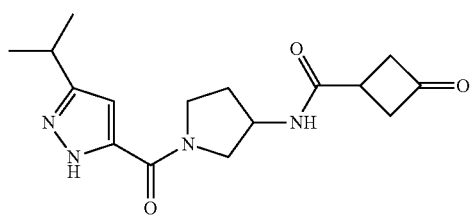
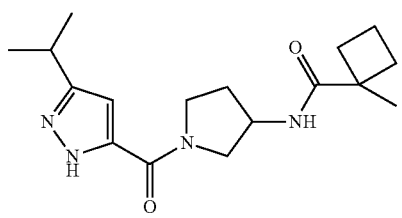
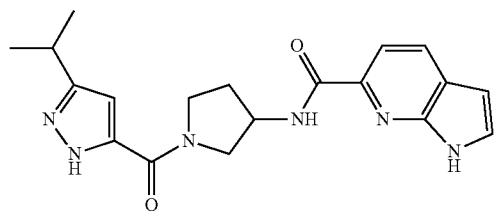
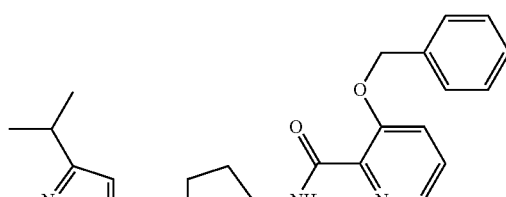
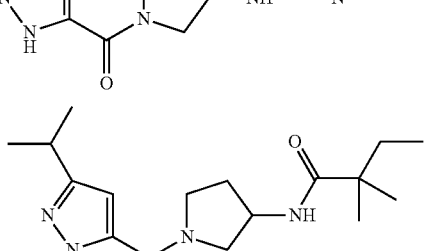
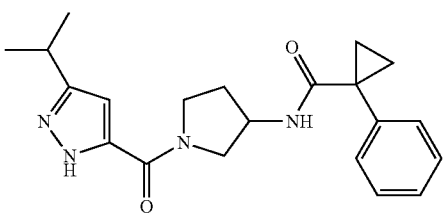

361
-continued
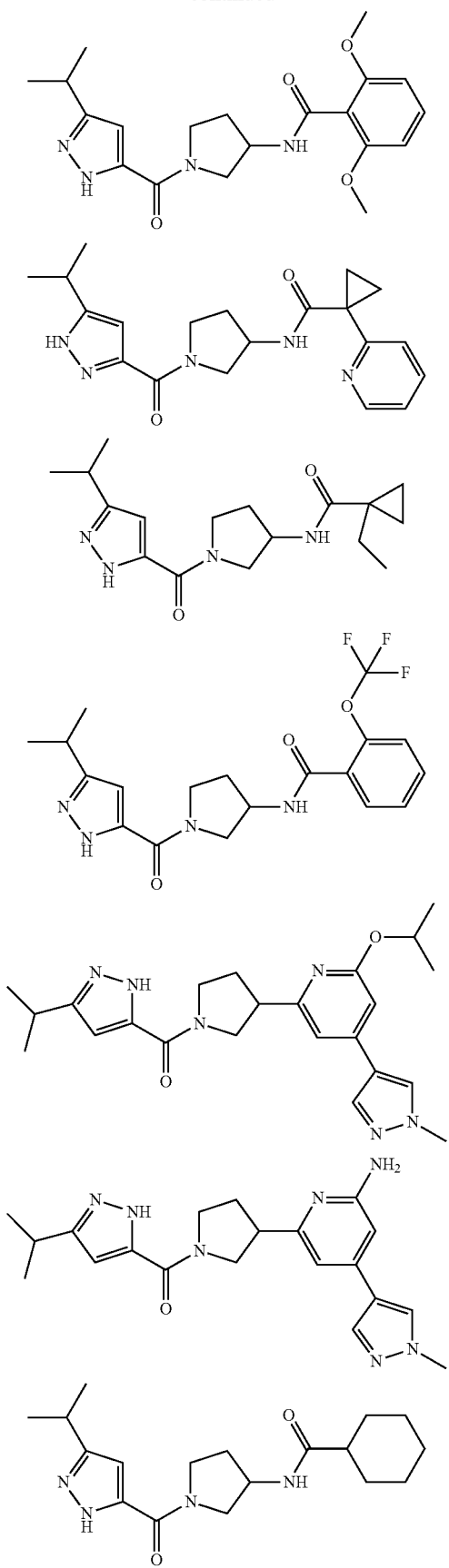
362
-continued
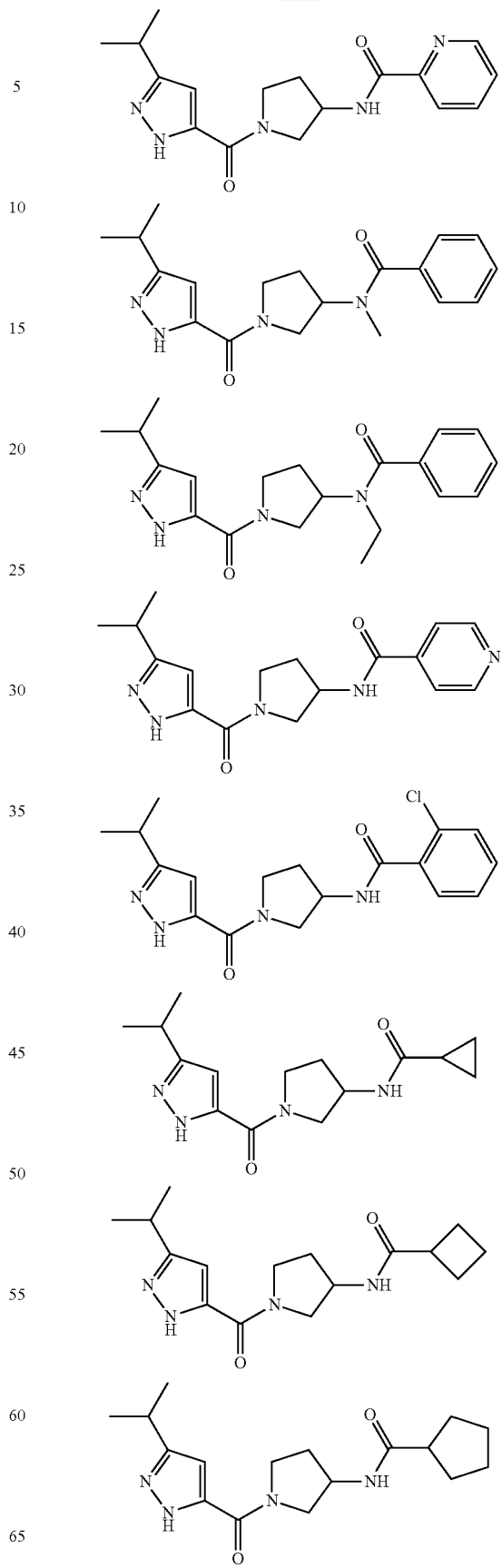

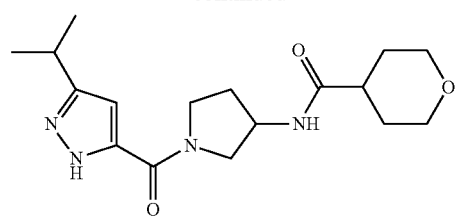
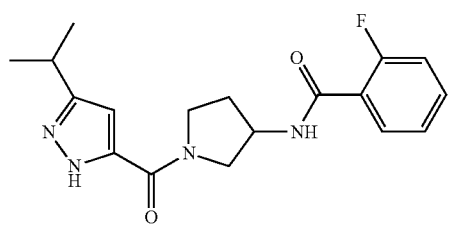
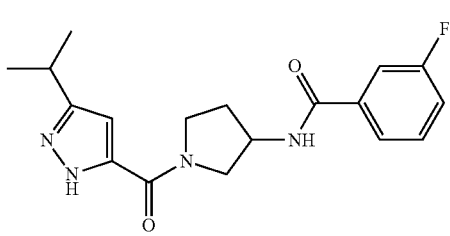
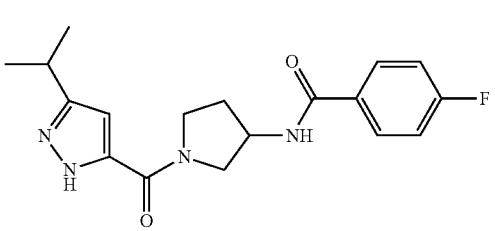
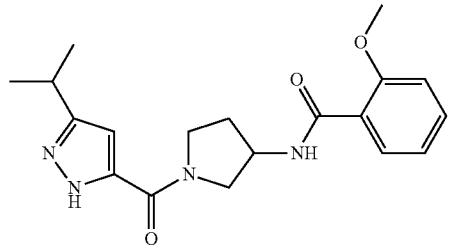
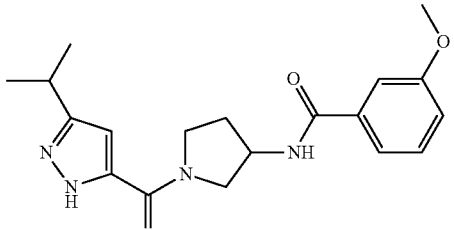
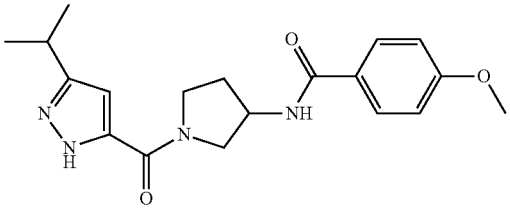
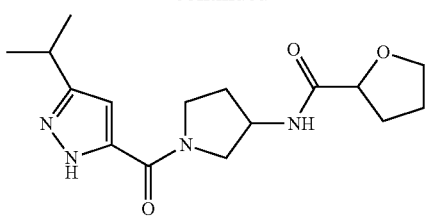
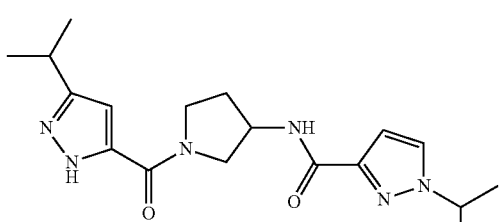
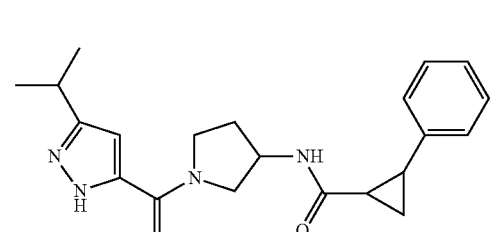
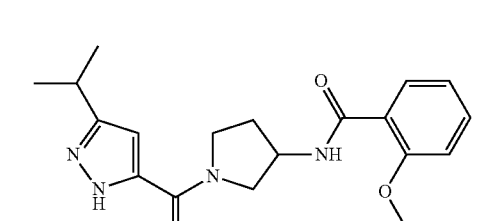
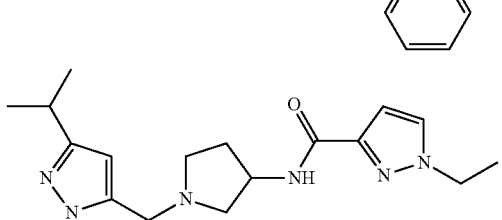
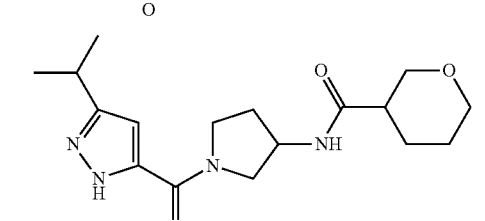
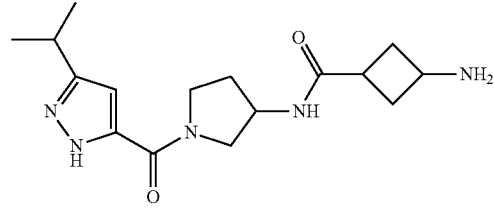

365
-continued
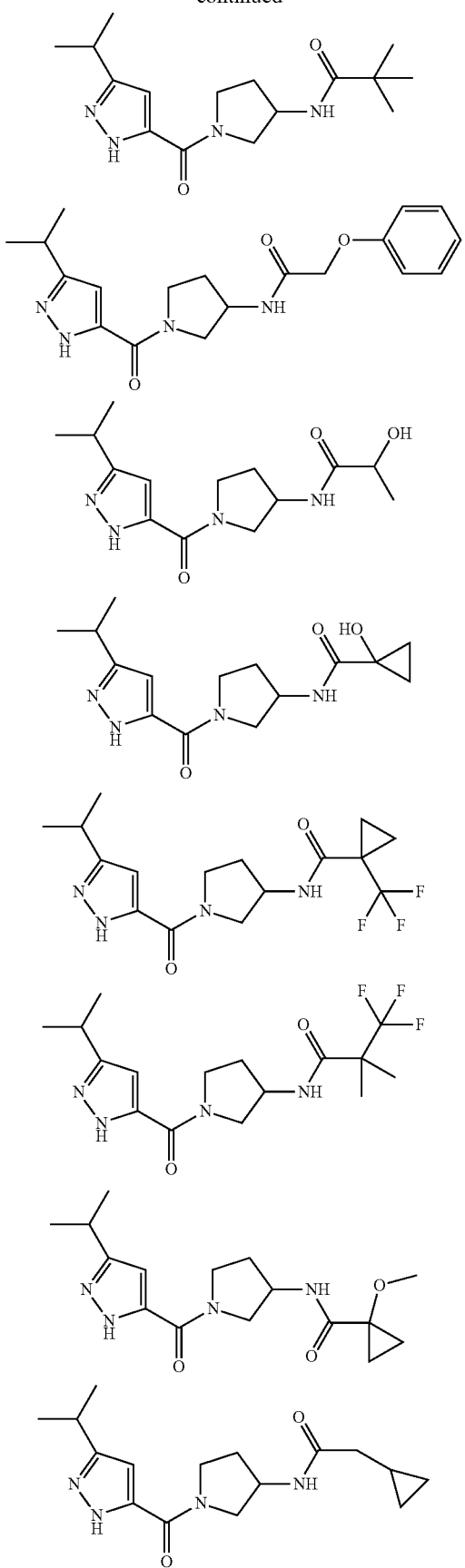
366
-continued
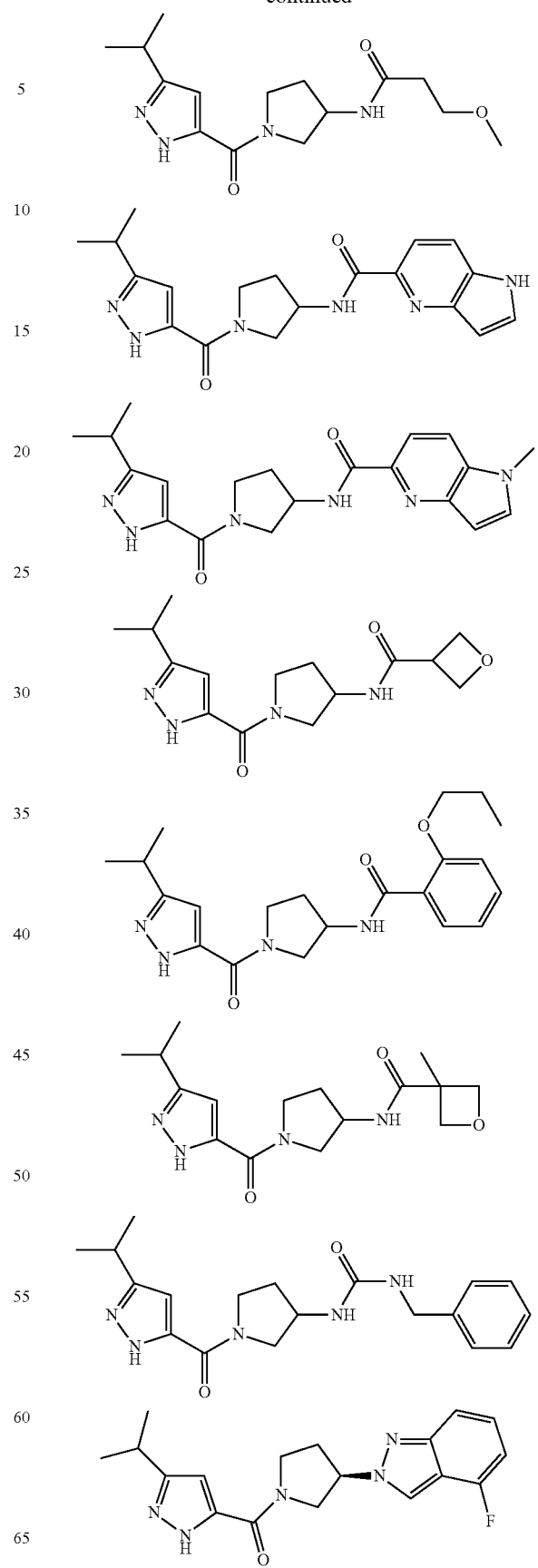

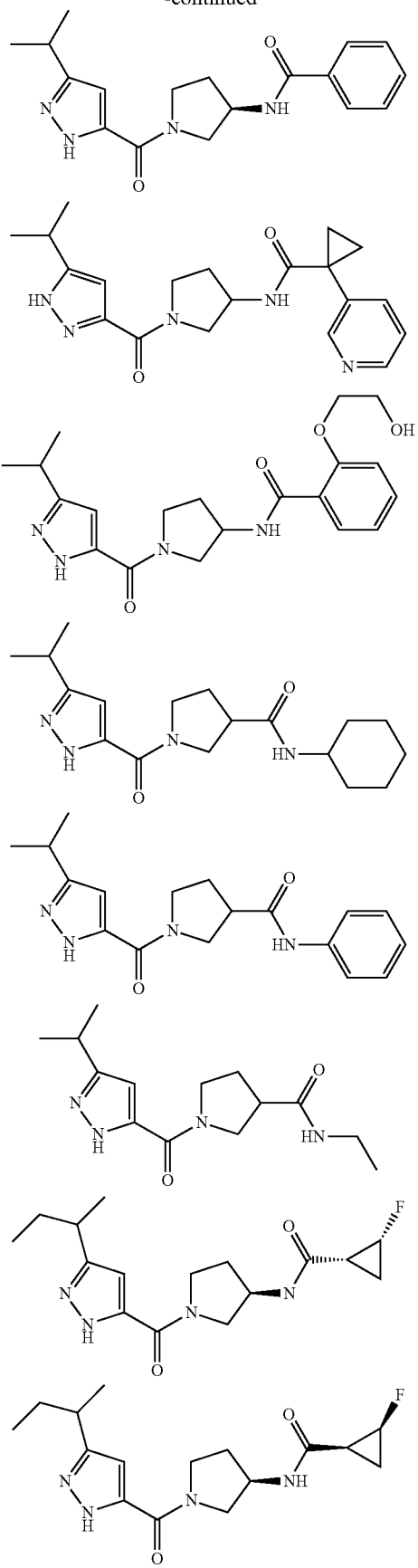
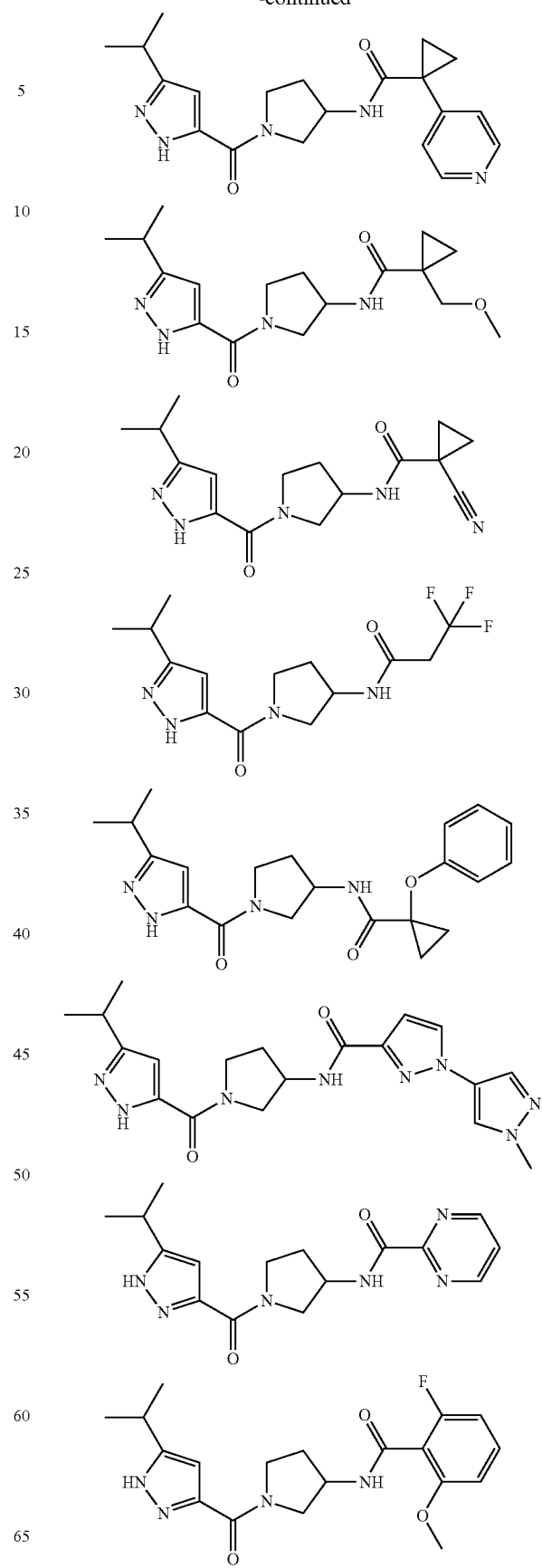

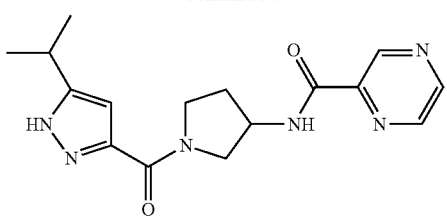
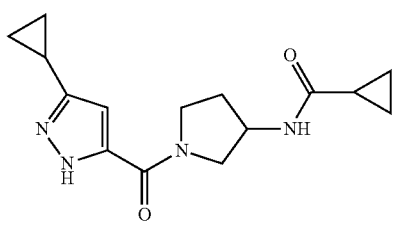
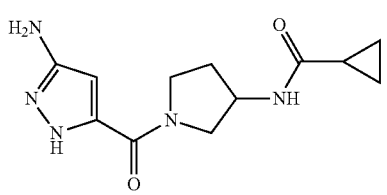
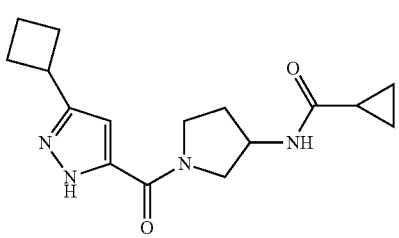
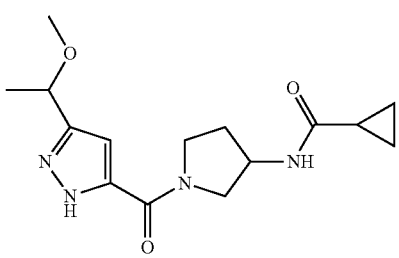
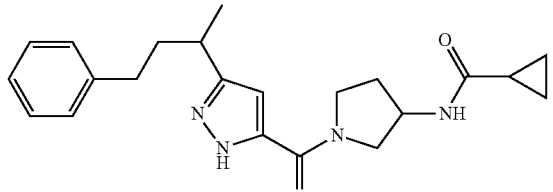
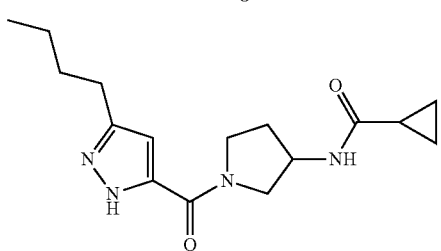
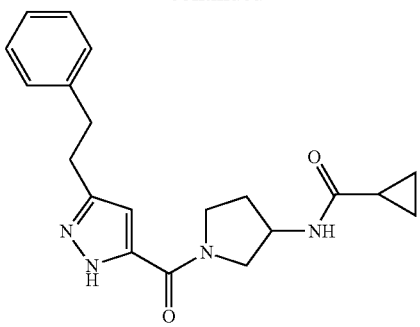
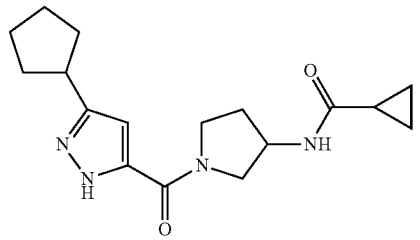
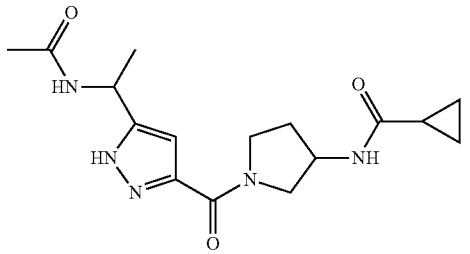
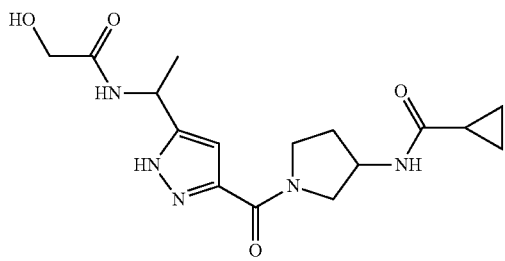
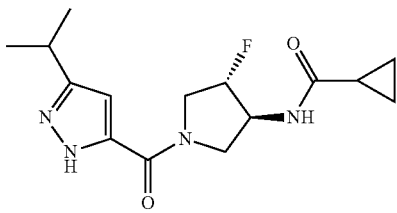
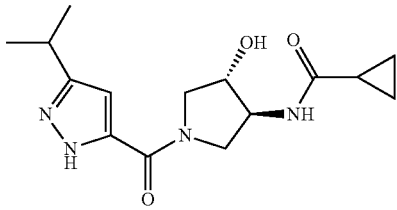
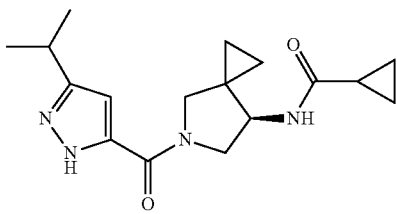

371
-continued
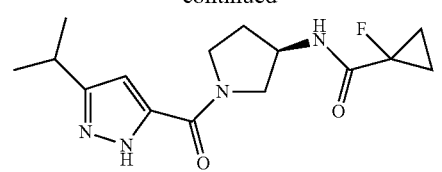
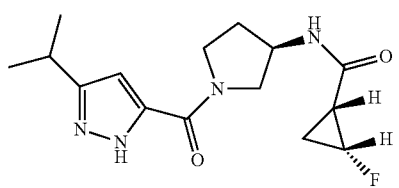
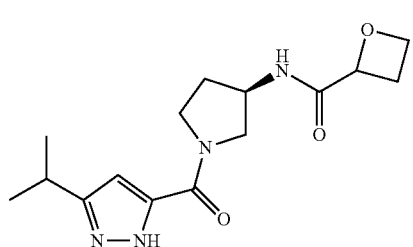
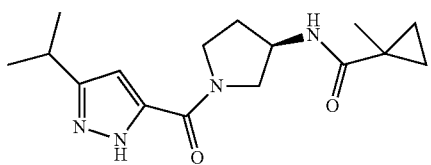
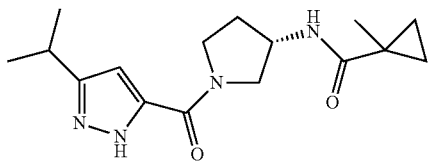
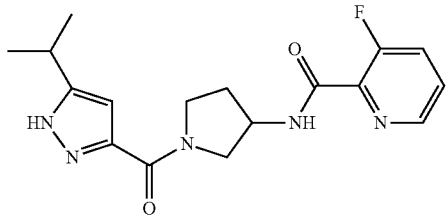
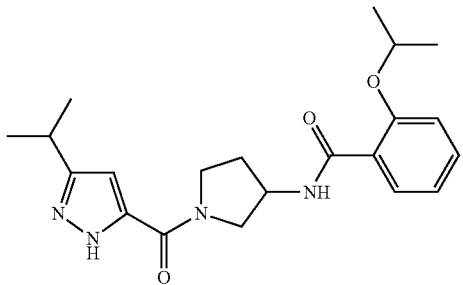
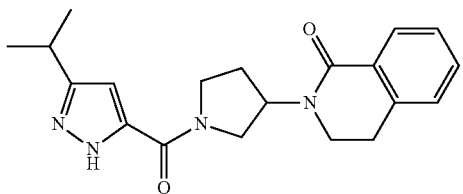
372
-continued
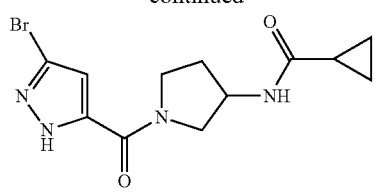
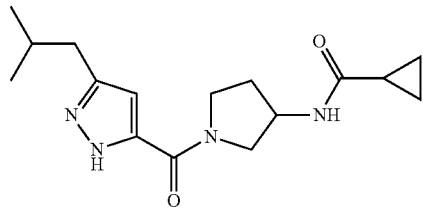
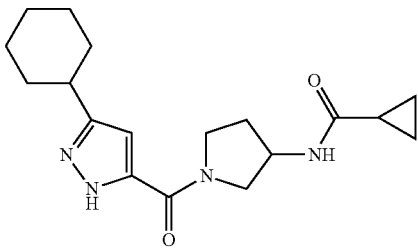
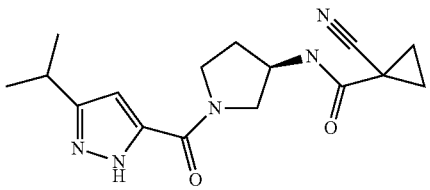
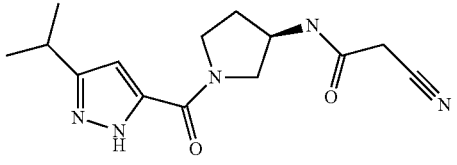
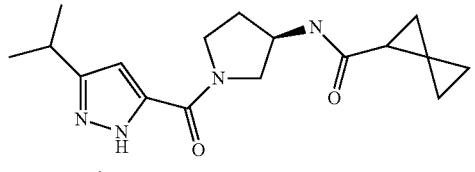
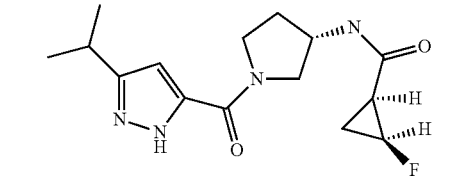
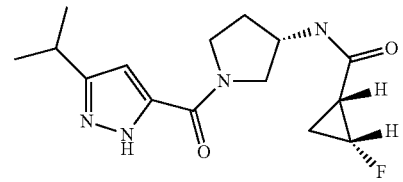
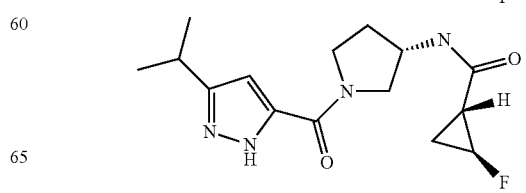

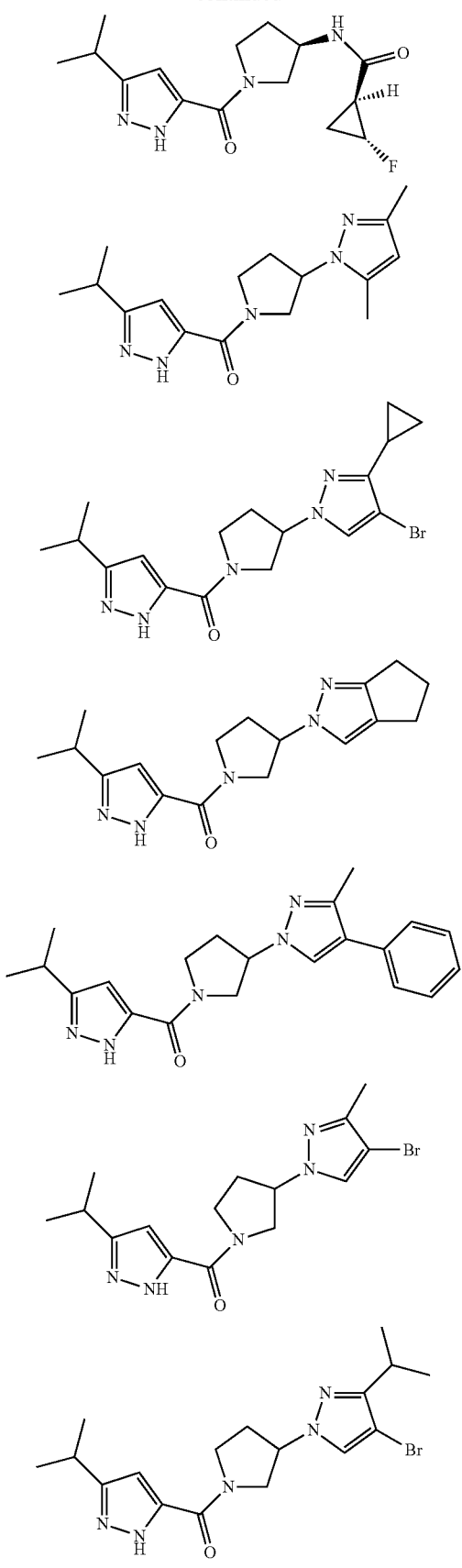
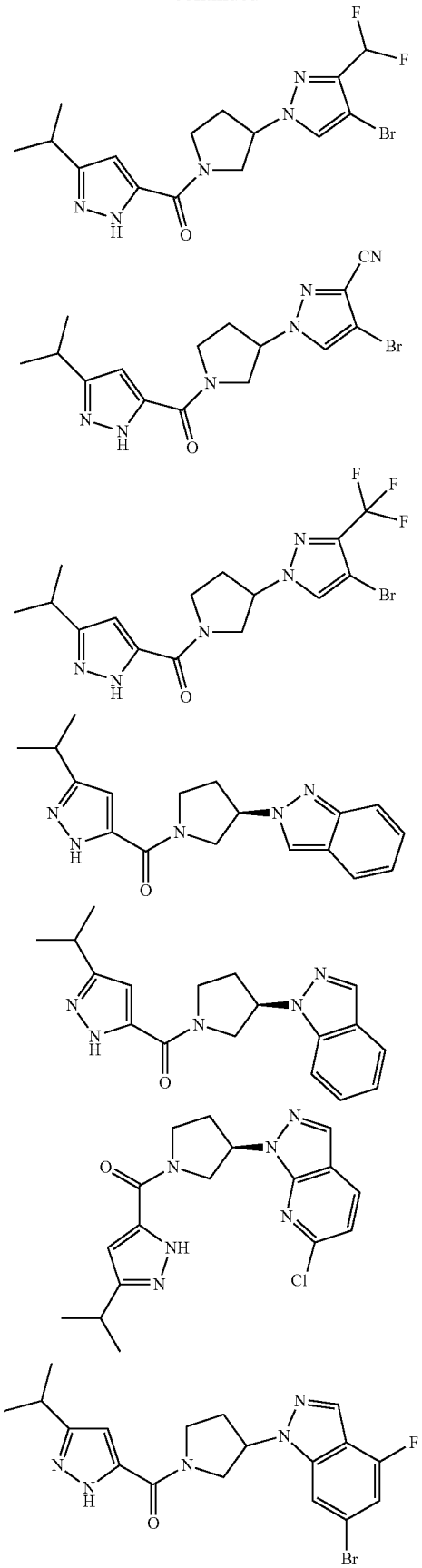

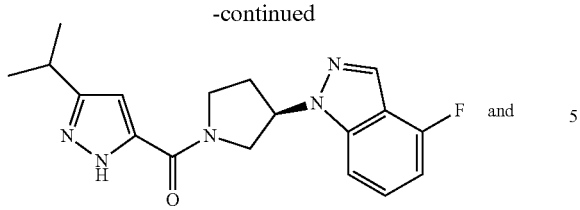 and
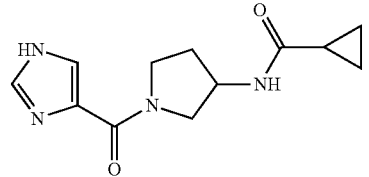
or a salt thereof.
20. A composition comprising a compound as described in claim 1 or a pharmaceutically acceptable salt thereof, and a pharmaceutically acceptable adjuvant, carrier, or vehicle.
* * * * *

UNITED STATES PATENT AND TRADEMARK OFFICE
CERTIFICATE OF CORRECTION

PATENT NO. : 10,022,354 B2
APPLICATION NO. : 15/482584
DATED : July 17, 2018
INVENTOR(S) : Kwong Wah Lai et al.

Page 1 of 2

It is certified that error appears in the above-identified patent and that said Letters Patent is hereby corrected as shown below:

In the Claims

Column 317, Lines 12-15, Claim 6, please delete the following compound:

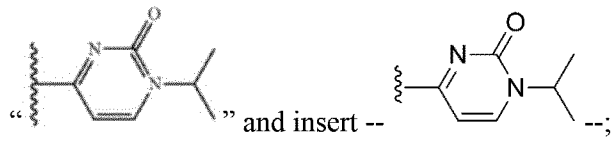

Column 317, Lines 30-34, Claim 6, please delete the following compound:

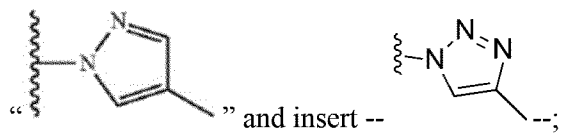

Column 317, Lines 53-59, Claim 6, please delete the following compound:

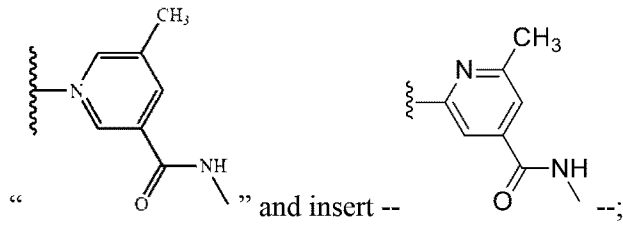

Column 323, Lines 18-26, Claim 6, please delete the following compound:

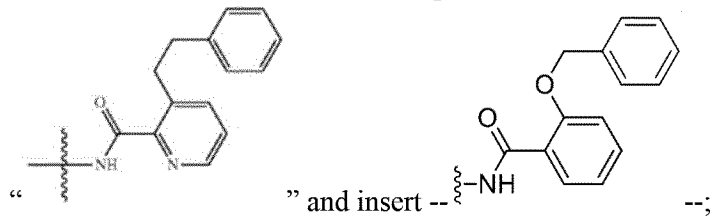

Signed and Sealed this
Second Day of October, 2018

Andrei Iancu
*Director of the United States Patent and Trademark Office*

CERTIFICATE OF CORRECTION (continued)
U.S. Pat. No. 10,022,354 B2

Column 326, Lines 37-42, Claim 6, please delete the following compound:

" 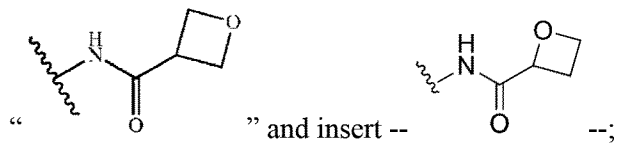 " and insert -- --;

Column 327, Lines 1-8, Claim 6, please delete the following compound:

" 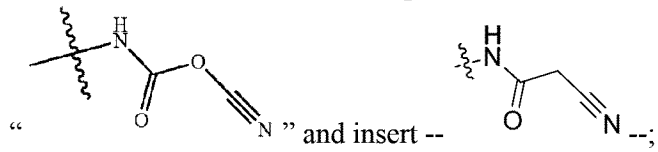 " and insert -- --;

Column 339, Lines 22-26, Claim 12, please delete the following compound:

" 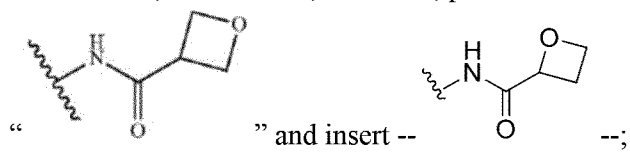 " and insert -- --;

Column 366, Lines 18-26, Claim 19, please delete the following compound:

" 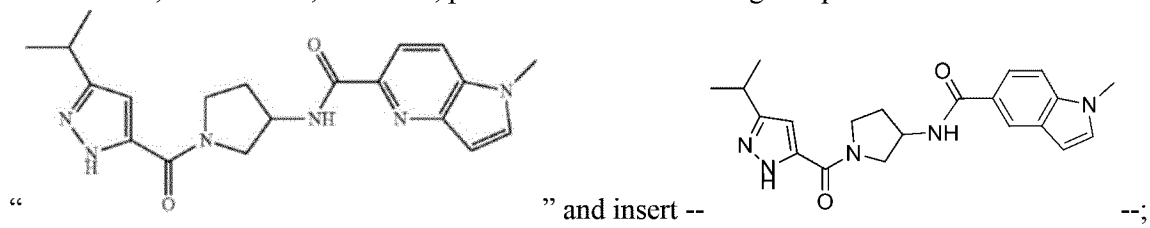 " and insert -- --;

Column 372, Lines 59-65, Claim 19, please delete the following compound:

" 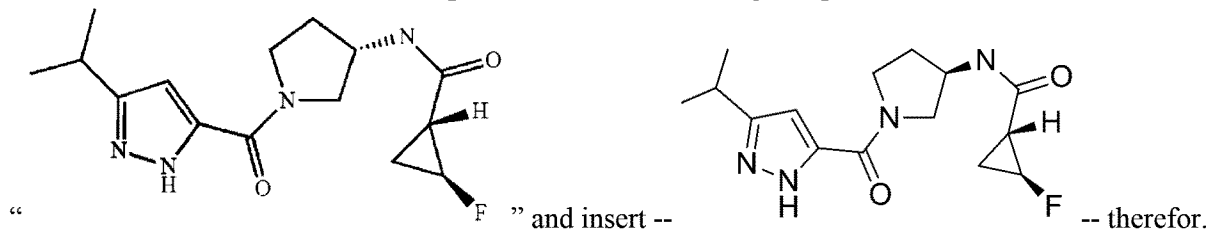 " and insert -- -- therefor.